US012502171B2

(12) United States Patent
Hall et al.

(10) Patent No.: US 12,502,171 B2
(45) Date of Patent: Dec. 23, 2025

(54) SURGICAL INSTRUMENTS WITH FLEXIBLE FIRING MEMBER ACTUATOR CONSTRAINT ARRANGEMENTS

(71) Applicant: Cilag GmbH International, Zug (CH)

(72) Inventors: Steven G. Hall, Cincinnati, OH (US); Spencer J. Witte, Los Altos, CA (US)

(73) Assignee: Cilag GmbH International, Zug (CH)

( * ) Notice: Subject to any disclaimer, the term of this patent is extended or adjusted under 35 U.S.C. 154(b) by 1083 days.

(21) Appl. No.: 17/360,220

(22) Filed: Jun. 28, 2021

(65) Prior Publication Data

US 2022/0031320 A1 Feb. 3, 2022

Related U.S. Application Data

(60) Provisional application No. 63/057,432, filed on Jul. 28, 2020, provisional application No. 63/057,430, filed on Jul. 28, 2020.

(51) Int. Cl.
*A61B 17/072* (2006.01)
*A61B 17/00* (2006.01)
(Continued)

(52) U.S. Cl.
CPC .... *A61B 17/0686* (2013.01); *A61B 17/00234* (2013.01); *A61B 17/068* (2013.01);
(Continued)

(58) Field of Classification Search
CPC .......... A61B 17/0686; A61B 17/00234; A61B 17/068; A61B 17/072; A61B 17/07207; A61B 17/29; A61B 17/320092; A61B 2034/301; A61B 2017/320094; A61B 2017/320095; A61B 2017/320097; A61B 2017/320093; A61B 2017/320071;
(Continued)

(56) References Cited

U.S. PATENT DOCUMENTS

| | | | |
|---|---|---|---|
| 66,052 | A | 6/1867 | Smith |
| 662,587 | A | 11/1900 | Blake |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

ASTM procedure D2240-00, "Standard Test Method for Rubber Property-Durometer Hardness," (Published Aug. 2000).

(Continued)

*Primary Examiner* — Anna K Kinsaul
*Assistant Examiner* — Mary C Hibbert-Copeland
(74) *Attorney, Agent, or Firm* — Frost Brown Todd LLP

(57) ABSTRACT

Articulatable surgical instruments that include a firing system configured to selectively move a firing member between a starting position and an ending position. The firing system includes a flexible upper drive member that axially passes through a flexible upper hollow member to provide upper axial drive motions to the firing member. The firing system also includes a flexible lower drive member that axially passes through a lower hollow member to provide lower axial drive motions to the firing member.

19 Claims, 136 Drawing Sheets

(51) Int. Cl.
*A61B 17/068* (2006.01)
*A61B 17/29* (2006.01)
*A61B 17/32* (2006.01)
*A61B 34/30* (2016.01)

(52) U.S. Cl.
CPC ...... *A61B 17/072* (2013.01); *A61B 17/07207* (2013.01); *A61B 17/29* (2013.01); *A61B 17/320092* (2013.01); *A61B 34/30* (2016.02); *A61B 2017/00314* (2013.01); *A61B 2017/00323* (2013.01); *A61B 2017/00336* (2013.01); *A61B 2017/00367* (2013.01); *A61B 2017/00389* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/320071* (2017.08); *A61B 2017/320093* (2017.08); *A61B 2017/320094* (2017.08); *A61B 2017/320095* (2017.08); *A61B 2017/320097* (2017.08); *A61B 2034/301* (2016.02)

(58) Field of Classification Search
CPC ........... A61B 2017/00314; A61B 2017/00323; A61B 2017/00336; A61B 2017/00367; A61B 2017/00389; A61B 2017/00398; A61B 2017/00477; A61B 2017/07214; A61B 2017/07257; A61B 2017/07271; A61B 2017/07278; A61B 2017/07285; A61B 2017/2927
USPC ........................................................ 227/175.1
See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |

(56) References Cited

U.S. PATENT DOCUMENTS

| | | | |
|---|---|---|---|
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,160,857 | A | 7/1979 | Nardella et al. |
| 4,169,476 | A | 10/1979 | Hiltebrandt |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,459,519 | A | 7/1984 | Erdman |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,476,864 | A | 10/1984 | Tezel |
| 4,478,220 | A | 10/1984 | Di Giovanni et al. |
| 4,480,641 | A | 11/1984 | Failla et al. |
| 4,481,458 | A | 11/1984 | Lane |
| 4,483,562 | A | 11/1984 | Schoolman |

(56) References Cited

U.S. PATENT DOCUMENTS 4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green

(56) References Cited

U.S. PATENT DOCUMENTS

| | | | |
|---|---|---|---|
| 4,821,939 | A | 4/1989 | Green |
| 4,827,552 | A | 5/1989 | Bojar et al. |
| 4,827,911 | A | 5/1989 | Broadwin et al. |
| 4,828,542 | A | 5/1989 | Hermann |
| 4,828,944 | A | 5/1989 | Yabe et al. |
| 4,830,855 | A | 5/1989 | Stewart |
| 4,832,158 | A | 5/1989 | Farrar et al. |
| 4,833,937 | A | 5/1989 | Nagano |
| 4,834,096 | A | 5/1989 | Oh et al. |
| 4,834,720 | A | 5/1989 | Blinkhorn |
| 4,838,859 | A | 6/1989 | Strassmann |
| 4,844,068 | A | 7/1989 | Arata et al. |
| 4,848,637 | A | 7/1989 | Pruitt |
| 4,856,078 | A | 8/1989 | Konopka |
| 4,860,644 | A | 8/1989 | Kohl et al. |
| 4,862,891 | A | 9/1989 | Smith |
| 4,863,423 | A | 9/1989 | Wallace |
| 4,865,030 | A | 9/1989 | Polyak |
| 4,868,530 | A | 9/1989 | Ahs |
| 4,868,958 | A | 9/1989 | Suzuki et al. |
| 4,869,414 | A | 9/1989 | Green et al. |
| 4,869,415 | A | 9/1989 | Fox |
| 4,873,977 | A | 10/1989 | Avant et al. |
| 4,875,486 | A | 10/1989 | Rapoport et al. |
| 4,880,015 | A | 11/1989 | Nierman |
| 4,890,613 | A | 1/1990 | Golden et al. |
| 4,892,244 | A | 1/1990 | Fox et al. |
| 4,893,622 | A | 1/1990 | Green et al. |
| 4,894,051 | A | 1/1990 | Shiber |
| 4,896,584 | A | 1/1990 | Stoll et al. |
| 4,896,678 | A | 1/1990 | Ogawa |
| 4,900,303 | A | 2/1990 | Lemelson |
| 4,903,697 | A | 2/1990 | Resnick et al. |
| 4,909,789 | A | 3/1990 | Taguchi et al. |
| 4,915,100 | A | 4/1990 | Green |
| 4,919,679 | A | 4/1990 | Averill et al. |
| 4,921,479 | A | 5/1990 | Grayzel |
| 4,925,082 | A | 5/1990 | Kim |
| 4,928,699 | A | 5/1990 | Sasai |
| 4,930,503 | A | 6/1990 | Pruitt |
| 4,930,674 | A | 6/1990 | Barak |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |
| 4,948,327 | A | 8/1990 | Crupi, Jr. |
| 4,949,707 | A | 8/1990 | LeVahn et al. |
| 4,949,927 | A | 8/1990 | Madocks et al. |
| 4,950,268 | A | 8/1990 | Rink |
| 4,951,860 | A | 8/1990 | Peters et al. |
| 4,951,861 | A | 8/1990 | Schulze et al. |
| 4,954,960 | A | 9/1990 | Lo et al. |
| 4,955,959 | A | 9/1990 | Tompkins et al. |
| 4,957,212 | A | 9/1990 | Duck et al. |
| 4,962,681 | A | 10/1990 | Yang |
| 4,962,877 | A | 10/1990 | Hervas |
| 4,964,559 | A | 10/1990 | Deniega et al. |
| 4,964,863 | A | 10/1990 | Kanshin et al. |
| 4,965,709 | A | 10/1990 | Ngo |
| 4,970,656 | A | 11/1990 | Lo et al. |
| 4,973,274 | A | 11/1990 | Hirukawa |
| 4,973,302 | A | 11/1990 | Armour et al. |
| 4,976,173 | A | 12/1990 | Yang |
| 4,978,049 | A | 12/1990 | Green |
| 4,978,333 | A | 12/1990 | Broadwin et al. |
| 4,979,952 | A | 12/1990 | Kubota et al. |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,001,649 | A | 3/1991 | Lo et al. |
| 5,002,543 | A | 3/1991 | Bradshaw et al. |
| 5,002,553 | A | 3/1991 | Shiber |
| 5,005,754 | A | 4/1991 | Van Overloop |
| 5,009,222 | A | 4/1991 | Her |
| 5,009,661 | A | 4/1991 | Michelson |
| 5,012,411 | A | 4/1991 | Policastro et al. |
| 5,014,898 | A | 5/1991 | Heidrich |
| 5,014,899 | A | 5/1991 | Presty et al. |
| 5,015,227 | A | 5/1991 | Broadwin et al. |
| 5,018,515 | A | 5/1991 | Gilman |
| 5,018,657 | A | 5/1991 | Pedlick et al. |
| 5,024,652 | A | 6/1991 | Dumenek et al. |
| 5,024,671 | A | 6/1991 | Tu et al. |
| 5,025,559 | A | 6/1991 | McCullough |
| 5,027,834 | A | 7/1991 | Pruitt |
| 5,030,226 | A | 7/1991 | Green et al. |
| 5,031,814 | A | 7/1991 | Tompkins et al. |
| 5,033,552 | A | 7/1991 | Hu |
| 5,035,040 | A | 7/1991 | Kerrigan et al. |
| 5,037,018 | A | 8/1991 | Matsuda et al. |
| 5,038,109 | A | 8/1991 | Goble et al. |
| 5,038,247 | A | 8/1991 | Kelley et al. |
| 5,040,715 | A | 8/1991 | Green et al. |
| 5,042,707 | A | 8/1991 | Taheri |
| 5,056,953 | A | 10/1991 | Marot et al. |
| 5,060,658 | A | 10/1991 | Dejter, Jr. et al. |
| 5,061,269 | A | 10/1991 | Muller |
| 5,062,491 | A | 11/1991 | Takeshima et al. |
| 5,062,563 | A | 11/1991 | Green et al. |
| 5,065,929 | A | 11/1991 | Schulze et al. |
| 5,069,569 | A | 12/1991 | Lieser |
| 5,071,052 | A | 12/1991 | Rodak et al. |
| 5,071,430 | A | 12/1991 | de Salis et al. |
| 5,074,454 | A | 12/1991 | Peters |
| 5,077,506 | A | 12/1991 | Krause |
| 5,079,006 | A | 1/1992 | Urquhart |
| 5,080,556 | A | 1/1992 | Carreno |
| 5,083,695 | A | 1/1992 | Foslien et al. |
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,094,247 | A | 3/1992 | Hernandez et al. |
| 5,098,004 | A | 3/1992 | Kerrigan |
| 5,098,360 | A | 3/1992 | Hirota |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,108,368 | A | 4/1992 | Hammerslag et al. |
| 5,109,722 | A | 5/1992 | Hufnagle et al. |
| 5,111,987 | A | 5/1992 | Moeinzadeh et al. |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,124,990 | A | 6/1992 | Williamson |
| 5,129,570 | A | 7/1992 | Schulze et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |

(56) References Cited

U.S. PATENT DOCUMENTS

D330,699 S 11/1992 Gill
5,163,598 A 11/1992 Peters et al.
5,164,652 A 11/1992 Johnson et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,174,276 A 12/1992 Crockard
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,188,126 A 2/1993 Fabian et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D338,729 S 8/1993 Sprecklemeier et al.
5,234,447 A 8/1993 Kaster et al.
5,236,269 A 8/1993 Handy
5,236,424 A 8/1993 Imran
5,236,440 A 8/1993 Hlavacek
5,236,629 A 8/1993 Mahabadi et al.
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,251,801 A 10/1993 Ruckdeschel et al.
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,269,794 A 12/1993 Rexroth
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,443 A 3/1994 Wentz
5,297,714 A 3/1994 Kramer
5,300,087 A 4/1994 Knoepfler
5,302,148 A 4/1994 Heinz
5,303,606 A 4/1994 Kokinda
5,304,204 A 4/1994 Bregen
D347,474 S 5/1994 Olson
5,307,976 A 5/1994 Olson et al.
5,308,353 A 5/1994 Beurrier
5,308,358 A 5/1994 Bond et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller et al.
5,314,466 A 5/1994 Stern et al.
5,318,221 A 6/1994 Green et al.
5,318,589 A 6/1994 Lichtman
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.

(56) References Cited

U.S. PATENT DOCUMENTS

| | | | |
|---|---|---|---|
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,738 | A | 1/1995 | Herbermann |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |
| 5,383,888 | A | 1/1995 | Zvenyatsky et al. |
| 5,383,895 | A | 1/1995 | Holmes et al. |
| 5,388,568 | A | 2/1995 | van der Heide |
| 5,389,072 | A | 2/1995 | Imran |
| 5,389,098 | A | 2/1995 | Tsuruta et al. |
| 5,389,102 | A | 2/1995 | Green et al. |
| 5,389,104 | A | 2/1995 | Hahnen et al. |
| 5,391,180 | A | 2/1995 | Tovey et al. |
| 5,392,979 | A | 2/1995 | Green et al. |
| 5,395,030 | A | 3/1995 | Kuramoto et al. |
| 5,395,033 | A | 3/1995 | Byrne et al. |
| 5,395,034 | A | 3/1995 | Allen et al. |
| 5,395,312 | A | 3/1995 | Desai |
| 5,395,384 | A | 3/1995 | Duthoit et al. |
| 5,397,046 | A | 3/1995 | Savage et al. |
| 5,397,324 | A | 3/1995 | Carroll et al. |
| 5,400,267 | A | 3/1995 | Denen et al. |
| 5,403,276 | A | 4/1995 | Schechter et al. |
| 5,403,312 | A | 4/1995 | Yates et al. |
| 5,404,106 | A | 4/1995 | Matsuda |
| 5,404,870 | A | 4/1995 | Brinkerhoff et al. |
| 5,404,960 | A | 4/1995 | Wada et al. |
| 5,405,072 | A | 4/1995 | Zlock et al. |
| 5,405,073 | A | 4/1995 | Porter |
| 5,405,344 | A | 4/1995 | Williamson et al. |
| 5,405,360 | A | 4/1995 | Tovey |
| 5,407,293 | A | 4/1995 | Crainich |
| 5,408,409 | A | 4/1995 | Glassman et al. |
| 5,409,498 | A | 4/1995 | Braddock et al. |
| 5,409,703 | A | 4/1995 | McAnalley et al. |
| D357,981 | S | 5/1995 | Green et al. |
| 5,411,481 | A | 5/1995 | Allen et al. |
| 5,411,508 | A | 5/1995 | Bessler et al. |
| 5,413,107 | A | 5/1995 | Oakley et al. |
| 5,413,267 | A | 5/1995 | Solyntjes et al. |
| 5,413,268 | A | 5/1995 | Green et al. |
| 5,413,272 | A | 5/1995 | Green et al. |
| 5,413,573 | A | 5/1995 | Koivukangas |
| 5,415,334 | A | 5/1995 | Williamson et al. |
| 5,415,335 | A | 5/1995 | Knodell, Jr. |
| 5,417,203 | A | 5/1995 | Tovey et al. |
| 5,417,361 | A | 5/1995 | Williamson, IV |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,423,835 | A | 6/1995 | Green et al. |
| 5,425,355 | A | 6/1995 | Kulick |
| 5,425,745 | A | 6/1995 | Green et al. |
| 5,427,298 | A | 6/1995 | Tegtmeier |
| 5,431,322 | A | 7/1995 | Green et al. |
| 5,431,323 | A | 7/1995 | Smith et al. |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,644 | A | 8/1995 | Pietrafitta et al. |
| 5,446,646 | A | 8/1995 | Miyazaki |
| 5,447,265 | A | 9/1995 | Vidal et al. |
| 5,447,417 | A | 9/1995 | Kuhl et al. |
| 5,447,513 | A | 9/1995 | Davison et al. |
| 5,449,355 | A | 9/1995 | Rhum et al. |
| 5,449,365 | A | 9/1995 | Green et al. |
| 5,449,370 | A | 9/1995 | Vaitekunas |
| 5,452,836 | A | 9/1995 | Huitema et al. |
| 5,452,837 | A | 9/1995 | Williamson, IV et al. |
| 5,454,378 | A | 10/1995 | Palmer et al. |
| 5,454,822 | A | 10/1995 | Schob et al. |
| 5,454,824 | A | 10/1995 | Fontayne et al. |
| 5,454,827 | A | 10/1995 | Aust et al. |
| 5,456,401 | A | 10/1995 | Green et al. |
| 5,456,917 | A | 10/1995 | Wise et al. |
| 5,458,279 | A | 10/1995 | Plyley |
| 5,458,579 | A | 10/1995 | Chodorow et al. |
| 5,462,215 | A | 10/1995 | Viola et al. |
| 5,464,013 | A | 11/1995 | Lemelson |
| 5,464,144 | A | 11/1995 | Guy et al. |

(56) References Cited

U.S. PATENT DOCUMENTS

| | | | |
|---|---|---|---|
| 5,464,300 | A | 11/1995 | Crainich |
| 5,465,819 | A | 11/1995 | Weilant et al. |
| 5,465,894 | A | 11/1995 | Clark et al. |
| 5,465,895 | A | 11/1995 | Knodel et al. |
| 5,465,896 | A | 11/1995 | Allen et al. |
| 5,466,020 | A | 11/1995 | Page et al. |
| 5,467,911 | A | 11/1995 | Tsuruta et al. |
| 5,468,253 | A | 11/1995 | Bezwada et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,470,010 | A | 11/1995 | Rothfuss et al. |
| 5,471,129 | A | 11/1995 | Mann |
| 5,472,132 | A | 12/1995 | Savage et al. |
| 5,472,442 | A | 12/1995 | Klicek |
| 5,473,204 | A | 12/1995 | Temple |
| 5,474,057 | A | 12/1995 | Makower et al. |
| 5,474,223 | A | 12/1995 | Viola et al. |
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,623 | A | 4/1996 | Tilton, Jr. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,509,596 | A | 4/1996 | Green et al. |
| 5,509,916 | A | 4/1996 | Taylor |
| 5,509,918 | A | 4/1996 | Romano |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,788 | A | 6/1996 | Kuzmak |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |

(56) References Cited

U.S. PATENT DOCUMENTS 5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella

(56) References Cited

U.S. PATENT DOCUMENTS 5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,746,770 A 5/1998 Zeitels et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,186 A 6/1998 Faraz et al.
5,766,188 A 6/1998 Igaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,798,752 A 8/1998 Buxton et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,240 A 9/1998 Robertson
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,816,770 A 10/1998 Itagaki
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A 11/1998 Kolesa et al.
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,183 A 12/1998 Chilcoat
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi

(56) References Cited

U.S. PATENT DOCUMENTS 5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,664 A 2/1999 Speier et al.
5,868,760 A 2/1999 McGuckin, Jr.
5,868,790 A 2/1999 Vincent et al.
5,871,135 A 2/1999 Williamson, IV et al.
5,873,817 A 2/1999 Kokish et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,881,943 A 3/1999 Heck et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,863 A 4/1999 Yoon
5,893,878 A 4/1999 Pierce
5,894,979 A 4/1999 Powell
5,897,552 A 4/1999 Edwards et al.
5,897,562 A 4/1999 Bolanos et al.
5,899,425 A 5/1999 Corey, Jr. et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,146 A 6/1999 Allotta et al.
5,916,147 A 6/1999 Boury
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,938,678 A 8/1999 Zirps et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,980,569 A 11/1999 Scirica
5,984,949 A 11/1999 Levin
5,988,479 A 11/1999 Palmer
5,990,379 A 11/1999 Gregory
5,993,466 A 11/1999 Yoon
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,275 A 2/2000 Horvitz et al.
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.

(56) References Cited

U.S. PATENT DOCUMENTS

RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
6,094,021 A 7/2000 Noro et al.
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
RE36,923 E 10/2000 Hiroi et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,149,660 A 11/2000 Laufer et al.
6,151,323 A 11/2000 O'Connell et al.
6,152,935 A 11/2000 Kammerer et al.
6,155,473 A 12/2000 Tompkins et al.
6,156,056 A 12/2000 Kearns et al.
6,157,169 A 12/2000 Lee
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,235,036 B1 5/2001 Gardner et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.

(56) References Cited

U.S. PATENT DOCUMENTS 6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,338,738 B1 1/2002 Bellotti et al.
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble

(56) References Cited

U.S. PATENT DOCUMENTS 6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,844 B2 4/2003 Lee et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,569,173 B1 5/2003 Blatter et al.
6,572,629 B2 6/2003 Kalloo et al.
6,575,969 B1 6/2003 Rittman, III et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,625,517 B1 9/2003 Bogdanov et al.
6,626,834 B2 9/2003 Dunne et al.
6,626,938 B1 9/2003 Butaric et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,676,676 B2 1/2004 Danitz et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,182 B2 3/2004 Pilvisto
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.

(56) References Cited

U.S. PATENT DOCUMENTS 6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,743,239 B1 6/2004 Kuehn et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 * 9/2004 Hoffman .......... A61B 17/07207 227/180.1
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,972 B2 11/2004 Snow
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,107 B2 2/2005 Wang et al.
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.

(56) References Cited

U.S. PATENT DOCUMENTS 6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski

(56) References Cited

U.S. PATENT DOCUMENTS

| | | | |
|---|---|---|---|
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,412 | B1 | 7/2006 | Reynolds et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,363 | B2 | 9/2006 | Nishizawa et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,201 | B2 | 9/2006 | Truckai et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,846 | B2 | 1/2007 | Dycus et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,146 | B2 | 1/2007 | Truckai et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,189,233 | B2 | 3/2007 | Truckai et al. |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |

(56) References Cited

U.S. PATENT DOCUMENTS 7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,250,028 B2 7/2007 Julian et al.
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,261,713 B2 8/2007 Langmaid et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,311,709 B2 12/2007 Truckai et al.
7,313,430 B2 12/2007 Urquhart et al.
7,314,473 B2 1/2008 Jinno et al.
7,320,700 B2 1/2008 Cooper et al.
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,398 B2 4/2008 Kanazawa
7,354,440 B2 4/2008 Truckal et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,817 B2 7/2008 Okada
7,404,822 B2 7/2008 Viart et al.

(56) References Cited

U.S. PATENT DOCUMENTS

D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,430,849 B1 10/2008 Coutts et al.
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
D580,942 S 11/2008 Oshiro et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,572,298 B2 8/2009 Roller et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle

(56) References Cited

U.S. PATENT DOCUMENTS

| | | | |
|---|---|---|---|
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Iio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |
| 7,625,662 | B2 | 12/2009 | Vaisnys et al. |
| 7,630,841 | B2 | 12/2009 | Comisky et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,635,922 | B2 | 12/2009 | Becker |
| 7,637,409 | B2 | 12/2009 | Marczyk |
| 7,637,410 | B2 | 12/2009 | Marczyk |
| 7,638,958 | B2 | 12/2009 | Philipp et al. |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,641,671 | B2 | 1/2010 | Crainich |
| 7,644,016 | B2 | 1/2010 | Nycz et al. |
| 7,644,484 | B2 | 1/2010 | Vereschagin |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,055 | B2 | 1/2010 | Marczyk |
| 7,648,457 | B2 | 1/2010 | Stefanchik et al. |
| 7,648,519 | B2 | 1/2010 | Lee et al. |
| 7,650,185 | B2 | 1/2010 | Maile et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,003 | B2 | 2/2010 | Lorang et al. |
| 7,655,004 | B2 | 2/2010 | Long |
| 7,655,288 | B2 | 2/2010 | Bauman et al. |
| 7,655,584 | B2 | 2/2010 | Biran et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,658,705 | B2 | 2/2010 | Melvin et al. |
| 7,659,219 | B2 | 2/2010 | Biran et al. |
| 7,661,448 | B2 | 2/2010 | Kim et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,666,195 | B2 | 2/2010 | Kelleher et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,670,337 | B2 | 3/2010 | Young |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,678,117 | B2 | 3/2010 | Hinman et al. |
| 7,678,121 | B1 | 3/2010 | Knodel |
| 7,682,307 | B2 | 3/2010 | Danitz et al. |
| 7,682,367 | B2 | 3/2010 | Shah et al. |
| 7,682,686 | B2 | 3/2010 | Curro et al. |
| 7,686,201 | B2 | 3/2010 | Csiky |
| 7,686,804 | B2 | 3/2010 | Johnson et al. |
| 7,686,826 | B2 | 3/2010 | Lee et al. |
| 7,688,028 | B2 | 3/2010 | Phillips et al. |
| 7,690,547 | B2 | 4/2010 | Racenet et al. |
| 7,691,098 | B2 | 4/2010 | Wallace et al. |
| 7,691,103 | B2 | 4/2010 | Fernandez et al. |
| 7,691,106 | B2 | 4/2010 | Schenberger et al. |
| 7,694,864 | B2 | 4/2010 | Okada et al. |
| 7,694,865 | B2 | 4/2010 | Scirica |
| 7,695,485 | B2 | 4/2010 | Whitman et al. |
| 7,695,493 | B2 | 4/2010 | Saadat et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,756 | B2 | 5/2010 | Nobis et al. |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,717,873 | B2 | 5/2010 | Swick |
| 7,717,915 | B2 | 5/2010 | Miyazawa |
| 7,717,926 | B2 | 5/2010 | Whitfield et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,932 | B2 | 5/2010 | Cole et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shalton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |
| 7,725,214 | B2 | 5/2010 | Diolaiti |
| 7,726,171 | B2 | 6/2010 | Langlotz et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,727,954 | B2 | 6/2010 | McKay |
| 7,728,553 | B2 | 6/2010 | Carrier et al. |
| 7,729,742 | B2 | 6/2010 | Govari |
| 7,731,072 | B2 | 6/2010 | Timm et al. |
| 7,731,073 | B2 | 6/2010 | Wixey et al. |
| 7,731,724 | B2 | 6/2010 | Huitema et al. |
| 7,735,703 | B2 | 6/2010 | Morgan et al. |
| 7,735,704 | B2 | 6/2010 | Bilotti |
| 7,736,254 | B2 | 6/2010 | Schena |
| 7,736,306 | B2 | 6/2010 | Brustad et al. |
| 7,736,356 | B2 | 6/2010 | Cooper et al. |
| 7,736,374 | B2 | 6/2010 | Vaughan et al. |

(56) References Cited

U.S. PATENT DOCUMENTS

| | | | |
|---|---|---|---|
| 7,738,971 | B2 | 6/2010 | Swayze et al. |
| 7,740,159 | B2 | 6/2010 | Shelton, IV et al. |
| 7,742,036 | B2 | 6/2010 | Grant et al. |
| 7,743,960 | B2 | 6/2010 | Whitman et al. |
| 7,744,624 | B2 | 6/2010 | Bettuchi |
| 7,744,627 | B2 | 6/2010 | Orban, III et al. |
| 7,744,628 | B2 | 6/2010 | Viola |
| 7,747,146 | B2 | 6/2010 | Milano et al. |
| 7,748,587 | B2 | 7/2010 | Haramiishi et al. |
| 7,748,632 | B2 | 7/2010 | Coleman et al. |
| 7,749,204 | B2 | 7/2010 | Dhanaraj et al. |
| 7,749,240 | B2 | 7/2010 | Takahashi et al. |
| 7,751,870 | B2 | 7/2010 | Whitman |
| 7,753,245 | B2 | 7/2010 | Boudreaux et al. |
| 7,753,246 | B2 | 7/2010 | Scirica |
| 7,753,904 | B2 | 7/2010 | Shelton, IV et al. |
| 7,757,924 | B2 | 7/2010 | Gerbi et al. |
| 7,758,594 | B2 | 7/2010 | Lamson et al. |
| 7,758,612 | B2 | 7/2010 | Shipp |
| 7,758,613 | B2 | 7/2010 | Whitman |
| 7,762,462 | B2 | 7/2010 | Gelbman |
| 7,762,998 | B2 | 7/2010 | Birk et al. |
| D622,286 | S | 8/2010 | Umezawa |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,770,658 | B2 | 8/2010 | Ito et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,772,725 | B2 | 8/2010 | Siman-Tov |
| 7,775,972 | B2 | 8/2010 | Brock et al. |
| 7,776,037 | B2 | 8/2010 | Odom |
| 7,776,060 | B2 | 8/2010 | Mooradian et al. |
| 7,776,065 | B2 | 8/2010 | Griffiths et al. |
| 7,778,004 | B2 | 8/2010 | Nerheim et al. |
| 7,779,614 | B1 | 8/2010 | McGonagle et al. |
| 7,779,737 | B2 | 8/2010 | Newman, Jr. et al. |
| 7,780,054 | B2 | 8/2010 | Wales et al. |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,785,252 | B2 | 8/2010 | Danitz et al. |
| 7,787,256 | B2 | 8/2010 | Chan et al. |
| 7,789,283 | B2 | 9/2010 | Shah |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,835,823 | B2 | 11/2010 | Sillman et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,425 | B2 | 11/2010 | Saeki et al. |
| 7,837,685 | B2 | 11/2010 | Weinberg et al. |
| 7,837,687 | B2 | 11/2010 | Harp |
| 7,837,694 | B2 | 11/2010 | Tethrake et al. |
| 7,838,789 | B2 | 11/2010 | Stoffers et al. |
| 7,839,109 | B2 | 11/2010 | Carmen, Jr. et al. |
| 7,840,253 | B2 | 11/2010 | Tremblay et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,843,158 | B2 | 11/2010 | Prisco |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,845,538 | B2 | 12/2010 | Whitman |
| 7,845,912 | B2 | 12/2010 | Sung et al. |
| 7,846,085 | B2 | 12/2010 | Silverman et al. |
| 7,846,149 | B2 | 12/2010 | Jankowski |
| 7,846,161 | B2 | 12/2010 | Dumbauld et al. |
| 7,848,066 | B2 | 12/2010 | Yanagishima |
| 7,850,623 | B2 | 12/2010 | Griffin et al. |
| 7,850,642 | B2 | 12/2010 | Moll et al. |
| 7,850,982 | B2 | 12/2010 | Stopek et al. |
| 7,853,813 | B2 | 12/2010 | Lee |
| 7,854,735 | B2 | 12/2010 | Houser et al. |
| 7,854,736 | B2 | 12/2010 | Ryan |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,502 | B2 | 1/2011 | Pool et al. |
| 7,862,546 | B2 | 1/2011 | Conlon et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,871,440 | B2 | 1/2011 | Schwartz et al. |
| 7,875,055 | B2 | 1/2011 | Cichocki, Jr. |
| 7,877,869 | B2 | 2/2011 | Mehdizadeh et al. |
| 7,879,063 | B2 | 2/2011 | Khosravi |
| 7,879,070 | B2 | 2/2011 | Ortiz et al. |
| 7,879,367 | B2 | 2/2011 | Heublein et al. |
| 7,883,461 | B2 | 2/2011 | Albrecht et al. |

(56) References Cited

U.S. PATENT DOCUMENTS

| | | | |
|---|---|---|---|
| 7,883,465 | B2 | 2/2011 | Donofrio et al. |
| 7,883,540 | B2 | 2/2011 | Niwa et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,887,536 | B2 | 2/2011 | Johnson et al. |
| 7,887,563 | B2 | 2/2011 | Cummins |
| 7,887,755 | B2 | 2/2011 | Mingerink et al. |
| 7,891,531 | B1 | 2/2011 | Ward |
| 7,891,532 | B2 | 2/2011 | Mastri et al. |
| 7,892,200 | B2 | 2/2011 | Birk et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,671 | B2 | 3/2011 | Kim et al. |
| 7,896,869 | B2 | 3/2011 | DiSilvestro et al. |
| 7,896,877 | B2 | 3/2011 | Hall et al. |
| 7,896,895 | B2 | 3/2011 | Boudreaux et al. |
| 7,896,897 | B2 | 3/2011 | Gresham et al. |
| 7,896,900 | B2 | 3/2011 | Frank et al. |
| 7,898,198 | B2 | 3/2011 | Murphree |
| 7,900,805 | B2 | 3/2011 | Shelton, IV et al. |
| 7,900,806 | B2 | 3/2011 | Chen et al. |
| 7,901,381 | B2 | 3/2011 | Birk et al. |
| 7,905,380 | B2 | 3/2011 | Shelton, IV et al. |
| 7,905,381 | B2 | 3/2011 | Baxter, III et al. |
| 7,905,881 | B2 | 3/2011 | Masuda et al. |
| 7,905,889 | B2 | 3/2011 | Catanese, III et al. |
| 7,905,890 | B2 | 3/2011 | Whitfield et al. |
| 7,905,902 | B2 | 3/2011 | Huitema et al. |
| 7,909,039 | B2 | 3/2011 | Hur |
| 7,909,191 | B2 | 3/2011 | Baker et al. |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,521 | B2 | 3/2011 | Wang et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,845 | B2 | 4/2011 | Saadat et al. |
| 7,918,848 | B2 | 4/2011 | Lau et al. |
| 7,918,861 | B2 | 4/2011 | Brock et al. |
| 7,918,867 | B2 | 4/2011 | Dana et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,926,692 | B2 | 4/2011 | Racenet et al. |
| 7,927,328 | B2 | 4/2011 | Orszulak et al. |
| 7,928,281 | B2 | 4/2011 | Augustine |
| 7,930,040 | B1 | 4/2011 | Kelsch et al. |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,931,877 | B2 | 4/2011 | Steffens et al. |
| 7,934,630 | B2 | 5/2011 | Shelton, IV et al. |
| 7,934,631 | B2 | 5/2011 | Balbierz et al. |
| 7,934,896 | B2 | 5/2011 | Schnier |
| 7,935,130 | B2 | 5/2011 | Williams |
| 7,935,773 | B2 | 5/2011 | Hadba et al. |
| 7,936,142 | B2 | 5/2011 | Otsuka et al. |
| 7,938,307 | B2 | 5/2011 | Bettuchi |
| 7,939,152 | B2 | 5/2011 | Haskin et al. |
| 7,941,865 | B2 | 5/2011 | Seman, Jr. et al. |
| 7,942,300 | B2 | 5/2011 | Rethy et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,945,798 | B2 | 5/2011 | Carlson et al. |
| 7,946,453 | B2 | 5/2011 | Voegele et al. |
| 7,947,011 | B2 | 5/2011 | Birk et al. |
| 7,948,381 | B2 | 5/2011 | Lindsay et al. |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,951,071 | B2 | 5/2011 | Whitman et al. |
| 7,951,166 | B2 | 5/2011 | Orban, III et al. |
| 7,952,464 | B2 | 5/2011 | Nikitin et al. |
| 7,954,682 | B2 | 6/2011 | Giordano et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,954,688 | B2 | 6/2011 | Argentine et al. |
| 7,955,253 | B2 | 6/2011 | Ewers et al. |
| 7,955,257 | B2 | 6/2011 | Frasier et al. |
| 7,955,322 | B2 | 6/2011 | Devengenzo et al. |
| 7,955,327 | B2 | 6/2011 | Sartor et al. |
| 7,955,380 | B2 | 6/2011 | Chu et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |

(56) References Cited

U.S. PATENT DOCUMENTS

| | | | |
|---|---|---|---|
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,052,697 B2 | 11/2011 | Phillips |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stem et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |

(56) References Cited

U.S. PATENT DOCUMENTS 8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,417 B2 5/2012 Danitz
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,472 B2 6/2012 Lau et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.

(56) References Cited

U.S. PATENT DOCUMENTS 8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,948 B2 1/2013 Bahney
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,409,234 B2 4/2013 Stahler et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.

(56) References Cited

U.S. PATENT DOCUMENTS 8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,439,830 B2 5/2013 McKinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Aller
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica

(56) References Cited

U.S. PATENT DOCUMENTS

| | | | |
|---|---|---|---|
| 8,585,583 | B2 | 11/2013 | Sakaguchi et al. |
| 8,585,598 | B2 | 11/2013 | Razzaque et al. |
| 8,585,721 | B2 | 11/2013 | Kirsch |
| 8,590,760 | B2 | 11/2013 | Cummins et al. |
| 8,590,762 | B2 | 11/2013 | Hess et al. |
| 8,590,764 | B2 | 11/2013 | Hartwick et al. |
| 8,591,400 | B2 | 11/2013 | Sugiyama |
| 8,596,515 | B2 | 12/2013 | Okoniewski |
| 8,597,745 | B2 | 12/2013 | Farnsworth et al. |
| 8,599,450 | B2 | 12/2013 | Kubo et al. |
| 8,602,125 | B2 | 12/2013 | King |
| 8,602,287 | B2 | 12/2013 | Yates et al. |
| 8,602,288 | B2 | 12/2013 | Shelton, IV et al. |
| 8,603,077 | B2 | 12/2013 | Cooper et al. |
| 8,603,089 | B2 | 12/2013 | Viola |
| 8,603,110 | B2 | 12/2013 | Maruyama et al. |
| 8,603,135 | B2 | 12/2013 | Mueller |
| 8,608,043 | B2 | 12/2013 | Scirica |
| 8,608,044 | B2 | 12/2013 | Hueil et al. |
| 8,608,045 | B2 | 12/2013 | Smith et al. |
| 8,608,046 | B2 | 12/2013 | Laurent et al. |
| 8,608,745 | B2 | 12/2013 | Guzman et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,431 | B2 | 12/2013 | Timm et al. |
| 8,617,155 | B2 | 12/2013 | Johnson et al. |
| 8,620,473 | B2 | 12/2013 | Diolaiti et al. |
| 8,622,274 | B2 | 1/2014 | Yates et al. |
| 8,622,275 | B2 | 1/2014 | Baxter, III et al. |
| 8,627,993 | B2 | 1/2014 | Smith et al. |
| 8,627,994 | B2 | 1/2014 | Zemlok et al. |
| 8,627,995 | B2 | 1/2014 | Smith et al. |
| 8,628,467 | B2 | 1/2014 | Whitman et al. |
| 8,628,518 | B2 | 1/2014 | Blumenkranz et al. |
| 8,628,544 | B2 | 1/2014 | Farascioni |
| 8,628,545 | B2 | 1/2014 | Cabrera et al. |
| 8,631,987 | B2 | 1/2014 | Shelton, IV et al. |
| 8,631,992 | B1 | 1/2014 | Hausen et al. |
| 8,631,993 | B2 | 1/2014 | Kostrzewski |
| 8,632,462 | B2 | 1/2014 | Yoo et al. |
| 8,632,525 | B2 | 1/2014 | Kerr et al. |
| 8,632,535 | B2 | 1/2014 | Shelton, IV et al. |
| 8,632,539 | B2 | 1/2014 | Twomey et al. |
| 8,632,563 | B2 | 1/2014 | Nagase et al. |
| 8,636,187 | B2 | 1/2014 | Hueil et al. |
| 8,636,190 | B2 | 1/2014 | Zemlok et al. |
| 8,636,191 | B2 | 1/2014 | Meagher |
| 8,636,193 | B2 | 1/2014 | Whitman et al. |
| 8,636,736 | B2 | 1/2014 | Yates et al. |
| 8,636,766 | B2 | 1/2014 | Milliman et al. |
| 8,639,936 | B2 | 1/2014 | Hu et al. |
| 8,640,788 | B2 | 2/2014 | Dachs, II et al. |
| 8,646,674 | B2 | 2/2014 | Schulte et al. |
| 8,647,258 | B2 | 2/2014 | Aranyi et al. |
| 8,652,120 | B2 | 2/2014 | Giordano et al. |
| 8,652,151 | B2 | 2/2014 | Lehman et al. |
| 8,652,155 | B2 | 2/2014 | Houser et al. |
| 8,656,929 | B2 | 2/2014 | Miller et al. |
| 8,657,174 | B2 | 2/2014 | Yates et al. |
| 8,657,175 | B2 | 2/2014 | Sonnenschein et al. |
| 8,657,176 | B2 | 2/2014 | Shelton, IV et al. |
| 8,657,177 | B2 | 2/2014 | Scirica et al. |
| 8,657,178 | B2 | 2/2014 | Hueil et al. |
| 8,657,482 | B2 | 2/2014 | Malackowski et al. |
| 8,657,808 | B2 | 2/2014 | McPherson et al. |
| 8,657,814 | B2 | 2/2014 | Werneth et al. |
| 8,657,821 | B2 | 2/2014 | Palermo |
| D701,238 | S | 3/2014 | Lai et al. |
| 8,662,370 | B2 | 3/2014 | Takei |
| 8,663,106 | B2 | 3/2014 | Stivoric et al. |
| 8,663,192 | B2 | 3/2014 | Hester et al. |
| 8,663,245 | B2 | 3/2014 | Francischelli et al. |
| 8,663,262 | B2 | 3/2014 | Smith et al. |
| 8,663,270 | B2 | 3/2014 | Donnigan et al. |
| 8,664,792 | B2 | 3/2014 | Rebsdorf |
| 8,668,129 | B2 | 3/2014 | Olson |
| 8,668,130 | B2 | 3/2014 | Hess et al. |
| 8,668,702 | B2 | 3/2014 | Awtar et al. |
| 8,672,206 | B2 | 3/2014 | Aranyi et al. |
| 8,672,207 | B2 | 3/2014 | Shelton, IV et al. |
| 8,672,208 | B2 | 3/2014 | Hess et al. |
| 8,672,209 | B2 | 3/2014 | Crainich |
| 8,672,922 | B2 | 3/2014 | Loh et al. |
| 8,672,935 | B2 | 3/2014 | Okada et al. |
| 8,672,951 | B2 | 3/2014 | Smith et al. |
| 8,673,210 | B2 | 3/2014 | Deshays |
| 8,675,820 | B2 | 3/2014 | Baic et al. |
| 8,678,263 | B2 | 3/2014 | Viola |
| 8,678,994 | B2 | 3/2014 | Sonnenschein et al. |
| 8,679,093 | B2 | 3/2014 | Farra |
| 8,679,098 | B2 | 3/2014 | Hart |
| 8,679,137 | B2 | 3/2014 | Bauman et al. |
| 8,679,154 | B2 | 3/2014 | Smith et al. |
| 8,679,156 | B2 | 3/2014 | Smith et al. |
| 8,679,454 | B2 | 3/2014 | Guire et al. |
| 8,684,248 | B2 | 4/2014 | Milliman |
| 8,684,249 | B2 | 4/2014 | Racenet et al. |
| 8,684,250 | B2 | 4/2014 | Bettuchi et al. |
| 8,684,253 | B2 | 4/2014 | Giordano et al. |
| 8,684,962 | B2 | 4/2014 | Kirschenman et al. |
| 8,685,004 | B2 | 4/2014 | Zemlock et al. |
| 8,685,020 | B2 | 4/2014 | Weizman et al. |
| 8,690,893 | B2 | 4/2014 | Deitch et al. |
| 8,695,866 | B2 | 4/2014 | Leimbach et al. |
| 8,696,665 | B2 | 4/2014 | Hunt et al. |
| 8,701,958 | B2 | 4/2014 | Shelton, IV et al. |
| 8,701,959 | B2 | 4/2014 | Shah |
| 8,706,316 | B1 | 4/2014 | Hoevenaar |
| 8,708,210 | B2 | 4/2014 | Zemlok et al. |
| 8,708,211 | B2 | 4/2014 | Zemlok et al. |
| 8,708,212 | B2 | 4/2014 | Williams |
| 8,708,213 | B2 | 4/2014 | Shelton, IV et al. |
| 8,709,012 | B2 | 4/2014 | Muller |
| 8,714,352 | B2 | 5/2014 | Farascioni et al. |
| 8,714,429 | B2 | 5/2014 | Demmy |
| 8,714,430 | B2 | 5/2014 | Natarajan et al. |
| 8,715,256 | B2 | 5/2014 | Greener |
| 8,715,302 | B2 | 5/2014 | Ibrahim et al. |
| 8,720,766 | B2 | 5/2014 | Hess et al. |
| 8,721,630 | B2 | 5/2014 | Ortiz et al. |
| 8,721,666 | B2 | 5/2014 | Schroeder et al. |
| 8,727,197 | B2 | 5/2014 | Hess et al. |
| 8,727,199 | B2 | 5/2014 | Wenchell |
| 8,727,200 | B2 | 5/2014 | Roy |
| 8,727,961 | B2 | 5/2014 | Ziv |
| 8,728,099 | B2 | 5/2014 | Cohn et al. |
| 8,728,119 | B2 | 5/2014 | Cummins |
| 8,733,470 | B2 | 5/2014 | Matthias et al. |
| 8,733,611 | B2 | 5/2014 | Milliman |
| 8,733,612 | B2 | 5/2014 | Ma |
| 8,733,613 | B2 | 5/2014 | Huitema et al. |
| 8,733,614 | B2 | 5/2014 | Ross et al. |
| 8,734,336 | B2 | 5/2014 | Bonadio et al. |
| 8,734,359 | B2 | 5/2014 | Ibanez et al. |
| 8,734,478 | B2 | 5/2014 | Widenhouse et al. |
| 8,734,831 | B2 | 5/2014 | Kim et al. |
| 8,739,033 | B2 | 5/2014 | Rosenberg |
| 8,739,417 | B2 | 6/2014 | Tokunaga et al. |
| 8,740,034 | B2 | 6/2014 | Morgan et al. |
| 8,740,037 | B2 | 6/2014 | Shelton, IV et al. |
| 8,740,038 | B2 | 6/2014 | Shelton, IV et al. |
| 8,740,987 | B2 | 6/2014 | Geremakis et al. |
| 8,746,529 | B2 | 6/2014 | Shelton, IV et al. |
| 8,746,530 | B2 | 6/2014 | Giordano et al. |
| 8,746,533 | B2 | 6/2014 | Whitman et al. |
| 8,746,535 | B2 | 6/2014 | Shelton, IV et al. |
| 8,747,238 | B2 | 6/2014 | Shelton, IV et al. |
| 8,747,441 | B2 | 6/2014 | Konieczynski et al. |
| 8,752,264 | B2 | 6/2014 | Ackley et al. |
| 8,752,699 | B2 | 6/2014 | Morgan et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |

(56) References Cited

U.S. PATENT DOCUMENTS 8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,855,822 B2 10/2014 Bartol et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roßkamp et al.
8,869,913 B2 10/2014 Matthias et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.

(56) References Cited

U.S. PATENT DOCUMENTS

| | | | |
|---|---|---|---|
| 8,911,471 | B2 | 12/2014 | Spivey et al. |
| 8,912,746 | B2 | 12/2014 | Reid et al. |
| 8,915,842 | B2 | 12/2014 | Weisenburgh, II et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,931,692 | B2 | 1/2015 | Sancak |
| 8,936,614 | B2 | 1/2015 | Allen, IV |
| 8,937,408 | B2 | 1/2015 | Ganem et al. |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,961,542 | B2 | 2/2015 | Whitfield et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |
| 9,055,941 | B2 | 6/2015 | Schmid et al. |
| 9,055,942 | B2 | 6/2015 | Balbierz et al. |
| 9,055,943 | B2 | 6/2015 | Zemlok et al. |
| 9,055,944 | B2 | 6/2015 | Hodgkinson et al. |
| 9,055,961 | B2 | 6/2015 | Manzo et al. |

(56) References Cited

U.S. PATENT DOCUMENTS 9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,771 B2 10/2015 Steger
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
9,221,179 B2 12/2015 Hinman
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.

(56) References Cited

U.S. PATENT DOCUMENTS 9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.

(56) References Cited

U.S. PATENT DOCUMENTS 9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,540 B2 10/2016 Stokes et al.
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,005 B2 12/2016 Williams et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.

(56) References Cited

U.S. PATENT DOCUMENTS 9,554,796 B2 1/2017 Kostrzewski
9,554,803 B2 1/2017 Smith et al.
9,554,812 B2 1/2017 Inkpen et al.
9,554,854 B2 1/2017 Yates et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,561,072 B2 2/2017 Ko
9,561,082 B2 2/2017 Yen et al.
9,566,061 B2 2/2017 Aronhalt et al.
9,566,062 B2 2/2017 Boudreaux
9,566,064 B2 2/2017 Williams et al.
9,566,065 B2 2/2017 Knodel
9,566,067 B2 2/2017 Milliman et al.
9,572,552 B1 2/2017 Bodor et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.
9,610,412 B2 4/2017 Zemlok et al.
9,614,258 B2 4/2017 Takahashi et al.
9,615,826 B2 4/2017 Shelton, IV et al.
9,622,745 B2 4/2017 Ingmanson et al.
9,622,746 B2 4/2017 Simms et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,651,032 B2 5/2017 Weaver et al.
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,111 B2 5/2017 Holsten et al.
9,662,116 B2 5/2017 Smith et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,872 B2 6/2017 Jankowski et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,700,381 B2 7/2017 Amat Girbau
9,702,823 B2 7/2017 Maher et al.
9,706,674 B2 7/2017 Collins et al.
9,706,981 B2 7/2017 Nicholas et al.
9,706,991 B2 7/2017 Hess et al.

(56) References Cited

U.S. PATENT DOCUMENTS 9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,757,856 B2 9/2017 Oyola et al.
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,994 B2 12/2017 Schena
D808,989 S 1/2018 Ayvazian et al.

(56) References Cited

U.S. PATENT DOCUMENTS

| | | | |
|---|---|---|---|
| 9,855,039 | B2 | 1/2018 | Racenet et al. |
| 9,855,040 | B2 | 1/2018 | Kostrzewski |
| 9,855,662 | B2 | 1/2018 | Ruiz Morales et al. |
| 9,861,261 | B2 | 1/2018 | Shahinian |
| 9,861,359 | B2 | 1/2018 | Shelton, IV et al. |
| 9,861,361 | B2 | 1/2018 | Aronhalt et al. |
| 9,861,362 | B2 | 1/2018 | Whitman et al. |
| 9,861,366 | B2 | 1/2018 | Aranyi |
| 9,861,382 | B2 | 1/2018 | Smith et al. |
| 9,861,446 | B2 | 1/2018 | Lang |
| 9,867,612 | B2 | 1/2018 | Parihar et al. |
| 9,867,613 | B2 | 1/2018 | Marczyk et al. |
| 9,867,615 | B2 | 1/2018 | Fanelli et al. |
| 9,867,617 | B2 | 1/2018 | Ma |
| 9,867,618 | B2 | 1/2018 | Hall et al. |
| 9,867,620 | B2 | 1/2018 | Fischvogt et al. |
| 9,868,198 | B2 | 1/2018 | Nicholas et al. |
| 9,872,682 | B2 | 1/2018 | Hess et al. |
| 9,872,683 | B2 | 1/2018 | Hopkins et al. |
| 9,872,684 | B2 | 1/2018 | Hall et al. |
| 9,872,722 | B2 | 1/2018 | Lech |
| 9,877,721 | B2 | 1/2018 | Schellin et al. |
| 9,877,722 | B2 | 1/2018 | Schellin et al. |
| 9,877,723 | B2 | 1/2018 | Hall et al. |
| 9,877,776 | B2 | 1/2018 | Boudreaux |
| D810,099 | S | 2/2018 | Riedel |
| 9,883,843 | B2 | 2/2018 | Garlow |
| 9,883,860 | B2 | 2/2018 | Leimbach et al. |
| 9,883,861 | B2 | 2/2018 | Shelton, IV et al. |
| 9,884,456 | B2 | 2/2018 | Schellin et al. |
| 9,888,914 | B2 | 2/2018 | Martin et al. |
| 9,888,919 | B2 | 2/2018 | Leimbach et al. |
| 9,888,921 | B2 | 2/2018 | Williams et al. |
| 9,888,924 | B2 | 2/2018 | Ebersole et al. |
| 9,889,230 | B2 | 2/2018 | Bennett et al. |
| 9,895,147 | B2 | 2/2018 | Shelton, IV |
| 9,895,148 | B2 | 2/2018 | Shelton, IV et al. |
| 9,895,813 | B2 | 2/2018 | Blumenkranz et al. |
| 9,901,339 | B2 | 2/2018 | Farascioni |
| 9,901,341 | B2 | 2/2018 | Kostrzewski |
| 9,901,342 | B2 | 2/2018 | Shelton, IV et al. |
| 9,901,344 | B2 | 2/2018 | Moore et al. |
| 9,901,345 | B2 | 2/2018 | Moore et al. |
| 9,901,346 | B2 | 2/2018 | Moore et al. |
| 9,901,358 | B2 | 2/2018 | Faller et al. |
| 9,901,406 | B2 | 2/2018 | State et al. |
| 9,901,412 | B2 | 2/2018 | Lathrop et al. |
| D813,899 | S | 3/2018 | Erant et al. |
| 9,907,456 | B2 | 3/2018 | Miyoshi |
| 9,907,552 | B2 | 3/2018 | Measamer et al. |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |
| 9,918,704 | B2 | 3/2018 | Shelton, IV et al. |
| 9,918,714 | B2 | 3/2018 | Gibbons, Jr. |
| 9,918,715 | B2 | 3/2018 | Menn |
| 9,918,716 | B2 | 3/2018 | Baxter, III et al. |
| 9,918,717 | B2 | 3/2018 | Czernik |
| 9,918,730 | B2 | 3/2018 | Trees et al. |
| 9,924,941 | B2 | 3/2018 | Burbank |
| 9,924,942 | B2 | 3/2018 | Swayze et al. |
| 9,924,943 | B2 | 3/2018 | Mohan Pinjala et al. |
| 9,924,944 | B2 | 3/2018 | Shelton, IV et al. |
| 9,924,945 | B2 | 3/2018 | Zheng et al. |
| 9,924,946 | B2 | 3/2018 | Vendely et al. |
| 9,924,947 | B2 | 3/2018 | Shelton, IV et al. |
| 9,924,961 | B2 | 3/2018 | Shelton, IV et al. |
| 9,931,106 | B2 | 4/2018 | Au et al. |
| 9,931,116 | B2 | 4/2018 | Racenet et al. |
| 9,931,117 | B2 | 4/2018 | Hathaway et al. |
| 9,931,118 | B2 | 4/2018 | Shelton, IV et al. |
| 9,931,120 | B2 | 4/2018 | Chen et al. |
| 9,936,949 | B2 | 4/2018 | Measamer et al. |
| 9,936,950 | B2 | 4/2018 | Shelton, IV et al. |
| 9,936,951 | B2 | 4/2018 | Hufnagel et al. |
| 9,936,952 | B2 | 4/2018 | Demmy |
| 9,936,954 | B2 | 4/2018 | Shelton, IV et al. |
| 9,937,626 | B2 | 4/2018 | Rockrohr |
| 9,943,309 | B2 | 4/2018 | Shelton, IV et al. |
| 9,943,310 | B2 | 4/2018 | Harris et al. |
| 9,943,312 | B2 | 4/2018 | Posada et al. |
| 9,949,754 | B2 | 4/2018 | Newhauser et al. |
| 9,953,193 | B2 | 4/2018 | Butler et al. |
| D819,072 | S | 5/2018 | Clediere |
| 9,955,954 | B2 | 5/2018 | Destoumieux et al. |
| 9,955,965 | B2 | 5/2018 | Chen et al. |
| 9,955,966 | B2 | 5/2018 | Zergiebel |
| 9,956,677 | B2 | 5/2018 | Baskar et al. |
| 9,962,129 | B2 | 5/2018 | Jerebko et al. |
| 9,962,157 | B2 | 5/2018 | Sapre |
| 9,962,158 | B2 | 5/2018 | Hall et al. |
| 9,962,159 | B2 | 5/2018 | Heinrich et al. |
| 9,962,161 | B2 | 5/2018 | Scheib et al. |
| 9,968,354 | B2 | 5/2018 | Shelton, IV et al. |
| 9,968,355 | B2 | 5/2018 | Shelton, IV et al. |
| 9,968,356 | B2 | 5/2018 | Shelton, IV et al. |
| 9,968,397 | B2 | 5/2018 | Taylor et al. |
| 9,974,529 | B2 | 5/2018 | Shelton, IV et al. |
| 9,974,538 | B2 | 5/2018 | Baxter, III et al. |
| 9,974,539 | B2 | 5/2018 | Yates et al. |
| 9,974,541 | B2 | 5/2018 | Calderoni |
| 9,974,542 | B2 | 5/2018 | Hodgkinson |
| 9,980,630 | B2 | 5/2018 | Larkin et al. |
| 9,980,713 | B2 | 5/2018 | Aronhalt et al. |
| 9,980,724 | B2 | 5/2018 | Farascioni et al. |
| 9,980,729 | B2 | 5/2018 | Moore et al. |
| 9,980,740 | B2 | 5/2018 | Krause et al. |
| 9,980,769 | B2 | 5/2018 | Trees et al. |
| D819,680 | S | 6/2018 | Nguyen |
| D819,682 | S | 6/2018 | Howard et al. |
| D819,684 | S | 6/2018 | Dart |
| D820,307 | S | 6/2018 | Jian et al. |
| D820,867 | S | 6/2018 | Dickens et al. |
| 9,987,000 | B2 | 6/2018 | Shelton, IV et al. |
| 9,987,003 | B2 | 6/2018 | Timm et al. |
| 9,987,006 | B2 | 6/2018 | Morgan et al. |
| 9,987,008 | B2 | 6/2018 | Scirica et al. |
| 9,987,095 | B2 | 6/2018 | Chowaniec et al. |
| 9,987,097 | B2 | 6/2018 | van der Weide et al. |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 9,993,284 | B2 | 6/2018 | Boudreaux |
| 9,999,408 | B2 | 6/2018 | Boudreaux et al. |
| 9,999,423 | B2 | 6/2018 | Schuckmann et al. |
| 9,999,426 | B2 | 6/2018 | Moore et al. |
| 9,999,431 | B2 | 6/2018 | Shelton, IV et al. |
| 9,999,472 | B2 | 6/2018 | Weir et al. |
| 10,004,497 | B2 | 6/2018 | Overmyer et al. |
| 10,004,498 | B2 | 6/2018 | Morgan et al. |
| 10,004,500 | B2 | 6/2018 | Shelton, IV et al. |
| 10,004,501 | B2 | 6/2018 | Shelton, IV et al. |
| 10,004,505 | B2 | 6/2018 | Moore et al. |
| 10,004,506 | B2 | 6/2018 | Shelton, IV et al. |
| 10,004,552 | B1 | 6/2018 | Kleyman et al. |
| D822,206 | S | 7/2018 | Shelton, IV et al. |
| 10,010,322 | B2 | 7/2018 | Shelton, IV et al. |
| 10,010,324 | B2 | 7/2018 | Huitema et al. |
| 10,010,395 | B2 | 7/2018 | Puckett et al. |
| 10,013,049 | B2 | 7/2018 | Leimbach et al. |
| 10,016,199 | B2 | 7/2018 | Baber et al. |
| 10,016,656 | B2 | 7/2018 | Devor et al. |
| 10,022,120 | B2 | 7/2018 | Martin et al. |
| 10,022,123 | B2 | 7/2018 | Williams et al. |
| 10,022,125 | B2 | 7/2018 | (Prommersberger) Stopek et al. |
| 10,024,407 | B2 | 7/2018 | Aranyi et al. |

(56) References Cited

U.S. PATENT DOCUMENTS 10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.
10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
D835,659 S 12/2018 Anzures et al.
D836,124 S 12/2018 Fan
10,143,474 B2 12/2018 Bucciaglia et al.
10,146,423 B1 12/2018 Reed et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.

(56) References Cited

U.S. PATENT DOCUMENTS 10,188,389 B2 1/2019 Vendely et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,911 B2 2/2019 Miller et al.
10,194,912 B2 2/2019 Scheib et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,645 B2 4/2019 Kostrzewski
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,285,724 B2 5/2019 Faller et al.
10,285,750 B2 5/2019 Coulson et al.
10,292,698 B2 5/2019 Meade et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,578 B2 6/2019 Leimbach et al.
10,314,579 B2 6/2019 Chowaniec et al.
10,314,580 B2 6/2019 Scheib et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.

(56) References Cited

U.S. PATENT DOCUMENTS

| | | | |
|---|---|---|---|
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,949 | B2 | 10/2019 | Decker et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,470,770 | B2 | 11/2019 | Shelton, IV et al. |
| 10,471,282 | B2 | 11/2019 | Kirk et al. |
| 10,471,576 | B2 | 11/2019 | Totsu |

(56) References Cited

U.S. PATENT DOCUMENTS

| | | | |
|---|---|---|---|
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,004 | B2 | 12/2019 | Hanuschik et al. |
| 10,500,309 | B2 | 12/2019 | Shah et al. |
| 10,507,034 | B2 | 12/2019 | Timm |
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,524,870 | B2 | 1/2020 | Saraliev et al. |
| 10,531,874 | B2 | 1/2020 | Morgan et al. |
| 10,531,887 | B2 | 1/2020 | Shelton, IV et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |
| 10,582,928 | B2 | 3/2020 | Hunter et al. |
| 10,588,231 | B2 | 3/2020 | Sgroi, Jr. et al. |
| 10,588,623 | B2 | 3/2020 | Schmid et al. |
| 10,588,625 | B2 | 3/2020 | Weaner et al. |
| 10,588,626 | B2 | 3/2020 | Overmyer et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,595,835 | B2 | 3/2020 | Kerr et al. |
| 10,595,862 | B2 | 3/2020 | Shelton, IV et al. |
| 10,595,882 | B2 | 3/2020 | Parfett et al. |
| 10,595,887 | B2 | 3/2020 | Shelton, IV et al. |
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,117 | B2 | 3/2020 | Schings et al. |
| 10,603,128 | B2 | 3/2020 | Zergiebel et al. |
| D882,783 | S | 4/2020 | Shelton, IV et al. |
| 10,610,224 | B2 | 4/2020 | Shelton, IV et al. |
| 10,610,225 | B2 | 4/2020 | Reed et al. |
| 10,610,236 | B2 | 4/2020 | Baril |
| 10,610,313 | B2 | 4/2020 | Bailey et al. |
| 10,610,346 | B2 | 4/2020 | Schwartz |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,617,438 | B2 | 4/2020 | O'Keefe et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,089 | B2 | 5/2020 | Manwaring et al. |
| 10,639,115 | B2 | 5/2020 | Shelton, IV et al. |
| 10,642,633 | B1 | 5/2020 | Chopra et al. |
| 10,645,905 | B2 | 5/2020 | Gandola et al. |
| 10,646,220 | B2 | 5/2020 | Shelton, IV et al. |
| 10,646,292 | B2 | 5/2020 | Solomon et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |

(56) References Cited

U.S. PATENT DOCUMENTS

| | | | |
|---|---|---|---|
| 10,667,408 | B2 | 5/2020 | Sgroi, Jr. et al. |
| D888,953 | S | 6/2020 | Baxter, III et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,818 | B2 | 6/2020 | McLain et al. |
| 10,674,895 | B2 | 6/2020 | Yeung et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,675,080 | B2 | 6/2020 | Woloszko et al. |
| 10,675,102 | B2 | 6/2020 | Forgione et al. |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,137 | B2 | 6/2020 | Stokes et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,812 | B2 | 6/2020 | Shelton, IV et al. |
| 10,687,813 | B2 | 6/2020 | Shelton, IV et al. |
| 10,687,817 | B2 | 6/2020 | Shelton, IV et al. |
| 10,687,819 | B2 | 6/2020 | Stokes et al. |
| 10,687,904 | B2 | 6/2020 | Harris et al. |
| 10,695,053 | B2 | 6/2020 | Hess et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,062 | B2 | 6/2020 | Leimbach et al. |
| 10,695,063 | B2 | 6/2020 | Morgan et al. |
| 10,695,074 | B2 | 6/2020 | Carusillo |
| 10,695,081 | B2 | 6/2020 | Shelton, IV et al. |
| 10,695,119 | B2 | 6/2020 | Smith |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| D893,717 | S | 8/2020 | Messerly et al. |
| 10,729,432 | B2 | 8/2020 | Shelton, IV et al. |
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,736,702 | B2 | 8/2020 | Harris et al. |
| 10,737,398 | B2 | 8/2020 | Remirez et al. |
| 10,743,849 | B2 | 8/2020 | Shelton, IV et al. |
| 10,743,850 | B2 | 8/2020 | Hibner et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,899 | B2 | 8/2020 | Worrell |
| 10,743,930 | B2 | 8/2020 | Nagtegaal |
| 10,751,048 | B2 | 8/2020 | Whitman et al. |
| 10,751,053 | B2 | 8/2020 | Harris et al. |
| 10,751,076 | B2 | 8/2020 | Laurent et al. |
| 10,751,138 | B2 | 8/2020 | Giordano et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |

(56) References Cited

U.S. PATENT DOCUMENTS

| | | | |
|---|---|---|---|
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,395 | B2 | 1/2021 | Merchant et al. |
| 10,881,396 | B2 | 1/2021 | Shelton, IV et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Biasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,980,575 | B2 | 4/2021 | Perrow et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,005,291 | B2 | 5/2021 | Calderoni |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |

(56) References Cited

U.S. PATENT DOCUMENTS

| | | | |
|---|---|---|---|
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 | 9/2021 | Beardsley |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner, II |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,089 | B2 | 12/2021 | Kostrzewski et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |

(56) References Cited

U.S. PATENT DOCUMENTS

| | | | |
|---|---|---|---|
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,697 | B2 | 4/2022 | Fanelli et al. |
| 11,304,699 | B2 | 4/2022 | Shelton, IV et al. |
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| 11,350,843 | B2 | 6/2022 | Shelton, IV et al. |
| 11,350,916 | B2 | 6/2022 | Shelton, IV et al. |
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,364,027 | B2 | 6/2022 | Harris et al. |
| 11,364,046 | B2 | 6/2022 | Shelton, IV et al. |
| 11,369,368 | B2 | 6/2022 | Shelton, IV et al. |
| 11,369,376 | B2 | 6/2022 | Simms et al. |
| 11,369,377 | B2 | 6/2022 | Boudreaux et al. |
| 11,373,755 | B2 | 6/2022 | Shelton, IV et al. |
| 11,376,001 | B2 | 7/2022 | Shelton, IV et al. |
| 11,376,082 | B2 | 7/2022 | Shelton, IV et al. |
| 11,376,098 | B2 | 7/2022 | Shelton, IV et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,628 | B2 | 7/2022 | Baxter, III et al. |
| 11,382,638 | B2 | 7/2022 | Harris et al. |
| 11,382,697 | B2 | 7/2022 | Shelton, IV et al. |
| 11,389,160 | B2 | 7/2022 | Shelton, IV et al. |
| 11,389,161 | B2 | 7/2022 | Shelton, IV et al. |
| 11,389,162 | B2 | 7/2022 | Baber et al. |
| 11,389,164 | B2 | 7/2022 | Yates et al. |
| 11,395,651 | B2 | 7/2022 | Shelton, IV et al. |
| 11,395,652 | B2 | 7/2022 | Parihar et al. |
| 11,399,828 | B2 | 8/2022 | Swayze et al. |
| 11,399,829 | B2 | 8/2022 | Leimbach et al. |
| 11,399,831 | B2 | 8/2022 | Overmyer et al. |
| 11,399,837 | B2 | 8/2022 | Shelton, IV et al. |
| 11,406,377 | B2 | 8/2022 | Schmid et al. |
| 11,406,378 | B2 | 8/2022 | Baxter, III et al. |
| 11,406,380 | B2 | 8/2022 | Yates et al. |
| 11,406,381 | B2 | 8/2022 | Parihar et al. |
| 11,406,382 | B2 | 8/2022 | Shelton, IV et al. |
| 11,406,386 | B2 | 8/2022 | Baber et al. |
| 11,406,390 | B2 | 8/2022 | Shelton, IV et al. |
| 11,406,442 | B2 | 8/2022 | Davison et al. |
| 11,410,259 | B2 | 8/2022 | Harris et al. |
| 11,413,042 | B2 | 8/2022 | Shelton, IV et al. |
| 11,413,102 | B2 | 8/2022 | Shelton, IV et al. |
| 11,419,606 | B2 | 8/2022 | Overmyer et al. |
| 11,419,630 | B2 | 8/2022 | Yates et al. |
| 11,424,027 | B2 | 8/2022 | Shelton, IV |
| 11,426,160 | B2 | 8/2022 | Shelton, IV et al. |
| 11,426,167 | B2 | 8/2022 | Shelton, IV et al. |
| 11,426,251 | B2 | 8/2022 | Kimball et al. |
| D964,564 | S | 9/2022 | Boudreaux |
| 11,432,816 | B2 | 9/2022 | Leimbach et al. |
| 11,432,885 | B2 | 9/2022 | Shelton, IV et al. |
| 11,439,391 | B2 | 9/2022 | Bruns et al. |
| 11,439,470 | B2 | 9/2022 | Spivey et al. |
| 11,446,029 | B2 | 9/2022 | Shelton, IV et al. |
| 11,446,034 | B2 | 9/2022 | Shelton, IV et al. |
| 11,452,528 | B2 | 9/2022 | Leimbach et al. |
| D966,512 | S | 10/2022 | Shelton, IV et al. |
| D967,421 | S | 10/2022 | Shelton, IV et al. |
| 11,457,918 | B2 | 10/2022 | Shelton, IV et al. |
| 11,464,511 | B2 | 10/2022 | Timm et al. |

(56) References Cited

U.S. PATENT DOCUMENTS

| | | | |
|---|---|---|---|
| 11,464,512 | B2 | 10/2022 | Shelton, IV et al. |
| 11,464,513 | B2 | 10/2022 | Shelton, IV et al. |
| 11,464,514 | B2 | 10/2022 | Yates et al. |
| 11,464,601 | B2 | 10/2022 | Shelton, IV et al. |
| 11,471,155 | B2 | 10/2022 | Shelton, IV et al. |
| 11,471,156 | B2 | 10/2022 | Shelton, IV et al. |
| 11,471,157 | B2 | 10/2022 | Baxter, III et al. |
| 11,478,241 | B2 | 10/2022 | Shelton, IV et al. |
| 11,478,242 | B2 | 10/2022 | Shelton, IV et al. |
| 11,478,244 | B2 | 10/2022 | DiNardo et al. |
| 11,478,247 | B2 | 10/2022 | Shelton, IV et al. |
| D971,232 | S | 11/2022 | Siebel et al. |
| 11,484,307 | B2 | 11/2022 | Hall et al. |
| 11,484,309 | B2 | 11/2022 | Harris et al. |
| 11,484,310 | B2 | 11/2022 | Shelton, IV et al. |
| 11,484,311 | B2 | 11/2022 | Shelton, IV et al. |
| 11,484,312 | B2 | 11/2022 | Shelton, IV et al. |
| 11,490,889 | B2 | 11/2022 | Overmyer et al. |
| 11,497,488 | B2 | 11/2022 | Leimbach et al. |
| 11,497,489 | B2 | 11/2022 | Baxter, III et al. |
| 11,497,492 | B2 | 11/2022 | Shelton, IV |
| 11,497,499 | B2 | 11/2022 | Shelton, IV et al. |
| 11,504,116 | B2 | 11/2022 | Schmid et al. |
| 11,504,119 | B2 | 11/2022 | Shelton, IV et al. |
| 11,504,122 | B2 | 11/2022 | Shelton, IV et al. |
| 11,504,192 | B2 | 11/2022 | Shelton, IV et al. |
| 11,510,671 | B2 | 11/2022 | Shelton, IV et al. |
| 11,510,741 | B2 | 11/2022 | Shelton, IV et al. |
| 11,517,304 | B2 | 12/2022 | Yates et al. |
| 11,517,306 | B2 | 12/2022 | Miller et al. |
| 11,517,309 | B2 | 12/2022 | Bakos et al. |
| 11,517,311 | B2 | 12/2022 | Lytle, IV et al. |
| 11,517,315 | B2 | 12/2022 | Huitema et al. |
| 11,517,325 | B2 | 12/2022 | Shelton, IV et al. |
| 11,517,390 | B2 | 12/2022 | Baxter, III |
| 11,523,821 | B2 | 12/2022 | Harris et al. |
| 11,523,822 | B2 | 12/2022 | Shelton, IV et al. |
| 11,523,823 | B2 | 12/2022 | Hunter et al. |
| 11,529,137 | B2 | 12/2022 | Shelton, IV et al. |
| 11,529,138 | B2 | 12/2022 | Jaworek et al. |
| 11,529,139 | B2 | 12/2022 | Shelton, IV et al. |
| 11,529,140 | B2 | 12/2022 | Shelton, IV et al. |
| 11,529,142 | B2 | 12/2022 | Leimbach et al. |
| 11,534,162 | B2 | 12/2022 | Shelton, IV |
| 11,534,259 | B2 | 12/2022 | Leimbach et al. |
| D974,560 | S | 1/2023 | Shelton, IV et al. |
| D975,278 | S | 1/2023 | Shelton, IV et al. |
| D975,850 | S | 1/2023 | Shelton, IV et al. |
| D975,851 | S | 1/2023 | Shelton, IV et al. |
| D976,401 | S | 1/2023 | Shelton, IV et al. |
| 11,540,824 | B2 | 1/2023 | Shelton, IV et al. |
| 11,540,829 | B2 | 1/2023 | Shelton, IV et al. |
| 11,547,403 | B2 | 1/2023 | Shelton, IV et al. |
| 11,547,404 | B2 | 1/2023 | Shelton, IV et al. |
| 11,553,911 | B2 | 1/2023 | Shelton, IV et al. |
| 11,553,916 | B2 | 1/2023 | Vendely et al. |
| 11,553,919 | B2 | 1/2023 | Shelton, IV et al. |
| 11,553,971 | B2 | 1/2023 | Shelton, IV et al. |
| 11,559,302 | B2 | 1/2023 | Timm et al. |
| 11,559,303 | B2 | 1/2023 | Shelton, IV et al. |
| 11,559,304 | B2 | 1/2023 | Boudreaux et al. |
| 11,559,307 | B2 | 1/2023 | Shelton, IV et al. |
| 11,559,308 | B2 | 1/2023 | Yates et al. |
| 11,559,496 | B2 | 1/2023 | Widenhouse et al. |
| 11,564,679 | B2 | 1/2023 | Parihar et al. |
| 11,564,682 | B2 | 1/2023 | Timm et al. |
| 11,564,686 | B2 | 1/2023 | Yates et al. |
| 11,564,688 | B2 | 1/2023 | Swayze et al. |
| 11,564,703 | B2 | 1/2023 | Shelton, IV et al. |
| 11,564,756 | B2 | 1/2023 | Shelton, IV et al. |
| 11,571,207 | B2 | 2/2023 | Shelton, IV et al. |
| 11,571,210 | B2 | 2/2023 | Shelton, IV et al. |
| 11,571,212 | B2 | 2/2023 | Yates et al. |
| 11,571,215 | B2 | 2/2023 | Shelton, IV et al. |
| 11,571,231 | B2 | 2/2023 | Hess et al. |
| 11,576,668 | B2 | 2/2023 | Shelton, IV et al. |
| 11,576,672 | B2 | 2/2023 | Shelton, IV et al. |
| 11,576,673 | B2 | 2/2023 | Shelton, IV |
| 11,576,677 | B2 | 2/2023 | Shelton, IV et al. |
| 11,583,274 | B2 | 2/2023 | Widenhouse et al. |
| 11,583,277 | B2 | 2/2023 | Shelton, IV et al. |
| 11,583,278 | B2 | 2/2023 | Shelton, IV et al. |
| 11,583,279 | B2 | 2/2023 | Smith et al. |
| 11,589,865 | B2 | 2/2023 | Shelton, IV et al. |
| 11,589,888 | B2 | 2/2023 | Shelton, IV et al. |
| 11,596,406 | B2 | 3/2023 | Huitema et al. |
| 11,602,340 | B2 | 3/2023 | Schmid et al. |
| 11,602,346 | B2 | 3/2023 | Shelton, IV |
| 11,602,366 | B2 | 3/2023 | Shelton, IV et al. |
| 11,607,219 | B2 | 3/2023 | Shelton, IV et al. |
| 11,607,239 | B2 | 3/2023 | Swensgard et al. |
| 11,607,278 | B2 | 3/2023 | Shelton, IV et al. |
| 11,612,393 | B2 | 3/2023 | Morgan et al. |
| 11,612,394 | B2 | 3/2023 | Morgan et al. |
| 11,612,395 | B2 | 3/2023 | Yates et al. |
| 11,617,575 | B2 | 4/2023 | Yates et al. |
| 11,617,576 | B2 | 4/2023 | Yates et al. |
| 11,617,577 | B2 | 4/2023 | Huang |
| 11,622,763 | B2 | 4/2023 | Parihar et al. |
| 11,622,766 | B2 | 4/2023 | Shelton, IV |
| 11,622,785 | B2 | 4/2023 | Hess et al. |
| 11,627,959 | B2 | 4/2023 | Shelton, IV et al. |
| 11,627,960 | B2 | 4/2023 | Shelton, IV et al. |
| 11,633,183 | B2 | 4/2023 | Parihar et al. |
| 11,638,581 | B2 | 5/2023 | Parihar et al. |
| 11,638,582 | B2 | 5/2023 | Bakos et al. |
| 11,638,583 | B2 | 5/2023 | Yates et al. |
| 11,638,587 | B2 | 5/2023 | Shelton, IV et al. |
| 11,642,125 | B2 | 5/2023 | Harris et al. |
| 11,642,128 | B2 | 5/2023 | Shelton, IV et al. |
| 11,648,005 | B2 | 5/2023 | Yates et al. |
| 11,648,006 | B2 | 5/2023 | Timm et al. |
| 11,648,008 | B2 | 5/2023 | Shelton, IV et al. |
| 11,648,009 | B2 | 5/2023 | Jenkins |
| 11,648,022 | B2 | 5/2023 | Shelton, IV |
| 11,648,024 | B2 | 5/2023 | Shelton, IV et al. |
| 11,653,914 | B2 | 5/2023 | Shelton, IV et al. |
| 11,653,915 | B2 | 5/2023 | Shelton, IV et al. |
| 11,653,917 | B2 | 5/2023 | Scott et al. |
| 11,653,918 | B2 | 5/2023 | Swayze et al. |
| 11,653,920 | B2 | 5/2023 | Shelton, IV et al. |
| 11,659,023 | B2 | 5/2023 | Shelton, IV et al. |
| 11,660,090 | B2 | 5/2023 | Bakos et al. |
| 11,660,110 | B2 | 5/2023 | Shelton, IV et al. |
| 11,660,163 | B2 | 5/2023 | Shelton, IV et al. |
| 11,666,332 | B2 | 6/2023 | Giordano et al. |
| 11,672,531 | B2 | 6/2023 | Timm et al. |
| 11,672,532 | B2 | 6/2023 | Shelton, IV et al. |
| 11,672,536 | B2 | 6/2023 | Shelton, IV et al. |
| 11,672,605 | B2 | 6/2023 | Messerly et al. |
| 11,678,877 | B2 | 6/2023 | Shelton, IV et al. |
| 11,678,880 | B2 | 6/2023 | Shelton, IV et al. |
| 11,678,881 | B2 | 6/2023 | Yates et al. |
| 11,678,882 | B2 | 6/2023 | Shelton, IV et al. |
| 11,684,360 | B2 | 6/2023 | Shelton, IV et al. |
| 11,684,361 | B2 | 6/2023 | Yates et al. |
| 11,684,365 | B2 | 6/2023 | Shelton, IV et al. |
| 11,684,369 | B2 | 6/2023 | Shelton, IV et al. |
| 11,684,434 | B2 | 6/2023 | Shelton, IV |
| 11,690,615 | B2 | 7/2023 | Parihar et al. |
| 11,690,623 | B2 | 7/2023 | Shelton, IV et al. |
| 11,696,757 | B2 | 7/2023 | Shelton, IV et al. |
| 11,696,759 | B2 | 7/2023 | Shelton, IV et al. |
| 11,696,761 | B2 | 7/2023 | Shelton, IV |
| 11,696,778 | B2 | 7/2023 | Shelton, IV et al. |
| 11,701,110 | B2 | 7/2023 | Yates et al. |
| 11,701,111 | B2 | 7/2023 | Shelton, IV et al. |
| 11,701,113 | B2 | 7/2023 | Shelton, IV et al. |
| 11,701,114 | B2 | 7/2023 | Shelton, IV et al. |
| 11,701,115 | B2 | 7/2023 | Harris et al. |
| 11,707,273 | B2 | 7/2023 | Kerr et al. |
| 11,712,244 | B2 | 8/2023 | Vendely et al. |
| 11,712,303 | B2 | 8/2023 | Shelton, IV et al. |
| 11,717,285 | B2 | 8/2023 | Yates et al. |

(56) References Cited

U.S. PATENT DOCUMENTS

| | | | |
|---|---|---|---|
| 11,717,291 | B2 | 8/2023 | Morgan et al. |
| 11,717,294 | B2 | 8/2023 | Huitema et al. |
| 11,737,748 | B2 | 8/2023 | Witte |
| 11,826,013 | B2 | 11/2023 | Parks |
| 11,857,182 | B2 | 1/2024 | Witte |
| 11,864,756 | B2 | 1/2024 | Witte et al. |
| 11,871,925 | B2 | 1/2024 | Hall et al. |
| 11,883,024 | B2 | 1/2024 | Bakos et al. |
| 11,974,741 | B2 | 5/2024 | Moubarak et al. |
| 12,064,107 | B2 | 8/2024 | Parks |
| 12,156,709 | B2 | 12/2024 | Traina |
| 12,220,126 | B2 | 2/2025 | Witte |
| 2001/0000531 | A1 | 4/2001 | Casscells et al. |
| 2001/0025183 | A1 | 9/2001 | Shahidi |
| 2001/0025184 | A1 | 9/2001 | Messerly |
| 2001/0030219 | A1 | 10/2001 | Green et al. |
| 2001/0034530 | A1 | 10/2001 | Malackowski et al. |
| 2001/0045442 | A1 | 11/2001 | Whitman |
| 2002/0014510 | A1 | 2/2002 | Richter et al. |
| 2002/0022810 | A1 | 2/2002 | Urich |
| 2002/0022836 | A1 | 2/2002 | Goble et al. |
| 2002/0022861 | A1 | 2/2002 | Jacobs et al. |
| 2002/0023126 | A1 | 2/2002 | Flavin |
| 2002/0029032 | A1 | 3/2002 | Arkin |
| 2002/0029036 | A1 | 3/2002 | Goble et al. |
| 2002/0042620 | A1 | 4/2002 | Julian et al. |
| 2002/0054158 | A1 | 5/2002 | Asami |
| 2002/0066764 | A1 | 6/2002 | Perry et al. |
| 2002/0082612 | A1 | 6/2002 | Moll et al. |
| 2002/0087048 | A1 | 7/2002 | Brock et al. |
| 2002/0087148 | A1 | 7/2002 | Brock et al. |
| 2002/0091374 | A1 | 7/2002 | Cooper |
| 2002/0095175 | A1 | 7/2002 | Brock et al. |
| 2002/0103494 | A1 | 8/2002 | Pacey |
| 2002/0111621 | A1 | 8/2002 | Wallace et al. |
| 2002/0111624 | A1 | 8/2002 | Witt et al. |
| 2002/0116063 | A1 | 8/2002 | Giannetti et al. |
| 2002/0117533 | A1 | 8/2002 | Milliman et al. |
| 2002/0117534 | A1 | 8/2002 | Green et al. |
| 2002/0127265 | A1 | 9/2002 | Bowman et al. |
| 2002/0128633 | A1 | 9/2002 | Brock et al. |
| 2002/0133236 | A1 | 9/2002 | Rousseau |
| 2002/0134811 | A1 | 9/2002 | Napier et al. |
| 2002/0135474 | A1 | 9/2002 | Sylliassen |
| 2002/0138086 | A1 | 9/2002 | Sixto et al. |
| 2002/0143340 | A1 | 10/2002 | Kaneko |
| 2002/0151770 | A1 | 10/2002 | Noll et al. |
| 2002/0158593 | A1 | 10/2002 | Henderson et al. |
| 2002/0161277 | A1 | 10/2002 | Boone et al. |
| 2002/0177848 | A1 | 11/2002 | Truckai et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0009193 | A1 | 1/2003 | Corsaro |
| 2003/0011245 | A1 | 1/2003 | Fiebig |
| 2003/0012805 | A1 | 1/2003 | Chen et al. |
| 2003/0018323 | A1 | 1/2003 | Wallace et al. |
| 2003/0028236 | A1 | 2/2003 | Gillick et al. |
| 2003/0039689 | A1 | 2/2003 | Chen et al. |
| 2003/0040670 | A1 | 2/2003 | Govari |
| 2003/0045835 | A1 | 3/2003 | Anderson et al. |
| 2003/0047230 | A1 | 3/2003 | Kim |
| 2003/0047582 | A1 | 3/2003 | Sonnenschein et al. |
| 2003/0050628 | A1 | 3/2003 | Whitman et al. |
| 2003/0050654 | A1 | 3/2003 | Whitman et al. |
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0135204 | A1 | 7/2003 | Lee et al. |
| 2003/0139741 | A1 | 7/2003 | Goble et al. |
| 2003/0144660 | A1 | 7/2003 | Mollenauer |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0158463 | A1 | 8/2003 | Julian et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0191494 | A1 | 10/2003 | Gray et al. |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0231870 | A1 | 11/2004 | McCormick et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |

(56) References Cited

U.S. PATENT DOCUMENTS

2004/0254455 A1 12/2004 Iddan
2004/0254566 A1 12/2004 Plicchi et al.
2004/0254590 A1 12/2004 Hoffman et al.
2004/0254680 A1 12/2004 Sunaoshi
2004/0260315 A1 12/2004 Dell et al.
2004/0267310 A1 12/2004 Racenet et al.
2005/0010158 A1 1/2005 Brugger et al.
2005/0010213 A1 1/2005 Stad et al.
2005/0021078 A1 1/2005 Vleugels et al.
2005/0023325 A1 2/2005 Gresham et al.
2005/0032511 A1 2/2005 Malone et al.
2005/0033352 A1 2/2005 Zepf et al.
2005/0044489 A1 2/2005 Yamagami et al.
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0067548 A1 3/2005 Inoue
2005/0070925 A1 3/2005 Shelton et al.
2005/0070929 A1 3/2005 Dalessandro et al.
2005/0075561 A1 4/2005 Golden
2005/0079088 A1 4/2005 Wirth et al.
2005/0080342 A1 4/2005 Gilreath et al.
2005/0085693 A1 4/2005 Belson et al.
2005/0085838 A1 4/2005 Thompson et al.
2005/0090709 A1 4/2005 Okada et al.
2005/0090817 A1 4/2005 Phan
2005/0096683 A1 5/2005 Ellins et al.
2005/0116673 A1 6/2005 Carl et al.
2005/0120836 A1 6/2005 Anderson
2005/0124855 A1 6/2005 Jaffe et al.
2005/0125897 A1 6/2005 Wyslucha et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131457 A1 6/2005 Douglas et al.
2005/0137454 A1 6/2005 Saadat et al.
2005/0137455 A1 6/2005 Ewers et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145672 A1 7/2005 Schwemberger et al.
2005/0150928 A1 7/2005 Kameyama et al.
2005/0154258 A1 7/2005 Tartaglia et al.
2005/0154406 A1 7/2005 Bombard et al.
2005/0159778 A1 7/2005 Heinrich et al.
2005/0165419 A1 7/2005 Sauer et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177249 A1 8/2005 Kladakis et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0191936 A1 9/2005 Marine et al.
2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0256452 A1 11/2005 DeMarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0274034 A1 12/2005 Hayashida et al.
2005/0283188 A1 12/2005 Loshakove et al.
2005/0283226 A1 12/2005 Haverkost
2006/0008787 A1 1/2006 Hayman et al.
2006/0011698 A1 1/2006 Okada et al.
2006/0015009 A1 1/2006 Jaffe et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0235368 A1 10/2006 Oz
2006/0241666 A1 10/2006 Briggs et al.
2006/0241691 A1 10/2006 Wilk
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.

(56) References Cited

U.S. PATENT DOCUMENTS

| | | | |
|---|---|---|---|
| 2006/0287576 | A1 | 12/2006 | Tsuji et al. |
| 2006/0289600 | A1 | 12/2006 | Wales et al. |
| 2006/0289602 | A1 | 12/2006 | Wales et al. |
| 2006/0291981 | A1 | 12/2006 | Viola et al. |
| 2007/0005045 | A1 | 1/2007 | Mintz et al. |
| 2007/0009570 | A1 | 1/2007 | Kim et al. |
| 2007/0010702 | A1 | 1/2007 | Wang et al. |
| 2007/0010838 | A1 | 1/2007 | Shelton et al. |
| 2007/0016235 | A1 | 1/2007 | Tanaka et al. |
| 2007/0018958 | A1 | 1/2007 | Tavakoli et al. |
| 2007/0026039 | A1 | 2/2007 | Drumheller et al. |
| 2007/0026040 | A1 | 2/2007 | Crawley et al. |
| 2007/0027459 | A1 | 2/2007 | Horvath et al. |
| 2007/0027468 | A1 | 2/2007 | Wales et al. |
| 2007/0027551 | A1 | 2/2007 | Farnsworth et al. |
| 2007/0043338 | A1 | 2/2007 | Moll et al. |
| 2007/0043387 | A1 | 2/2007 | Vargas et al. |
| 2007/0049951 | A1 | 3/2007 | Menn |
| 2007/0049966 | A1 | 3/2007 | Bonadio et al. |
| 2007/0051375 | A1 | 3/2007 | Milliman |
| 2007/0055228 | A1 | 3/2007 | Berg et al. |
| 2007/0055305 | A1 | 3/2007 | Schnyder et al. |
| 2007/0073341 | A1 | 3/2007 | Smith et al. |
| 2007/0073389 | A1 | 3/2007 | Bolduc et al. |
| 2007/0078328 | A1 | 4/2007 | Ozaki et al. |
| 2007/0078484 | A1 | 4/2007 | Talarico et al. |
| 2007/0084897 | A1 | 4/2007 | Shelton et al. |
| 2007/0088376 | A1 | 4/2007 | Zacharias |
| 2007/0090788 | A1 | 4/2007 | Hansford et al. |
| 2007/0093869 | A1 | 4/2007 | Bloom et al. |
| 2007/0102472 | A1 | 5/2007 | Shelton |
| 2007/0103437 | A1 | 5/2007 | Rosenberg |
| 2007/0106113 | A1 | 5/2007 | Ravo |
| 2007/0106317 | A1 | 5/2007 | Shelton et al. |
| 2007/0118115 | A1 | 5/2007 | Artale et al. |
| 2007/0134251 | A1 | 6/2007 | Ashkenazi et al. |
| 2007/0135686 | A1 | 6/2007 | Pruitt et al. |
| 2007/0135803 | A1 | 6/2007 | Belson |
| 2007/0152612 | A1 | 7/2007 | Chen et al. |
| 2007/0152829 | A1 | 7/2007 | Lindsay et al. |
| 2007/0155010 | A1 | 7/2007 | Farnsworth et al. |
| 2007/0162056 | A1 | 7/2007 | Gerbi et al. |
| 2007/0170225 | A1 | 7/2007 | Shelton et al. |
| 2007/0173687 | A1 | 7/2007 | Shima et al. |
| 2007/0173813 | A1 | 7/2007 | Odom |
| 2007/0173872 | A1 | 7/2007 | Neuenfeldt |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0179477 | A1 | 8/2007 | Danger |
| 2007/0185545 | A1 | 8/2007 | Duke |
| 2007/0187857 | A1 | 8/2007 | Riley et al. |
| 2007/0190110 | A1 | 8/2007 | Pameijer et al. |
| 2007/0191868 | A1 | 8/2007 | Theroux et al. |
| 2007/0191915 | A1 | 8/2007 | Strother et al. |
| 2007/0194079 | A1 | 8/2007 | Hueil et al. |
| 2007/0194081 | A1 | 8/2007 | Hueil et al. |
| 2007/0194082 | A1 | 8/2007 | Morgan et al. |
| 2007/0197954 | A1 | 8/2007 | Keenan |
| 2007/0198039 | A1 | 8/2007 | Jones et al. |
| 2007/0203510 | A1 | 8/2007 | Bettuchi |
| 2007/0207010 | A1 | 9/2007 | Caspi |
| 2007/0208359 | A1 | 9/2007 | Hoffman |
| 2007/0208375 | A1 | 9/2007 | Nishizawa et al. |
| 2007/0213750 | A1 | 9/2007 | Weadock |
| 2007/0221701 | A1 | 9/2007 | Ortiz et al. |
| 2007/0225562 | A1 | 9/2007 | Spivey et al. |
| 2007/0233163 | A1 | 10/2007 | Bombard et al. |
| 2007/0243227 | A1 | 10/2007 | Gertner |
| 2007/0244471 | A1 | 10/2007 | Malackowski |
| 2007/0244496 | A1 | 10/2007 | Hellenkamp |
| 2007/0246505 | A1 | 10/2007 | Pace-Floridia et al. |
| 2007/0260132 | A1 | 11/2007 | Sterling |
| 2007/0260242 | A1 | 11/2007 | Dycus et al. |
| 2007/0262592 | A1 | 11/2007 | Hwang et al. |
| 2007/0270660 | A1 | 11/2007 | Caylor et al. |
| 2007/0275035 | A1 | 11/2007 | Herman et al. |
| 2007/0276409 | A1 | 11/2007 | Ortiz et al. |
| 2007/0279011 | A1 | 12/2007 | Jones et al. |
| 2007/0286892 | A1 | 12/2007 | Herzberg et al. |
| 2007/0290027 | A1 | 12/2007 | Maatta et al. |
| 2007/0296286 | A1 | 12/2007 | Avenell |
| 2008/0000941 | A1 | 1/2008 | Sonnenschein et al. |
| 2008/0003196 | A1 | 1/2008 | Jonn et al. |
| 2008/0007237 | A1 | 1/2008 | Nagashima et al. |
| 2008/0015598 | A1 | 1/2008 | Prommersberger |
| 2008/0021486 | A1 | 1/2008 | Oyola et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0030170 | A1 | 2/2008 | Dacquay et al. |
| 2008/0039746 | A1 | 2/2008 | Hissong et al. |
| 2008/0042861 | A1 | 2/2008 | Dacquay et al. |
| 2008/0046000 | A1 | 2/2008 | Lee et al. |
| 2008/0051833 | A1 | 2/2008 | Gramuglia et al. |
| 2008/0064920 | A1 | 3/2008 | Bakos et al. |
| 2008/0064921 | A1 | 3/2008 | Larkin et al. |
| 2008/0065153 | A1 | 3/2008 | Allard et al. |
| 2008/0069736 | A1 | 3/2008 | Mingerink et al. |
| 2008/0071328 | A1 | 3/2008 | Haubrich et al. |
| 2008/0077158 | A1 | 3/2008 | Haider et al. |
| 2008/0078802 | A1 | 4/2008 | Hess et al. |
| 2008/0081948 | A1 | 4/2008 | Weisenburgh et al. |
| 2008/0082114 | A1 | 4/2008 | McKenna et al. |
| 2008/0082125 | A1 | 4/2008 | Murray et al. |
| 2008/0082126 | A1 | 4/2008 | Murray et al. |
| 2008/0083807 | A1 | 4/2008 | Beardsley et al. |
| 2008/0083811 | A1 | 4/2008 | Marczyk |
| 2008/0085296 | A1 | 4/2008 | Powell et al. |
| 2008/0086078 | A1 | 4/2008 | Powell et al. |
| 2008/0091072 | A1 | 4/2008 | Omori et al. |
| 2008/0094228 | A1 | 4/2008 | Welch et al. |
| 2008/0108443 | A1 | 5/2008 | Jinno et al. |
| 2008/0114250 | A1 | 5/2008 | Urbano et al. |
| 2008/0125634 | A1 | 5/2008 | Ryan et al. |
| 2008/0125749 | A1 | 5/2008 | Olson |
| 2008/0126984 | A1 | 5/2008 | Fleishman et al. |
| 2008/0128469 | A1 | 6/2008 | Dalessandro et al. |
| 2008/0129253 | A1 | 6/2008 | Shiue et al. |
| 2008/0135600 | A1 | 6/2008 | Hiranuma et al. |
| 2008/0140115 | A1 | 6/2008 | Stopek |
| 2008/0140159 | A1 | 6/2008 | Bornhoft et al. |
| 2008/0149682 | A1 | 6/2008 | Uhm |
| 2008/0154299 | A1 | 6/2008 | Livneh |
| 2008/0154335 | A1 | 6/2008 | Thrope et al. |
| 2008/0169328 | A1 | 7/2008 | Shelton |
| 2008/0169332 | A1 | 7/2008 | Shelton et al. |
| 2008/0169333 | A1 | 7/2008 | Shelton et al. |
| 2008/0172087 | A1 | 7/2008 | Fuchs et al. |
| 2008/0177392 | A1 | 7/2008 | Williams et al. |
| 2008/0190989 | A1 | 8/2008 | Crews et al. |
| 2008/0196253 | A1 | 8/2008 | Ezra et al. |
| 2008/0196419 | A1 | 8/2008 | Dube |
| 2008/0197167 | A1 | 8/2008 | Viola et al. |
| 2008/0200755 | A1 | 8/2008 | Bakos |
| 2008/0200762 | A1 | 8/2008 | Stokes et al. |
| 2008/0200835 | A1 | 8/2008 | Monson et al. |
| 2008/0200911 | A1 | 8/2008 | Long |
| 2008/0200933 | A1 | 8/2008 | Bakos et al. |
| 2008/0200934 | A1 | 8/2008 | Fox |
| 2008/0206186 | A1 | 8/2008 | Butler et al. |
| 2008/0208058 | A1 | 8/2008 | Sabata et al. |
| 2008/0216704 | A1 | 9/2008 | Eisenbeis et al. |
| 2008/0234709 | A1 | 9/2008 | Houser |
| 2008/0234866 | A1 | 9/2008 | Kishi et al. |
| 2008/0242939 | A1 | 10/2008 | Johnston |
| 2008/0243088 | A1 | 10/2008 | Evans |
| 2008/0249536 | A1 | 10/2008 | Stahler et al. |
| 2008/0249608 | A1 | 10/2008 | Dave |
| 2008/0255413 | A1 | 10/2008 | Zemlok et al. |
| 2008/0255420 | A1 | 10/2008 | Lee et al. |
| 2008/0255421 | A1 | 10/2008 | Hegeman et al. |
| 2008/0255663 | A1 | 10/2008 | Akpek et al. |

(56) References Cited

U.S. PATENT DOCUMENTS

| | | | |
|---|---|---|---|
| 2008/0262654 | A1 | 10/2008 | Omori et al. |
| 2008/0269596 | A1 | 10/2008 | Revie et al. |
| 2008/0281171 | A1 | 11/2008 | Fennell et al. |
| 2008/0281332 | A1 | 11/2008 | Taylor |
| 2008/0287944 | A1 | 11/2008 | Pearson et al. |
| 2008/0293910 | A1 | 11/2008 | Kapiamba et al. |
| 2008/0294179 | A1 | 11/2008 | Balbierz et al. |
| 2008/0296346 | A1 | 12/2008 | Shelton, IV et al. |
| 2008/0296347 | A1 | 12/2008 | Shelton, IV et al. |
| 2008/0297287 | A1 | 12/2008 | Shachar et al. |
| 2008/0298784 | A1 | 12/2008 | Kastner |
| 2008/0308504 | A1 | 12/2008 | Hallan et al. |
| 2008/0308602 | A1 | 12/2008 | Timm et al. |
| 2008/0308603 | A1 | 12/2008 | Shelton et al. |
| 2008/0308607 | A1 | 12/2008 | Timm et al. |
| 2008/0308807 | A1 | 12/2008 | Yamazaki et al. |
| 2008/0312686 | A1 | 12/2008 | Ellingwood |
| 2008/0312687 | A1 | 12/2008 | Blier |
| 2008/0315829 | A1 | 12/2008 | Jones et al. |
| 2009/0001121 | A1 | 1/2009 | Hess et al. |
| 2009/0001130 | A1 | 1/2009 | Hess et al. |
| 2009/0004455 | A1 | 1/2009 | Gravagna et al. |
| 2009/0005809 | A1 | 1/2009 | Hess et al. |
| 2009/0007014 | A1 | 1/2009 | Coomer et al. |
| 2009/0012534 | A1 | 1/2009 | Madhani et al. |
| 2009/0015195 | A1 | 1/2009 | Loth-Krausser |
| 2009/0020958 | A1 | 1/2009 | Soul |
| 2009/0048583 | A1 | 2/2009 | Williams et al. |
| 2009/0048589 | A1 | 2/2009 | Takashino et al. |
| 2009/0076506 | A1 | 3/2009 | Baker |
| 2009/0078736 | A1 | 3/2009 | Van Lue |
| 2009/0081313 | A1 | 3/2009 | Aghion et al. |
| 2009/0088659 | A1 | 4/2009 | Graham et al. |
| 2009/0090763 | A1 | 4/2009 | Zemlok et al. |
| 2009/0099579 | A1 | 4/2009 | Nentwick et al. |
| 2009/0099876 | A1 | 4/2009 | Whitman |
| 2009/0110533 | A1 | 4/2009 | Jinno |
| 2009/0112234 | A1 | 4/2009 | Crainich et al. |
| 2009/0114701 | A1 | 5/2009 | Zemlok et al. |
| 2009/0118762 | A1 | 5/2009 | Crainch et al. |
| 2009/0119011 | A1 | 5/2009 | Kondo et al. |
| 2009/0120994 | A1 | 5/2009 | Murray et al. |
| 2009/0131819 | A1 | 5/2009 | Ritchie et al. |
| 2009/0132400 | A1 | 5/2009 | Conway |
| 2009/0135280 | A1 | 5/2009 | Johnston et al. |
| 2009/0138003 | A1 | 5/2009 | Deville et al. |
| 2009/0143797 | A1 | 6/2009 | Smith et al. |
| 2009/0143855 | A1 | 6/2009 | Weber et al. |
| 2009/0149871 | A9 | 6/2009 | Kagan et al. |
| 2009/0167548 | A1 | 7/2009 | Sugahara |
| 2009/0171147 | A1 | 7/2009 | Lee et al. |
| 2009/0177218 | A1 | 7/2009 | Young et al. |
| 2009/0177226 | A1 | 7/2009 | Reinprecht et al. |
| 2009/0181290 | A1 | 7/2009 | Baldwin et al. |
| 2009/0188964 | A1 | 7/2009 | Orlov |
| 2009/0192534 | A1 | 7/2009 | Ortiz et al. |
| 2009/0198272 | A1 | 8/2009 | Kerver et al. |
| 2009/0204108 | A1 | 8/2009 | Steffen |
| 2009/0204109 | A1 | 8/2009 | Grove et al. |
| 2009/0204126 | A1 | 8/2009 | Le |
| 2009/0204925 | A1 | 8/2009 | Bhat et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh, II et al. |
| 2009/0206133 | A1 | 8/2009 | Morgan et al. |
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0221993 | A1 | 9/2009 | Sohi et al. |
| 2009/0227834 | A1 | 9/2009 | Nakamoto et al. |
| 2009/0234273 | A1 | 9/2009 | Intoccia et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248100 | A1 | 10/2009 | Vaisnys et al. |
| 2009/0253959 | A1 | 10/2009 | Yoshie et al. |
| 2009/0255974 | A1 | 10/2009 | Viola |
| 2009/0259141 | A1 | 10/2009 | Ewers et al. |
| 2009/0261141 | A1 | 10/2009 | Stratton et al. |
| 2009/0262078 | A1 | 10/2009 | Pizzi |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076483 | A1 | 3/2010 | Imuta |
| 2010/0076489 | A1 | 3/2010 | Stopek et al. |
| 2010/0081883 | A1 | 4/2010 | Murray et al. |
| 2010/0094312 | A1 | 4/2010 | Ruiz Morales et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241137 | A1 | 9/2010 | Doyle et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |

(56) References Cited

U.S. PATENT DOCUMENTS

| | | | |
|---|---|---|---|
| 2010/0298636 | A1 | 11/2010 | Castro et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | El-Galley et al. |
| 2011/0125176 | A1 | 5/2011 | Yates et al. |
| 2011/0127945 | A1 | 6/2011 | Yoneda |
| 2011/0129706 | A1 | 6/2011 | Takahashi et al. |
| 2011/0144764 | A1 | 6/2011 | Bagga et al. |
| 2011/0147433 | A1 | 6/2011 | Shelton, IV et al. |
| 2011/0160725 | A1 | 6/2011 | Kabaya et al. |
| 2011/0163146 | A1 | 7/2011 | Ortiz et al. |
| 2011/0172495 | A1 | 7/2011 | Armstrong |
| 2011/0174861 | A1 | 7/2011 | Shelton, IV et al. |
| 2011/0192882 | A1 | 8/2011 | Hess et al. |
| 2011/0198381 | A1 | 8/2011 | McCardle et al. |
| 2011/0199225 | A1 | 8/2011 | Touchberry et al. |
| 2011/0218400 | A1 | 9/2011 | Ma et al. |
| 2011/0218550 | A1 | 9/2011 | Ma |
| 2011/0220381 | A1 | 9/2011 | Friese et al. |
| 2011/0224543 | A1 | 9/2011 | Johnson et al. |
| 2011/0225105 | A1 | 9/2011 | Scholer et al. |
| 2011/0230713 | A1 | 9/2011 | Kleemann et al. |
| 2011/0235168 | A1 | 9/2011 | Sander |
| 2011/0238044 | A1 | 9/2011 | Main et al. |
| 2011/0241597 | A1 | 10/2011 | Zhu et al. |
| 2011/0251606 | A1 | 10/2011 | Kerr |
| 2011/0256266 | A1 | 10/2011 | Orme et al. |
| 2011/0271186 | A1 | 11/2011 | Owens |
| 2011/0275901 | A1 | 11/2011 | Shelton, IV |
| 2011/0276083 | A1 | 11/2011 | Shelton, IV et al. |
| 2011/0278035 | A1 | 11/2011 | Chen |
| 2011/0278343 | A1 | 11/2011 | Knodel et al. |
| 2011/0279268 | A1 | 11/2011 | Konishi et al. |
| 2011/0285507 | A1 | 11/2011 | Nelson |
| 2011/0290856 | A1 | 12/2011 | Shelton, IV et al. |
| 2011/0290858 | A1 | 12/2011 | Whitman et al. |
| 2011/0292258 | A1 | 12/2011 | Adler et al. |
| 2011/0293690 | A1 | 12/2011 | Griffin et al. |
| 2011/0295295 | A1 | 12/2011 | Shelton, IV et al. |
| 2011/0295299 | A1 | 12/2011 | Braithwaite et al. |
| 2011/0313894 | A1 | 12/2011 | Dye et al. |
| 2011/0315413 | A1 | 12/2011 | Fisher et al. |
| 2012/0004636 | A1 | 1/2012 | Lo |
| 2012/0007442 | A1 | 1/2012 | Rhodes et al. |
| 2012/0008880 | A1 | 1/2012 | Toth |
| 2012/0016239 | A1 | 1/2012 | Barthe et al. |
| 2012/0016413 | A1 | 1/2012 | Timm et al. |
| 2012/0016467 | A1 | 1/2012 | Chen et al. |
| 2012/0029272 | A1 | 2/2012 | Shelton, IV et al. |
| 2012/0029550 | A1 | 2/2012 | Forsell |
| 2012/0033360 | A1 | 2/2012 | Hsu |
| 2012/0059286 | A1 | 3/2012 | Hastings et al. |
| 2012/0064483 | A1 | 3/2012 | Lint et al. |
| 2012/0074200 | A1 | 3/2012 | Schmid et al. |
| 2012/0078243 | A1 | 3/2012 | Worrell et al. |
| 2012/0078244 | A1 | 3/2012 | Worrell et al. |
| 2012/0080336 | A1 | 4/2012 | Shelton, IV et al. |
| 2012/0080344 | A1 | 4/2012 | Shelton, IV |
| 2012/0080478 | A1 | 4/2012 | Morgan et al. |
| 2012/0080491 | A1 | 4/2012 | Shelton, IV et al. |
| 2012/0080498 | A1 | 4/2012 | Shelton, IV et al. |
| 2012/0086276 | A1 | 4/2012 | Sawyers |
| 2012/0095458 | A1 | 4/2012 | Cybulski et al. |
| 2012/0101488 | A1 | 4/2012 | Aldridge et al. |
| 2012/0109186 | A1 | 5/2012 | Parrott et al. |
| 2012/0116261 | A1 | 5/2012 | Mumaw et al. |
| 2012/0116262 | A1 | 5/2012 | Houser et al. |
| 2012/0116265 | A1 | 5/2012 | Houser et al. |
| 2012/0116266 | A1 | 5/2012 | Houser et al. |
| 2012/0116381 | A1 | 5/2012 | Houser et al. |
| 2012/0118595 | A1 | 5/2012 | Pellenc |
| 2012/0123463 | A1 | 5/2012 | Jacobs |
| 2012/0125792 | A1 | 5/2012 | Cassivi |
| 2012/0130217 | A1 | 5/2012 | Kauphusman et al. |
| 2012/0132286 | A1 | 5/2012 | Lim et al. |
| 2012/0132663 | A1 | 5/2012 | Kasvikis et al. |
| 2012/0143175 | A1 | 6/2012 | Hermann et al. |
| 2012/0171539 | A1 | 7/2012 | Rejman et al. |
| 2012/0175398 | A1 | 7/2012 | Sandborn et al. |
| 2012/0190964 | A1 | 7/2012 | Hyde et al. |
| 2012/0197239 | A1 | 8/2012 | Smith et al. |
| 2012/0197272 | A1 | 8/2012 | Oray et al. |
| 2012/0203213 | A1 | 8/2012 | Kimball et al. |
| 2012/0211542 | A1 | 8/2012 | Racenet |
| 2012/0220990 | A1 | 8/2012 | Mckenzie et al. |
| 2012/0233298 | A1 | 9/2012 | Verbandt et al. |
| 2012/0234895 | A1 | 9/2012 | O'Connor et al. |
| 2012/0234897 | A1 | 9/2012 | Shelton, IV et al. |
| 2012/0239068 | A1 | 9/2012 | Morris et al. |
| 2012/0241494 | A1 | 9/2012 | Marczyk |
| 2012/0248169 | A1 | 10/2012 | Widenhouse et al. |
| 2012/0251861 | A1 | 10/2012 | Liang et al. |
| 2012/0253328 | A1 | 10/2012 | Cunningham et al. |
| 2012/0256494 | A1 | 10/2012 | Kesler et al. |
| 2012/0271327 | A1 | 10/2012 | West et al. |
| 2012/0283707 | A1 | 11/2012 | Giordano et al. |
| 2012/0286019 | A1 | 11/2012 | Hueil et al. |
| 2012/0289811 | A1 | 11/2012 | Viola et al. |
| 2012/0289979 | A1 | 11/2012 | Eskaros et al. |
| 2012/0292367 | A1 | 11/2012 | Morgan et al. |
| 2012/0296316 | A1 | 11/2012 | Imuta |
| 2012/0296342 | A1 | 11/2012 | Haglund Wendelschafer |
| 2012/0298722 | A1 | 11/2012 | Hess et al. |
| 2012/0301498 | A1 | 11/2012 | Altreuter et al. |
| 2012/0310254 | A1 | 12/2012 | Manzo et al. |
| 2012/0316424 | A1 | 12/2012 | Stopek |
| 2012/0330329 | A1 | 12/2012 | Harris et al. |
| 2013/0006227 | A1 | 1/2013 | Takashino |
| 2013/0008937 | A1 | 1/2013 | Viola |
| 2013/0012983 | A1 | 1/2013 | Kleyman |
| 2013/0018400 | A1 | 1/2013 | Milton et al. |
| 2013/0020375 | A1 | 1/2013 | Shelton, IV et al. |
| 2013/0020376 | A1 | 1/2013 | Shelton, IV et al. |
| 2013/0023861 | A1 | 1/2013 | Shelton, IV et al. |
| 2013/0023910 | A1 | 1/2013 | Solomon et al. |
| 2013/0026208 | A1 | 1/2013 | Shelton, IV et al. |
| 2013/0026210 | A1 | 1/2013 | Shelton, IV et al. |
| 2013/0030462 | A1 | 1/2013 | Keating et al. |
| 2013/0041292 | A1 | 2/2013 | Cunningham |

(56) References Cited

U.S. PATENT DOCUMENTS

| | | | |
|---|---|---|---|
| 2013/0057162 | A1 | 3/2013 | Pollischansky |
| 2013/0068816 | A1 | 3/2013 | Mandakolathur Vasudevan et al. |
| 2013/0069088 | A1 | 3/2013 | Speck et al. |
| 2013/0075447 | A1 | 3/2013 | Weisenburgh, II et al. |
| 2013/0087597 | A1 | 4/2013 | Shelton, IV et al. |
| 2013/0090534 | A1 | 4/2013 | Burns et al. |
| 2013/0096568 | A1 | 4/2013 | Justis |
| 2013/0098970 | A1 | 4/2013 | Racenet et al. |
| 2013/0106352 | A1 | 5/2013 | Nagamine |
| 2013/0112729 | A1 | 5/2013 | Beardsley et al. |
| 2013/0116669 | A1 | 5/2013 | Shelton, IV et al. |
| 2013/0123816 | A1 | 5/2013 | Hodgkinson et al. |
| 2013/0126202 | A1 | 5/2013 | Oomori et al. |
| 2013/0131476 | A1 | 5/2013 | Siu et al. |
| 2013/0131651 | A1 | 5/2013 | Strobl et al. |
| 2013/0136969 | A1 | 5/2013 | Yasui et al. |
| 2013/0153639 | A1 | 6/2013 | Hodgkinson et al. |
| 2013/0153641 | A1 | 6/2013 | Shelton, IV et al. |
| 2013/0158390 | A1 | 6/2013 | Tan et al. |
| 2013/0162198 | A1 | 6/2013 | Yokota et al. |
| 2013/0165908 | A1 | 6/2013 | Purdy et al. |
| 2013/0169217 | A1 | 7/2013 | Watanabe et al. |
| 2013/0172713 | A1 | 7/2013 | Kirschenman |
| 2013/0172878 | A1 | 7/2013 | Smith |
| 2013/0175315 | A1 | 7/2013 | Milliman |
| 2013/0175317 | A1 | 7/2013 | Yates et al. |
| 2013/0183769 | A1 | 7/2013 | Tajima |
| 2013/0211244 | A1 | 8/2013 | Nathaniel |
| 2013/0214025 | A1 | 8/2013 | Zemlok et al. |
| 2013/0215449 | A1 | 8/2013 | Yamasaki |
| 2013/0231681 | A1 | 9/2013 | Robinson et al. |
| 2013/0233906 | A1 | 9/2013 | Hess et al. |
| 2013/0238021 | A1 | 9/2013 | Gross et al. |
| 2013/0248578 | A1 | 9/2013 | Arteaga Gonzalez |
| 2013/0253480 | A1 | 9/2013 | Kimball et al. |
| 2013/0256373 | A1 | 10/2013 | Schmid et al. |
| 2013/0256380 | A1 | 10/2013 | Schmid et al. |
| 2013/0267950 | A1 | 10/2013 | Rosa et al. |
| 2013/0267978 | A1 | 10/2013 | Trissel |
| 2013/0270322 | A1 | 10/2013 | Scheib et al. |
| 2013/0277410 | A1 | 10/2013 | Fernandez et al. |
| 2013/0284792 | A1 | 10/2013 | Ma |
| 2013/0289565 | A1 | 10/2013 | Hassler, Jr. |
| 2013/0293353 | A1 | 11/2013 | McPherson et al. |
| 2013/0303845 | A1 | 11/2013 | Skula et al. |
| 2013/0304084 | A1 | 11/2013 | Beira et al. |
| 2013/0306704 | A1 | 11/2013 | Balbierz et al. |
| 2013/0327552 | A1 | 12/2013 | Lovelass et al. |
| 2013/0333910 | A1 | 12/2013 | Tanimoto et al. |
| 2013/0334280 | A1 | 12/2013 | Krehel et al. |
| 2013/0334283 | A1 | 12/2013 | Swayze et al. |
| 2013/0334285 | A1 | 12/2013 | Swayze et al. |
| 2013/0341374 | A1 | 12/2013 | Shelton, IV et al. |
| 2014/0001231 | A1 | 1/2014 | Shelton, IV et al. |
| 2014/0001234 | A1 | 1/2014 | Shelton, IV et al. |
| 2014/0002322 | A1 | 1/2014 | Kanome et al. |
| 2014/0005550 | A1 | 1/2014 | Lu et al. |
| 2014/0005640 | A1 | 1/2014 | Shelton, IV et al. |
| 2014/0005678 | A1 | 1/2014 | Shelton, IV et al. |
| 2014/0005702 | A1 | 1/2014 | Timm et al. |
| 2014/0005718 | A1 | 1/2014 | Shelton, IV et al. |
| 2014/0008289 | A1 | 1/2014 | Williams et al. |
| 2014/0014704 | A1 | 1/2014 | Onukuri et al. |
| 2014/0014705 | A1 | 1/2014 | Baxter, III |
| 2014/0014707 | A1 | 1/2014 | Onukuri et al. |
| 2014/0018832 | A1 | 1/2014 | Shelton, IV |
| 2014/0022283 | A1 | 1/2014 | Chan et al. |
| 2014/0039549 | A1 | 2/2014 | Belsky et al. |
| 2014/0041191 | A1 | 2/2014 | Knodel |
| 2014/0048580 | A1 | 2/2014 | Merchant et al. |
| 2014/0069240 | A1 | 3/2014 | Dauvin et al. |
| 2014/0078715 | A1 | 3/2014 | Pickard et al. |
| 2014/0081176 | A1 | 3/2014 | Hassan |
| 2014/0088614 | A1 | 3/2014 | Blumenkranz |
| 2014/0094681 | A1 | 4/2014 | Valentine et al. |
| 2014/0100558 | A1 | 4/2014 | Schmitz et al. |
| 2014/0107697 | A1 | 4/2014 | Patani et al. |
| 2014/0110453 | A1 | 4/2014 | Wingardner et al. |
| 2014/0115229 | A1 | 4/2014 | Kothamasu et al. |
| 2014/0131418 | A1 | 5/2014 | Kostrzewski |
| 2014/0131419 | A1 | 5/2014 | Bettuchi |
| 2014/0135832 | A1 | 5/2014 | Park et al. |
| 2014/0148803 | A1 | 5/2014 | Taylor |
| 2014/0151433 | A1 | 6/2014 | Shelton, IV et al. |
| 2014/0155916 | A1 | 6/2014 | Hodgkinson et al. |
| 2014/0158747 | A1 | 6/2014 | Measamer et al. |
| 2014/0166718 | A1 | 6/2014 | Swayze et al. |
| 2014/0166723 | A1 | 6/2014 | Beardsley et al. |
| 2014/0166724 | A1 | 6/2014 | Schellin et al. |
| 2014/0166725 | A1 | 6/2014 | Schellin et al. |
| 2014/0166726 | A1 | 6/2014 | Schellin et al. |
| 2014/0175147 | A1 | 6/2014 | Manoux et al. |
| 2014/0175150 | A1 | 6/2014 | Shelton, IV et al. |
| 2014/0175152 | A1 | 6/2014 | Hess et al. |
| 2014/0181710 | A1 | 6/2014 | Baalu et al. |
| 2014/0183244 | A1 | 7/2014 | Duque et al. |
| 2014/0188091 | A1 | 7/2014 | Vidal et al. |
| 2014/0188101 | A1 | 7/2014 | Bales, Jr. et al. |
| 2014/0188159 | A1 | 7/2014 | Steege |
| 2014/0207124 | A1 | 7/2014 | Aldridge et al. |
| 2014/0209658 | A1 | 7/2014 | Skalla et al. |
| 2014/0224857 | A1 | 8/2014 | Schmid |
| 2014/0228632 | A1 | 8/2014 | Sholev et al. |
| 2014/0228867 | A1 | 8/2014 | Thomas et al. |
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch, Jr. et al. |
| 2014/0249573 | A1 | 9/2014 | Arav |
| 2014/0262408 | A1 | 9/2014 | Woodard |
| 2014/0263541 | A1 | 9/2014 | Leimbach et al. |
| 2014/0263552 | A1 | 9/2014 | Hall et al. |
| 2014/0263558 | A1 | 9/2014 | Hausen et al. |
| 2014/0276730 | A1 | 9/2014 | Boudreaux et al. |
| 2014/0284371 | A1 | 9/2014 | Morgan et al. |
| 2014/0287703 | A1 | 9/2014 | Herbsommer et al. |
| 2014/0288460 | A1 | 9/2014 | Ouyang et al. |
| 2014/0291379 | A1 | 10/2014 | Schellin et al. |
| 2014/0291383 | A1 | 10/2014 | Spivey et al. |
| 2014/0299648 | A1 | 10/2014 | Shelton, IV et al. |
| 2014/0303645 | A1 | 10/2014 | Morgan et al. |
| 2014/0303660 | A1 | 10/2014 | Boyden et al. |
| 2014/0330161 | A1 | 11/2014 | Swayze et al. |
| 2014/0330298 | A1 | 11/2014 | Arshonsky et al. |
| 2014/0330579 | A1 | 11/2014 | Cashman et al. |
| 2014/0358163 | A1 | 12/2014 | Farin et al. |
| 2014/0367445 | A1 | 12/2014 | Ingmanson et al. |
| 2014/0371764 | A1 | 12/2014 | Oyola et al. |
| 2014/0373003 | A1 | 12/2014 | Grez et al. |
| 2014/0374130 | A1 | 12/2014 | Nakamura et al. |
| 2014/0378950 | A1 | 12/2014 | Chiu |
| 2015/0001272 | A1 | 1/2015 | Sniffin et al. |
| 2015/0002089 | A1 | 1/2015 | Rejman et al. |
| 2015/0022012 | A1 | 1/2015 | Kim et al. |
| 2015/0025549 | A1 | 1/2015 | Kilroy et al. |
| 2015/0025571 | A1 | 1/2015 | Suzuki et al. |
| 2015/0034697 | A1 | 2/2015 | Mastri et al. |
| 2015/0039010 | A1 | 2/2015 | Beardsley et al. |
| 2015/0053737 | A1 | 2/2015 | Leimbach et al. |
| 2015/0053743 | A1 | 2/2015 | Yates et al. |
| 2015/0053746 | A1 | 2/2015 | Shelton, IV et al. |
| 2015/0053748 | A1 | 2/2015 | Yates et al. |
| 2015/0060516 | A1 | 3/2015 | Collings et al. |
| 2015/0060519 | A1 | 3/2015 | Shelton, IV et al. |
| 2015/0060520 | A1 | 3/2015 | Shelton, IV et al. |
| 2015/0060521 | A1 | 3/2015 | Weisenburgh, II et al. |
| 2015/0066000 | A1 | 3/2015 | An et al. |
| 2015/0067582 | A1 | 3/2015 | Donnelly et al. |
| 2015/0076208 | A1 | 3/2015 | Shelton, IV |
| 2015/0076209 | A1 | 3/2015 | Shelton, IV et al. |
| 2015/0076210 | A1 | 3/2015 | Shelton, IV et al. |
| 2015/0076211 | A1 | 3/2015 | Irka et al. |
| 2015/0080883 | A1 | 3/2015 | Haverkost et al. |

(56) References Cited

U.S. PATENT DOCUMENTS

2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272606 A1 10/2015 Nobis
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297824 A1 10/2015 Cabiri et al.
2015/0303417 A1 10/2015 Koeder et al.
2015/0305743 A1 10/2015 Casasanta et al.
2015/0313594 A1 11/2015 Shelton, IV et al.
2015/0324317 A1 11/2015 Collins et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0081678 A1 3/2016 Kappel et al.
2016/0082161 A1 3/2016 Zilberman et al.
2016/0089175 A1 3/2016 Hibner et al.
2016/0118201 A1 4/2016 Nicholas et al.
2016/0132026 A1 5/2016 Wingardner et al.
2016/0135835 A1 5/2016 Onuma
2016/0135895 A1 5/2016 Faasse et al.
2016/0139666 A1 5/2016 Rubin et al.
2016/0174969 A1 6/2016 Kerr et al.
2016/0174972 A1* 6/2016 Shelton, IV ......... A61B 17/072
227/180.1
2016/0174983 A1 6/2016 Shelton, IV et al.
2016/0183939 A1 6/2016 Shelton, IV et al.
2016/0183944 A1 6/2016 Swensgard et al.
2016/0192927 A1 7/2016 Kostrzewski
2016/0192960 A1 7/2016 Bueno et al.
2016/0199063 A1 7/2016 Mandakolathur Vasudevan et al.
2016/0199956 A1 7/2016 Shelton, IV et al.
2016/0220150 A1 8/2016 Sharonov
2016/0235494 A1 8/2016 Shelton, IV et al.
2016/0242783 A1 8/2016 Shelton, IV et al.
2016/0242855 A1 8/2016 Fichtinger et al.
2016/0249910 A1 9/2016 Shelton, IV et al.
2016/0249922 A1 9/2016 Morgan et al.
2016/0249929 A1 9/2016 Cappola et al.
2016/0256159 A1 9/2016 Pinjala et al.
2016/0256184 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0345972 A1 12/2016 Beardsley et al.
2016/0367122 A1 12/2016 Ichimura et al.
2016/0374669 A1 12/2016 Overmyer et al.
2016/0374716 A1 12/2016 Kessler
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0020616 A1 1/2017 Vale et al.
2017/0035419 A1 2/2017 Decker et al.
2017/0055819 A1 3/2017 Hansen et al.
2017/0055980 A1 3/2017 Vendely et al.
2017/0056008 A1 3/2017 Shelton, IV et al.
2017/0056016 A1 3/2017 Barton et al.
2017/0056018 A1 3/2017 Zeiner et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086930 A1 3/2017 Thompson et al.
2017/0086932 A1 3/2017 Auld et al.
2017/0095922 A1 4/2017 Licht et al.
2017/0105727 A1 4/2017 Scheib et al.
2017/0105733 A1 4/2017 Scheib et al.
2017/0105786 A1 4/2017 Scheib et al.
2017/0106302 A1 4/2017 Cummings et al.
2017/0135711 A1 5/2017 Overmyer et al.
2017/0135717 A1 5/2017 Boudreaux et al.
2017/0135747 A1 5/2017 Broderick et al.
2017/0168187 A1 6/2017 Calderoni et al.
2017/0172382 A1 6/2017 Nir et al.
2017/0172549 A1 6/2017 Smaby et al.
2017/0172662 A1 6/2017 Panescu et al.
2017/0182195 A1 6/2017 Wagner
2017/0182211 A1 6/2017 Raxworthy et al.
2017/0196558 A1 7/2017 Morgan et al.
2017/0196649 A1 7/2017 Yates et al.
2017/0202607 A1 7/2017 Shelton, IV et al.
2017/0202770 A1 7/2017 Friedrich et al.
2017/0224332 A1 8/2017 Hunter et al.
2017/0231628 A1 8/2017 Shelton, IV et al.
2017/0231629 A1 8/2017 Stopek et al.
2017/0238962 A1 8/2017 Hansen et al.
2017/0242455 A1 8/2017 Dickens
2017/0245949 A1 8/2017 Randle
2017/0249431 A1 8/2017 Shelton, IV et al.
2017/0252060 A1 9/2017 Ellingson et al.
2017/0255799 A1 9/2017 Zhao et al.
2017/0262110 A1 9/2017 Polishchuk et al.
2017/0265774 A1 9/2017 Johnson et al.
2017/0281186 A1 10/2017 Shelton, IV et al.
2017/0296173 A1 10/2017 Shelton, IV et al.
2017/0296185 A1 10/2017 Swensgard et al.

(56) References Cited

U.S. PATENT DOCUMENTS

2017/0303984 A1 10/2017 Malackowski
2017/0312042 A1 11/2017 Giordano et al.
2017/0319047 A1 11/2017 Poulsen et al.
2017/0319201 A1 11/2017 Morgan et al.
2017/0333034 A1 11/2017 Morgan et al.
2017/0333035 A1 11/2017 Morgan et al.
2017/0348010 A1 12/2017 Chiang
2017/0348043 A1 12/2017 Wang et al.
2017/0354413 A1 12/2017 Chen et al.
2017/0358052 A1 12/2017 Yuan
2017/0360441 A1 12/2017 Sgroi
2018/0008265 A1 1/2018 Hatanaka et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.
2018/0067004 A1 3/2018 Sgroi, Jr.
2018/0078247 A1 3/2018 Nakadate et al.
2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271553 A1 9/2018 Worrell
2018/0271604 A1 9/2018 Grout et al.
2018/0273597 A1 9/2018 Stimson
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0317905 A1 11/2018 Olson et al.
2018/0317915 A1 11/2018 McDonald, II
2018/0325514 A1 11/2018 Harris et al.
2018/0333169 A1 11/2018 Leimbach et al.
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000481 A1 1/2019 Harris et al.
2019/0000535 A1 1/2019 Messerly et al.
2019/0000536 A1 1/2019 Yates et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0038281 A1 2/2019 Shelton, IV et al.
2019/0038283 A1 2/2019 Shelton, IV et al.
2019/0038285 A1 2/2019 Mozdzierz
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117224 A1 4/2019 Setser et al.
2019/0125320 A1 5/2019 Shelton, IV et al.
2019/0125336 A1 5/2019 Deck et al.
2019/0125338 A1 5/2019 Shelton, IV et al.
2019/0125342 A1 5/2019 Beardsley et al.
2019/0125344 A1 5/2019 DiNardo et al.
2019/0125361 A1 5/2019 Shelton, IV et al.
2019/0125378 A1 5/2019 Shelton, IV et al.
2019/0125388 A1 5/2019 Shelton, IV et al.
2019/0125432 A1 5/2019 Shelton, IV et al.
2019/0125454 A1 5/2019 Stokes et al.
2019/0125476 A1 5/2019 Shelton, IV et al.
2019/0133422 A1 5/2019 Nakamura
2019/0133577 A1 5/2019 Weadock et al.
2019/0138770 A1 5/2019 Compaijen et al.
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183502 A1 6/2019 Shelton, IV et al.
2019/0192147 A1 6/2019 Shelton, IV et al.
2019/0192148 A1 6/2019 Shelton, IV et al.
2019/0192151 A1 6/2019 Shelton, IV et al.
2019/0192153 A1 6/2019 Shelton, IV et al.
2019/0192155 A1 6/2019 Shelton, IV et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.
2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201025 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.

(56) References Cited

U.S. PATENT DOCUMENTS

2019/0201034 A1 7/2019 Shelton, IV et al.
2019/0201045 A1 7/2019 Yates et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201158 A1 7/2019 Shelton, IV et al.
2019/0201594 A1 7/2019 Shelton, IV et al.
2019/0205567 A1 7/2019 Shelton, IV et al.
2019/0206555 A1 7/2019 Morgan et al.
2019/0206561 A1 7/2019 Shelton, IV et al.
2019/0206564 A1 7/2019 Shelton, IV et al.
2019/0206569 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0239877 A1* 8/2019 Ragosta ........... A61B 17/07207
2019/0261982 A1 8/2019 Holsten
2019/0261983 A1 8/2019 Granger et al.
2019/0261984 A1 8/2019 Nelson et al.
2019/0261987 A1 8/2019 Viola et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0282233 A1 9/2019 Burbank et al.
2019/0290264 A1 9/2019 Morgan et al.
2019/0290266 A1 9/2019 Scheib et al.
2019/0290267 A1 9/2019 Baxter, III et al.
2019/0290297 A1 9/2019 Haider et al.
2019/0298353 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0314015 A1 10/2019 Shelton, IV et al.
2019/0321062 A1 10/2019 Williams
2019/0328387 A1 10/2019 Overmyer et al.
2019/0388091 A1 12/2019 Eschbach et al.
2020/0000531 A1 1/2020 Giordano et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015915 A1 1/2020 Swayze et al.
2020/0037939 A1 2/2020 Castagna et al.
2020/0038016 A1 2/2020 Shelton, IV et al.
2020/0038018 A1 2/2020 Shelton, IV et al.
2020/0046355 A1 2/2020 Harris et al.
2020/0046356 A1 2/2020 Baxter, III et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060713 A1 2/2020 Leimbach et al.
2020/0061385 A1 2/2020 Schwarz et al.
2020/0085435 A1 3/2020 Shelton, IV et al.
2020/0085518 A1 3/2020 Giordano et al.
2020/0093484 A1 3/2020 Shelton, IV et al.
2020/0093506 A1 3/2020 Leimbach et al.
2020/0093550 A1 3/2020 Spivey et al.
2020/0107829 A1 4/2020 Shelton, IV et al.
2020/0114505 A1 4/2020 Kikuchi
2020/0138507 A1 5/2020 Davison et al.
2020/0138534 A1 5/2020 Garcia Kilroy et al.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0229814 A1 7/2020 Amariglio et al.
2020/0237371 A1 7/2020 Huitema et al.
2020/0261086 A1 8/2020 Zeiner et al.
2020/0268377 A1 8/2020 Schmid et al.
2020/0275927 A1 9/2020 Shelton, IV et al.
2020/0280219 A1 9/2020 Laughery et al.
2020/0289112 A1 9/2020 Whitfield et al.
2020/0305863 A1 10/2020 Yates et al.
2020/0305864 A1 10/2020 Yates et al.
2020/0305872 A1 10/2020 Weidner et al.
2020/0315623 A1 10/2020 Eisinger et al.
2020/0323526 A1 10/2020 Huang et al.
2020/0330181 A1 10/2020 Junger et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0367886 A1 11/2020 Shelton, IV et al.
2020/0375585 A1 12/2020 Swayze et al.
2020/0375597 A1 12/2020 Shelton, IV et al.
2020/0390444 A1 12/2020 Harris et al.
2020/0397430 A1 12/2020 Patel et al.
2020/0405292 A1 12/2020 Shelton, IV et al.
2020/0405296 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405403 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0015480 A1 1/2021 Shelton, IV et al.
2021/0030416 A1 2/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068829 A1 3/2021 Miller et al.
2021/0068835 A1 3/2021 Shelton, IV et al.
2021/0077099 A1 3/2021 Shelton, IV et al.
2021/0077109 A1 3/2021 Harris et al.
2021/0085313 A1 3/2021 Morgan et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.
2021/0093321 A1 4/2021 Auld et al.
2021/0093323 A1 4/2021 Scirica et al.
2021/0100541 A1 4/2021 Shelton, IV et al.
2021/0100982 A1 4/2021 Laby et al.
2021/0107031 A1 4/2021 Bales, Jr. et al.
2021/0121175 A1 4/2021 Yates et al.

(56) References Cited

U.S. PATENT DOCUMENTS

2021/0128153 A1 5/2021 Sgroi
2021/0137522 A1 5/2021 Shelton, IV et al.
2021/0153866 A1 5/2021 Knapp et al.
2021/0177401 A1 6/2021 Abramek et al.
2021/0177411 A1 6/2021 Williams
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212691 A1 7/2021 Smith et al.
2021/0212776 A1 7/2021 Schmitt et al.
2021/0228209 A1 7/2021 Shelton, IV et al.
2021/0236124 A1 8/2021 Shelton, IV et al.
2021/0244407 A1 8/2021 Shelton, IV et al.
2021/0244410 A1 8/2021 Swayze et al.
2021/0244411 A1 8/2021 Smith et al.
2021/0259681 A1 8/2021 Shelton, IV et al.
2021/0259687 A1 8/2021 Gonzalez et al.
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0353284 A1 11/2021 Yang et al.
2021/0369271 A1 12/2021 Schings et al.
2021/0378669 A1 12/2021 Shelton, IV et al.
2021/0393261 A1 12/2021 Harris et al.
2021/0393262 A1 12/2021 Shelton, IV et al.
2021/0393366 A1 12/2021 Shelton, IV et al.
2022/0000478 A1 1/2022 Shelton, IV et al.
2022/0000479 A1 1/2022 Shelton, IV et al.
2022/0015760 A1 1/2022 Beardsley et al.
2022/0031313 A1 2/2022 Bakos et al.
2022/0031315 A1 2/2022 Bakos et al.
2022/0031319 A1 2/2022 Witte et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0104816 A1 4/2022 Fernandes et al.
2022/0117602 A1 4/2022 Wise et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133312 A1 5/2022 Huang
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160358 A1 5/2022 Wixey
2022/0167968 A1 6/2022 Worthington et al.
2022/0167970 A1 6/2022 Aronhalt et al.
2022/0167972 A1 6/2022 Shelton, IV et al.
2022/0167973 A1 6/2022 Shelton, IV et al.
2022/0167975 A1 6/2022 Shelton, IV et al.
2022/0167977 A1 6/2022 Shelton, IV et al.
2022/0167979 A1 6/2022 Yates et al.
2022/0167981 A1 6/2022 Shelton, IV et al.
2022/0167982 A1 6/2022 Shelton, IV et al.
2022/0167983 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0211367 A1 7/2022 Schmid et al.
2022/0218332 A1 7/2022 Shelton, IV et al.
2022/0218336 A1 7/2022 Timm et al.
2022/0218338 A1 7/2022 Shelton, IV et al.
2022/0218344 A1 7/2022 Leimbach et al.
2022/0218345 A1 7/2022 Shelton, IV et al.
2022/0218346 A1 7/2022 Shelton, IV et al.
2022/0218347 A1 7/2022 Shelton, IV et al.
2022/0218348 A1 7/2022 Swensgard et al.
2022/0218349 A1 7/2022 Shelton, IV et al.
2022/0218350 A1 7/2022 Shelton, IV et al.
2022/0218351 A1 7/2022 Shelton, IV et al.
2022/0218376 A1 7/2022 Shelton, IV et al.
2022/0218381 A1 7/2022 Leimbach et al.
2022/0218382 A1 7/2022 Leimbach et al.
2022/0225986 A1 7/2022 Shelton, IV et al.
2022/0225993 A1 7/2022 Huitema et al.
2022/0225994 A1 7/2022 Setser et al.
2022/0226013 A1 7/2022 Hall et al.
2022/0233186 A1 7/2022 Timm et al.
2022/0233188 A1 7/2022 Timm et al.
2022/0233194 A1 7/2022 Baxter, III et al.
2022/0233195 A1 7/2022 Shelton, IV et al.

(56) References Cited

U.S. PATENT DOCUMENTS

| | | | |
|---|---|---|---|
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0249095 | A1 | 8/2022 | Shelton, IV et al. |
| 2022/0265272 | A1 | 8/2022 | Li et al. |
| 2022/0273291 | A1 | 9/2022 | Shelton, IV et al. |
| 2022/0273292 | A1 | 9/2022 | Shelton, IV et al. |
| 2022/0273293 | A1 | 9/2022 | Shelton, IV et al. |
| 2022/0273294 | A1 | 9/2022 | Creamer et al. |
| 2022/0273299 | A1 | 9/2022 | Shelton, IV et al. |
| 2022/0273300 | A1 | 9/2022 | Shelton, IV et al. |
| 2022/0273301 | A1 | 9/2022 | Creamer et al. |
| 2022/0273303 | A1 | 9/2022 | Creamer et al. |
| 2022/0273304 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0278438 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296236 | A1 | 9/2022 | Bakos et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |

(56) References Cited

FOREIGN PATENT DOCUMENTS

| | | | |
|---|---|---|---|
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |

(56) References Cited

FOREIGN PATENT DOCUMENTS

| | | | |
|---|---|---|---|
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-146345 | A | 6/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008-220972 | A | 9/2008 |
| JP | 2008220032 | A | 9/2008 |
| JP | 2009507526 | A | 2/2009 |
| JP | 2009-189703 | A | 8/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016530949 | A | 10/2016 |
| JP | 2017513563 | A | 6/2017 |
| JP | D1593236 | S | 12/2017 |
| JP | 1601498 | S | 4/2018 |
| JP | D1618301 | S | 11/2018 |
| JP | 2019513530 | A | 5/2019 |
| JP | D1646991 | S | 12/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | A1 | 5/1993 |

(56) References Cited

FOREIGN PATENT DOCUMENTS

| | | | |
|---|---|---|---|
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

(56) References Cited

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.

(56) References Cited

OTHER PUBLICATIONS

Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," *Online Article*, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, *Article ID 879294, Hindawi Publishing Corporation*.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure. 12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.
Chinese First Office Action and Search Report dated May 21, 2025, for Application No. 202180066187.3, 7 pages.
International Search Report and Written Opinion dated Nov. 24, 2021, for International Application No. PCT/IB2021/056757, 14 pages.
International Search Report and Written Opinion dated Oct. 28, 2021, for International Application No. PCT/IB2021/056755, 12 pages.
Japanese First Office Action dated Mar. 5, 2025, for Application No. 2023-505953, 5 pages.
Japanese First Office Action dated Mar. 18, 2025, for Application No. 2023-505964, 7 pages.
U.S. Appl. No. 12/031,573, entitled "Surgical Cutting and Fastening Instrument Having Electrodes," filed Feb. 14, 2008.

* cited by examiner

SURGICAL INSTRUMENTS WITH FLEXIBLE FIRING MEMBER ACTUATOR CONSTRAINT ARRANGEMENTS

CROSS-REFERENCE TO RELATED APPLICATIONS

This non-provisional application claims the benefit under 35 U.S.C. § 119(e) of U.S. Provisional Patent Application Ser. No. 63/057,430, entitled SURGICAL INSTRUMENTS WITH TORSION SPINE DRIVE ARRANGEMENTS, filed Jul. 28, 2020, of U.S. Provisional Patent Application Ser. No. 63/057,432, entitled ARTICULATION JOINT ARRANGEMENTS FOR SURGICAL INSTRUMENTS, filed Jul. 28, 2020, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 119 is an exploded assembly perspective view of a portion of the surgical instrument of FIG. 115;

FIG. 120 is a bottom cross sectional view of an articulation joint and portions of the anvil of the surgical instrument of FIG. 115;

FIG. 121 is an exploded assembly view of the articulation joint of FIG. 120;

FIG. 122 is a side view of an annular disc member of the articulation joint of FIG. 121;

FIG. 123 is a perspective view of the annular disc member of FIG. 122;

FIG. 124 is a view of a distal face of the annular disc member of FIG. 122;

FIG. 125 is a view of a proximal face of the annular disc member of FIG. 122;

FIG. 126 is a top view of a pulley unit of the surgical instrument of FIG. 115;

FIG. 127 is a perspective view of a portion of the articulation joint and elongate shaft assembly of the surgical instrument of FIG. 115, with an outer shaft tube omitted for clarity;

FIG. 128 is a side elevational view of the pulley unit of FIG. 126;

FIG. 129 is another side elevational view of the pulley unit of FIG. 126;

FIG. 130 is a perspective view of the pulley unit of FIG. 126 and a continuum shaft of the articulation joint of the surgical instrument of FIG. 115;

Figure 115:
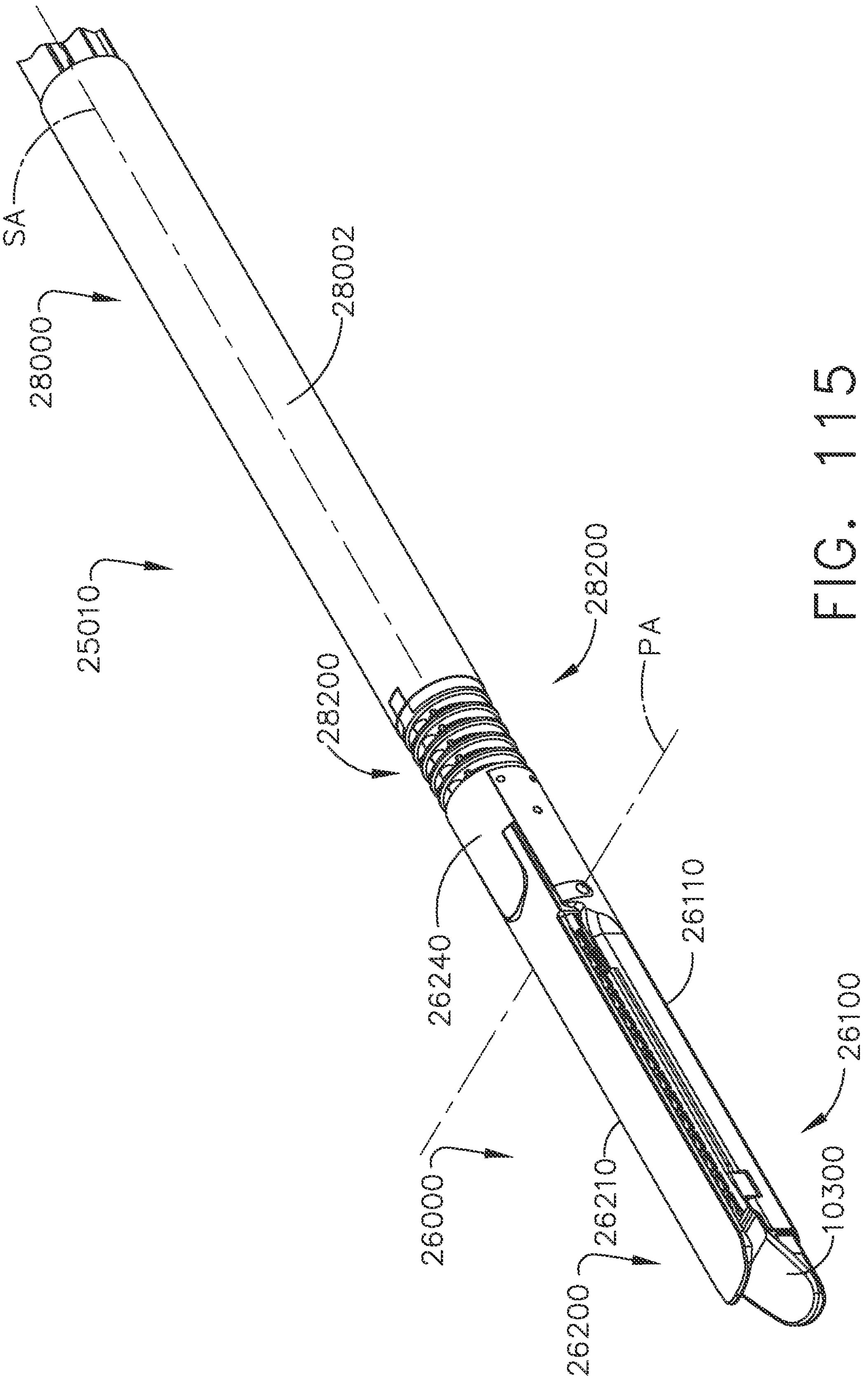
FIG. 115 is a perspective view of a portion of another surgical instrument embodiment.
Figure 116:
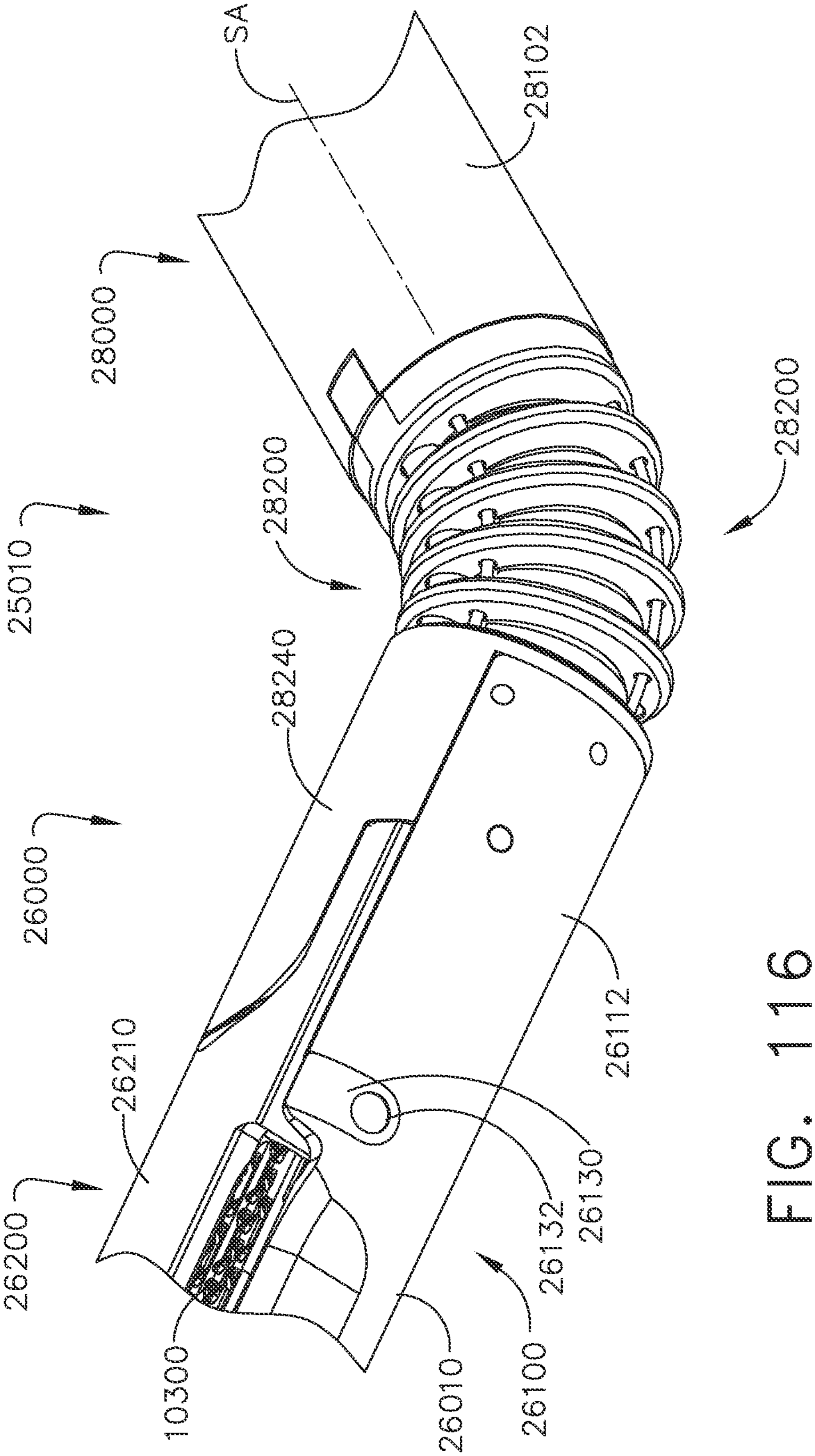
FIG. 116 is a perspective view of a portion of the surgical instrument of FIG. 115 with a surgical end effector portion thereof in an articulated position relative to an elongate shaft portion thereof.
Figure 117:
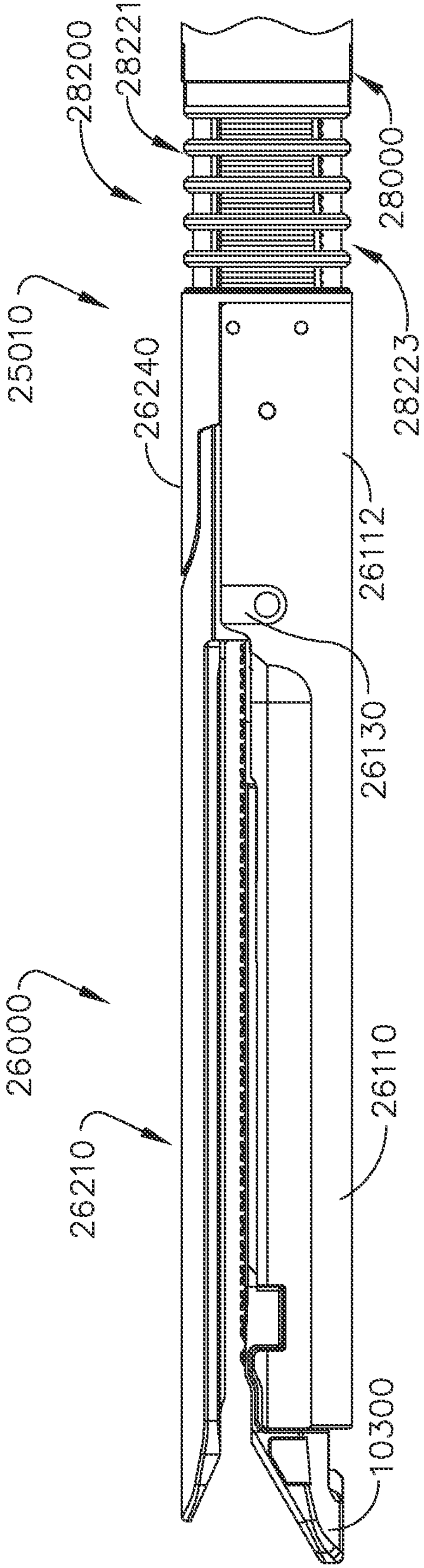
FIG. 117 is a side elevational view of the surgical end effector of FIG. 116, with an anvil thereof in a closed position.
Figure 118:
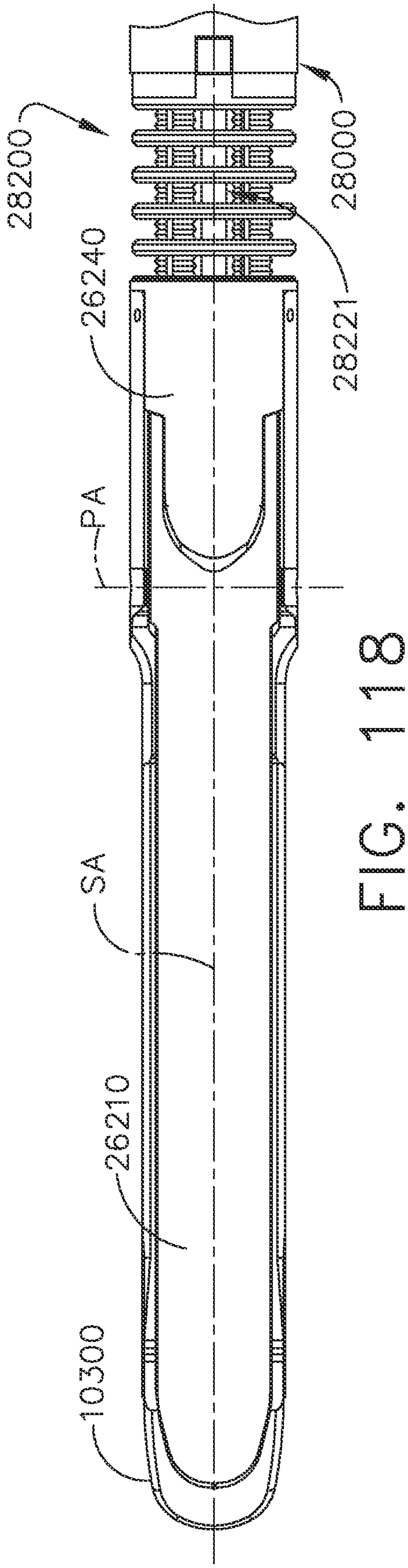
FIG. 118 is a top view of the surgical end effector of FIG. 117.
Figure 126:
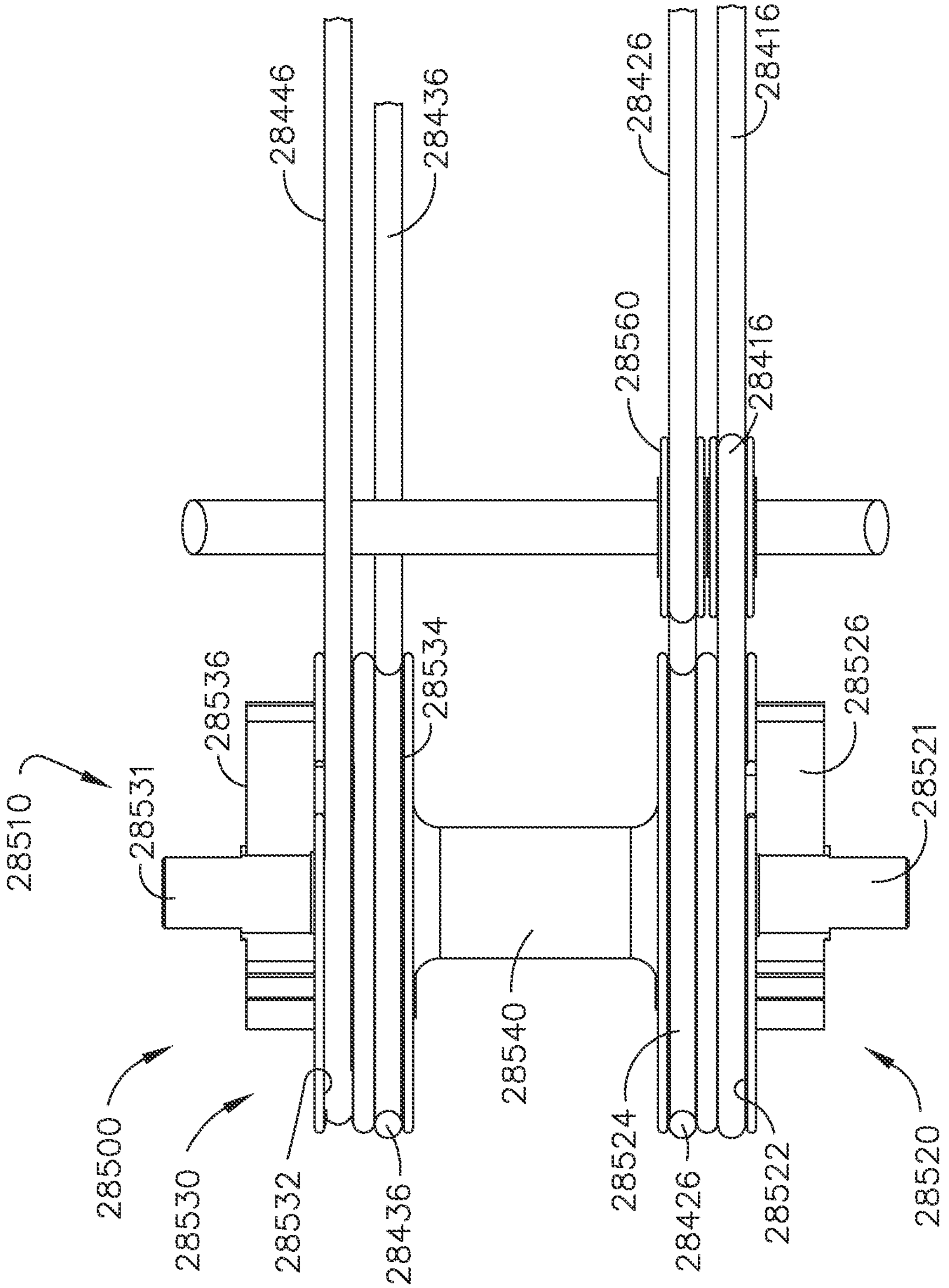
Figure 131:
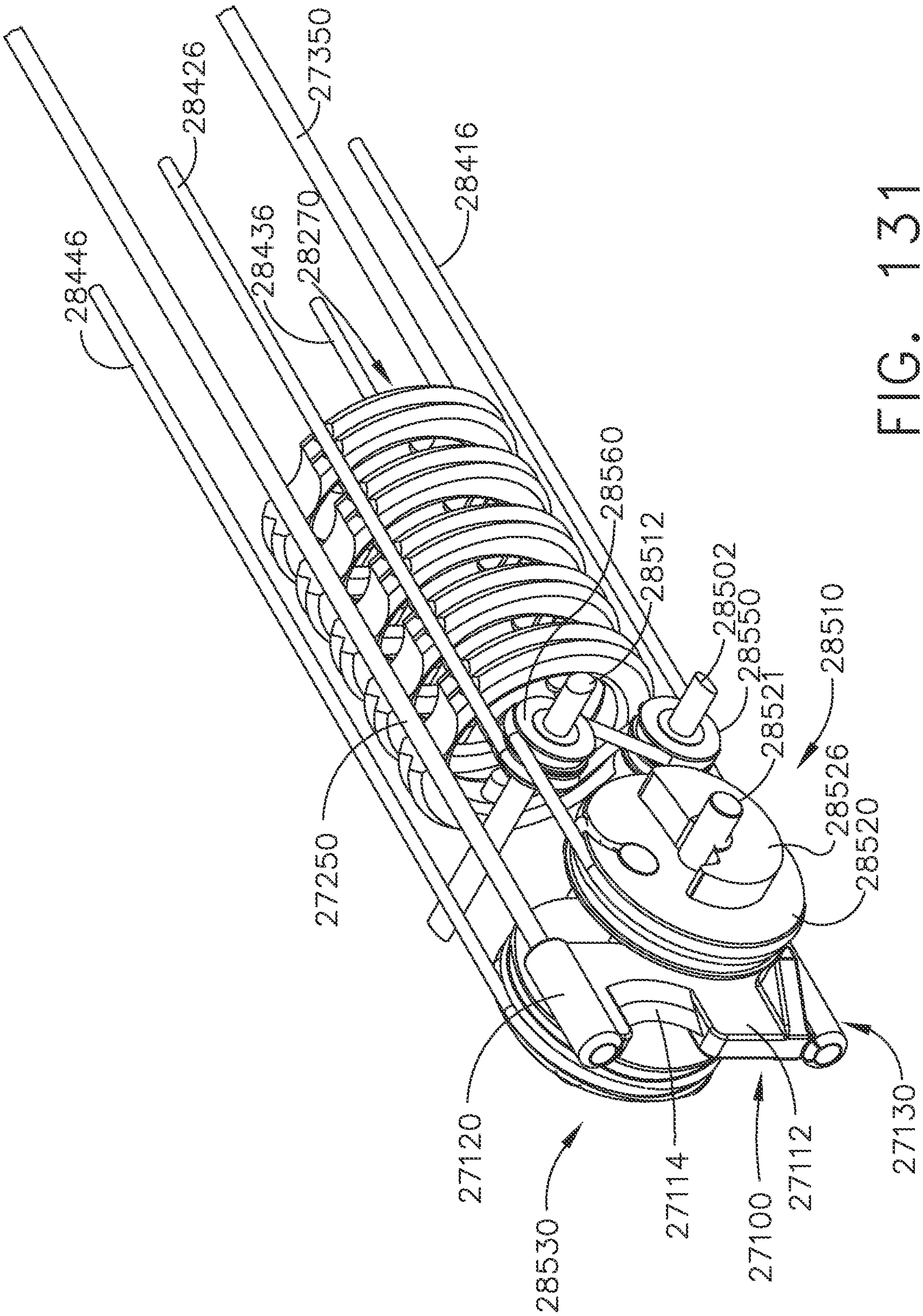
Figure 132:
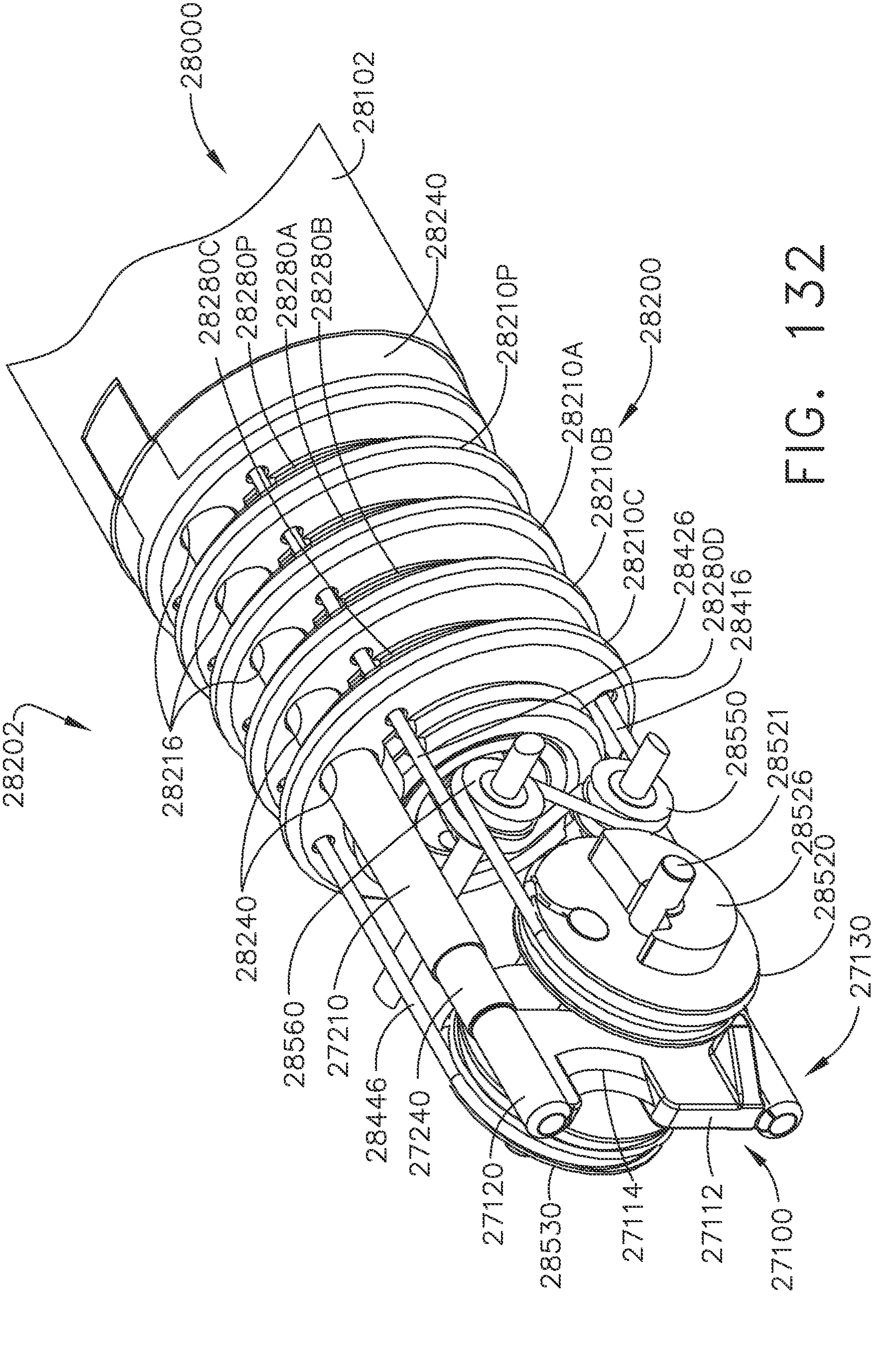
Figure 133:
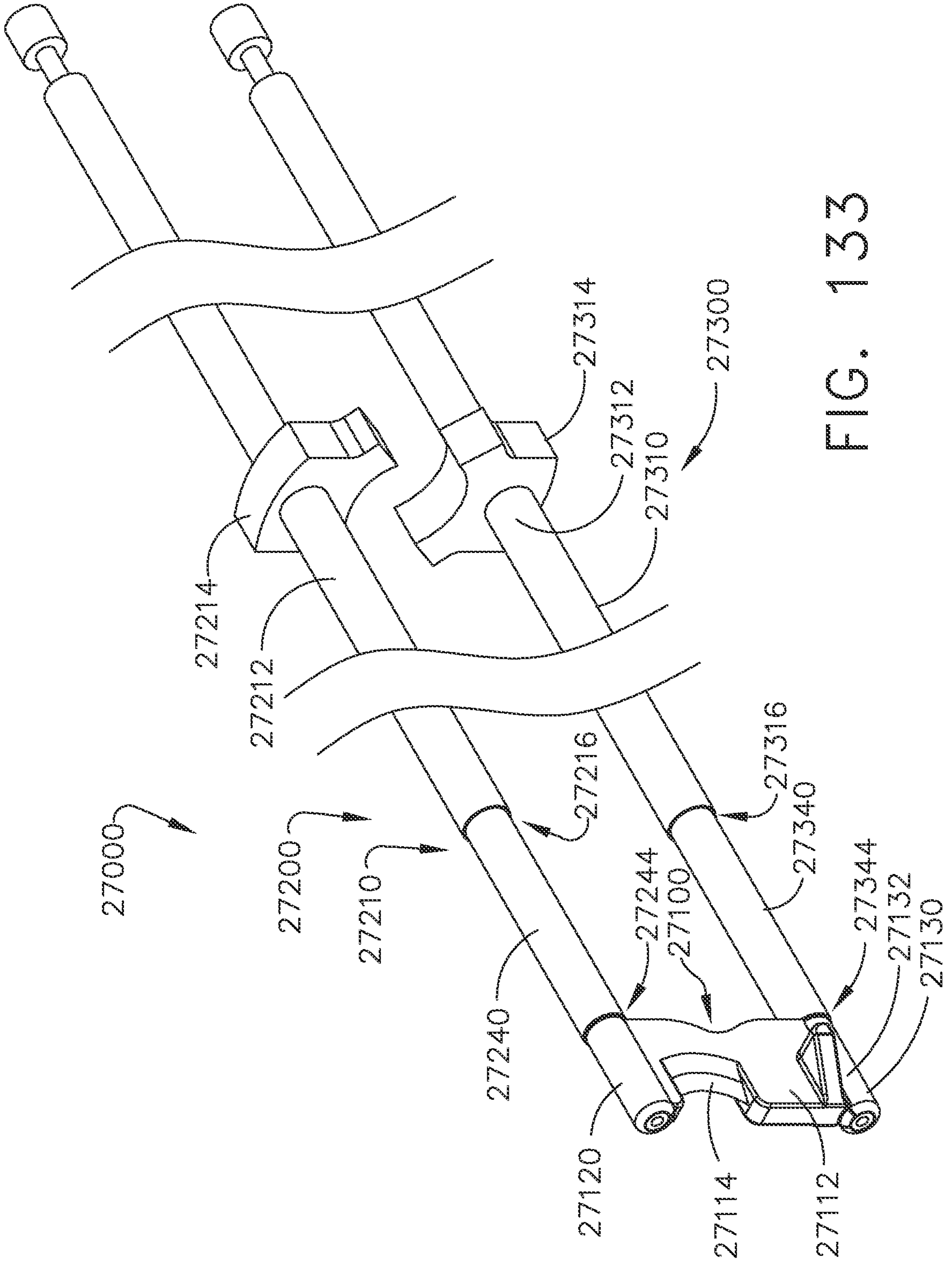
Figure 134:
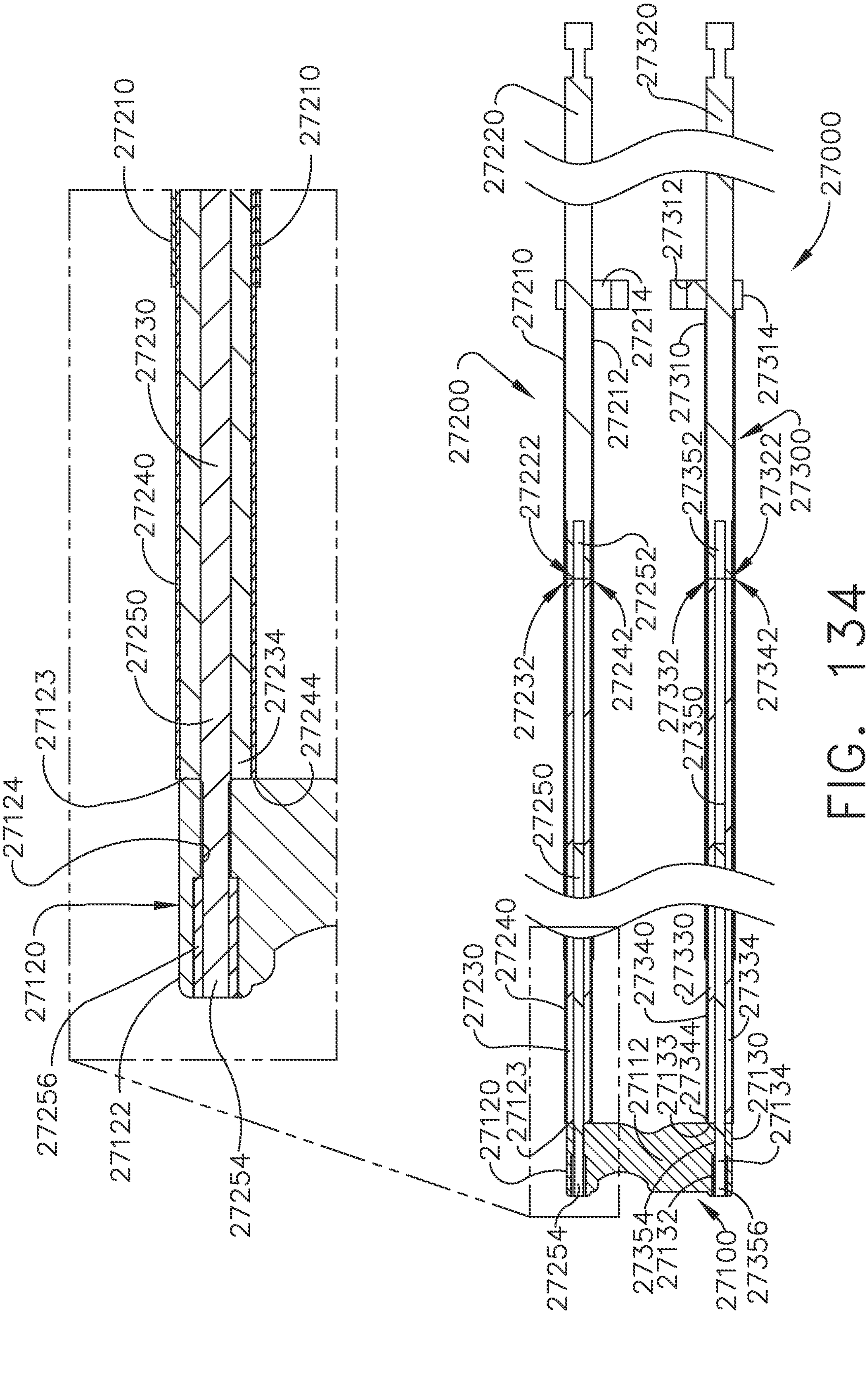
Figure 135:
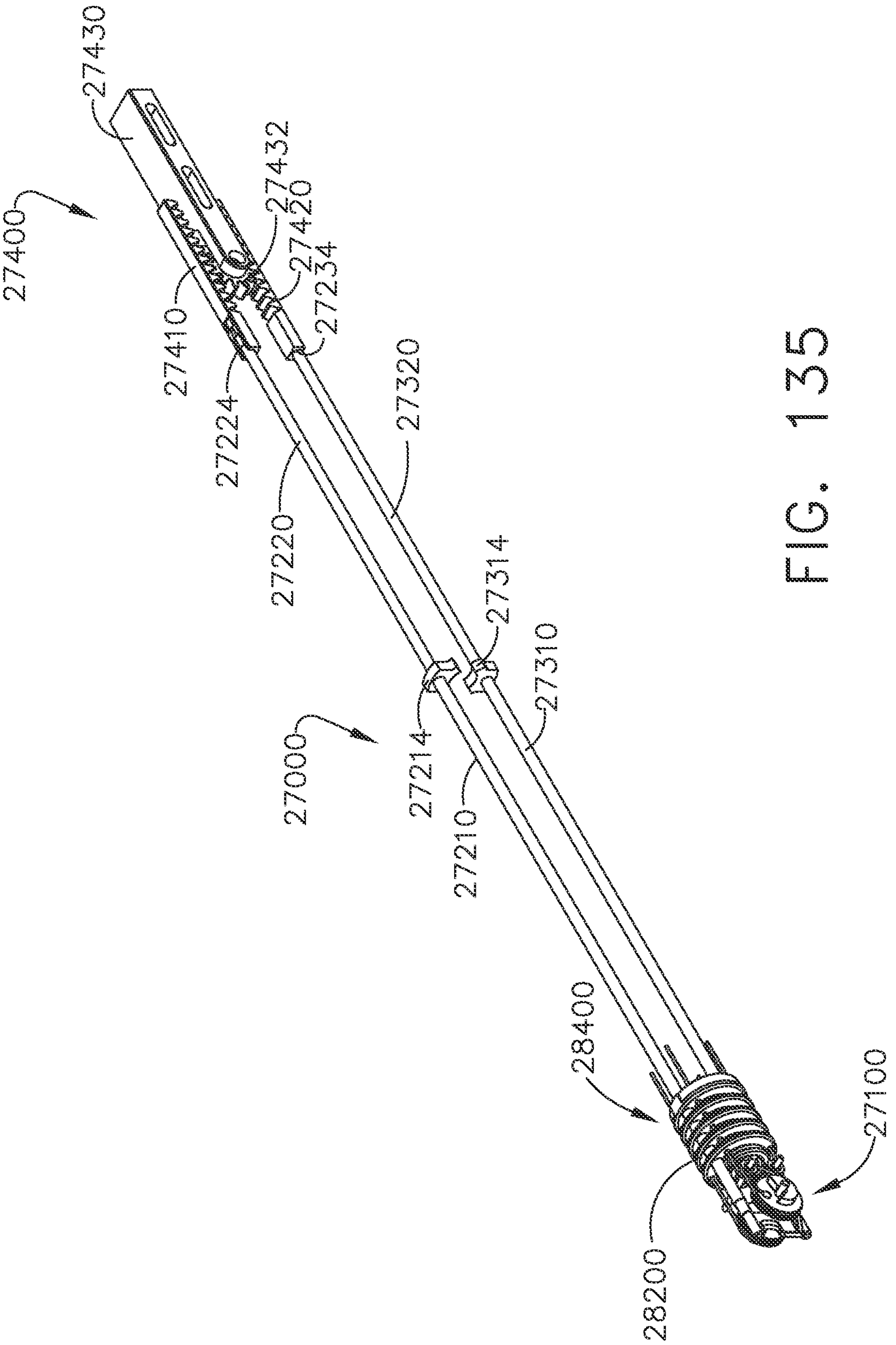
Figure 136:
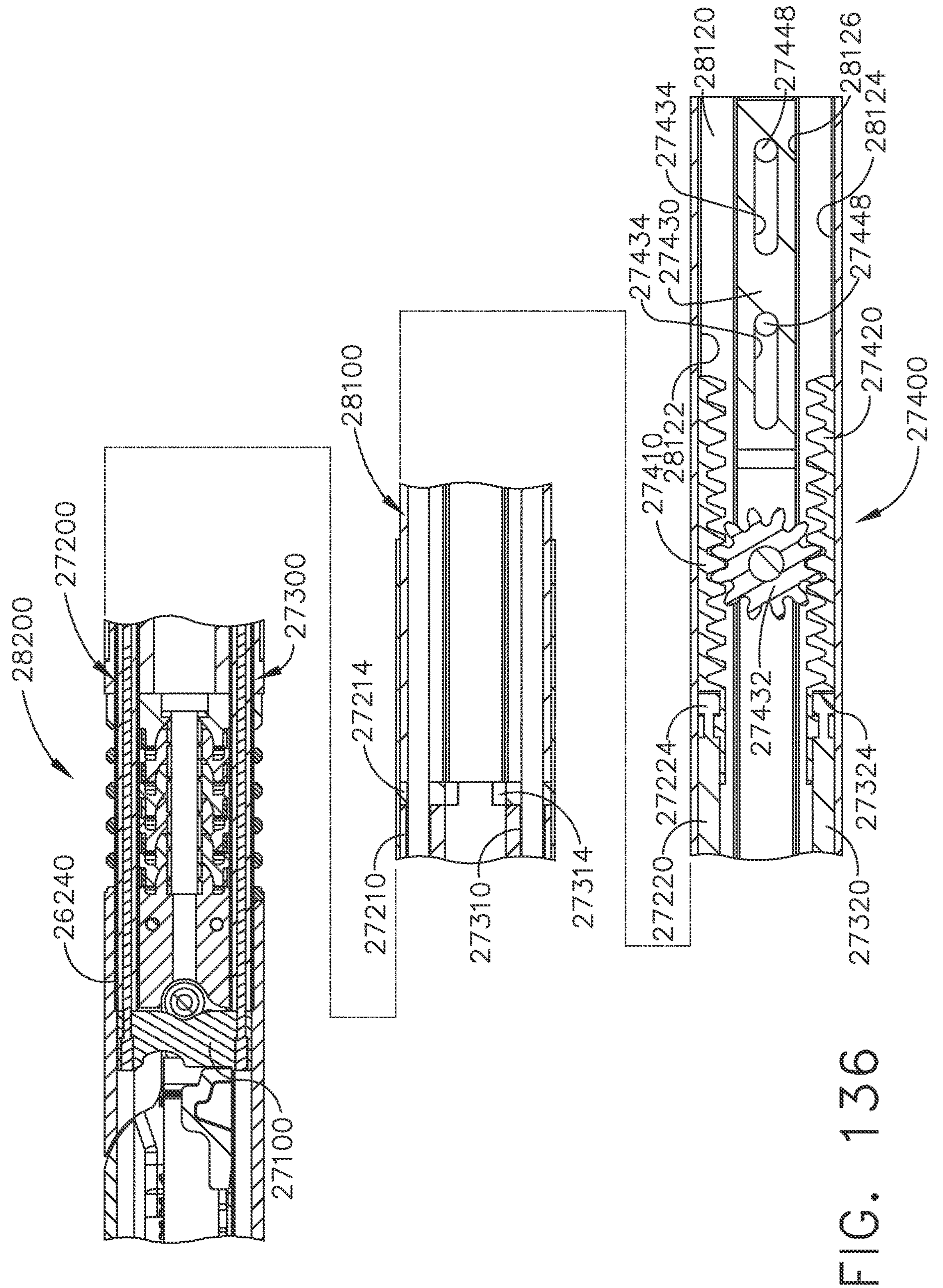
Figure 137:
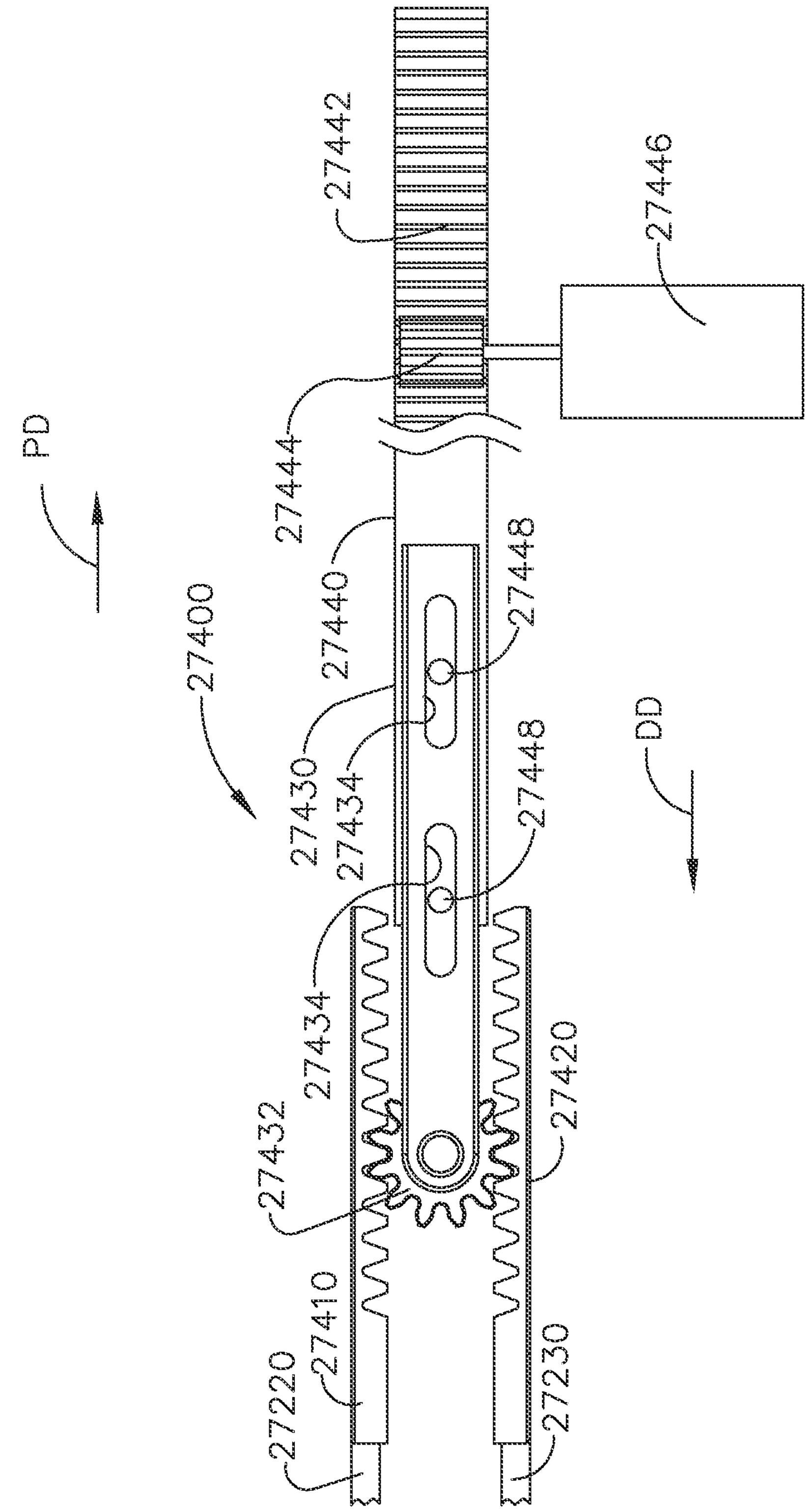
Figure 138:
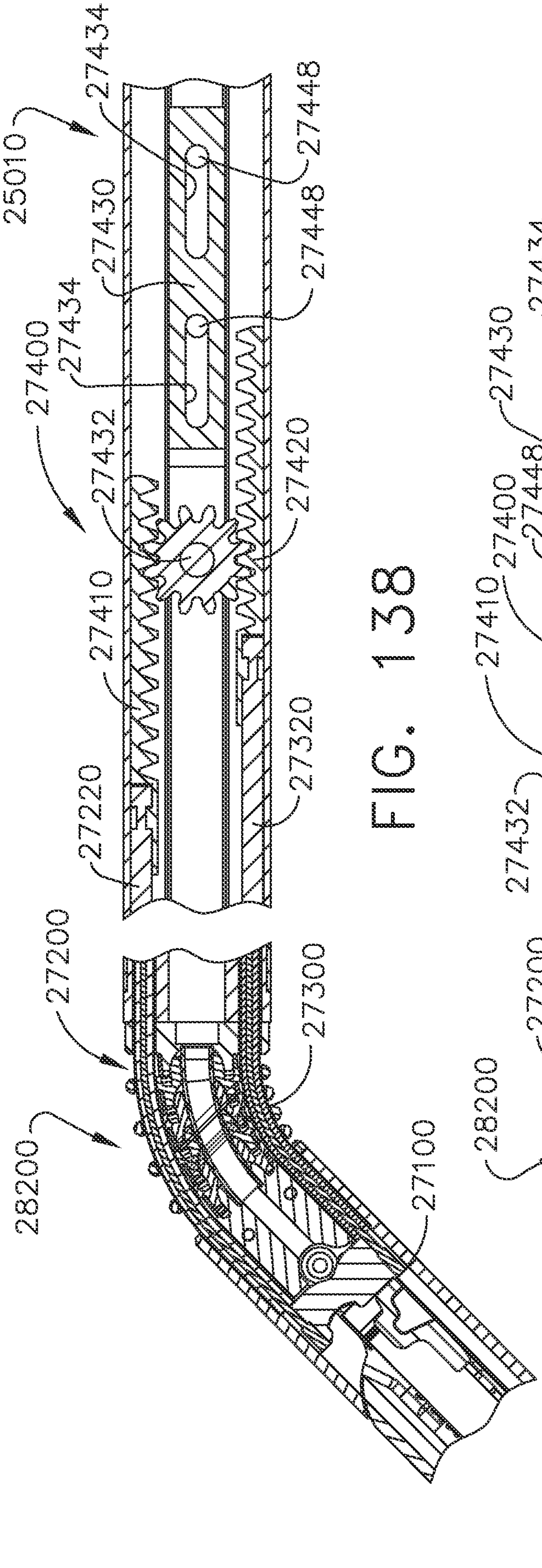
Figure 139:
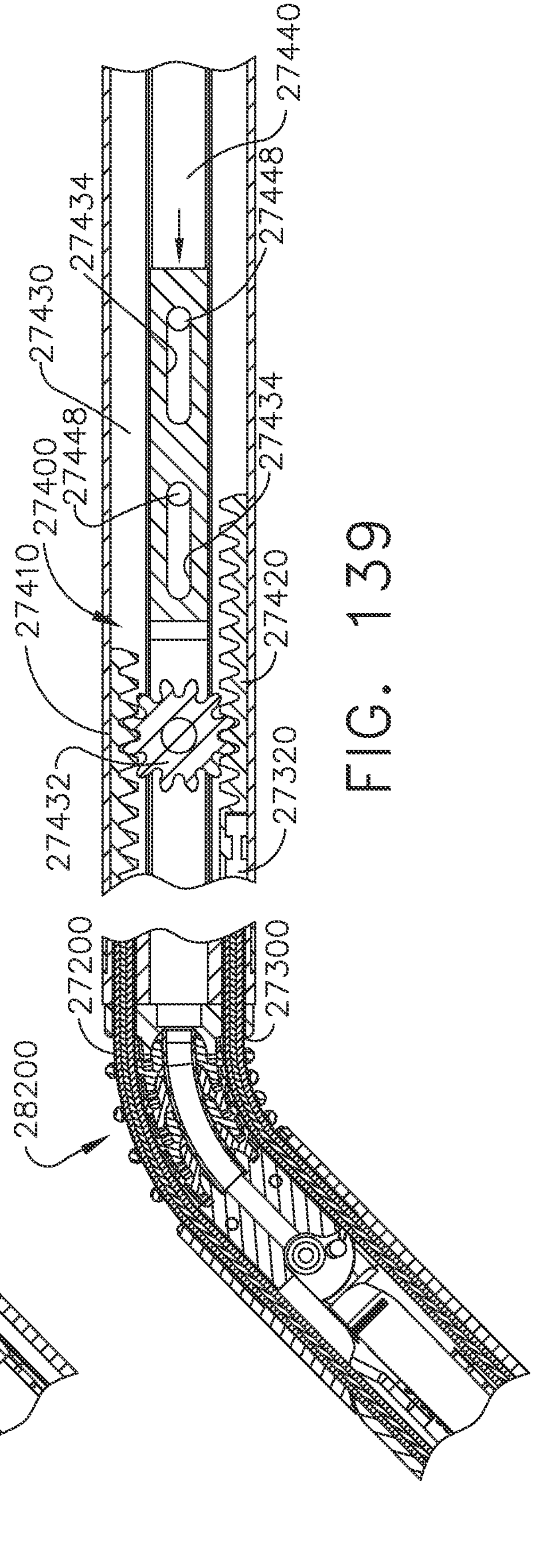
Figure 140:
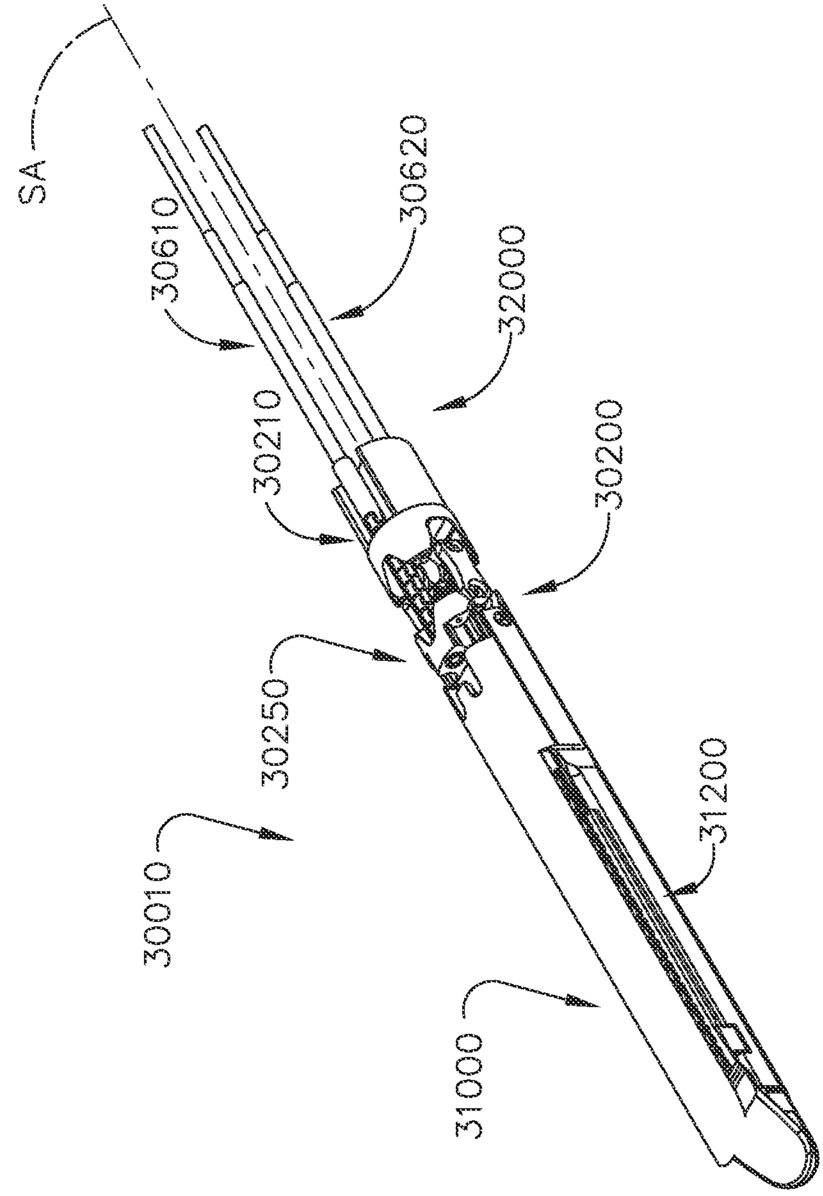
Figure 141:
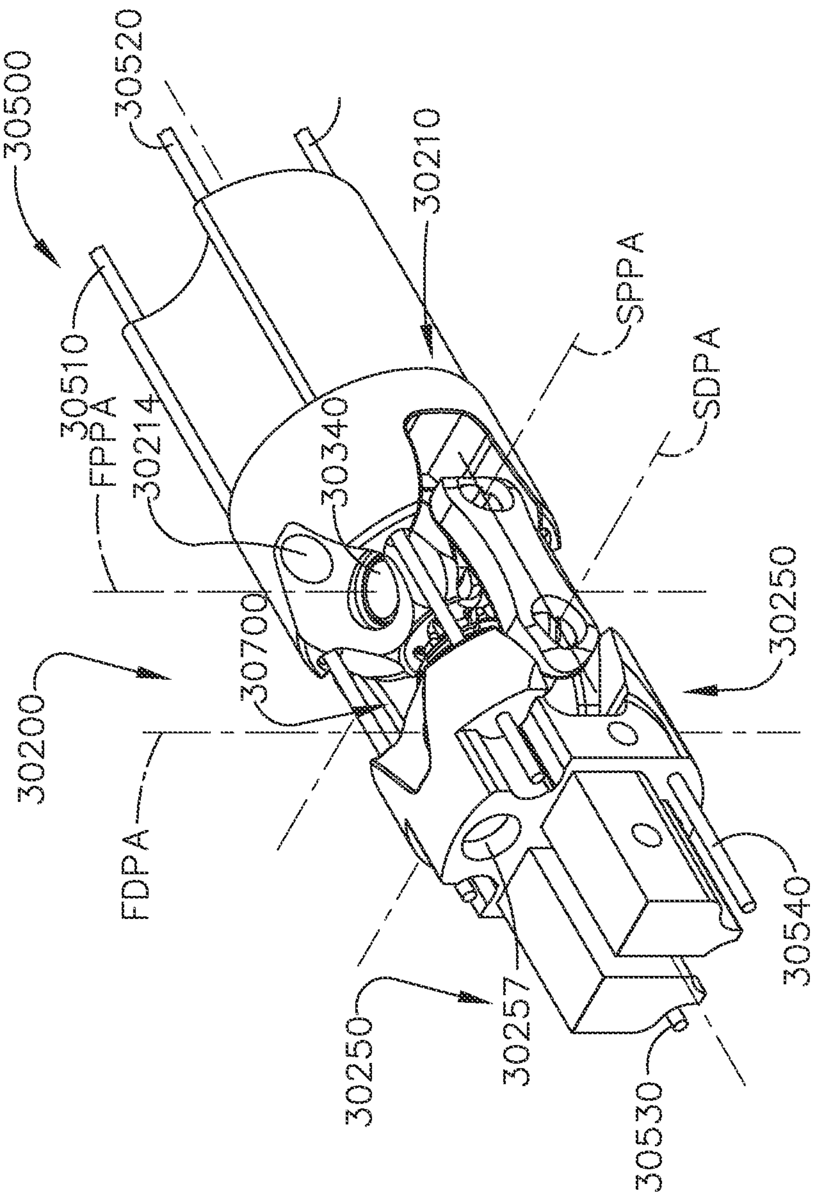
Figure 142:
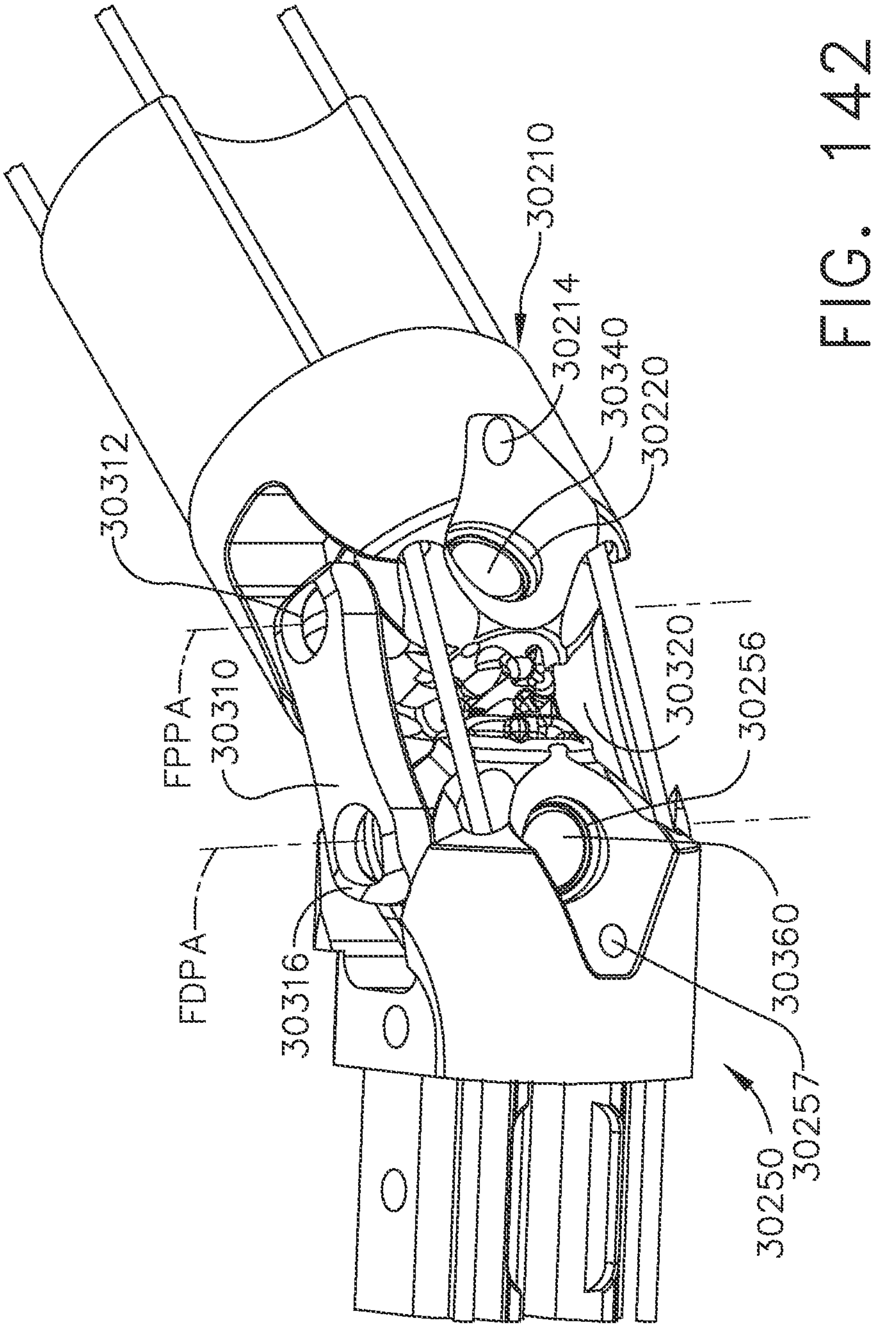
Figure 143:
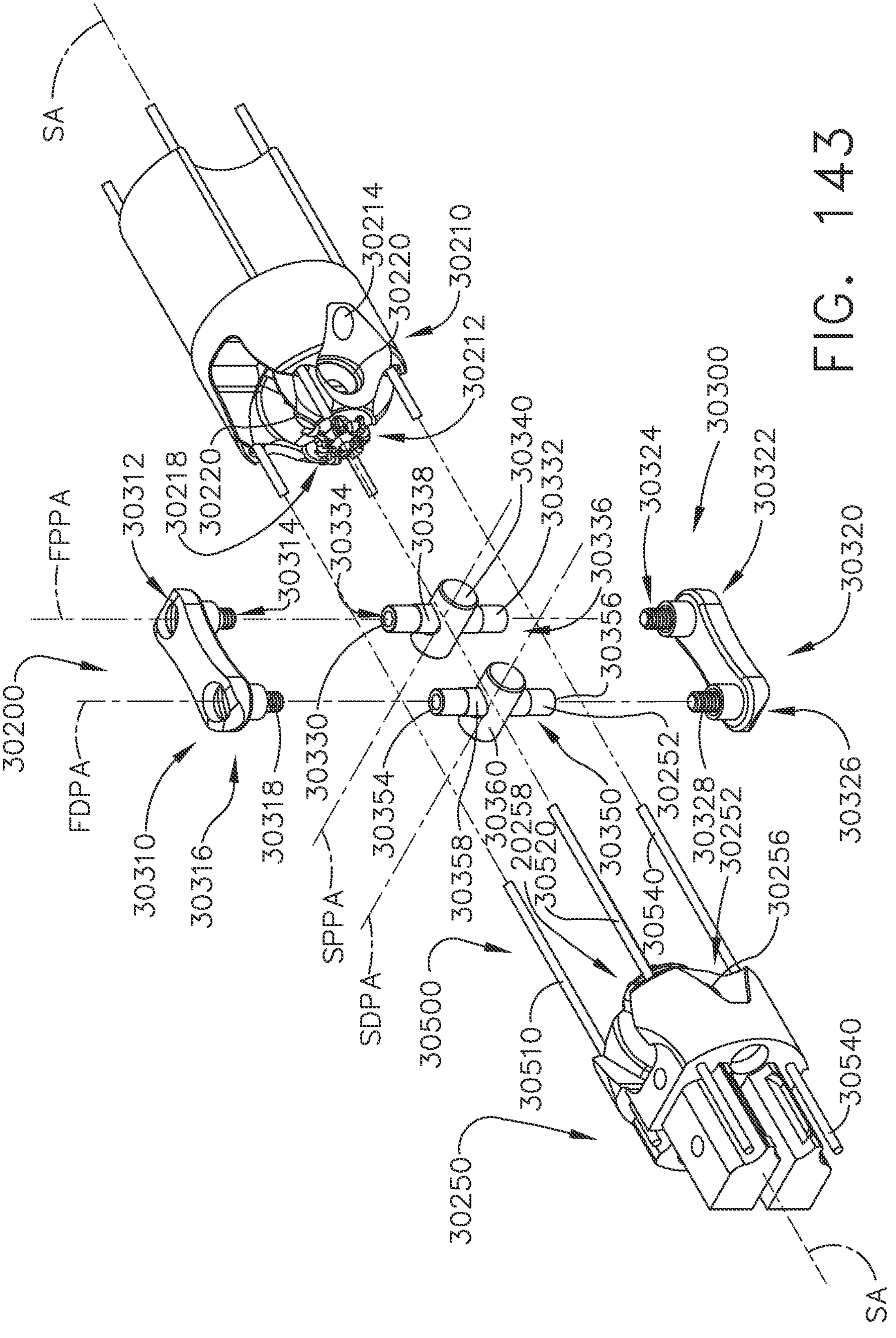
Figure 144:
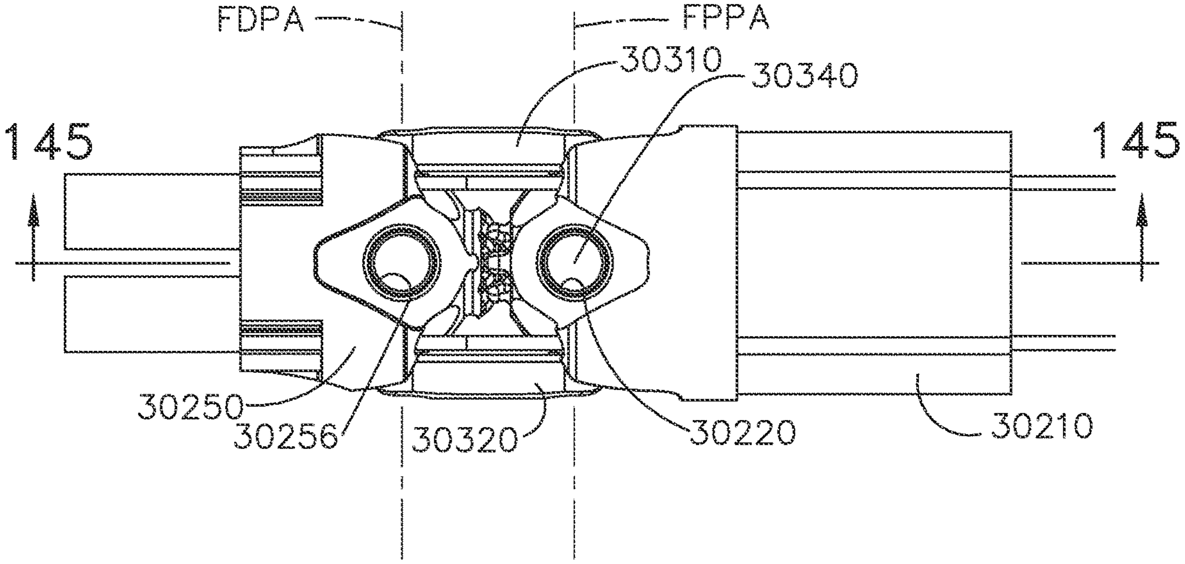
Figure 145:
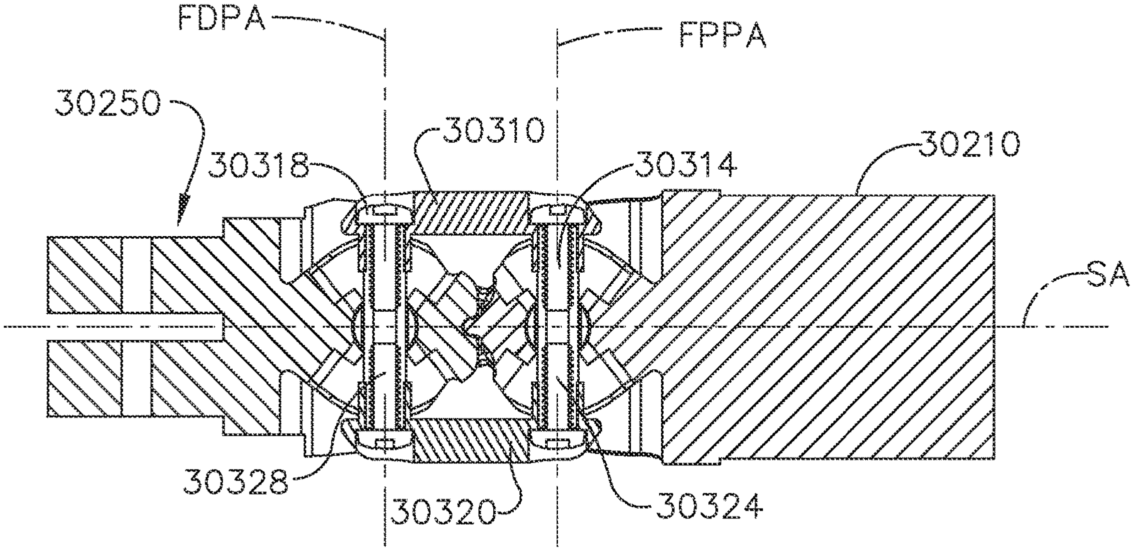
Figure 146:
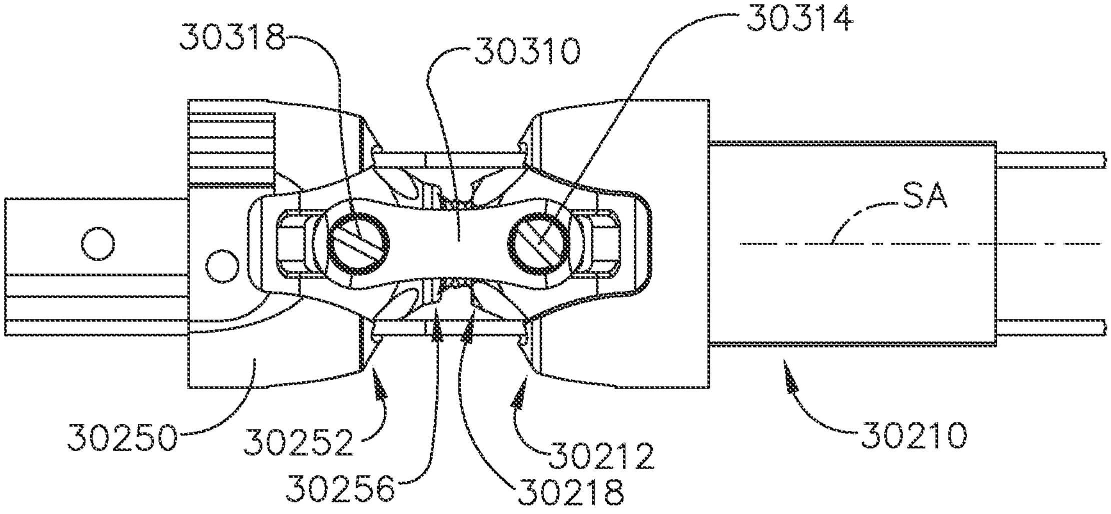
Figure 147:
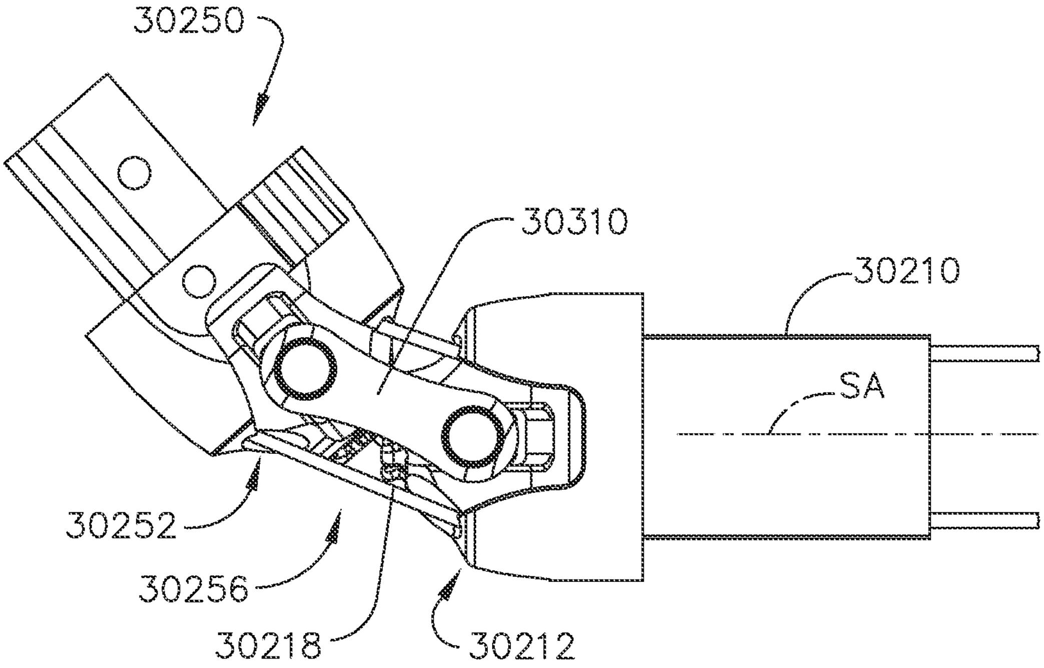
Figure 148:
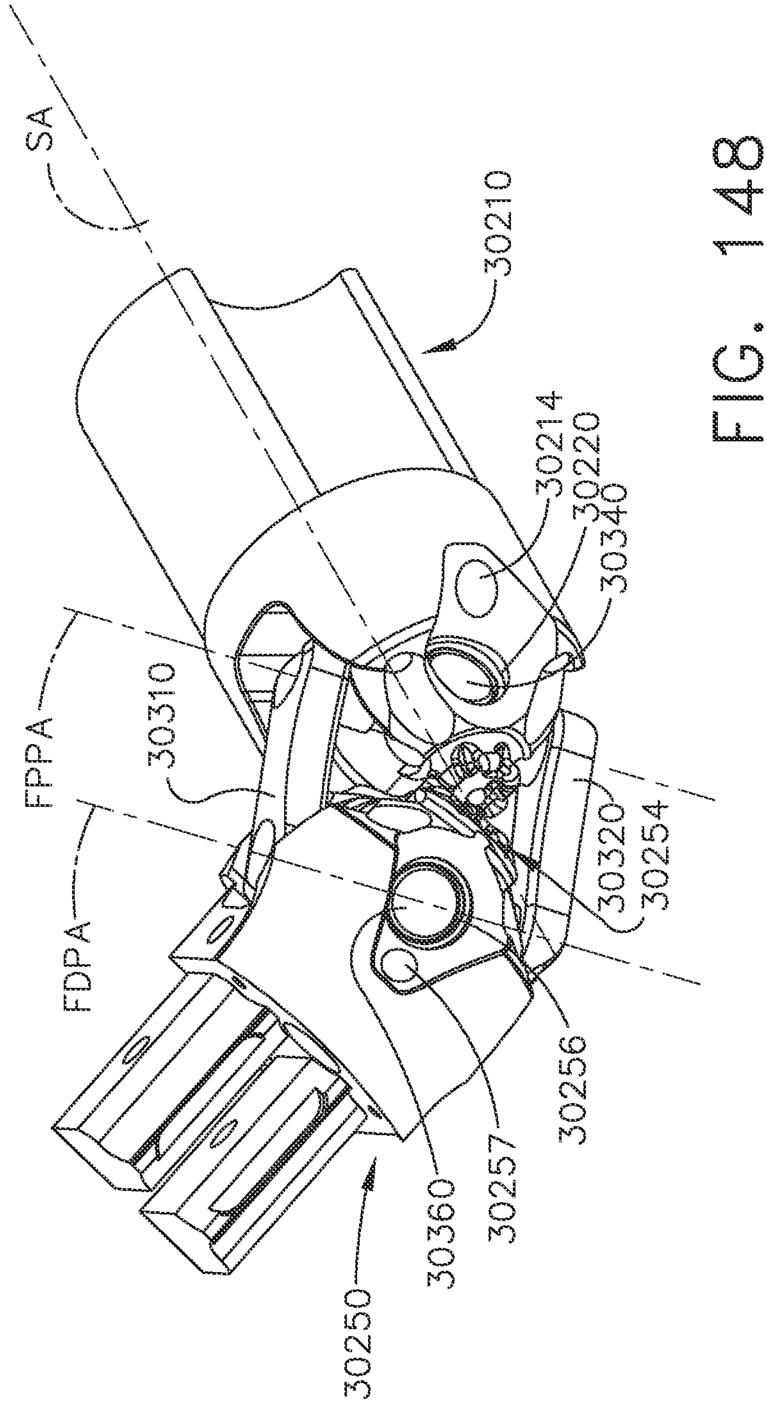
Figure 149:
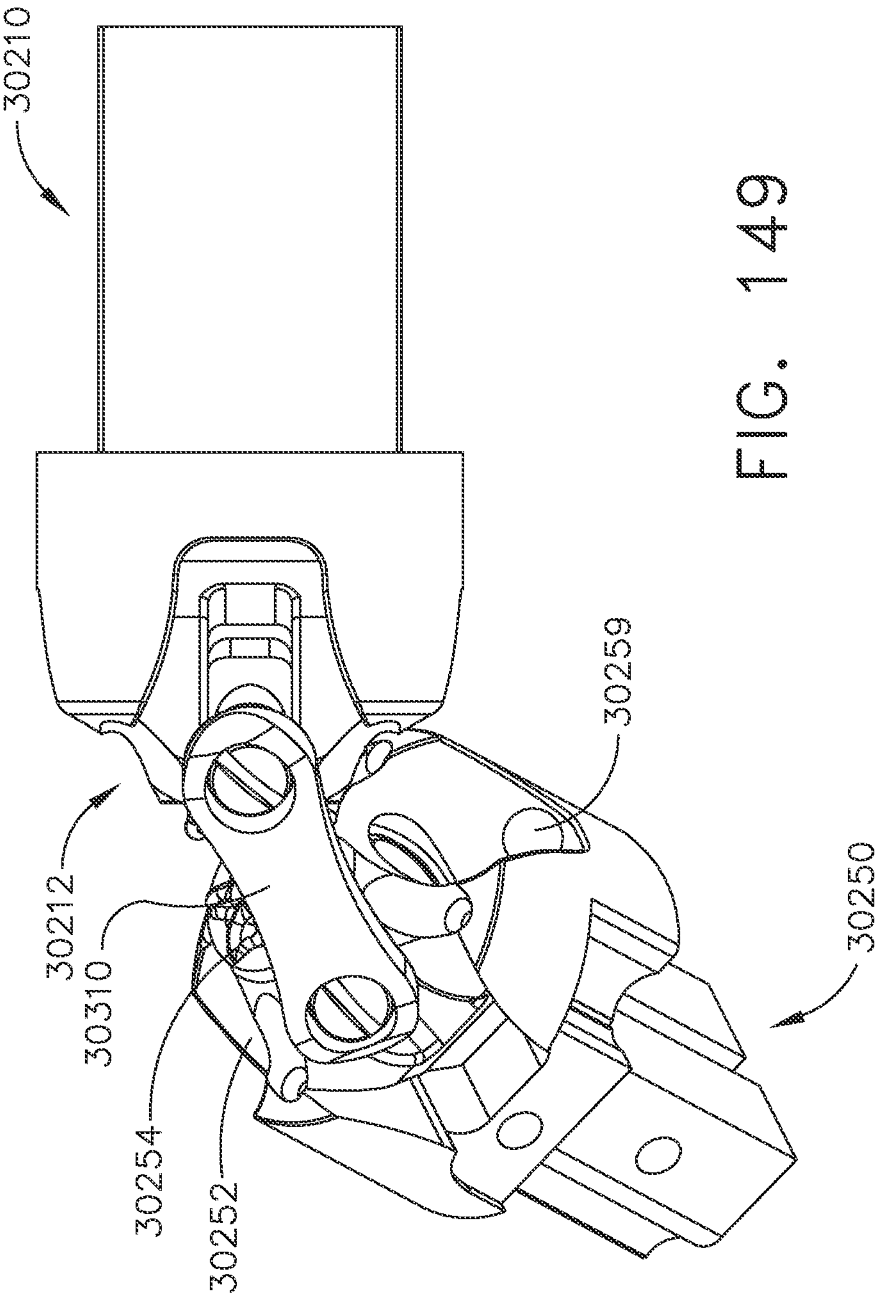
Figure 151:
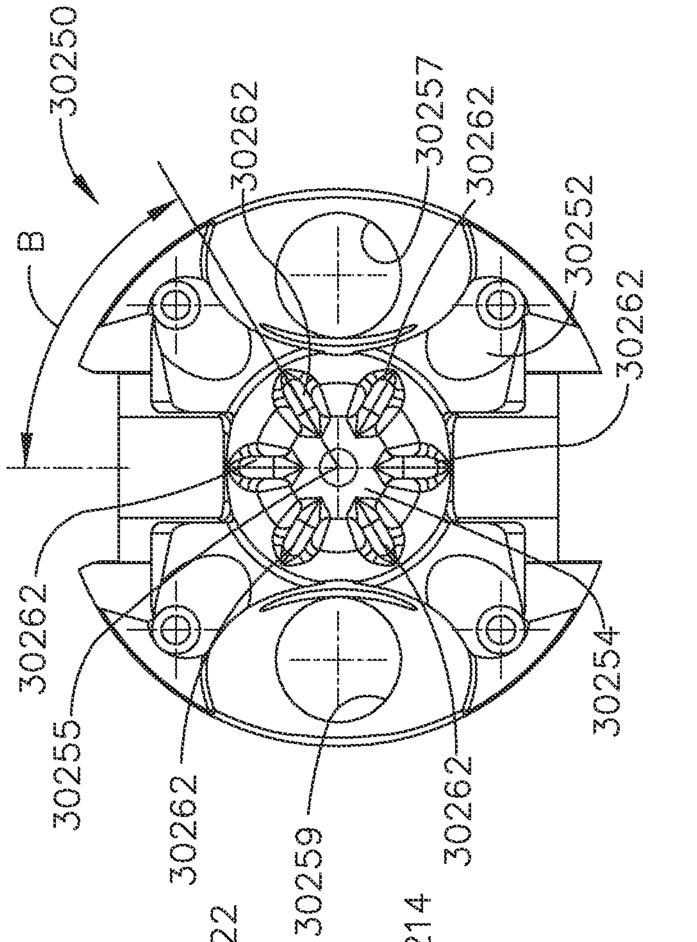
Figure 150:
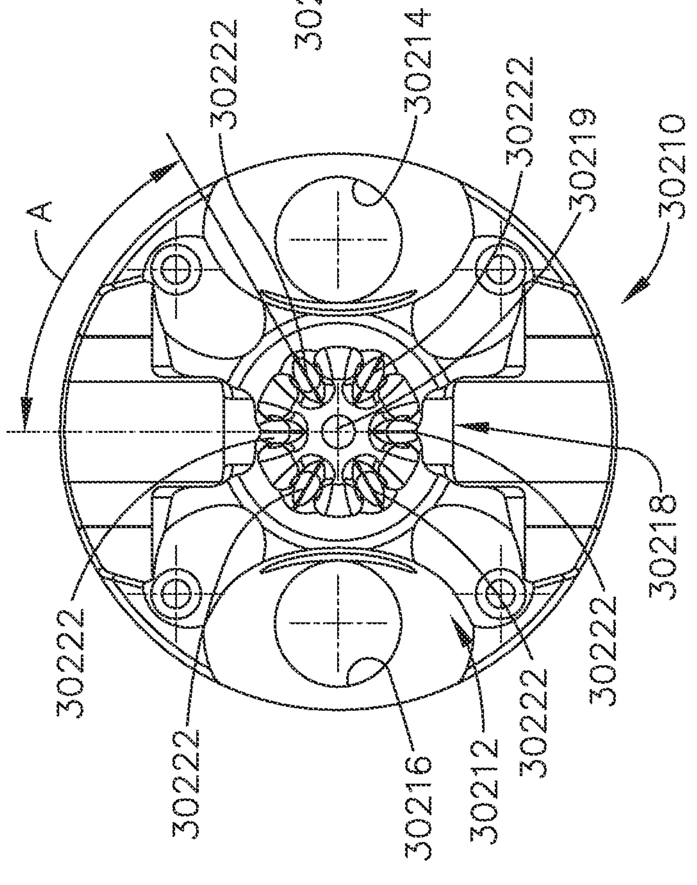
Figure 152:
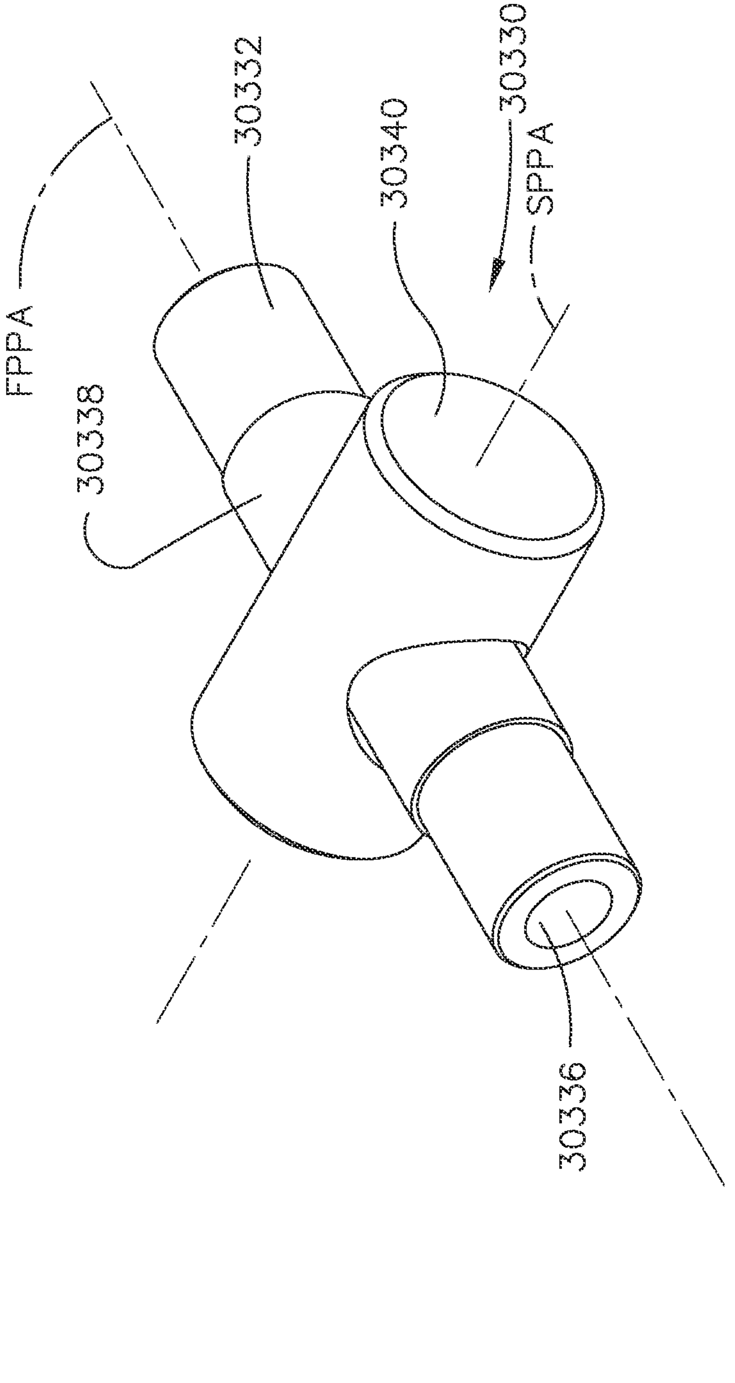
Figure 153:
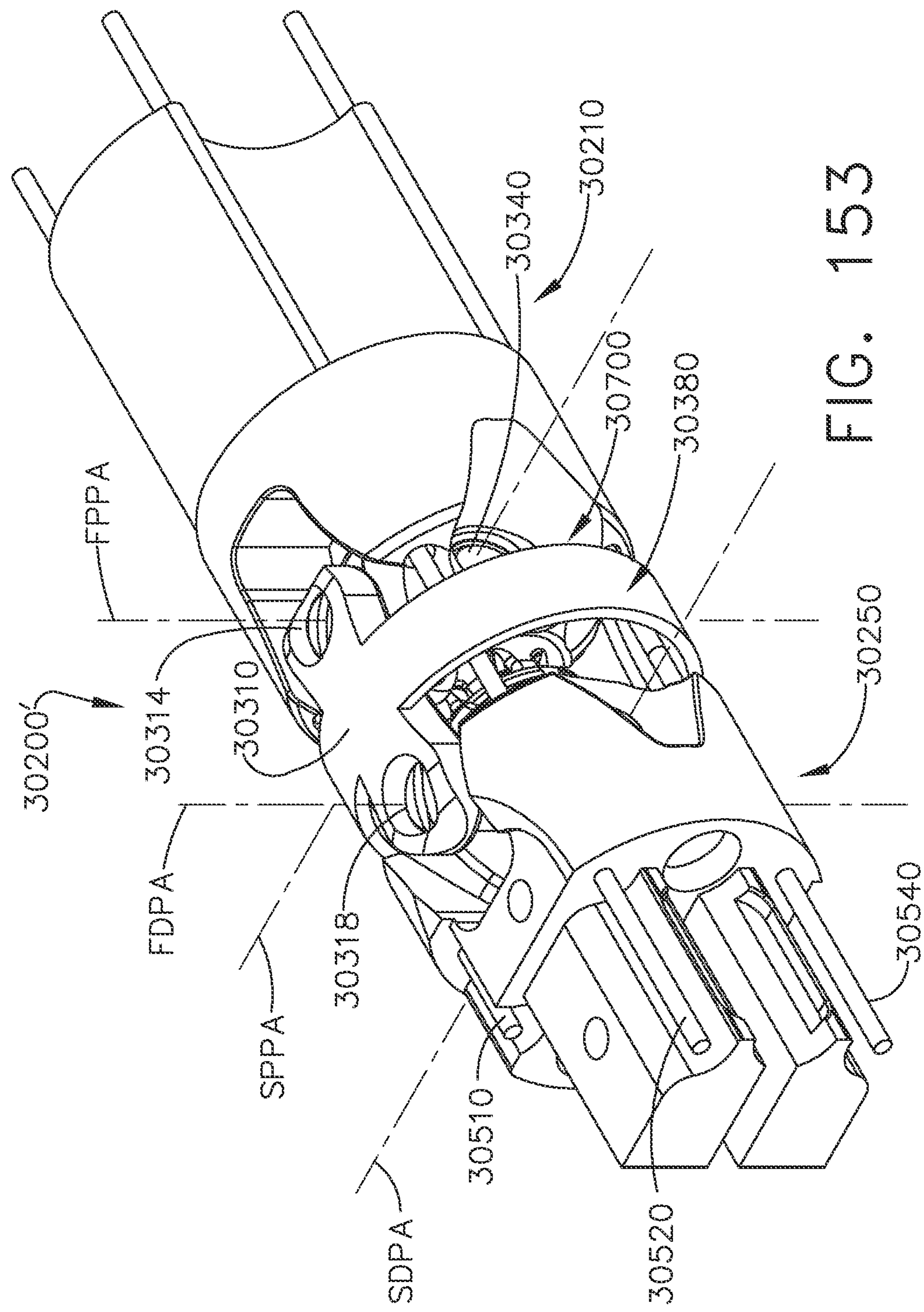
Figure 154:
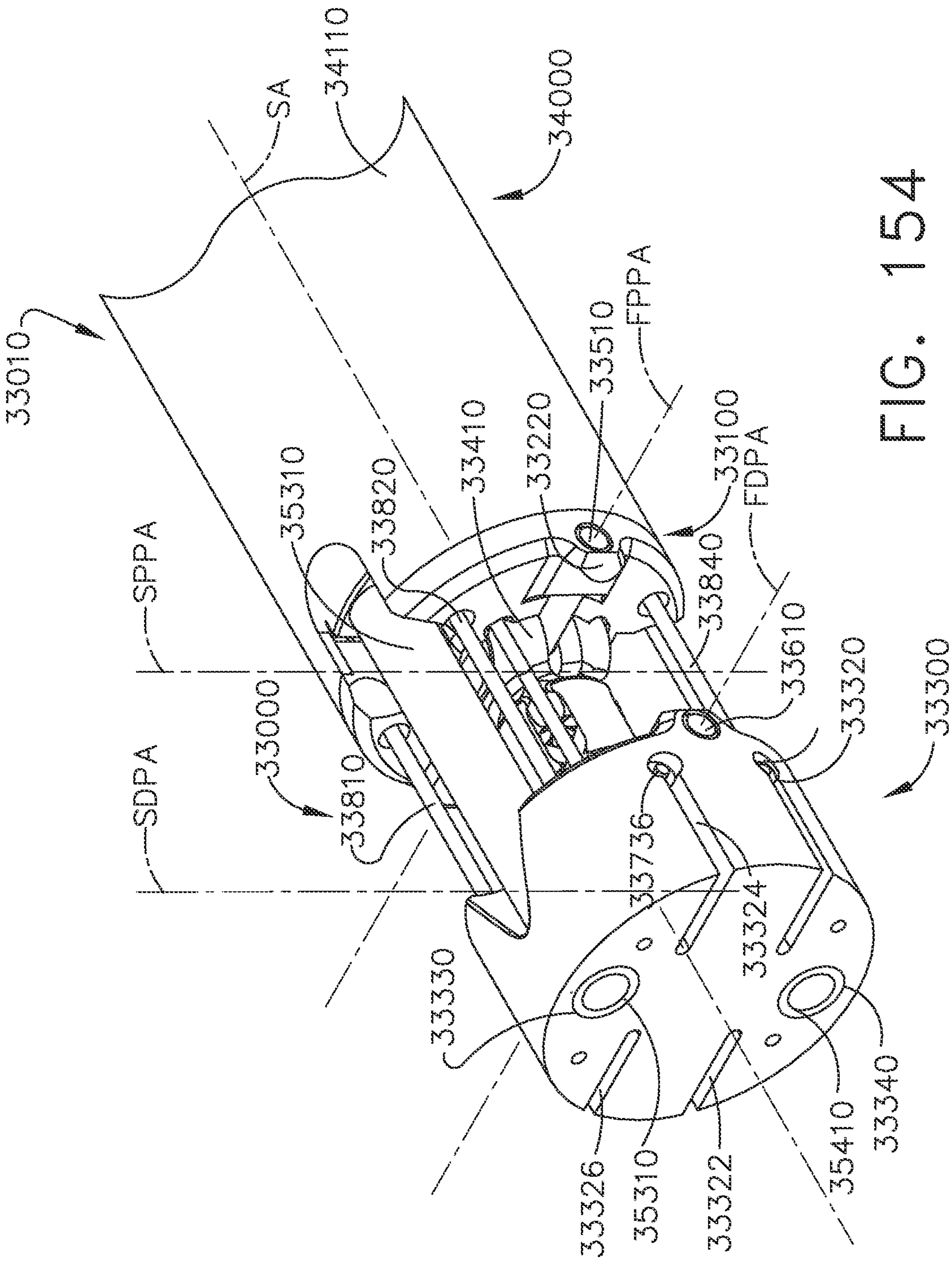
Figure 155:
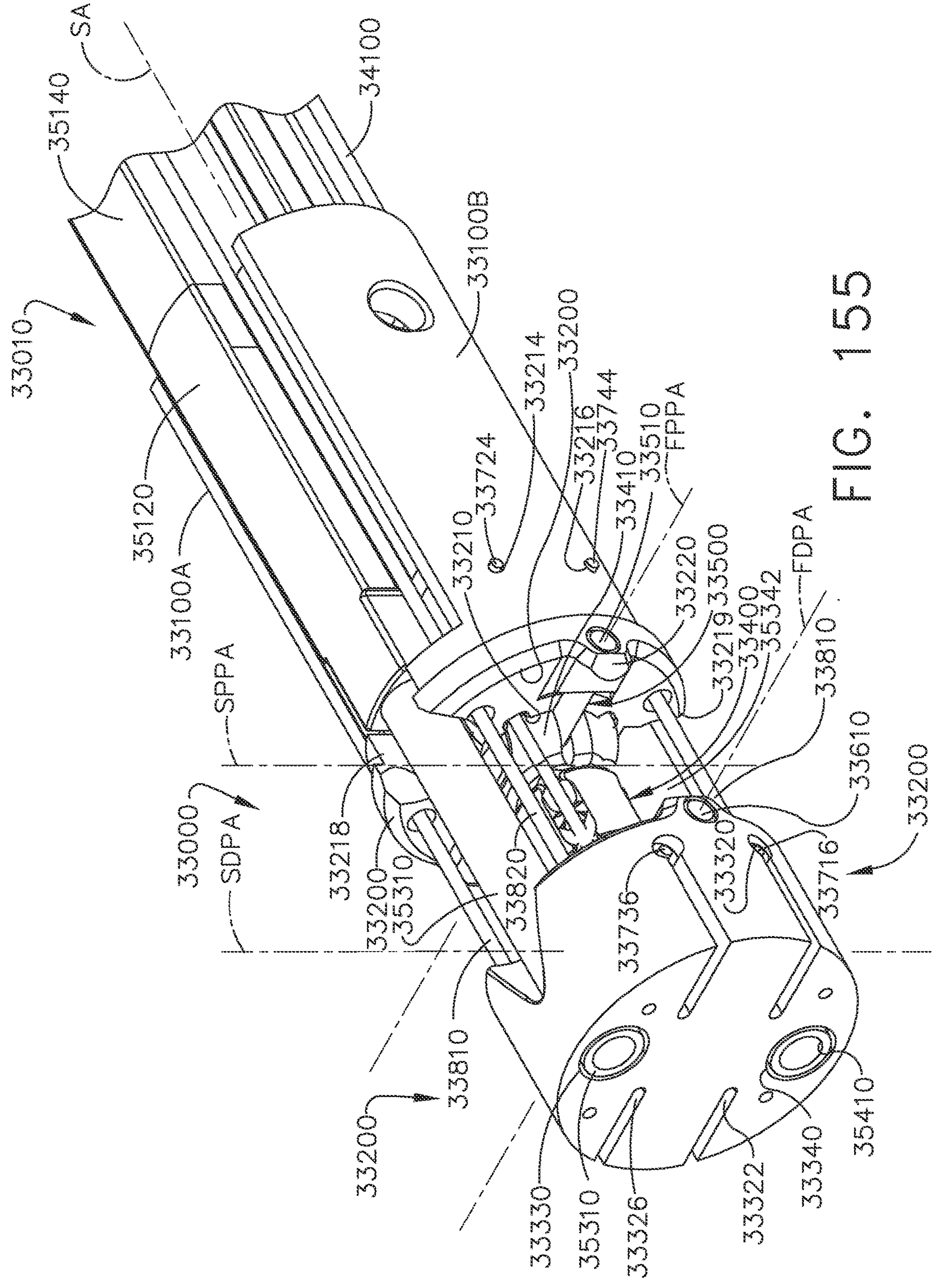
Figure 156:
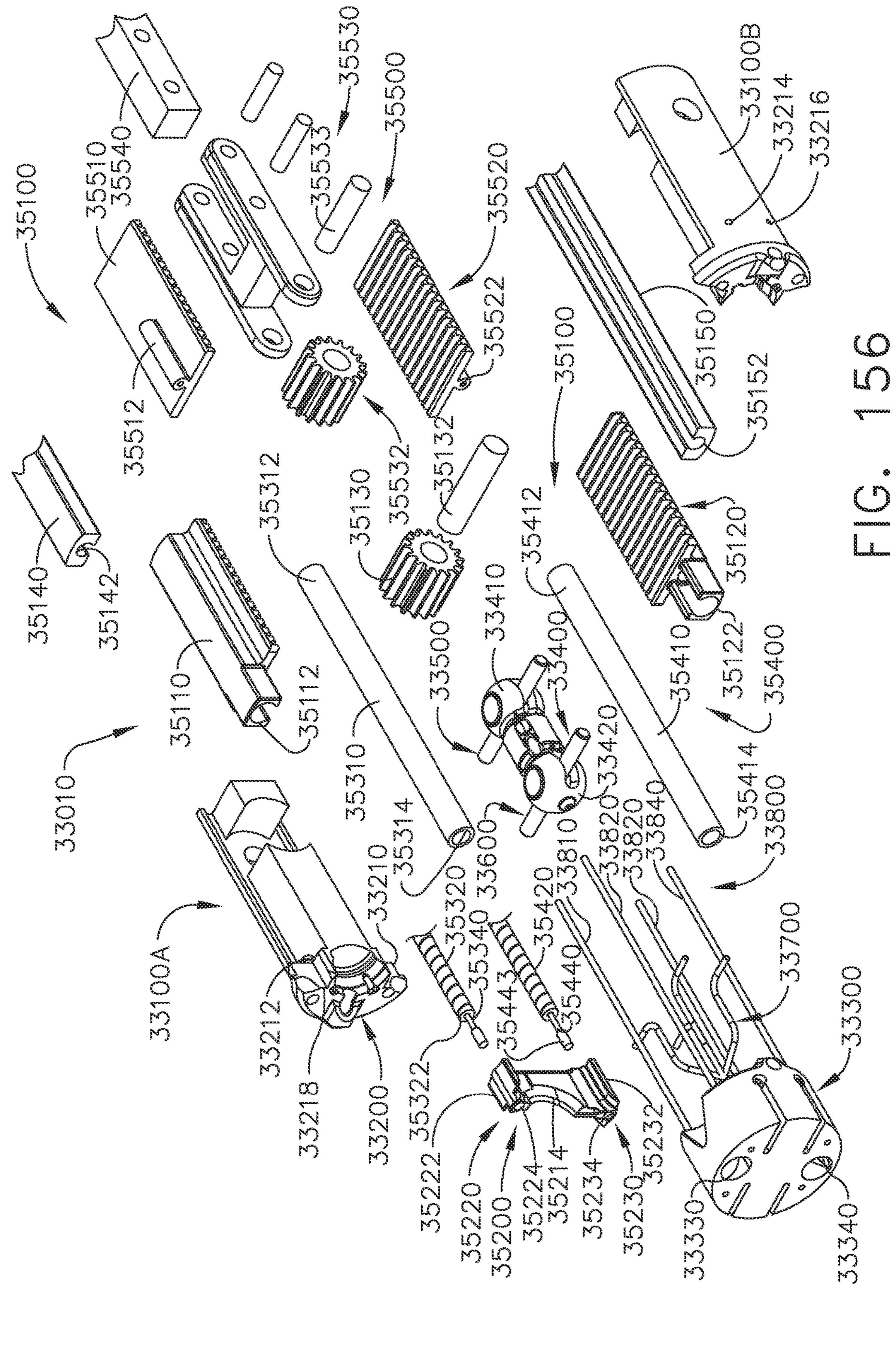
Figure 157:
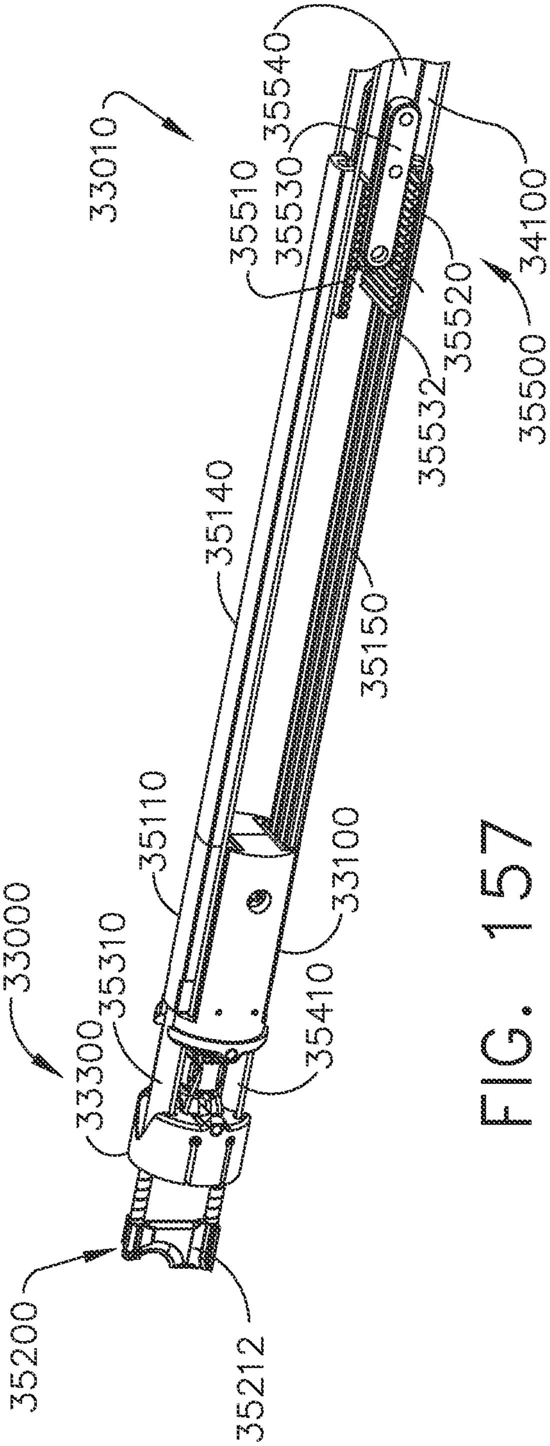
Figure 158:
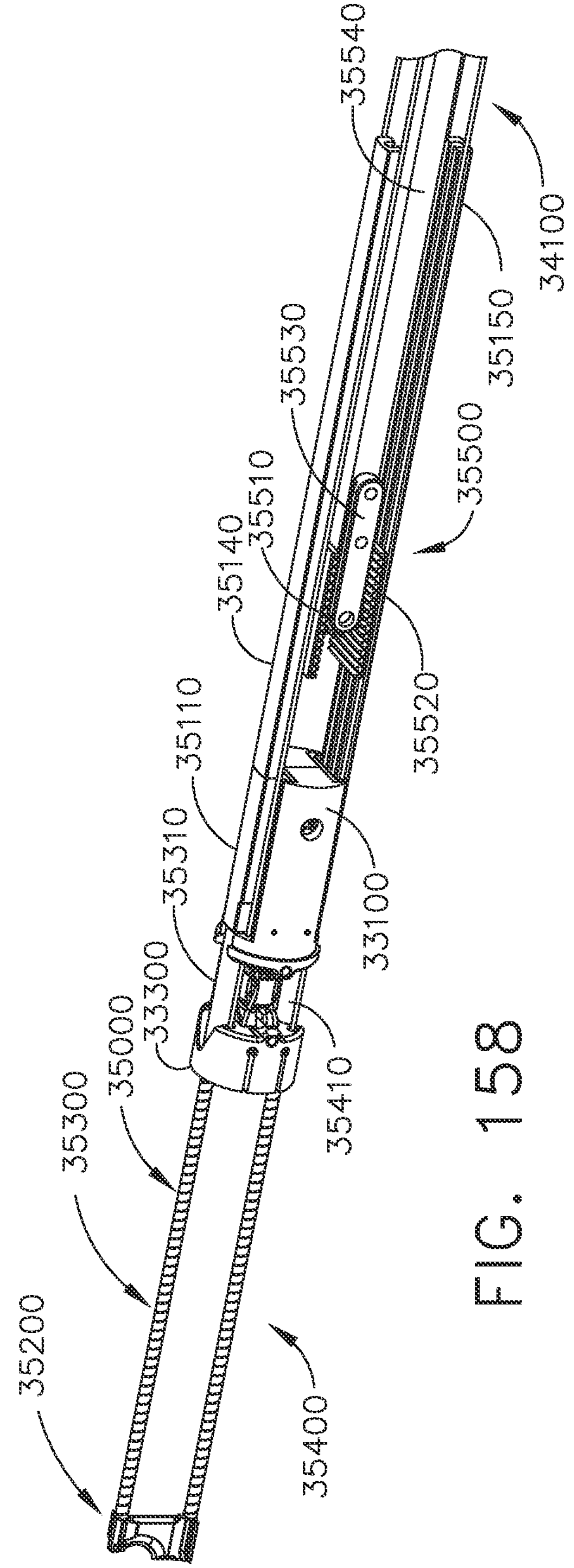
Figure 159:
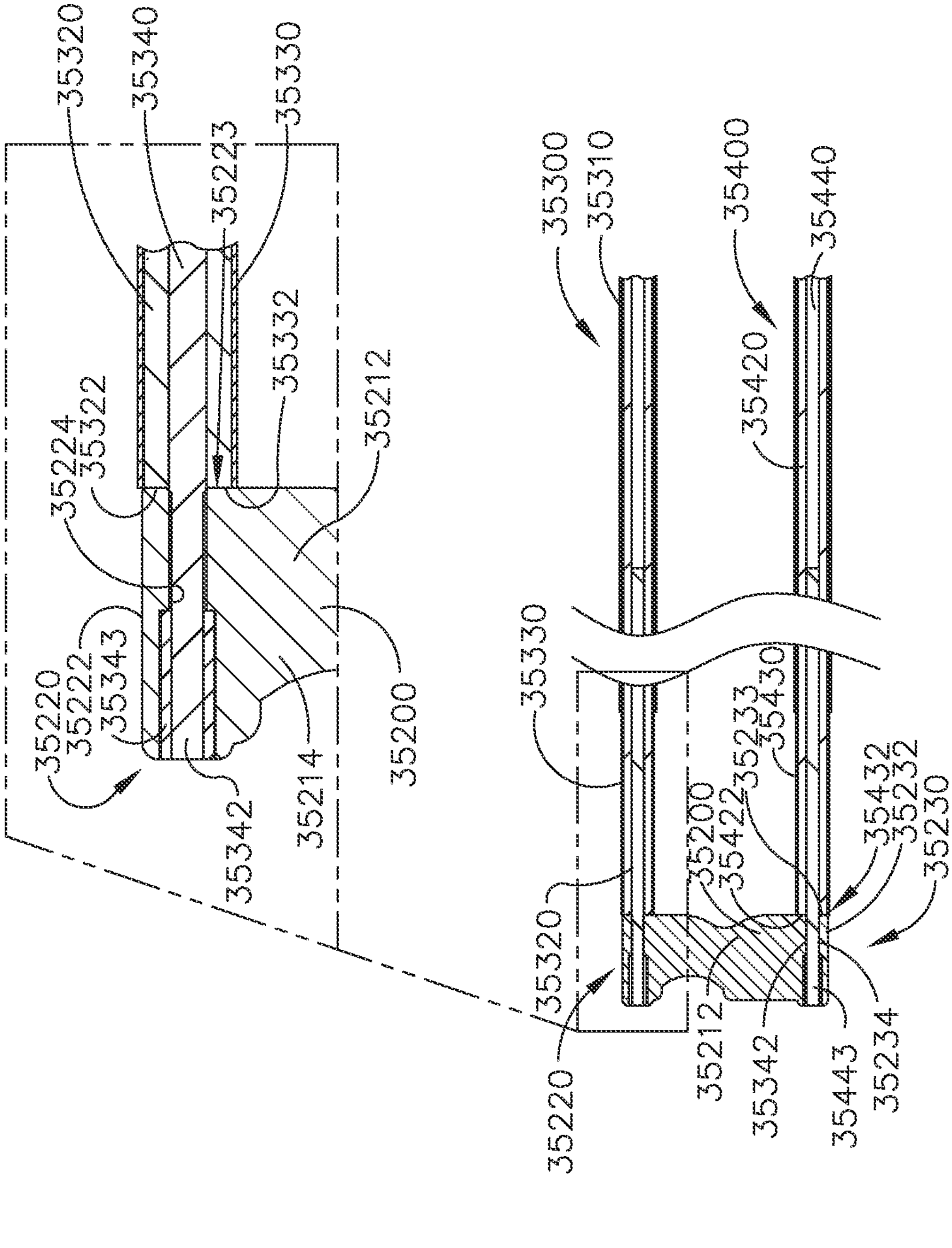
Figure 160:
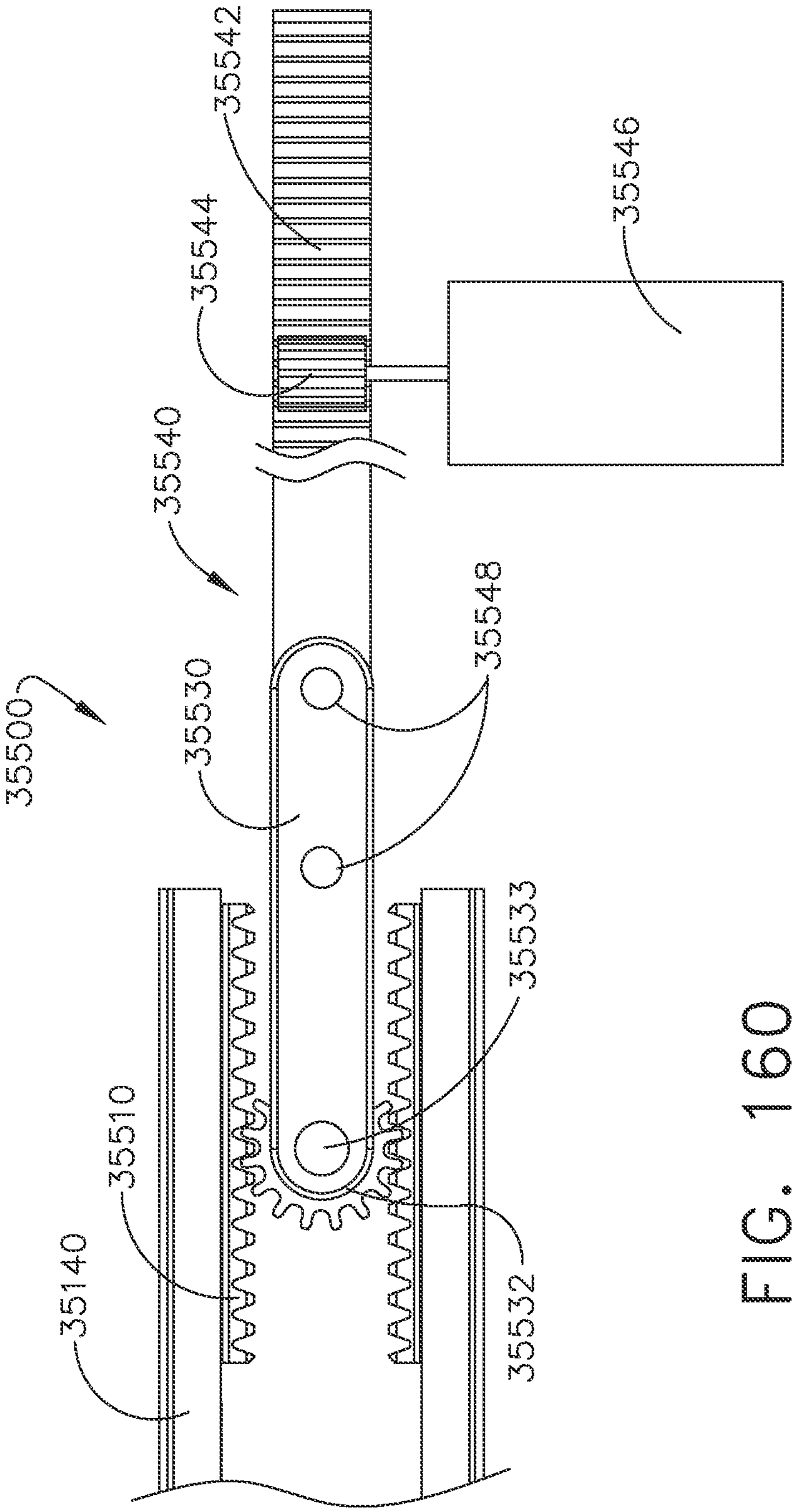
Figure 161:
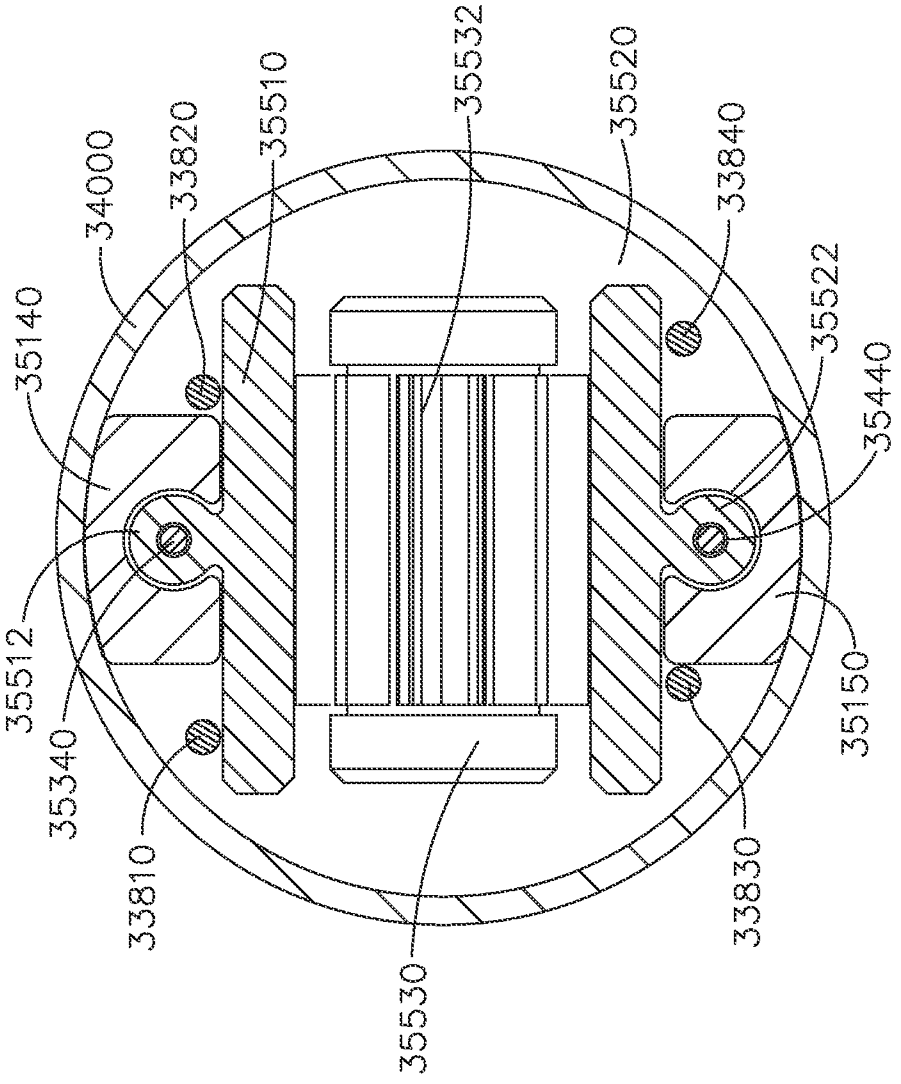
Figure 162:
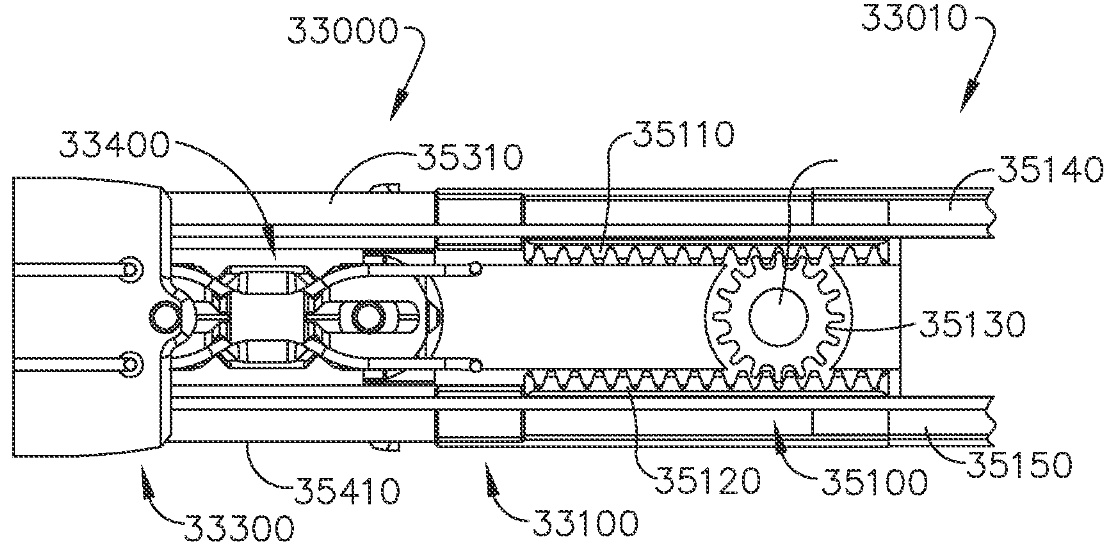
Figure 163:
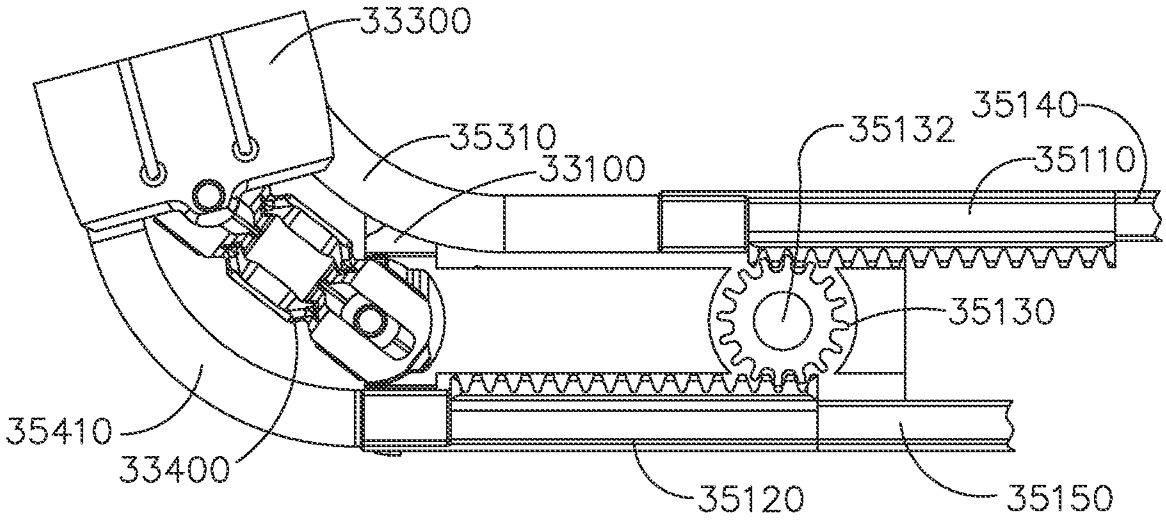
Figure 164:
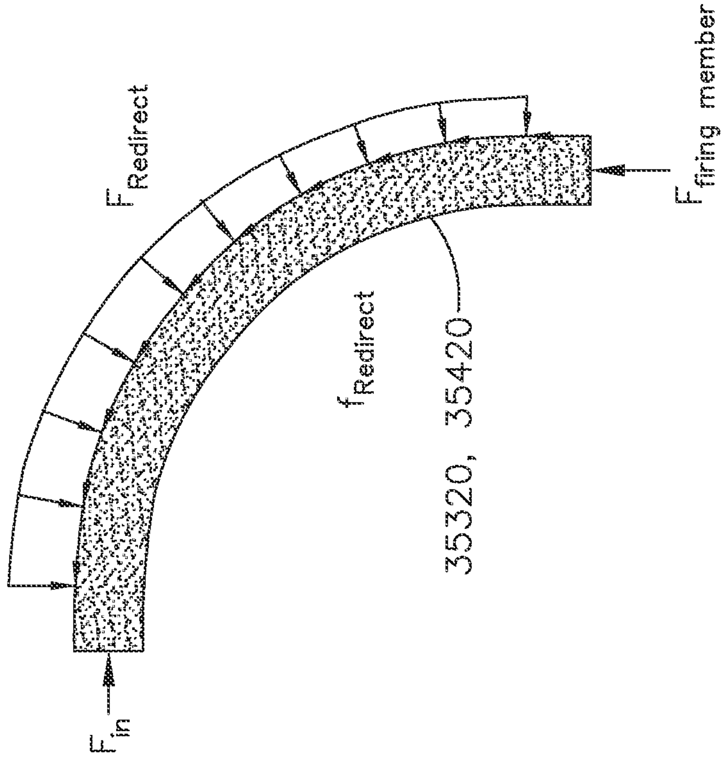
Figure 165:
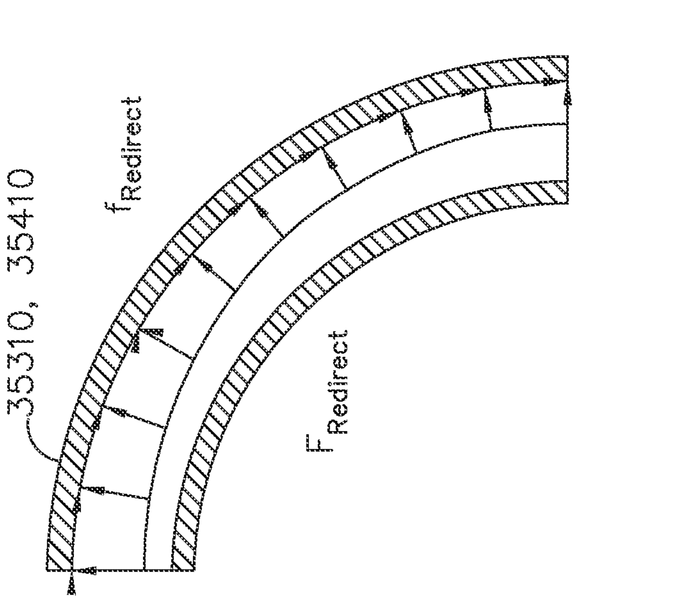
Figure 166:
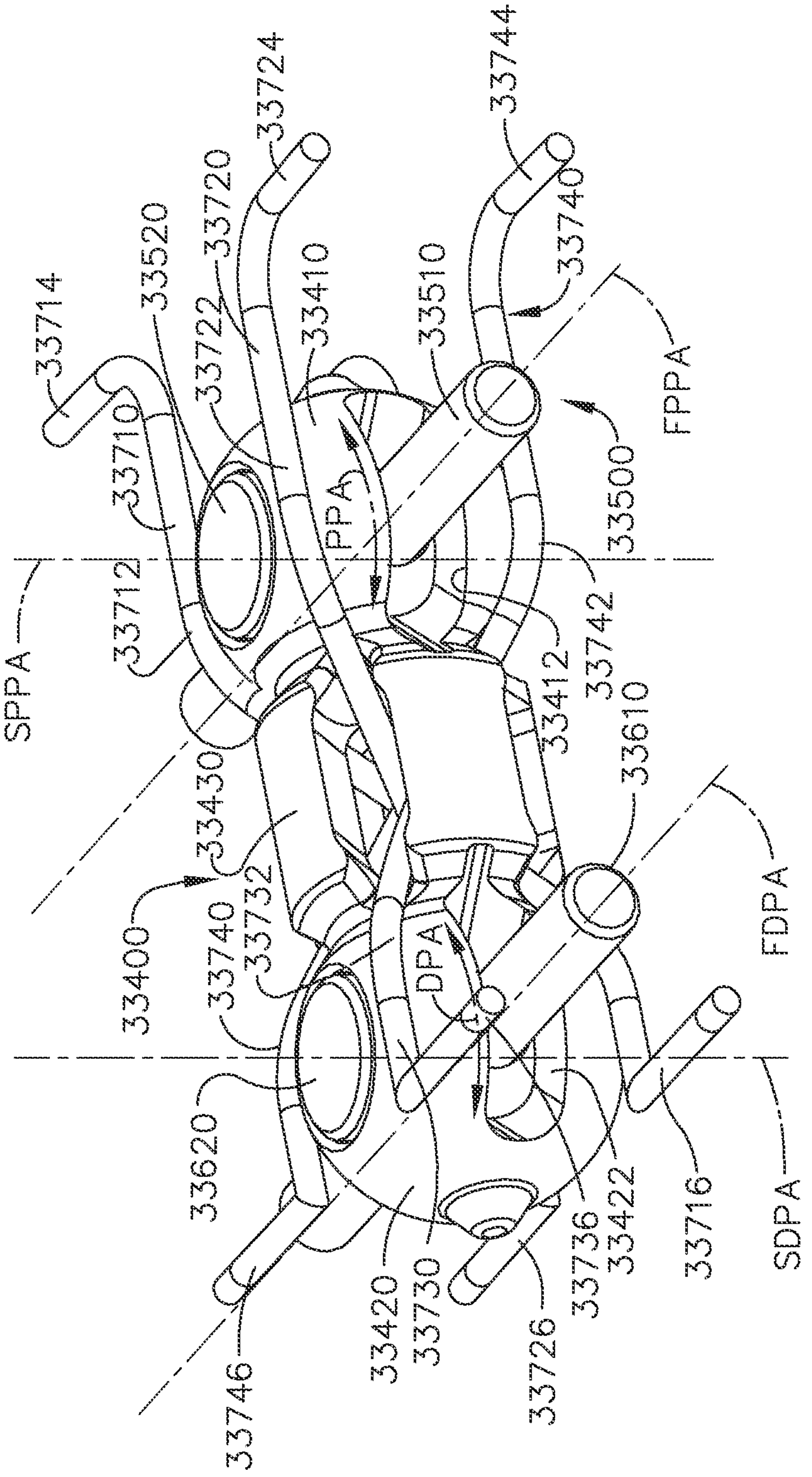
Figure 167:
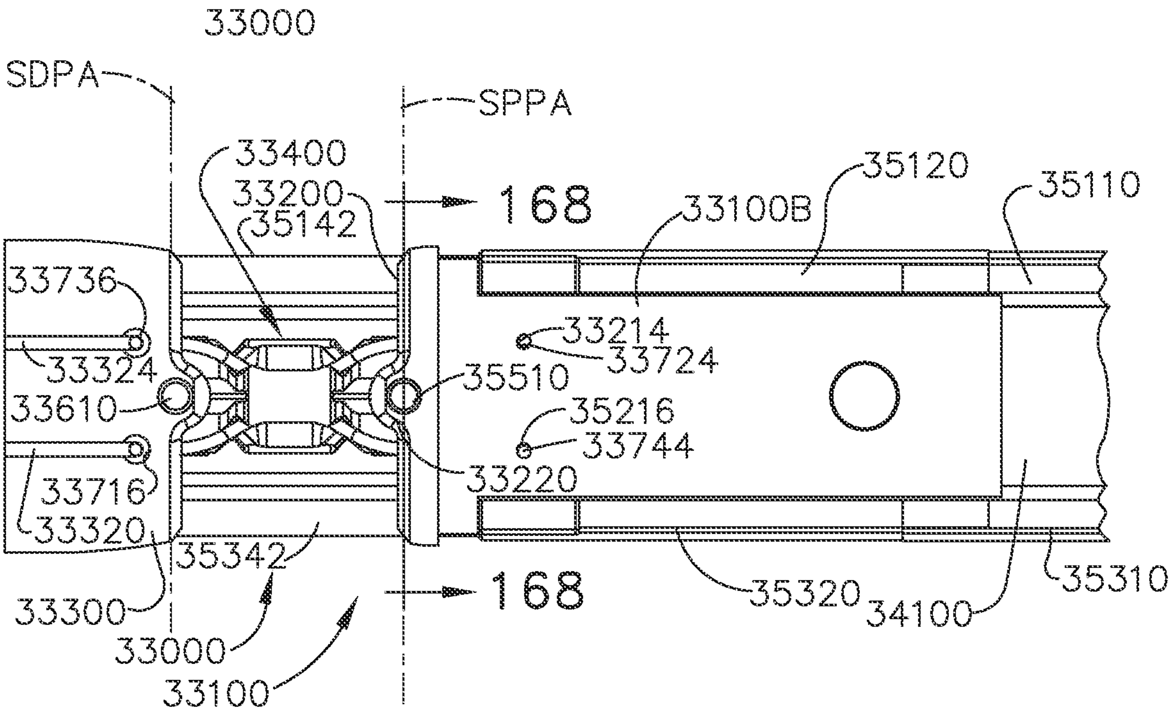
Figure 168:
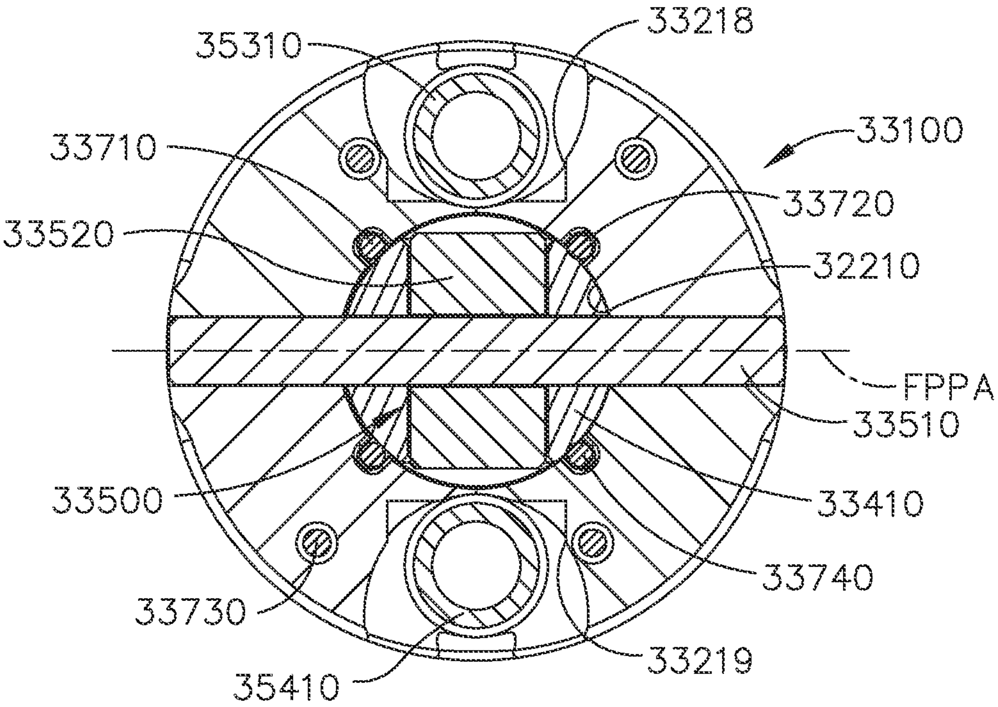
Figure 169:
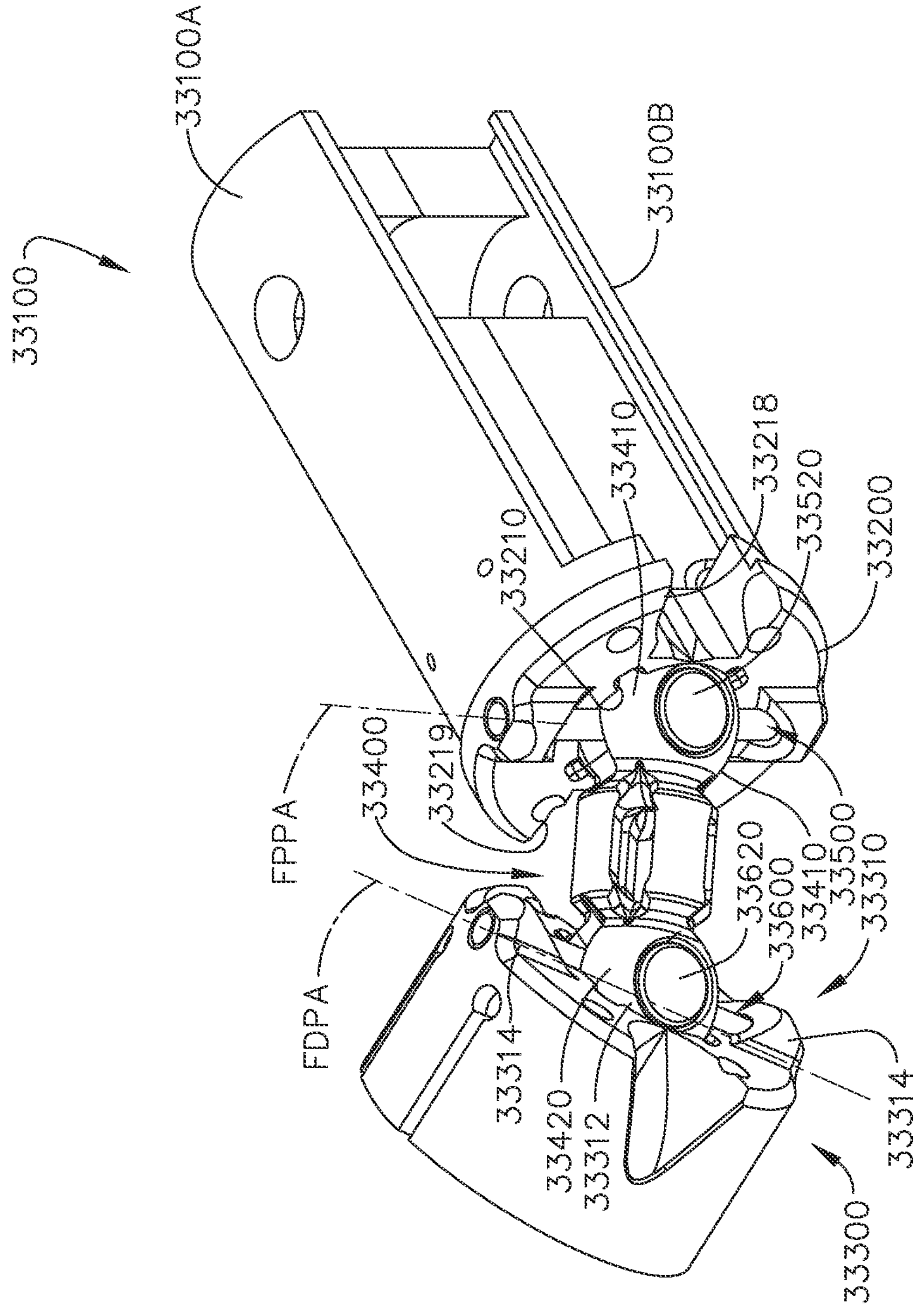

FIG. 131 is another perspective view of the pulley unit of FIG. 126 and a series of elastomeric annular spacer members of the articulation joint of the surgical instrument of FIG. 115;

FIG. 132 is another perspective view of the pulley unit, portions of a firing system and the articulation joint of the surgical instrument of FIG. 115;

FIG. 133 is a perspective view of a portion of a firing system of the surgical instrument of FIG. 115;

FIG. 134 is a partial cross-sectional view of the firing system of FIG. 133;

FIG. 135 is a perspective view of the firing system, articulation joint, and a closure system of the surgical instrument of FIG. 115;

FIG. 136 is a partial cross sectional view of the surgical instrument of FIG. 115 with the surgical end effector thereof in an unarticulated position;

FIG. 137 is a partial view of a differential drive assembly embodiment of the firing system of the surgical instrument of FIG. 115;

FIG. 138 is another partial cross sectional view of the surgical instrument of FIG. 115 with the surgical end effector thereof in an articulated position;

FIG. 139 is another partial cross sectional view of the surgical instrument of FIG. 115 with the surgical end effector thereof in an articulated position;

FIG. 140 is a perspective of a portion of another surgical instrument embodiment;

FIG. 141 is a perspective view of an articulation joint of the surgical instrument of FIG. 140 in an unarticulated orientation;

FIG. 142 is another perspective view of the articulation joint of FIG. 141 in another articulated orientation;

FIG. 143 is an exploded perspective view of the articulation joint of FIG. 141;

FIG. 144 is a top view of the articulation joint of FIG. 141;

FIG. 145 is a cross-sectional view of the articulation joint of FIG. 144 taken along line 145-145 in FIG. 144;

FIG. 146 is a side elevational view of the articulation joint of FIG. 144;

FIG. 147 is another side elevation al view of the articulation joint of FIG. 146 in an articulated orientation;

FIG. 148 is a perspective view of the articulation join of FIG. 141 in another articulated orientation;

FIG. 149 is another perspective view of the articulation join of FIG. 141 in another articulated orientation;

FIG. 150 is an end view of the proximal joint member of the articulation joint of FIG. 141;

FIG. 151 is an end view of the distal joint member of the articulation joint of FIG. 141;

FIG. 152 is a perspective view of a proximal cross pin assembly of the articulation joint of FIG. 141;

FIG. 153 is a perspective view of another articulation joint embodiment;

FIG. 154 is a perspective view of an articulation joint portion of another surgical instrument embodiment;

FIG. 155 is another perspective view of the articulation joint arrangement of FIG. 154 with an outer shaft tube omitted for clarity;

FIG. 156 is an exploded perspective assembly view of the articulation joint arrangement and firing drive system of the surgical instrument of FIG. 154;

FIG. 157 is a perspective view of the articulation joint and firing system arrangement of FIG. 156 with an outer shaft tube omitted for clarity and wherein a firing member is in a starting position;

FIG. 158 is another perspective view of the articulation joint and firing system of FIG. 157 after the firing member has been advanced to a distal position;

FIG. 159 is a partial cross-sectional view of a portion of the firing system of the surgical instrument of FIG. 154;

FIG. 160 is a partial view of a proximal differential drive assembly of the surgical instrument embodiment of FIG. 154;

FIG. 161 is a cross sectional end view through the proximal differential drive assembly of FIG. 160;

FIG. 162 is a side elevational view of the articulation joint and distal differential drive assembly of the surgical instrument of FIG. 154;

FIG. 163 is another side elevational view of the articulation joint and distal differential drive assembly of FIG. 162 in an articulated orientation;

FIG. 164 is a partial graphical depiction of reactive forces acting on push coils of the surgical instrument of FIG. 154 when the articulation joint thereof is in an articulated orientation and the firing member is being distally advanced;

FIG. 165 is another partial graphical depiction of reactive forces acting on flexible outer tubes of the surgical instrument of FIG. 154 when the articulation joint thereof is in an articulated orientation;

FIG. 166 is a perspective view of a central link member and flexible joint support assembly of the surgical instrument of FIG. 154;

FIG. 167 is a side elevational view of the articulation joint of the surgical instrument of FIG. 154 in an unarticulated orientation;

FIG. 168 is a cross-sectional view of the articulation joint of FIG. 167 taken along line 168-168 in FIG. 167; and FIG. 169 is a partial perspective view of the articulation joint of the surgical instrument of FIG. 154 in an articulated orientation with the flexible joint support assembly omitted for clarity.

DETAILED DESCRIPTION

Applicant of the present application owns the following U.S. patent applications that were filed on even date herewith and which are each herein incorporated by reference in their respective entireties:

U.S. Pat. No. 11,638,582, entitled SURGICAL INSTRUMENTS WITH TORSION SPINE DRIVE ARRANGEMENTS, issued on May 2, 2023;
U.S. Pat. No. 11,86,013, entitled SURGICAL INSTRUMENTS WITH FIRING MEMBER CLOSURE FEATURES, issued on Nov. 28, 2023;
U.S. Pat. No. 11,660,090, entitled SURGICAL INSTRUMENTS WITH SEGMENTED FLEXIBLE DRIVE ARRANGEMENTS, issued on May 30, 2023;
U.S. Pat. No. 11,864,756, entitled SURGICAL INSTRUMENTS WITH FLEXIBLE BALL CHAIN DRIVE ARRANGEMENTS, issued on Jan. 9, 2024;
U.S. Pat. No. 11,737,748, entitled SURGICAL INSTRUMENTS WITH DOUBLE SPHERICAL ARTICULATION JOINTS WITH PIVOTABLE LINKS, issued on Aug. 29, 2023;
U.S. Pat. No. 12,220,126, entitled SURGICAL INSTRUMENTS WITH DOUBLE PIVOT ARTICULATION JOINT ARRANGEMENTS, issued on Feb. 11, 2025;
U.S. Pat. No. 11,857,182, entitled SURGICAL INSTRUMENTS WITH COMBINATION FUNCTION ARTICULATION JOINT ARRANGEMENTS, issued on Jan. 2, 2024;
U.S. Pat. No. 11,883,024, entitled METHOD OF OPERATING A SURGICAL INSTRUMENT, issued on Jan. 30, 2024;
U.S. Pat. No. 11,871,925, entitled SURGICAL INSTRUMENTS WITH DUAL SPHERICAL ARTICULATION JOINT ARRANGEMENTS, issued on Jan. 16, 2024;
U.S. Pat. No. 12,064,107, entitled ARTICULATABLE SURGICAL INSTRUMENTS WITH ARTICULATION JOINTS COMPRISING FLEXIBLE EXOSKELETON ARRANGEMENTS, issued on Aug. 20, 2024; and
U.S. Pat. No. 11,974,741, entitled SURGICAL INSTRUMENTS WITH DIFFERENTIAL ARTICULATION JOINT ARRANGEMENTS FOR ACCOMMODATING FLEXIBLE ACTUATORS, issued on May 7, 2024.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted.

The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

FIGS. 1-4 illustrate one form of a surgical instrument 10 that may address many of the challenges facing surgical instruments with articulatable end effectors that are configured to cut and fasten tissue. In various embodiments, the surgical instrument 10 may comprise a handheld device. In other embodiments, the surgical instrument 10 may comprises an automated system sometimes referred to as a robotically-controlled system, for example. In various forms, the surgical instrument 10 comprises a surgical end effector 1000 that is operably coupled to an elongate shaft assembly 2000. The elongate shaft assembly 2000 may be operably attached to a housing 2002. In one embodiment, the housing 2002 may comprise a handle that is configured to be grasped, manipulated, and actuated by the clinician. In other embodiments, the housing 2002 may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 1000 comprises a first jaw 1100 and a second jaw 1200. In the illustrated arrangement, the first jaw 1100 comprises an elongate channel 1110 that comprises a proximal end 1112 and a distal end 1114 and is configured to operably support a surgical staple cartridge 1300 therein. The surgical staple cartridge 1300 comprises a cartridge body 1302 that has an elongate slot 1304 therein. A plurality of surgical staples or fasteners (not shown) are stored therein on drivers (not shown) that are arranged in rows on each side of the elongate slot 1304. The drivers are each associated with corresponding staple cavities 1308 that open through a cartridge deck surface 1306. The surgical staple cartridge 1300 may be replaced after the staples/fasteners have been discharged therefrom. Other embodiments are contemplated wherein the elongate channel 1110 and/or the entire surgical end effector 1000 may is discarded after the surgical staple cartridge 1300 has been used. Such end effector arrangements may be referred to as "disposable loading units", for example.

In the illustrated arrangement, the second jaw 1200 comprises an anvil 1210 that comprises an elongate anvil body 1212 that comprises a proximal end 1214 and a distal end 1216. In one arrangement, a pair of stiffening rods or members 1213 may be supported in the anvil body 1212 to provide the anvil body 1212 with added stiffness and rigidity. The anvil body 1212 comprises a staple-forming undersurface 1218 that faces the first jaw 1100 and may include a series of staple-forming pockets (not shown) that corresponds to each of the staples or fasteners in the surgical staple cartridge 1300. The anvil body 1212 may further include a pair of downwardly extending tissue stop features 1220 that are formed adjacent the proximal end 1214 of the anvil body 1212. One tissue stop feature 1220 extends from each side of the anvil body 1212 such that a distal end 1222 on each tissue stop corresponds to the proximal-most staples/fasteners in the surgical staple cartridge 1300. When the anvil 1210 is moved to a closed position onto tissue positioned between the staple-forming undersurface 1218 of the anvil 1210 and the cartridge deck surface 1306 of the surgical staple cartridge 1300, the tissue contacts the distal ends 1222 of the tissue stop features 1220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 1308 through the clamped tissue and into forming contact with the staple-forming undersurface 1218 of the anvil 1210.

Figure 1:
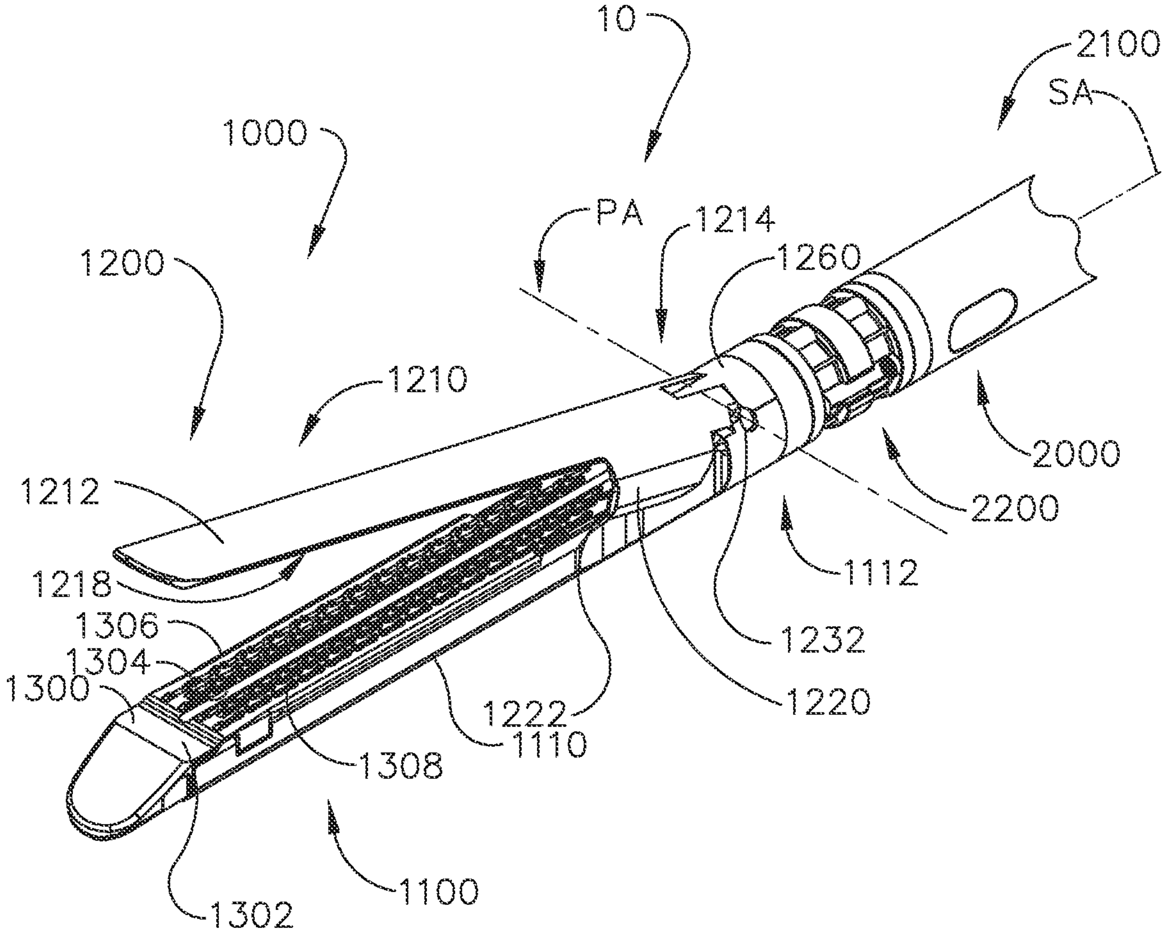
FIG. 1 is a perspective view of a surgical end effector portion of a surgical instrument in accordance with at least one aspect of the present disclosure.
Figure 2:
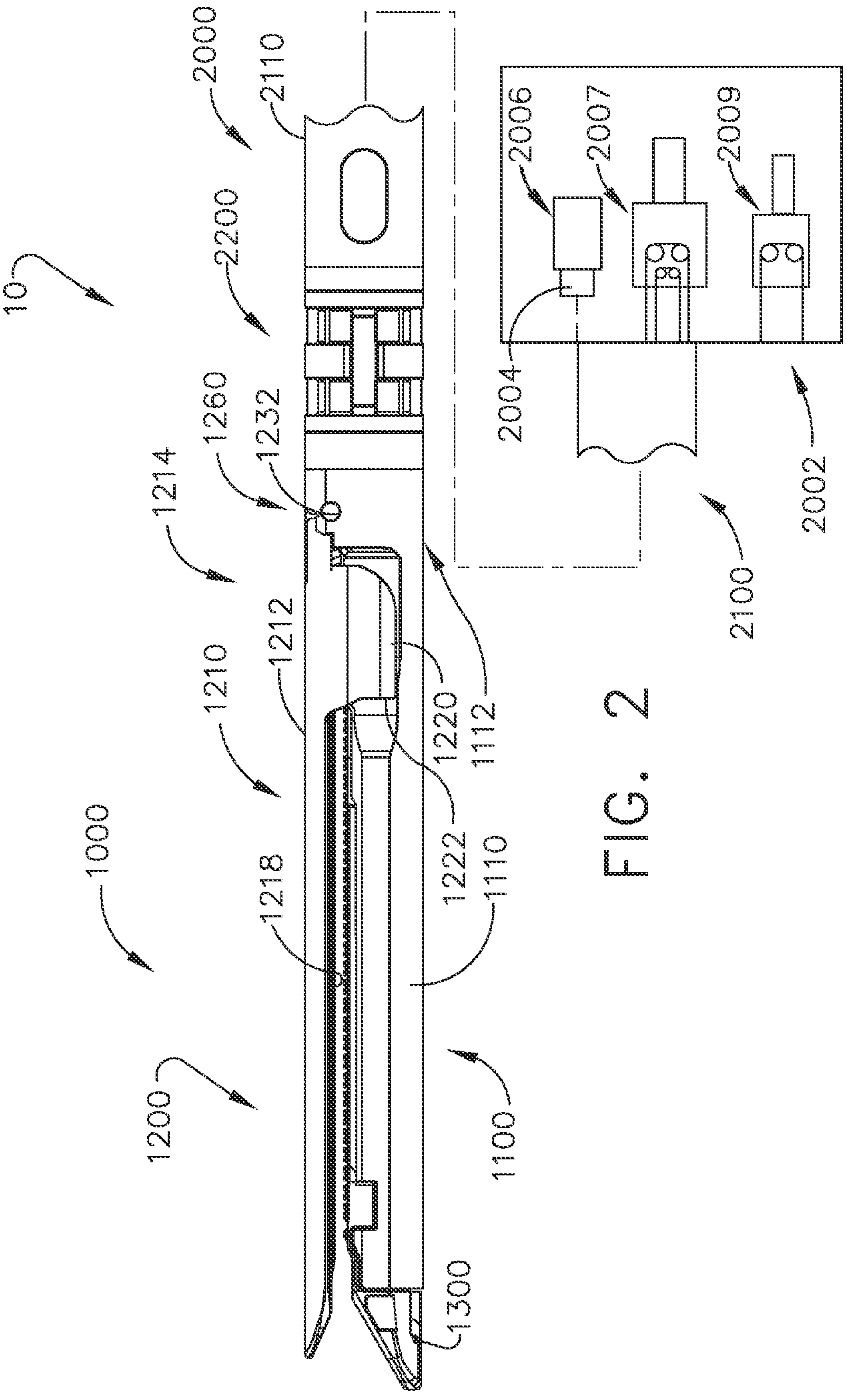
FIG. 2 is a side view of the surgical end effector portion instrument of FIG. 1 in a closed orientation.
Figure 3:
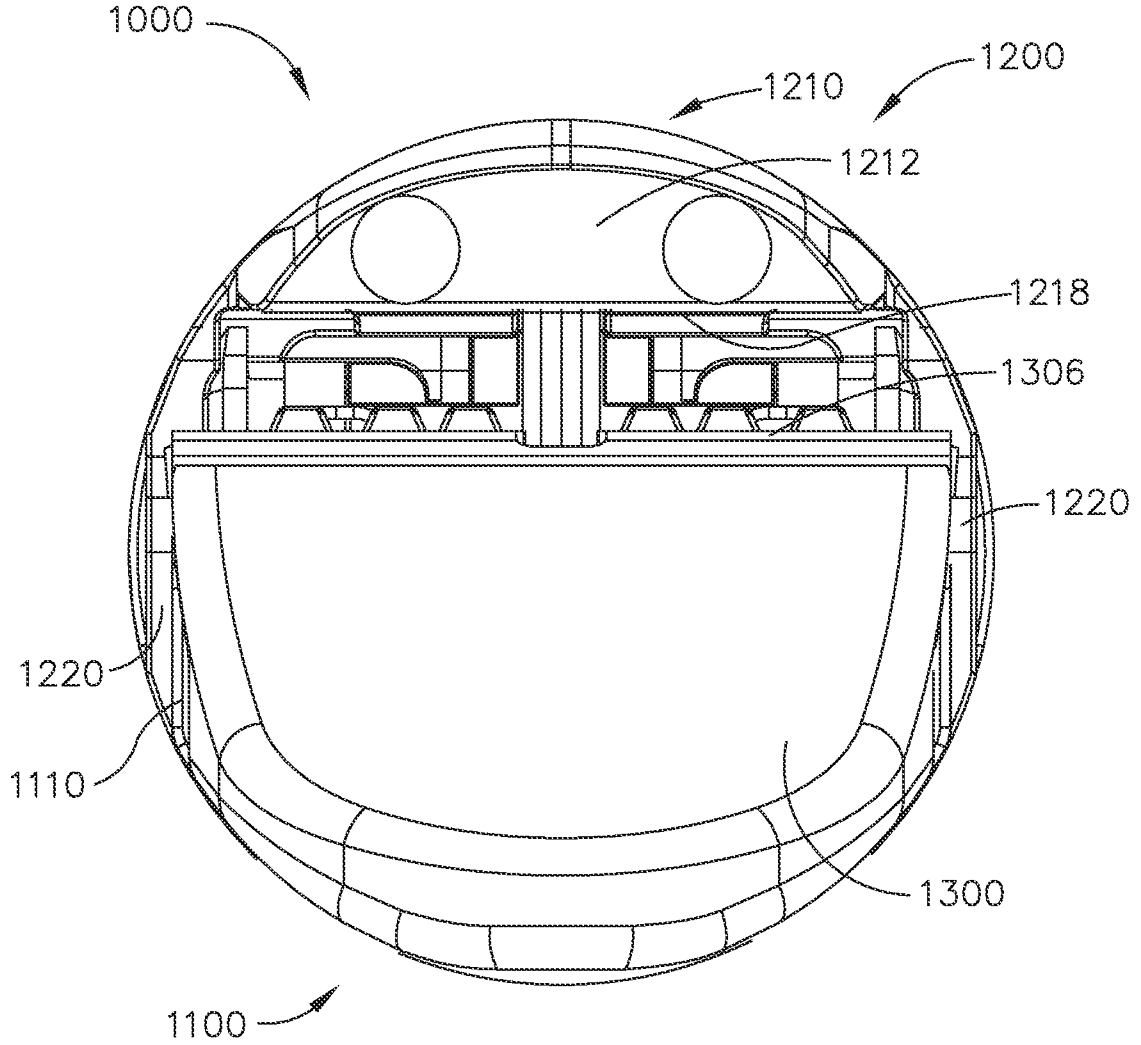
FIG. 3 is an end view of the surgical end effector of FIG. 2.
Figure 4:
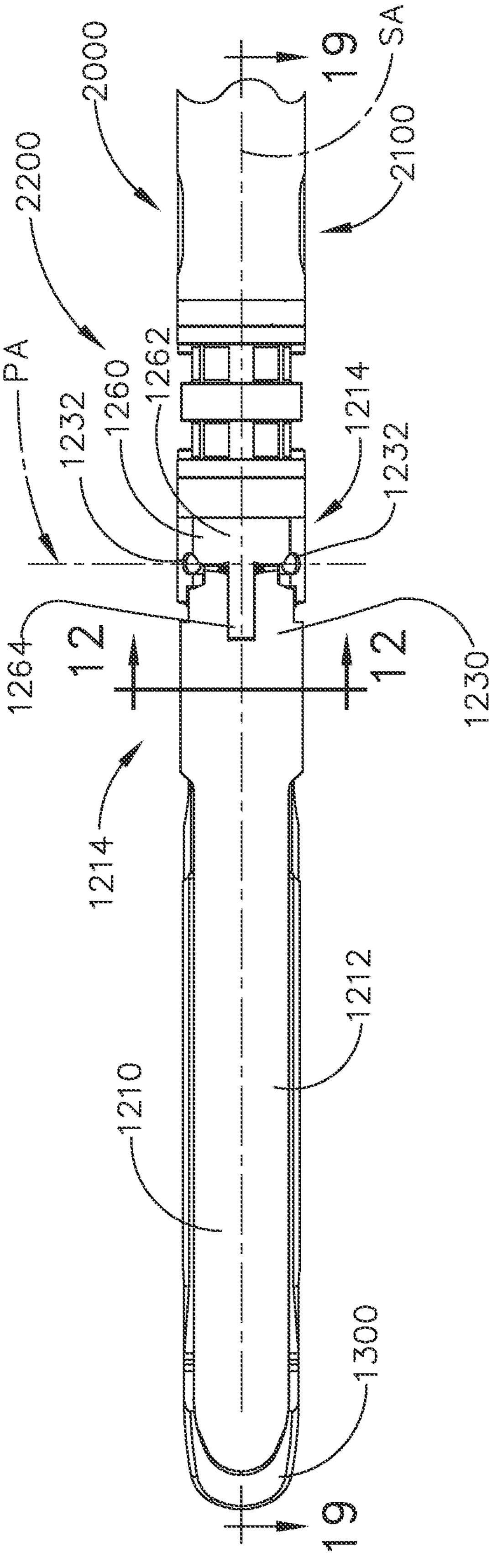
FIG. 4 is a top view of the surgical end effector of FIG. 2.
Figure 5:
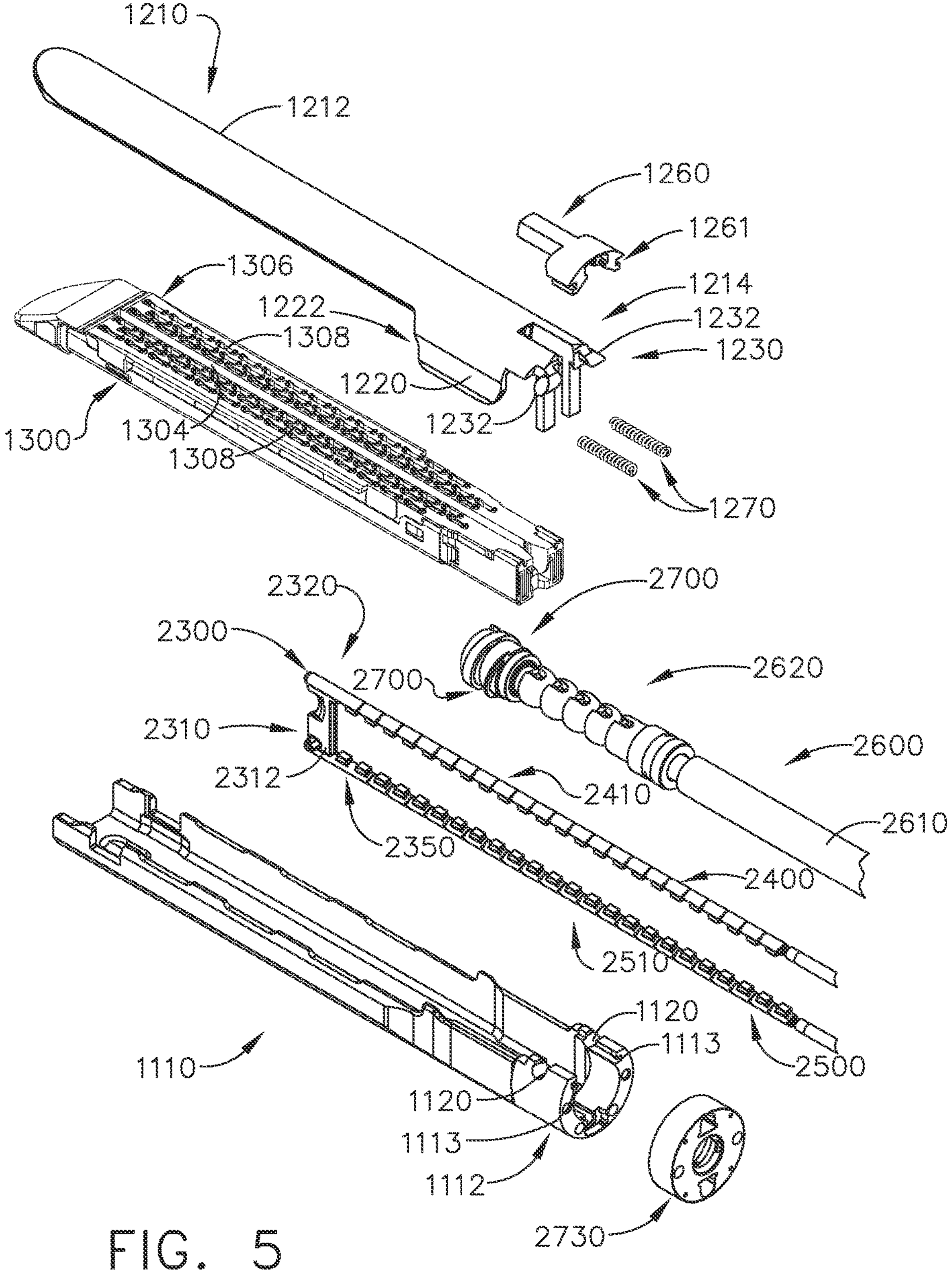
FIG. 5 is an exploded assembly view of a portion of the surgical instrument of FIG. 1.
Figure 6:
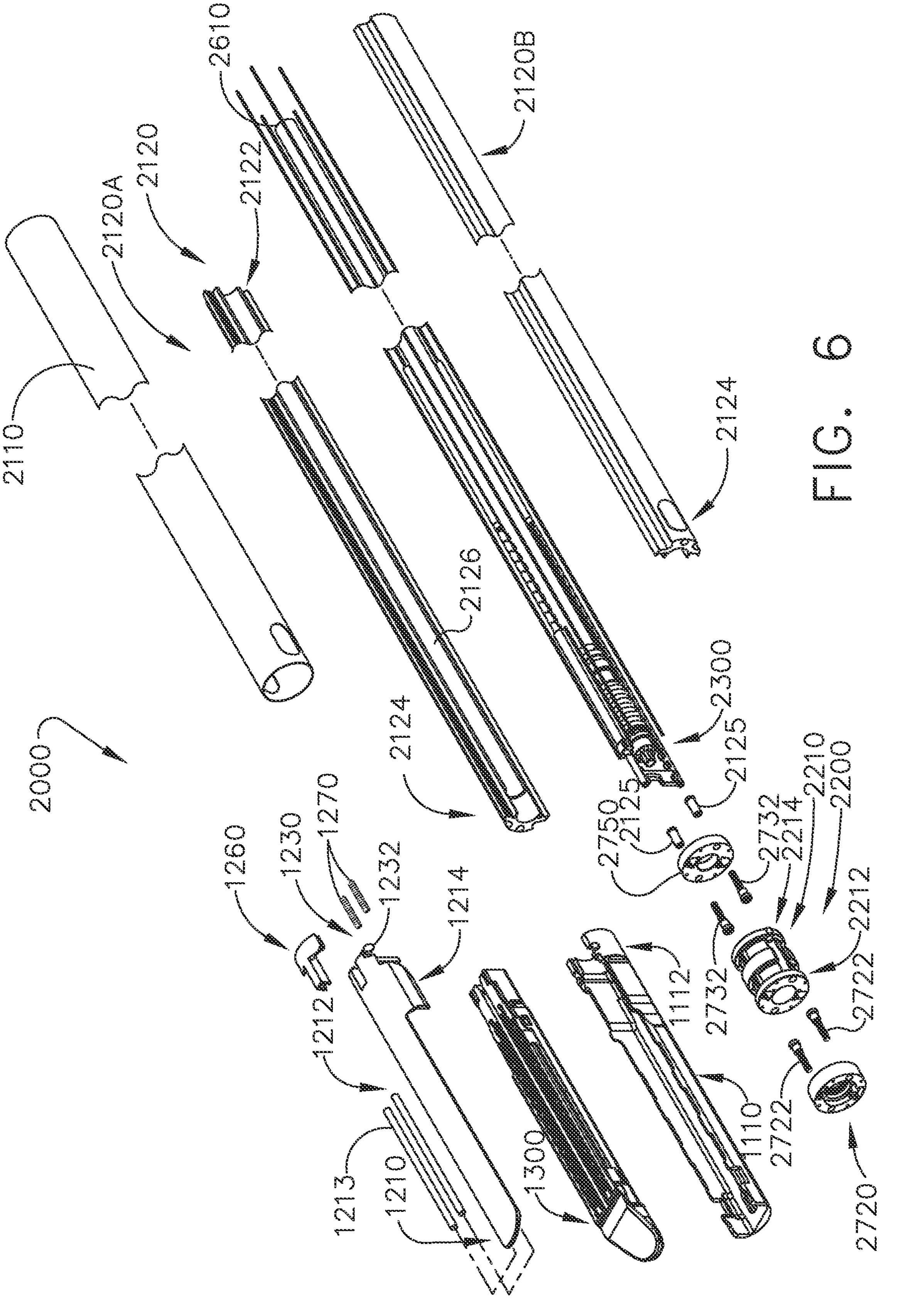
FIG. 6 is an exploded assembly view of an elongate shaft assembly of the surgical instrument of FIG. 1.

As can be seen in FIGS. 5 and 6, the proximal end 1214 of the anvil body 1212 comprises an anvil mounting portion 1230 that includes a pair of laterally extending mounting pins 1232 that are configured to be received in corresponding mounting cradles or pivot cradles 1120 formed in the proximal end 1112 of the elongate channel 1110. The mounting pins 1232 are pivotally retained within the mounting cradles 1120 by an anvil cap 1260 that may be attached to the proximal end 1112 of the elongate channel 1110 by mechanical snap features 1261 that are configured to engage retention formations 1113 on the elongate channel 1110. See FIG. 5. In other arrangements, the anvil cap 1260 may be attached to the elongate channel 1110 by welding, adhesive, etc. Such arrangement facilitates pivotal travel of the anvil 1210 relative to the surgical staple cartridge 1300 mounted in the elongate channel 1110 about a pivot axis PA between an open position (FIG. 1) and a closed position (FIGS. 2-5). Such pivot axis PA may be referred to herein as being "fixed" in that the pivot axis does not translate or otherwise move as the anvil 1200 is pivoted from an open position to a closed position.

In the illustrated arrangement, the elongate shaft assembly 2000 defines a shaft axis SA and comprises a proximal shaft portion 2100 that may operably interface with a housing of the control portion (e.g., handheld unit, robotic tool driver, etc.) of the surgical instrument 10. The elongate shaft assembly 2000 further comprises an articulation joint 2200 that is attached to the proximal shaft portion 2100 and the surgical end effector 1000. In various instances, the proximal shaft portion 2100 comprises a hollow outer tube 2110 that may be operably coupled to a housing 2002. See FIG. 2. As can be seen in FIG. 6, the proximal shaft portion 2100 may further comprise a rigid proximal support shaft 2120 that is supported within the hollow outer tube 2110 and extends from the housing to the articulation joint 2200. The proximal support shaft 2120 may comprise a first half 2120A and a second half 2120B that may be coupled together by, for example, welding, adhesive, etc. The proximal support member 2120 comprises a proximal end 2122 and a distal end 2124 and includes an axial passage 2126 that extends therethrough from the proximal end 2122 to the distal end 2124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 10 employs a firing system 2300 that may address many if not all of these issues as well as others.

As can be seen in FIGS. 5-11, in at least one embodiment, the firing system 2300 comprises a firing member 2310 that includes a vertically-extending firing member body 2312 that comprises a top firing member feature 2320 and a bottom firing member feature 2350. A tissue cutting blade 2314 is attached to or formed in the vertically-extending firing member body 2312. See FIGS. 9 and 11. In at least one arrangement, it is desirable for the firing member 2310 to pass through the anvil body 1212 with low friction, high strength and high stiffness. In the illustrated arrangement, the top firing member feature 2320 comprises a top tubular body 2322 that has a top axial passage 2324 extending therethrough. See FIG. 10. The bottom firing member feature 2350 comprises a bottom tubular body 2352 that has a bottom axial passage 2354 extending therethrough. In at least one arrangement, the top firing member feature 2320 and the bottom firing member feature 2350 are integrally formed with the vertically-extending firing member body 2312. As can be seen in FIG. 12, the anvil body 1212 comprises an axially extending anvil slot 1240 that has a cross-sectional shape that resembles a "keyhole". Similarly, the elongate channel 1110 comprises an axially extending channel slot 1140 that also has a keyhole cross-sectional shape.

Traditional firing member arrangements employ long flexible cantilever wings that extend from a top portion and a bottom portion of the firing member. These cantilever wings slidably pass through slots in the anvil and channel that are commonly cut with a rectangular t-cutter which tended to produce higher friction surfaces. Such long cantilever wings have minimum surface area contact with the anvil and channel and can result in galling of those components. The keyhole-shaped channel slot 1140 and keyhole-shaped anvil slot 1240 may be cut with a round t-cutter and may be finished with a reamer/borer which will result in the creation of a lower friction surface. In addition, the top tubular body 2322 and the bottom tubular body 2352 are stiffer than the prior cantilever wing arrangements and have increased surface area contact with the anvil and channel, respectively which can reduce galling and lead to a stronger sliding connection. Stated another way, because the anvil slot 1240 and the channel slot 1140 are keyhole-shaped and have less material removed than a traditional rectangular slot, the geometry and increased material may result in a stiffer anvil and channel when compared to prior arrangements.

Figure 9:
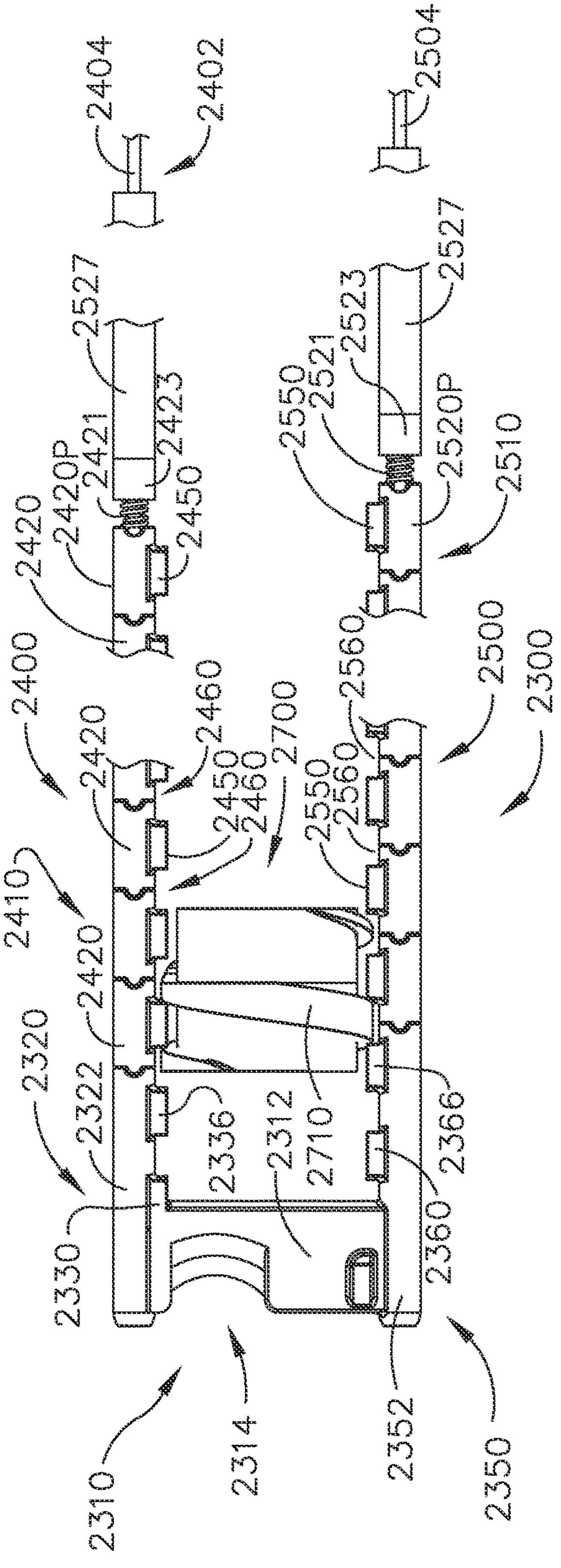
FIG. 9 is a side view of a firing member and upper and lower flexible spine assemblies of the firing system in engagement with a rotary drive screw of the rotary drive system of FIG. 8.
Figure 10:
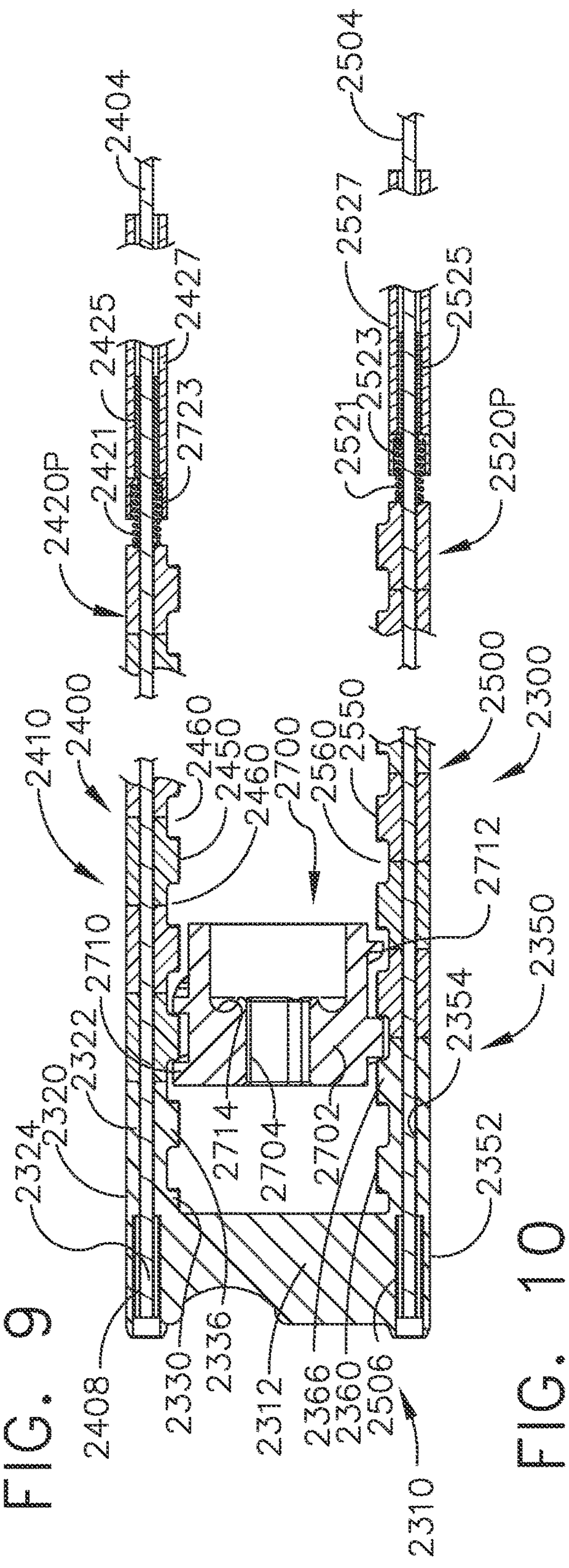
FIG. 10 is a cross-sectional view of the firing member and upper and lower flexible spine assemblies of FIG. 9.
Figure 11:
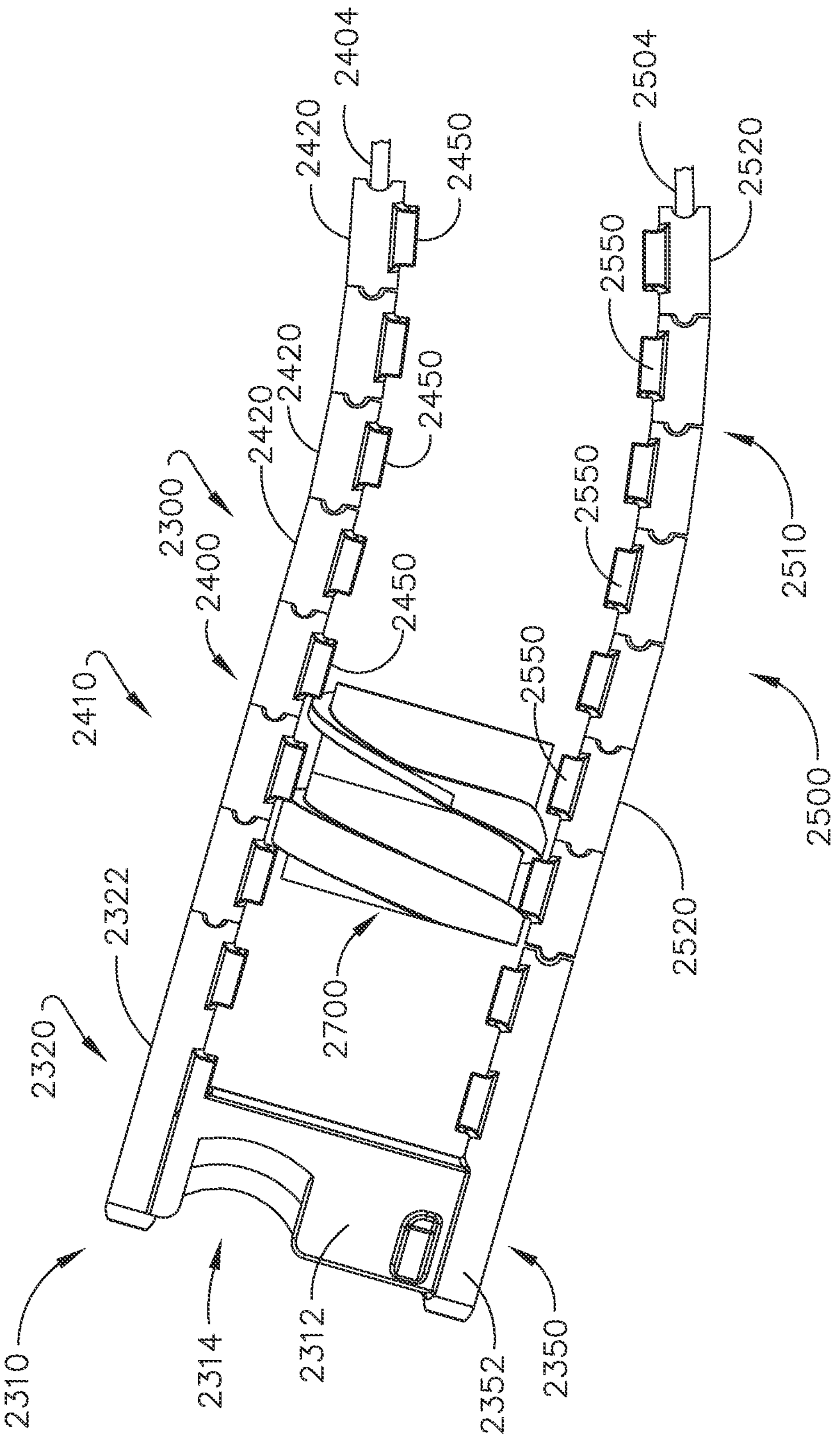
FIG. 11 is a side elevational view of the firing member and upper and lower flexible spine assemblies in engagement with the rotary drive screw of FIG. 9.
Figure 12:
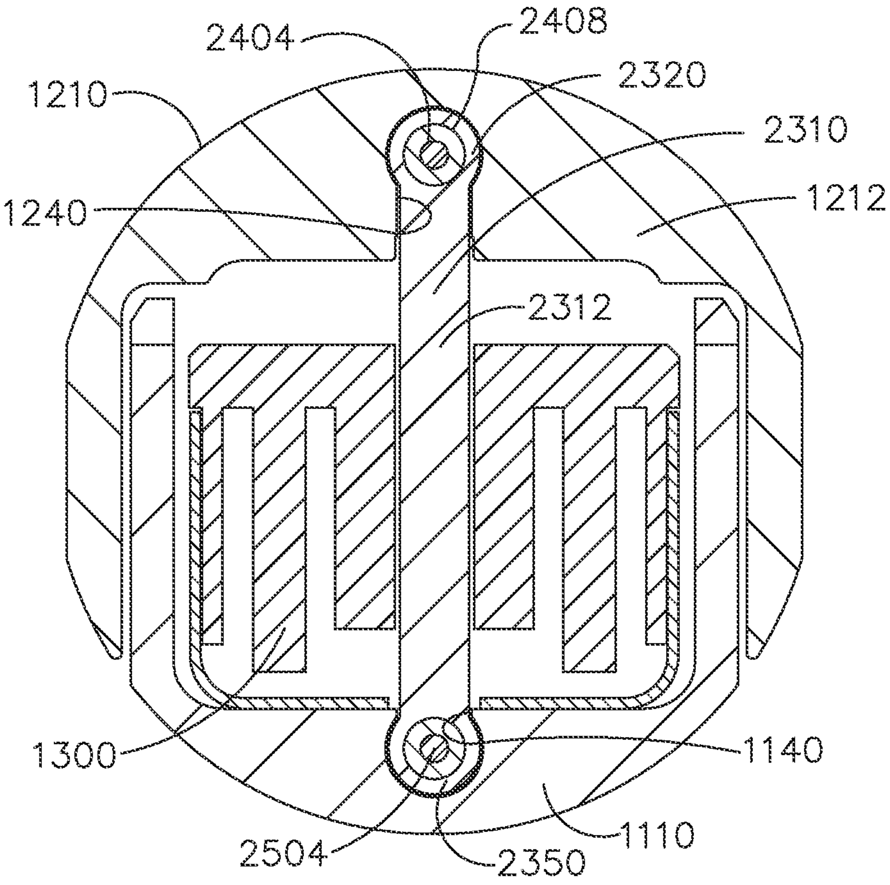
FIG. 12 is a cross-sectional end view of the surgical end effector of FIG. 4 taken along line 12-12 in FIG. 4.

Turning to FIGS. 9-11, in one arrangement, the firing system 2300 further comprises an upper flexible spine assembly 2400 that is operably coupled to the top firing member feature 2320 and a lower flexible spine assembly 2500 that is operably coupled to the bottom firing member feature 2350. In at least one embodiment, the upper flexible spine assembly 2400 comprises an upper series 2410 of upper vertebra members 2420 that are loosely coupled together by an upper flexible coupler member 2402 that is attached to the top firing member feature 2320. The upper flexible coupler member 2402 may comprises a top cable 2404 that extends through the top axial passage 2324 in the top firing member feature 2320 and a distal end 2406 of the top cable 2404 is attached to a retainer ferrule 2408 that is secured with the top axial passage 2324.

Figure 13:
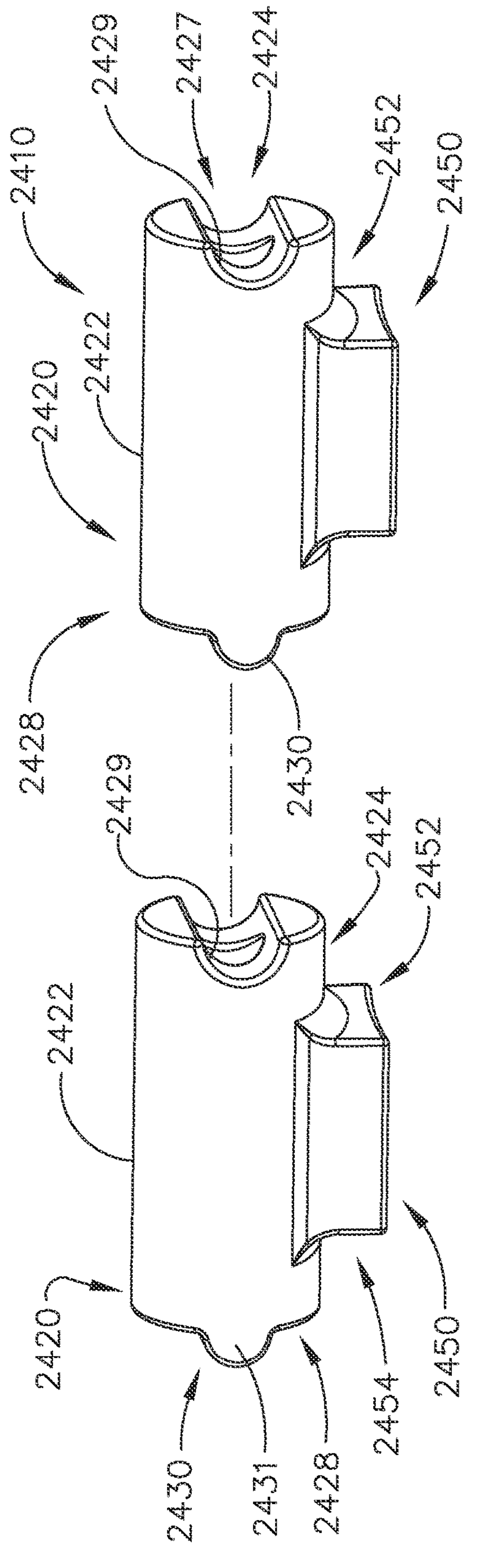
FIG. 13 is an exploded perspective view of two adjacent upper vertebra members of the upper flexible spine assembly of FIG. 10.

As can be seen in FIG. 13, each upper vertebra member 2420 comprises an upper vertebra body portion 2422 that has a proximal end 2424 and a distal end 2428. An upper hollow passage 2429 extends through the upper vertebra body portion 2422 to accommodate passage of the upper flexible coupler member 2402 therethrough. Each upper vertebra member 2420 further comprises a downwardly extending upper drive feature or upper vertebra member tooth 2450 that protrudes from the upper vertebra body portion 2422. Each upper vertebra member tooth 2450 has a helix-shaped proximal upper face portion 2452 and a helix-shaped distal upper face portion 2454. Each proximal end 2424 of the upper vertebra body portions 2422 has an upper proximal mating feature 2426 therein and each distal end 2428 has an upper distal mating feature 2430 formed therein. In at least one embodiment, the upper proximal mating feature 2426 comprises a concave recess 2427 and each upper distal mating feature 2430 comprises a convex mound 2431. When arranged in the upper series 2410, the convex mound 2431 on one upper vertebra member 2420 contacts and mates with the concave recess 2427 on an adjacent upper vertebra member 2420 in the upper series 2410 to maintain the upper vertebra members 2420 roughly in alignment so that the helix-shaped proximal upper face portion 2452 and a helix-shaped distal upper face portion 2454 on each respective upper tooth 2450 can be drivingly engaged by a rotary drive screw 2700 as will be discussed in further detail below.

Similarly, in at least one embodiment, the lower flexible spine assembly 2500 comprises a lower series 2510 of lower vertebra members 2520 that are loosely coupled together by a lower flexible coupler member 2502 that is attached to the bottom firing member feature 2350. The lower flexible coupler member 2502 may comprises a lower cable 2504 that extends through the bottom axial passage 2354 in the bottom firing member feature 2350 and a distal end 2506 of the bottom cable 2504 is attached to a retainer ferrule 2508 that is secured with the bottom axial passage 2354.

Figure 14:
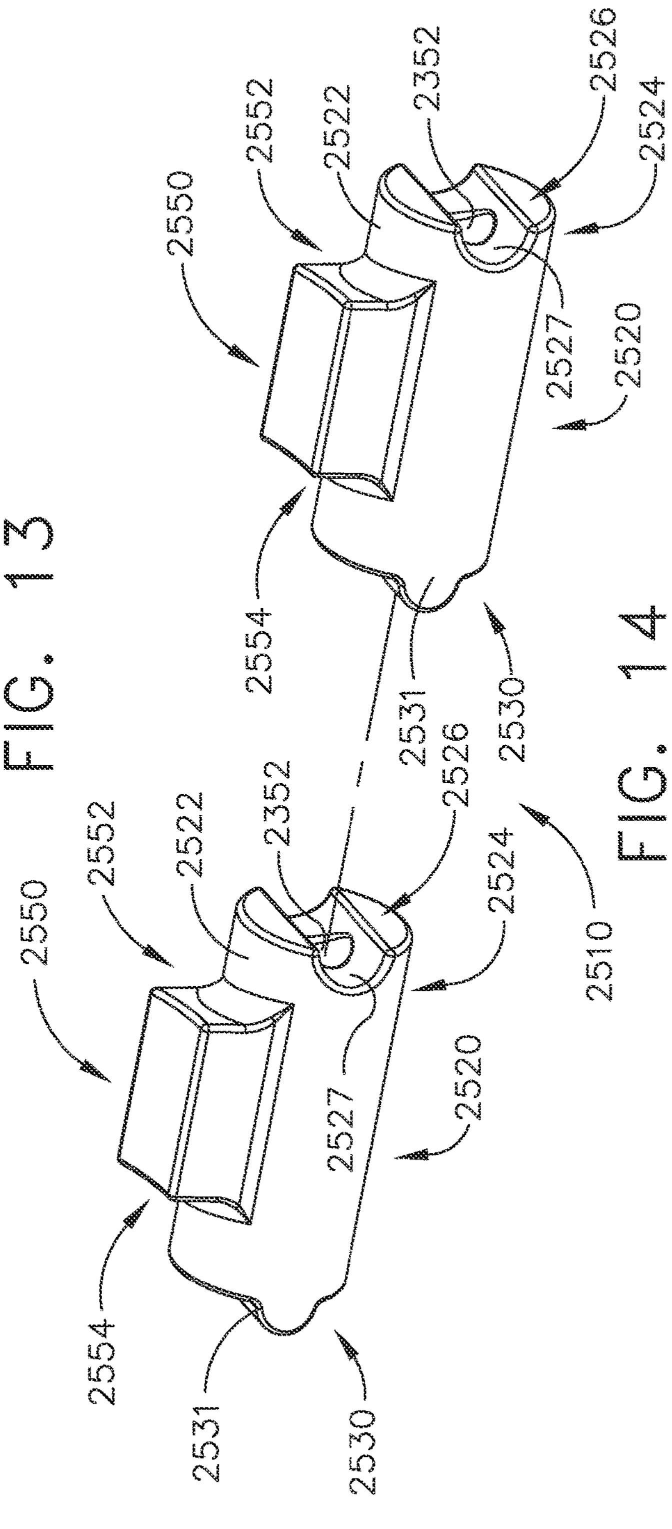
FIG. 14 is an exploded perspective view of two adjacent lower vertebra members of the lower flexible spine assembly of FIG. 10.

As can be seen in FIG. 14, each lower vertebra member 2520 comprises a lower vertebra body portion 2522 that has a proximal end 2524 and a distal end 2528. A lower hollow passage 2529 extends through the lower vertebra body portion 2522 to accommodate passage of the lower flexible coupler member 2502 therethrough. Each lower vertebra member 2520 further comprises an upwardly extending lower drive feature or lower vertebra member tooth 2550 that protrudes upward from the lower vertebra body portion 2522. Each lower vertebra member tooth 2550 has a helix-shaped proximal lower face portion 2552 and a helix-shaped distal lower face portion 2554. Each proximal end 2524 of the lower vertebra body portions 2522 has a lower proximal mating feature 2526 therein and each distal end 2528 has a lower distal mating feature 2530 formed therein. In at least one embodiment, the lower proximal mating feature 2526 comprises a concave recess 2527 and each lower distal mating feature 2530 comprises a convex mound 2531. When arranged in the lower series 2510, the convex mound 2531 on one lower vertebra member 2520 contacts and mates with the concave recess 2527 on an adjacent lower vertebra member 2520 in the lower series 2510 to maintain the lower vertebra members 2520 roughly in alignment so that the helix-shaped proximal lower face portion 2552 and a helix-shaped distal lower face portion 2554 on each respective lower vertebra member tooth 2550 can be drivingly engaged by a rotary drive screw 2700 as will be discussed in further detail below.

Figure 7:
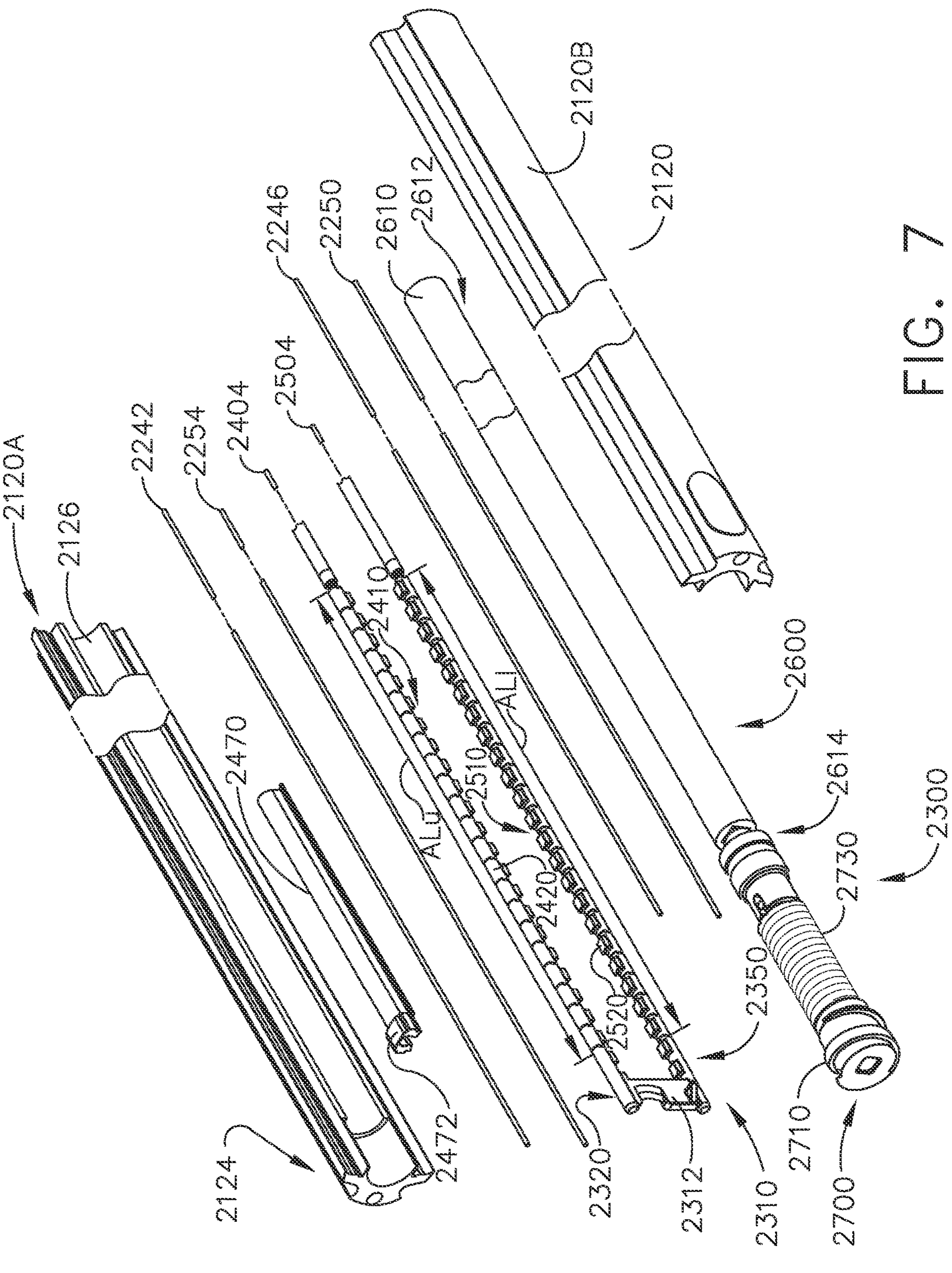
FIG. 7 is another exploded assembly view of the elongate shaft assembly of FIG. 6.
Figure 8:
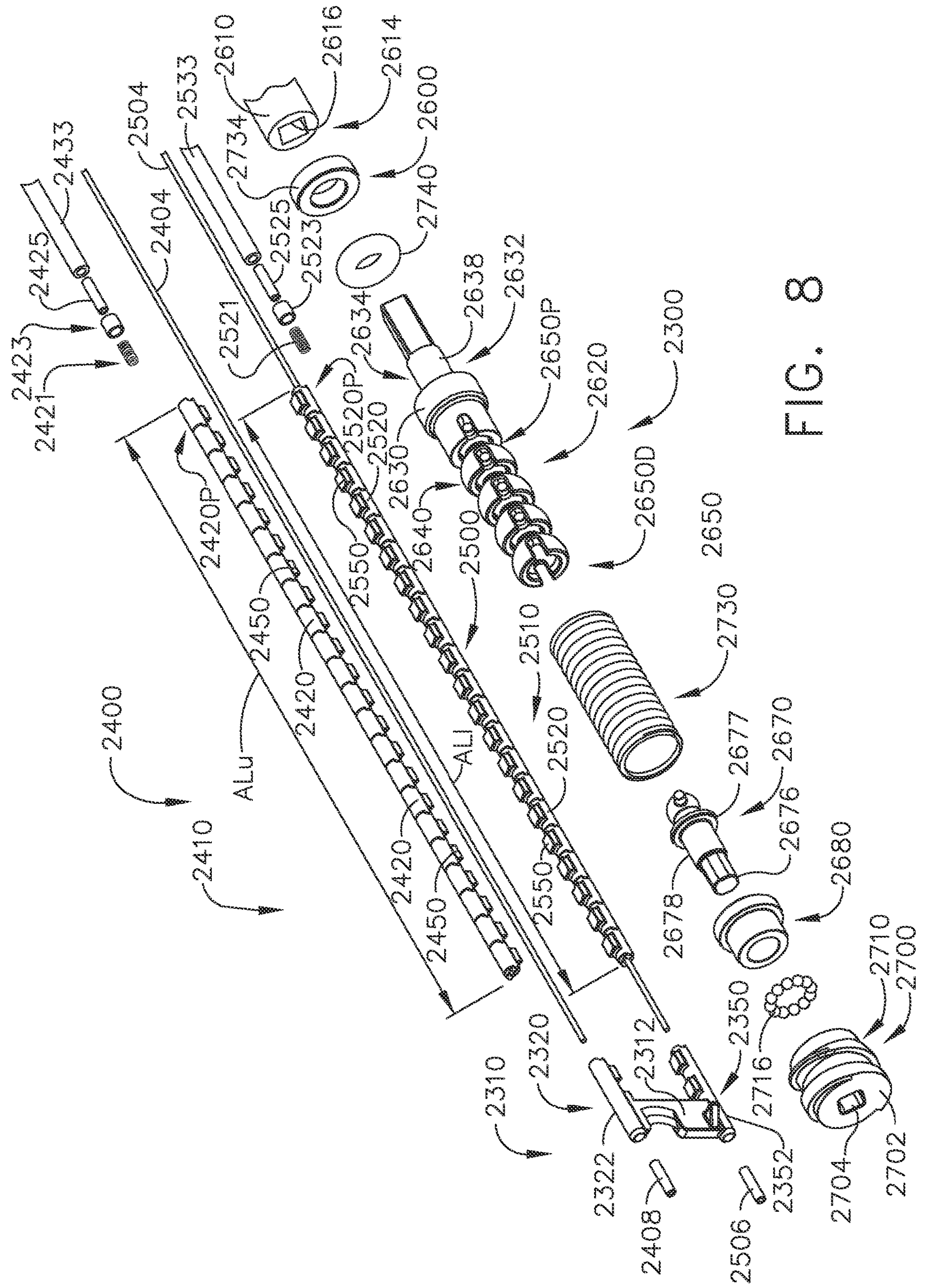
FIG. 8 is an exploded assembly view of a firing system and a rotary drive system according to at least one aspect of the present disclosure.

Now turning to FIGS. 5, 7, and 8, in at least one arrangement, the firing drive system 2300 further comprises a rotary drive screw 2700 that is configured to drivingly interface with the upper series 2410 of upper vertebra members 2420 and the lower series 2510 of lower vertebra members 2520. In the illustrated arrangement, the rotary drive screw 2700 is driven by a rotary drive system 2600 that comprises a proximal rotary drive shaft 2610 that is rotatably supported within the axial passage 2126 within the proximal support shaft 2120. See FIG. 7. The proximal rotary drive shaft 2610 comprises a proximal end 2612 and a distal end 2614. The proximal end 2612 may interface with a gear box 2004 or other arrangement that is driven by a motor 2006 or other source of rotary motion housed in the housing of the surgical instrument. See FIG. 2. Such source of rotary motion causes the proximal rotary drive shaft to rotate about the shaft axis SA within the axial passage 2126 in the proximal support shaft 2120.

Figure 16:
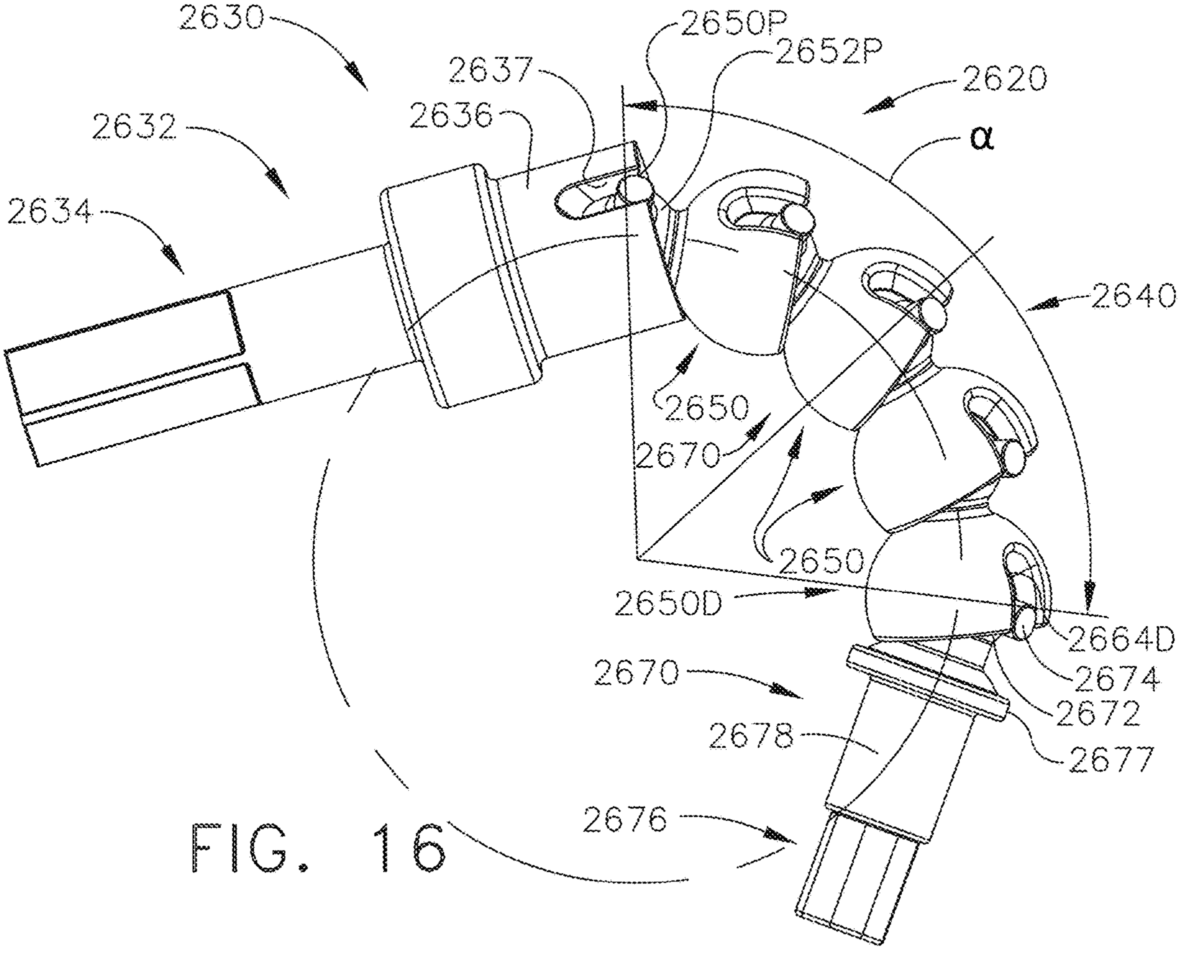
FIG. 16 is a perspective view of a CV drive shaft assembly of the rotary drive system of FIG. 8 in an articulated orientation.
Figure 17:
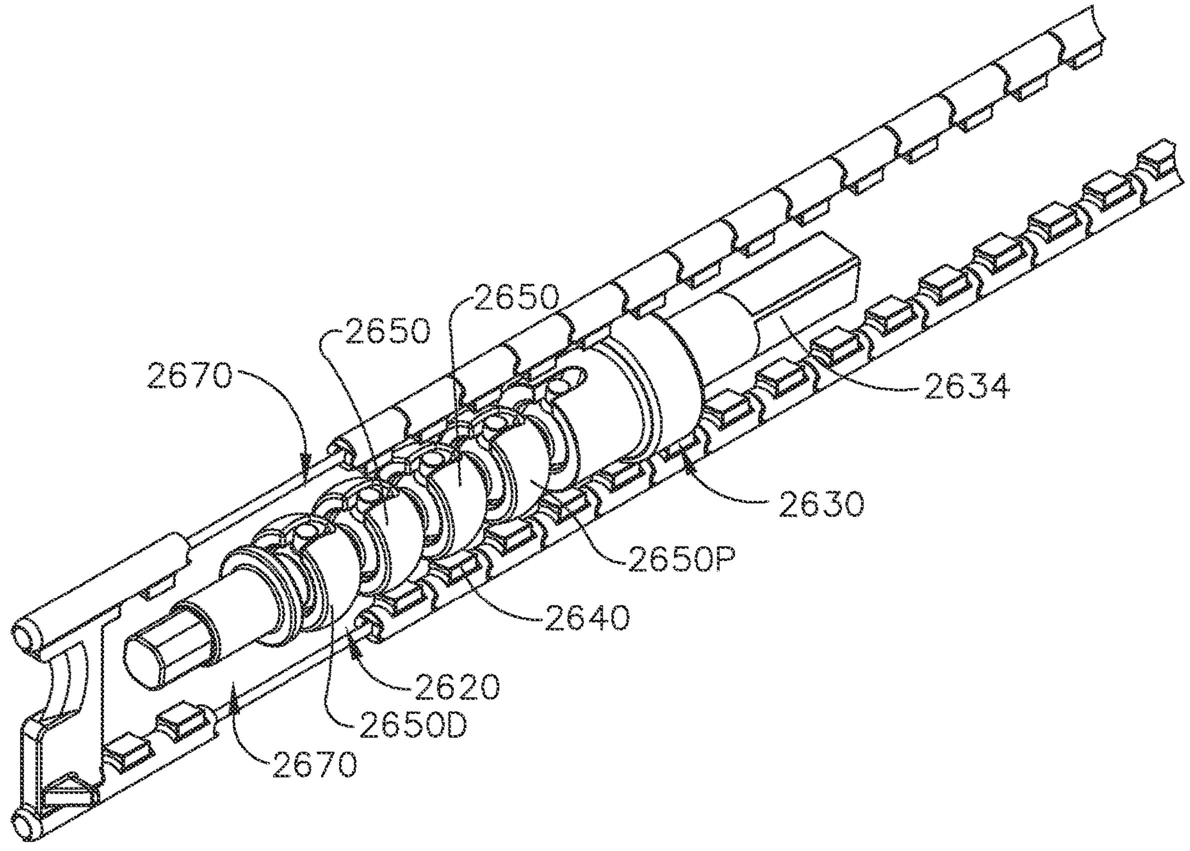
FIG. 17 is a perspective view of the firing system of FIG. 8 in driving engagement with the CV drive shaft assembly of FIG. 16 in accordance with at least one aspect of the present disclosure.

The proximal rotary drive shaft 2610 is operably supported within the elongate shaft assembly 2000 in a location that is proximal to the articulation joint 2200 and operably interfaces with a constant velocity (CV) drive shaft assembly 2620 that spans or extends axially through the articulation joint 2200. As can be seen in FIGS. 8, 16, and 17, in at least one arrangement, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650.

Figure 18:
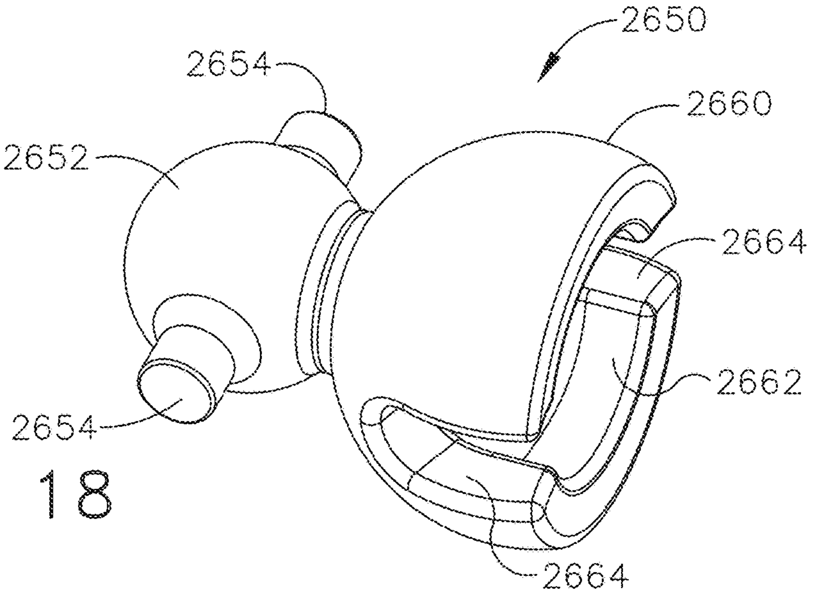
FIG. 18 is a perspective view of a drive joint of the CV drive shaft assembly of FIG. 16.

As can be seen in FIG. 18, in at least one arrangement, each drive joint 2650 comprises a first or distal sphere portion 2660 and a second or proximal sphere portion 2652. The distal sphere portion 2660 is larger than the proximal sphere portion 2652. The distal sphere portion 2660 comprises a socket cavity 2662 that is configured to rotatably receive a proximal sphere portion 2652 of an adjacent drive joint 2650 therein. Each proximal sphere portion 2652 comprises a pair of diametrically opposed joint pins 2654 that are configured to be movably received in corresponding pin slots 2664 in the distal sphere portion 2660 of an adjacent drive joint 2650 as can be seen in FIG. 16. A proximal sphere portion 2652P of a proximal-most drive joint 2650P is rotatably received in a distal socket portion 2636 of the proximal shaft segment 2632 as shown in FIG. 16. The joint pins 2654P are received within corresponding pin slots 2637 in the distal socket portion 2636. As can be further seen in FIG. 16, a distal-most drive joint 2650D in the series 2640 of movably coupled drive joints 2650 is movably coupled to a distal CV drive shaft 2670.

In at least one arrangement, the distal CV drive shaft 2670 comprises a proximal sphere portion 2672 that is sized to be movably received in the socket cavity 2662D in the distal-most drive joint 2650D. The proximal sphere portion 2672 includes joint pins 2674 that are movably received in the pin slots 2664D in the distal-most drive joint 2650D. The distal CV drive shaft 2670 further comprises a distally extending shaft stem 2676 that is configured to be non-rotatably coupled to the rotary drive screw 2700 that is positioned distal to the articulation joint 2200. The distal CV drive shaft 2670 includes a flange 2677 and a mounting barrel portion 2678 for receiving a thrust bearing housing 2680 thereon.

In the illustrated arrangement, when the series 2640 of movably coupled drive joints 2650 articulates, the joint pins 2674 remain in the corresponding pin slots 2664 of an adjacent drive joint 2650. In the example illustrated in FIG. 18, each drive joint may be capable of approximately eighteen degrees of articulation in the pitch and yaw directions. FIG. 16 illustrates an angle of the series of 2640 of drive joints 2650 when each drive joint 2650 in the series are fully articulated ninety degrees in pitch and yaw which yields an angle $\alpha$ of approximately 100.9 degrees. In such arrangement, the outer surface of each distal sphere portion 2660 clears the outer surface of the adjacent or adjoining proximal sphere portion 2652 allowing for unrestricted motion until the eighteen degree limit is reached. The rigid design and limited small angles allow the series 2640 of movably coupled drive joints 2650 to carry high loads torsionally at an overall large angle.

In the illustrated arrangement, the articulation joint 2200 comprises an articulation joint spring 2230 that is supported within an outer elastomeric joint assembly 2210. The outer elastomeric joint assembly 2210 comprises a distal end 2212 that is attached to the proximal end 1112 of the elongate channel 1110. For example, as can be seen in FIG. 6, the distal end 2212 of the outer elastomeric joint assembly 2210 is attached to the proximal end 1112 of the elongate channel 1110 by a pair of cap screws 2722 that extend through a distal mounting bushing 2720 to be threadably received in the proximal end 1112 of the elongate channel 1110. A proximal end 2214 of the elastomeric joint assembly 2210 is attached to the distal end 2124 of the proximal support shaft 2120. The proximal end 2214 of the elastomeric joint assembly 2210 is attached to the distal end 2124 of the proximal support member 2120 by a pair of cap screws 2732 that extend through a proximal mounting bushing 2750 to be threadably received in threaded inserts 2125 mounted within the distal end 2124 of the proximal support shaft 2120.

To prevent the drive joints 2650 from buckling during articulation, the series 2640 of movably coupled drive joints 2650 extend through at least one low friction articulation joint spring 2730 that is supported within the outer elastomeric joint assembly 2210. See FIG. 19. The articulation joint spring 2730 is sized relative to the drive joints 2650 such that a slight radial clearance is provided between the articulation joint spring 2730 and the drive joints 2650. The articulation joint spring 2730 is designed to carry articulation loads axially which may be significantly lower than the torsional firing loads. The joint spring(s) is longer than the series 2640 of drive joints 2650 such that the drive joints are axially loose. If the "hard stack" of the series 2640 of drive joints 2650 is longer than the articulation joint spring(s) 2730 hard stack, then the drive joints 2650 may serve as an articulation compression limiter causing firing loads and articulation loads to resolve axially through the series 2640 of the drive joints 2650. When the firing loads resolve axially through the series 2640 of the drive joints 2650, the loads may try to straighten the articulation joint 2200 or in other words cause de-articulation. If the hard stack of the articulation joint spring(s) 2730 is longer than the hard stack of the series 2640 of the drive joints 2650, the firing loads will then be contained within the end effector and no firing loads will resolve through the drive joints 2650 or through the springs(s) 2730.

Figure 19:
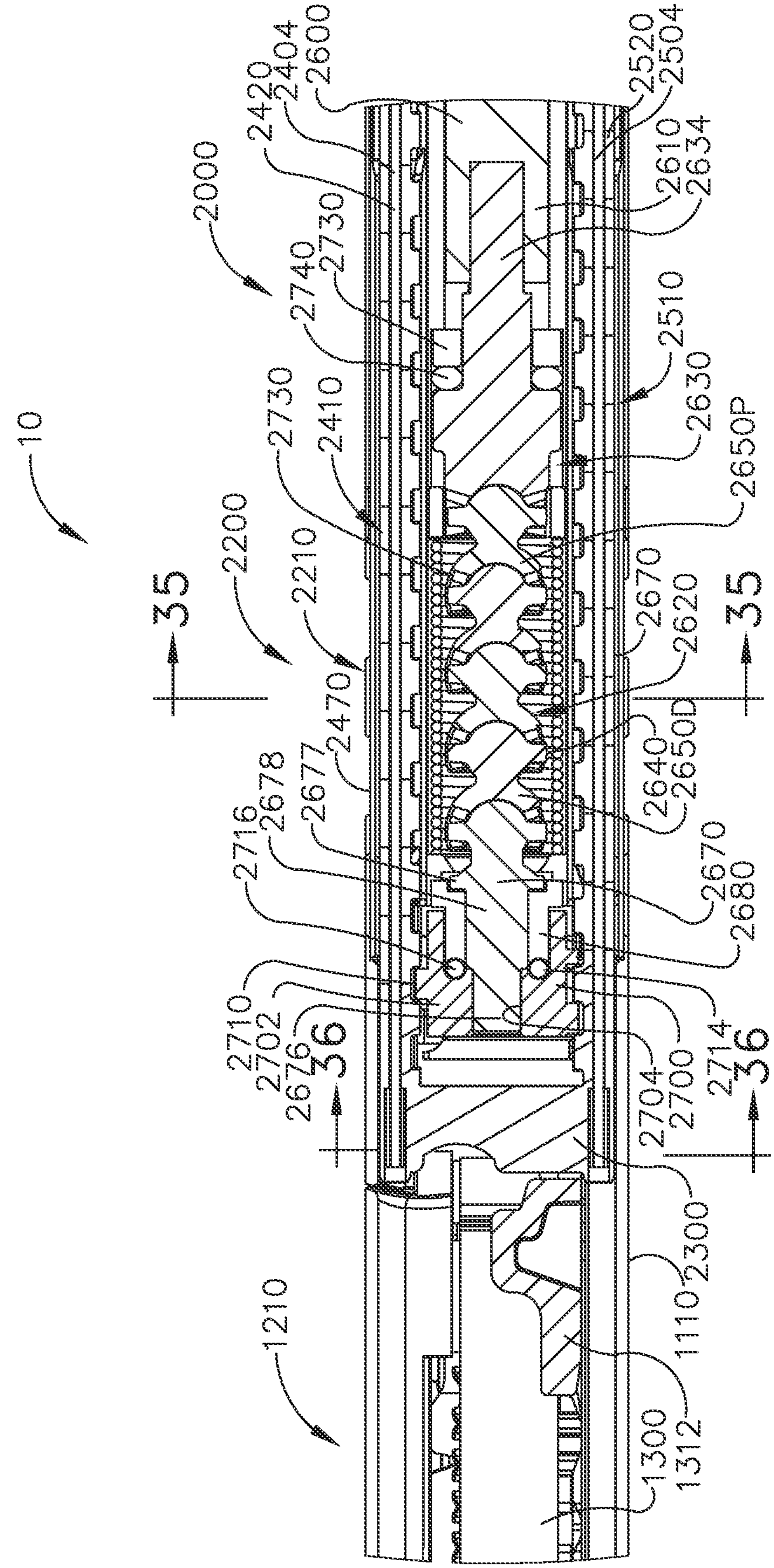
FIG. 19 is a cross-sectional view of a portion of the surgical instrument of FIG. 4 taken along line 19-19 in FIG. 4.
Figure 20:
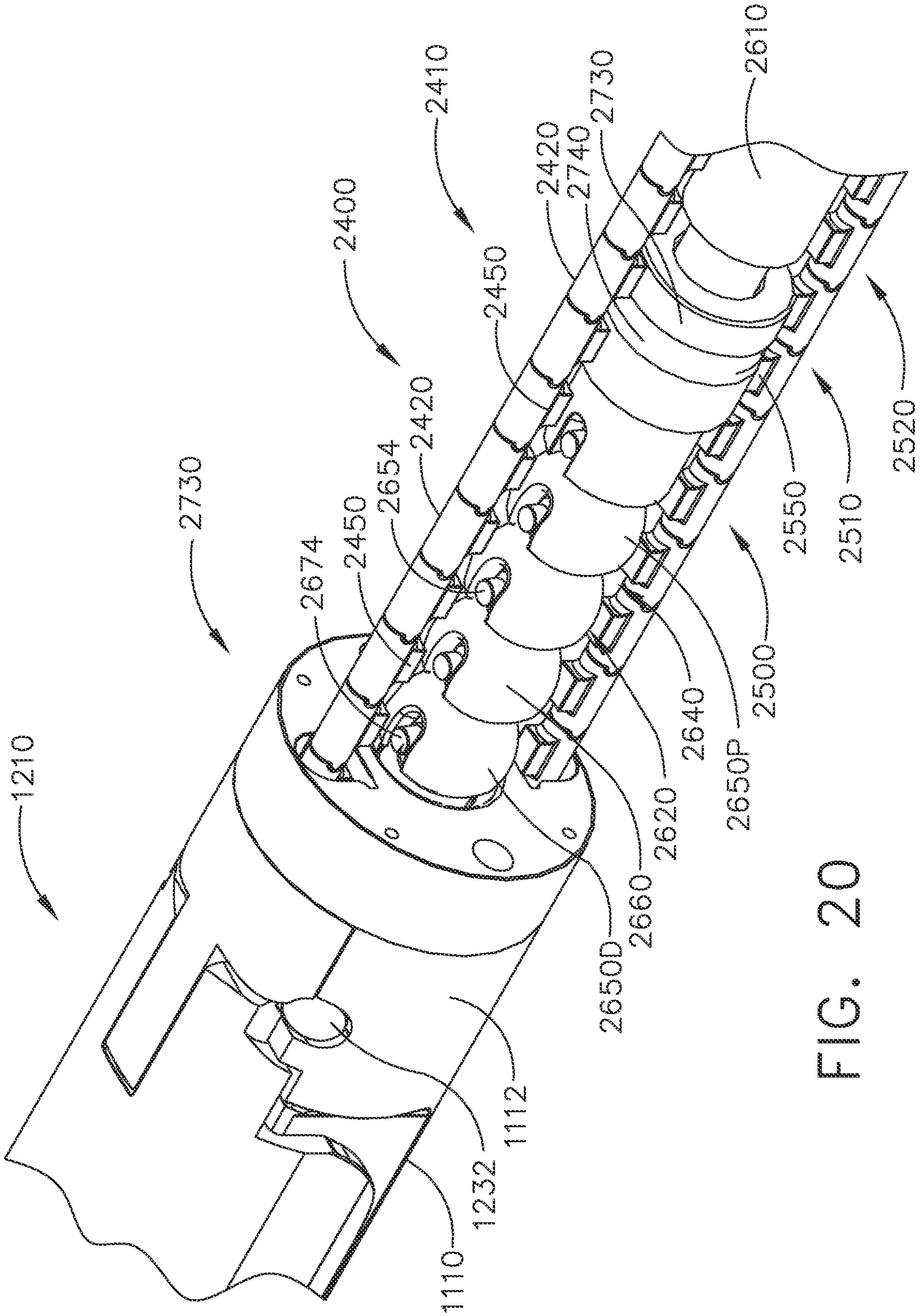
FIG. 20 is a partial perspective view of a proximal end portion of the surgical end effector and portions of the firing system and the rotary drive system of the surgical instrument of FIG. 1.
Figure 21:
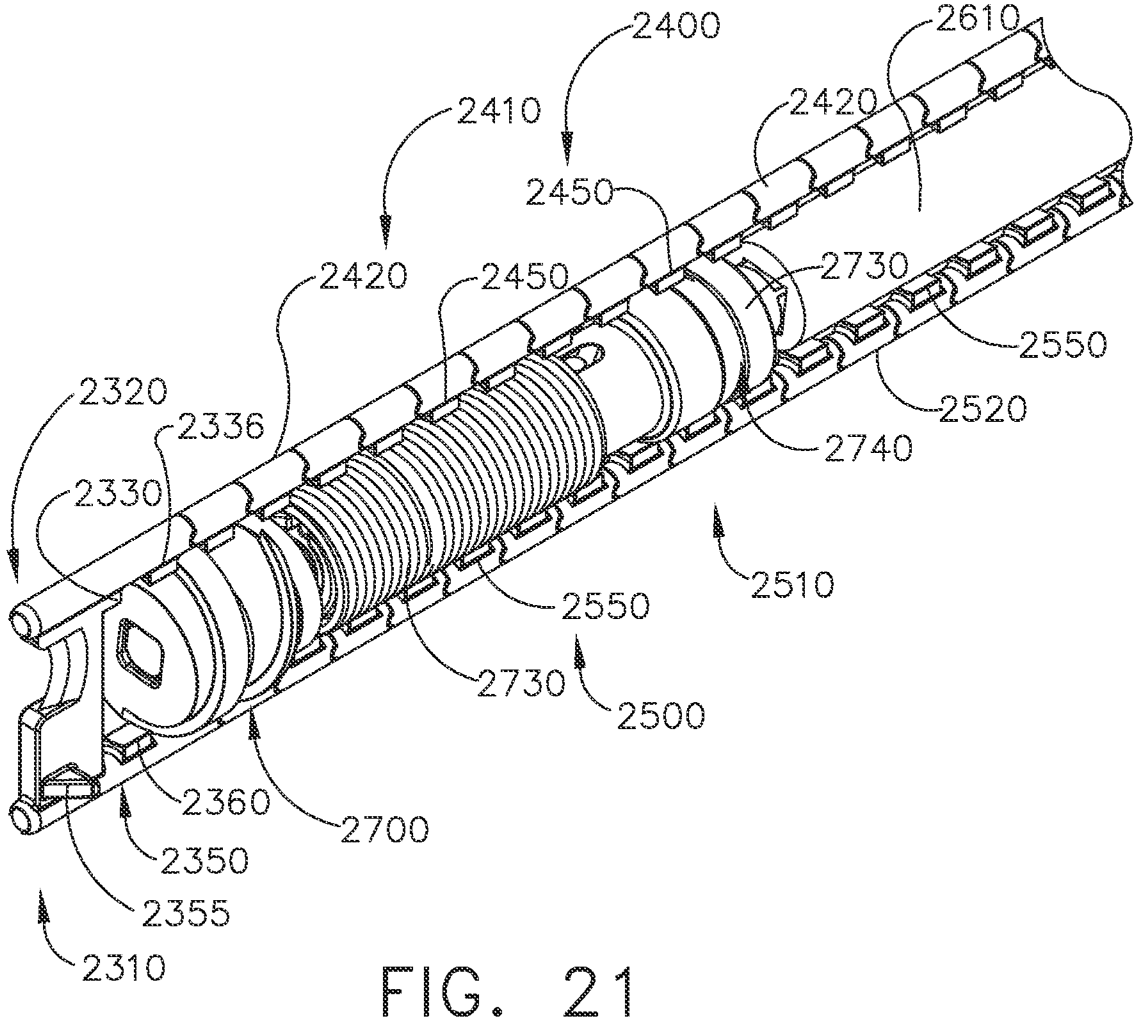
FIG. 21 is a perspective view of the rotary drive system of the surgical instrument of FIG. 1 in driving engagement with the firing system thereof in accordance with at least one aspect of the present disclosure.

To further ensure that the drive joints 2650 are always engaged with each other, a proximal drive spring 2740 is employed to apply an axial biasing force to the series 2640 of drive joints 2650. For example, as can be seen in FIGS. 8, 19, and 20, the proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring/bushing received on the proximal barrel portion 2638 of the proximal shaft segment 2632. The proximal drive spring 2740 lightly biases the drive joints 2650 together to decrease any gaps that may occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

As can be seen in FIGS. 9 and 10, the top firing member feature 2320 on the firing member 2310 comprises a distal upper firing member tooth segment 2330 that is equivalent to one half of an upper tooth 2450 on each upper vertebra member 2420. In addition, a proximal upper firing member tooth 2336 that is identical to an upper tooth 2450 on each upper vertebra member 2420 is spaced from the distal upper firing member tooth segment 2330. The distal upper firing member tooth segment 2330 and the proximal upper firing member tooth 2336 may be integrally formed with the top firing member feature 2320 of the firing member 2310. Likewise, the bottom firing member feature 2350 of the firing member 2310 comprises a distal lower firing member tooth 2360 and a proximal lower firing member tooth 2366 that are integrally formed on the bottom firing member feature 2350. For example, in at least one arrangement, the firing member 2310 with the rigidly attached teeth 2330, 2336, 2360, and 2366 may be fabricated at one time as one unitary component using conventional metal injection molding techniques.

As indicated above, each of the upper vertebra members 2520 is movably received on an upper flexible coupler member 2402 in the form of a top cable 2404. As was described above, the distal end 2406 of the top cable 2404 is secured to the top firing member feature 2320 of the firing member 2310. Similarly, each of the lower vertebra members 2520 is movably received on a lower flexible coupler member 2502 in the form of a lower cable 2504. A distal end 2506 of the lower cable 2504 is secured to the bottom firing member feature 2350 of the firing member 2310. In at least one arrangement, the top cable 2404 and the bottom cable 2504 extend through the proximal shaft portion 2100 and, as will be discussed in further detail below, may interface with a bailout arrangement supported in the housing for retracting the firing member 2310 back to its home or starting position should the firing member drive system fail.

Turning again to FIG. 8, the axial length $AL_u$ of the upper series 2410 of upper vertebra members 2420 and the axial length $AL_l$ of the lower series 2510 of lower vertebra members 2520 are equal and must be sufficiently long enough to facilitate the complete distal advancement of the firing member 2310 from the home or starting position to a distal-most ending position within the staple cartridge while the proximal-most upper vertebra members 2420 in the upper series 2410 of upper vertebra members 2420 and the proximal-most lower vertebra members 2520 in the lower series 2510 of lower vertebra members 2520 remain in driving engagement with the rotary drive screw 2700. As can be seen in FIG. 8, an upper compression limiting spring 2421 is configured to interface with a proximal-most upper vertebra member 2420P in the upper series 2410 of upper vertebra members 2420. The upper compression limiting spring 2421 is journaled on the top cable 2404 and is retained in biasing engagement with the proximal-most upper vertebra member 2420P by an upper spring holder 2423 that is retained in position by an upper ferrule 2425 that is crimped onto the top cable 2404. The top cable 2404 extends through an upper hypotube 2433 that is supported in the proximal support shaft. Likewise, a lower compression limiting spring 2521 is configured to interface with a proximal-most, lower vertebra member 2520P in the lower series 2510 of lower vertebra members 2520. The lower compression spring 2521 is journaled on the lower cable 2504 and is retained in biasing engagement with the proximal-most, lower vertebra member 2520P by a lower spring holder 2523 that is retained in position by a lower ferrule 2525 that is crimped onto the lower cable 2504. The lower cable 2504 extends through a lower hypotube 2533 that is supported in the proximal support shaft.

When the upper vertebra members 2420 and the lower vertebra members 2520 angle through the articulation joint (after the end effector has been positioned in an articulated position), the gaps between the respective vertebra members 2420, 2520 increase in each series 2410, 2510 which causes the springs 2421, 2521 to become tighter. The compression limiting springs 2421, 2521 provide enough slack in the cables 2404, 2504, respectively to enable the vertebra members 2420, 2520 angle through the most extreme articulation angles. If the cables 2404, 2504 are pulled too tight, the spring holders 2423, 2523 will contact their respective proximal-most vertebra members 2420P, 2520P. Such compression limiting arrangements ensure that the vertebra members 2420, 2520 in their respective series 2410, 2510 always remain close enough together so that the rotary drive screw 2700 will always drivingly engage them in the manner discussed in further detail below. When the vertebra members 2420, 2520 are aligned straight again, the compression limiting springs 2421, 2521 may partially relax while still maintaining some compression between the vertebra members.

As indicated above, when the upper vertebra members 2420 are arranged in the upper series 2410 and lower vertebra members 2520 are arranged in the lower series 2510, the convex mounds and concave recesses in each vertebra member as well as the compression limiter springs serve to maintain the upper and lower vertebra members in relatively linear alignment for driving engagement by the rotary drive screw 2700. As can be seen in FIGS. 9 and 10, when the upper vertebra members 2420 are in linear alignment, the upper teeth 2450 are spaced from each other by an opening space generally designated as 2460 that facilitates driving engagement with the helical drive thread 2170 on the rotary drive screw. Similarly, when the lower vertebra members 2520 are in linear alignment, the lower vertebra member teeth 2550 are spaced from each other by an opening space generally designated as 2560 that facilitates driving engagement with the helical drive thread 2170 of the rotary drive screw 2700.

Figure 22:
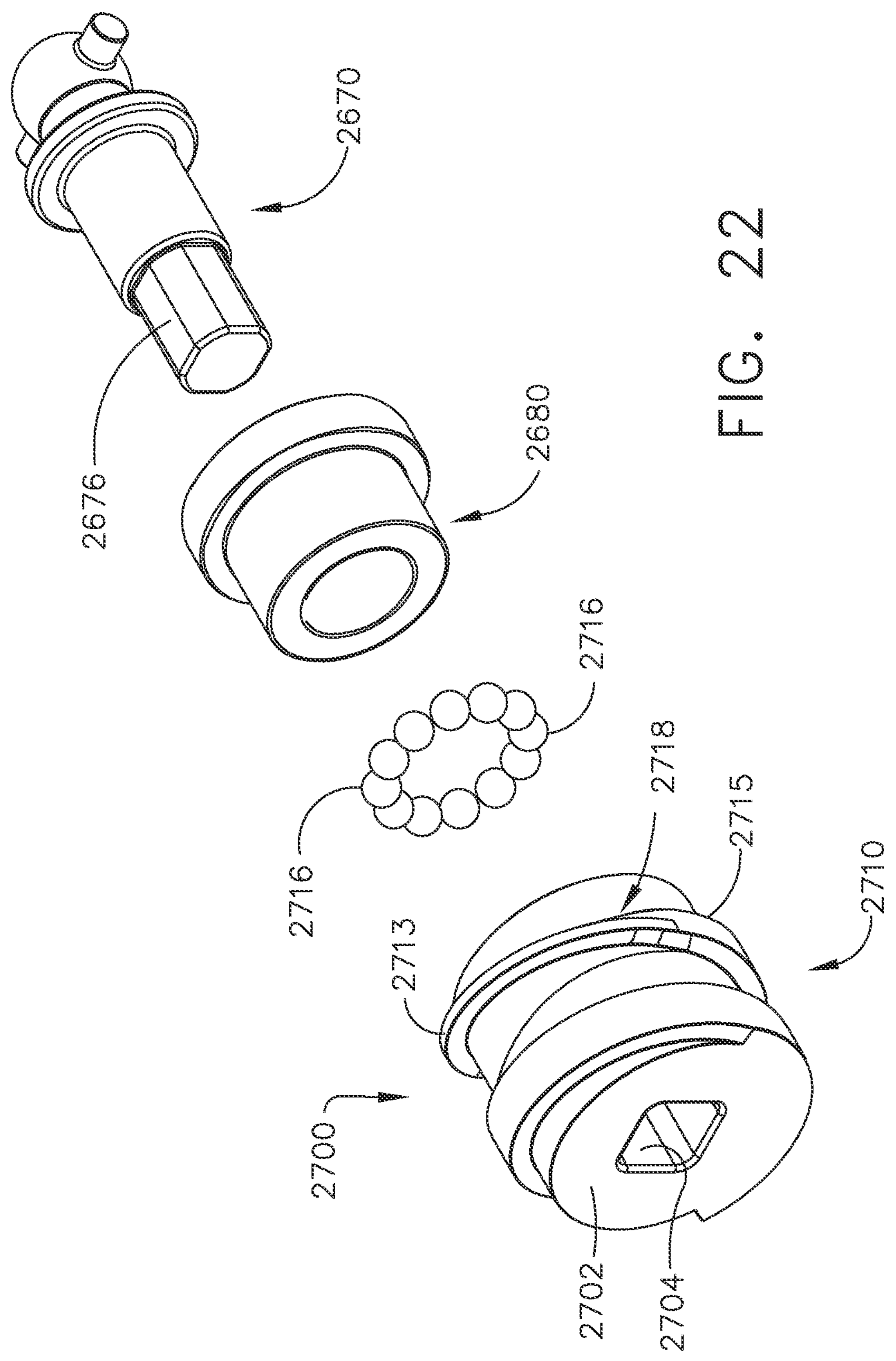
FIG. 22 is an exploded perspective view of the rotary drive screw and thrust bearing arrangement of the firing system of FIG. 21.

Turning to FIGS. 8 and 22, the rotary drive screw 2700 comprises a screw body 2702 that has a socket 2704 therein for receiving the distally extending shaft stem 2676 of the distal CV drive shaft 2670. An internal radial groove 2714 (FIG. 10) is formed in the screw body 2702 for supporting a plurality of ball bearings 2716 therein. In one arrangement, for example, 12 ball bearings 2716 are employed. The radial groove 2714 supports the ball bearings 2716 between the screw body 2702 and a distal end of the thrust bearing housing 2680. The ball bearings 2716 serve to distribute the axial load of the rotary drive screw 2700 and significantly reduce friction through the balls' rolling motion.

Figure 24:
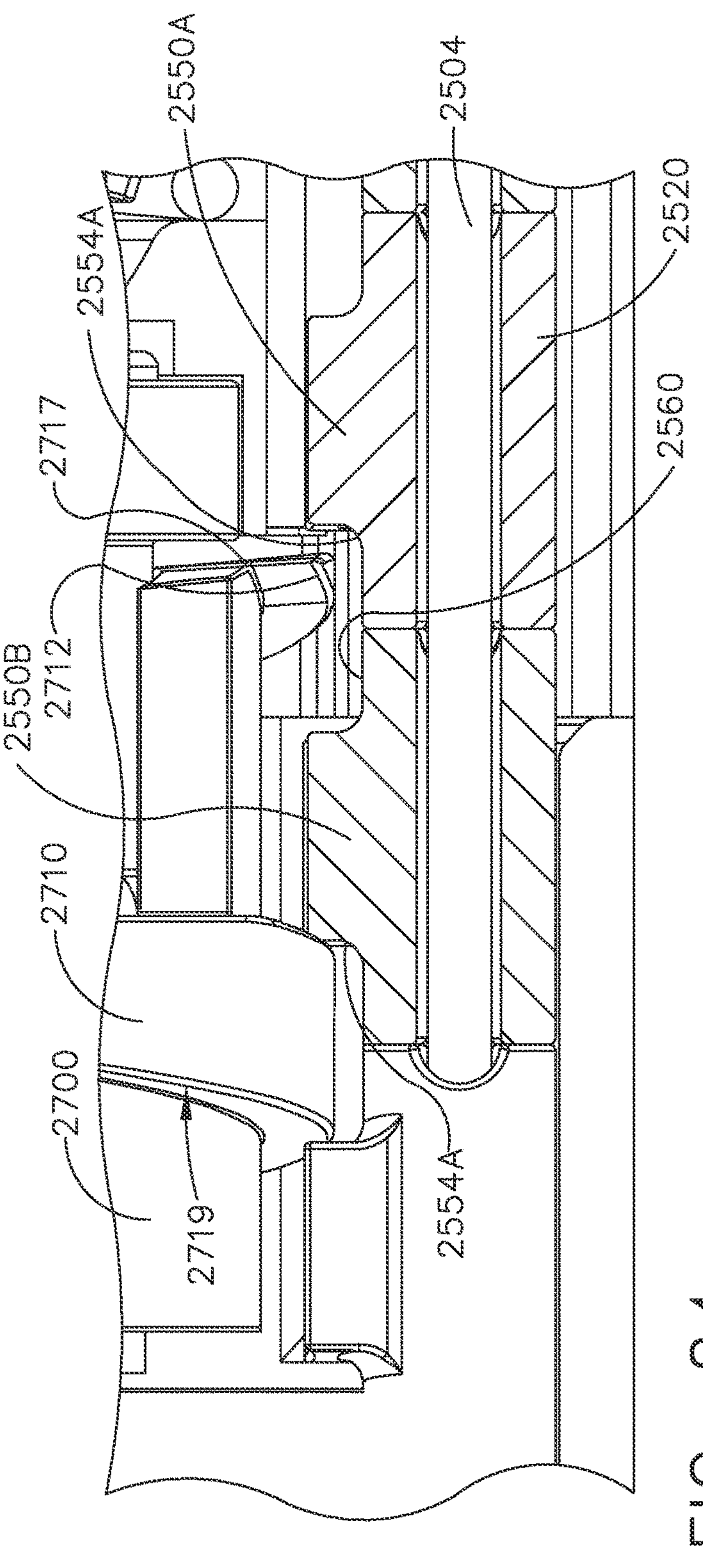
FIG. 24 is a partial cross-sectional side view of a portion of the lower flexible spine assembly and a portion of the firing member of FIG. 21 in driving engagement with a portion of the rotary drive screw.
Figure 23:
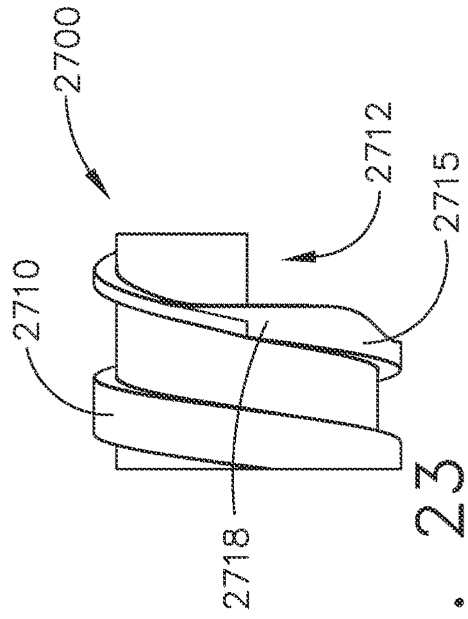
FIG. 23 is a side view of the rotary drive screw of FIG. 22.

As can be seen in FIG. 23, a helical drive thread 2710 is provided around the screw body 2702 and serves to form a proximal thread scoop feature 2712. The proximal thread scoop feature 2712 is formed with a first pitch 2713 and the remaining portion of the helical drive thread 2710 is formed with a second pitch 2715 that differs from the first pitch 2713. In FIGS. 22 and 23, area 2718 illustrates where the first pitch 2713 and the second pitch 2715 converge. In at least one embodiment, the first pitch 2713 is larger than the second pitch 2715 to ensure that the rotary drive screw 2700 captures and "scoops up" or drivingly engages every upper vertebra member 2420 and every lower vertebra member 2520. As can be seen in FIG. 24, a proximal end 2717 of the helical drive thread 2710 that has the first pitch 2713 has scooped into the into the opening space 2560 between two adjacent lower vertebra member teeth 2550A and 2550B while the center portion 2719 of the helical drive thread 2710 that has the second pitch 2715 is in driving engagement with the helix-shaped distal lower face portion 2554 on the lower vertebra member tooth 2550B and the helix-shaped proximal lower face portion 2552 on the proximal lower firing member tooth 2366. As can also be appreciated, the scoop feature 2712 may not contact the helix-shaped distal lower face portion 2554A of the lower vertebra member tooth 2550A as it scoops up the lower vertebra member tooth 2550B when driving the firing member 2310 distally. The helical drive thread 2710 interacts with the teeth 2450 of the upper vertebra members 2420 in a similar manner.

A power screw is a threaded rod with a full three hundred sixty degree nut around it. Rotation of the power screw causes the nut to advance or move longitudinally. In the present arrangements, however, due to space constraints, a full three hundred sixty degree nut cannot fit inside the end effector. In a general sense, the upper flexible spine assembly 2400 and the lower flexible spine assembly 2500 comprise a radially/longitudinally segmented "power screw nut" that is rotatably driven by the rotary drive screw 2700. When the rotary drive screw is rotated in a first rotary direction, the rotary drive screw 2700 drives one or more vertebra members in each of the upper series and lower series of vertebra members longitudinally while the vertebra members 2420, 2520 stay in the same locations radially. The upper series 2410 and lower series 2510 are constrained from rotating around the rotary drive screw 2700 and can only move longitudinally. In one arrangement, the upper vertebra members 2420 in the upper series 2410 and the lower vertebra members 2520 in the lower series 2510 only surround the rotary drive screw 2700 with less than ten degrees each.

Figure 25:
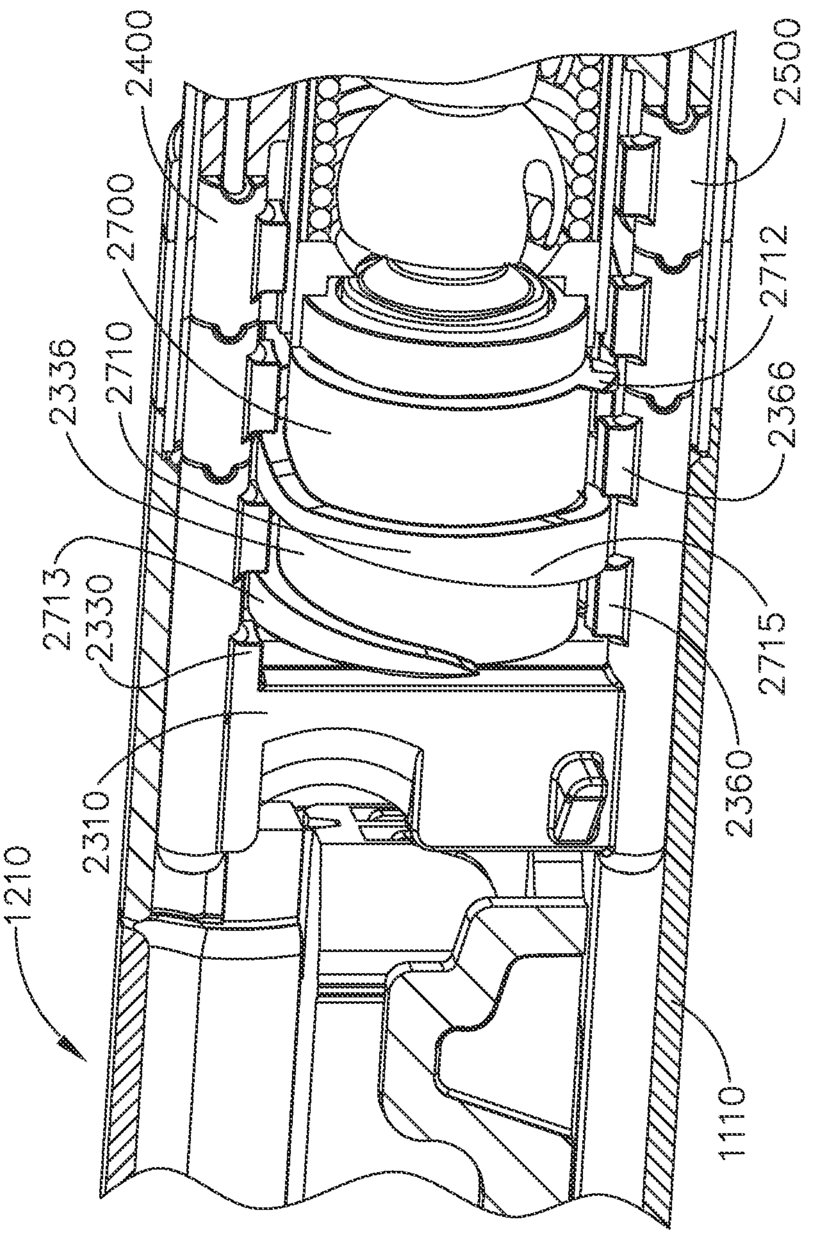
FIG. 25 is a perspective view of the firing member in a home or starting position within the surgical end effector of the surgical instrument of FIG. 1.
Figure 26:
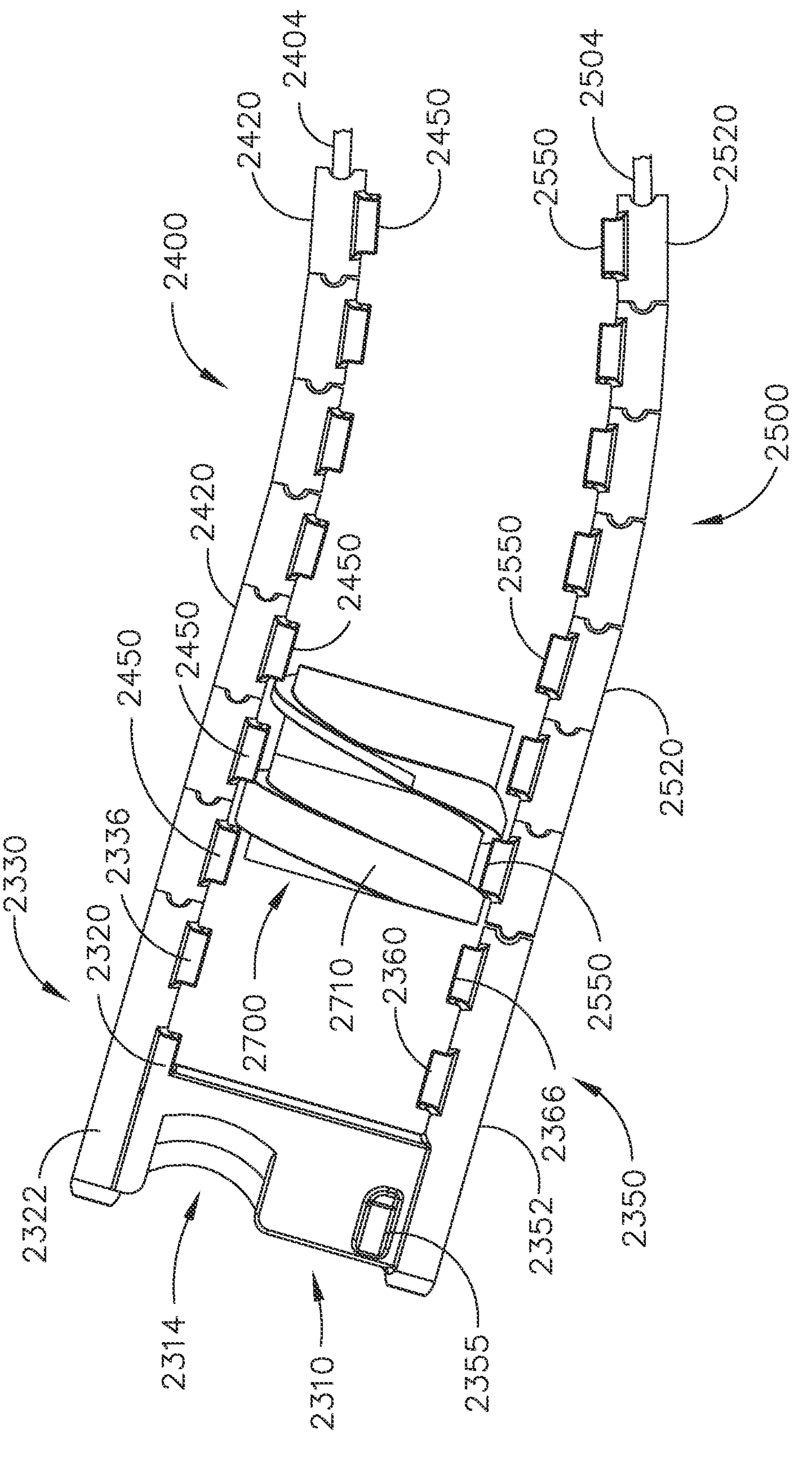
FIG. 26 is a side view illustrating the upper flexible spine assembly and the lower flexible spine assembly of FIG. 21 in driving engagement with the rotary drive screw after the firing member has been driven distally from a home or starting position.

FIG. 25 illustrates the firing member 2310 in the home or starting position. As can be seen in FIG. 25, a portion of the helical drive thread 2710 on the rotary drive screw 2700 is engaged between the distal upper firing member tooth segment 2330 and the proximal upper firing member tooth 2336 and another portion of the helical drive thread 2710 is engaged between the distal lower firing member tooth 2360 and a proximal lower firing member tooth 2366 on the firing member 2310. Such arrangement enables the rotary drive screw 2700 to precisely control the distal and proximal movement of the firing member 2310 which, as will be discussed in further detail below, can result in the precise movement of the anvil 1210. Once the firing member 2310 has been sufficiently distally advanced during a firing stroke, the helical drive thread 2710 operably engages the teeth on the upper and lower vertebras. See FIG. 26.

Figure 27:
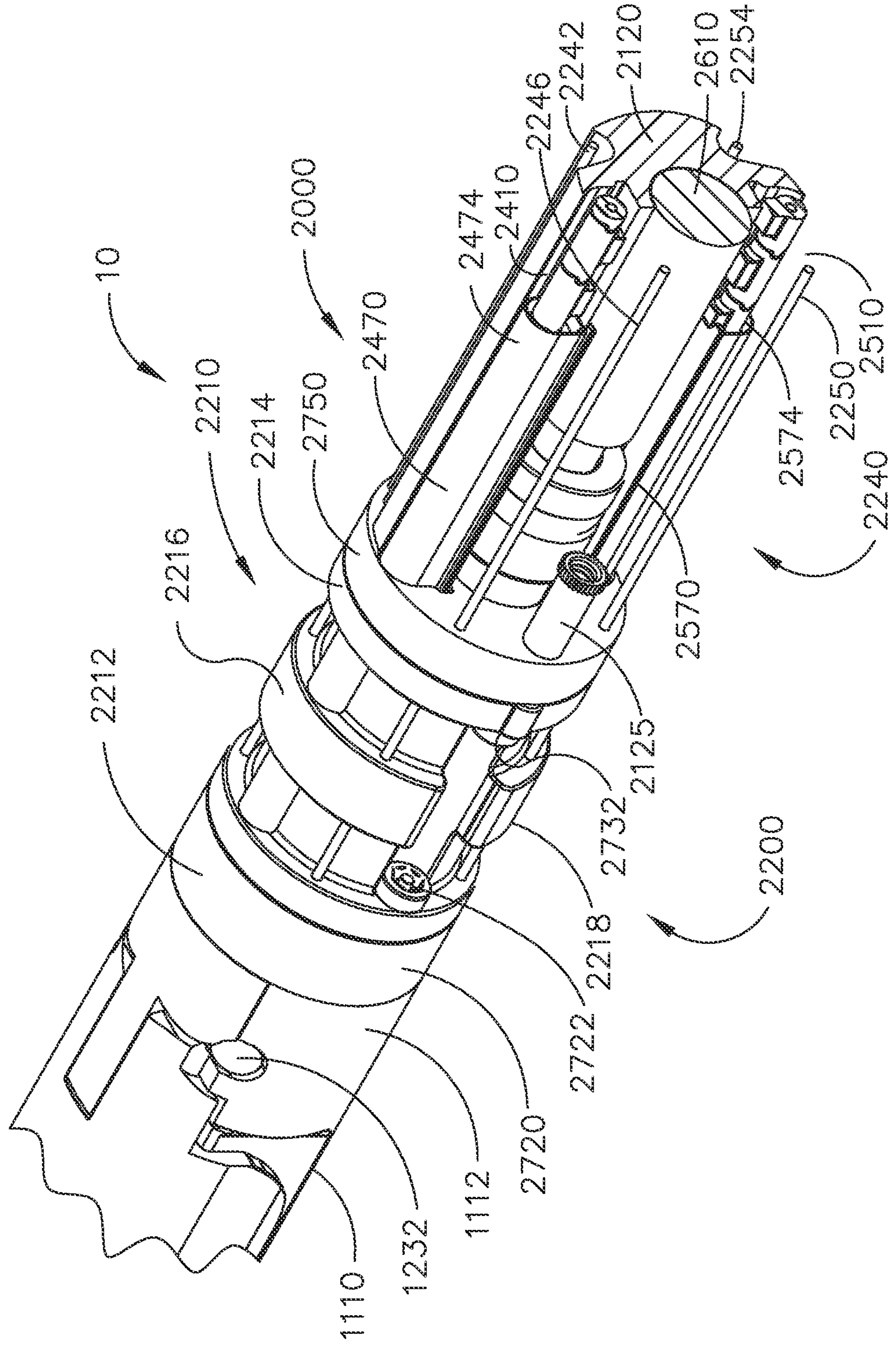
FIG. 27 is a partial cross-sectional perspective view of a portion of the surgical end effector, firing system and rotary drive system of the surgical instrument of FIG. 1 according to at least one aspect of the present disclosure with an outer elastomeric joint assembly of an articulation joint omitted for clarity.
Figure 29:
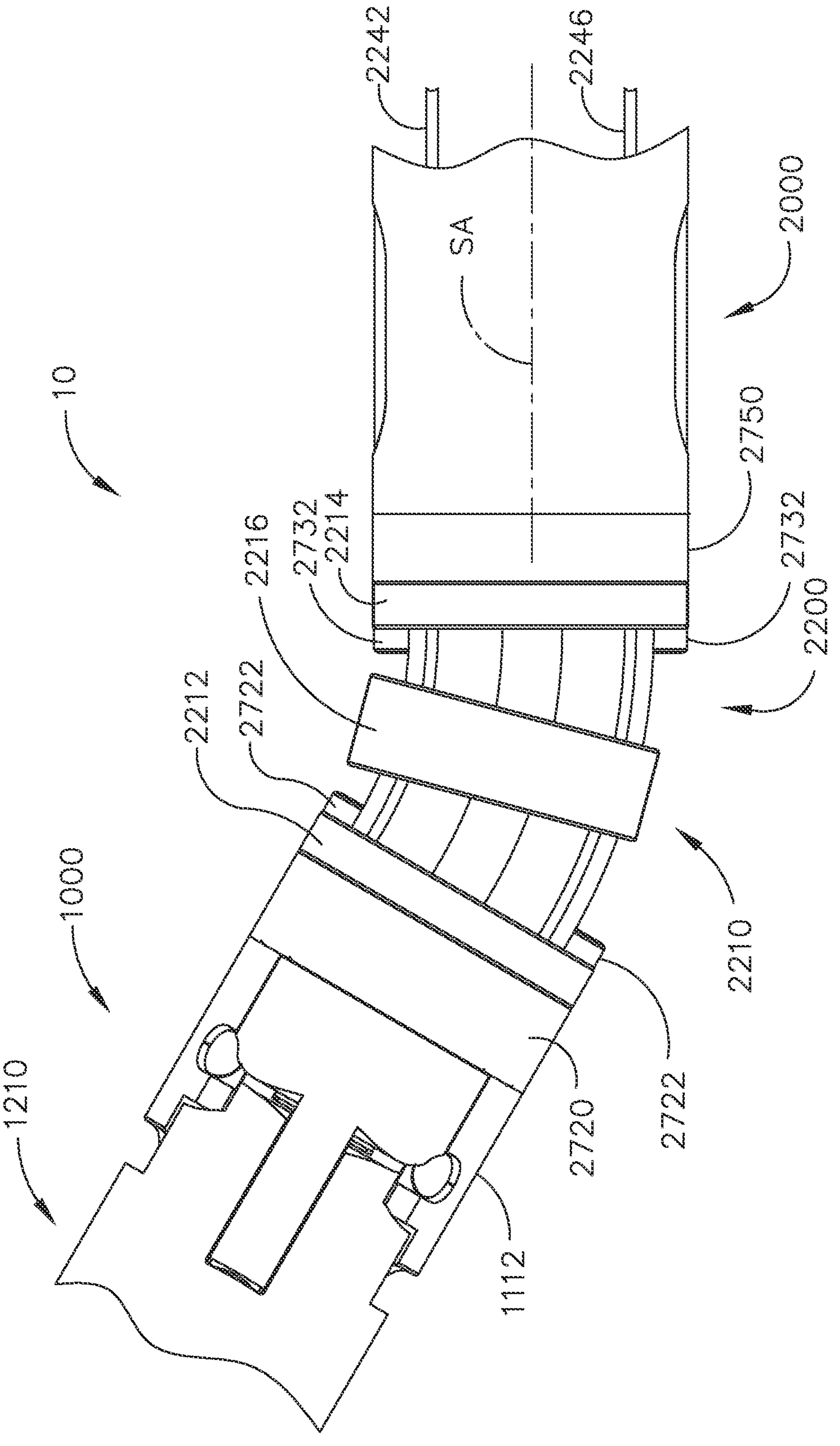
FIG. 29 is a top view of the surgical end effector of FIG. 27 articulated in a first direction relative to a portion of the elongate shaft assembly in accordance with at least one aspect of the present disclosure.
Figure 30:
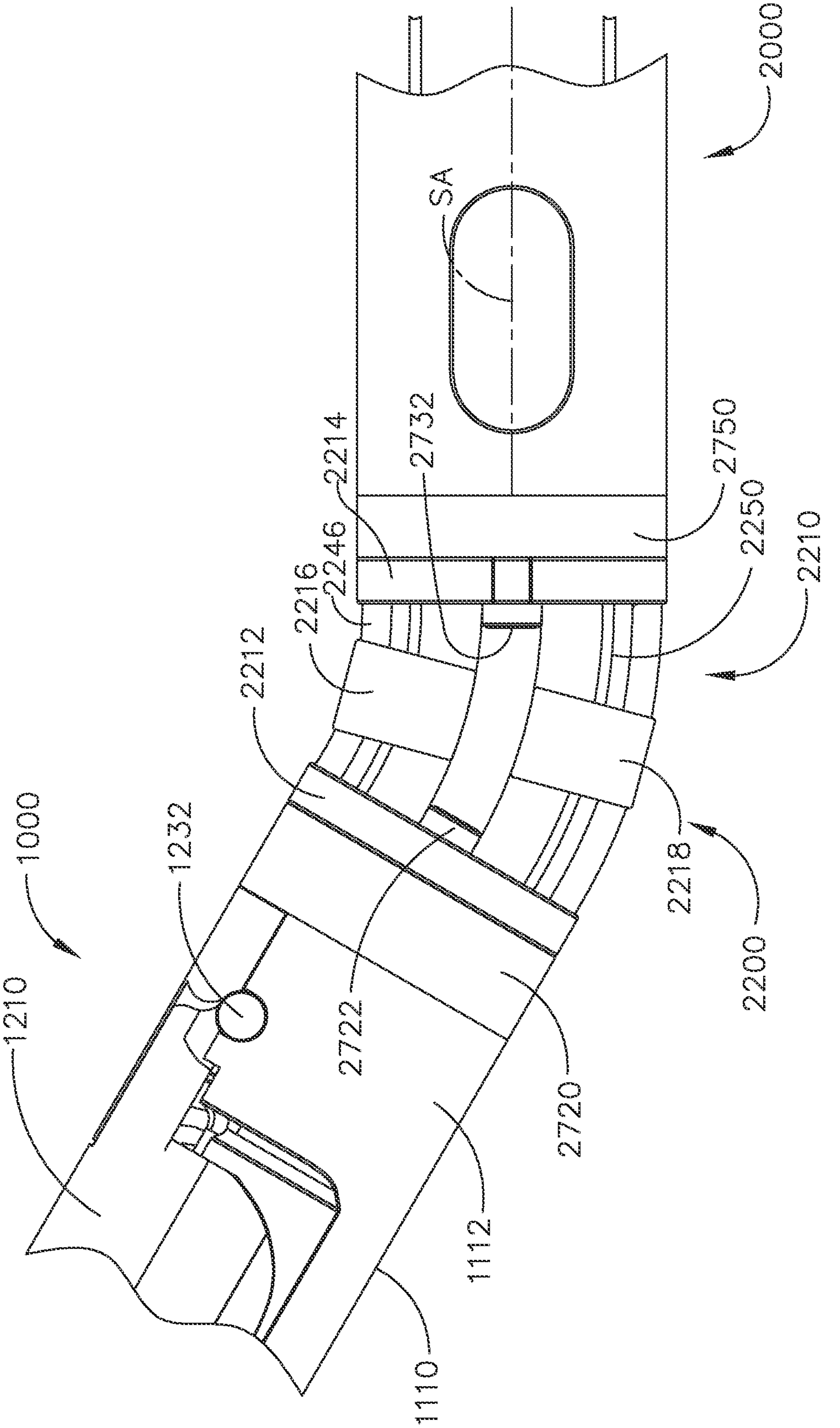
FIG. 30 is a side view of the surgical end effector of FIG. 29 articulated in another direction relative to a portion of the elongate shaft assembly in accordance with at least one aspect of the present disclosure.
Figure 31:
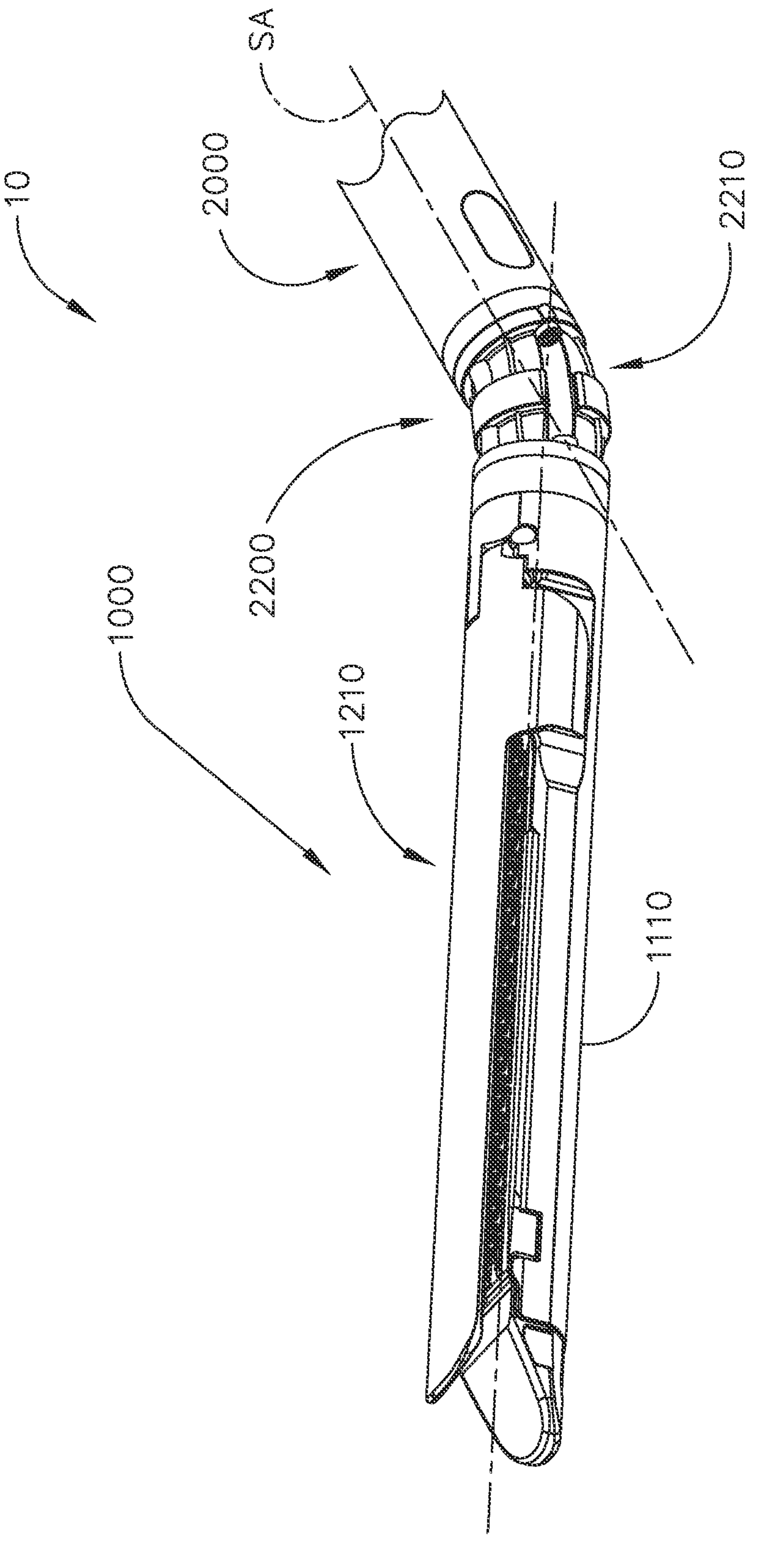
FIG. 31 is a perspective view of the surgical end effector of FIG. 29 articulated in multiple planes with respect to a portion of the elongate shaft assembly in accordance with at least one aspect of the present disclosure.

The surgical instrument 10 also comprises an articulation system 2240 that is configured to apply articulation motions to the surgical end effector 1000 to articulate the surgical end effector relative to the elongate shaft assembly 2000. In at least one arrangement, for example, the articulation system comprises four articulation cables 2242, 2246, 2250, and 2254 that extend through the elongate shaft assembly 2000. See FIG. 27. In the illustrated arrangement, the articulation cables 2242, 2246 pass through the proximal mounting bushing 2750, the proximal end 2214 of the elastomeric joint assembly 2210, as well as a central rib segment 2216 to be secured to the distal end 2212 of the elastomeric joint assembly 2210 or other portion of the surgical instrument. Likewise, the articulation cables 2250 and 2254 extend through the proximal mounting bushing 2750, the proximal end 2214 of the elastomeric joint assembly 2210, as well as a central rib segment 2218 to be secured to the distal end 2212 of the elastomeric joint assembly 2210 or other portion of the surgical end effector. The cables 2242, 2246, 2250, and 2254 operably interface with an articulation control system that is supported in the housing of the surgical instrument 10. For example, a proximal portion of each cable 2242, 2246, 2250, and 2254 may be spooled on a corresponding rotary spool or cable-management system 2007 (FIG. 2) in the housing portion of the surgical instrument 10 that is configured to payout and retract each cable 2242, 2246, 2250, and 2254 in desired manners. The spools/cable management system may be motor powered or manually powered (ratchet arrangement, etc.). FIG. 29 illustrates articulation of the surgical end effector 1000 through a first articulation plane relative to the elongate shaft assembly 2000. FIG. 30 illustrates articulation of the surgical end effector 1000 through a second articulation plane relative to the elongate shaft assembly 2000. FIG. 31 illustrates articulation of the surgical end effector 1000 through multiple articulation planes relative to the elongate shaft assembly 2000.

Figure 32:
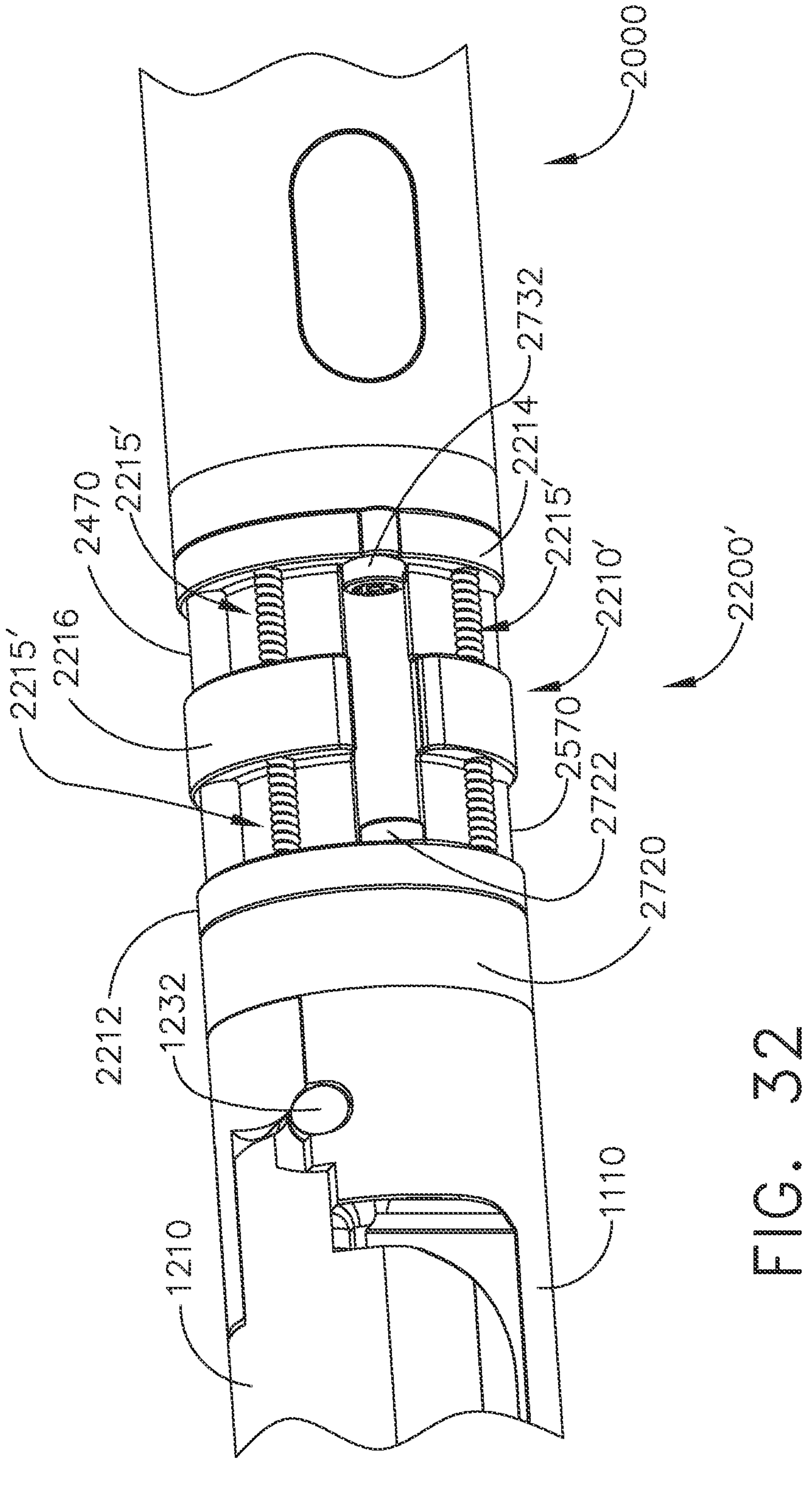
FIG. 32 is a side elevational view of a portion of another surgical instrument that employs another outer elastomeric joint assembly in accordance with at least one aspect of the present disclosure.
Figure 33:
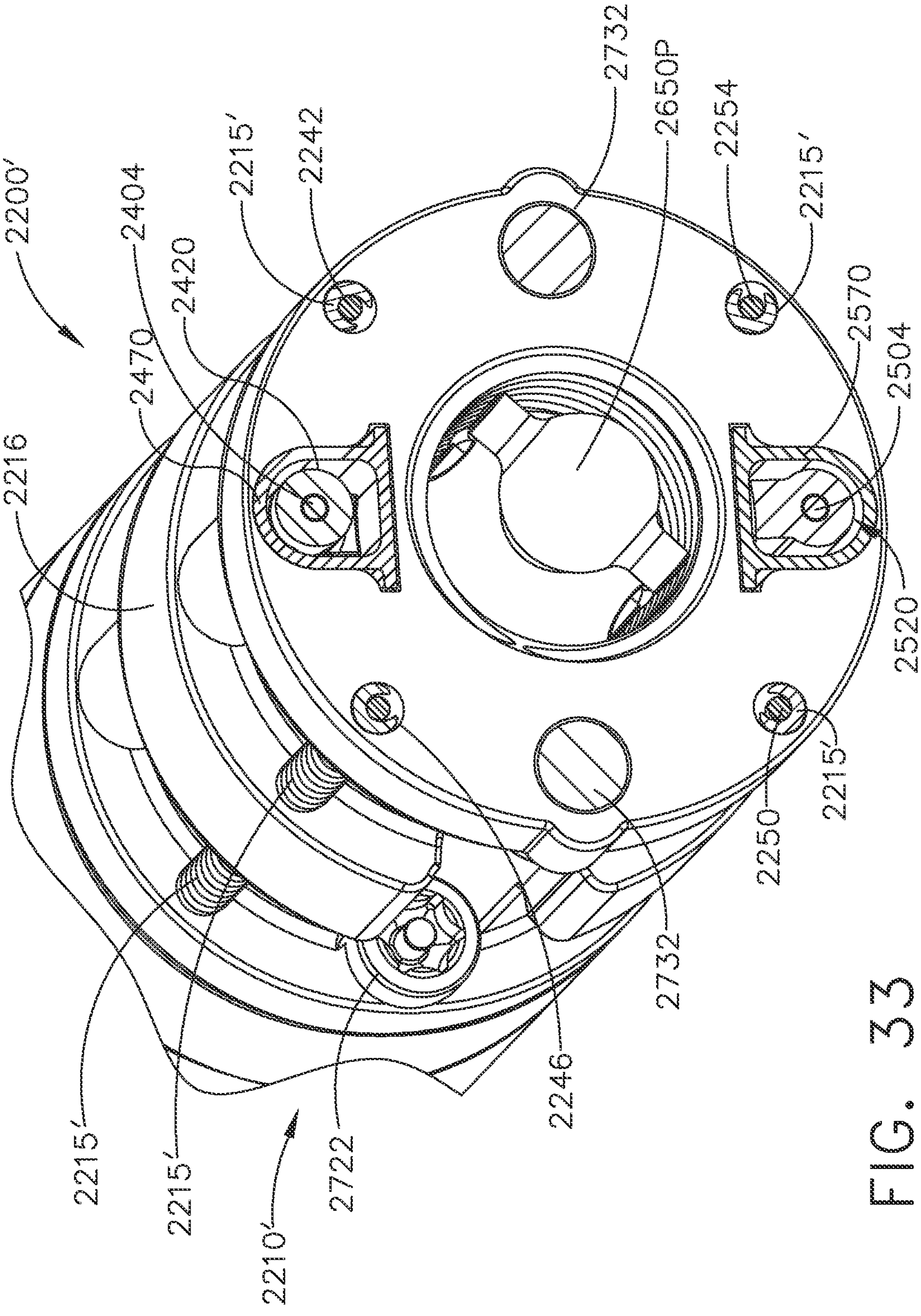
FIG. 33 is a partial cross-sectional perspective view of the surgical instrument of FIG. 32.
Figure 34:
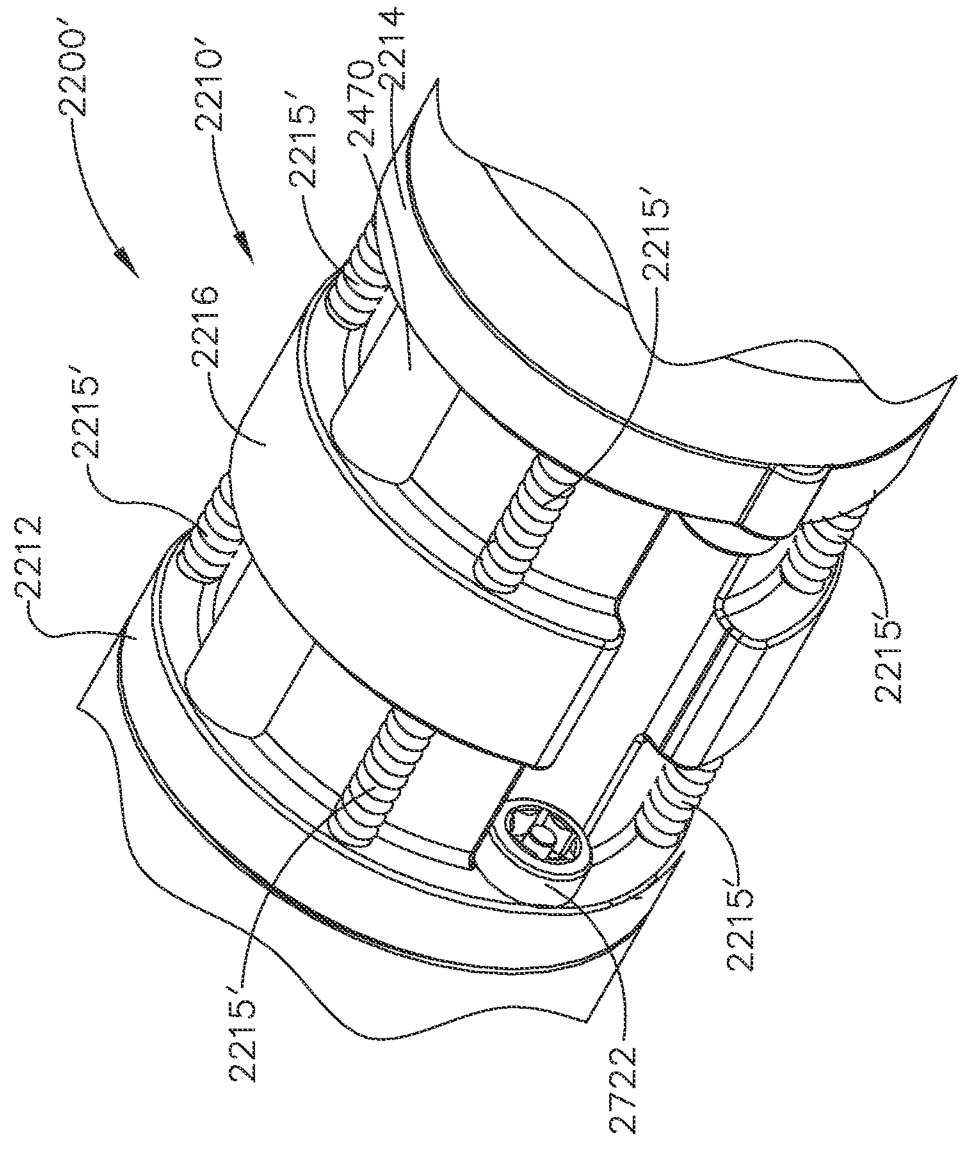
FIG. 34 is a perspective view of a portion of the outer elastomeric joint assembly of FIG. 32.

FIGS. 32-34 illustrate an alternative articulation joint 2200' in the form of an elastomeric joint assembly 2210'. As can be seen in FIG. 33, each articulation cable passes through a corresponding spring 2215' that is mounted in the ribs 2216' of the elastomeric joint assembly 2210'. For example, cable 2242 extends through spring 2244. Cable 2246 extends through spring 2248. Cable 2250 extends through spring 2252 and cable 2254 extends through spring 2256. As indicated above, the end effector is articulated by pulling on and relaxing the appropriate cables 2242, 2246, 2250 and 2254. To achieve higher articulation angles with greater joint stability, each of the springs 2244, 2248, 2252, and 2256 can slide through the ribs of the elastomeric joint to push the end effector and pull on the cables extending therethrough. The springs 2244, 2248, 2252, and 2256 will also retract into the ribs when the cables 2242, 2246, 2250, and 2254 are pulled tight. Each of the springs 2244, 2248, 2252, and 2256 loosely seat over the particular cable that passes therethrough. Each cable and corresponding spring may terminate or otherwise be coupled to a corresponding solid rod that is supported in the elongate shaft assembly 2000 and may be pushed and pulled from its proximal end. When the cable is pulled, the corresponding spring would carry little to no load. When the spring is pushed, the cable would carry little load, but will help limit the end effector movement. This interaction between the cable and spring may facilitate higher articulation angles that may approach ninety degrees, for example.

Figure 28:
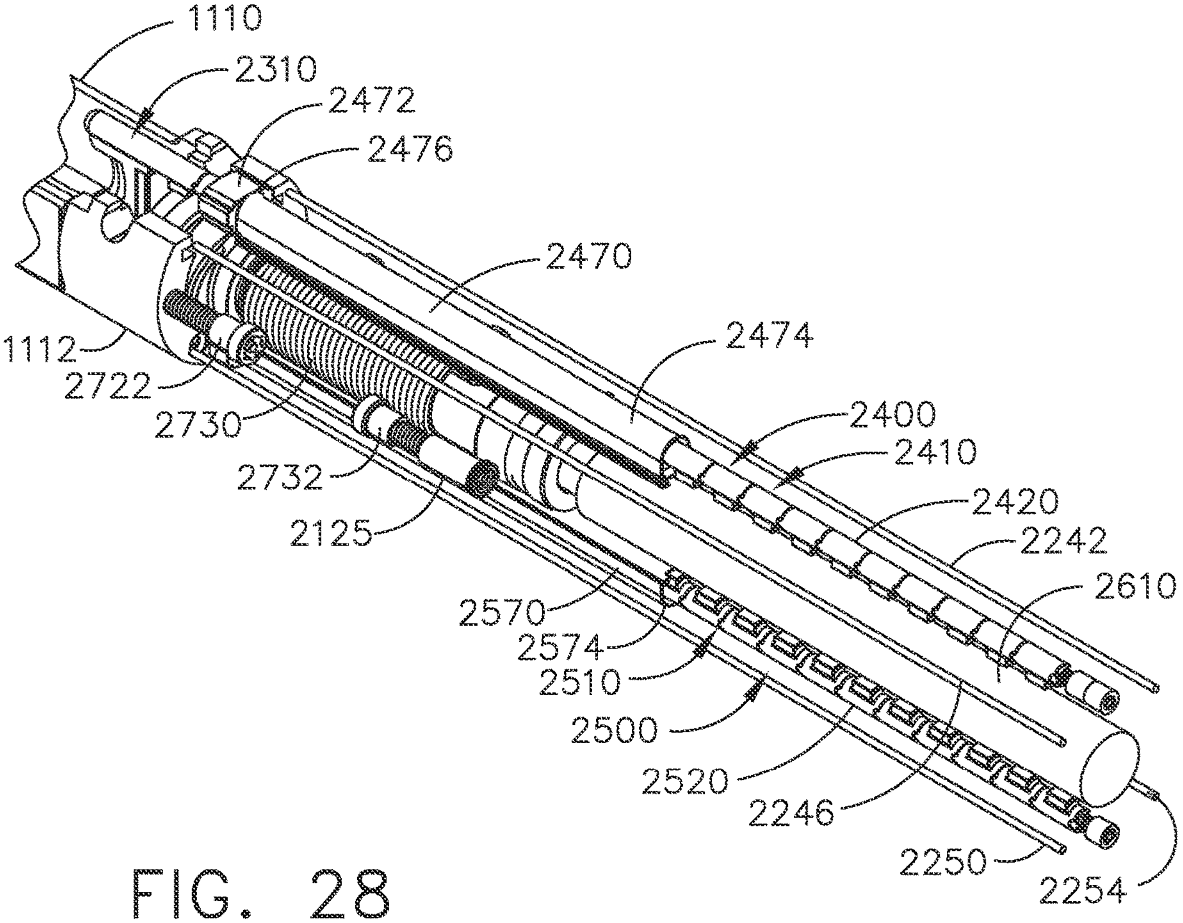
FIG. 28 is another partial perspective view of a portion of the surgical end effector, firing system and rotary drive system of FIG. 27 with an outer elastomeric joint assembly of an articulation joint and portions of the elongate shaft assembly omitted for clarity.
Figure 35:
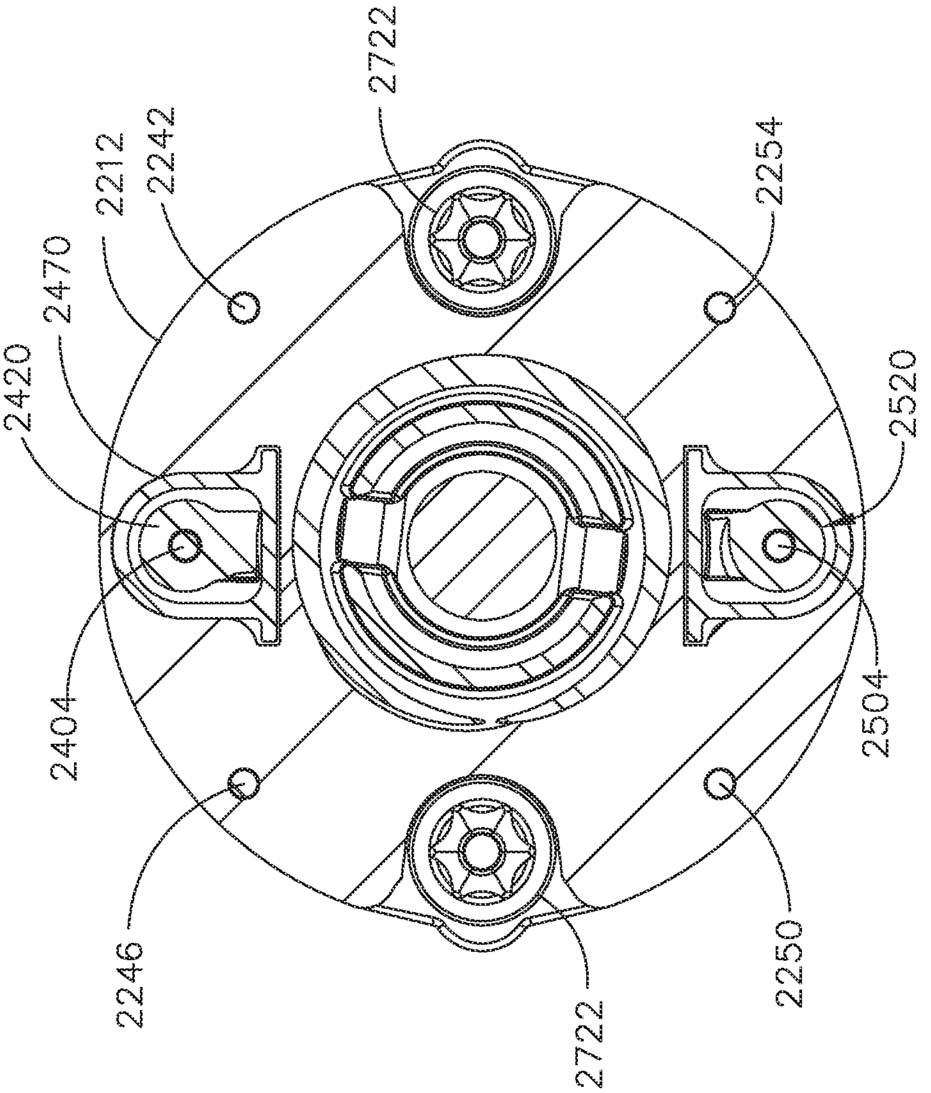
FIG. 35 is a cross-sectional end view of a portion of the surgical instrument of FIG. 19 taken along lines 35-35 in FIG. 19.

Because the radially/longitudinally segmented power screw nut arrangement disclosed herein does not have the same constraints as a three hundred sixty degree nut, the upper vertebra members 2420 in the upper series 2410 and the lower vertebra members 2520 in the lower series 2510 are constrained to ensure that their loads are transferred to the firing member in a longitudinal direction. To maintain each of the upper vertebra members 2420 in the desired orientation and to prevent the upper vertebra members 2420 from becoming snagged or disoriented when traversing through the articulation joint 2200, the upper vertebra members 2420 are aligned to pass through an upper sleeve 2470 that extends through an upper portion of the outer elastomeric joint assembly 2210 of the articulation joint 2200. See FIGS. 27, 28, and 35. A distal end 2472 of the upper sleeve 2470 is supported in the proximal end 1112 of the elongate channel 1110 and a proximal end 2474 of the upper sleeve 2470 is supported in the distal end of the proximal support shaft 2120. The upper sleeve 2470 is fabricated from a polymer or plastic material that has a low coefficient of friction and is flexible to enable the upper sleeve 2470 to flex with the outer elastomeric joint assembly 2210. The upper sleeve 2470 protects the upper vertebra members 2420 from contacting the outer elastomeric joint assembly 2210 that is fabricated from an elastomeric material that may have a higher coefficient of friction than the coefficient of friction of the material of the upper sleeve 2470. Stated another way, the upper sleeve 2470 forms a low friction, flexible, continuous, uninterrupted, and fully encapsulating path for the upper vertebra members 2420 as they traverse the articulation joint 2200.

Similarly, a lower sleeve 2570 is employed to support the lower vertebra members 2520 as they pass through the articulation joint 2200. A distal end 2572 of the lower sleeve 2570 is supported in the proximal end of the elongate channel and a proximal end of the lower sleeve 2570 is supported in the distal end of the proximal support shaft 2120. Like the upper sleeve 2470, the lower sleeve 2570 is fabricated from a polymer or plastic material that has a low coefficient of friction and is flexible to enable the lower sleeve 2570 to flex with the outer elastomeric joint assembly 2210. The lower sleeve 2570 protects the lower vertebra members 2520 from contacting the outer elastomeric joint assembly 2210 as they pass through the articulation joint 2200. Stated another way, the lower sleeve 2570 forms a low friction, flexible, continuous, uninterrupted, and fully encapsulating path for the lower vertebra members 2520 as they traverse the articulation joint 2200. In various embodiments, the upper sleeve 2470 and the lower sleeve 2570 are configured to bend freely without creating a kink. To prevent the formation of kinks in the sleeves, in at least one arrangement, the sleeves 2470, 2570 are supported within the outer elastomeric joint assembly 2210 such that the sleeves may move axially. For example, when the articulation joint angles up, the lower sleeve 2570 may slide distally and have a large bend radius; the upper sleeve 2470 in the same example, may slide proximally and have a tighter bend radius. By moving axially, the amount of material exposed outside of the joint assembly 2210 which might otherwise be susceptible to kinking under a tight bend radius is reduced. In at least one arrangement, the distal end 2472 of the upper sleeve 2470 is formed with an upper scoop 2476 that is configured to funnel the upper vertebra members 2420 into the anvil cap 1260. Similarly, the distal end of the lower sleeve 2570 may be formed with a lower scoop that is configured to funnel the lower vertebra members 2520 into the channel slot 1140 in the elongate channel 1110.

Figure 36:
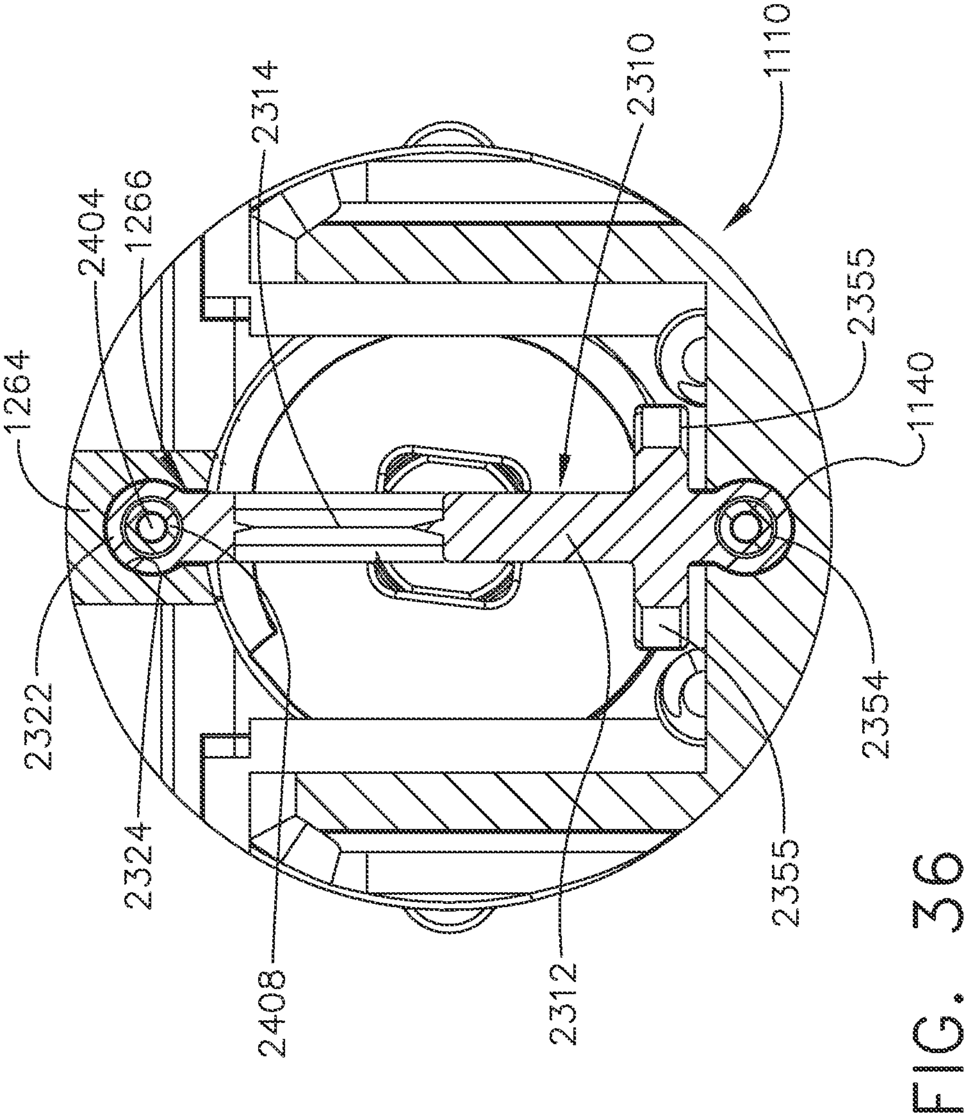
FIG. 36 is a cross-sectional end view of a portion of the surgical instrument of FIG. 19 taken along lines 36-36 in FIG. 19.
Figure 37:
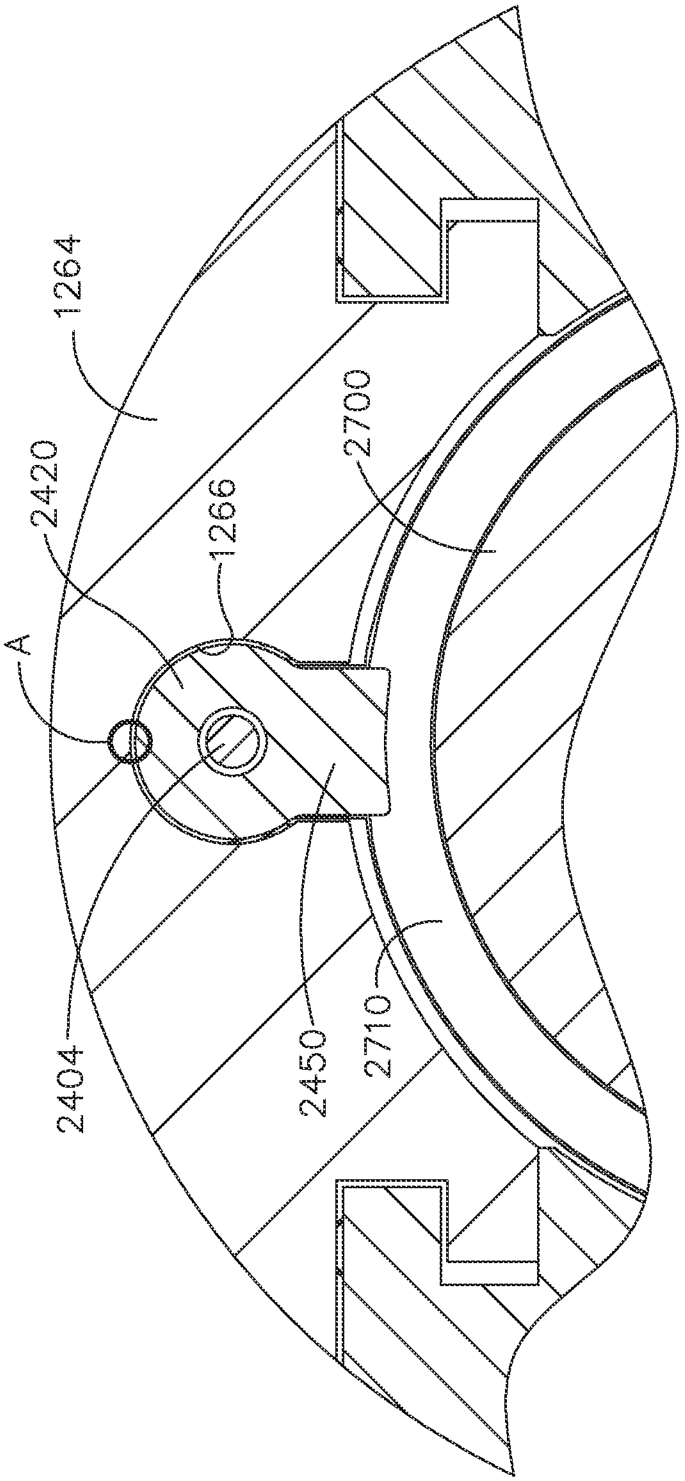
FIG. 37 is a partial cross-sectional view of a portion of an anvil cap and an upper vertebra member of the surgical instrument of FIG. 19 in accordance with at least one aspect of the present disclosure.

As indicated above, the anvil mounting portion 1230 comprises a pair of laterally extending mounting pins 1232 that are configured to be received in corresponding mounting cradles or pivot cradles 1120 that are formed in the proximal end 1112 of the elongate channel 1110. The mounting pins 1232 are pivotally retained within the mounting cradles 1120 by an anvil cap 1260 that is attached to the proximal end 1112 of the elongate channel 1110 in the above-described manners. The anvil cap 1260 comprises a proximal end 1262 and a distal end 1264 and has a keyhole-shaped vertebra passage 1266 extending therethrough to accommodate passage of the top firing member feature 2320 and upper vertebra members 2420 therethrough. FIG. 36 illustrates the vertebra passage 1266 in the anvil cap 1260. When the rotary drive screw 2700 applies load to the upper vertebra members 2420, the vertebra members 2420 will tend to tilt about the area A in FIG. 37, so the upper vertebra member tooth 2450 is no longer square with the rotary drive screw 2700 and may instead experience a higher-pressure line contact. Areas B in FIG. 37 show where the upper vertebra member 2420 stops tilting. To ensure that most of the loads stay in the longitudinal direction to perform useful work, the upper vertebra member tooth 2450 must be angled the same amount as the upper vertebra member 2420 tilts. Thus, when the upper vertebra member 2420 tilts, the upper vertebra member tooth 2450 will still maintain surface contact with the helical drive member 2710 on the rotary drive screw 2700 and all loads will be directed longitudinally and not vertically. The slightly angled upper vertebra member tooth 2450 may behave like a square thread when the vertebra member 2420 is tilted and better distributes loads to lower the pressure contact. By directing most of the loads in the longitudinal direction, vertical loads are avoided which could result in the establishment of friction that would counter the longitudinal loads. The upper vertebra members 2420 react similarly as they pass down the keyhole-shaped anvil slot 1240. Likewise, the lower vertebra members 2520 react similarly as they pass through the keyhole-shaped axially extending channel slot 1140 in the elongate channel 1110.

Figure 38:
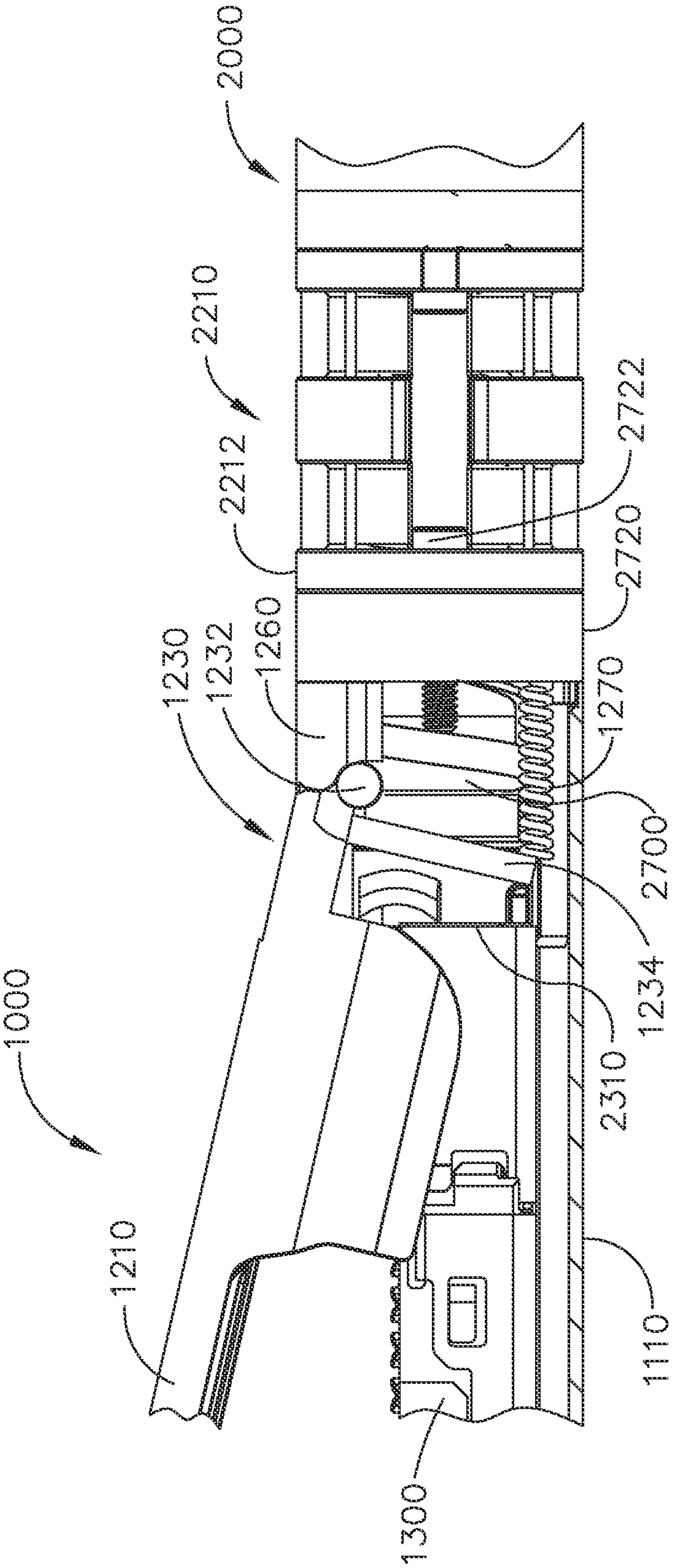
FIG. 38 is a side view of a portion of the surgical end effector of the surgical instrument of FIG. 19 with an anvil thereof in an open position in accordance with at least one aspect of the present disclosure and with portions of the surgical end effector omitted for clarity.

In the illustrated arrangement, the anvil 1210 is moved to the open position by a pair of anvil springs 1270 that are supported within the proximal end of the elongate channel. See FIGS. 38, 42, and 43. The springs 1270 are positioned to apply a pivotal biasing force to corresponding anvil control arms 1234 that may be integrally formed with anvil mounting portion 1230 and extend downwardly therefrom. See FIG. 38.

Figure 39:
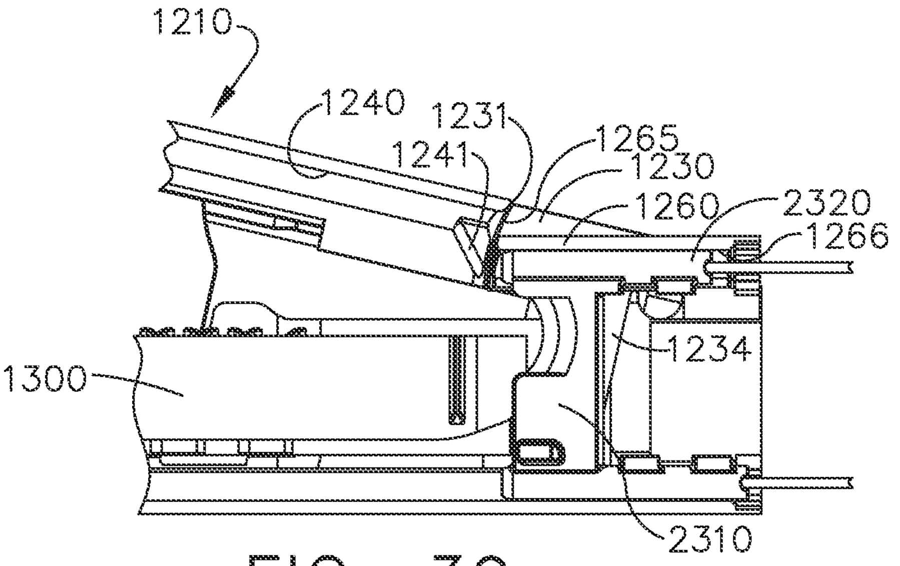
FIG. 39 is a partial cross-sectional side view of the surgical end effector of FIG. 38 with the anvil in an open position and the firing member in the home or starting position in accordance with at least one aspect of the present disclosure.
Figure 40:
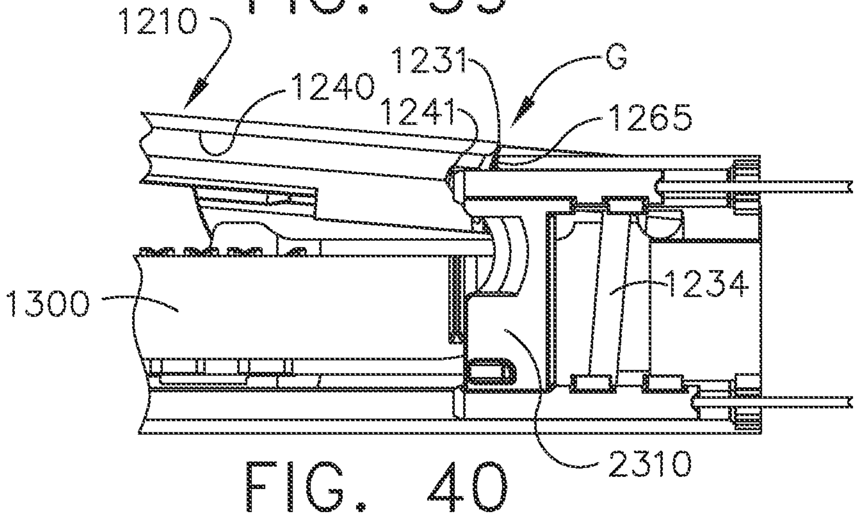
FIG. 40 is another partial cross-sectional side view of the surgical end effector of FIG. 39 with the anvil in a partially closed position.
Figure 41:
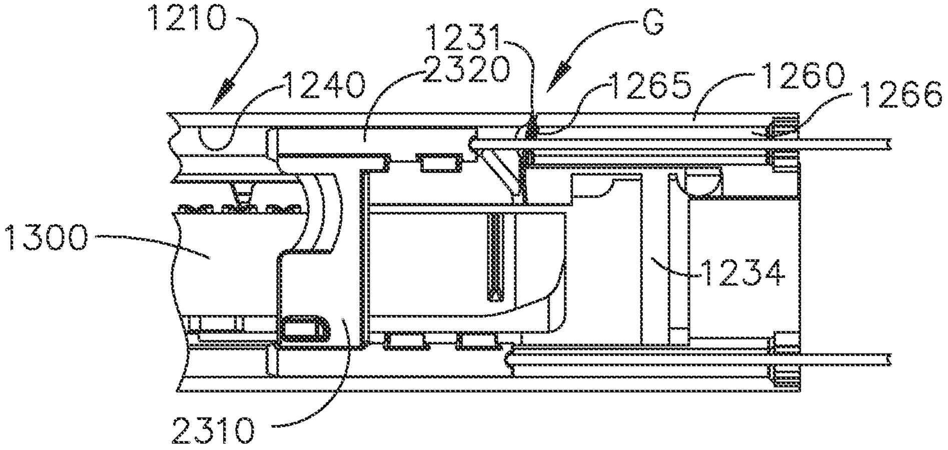
FIG. 41 is another partial cross-sectional side view of the surgical end effector of FIG. 39 with the anvil in a fully closed position and the firing member distally advancing through the surgical end effector.

FIGS. 39-41 illustrate portions of the anvil 1210, the firing member 2310, and the anvil cap 1260 when the anvil 1210 is open (FIG. 39), when the anvil 1210 is partially closed (FIG. 40) and after the firing member has been advanced distally from the home or starting position (FIG. 41). As can be seen in FIG. 39, when the firing member 2310 is in the home or starting position, the top firing member feature 2320 is completely received within the vertebra passage 1266 in the anvil cap 1260. During a firing stroke, the top firing member feature 2320 and the upper vertebra members 2420 in the upper series 2410 must transition from the vertebra passage 1266 in the anvil cap 1260 to the keyhole-shaped anvil slot 1240. Thus, it is desirable to minimize any gap "G" between the anvil mounting portion 1230 and a distal end 1264 of the anvil cap 1260. To minimize this gap G while facilitate unimpeded pivotal travel of the anvil 1210, the distal end 1264 of the anvil cap 1260 is formed with a curved cap surface 1265 that matches a curved mating surface 1231 on the anvil mounting portion 1230. Both surfaces 1265, 1231 are curved and concentric about the pivot axis PA or some other reference point. Such arrangement allows the anvil 1210 to move radially and not interfere with the anvil cap 1260 while maintaining a minimal gap G therebetween. The gap G between the anvil mounting portion 1230 and the distal end 1264 of the anvil cap 1260 is significantly shorter than a length of an upper vertebra member 2420 which facilitates easy transition of each upper vertebra member 2420 from the vertebra passage 1266 in the anvil cap 1260 to the keyhole-shaped anvil slot 1240. In addition, to further assist with the transition of the top firing member feature 2320 into the keyhole-shaped anvil slot 1240, a ramped surface 1241 is formed adjacent the curved mating surface 1231 on the anvil mounting portion 1230. As the firing member 2310 is initially advanced distally from the home or starting position, a distal end of the top firing member feature 2320 contacts the ramped surface 1241 and begins to apply a closing motion to the anvil 1210 as can be seen in FIG. 40. Further distal advancement of the firing member 2310 during the firing stroke or firing sequence causes the top firing member feature to enter the keyhole shaped anvil slot 1240 to completely close the anvil 1210 and retain the anvil 1210 in the closed position during the firing sequence. See FIG. 41.

Figure 15:
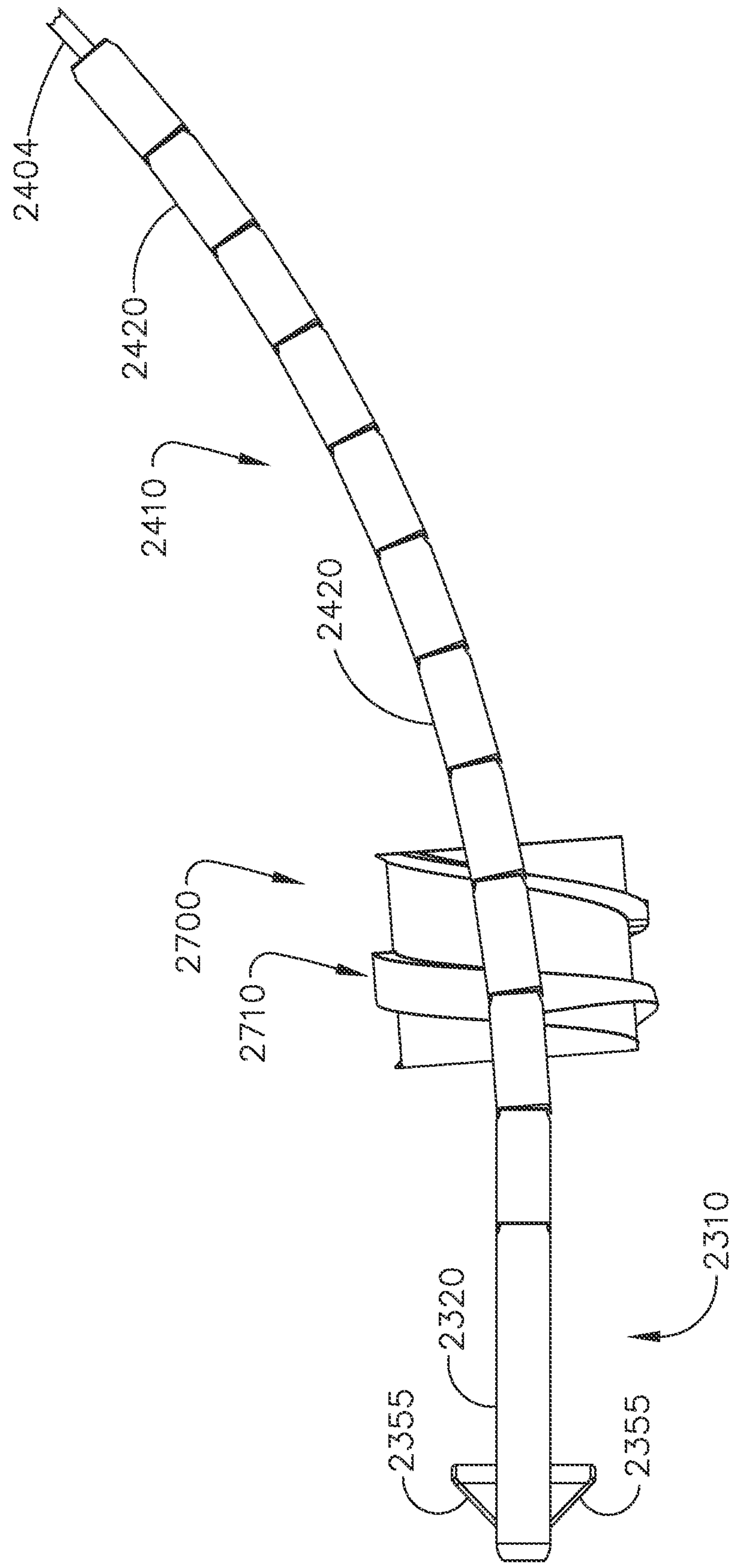
FIG. 15 is a top view of a firing member and upper and lower flexible spine assemblies in engagement with the rotary drive screw of FIG. 9.
Figure 42:
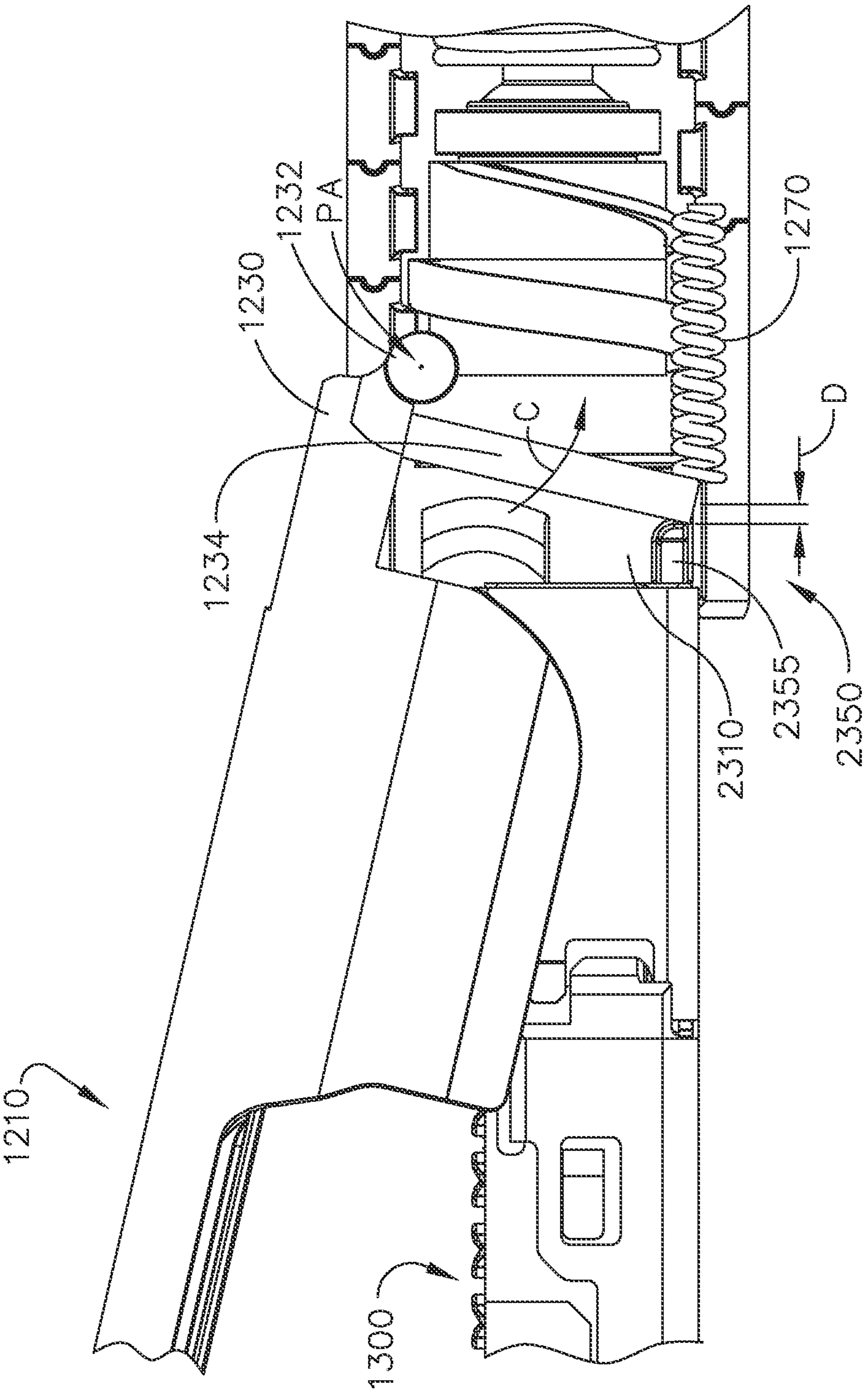
FIG. 42 is a partial side elevational view of the surgical end effector of FIG. 19 with portions thereof omitted for clarity to illustrate the anvil opening springs applying an opening motion to the anvil and with the firing member in a home or starting position.
Figure 43:
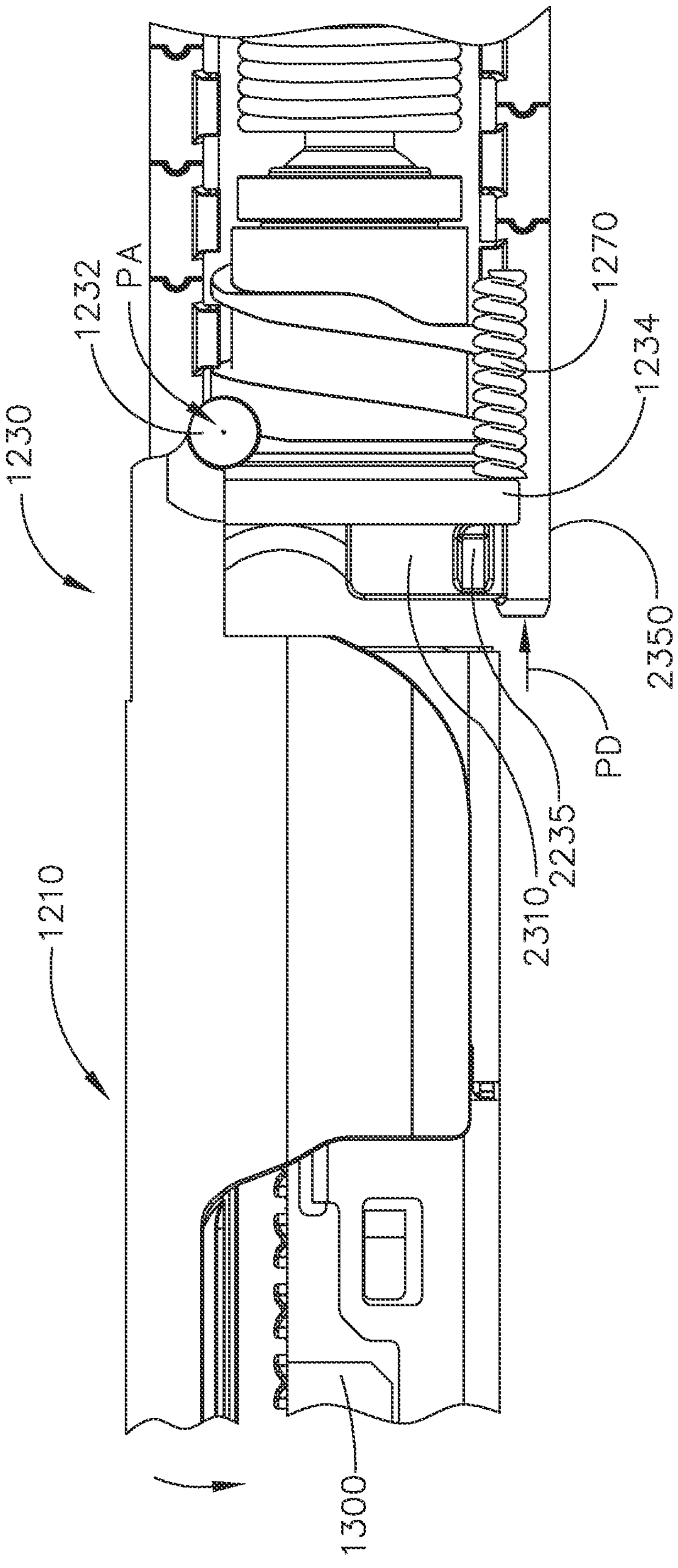
FIG. 43 is another partial side view of the surgical end effector of FIG. 42, after the firing member has moved proximally a short distance to apply a quick closure motion to the anvil for grasping purposes.

In general, the highest firing forces established in an endocutter are associated with cutting and stapling tissue. If those same forces can be used to close the anvil, then the forces generated during pre-clamping and grasping of tissue can be high as well. In at least one arrangement, the firing member body 2312 further comprises a firing member wing or tab 2355 that extends laterally from each lateral side of the firing member body 2312. See FIGS. 15 and 36. The firing member wings 2355 are positioned to contact the corresponding anvil control arms 1234 when the firing member 2310 is driven in the proximal direction PD from the home or starting position to quickly close the anvil 1210 for grasping purposes. In at least one arrangement, when the firing member 2310 is in the home or starting position, the firing member wings 2355 are located distal to the anvil control arms 1234 as shown in FIG. 42. When the firing member 3210 is moved proximally, the firing member wings 2355 push the anvil control arms 1234 (pivotal direction C) against the bias of the anvil springs 1270. See FIG. 42. In one arrangement, the firing member 2310 only has to move a short distance D to pivot the anvil 1210 to a closed position. In one embodiment, distance D may be approximately 0.070 inches long, for example. This short movement allows for a quick response. Because the anvil pivot point or pivot axis PA is relatively far from the firing member wings 2355 which creates a substantial moment arm, the proximal movement of the firing member 2310 (and firing member wings 2355) results in an application of high pre-compression torque to the anvil 1210 to move the anvil 1210 to a closed position. Thus, the firing member wings 2355 may be referred to herein as "pre-compression features". See FIG. 43. Thus, the clinician may use the surgical end effector 1000 to grasp and manipulate tissue between the anvil 1210 and the surgical staple cartridge 1300 without cutting the tissue and forming the staples, by advancing the firing member 2310 proximally the short distance D to cause the anvil 1210 to quickly pivot to a closed position.

The firing member 2310 may be moved in the proximal direction PD by rotating the rotary drive screw 2700 in a second rotary direction. Thus, when the firing member 2310 is in the "home" or starting position, the anvil 1210 may be biased into the fully open position by the anvil springs 1270. Activation of the rotary drive system 2600 to apply a rotary motion to the rotary drive screw 2700 in a first rotary direction will cause the firing member 2310 to be advanced distally from the home or starting position to apply an anvil closure motion to the anvil 1210 to move the anvil closed to clamp the target tissue between the anvil 1210 and the surgical staple cartridge 1300. Continued rotation of the rotary drive screw in the first rotary direction will cause the firing member 2310 to continue to distally advance through the surgical end effector 1000. As the firing member 2310 moves distally, the firing member 2310 contacts a sled 1312 (FIG. 19) that is supported in the surgical staple cartridge 1300 and drives the sled 1312 distally through the staple cartridge body 1302. When the firing member 2310 is in the home or starting position, the surgeon may wish to use the surgical end effector to grasp and manipulate tissue. To do so, the rotary drive system is actuated to apply a second rotary drive motion to the rotary drive screw 2700 in a second rotary direction that is opposite to the first rotary direction. Such rotary movement of the rotary drive screw 2700 in the second rotary direction will drive the firing member 2310 proximally from the starting position and cause the anvil 1210 to quickly pivot to the closed position. Thus, in accordance with at least one embodiment, the "home or starting position" of the firing member 2310 is not its proximal-most position.

If during the firing process, the rotary drive system 2600 quits rotating, the firing member 2310 may become stuck within the surgical end effector. In such instance, the top firing member feature 2320 may remain engaged with the anvil 1210 and the bottom firing member feature 2350 may remain engaged with the elongate channel 1110 and thereby prevent the surgeon from moving the anvil 1210 to an open position to release the tissue clamped between anvil 1210 and surgical staple cartridge 1300. This could occur, for example, if the motor or other control arrangement supplying the rotary drive motions to the rotary drive shaft 2610 fails or otherwise becomes inoperative. In such instances, the firing member 2310 may be retracted back to the home or starting position within the surgical end effector 1000 by pulling the top cable 2404 and the lower cable 2504 in a proximal direction. For example, a proximal portion of the top cable 2404 and a proximal portion of the lower cable 2505 may be spooled on a rotary spool or cable-management system 2009 (FIG. 2) in the housing portion of the surgical instrument 10 that is configured to payout the top cable 2404 and lower cable 2504 during the firing stroke and also retract the cables 2404, 2504 in a proximal direction should the firing member 2310 need to be retracted. The cable management system 2009 may be motor powered or manually powered (ratchet arrangement, etc.) to apply retraction motions to the cables 2404, 2504. When the cables 2404, 2504 are retracted, the upper vertebra members 2420 and lower vertebra members 2520 will cause the rotary drive screw 2700 to spin in reverse.

The following equation may be used to determine whether the rotary drive screw 2700 will spin in reverse depending upon the lead (L), pitch diameter ($d_p$), tooth angle ($\alpha$) and friction ($\mu$):

$$\mu \geq \frac{L}{\pi d_p}\cos\alpha$$

The rotary drive screw 2700 may self-lock if the above equation is true. For the most part, in many instances, the pitch diameter is mostly fixed for an endocutter, but the lead and tooth angle are variable. Because the upper vertebra member teeth 2450 and lower vertebra member teeth 2550 are mostly square, the rotary drive screw 2700 is more likely to be back drivable (cos (90)=1). The leads of the upper vertebra member teeth 2450 and lower vertebra member teeth 2550 may also be advantageous in that the rolling friction between the vertebra members 2420, 2520 and the rotary drive screw 2700 is more likely to enable the rotary drive screw 2700 to be back driven. Thus, in the event of an emergency, the surgeon can pull on the upper and lower cables 2404, 2504 in the proximal direction to cause the firing member 2310 to fully retract for a quick "bailout".

As indicated above, the relative control motions for the rotary drive system 2600, as well as the various cable-management systems employed in connection with the firing system 2300 and the articulation control system 2240, may be supported within a housing 2002 which may be handheld or comprise a portion of a larger automated surgical system. The firing system 2300, articulation control system 2240, and the rotary drive system 2600 may, for example, be motor-controlled and operated by one or more control circuits.

Figure 44:
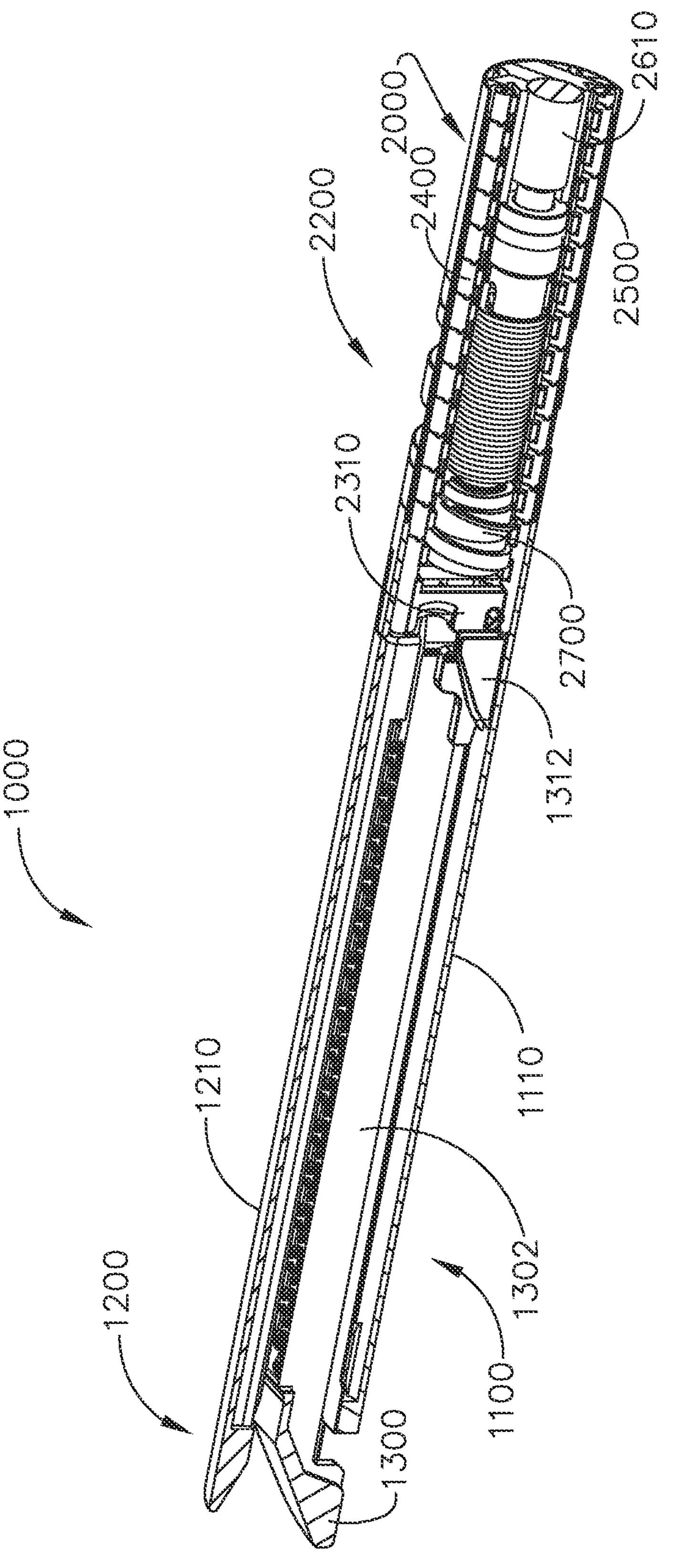
FIG. 44 is a cross-sectional view of the surgical end effector of FIG. 19 with the jaws thereof in a closed position and the firing member thereof in a proximal-most position.

One method of using the surgical instrument 10 may involve the use of the surgical instrument 10 to cut and staple target tissue within a patient using laparoscopic techniques. For example, one or more trocars may have been placed through the abdominal wall of a patient to provide access to a target tissue within the patient. The surgical end effector 1000 may be inserted through one trocar and one or more cameras or other surgical instruments may be inserted through the other trocar(s). To enable the surgical end effector 1000 to pass through the trocar cannula, the surgical end effector 1000 is positioned in an unarticulated orientation and the jaws 1100 and 1200 must be closed. To retain the jaws 1100 and 1200 in the closed position for insertion purposes, for example, the rotary drive system 2600 may be actuated to apply the second rotary motion to the rotary drive screw 2700 to cause the firing member 2310 to move proximally from the starting position to move the anvil 1210 (jaw 1200) to the closed position. See FIG. 44. The rotary drive system 2600 is deactivated to retain the firing member 2310 in that position. Once the surgical end effector has passed into the abdomen through the trocar, the rotary drive system 2600 may be activated to cause the rotary drive screw 2700 to drive the firing member 2310 distally back to the starting position wherein the anvil springs 1270 will pivot the anvil 1210 to the open position. See FIG. 38.

Once inside the abdomen and before engaging the target tissue, the surgeon may need to articulate the surgical end effector 1000 into an advantageous position. The articulation control system 2240 is then actuated to articulate the surgical end effector in one or more planes relative to a portion of the elongate shaft assembly 2000 that is received within the cannula of the trocar. Once the surgeon has oriented the surgical end effector 1000 in a desirable position, the articulation control system 2240 is deactivated to retain the surgical end effector 1000 in the articulated orientation. The surgeon may then use the surgical end effector to grasp the target tissue or adjacent tissue by activating the rotary drive system to rotate the rotary drive screw in the second rotary direction to move the firing member proximally to cause the anvil 1210 to rapidly close to grasp the tissue between the anvil 1210 and the surgical staple cartridge 1300. The anvil 1210 may be opened by reversing the rotation of the rotary drive screw 2700. This process may be repeated as necessary until the target tissue has be properly positioned between the anvil 1210 and the surgical staple cartridge 1300.

Once the target tissue has been positioned between the anvil 1210 and the surgical staple cartridge, the surgeon may commence the closing and firing process by activating the rotary drive system 2600 to drive the firing member 2310 distally from the starting position. As the firing member 2310 moves distally from the starting position, the firing member 2310 applies a closure motion to the anvil 1210 and moves the anvil 1210 from the open position to the closed position in the manners discussed above. As the firing member 2310 moves distally, the firing member 2310 retains the anvil 1210 in the closed position thereby clamping the target tissue between the anvil 1210 and the surgical staple cartridge 1300. As the firing member 2310 moves distally, the firing member 2310 contacts a sled 1312 supported in the surgical staple cartridge 1300 and also drives the sled 1312 distally through the staple cartridge body 1302. The sled 1312 serially drives rows of drivers supported in the staple cartridge toward the clamped target tissue. Each driver has supported thereon one or more surgical staples or fasteners which are then driven through the target tissue and into forming contact with the underside of the anvil 1210. As the firing member 2310 moves distally, the tissue cutting edge 2314 thereon cuts through the stapled tissue.

Figure 45:
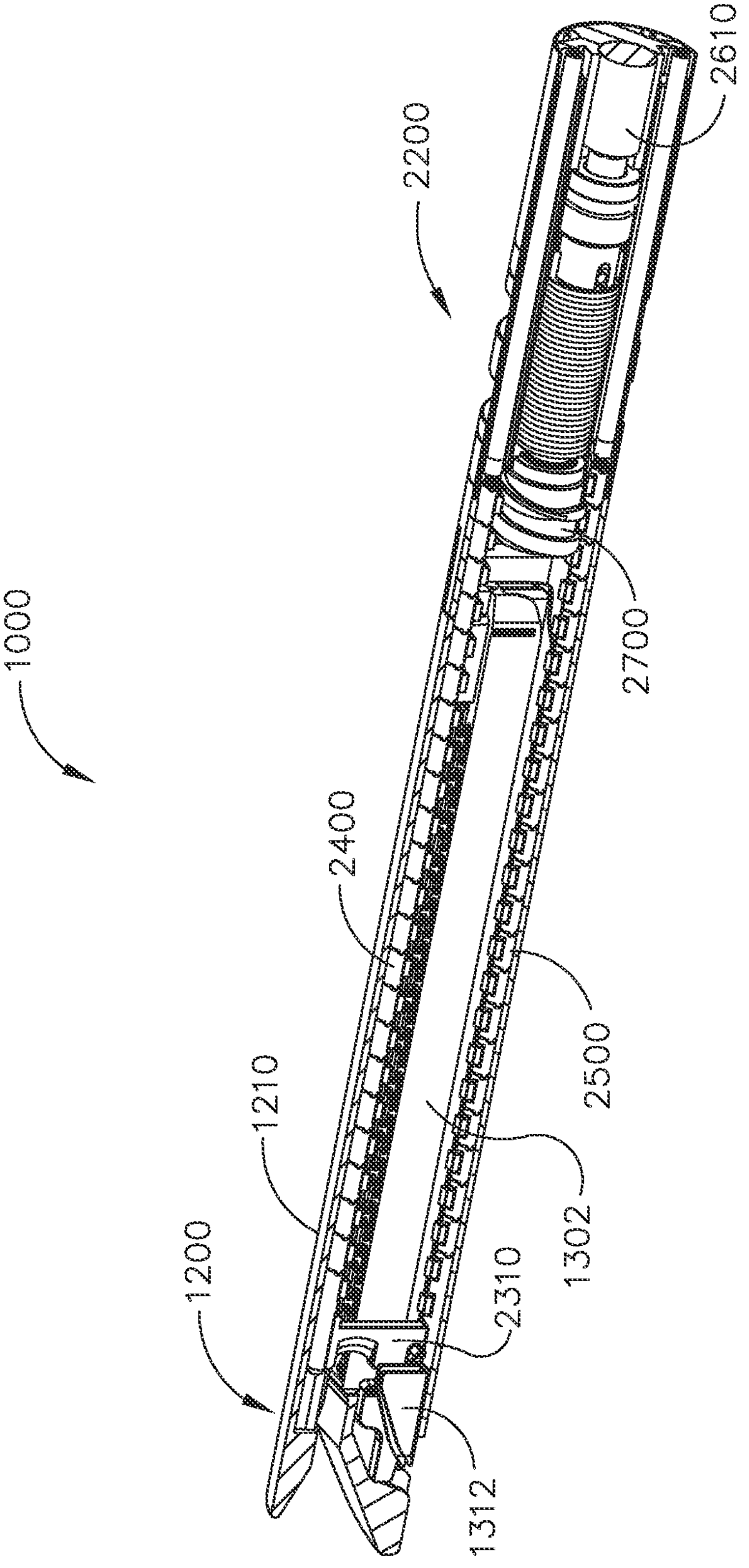
FIG. 45 is another cross-sectional view of the surgical end effector of FIG. 44, after the firing member has been distally advanced to the ending position within the surgical end effector.
Figure 46:
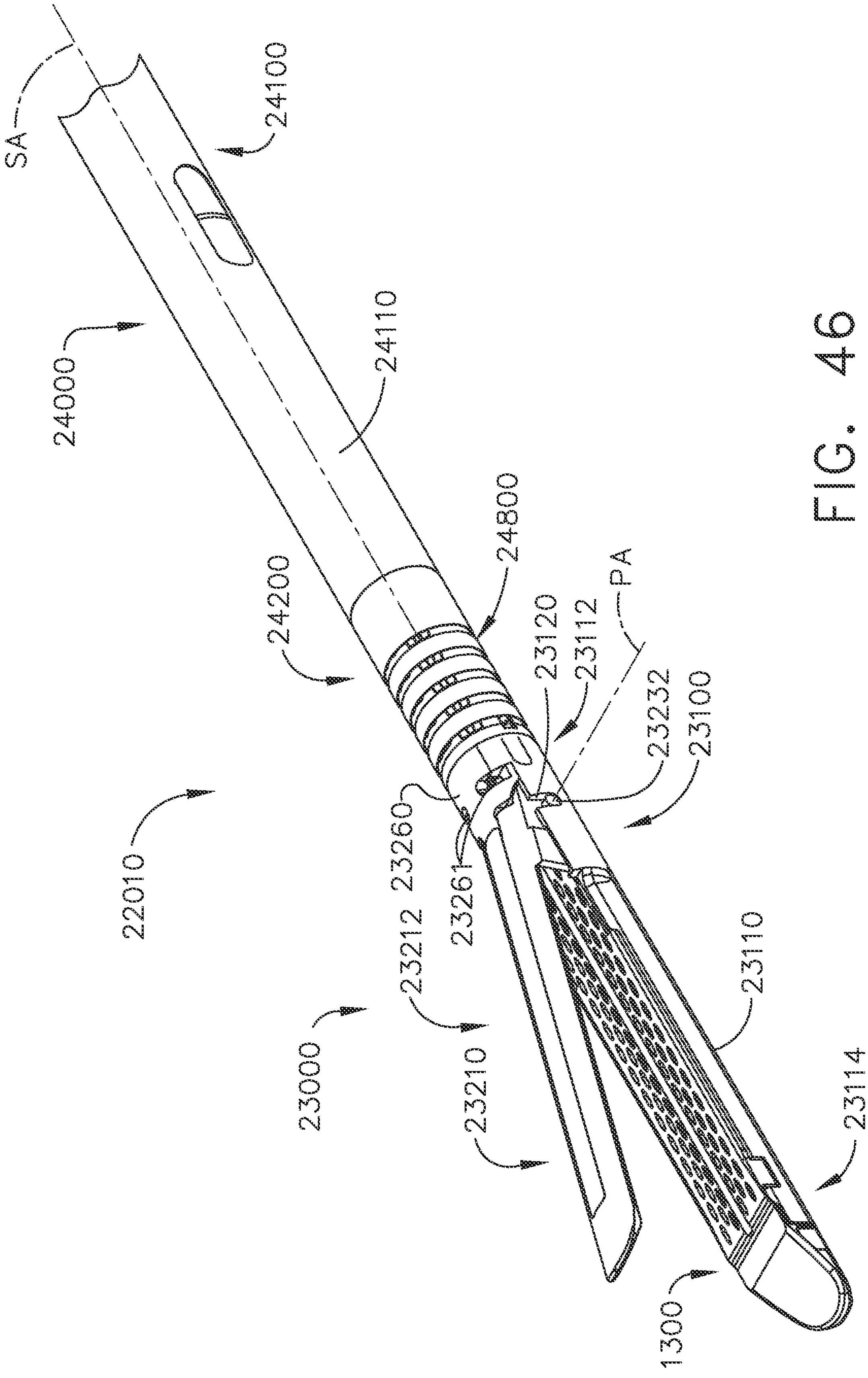
FIG. 46 is a perspective view of a portion of another surgical instrument.
Figure 47:
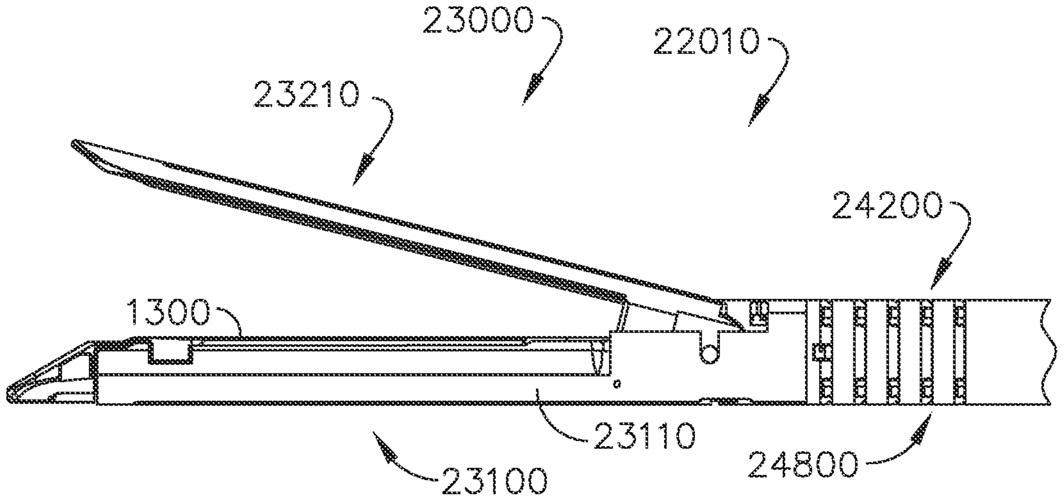
FIG. 47 is a side elevational view of a surgical end effector of the surgical instrument of FIG. 46, with the jaws thereof in an open position.

After the firing member 2310 has been driven distally to the ending position within the surgical end effector 1000 (FIG. 45), the rotary drive system 2600 is reversed which causes the firing member 2310 to retract proximally back to the home or starting position. Once the firing member 2310 has returned to the starting position, the anvil springs 1270 will pivot the anvil 1210 to the open position to enable the surgeon to release the stapled tissue from the surgical end effector 1000. Once the stapled tissue has been released, the surgical end effector may be withdrawn out of the patient through the trocar cannula. To do so, the surgeon must first actuate the articulation control system 2240 to return the surgical end effector 1000 to an unarticulated position and actuate the rotary drive system to drive the firing member 2310 proximally from the home or starting position to close the jaws. Thereafter, the surgical end effector 1000 may be withdrawn through the trocar cannula. If during the firing process or during the retraction process, the firing system becomes inoperative, the surgeon may retract the firing member 2310 back to the starting position by applying a pulling motion to the cables 2404, 2505 in the proximal direction in the various manners described herein.

FIGS. 46-68 illustrate another surgical instrument 22010 that in many aspects is identical or very similar to the surgical instrument 10 described above, except for the various differences discussed below. Like surgical instrument 10, surgical instrument 22010 may address many of the challenges facing surgical instruments with articulatable end effectors that are configured to cut and fasten tissue. In various embodiments, the surgical instrument 22010 may comprise a handheld device. In other embodiments, the surgical instrument 22010 may comprises an automated system sometimes referred to as a robotically-controlled system, for example. In various forms, the surgical instrument 22010 comprises a surgical end effector 23000 that is operably coupled to an elongate shaft assembly 24000. The elongate shaft assembly 24000 may be operably attached to a housing that is handheld or otherwise comprises a portion of a robotic system as was discussed above.

Figure 48:
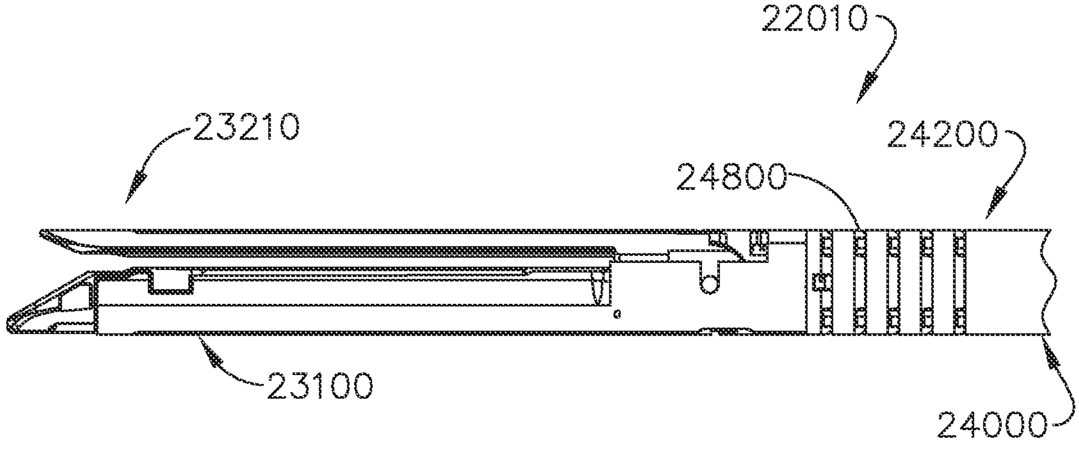
FIG. 48 is another side view of the surgical end effector of FIG. 48 with the jaws thereof in a closed position.
Figure 49:
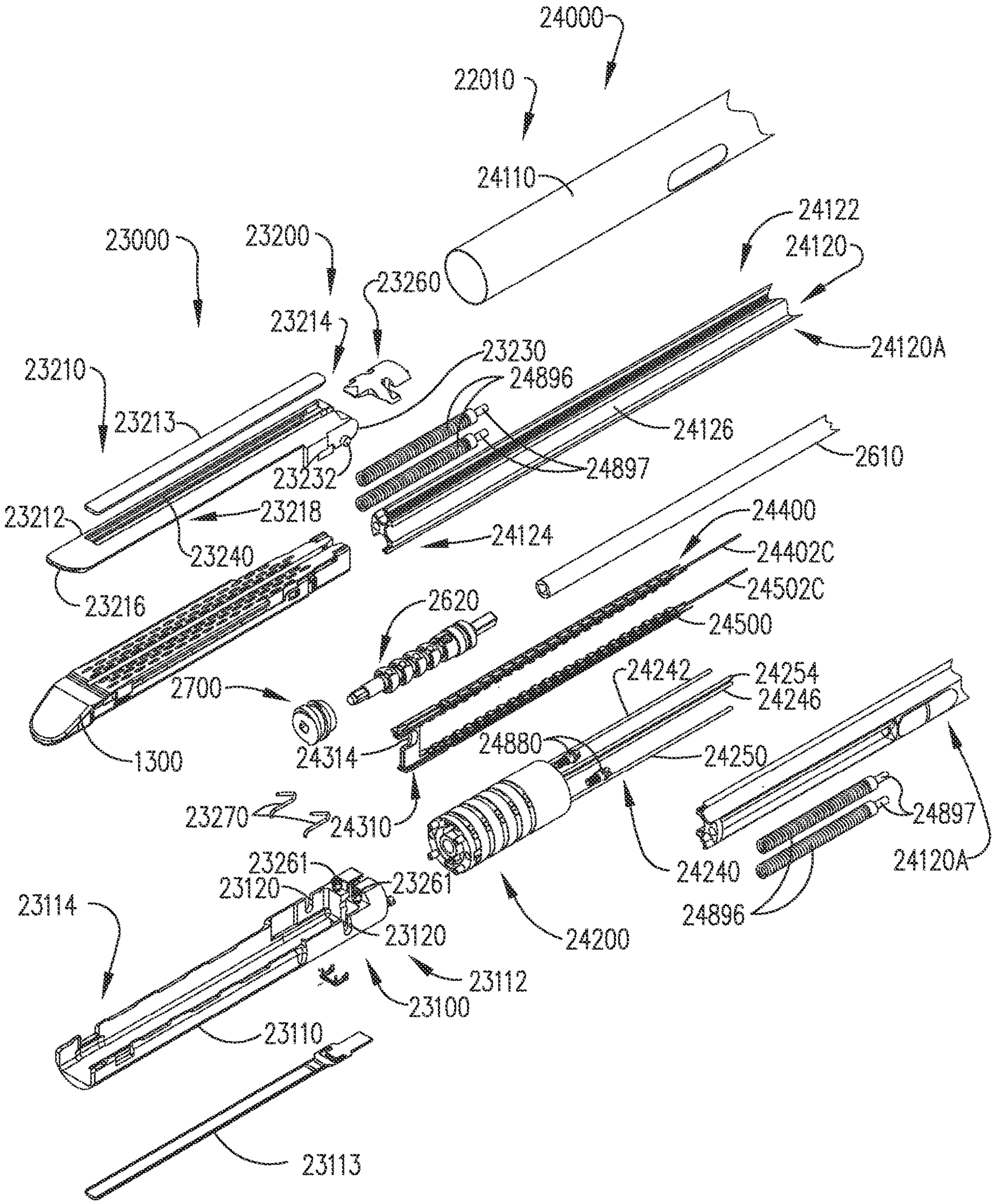
FIG. 49 is an exploded assembly view of a portion of the surgical instrument of FIG. 46.
Figure 50:
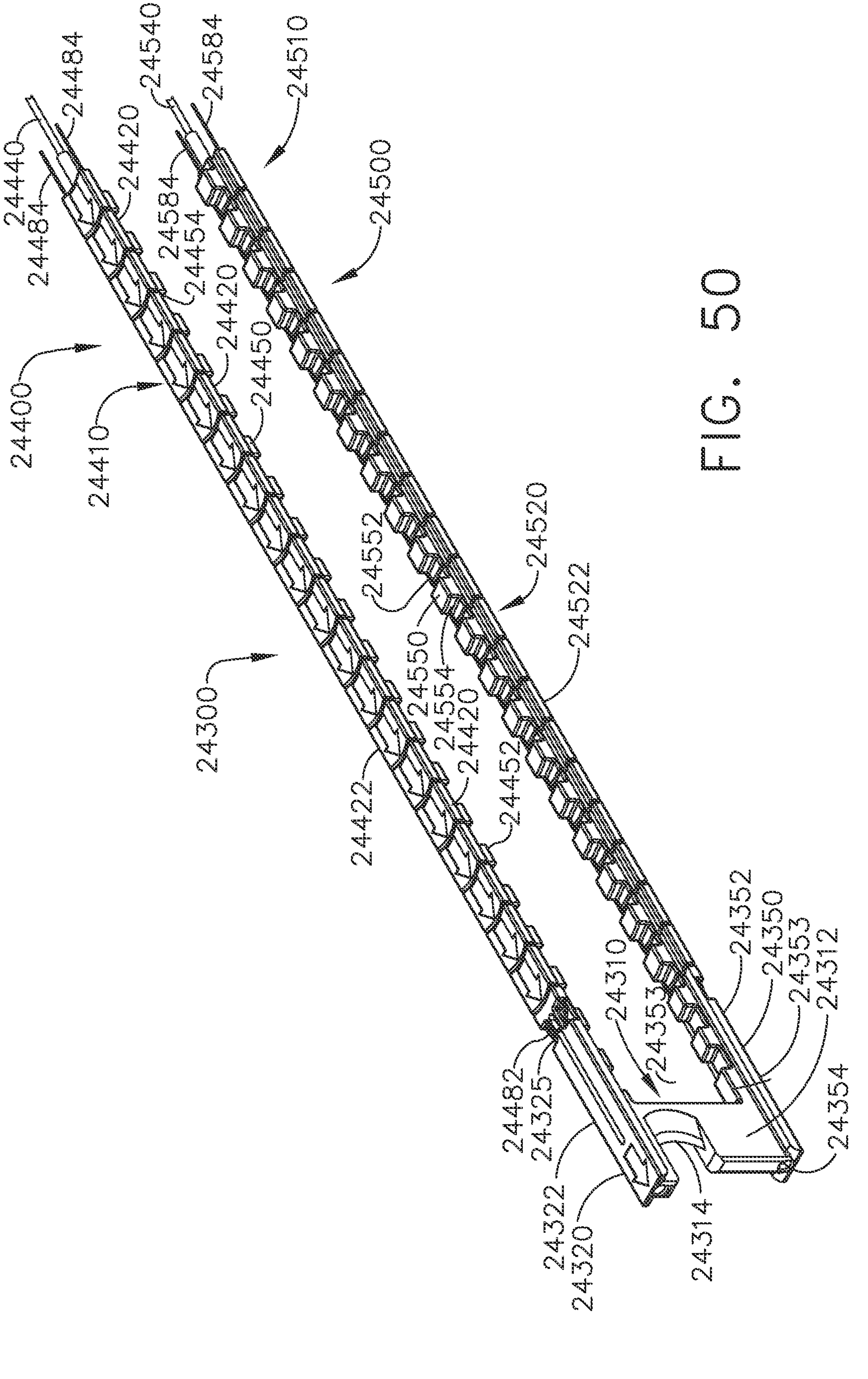
FIG. 50 is a perspective view of a firing member and portions of an upper flexible spine assembly and a lower flexible spine assembly of a firing system of the surgical instrument of FIG. 46.

As can be seen in FIG. 49, in one form, the surgical end effector 23000 comprises a first jaw 23100 and a second jaw 23200. In the illustrated arrangement, the first jaw 23100 comprises an elongate channel 23110 that comprises a proximal end 23112 and a distal end 23114 and is configured to operably support a surgical staple cartridge 1300 therein. The elongate channel 23110 has an open bottom to facilitate ease of assembly and has a channel cover 23113 that is configured to be attached thereto (welded, etc.) to cover the opening and add rigidity to the elongate channel 23110. In the illustrated arrangement, the second jaw 23200 comprises an anvil 23210 that comprises an elongate anvil body 23212 that comprises a proximal end 23214 and a distal end 23216. In one arrangement, an anvil cover 23213 is provided to facilitate assembly of the device and add rigidity to the anvil 23210 when it is attached (welded, etc.) to the anvil body 23212. The anvil body 23212 comprises a staple-forming undersurface 23218 that faces the first jaw 23100 and may include a series of staple-forming pockets (not shown) that corresponds to each of the staples or fasteners in the surgical staple cartridge 1300. The proximal end 23214 of the anvil body 23212 comprises an anvil mounting portion 23230 that includes a pair of laterally extending mounting pins 23232 that are configured to be received in corresponding mounting cradles or pivot cradles 23120 formed in the proximal end 23112 of the elongate channel 23110. The mounting pins 23232 are pivotally retained within the mounting cradles 23120 by an anvil cap 23260 that may be attached to the proximal end 23112 of the elongate channel 23110 by screws 23261. In other arrangements, the anvil cap 23260 may be attached to the elongate channel 23110 by welding, adhesive, etc. Such arrangement facilitates pivotal travel of the anvil 23210 relative to the surgical staple cartridge 1300 mounted in the elongate channel 23110 about a pivot axis PA between an open position (FIG. 47) and a closed position (FIG. 48). Such pivot axis PA may be referred to herein as being “fixed” in that the pivot axis does not translate or otherwise move as the anvil 23210 is pivoted from an open position to a closed position.

In the illustrated arrangement, the anvil 23210 is moved to the open position by a pair of anvil springs 23270 that are supported within the proximal end 23112 of the elongate channel 23110. See FIGS. 49 and 62. The springs 23270 are positioned to apply a pivotal biasing force to corresponding portions of the anvil 23210 to apply opening forces thereto. See FIG. 47.

In the illustrated arrangement, the elongate shaft assembly 24000 defines a shaft axis SA and comprises a proximal shaft portion 24100 that may operably interface with a housing of the control portion (e.g., handheld unit, robotic tool driver, etc.) of the surgical instrument 22010. The elongate shaft assembly 24000 further comprises an articulation joint 24200 that is attached to the proximal shaft portion 24100 and the surgical end effector 23000. In various instances, the proximal shaft portion 24100 comprises a hollow outer tube 24110 that may be operably coupled to a housing in the various manners discussed above. As can be seen in FIG. 49, the proximal shaft portion 24100 may further comprise a rigid proximal support shaft 24120 that is supported within the hollow outer tube 24110 and extends from the housing to the articulation joint 24200. The rigid proximal support shaft 24120 may comprise a first half 24120A and a second half 24120B that may be coupled together by, for example, welding, adhesive, etc. The rigid proximal support shaft 24120 comprises a proximal end 24122 and a distal end 24124 and includes an axial passage 24126 that extends therethrough from the proximal end 24122 to the distal end 24124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 22010 employs a firing system 24300 that is identical to or very similar in many aspects as firing system 2300 described above. As such, only those aspects of the firing system 24300 needed to understand the operation of the surgical instrument 22010 will be discussed below.

Figure 54:
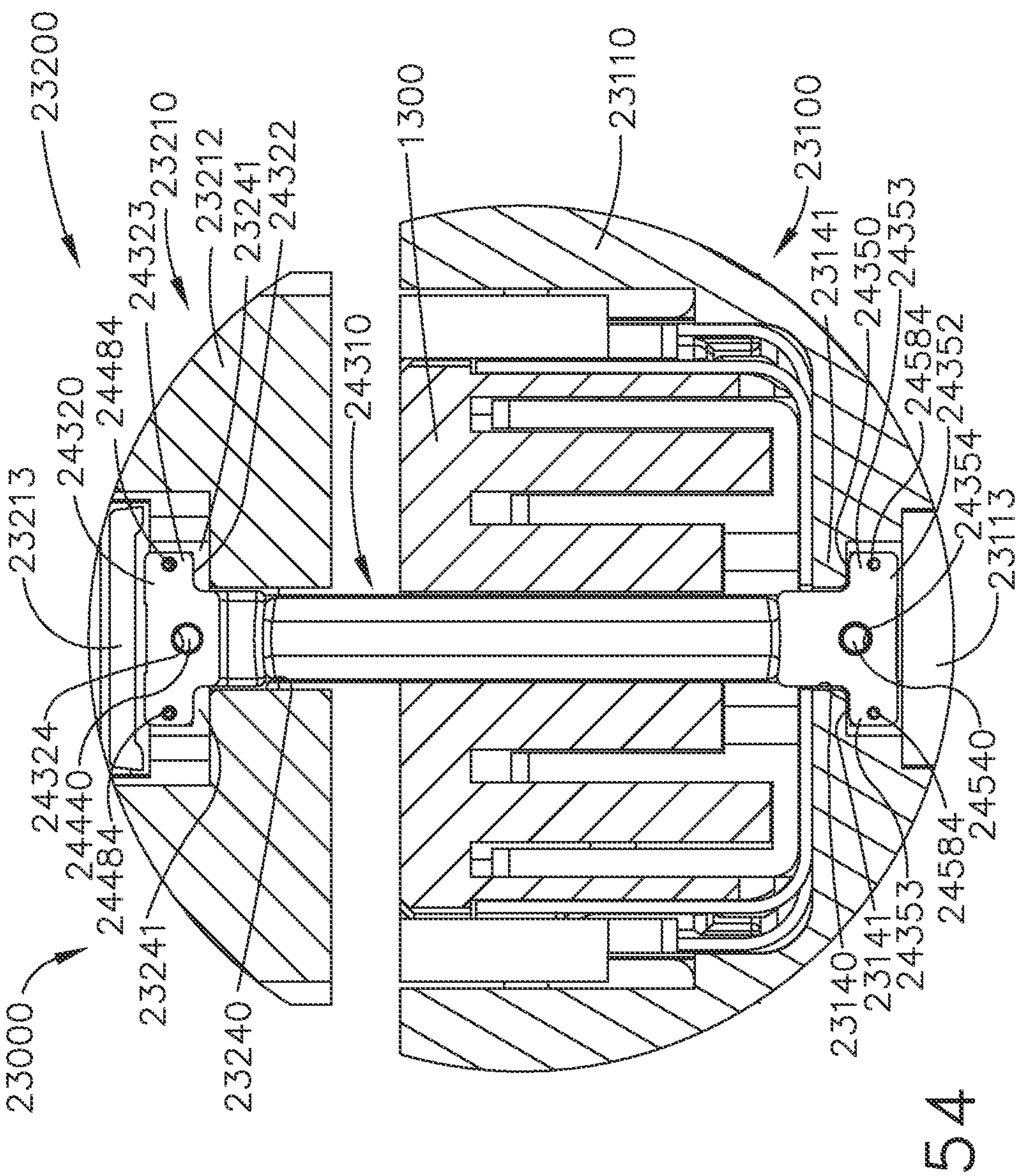
FIG. 54 is a cross-sectional end view of the surgical end effector of the surgical instrument of FIG. 46, with the jaws thereof in a closed position.

As can be seen in FIGS. 50-54, in at least one embodiment, the firing system 24300 comprises a firing member 24310 that includes a vertically-extending firing member body 24312 that comprises a top firing member feature 24320 and a bottom firing member feature 24350. A tissue cutting blade 24314 is attached to or formed in the vertically-extending firing member body 24312. See FIGS. 50 and 51. In at least one arrangement, it is desirable for the firing member 24310 to pass through the anvil body 23212 with low friction, high strength and high stiffness. In the illustrated arrangement, the top firing member feature 24320 comprises a T-shaped body 24322 that has two laterally extending tabs 24323 protruding therefrom and a top axial passage 24324 extending therethrough. See FIG. 53. The bottom firing member feature 24350 comprises a T-shaped body 24352 that has two laterally extending tabs 24353 protruding therefrom and a bottom axial passage 24354 extending therethrough. See FIG. 50. In at least one arrangement, the top firing member feature 24320 and the bottom firing member feature 24350 are integrally formed with the vertically-extending firing member body 24312. As can be seen in FIG. 54, the anvil body 23212 comprises an axially extending anvil slot 23240 that defines two opposed ledges 23241 for slidably receiving the laterally extending tabs 24323 thereon. Similarly, the elongate channel 23110 comprises an axially extending channel slot 23140 that defines axially extending channel ledges 23141 that are configured to slidably receive the laterally extending tabs 24353 thereon.

In the illustrated arrangement, the firing system 24300 comprises an upper flexible spine assembly 24400 that is operably coupled to the top firing member feature 24320 of the firing member 24310. In at least one embodiment, the upper flexible spine assembly 24400 comprises an upper series 24410 of upper vertebra members 24420 that are loosely coupled together by an upper flexible coupler member 24440 that extends through each of the upper vertebra members 24420 and is attached to the top firing member feature 24320.

Figure 52:
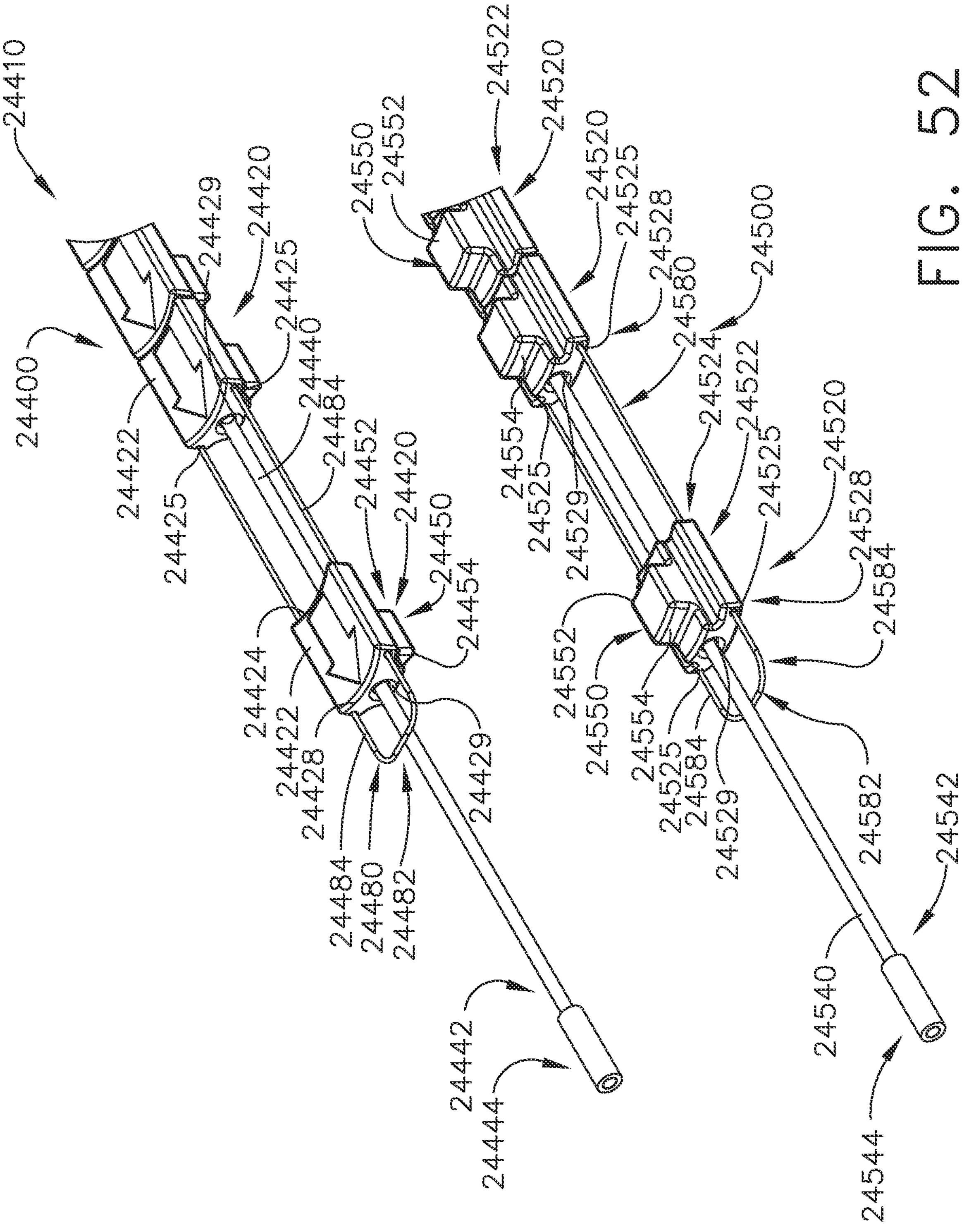
FIG. 52 is a partial exploded assembly view of the upper flexible spine assembly and lower flexible spine assembly depicted in FIG. 51.
Figure 53:
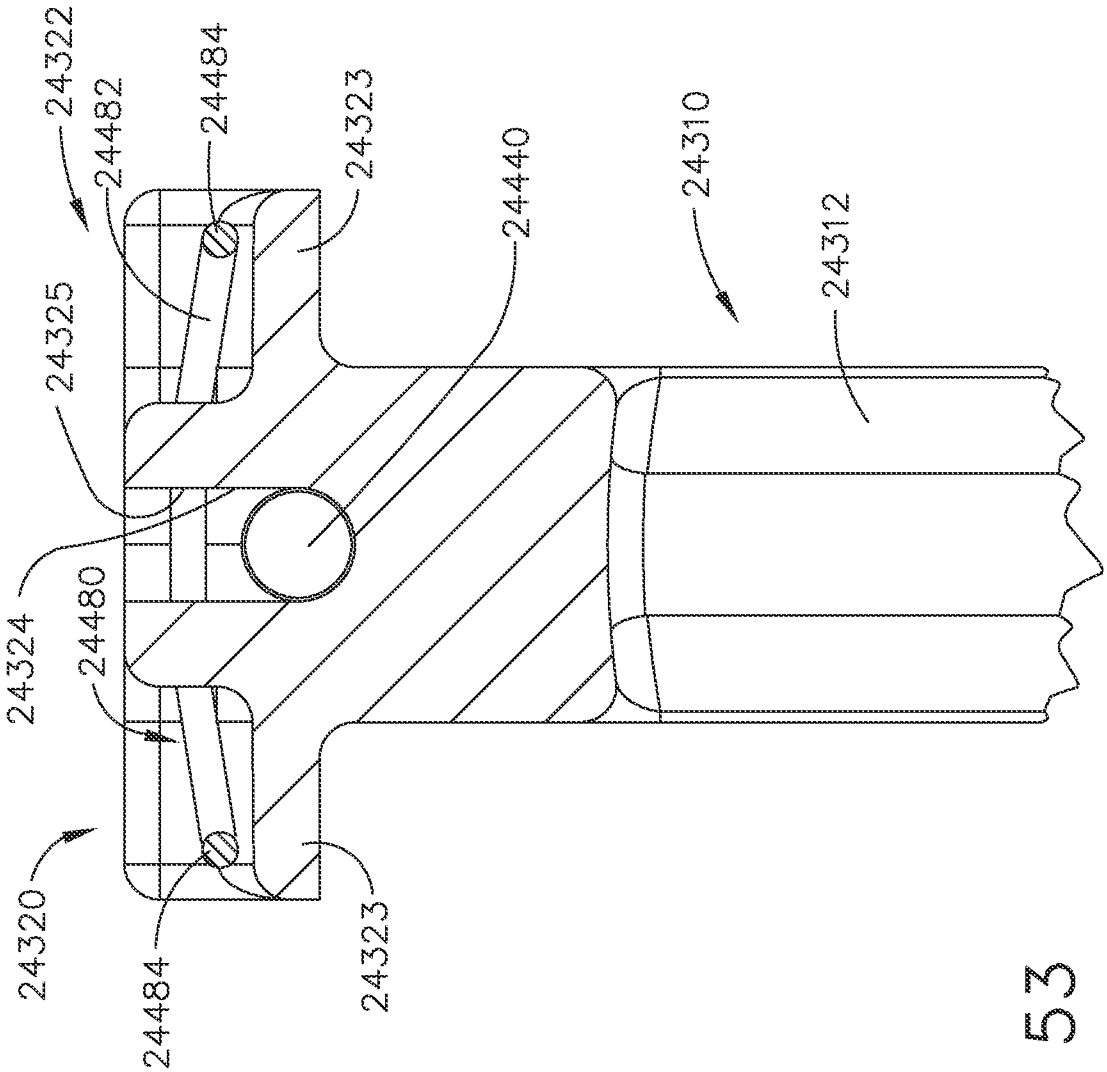
FIG. 53 is a partial cross-sectional end view of an upper portion of the firing member depicted in FIG. 50.

As can be seen in FIG. 52, each upper vertebra member 24420 is substantially T-shaped when viewed from an end thereof. In one aspect, each upper vertebra member 24420 comprises an upper vertebra body portion 24422 that has a proximal end 24424 and a distal end 24428. Each upper vertebra member 24420 further comprises a downwardly extending upper drive feature or upper vertebra member tooth 24450 that protrudes from the upper vertebra body portion 24422. Each upper vertebra member tooth 24450 has a helix-shaped proximal upper face portion 24452 and a helix-shaped distal upper face portion 24454. Each proximal end 24424 of the upper vertebra body portions 24422 has an arcuate or slightly concave curved shape and each distal end 24428 has an arcuate or slightly convex curved shape. When arranged in the upper series 24410, the convex distal end 24428 on one upper vertebra member 24420 contacts and mates with the concave proximal end 24424 on an adjacent upper vertebra member 24420 in the upper series 24410 to maintain the upper vertebra members 24420 roughly in alignment so that the helix-shaped proximal upper face portion 24452 and a helix-shaped distal upper face portion 24454 on each respective upper vertebra member tooth 24450 can be drivingly engaged by a rotary drive screw 2700 in the various manners disclosed herein. These curved mating surfaces on the upper vertebra members 24420 allow the upper vertebras members 24420 to better transfer loads between themselves even when they tilt.

In at least one embodiment, an upper alignment member 24480 is employed to assist with the alignment of the upper vertebra members 24420 in the upper series 24410. In one arrangement, the alignment member 24480 comprises a spring member or metal cable which may be fabricated from Nitinol wire, spring steel, etc., and be formed with a distal upper looped end 24482 and two upper leg portions 24484 that extend through corresponding upper passages 24425 in each upper vertebra body portion 24422. The upper flexible coupler member 24440 extends through an upper passage 24429 in each of the upper vertebra members 24420 to be attached to the firing member 24310. In particular, a distal end portion 24442 extends through the top axial passage 24324 in the top firing member feature 24320 and is secured therein by an upper retention lug 24444. A proximal portion of the upper flexible coupler member 24440 may interface with a corresponding rotary spool or cable-management system of the various types and designs disclosed herein that serve to payout and take up the upper flexible coupler member 24440 to maintain a desired amount of tension therein during operation and articulation of the surgical end effector 23000. The cable management system may be motor powered or manually powered (ratchet arrangement, etc.) to maintain a desired amount of tension in the upper flexible coupler member 24440. The amount of tension in each flexible coupler member may vary depending upon the relative positioning of the surgical end effector 23000 to the elongate shaft assembly 24000.

The firing system 24300 further comprises a lower flexible spine assembly 24500 that is operably coupled to the bottom firing member feature 24350. The lower flexible spine assembly 24500 comprises a lower series 24510 of lower vertebra members 24520 that are loosely coupled together by a lower flexible coupler member 24540 that extends through each of the lower vertebra members 24520 and is attached to the bottom firing member feature 24350.

As can be seen in FIG. 52, each lower vertebra member 24520 is substantially T-shaped when viewed from an end thereof. In one aspect, each lower vertebra member 24520 comprises a lower vertebra body portion 24522 that has a proximal end 24524 and a distal end 24528. Each lower vertebra member 24520 further comprises an upwardly extending lower drive feature or lower vertebra member tooth 24550 that protrudes from the lower vertebra body portion 24522. Each lower vertebra member tooth 24550 has a helix-shaped proximal lower face portion 24552 and a helix-shaped distal lower face portion 24554. The proximal end 24524 of each lower vertebra body portions 24522 has an arcuate or slightly concave curved shape and each distal end 24528 has an arcuate or slightly convex curved shape. When arranged in the lower series 24510, the convex distal end 24528 on one lower vertebra member 24520 contacts and mates with the concave proximal end 24524 on an adjacent lower vertebra member 24520 in the lower series 24510 to maintain the lower vertebra members 24520 roughly in alignment so that the helix-shaped proximal lower face portion 24552 and a helix-shaped distal lower face portion 24554 on each respective lower vertebra member tooth 24550 can be drivingly engaged by the rotary drive screw 2700 in the various manners disclosed herein. These curved mating surfaces on the lower vertebra members 24520 allow the lower vertebra members 24520 to better transfer loads between themselves even when they tilt.

In at least one embodiment, a lower alignment member 24580 is employed to assist with the alignment of the lower vertebra members 24520 in the lower series 24510. In one arrangement, the lower alignment member 24580 comprises a spring member or metal cable which may be fabricated from Nitinol wire, spring steel, etc., and be formed with a distal lower looped end 24582 and two lower leg portions 24584 that extend through corresponding lower passages 24525 in each lower vertebra body portion 24522. The lower flexible coupler member 24540 extends through the bottom axial passage 24529 in each of the lower vertebra members 24520 to be attached to the firing member 24310. In particular, a distal end portion 24542 of the lower flexible coupler member 24540 extends through the bottom axial passage 24354 in the bottom firing member feature 24350 and is secured therein by a lower retention lug 24544. A proximal portion of the lower flexible coupler member 24540 may interface with a corresponding rotary spool or cable-management system of the various types and designs disclosed herein that serve to payout and take up the lower flexible coupler member 24540 to maintain a desired amount of tension therein during operation and articulation of the surgical end effector 23000. The cable management system may be motor powered or manually powered (ratchet arrangement, etc.) to maintain a desired amount of tension in the lower flexible coupler member 24540. The amount of tension in each flexible coupler member may vary depending upon the relative positioning of the surgical end effector 23000 to the elongate shaft assembly 24000.

In accordance with at least one aspect, a large surface area is advantageous for distributing the force between the vertebra members when they push so that the vertebra members cannot twist relative to each other. The available area in the anvil and channel is limited and the anvil and channel must remain stiff. The T-shaped upper vertebra members 24420 and the T-shaped lower vertebra members 24520 are designed to fit in the limited spaces available in the anvil 23210 and the elongate channel 23110 while ensuring that there is a large amount of area to distribute the firing loads. The curved surfaces on each upper vertebra member 24420 and each lower vertebra member 24520 allow each of those vertebras to better transfer loads between themselves even when they tilt. The upper alignment member 24480 and the lower alignment member 24580 may also serve to prevent the upper vertebra members 24420 and the lower vertebra members 24520 from twisting relative to each other. The large surface area may also help to prevent galling of the vertebra members and/or the anvil and channel. The upper flexible spine assembly 24400 and the lower flexible spine assembly 24500 otherwise operably interface with the rotary drive screw 2700 arrangements as disclosed herein. The upper flexible coupler member 24440 and the lower flexible coupler member 24540 may also be used in the manners discussed above to retract the firing member 24310 back to its starting position if, during a firing stroke, the firing drive system 24300 fails.

Figure 51:
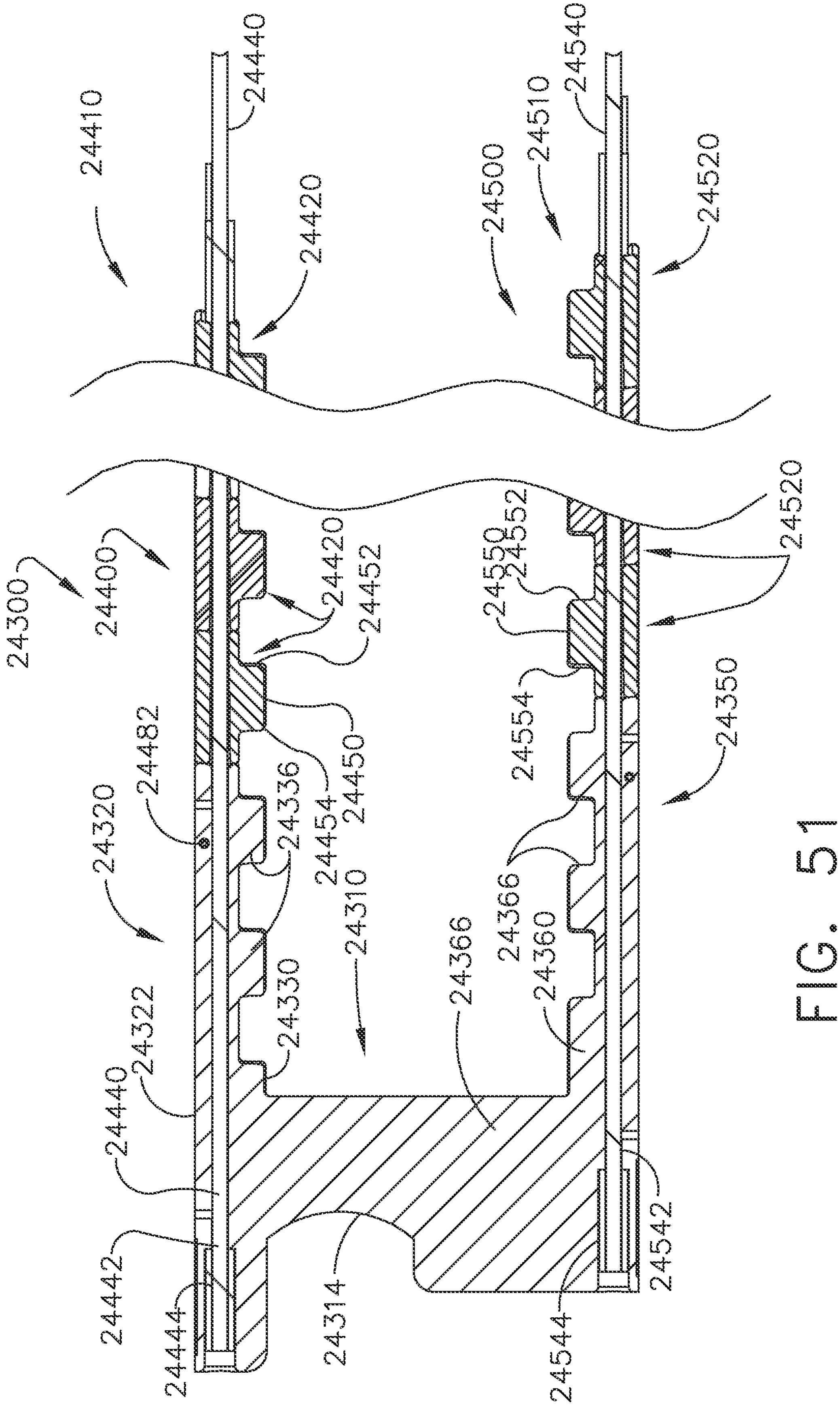
FIG. 51 is a cross-sectional side view of the portions of the firing system depicted in FIG. 50.

As can be seen in FIG. 51, the top firing member feature 24320 on the firing member 24310 comprises a distal upper firing member tooth segment 24330 that is equivalent to one half of an upper vertebra member tooth 24450 on each upper vertebra member 24420. In addition, two proximal upper firing member teeth 24336 that are identical to an upper vertebra member tooth 24450 on each upper vertebra member 24420 are spaced from the distal upper firing member tooth segment 24330. The distal upper firing member tooth segment 24330 and the proximal upper firing member teeth 24336 may each be integrally formed with the top firing member feature 24320 of the firing member 24310. Likewise, the bottom firing member feature 24350 of the firing member 24310 comprises a distal lower firing member tooth 24360 and two proximal lower firing member teeth 24366 that are integrally formed on the bottom firing member feature 24350. For example, in at least one arrangement, the firing member 24310 with the rigidly attached teeth 24330, 24336, 24360, and 24366 may be fabricated at one time as one unitary component using conventional metal injection molding techniques. The person of ordinary skill in the art will recognize that the firing member 24310 operates in essentially the same manner as the firing member 2310 as was described in detail herein.

Figure 56:
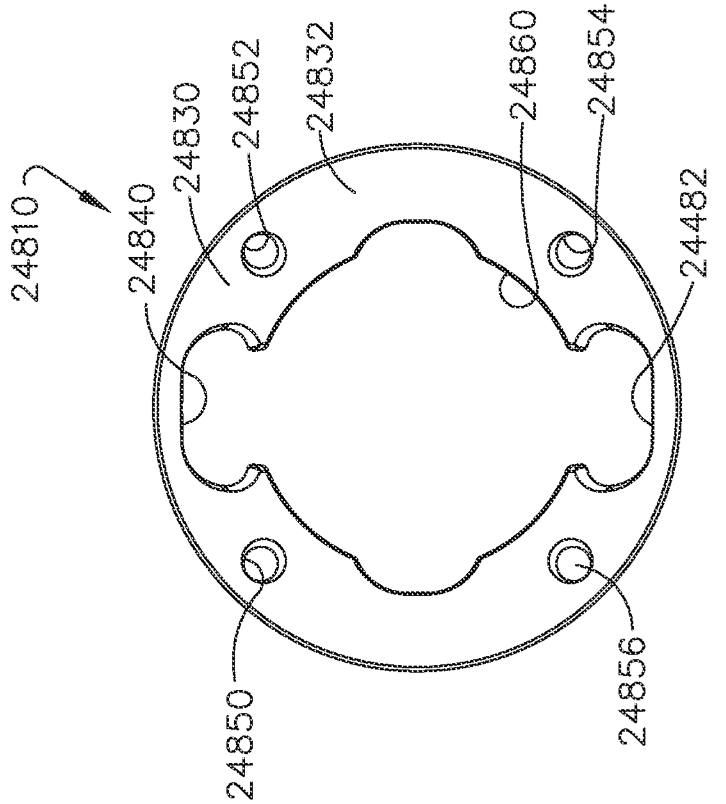
FIG. 56 is a view of a distal face of the annular rib member of FIG. 55.
Figure 55:
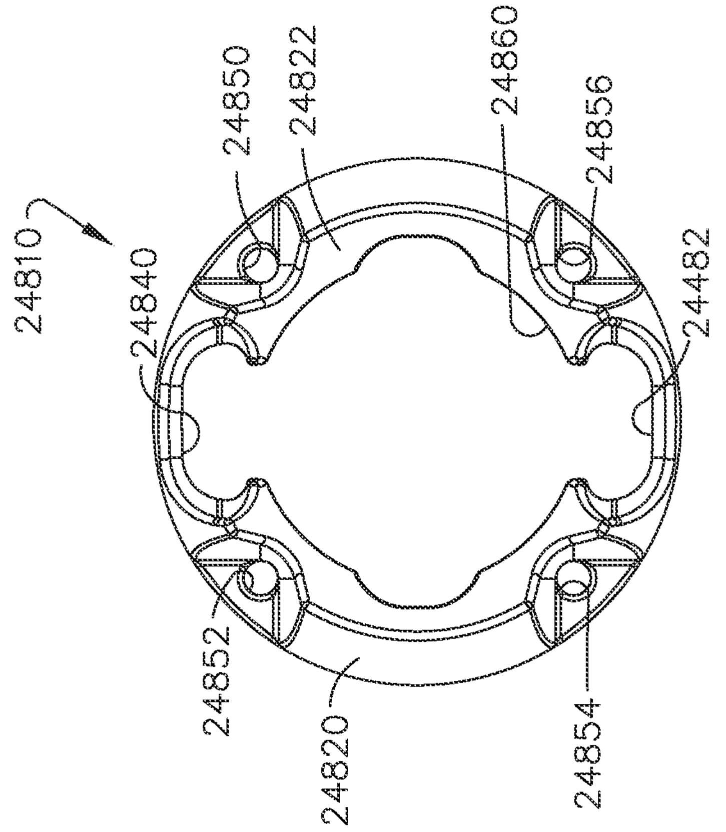
FIG. 55 is a view of a proximal face of an annular rib member of a movable exoskeleton assembly of the surgical instrument of FIG. 46.
Figure 57:
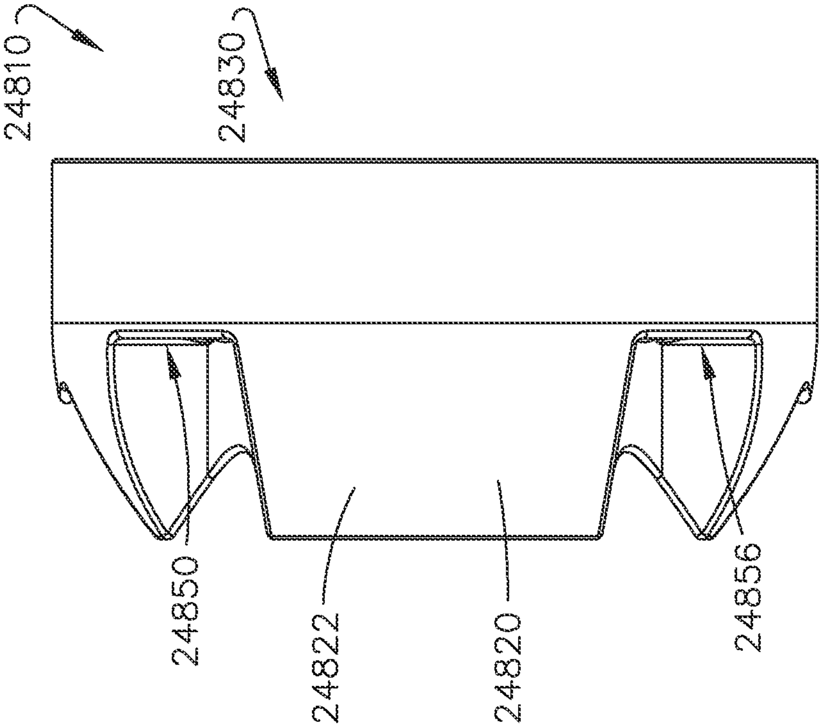
FIG. 57 is a side view of the annular rib member of FIGS. 55 and 56.

Turning now to FIGS. 55-58, in accordance with at least one aspect, the articulation joint 24200 comprises a movable exoskeleton assembly 24800. In one form, the movable exoskeleton assembly 24800 comprises a series 24802 of movably interfacing annular rib members 24810. As can be seen in FIGS. 55-57, each annular rib member 24810 comprises a first or proximal face 24820 that comprises a convex or domed portion 24822. Each annular rib member 24810 further comprises a second or distal face 24830 that is concave or dished. Each annular rib member 24810 further comprises an upper spine passage 24840 that is configured to accommodate passage of the upper flexible spine assembly 24400 therethrough and a lower spine passage 24842 that is configured to accommodate passage of the lower flexible spine assembly 24500 therethrough. In addition, each annular rib member 24810 further comprises four articulation passages 24850, 24852, 24854, and 24856 to accommodate passage of articulation actuators in the form of articulation cables 24242, 22446, 24250, and 24254 therethrough. See FIG. 49. Each annular rib member 24810 further comprises a central drive passage 24860 that is configured to accommodate passage of the constant velocity (CV) drive shaft assembly 2620 therethrough.

Figure 58:
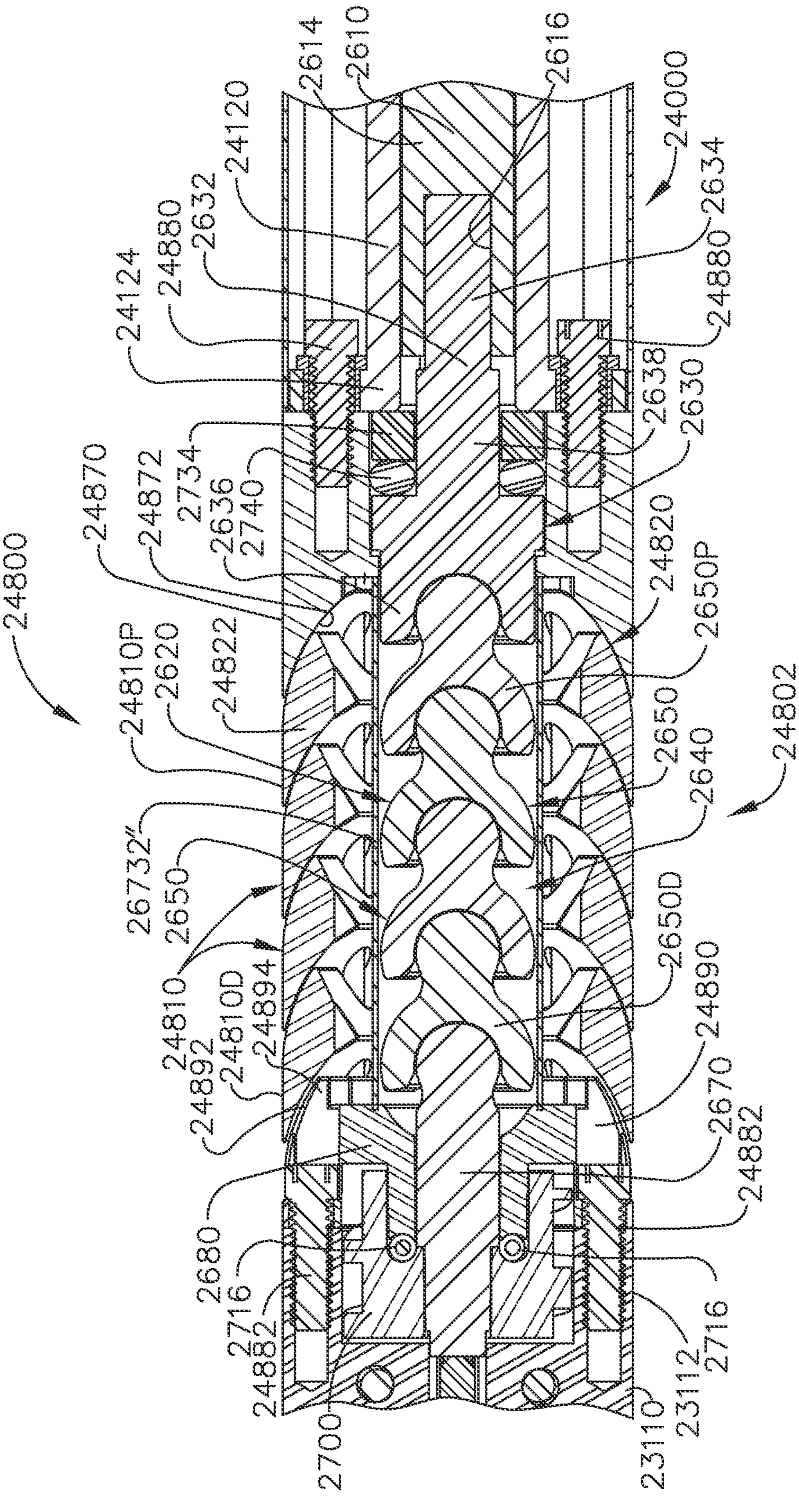
FIG. 58 is a partial cross-sectional view of a portion of the surgical instrument of FIG. 46.

As can be seen in FIG. 58, the movable exoskeleton assembly 24800 comprises a proximal attachment rib 24870 that is configured to attach the movable exoskeleton assembly 24800 to the distal end 24124 of the proximal support shaft 24120 by cap screws 24880 or other suitable fastener arrangements. The proximal attachment rib 24870 comprises a first or distal face 24872 that is concave or dished to receive or movably interface with the convex or domed portion 24822 of the proximal face 24820 of a proximal-most annular rib member 24810P. Similarly, the movable exoskeleton assembly 24800 comprises a distal attachment rib 24890 that is configured to attach the movable exoskeleton assembly 24800 to the proximal end 23112 of the elongate channel 23110 by cap screws 24882 or other suitable fasteners. The distal attachment rib 24890 comprises a first or proximal face 24892 that comprises a convex or domed portion 24894 that configured to be received in or movably interface with the concave or dished distal face 24832 of a distal-most annular rib member 24810D. In various embodiments, the annular rib members 24810, 24810P, and 24810D may be fabricated from any suitable metal (e.g., stainless steel, titanium, etc.) or other suitable material. The annular rib members 24810, 24810P, and 24810D may be formed by suitable drawing or forming operations, by machining or casting. The proximal faces 24820 and the distal faces 24830 may be polished or otherwise finished to a desirable smooth finish to reduce friction and facilitate movement between the annular rib members 24810, 24810P, and 24810D. In accordance with one aspect, all edges on each annular rib member 24810, 24810P, 24810D are rounded to facilitate relative movement between the annular rib members. The proximal attachment rib 24870 and the distal attachment rib 24890 may be formed with similar attributes.

The surgical instrument 22010 also comprises an articulation system 24240 that is configured to apply articulation motions to the surgical end effector 23000 to articulate the surgical end effector 23000 relative to the elongate shaft assembly 24000. In at least one arrangement, for example, as mentioned above, the articulation system 24240 comprises four articulation cables 24242, 24246, 24250, and 24254 that extend through the elongate shaft assembly 2400. See FIG. 49. In the illustrated arrangement, the articulation cables 24242, 24246 pass through the proximal attachment rib 24870 and through each of the annular rib members 24810P, 24810, and 24810D to be secured to the distal attachment rib 24890. In one arrangement for example, each of the articulation cables 24242, 24246 are secured to the distal attachment rib 24890 by corresponding attachment lugs 24243. See FIGS. 61 and 63. Likewise, the articulation cables 24250 and 24254 extend through the proximal attachment rib 24870 and through each of the annular rib members 24810P, 24810, and 24810D to be secured to the distal attachment rib 24890 by corresponding attachment lugs 24243.

Figure 59:
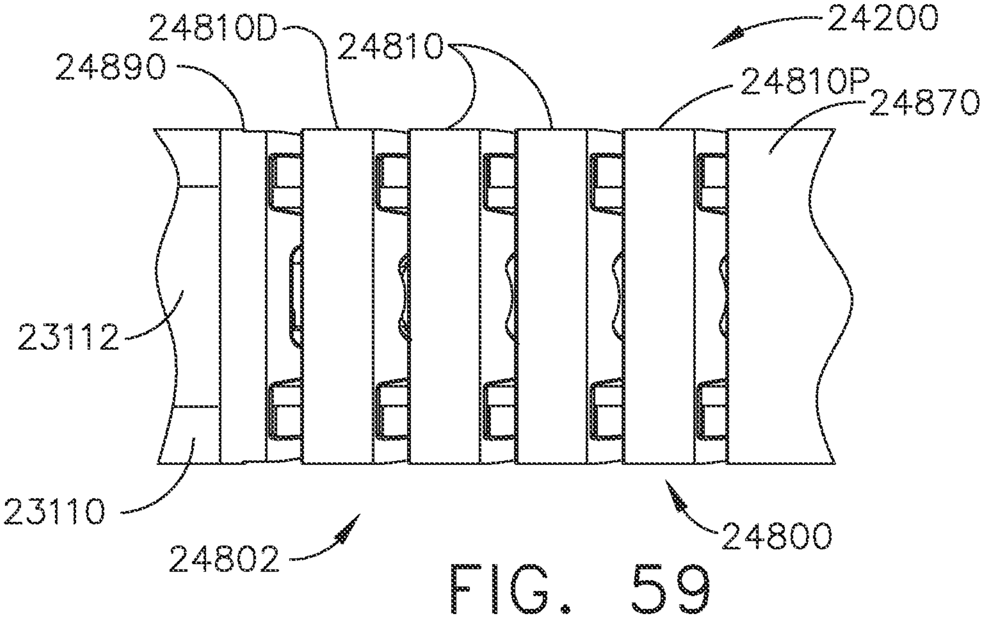
FIG. 59 is a side view of an articulation joint of the surgical instrument of FIG. 46 when the surgical end effector thereof is in an unarticulated position.
Figure 60:
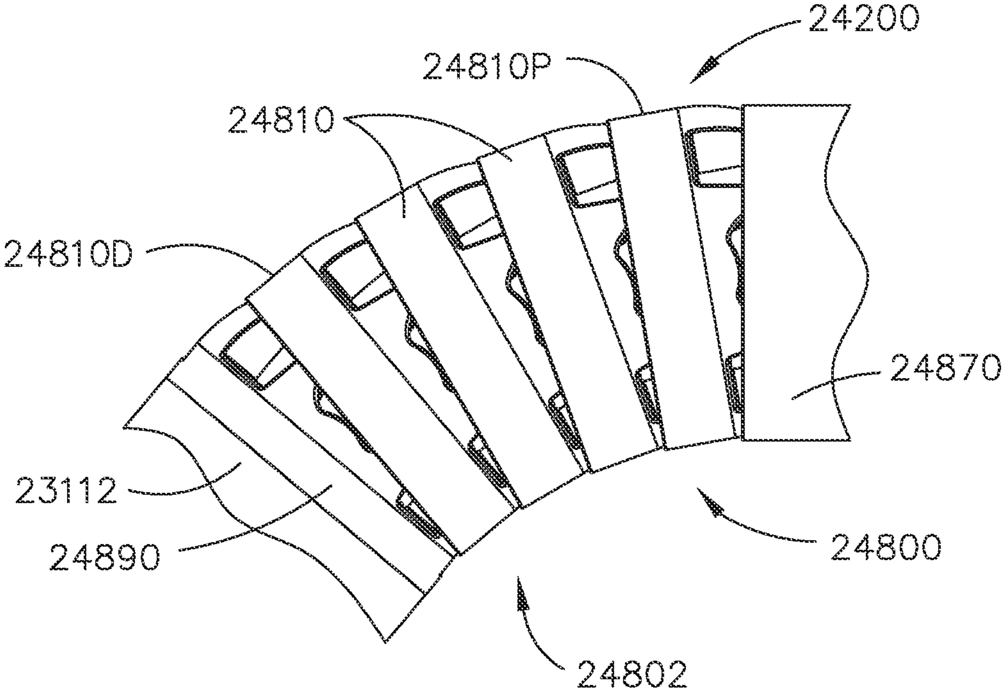
FIG. 60 is another side view of the articulation joint of FIG. 59 when the surgical end effector is in an articulated position.
Figure 61:
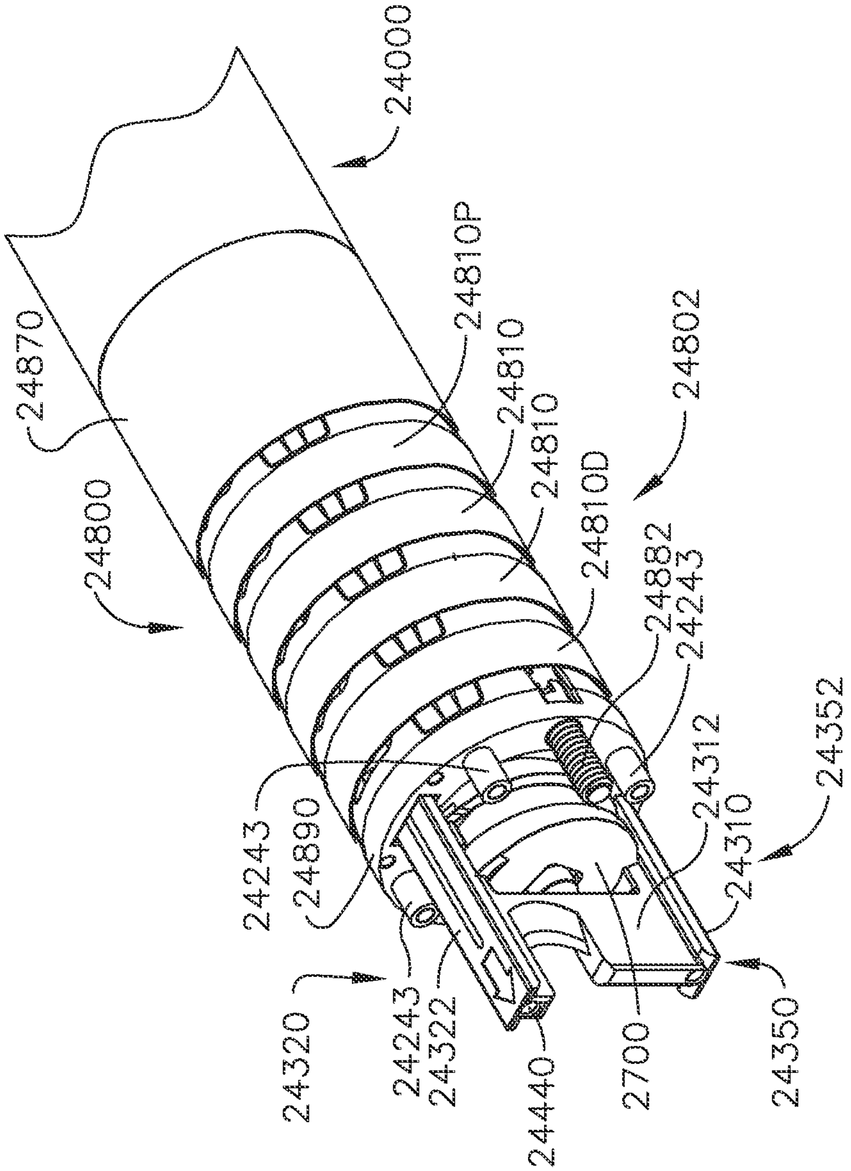
FIG. 61 is partial perspective view of a portion of the surgical instrument of FIG. 46 with the surgical end effector omitted for clarity.
Figure 62:
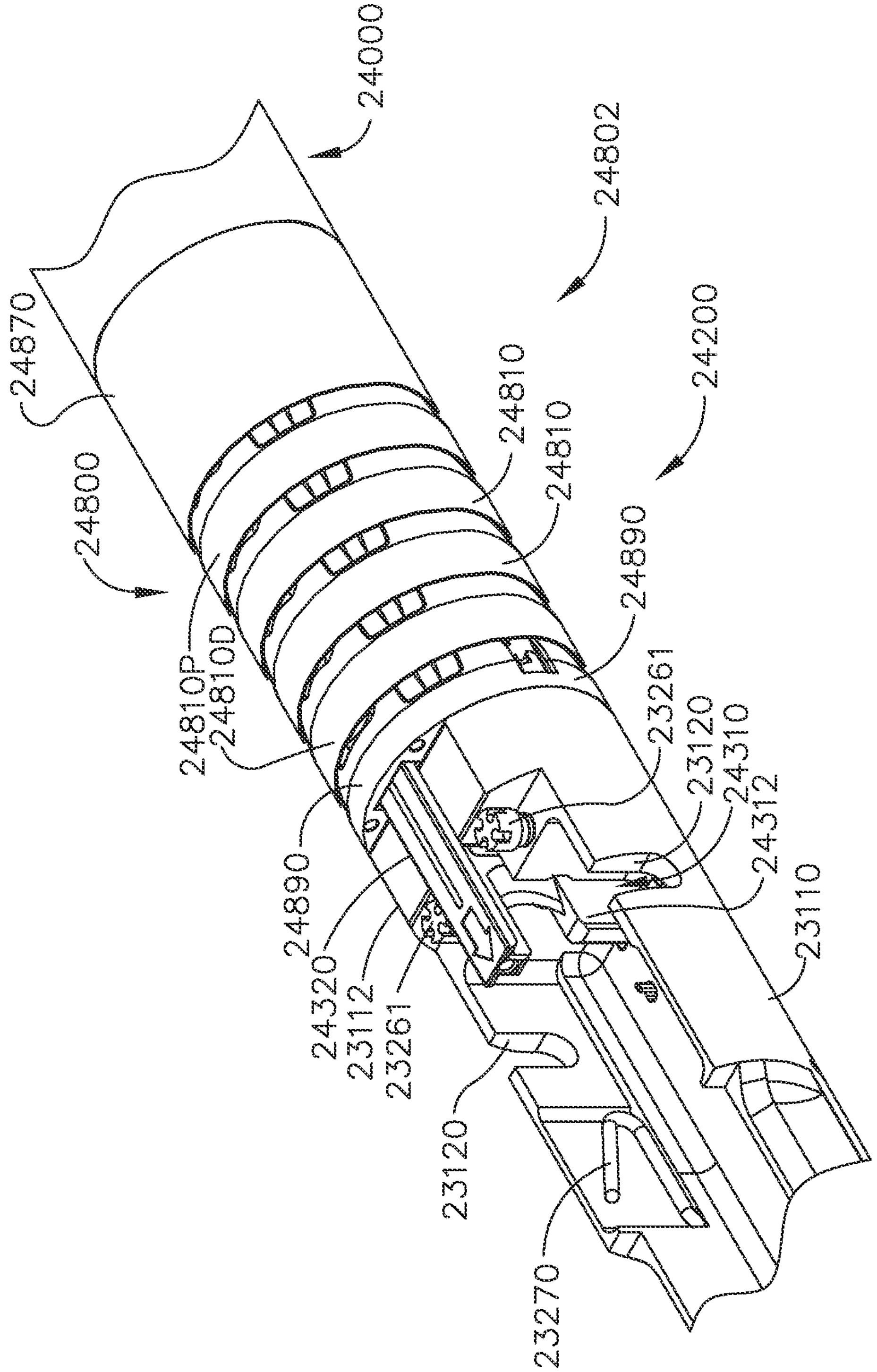
FIG. 62 is another partial perspective view of a portion of the surgical instrument of FIG. 46.
Figure 63:
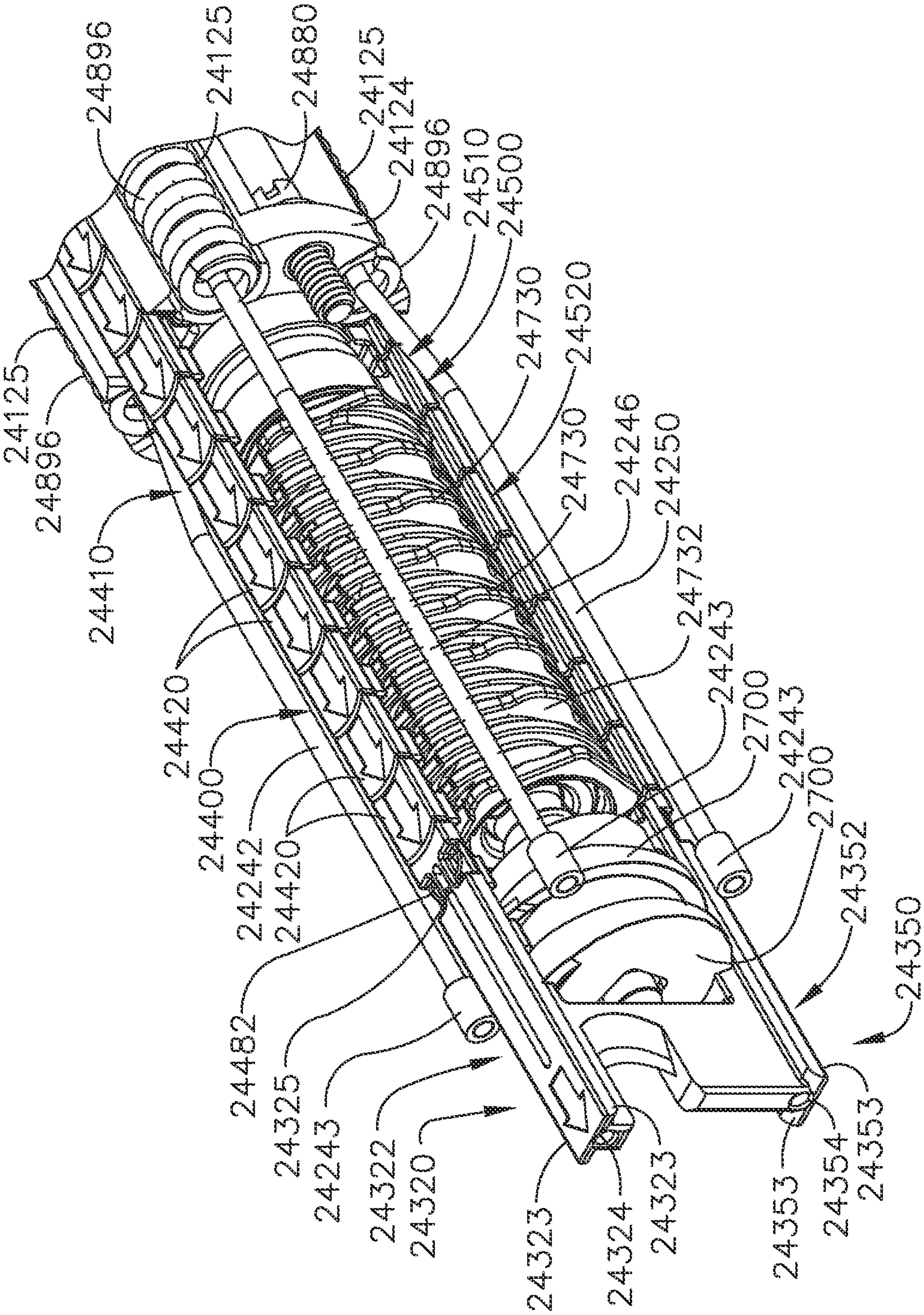
FIG. 63 is another partial perspective view of a portion of the surgical instrument of FIG. 46.

In one arrangement, each of the articulation cables 24242, 24246, 24250, and 24254 extend through corresponding coil springs 24896 that are supported in cavities 24125 in the distal end 24124 of the rigid proximal support shaft 24120. In addition, each coil spring 24896 is associated with a tensioning lug 24897 that is also journaled onto each respective articulation cable 24242, 24246, 24250, and 24524 and is secured thereon to attain a desired amount of compression in each spring 24896 which serves to retain the annular rib members 24810P, 24810, and 24810D in movable engagement with each other and with the proximal attachment rib 24870 and the distal attachment rib 24890. The cables 24242, 24246, 24250, and 24254 operably interface with an articulation control system that is supported in the housing of the surgical instrument 22010. For example, as was discussed above, a proximal portion of each cable 24242, 24246, 24250, and 24254 may be spooled on a corresponding rotary spool or cable-management system 2007 (FIG. 2) in the housing portion of the surgical instrument 22010 that is configured to payout and retract each cable 24242, 24246, 24250, and 24254 in desired manners. The spools/cable management system may be motor powered or manually powered (ratchet arrangement, etc.). FIG. 59 illustrates the articulation joint 24200 in an unarticulated position and FIG. 60 illustrates the articulation joint in one articulated configuration. Such arrangement permits the surgical end effector 23000 to be articulated through multiple articulation planes relative to the elongate shaft assembly 24000.

Figure 64:
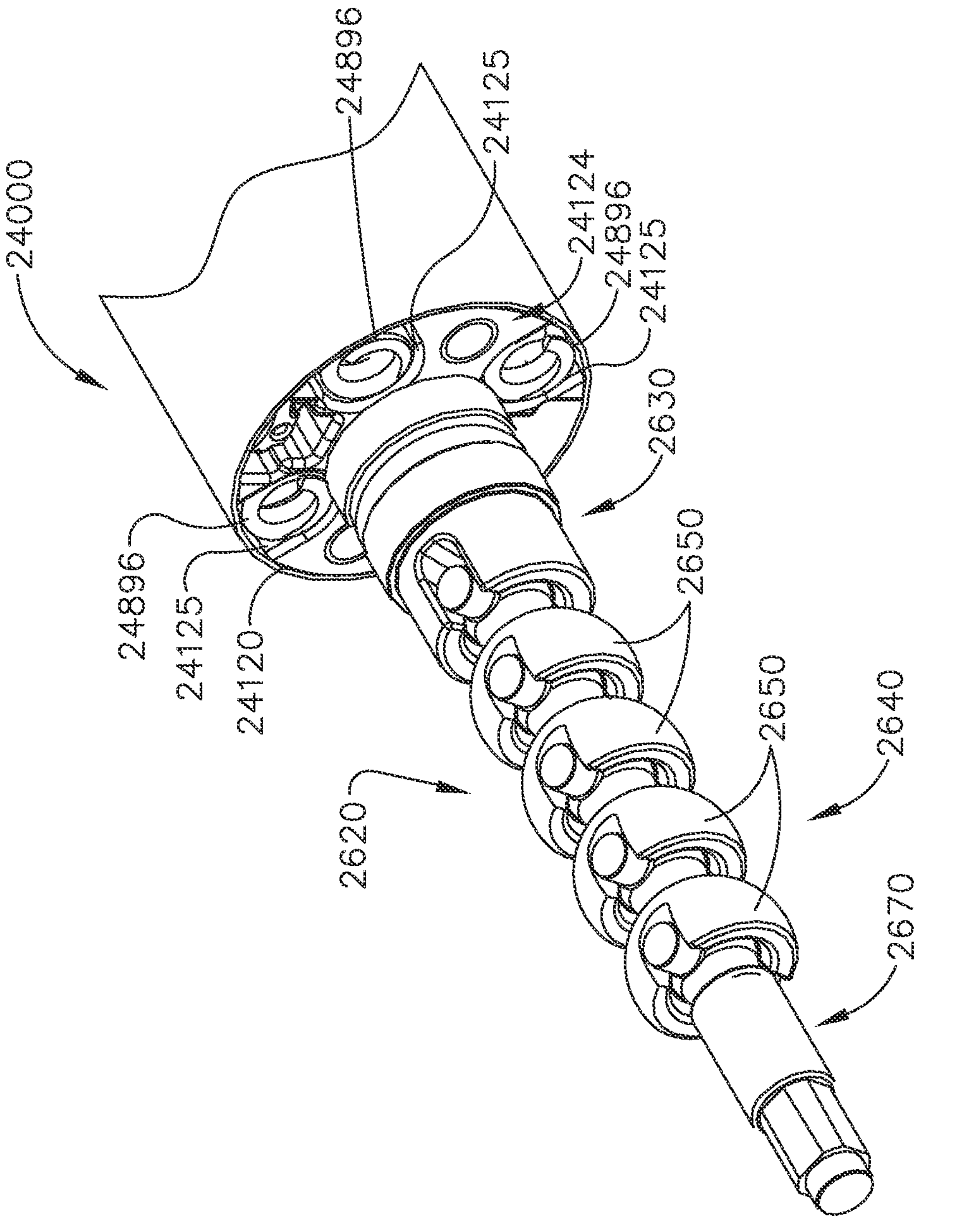
FIG. 64 is a perspective view of a CV drive shaft assembly and a portion of the elongate shaft assembly of the surgical instrument of FIG. 46.
Figure 65:
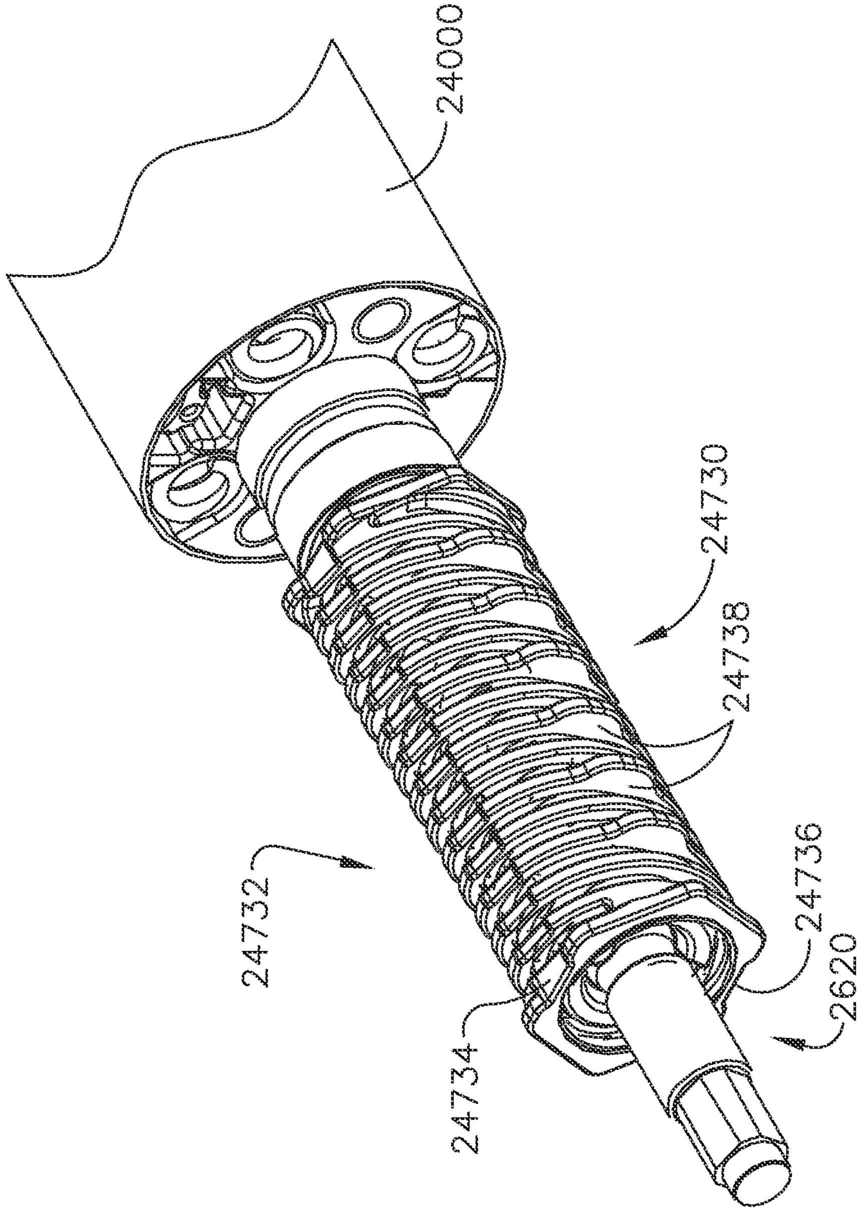
FIG. 65 is another perspective view of the CV drive shaft assembly and elongated shaft assembly of FIG. 64 with a drive cover embodiment installed around the CV drive shaft assembly.

As can be seen in FIGS. 49, 58, and 64, the surgical instrument 22010 employs a constant velocity (CV) drive shaft assembly 2620 that spans or extends axially through the articulation joint 24200. The operation and construction of the CV drive shaft assembly 2620 was described in detail above and will not be repeated here beyond what is necessary to understand the operation of the surgical instrument 22010. Briefly as described above, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650. As can be seen in FIG. 58 as was also described previously, to ensure that the drive joints 2650 are engaged with each other, a proximal drive spring 2740 is employed to apply an axial biasing force to the series 2640 of drive joints 2650. For example, as can be seen in FIG. 58, proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring received on the proximal barrel portion 2638 of the proximal shaft segment 2632. The proximal drive spring 2740 lightly biases the drive joints 2650 together to decrease any gaps that occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

Figure 66:
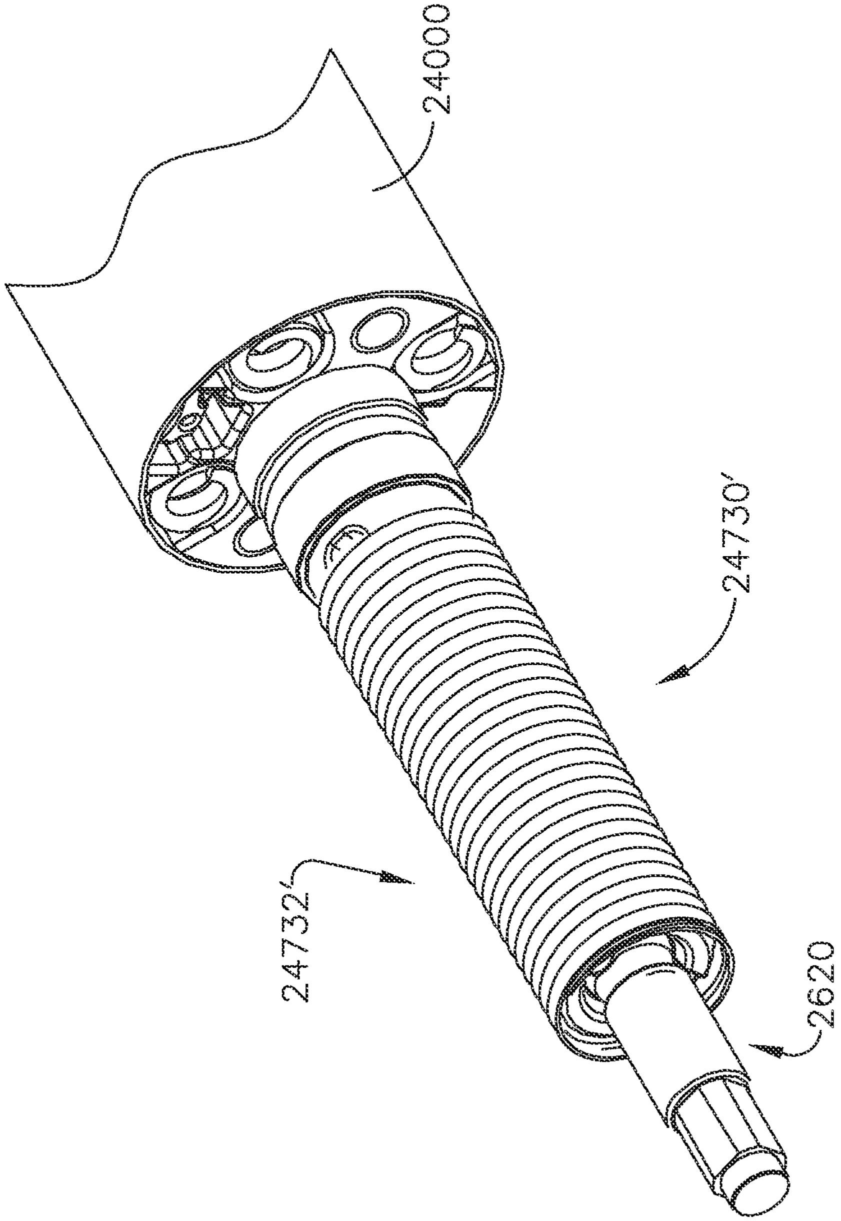
FIG. 66 is another perspective view of the CV drive shaft assembly and elongated shaft assembly of FIG. 64 with another drive cover embodiment installed around the CV drive shaft assembly.
Figure 67:
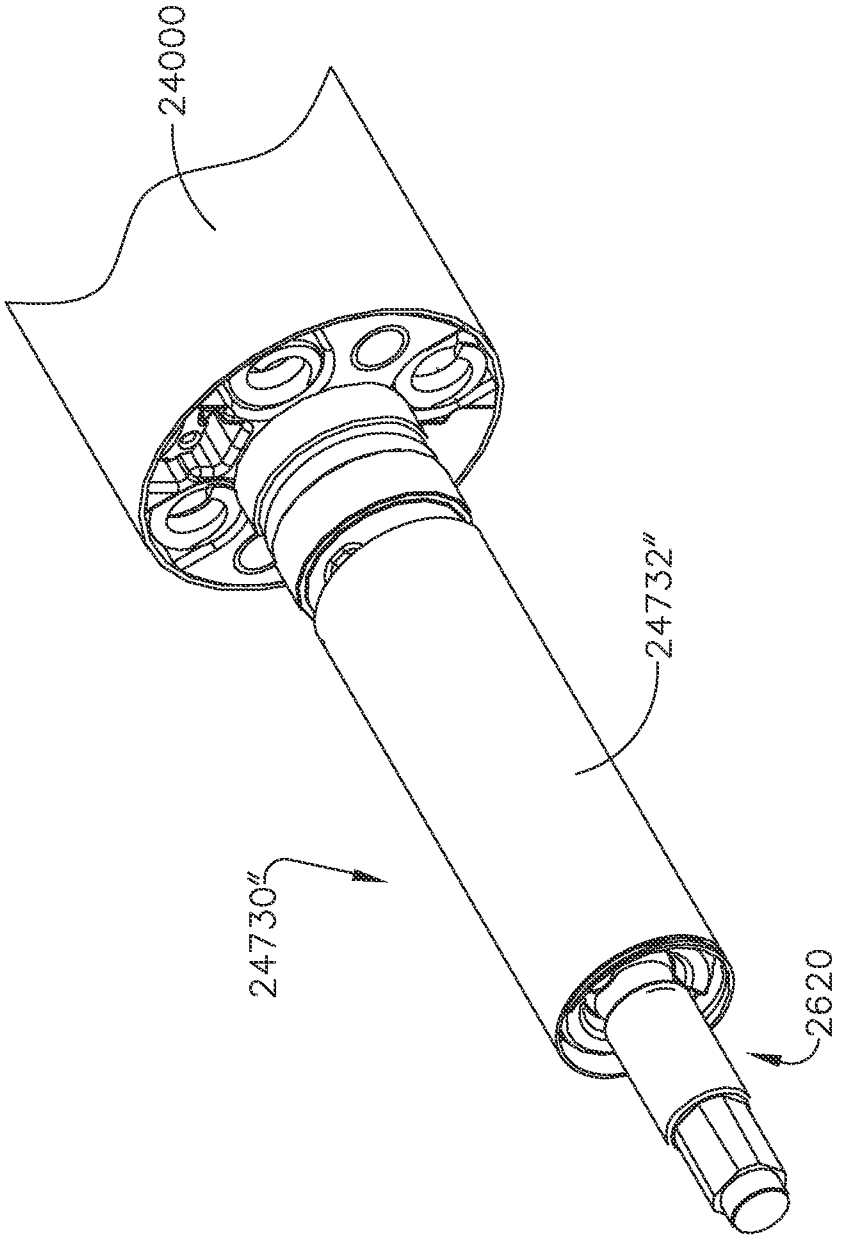
FIG. 67 is another perspective view of the CV drive shaft assembly and elongated shaft assembly of FIG. 64 with another drive cover embodiment installed around the CV drive shaft assembly.
Figure 68:
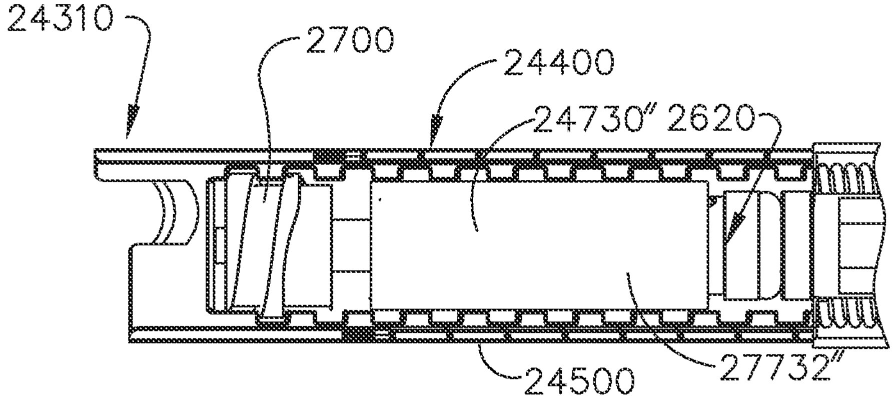
FIG. 68 is a side view of a portion of the firing system of the surgical instrument of FIG. 46 with the drive cover of FIG. 67 installed around the CV drive shaft assembly.
Figure 69:
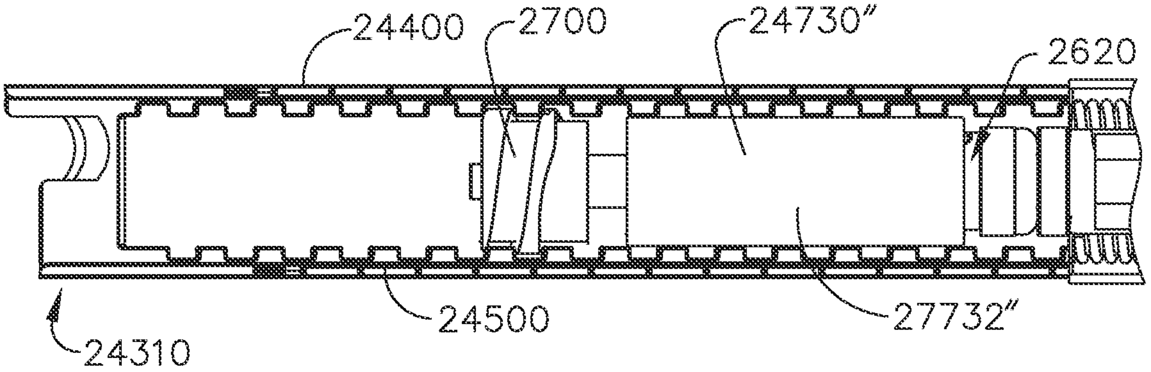
FIG. 69 is another side view of the portion of the firing system and drive cover of FIG. 68.
Figure 70:
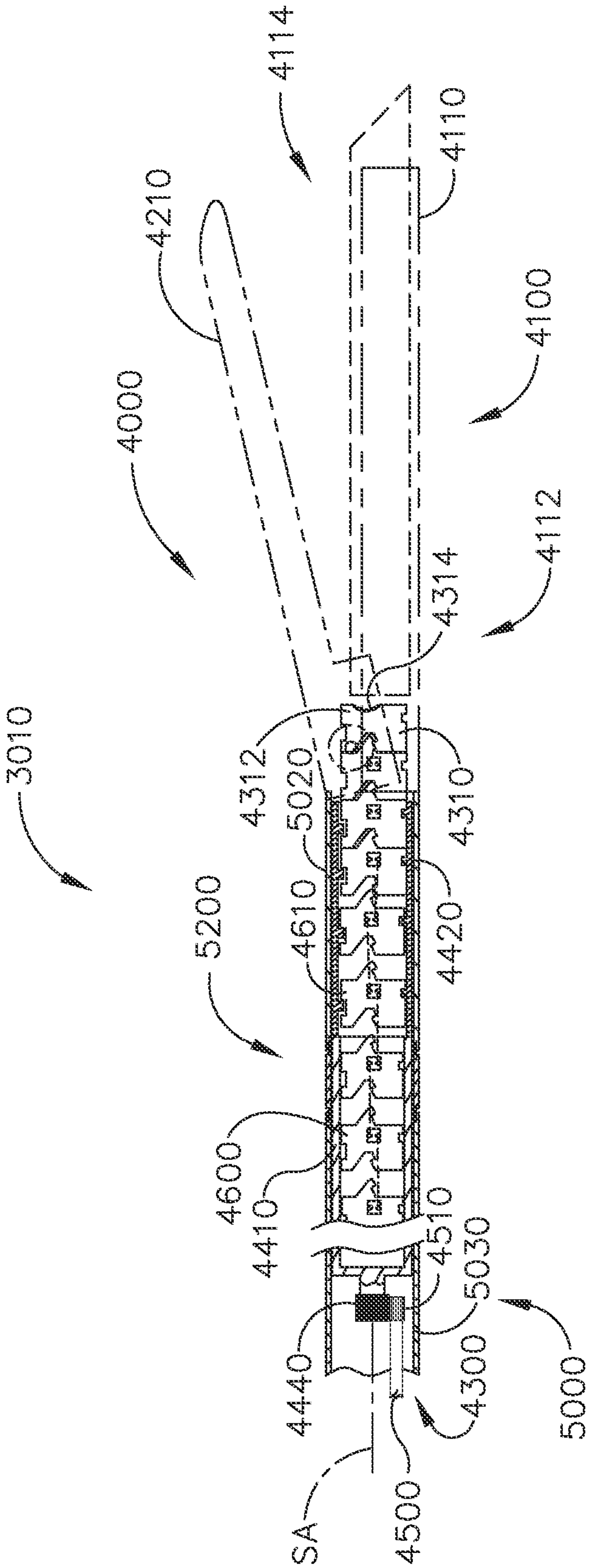
FIG. 70 is a cross-sectional view of a portion of another surgical instrument.
Figure 71:
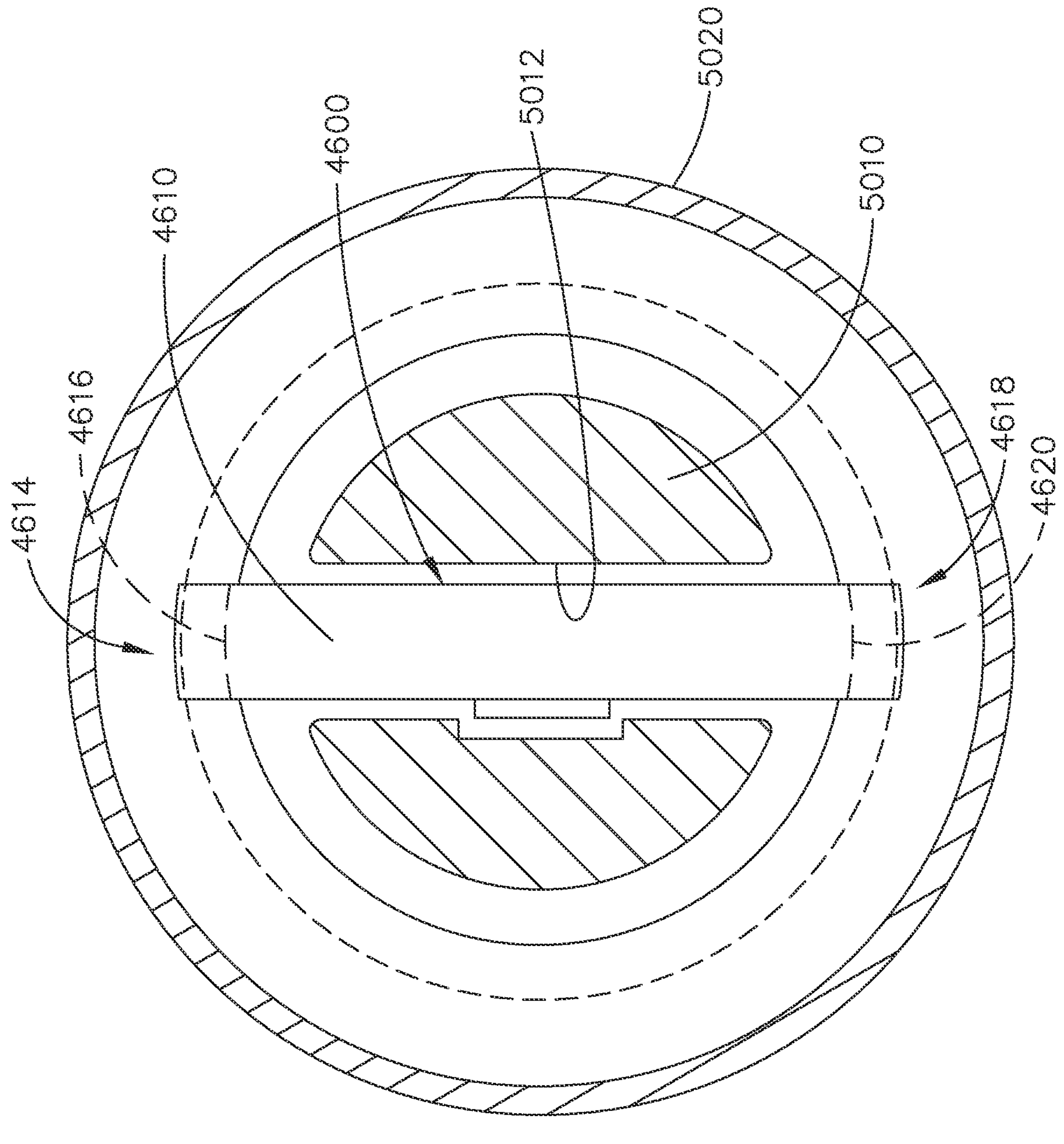
FIG. 71 is a cross-sectional end view of a surgical end effector of the surgical instrument of FIG. 70.

To further prevent the drive joints 2650 from buckling during articulation, the series 2640 of movably coupled drive joints 2650 extend through at least one low friction drive cover 24730 that extends through the central drive passage 24860 in each of the annular rib members 24810. In the arrangement depicted in FIGS. 63 and 65, the drive cover 24730 comprises an outer and inner cut hypotube 24732. Such hypotube 24732 may be fashioned from metal (e.g., stainless steel, etc.) and have multiple series of cuts or slits therein that may be made using laser cutter arrangements. In the illustrated arrangement, the hypotube 24732 may be fabricated with an upper relief passage 24734 that provides clearance for the upper flexible spine assembly 24400 to pass thereover during operation while the surgical end effector 23000 is in an articulated position and articulated positions. In addition, the hypotube 24732 may have a lower relief passage 24736 to provide similar clearance for the lower flexible spine assembly 24500. As can also be seen in FIG. 65, the hypotube 24732 may be shaped with diametrically opposed lateral tab portions 24738 to provide lateral stability during articulation. FIG. 66 illustrates an alternative drive cover 24730' that comprises an inner cut hypotube 24732'. FIGS. 58, 67, 68, and 69 illustrate an alternative drive cover 24730" that comprises flexible heat shrink tubing 24732" that is applied over the constant velocity (CV) drive shaft assembly 2620. In still other arrangements, the drive cover may comprise a coiled spring or coiled member as well.

Various embodiments of the present disclosure provide advantages over previous surgical endocutter configurations that are capable of articulation. For example, pushing a firing member forward in an articulating end effector generally requires a lot of force and that force must be balanced. For example, when firing the firing member at an angle of greater than sixty degrees, it becomes very difficult to push a beam through the articulation joint. The joint also experiences significant loads which may cause the articulation joint to de-articulate. By employing an upper flexible drive arrangement and a lower flexible drive arrangement that are each flexible through the articulation joint, but then become rigid when they are distal to the articulation joint can allow for a large degree of articulation (e.g., articulation angles over seventy degrees) while applying balanced loads to the firing member that are constrained to the firing member and not to the articulation joint. Stated another way, torsional loads are applied proximal to the articulation joint instead of longitudinal loads which could lead to de-articulation of the end effector. The torsional loads are converted to longitudinal loads at a position that is distal to the articulation joint. Thus, the rotary drive screw serves to actually convert torsional motion or loads to longitudinal loads that are applied to the firing member at a location that is distal to the articulation joint.

Further, by longitudinally breaking up the threaded drive arrangements, the threaded drive arrangements pass through the articulation joint while also effectively decreasing the length of the surgical end effector. For example, each single vertebra tooth is significantly shorter than multiple pitches rigidly connected. The vertebra can angle as they pass through the articulation joint. This flexible interconnection enables the rotary drive screw to be closely positioned to the articulation joint as compared to being significantly spaced therefrom if all of the pitches were rigidly connected.

FIGS. 70-73 illustrate another surgical end effector 4000 that may be employed with a surgical instrument 3010 that may be similar to the surgical instrument 10 in many aspects. The surgical end effector 4000 may be similar to the surgical end effector 1000 except for the differences discussed below. The surgical end effector 4000 is operably coupled to an elongate shaft assembly 5000. The elongate shaft assembly 5000 may be operably attached to a housing portion of the surgical instrument 3010. The housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents.

In at least one form, the surgical end effector 4000 comprises a first jaw 4100 and a second jaw 4200. In the illustrated arrangement, the first jaw 4100 comprises an elongate channel 4110 that comprises a proximal end 4112 and a distal end 4114 and is configured to operably support a surgical staple cartridge 1300 therein. In the illustrated arrangement, the second jaw 4200 comprises an anvil 4210 that may be similar to anvil 1210 described above. In the illustrated arrangement, the elongate shaft assembly 5000 defines a shaft axis SA and comprises a proximal shaft segment that operably interfaces with a housing of the control portion (e.g., handheld unit, robotic tool driver, etc.) of the surgical instrument 3010. The elongate shaft assembly 5000 further comprises an articulation joint 5200 that is attached to a proximal shaft portion and the surgical end effector 4000.

The elongate shaft assembly 5000 may comprise a distal spine assembly 5010 that is attached to the proximal end 4112 of the elongate channel 4110 and the articulation joint 5200. See FIG. 70. The distal spine assembly 5010 is non-movably supported in a distal outer tube segment 5020 that operably interfaces with the surgical end effector 4000. The elongate shaft assembly 5000 further includes a proximal spine member (not shown) that operably interfaces with a proximal end of the articulation joint 5200 and may be attached to or otherwise operably interface with the housing of the surgical instrument 3010. A proximal outer tube segment 5030 extends from the articulation joint 5200 back to the housing to operably interface therewith.

The surgical instrument 3010 employs a firing drive system 4300 that comprises a firing member 4310 that includes a vertically-extending firing member body 4312 that comprises a top firing member feature and a bottom firing member feature. A tissue cutting blade 4314 is attached to or formed in the vertically-extending firing member body 4312. The firing drive system 4300 comprises a rotary drive nut 4400 that is configured to rotatably drive a series 4600 of drive components 4610 that operably interface with the firing member 4310. The rotary drive nut 4400 comprises a flexible proximal segment 4410 that spans the articulation joint 5200 and a threaded distal segment 4420 that is distal to the articulation joint 5200. The threaded distal segment 4420 comprises a series of variable pitched threads 4430, with coarse spacing 4432 at the proximal end, and tighter spacing 4434 at the distal or exit end. See FIG. 72. The threaded rotary drive nut 4400 comprises a proximal drive gear 4440 that meshingly interfaces with a distal drive gear 4510 that is attached to a rotary drive shaft 4500. See FIG. 70. The rotary drive shaft 4500 may interface with a gearbox/motor arrangement supported in the housing of the surgical instrument 3010. Rotation of the rotary drive shaft 4500 causes the drive nut 4400 to rotate about the shaft axis SA.

The rotary drive nut 4400 comprises a proximal segment 4410 and a threaded distal segment 4420. The threaded distal segment 4420 is located distal to the articulation joint 5200 and is configured to threadably engage a series 4600 of drive components 4610 that are loosely linked together by flexible tethers 4640. In at least one arrangement, for example, each drive component 4610 comprises a vertically extending plate member 4612 that each includes a top end 4614 and a bottom end 4618. The top end 4614 includes a top thread segment 4616 and the bottom end 4418 includes a bottom thread segment 4620. The top thread segment 4616 and the bottom thread segment 4620 are configured to threadably engage the threads 4430 of the rotary drive nut 4400. The series 4600 of drive components 4610 is configured to flexibly pass through the articulation joint 5200 and into a vertical passage 5012 in the distal spine assembly 5010. Rotation of the rotary drive nut 4400 in a first rotary direction causes the series 4600 of drive components 4610 to move axially in the distal direction and rotation of the rotary drive nut 4400 in a second rotary direction will cause the series 4600 of drive components 4610 to move axially in the proximal direction.

Figure 72:
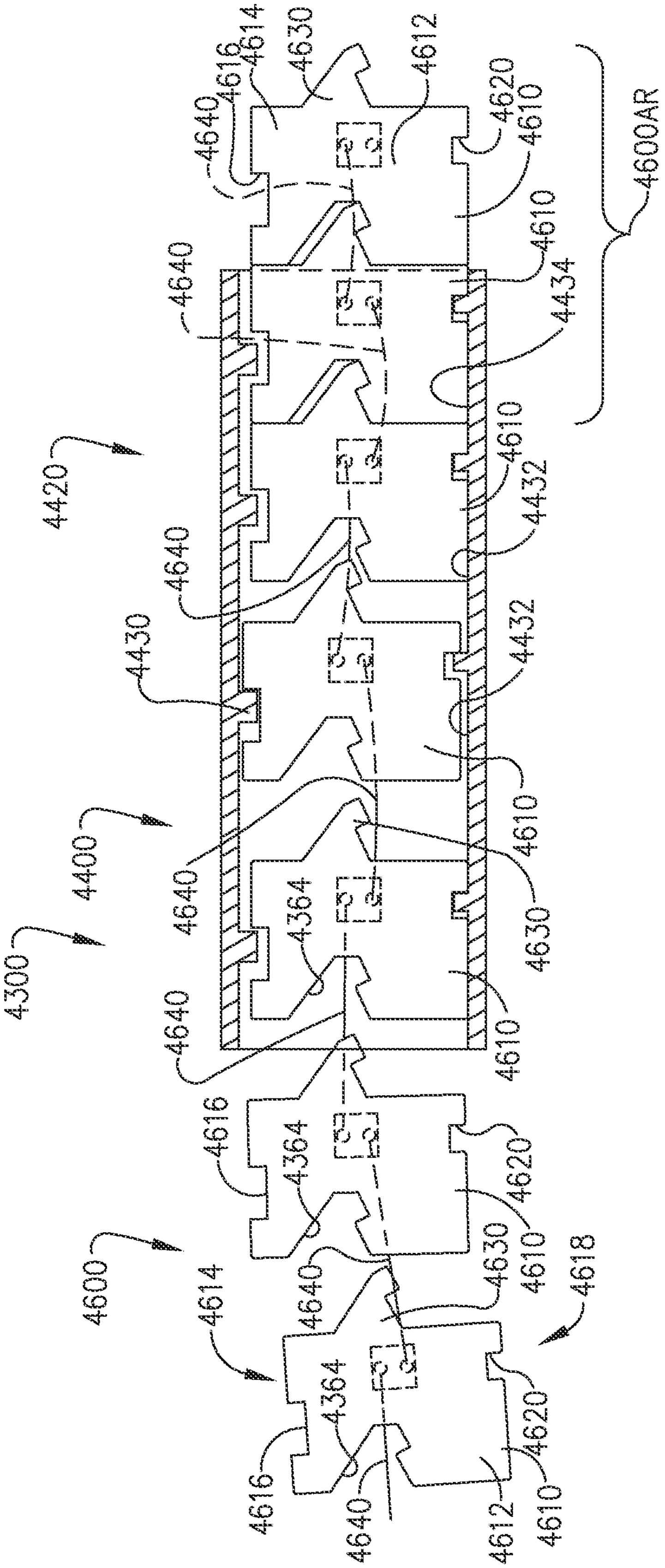
FIG. 72 is a cross-sectional side view of a rotary drive nut in engagement with drive components of the surgical instrument of FIG. 70.

Turning to FIG. 72, in at least one arrangement, each drive component 4610 further comprises a distally protruding latch feature 4630. Each latch feature 4360 is configured to be releasably received in latching engagement within a latch cavity 4364 that is formed in the adjacent drive component 4610 that is immediately distal thereto. When the drive components 4610 are latched together, they form an axially rigid series 4600AR of drive components for applying an axial drive motion to the firing member 5310 to drive the firing member 5310 through the surgical end effector 4000 from a starting to an ending position and then from the ending position back to the starting position. As can be seen in FIG. 72, as the drive components 4610 enter the threaded distal segment 4420 of the rotary drive nut 4400, they are loosely linked together. As the drive components 4610 threadably engage the finely pitched threads 4430 in the threaded distal segment 4420 of the rotary drive nut 4400, the latch features 4630 are latchingly received within the corresponding latch cavity 4364 in the distally adjacent drive component 4610 to form the axially rigid series 4600AR of drive components 4610. In one arrangement, a distal-most drive component 4610 may be configured to latchingly engage the firing member 4310 in a similar manner or in alternative arrangements, the distal-most drive component may be non-removably attached to the firing member 4310.

In the illustrated example, the drive components 4610 in the series 4600 of drive components are flexibly linked together such that they can move relative to each other to accommodate the articulation joint and without the need for reinforcing and support plates that are commonly required when pushing a firing beam through an articulated joint. As the series of drive components 4610 enters and is drivingly engaged by the threaded distal segment 4420 which is distal to the articulation joint, the drive components 4610 form the axially rigid series of drive components for driving the firing member 4310 through the surgical end effector 4000. The anvil 4210 may be pivoted into an open position by a spring or other arrangement in the various manners disclosed herein and then closed by the firing member 4310 as the firing member 4310 is driven distally from a starting position to an ending position in the various manners discussed herein. Other jaw control arrangements may also be employed to control the opening and closing of the jaws.

FIGS. 73-76 illustrate another surgical end effector 6000 that employs a drive system 6300 that comprises a series 6600 of flexibly linked drive components 6610 that can be used to traverse an articulation joint 6200 and rigidly advance a firing member 6130 through the surgical end effector 6000. The surgical end effector 6000 may comprise a channel 6010 that is configured to operably support a surgical staple cartridge (not shown) therein. An anvil 6020 may be pivotally coupled to the channel 6010 and is movable between an open position and a closed position by the firing member 6130 or other closure system arrangement. The anvil 6020 may be moved to an open position by a spring or other arrangement in the various manners disclosed herein.

Figure 74:
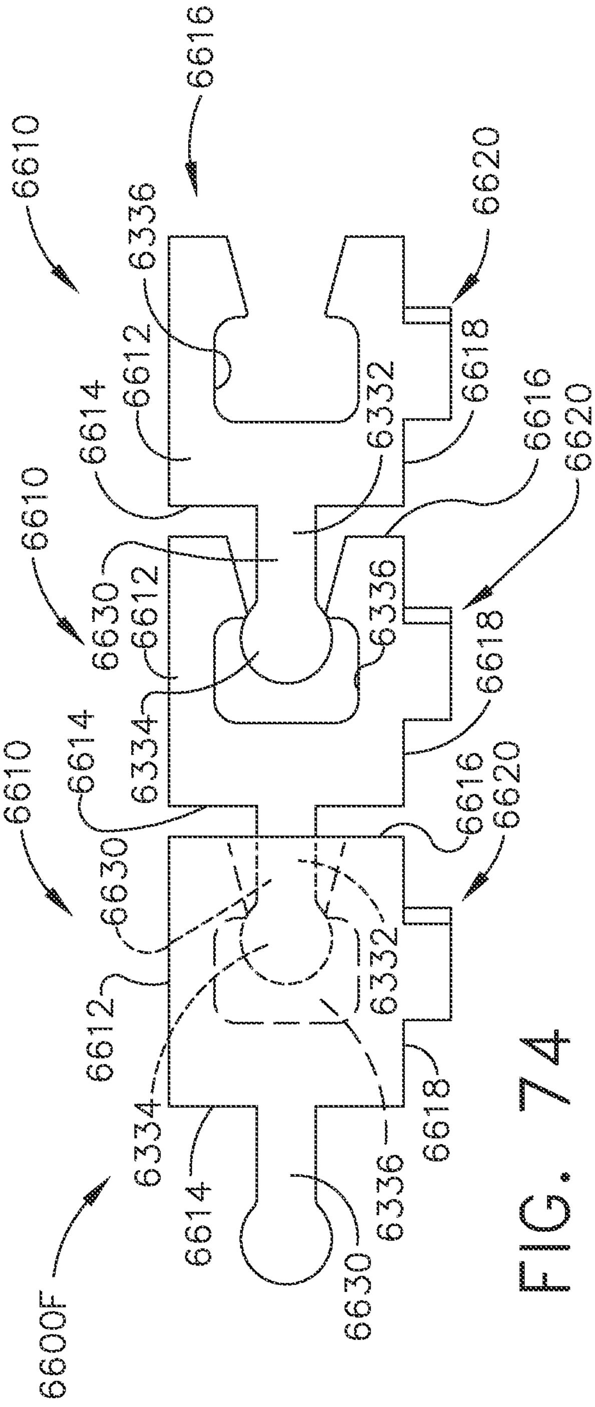
FIG. 74 is a side view of a portion of the series of flexibly linked drive components of the surgical instrument of FIG. 73 prior to engagement with a rotary drive gear in the surgical end effector.
Figure 75:
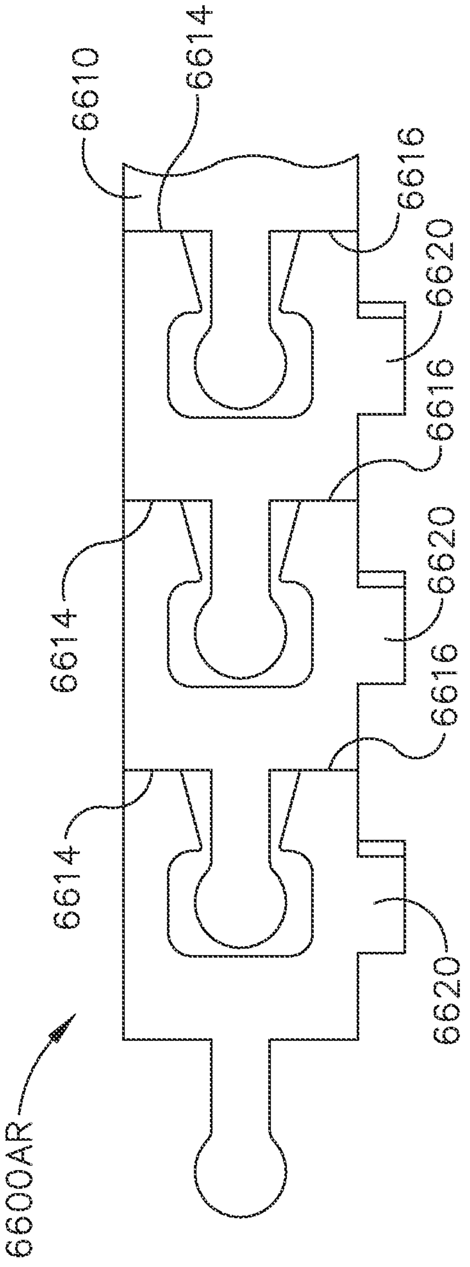
FIG. 75 is another side view of the portion of drive components of FIG. 74 after being engaged with the rotary drive gear to form a rigid series of drive components.
Figure 76:
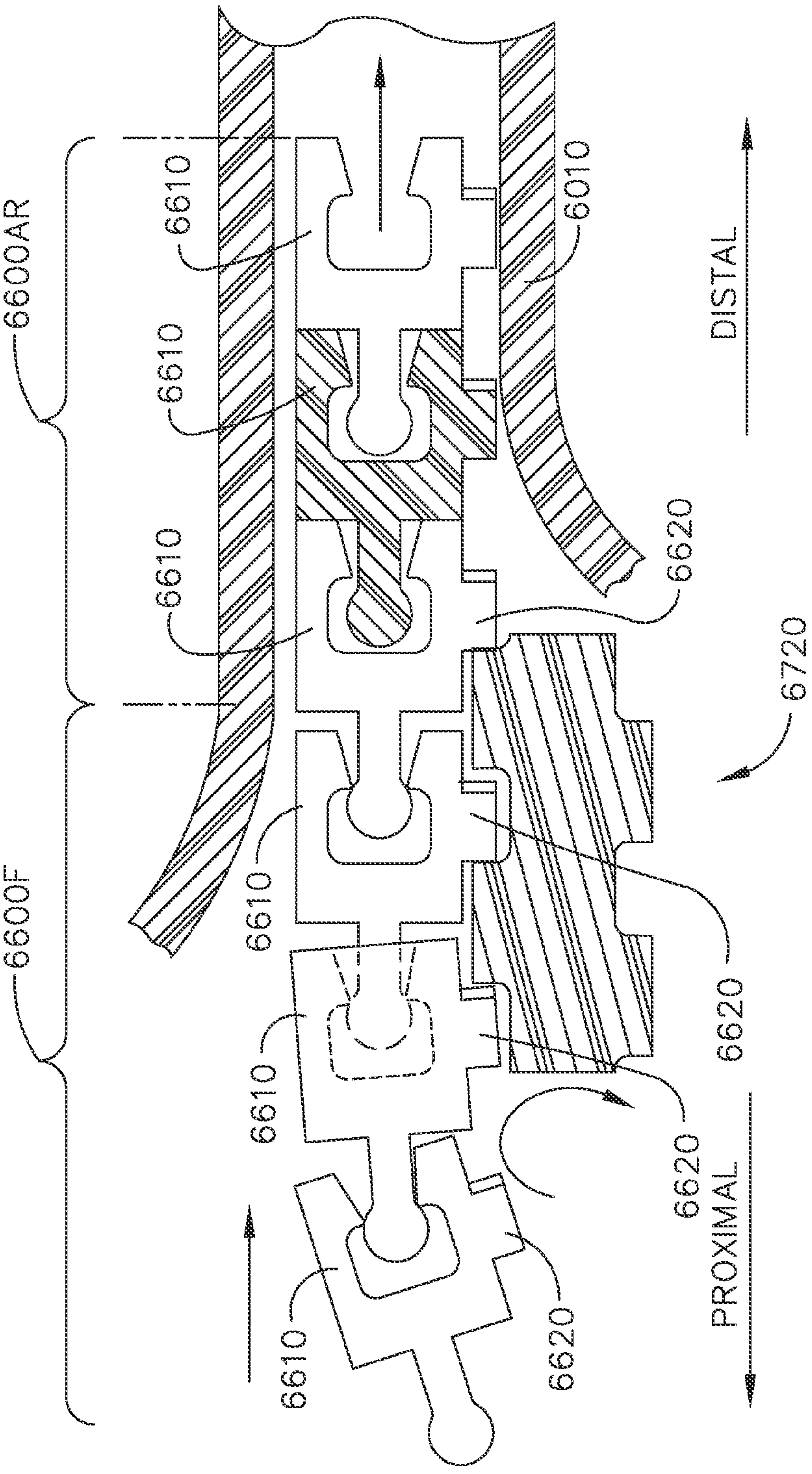
FIG. 76 is a partial cross-sectional view of the rotary drive system of the surgical instrument of FIG. 74 with components in the series of flexible drive components in driving engagement with the rotary drive gear thereof.

Turning to FIG. 74, in at least one arrangement, each drive component 6610 comprises a drive component body 6612 that has a proximal face 6614, a distal face 6616, and thread segment 6620 that is formed on a bottom surface 6618. Each drive component 6610 further comprises a proximally protruding latch feature 6630. Each latch feature 6630 comprises a neck feature 6632 that has a spherical latch head 6634 formed on an end thereof. The latch feature 6630 is configured to be movably received within a latch cavity

6336 that is formed in the adjacent drive component 6610 that is immediately distal thereto. To facilitate movable attachment of the drive components 6610 in movable serial arrangement, the spherical latch head 6634 is inserted through a tapered passage 6338 in the drive component body 6612 and into the latch cavity 6636. The spherical latch head 6634 is sized and shaped relative to the latch cavity 6636 to permit relative movement between the drive components 6610 when arranged as shown in FIG. 74. However, when the drive components are axially aligned such that the distal face 6616 of one drive component 6610 is in abutting engagement with the proximal face 6614 of the drive component that is immediately distal thereto, the drive components 6610 form an axially rigid series 6600AR of drive components that can drive the firing member 6130 through the surgical end effector 6000.

Figure 73:
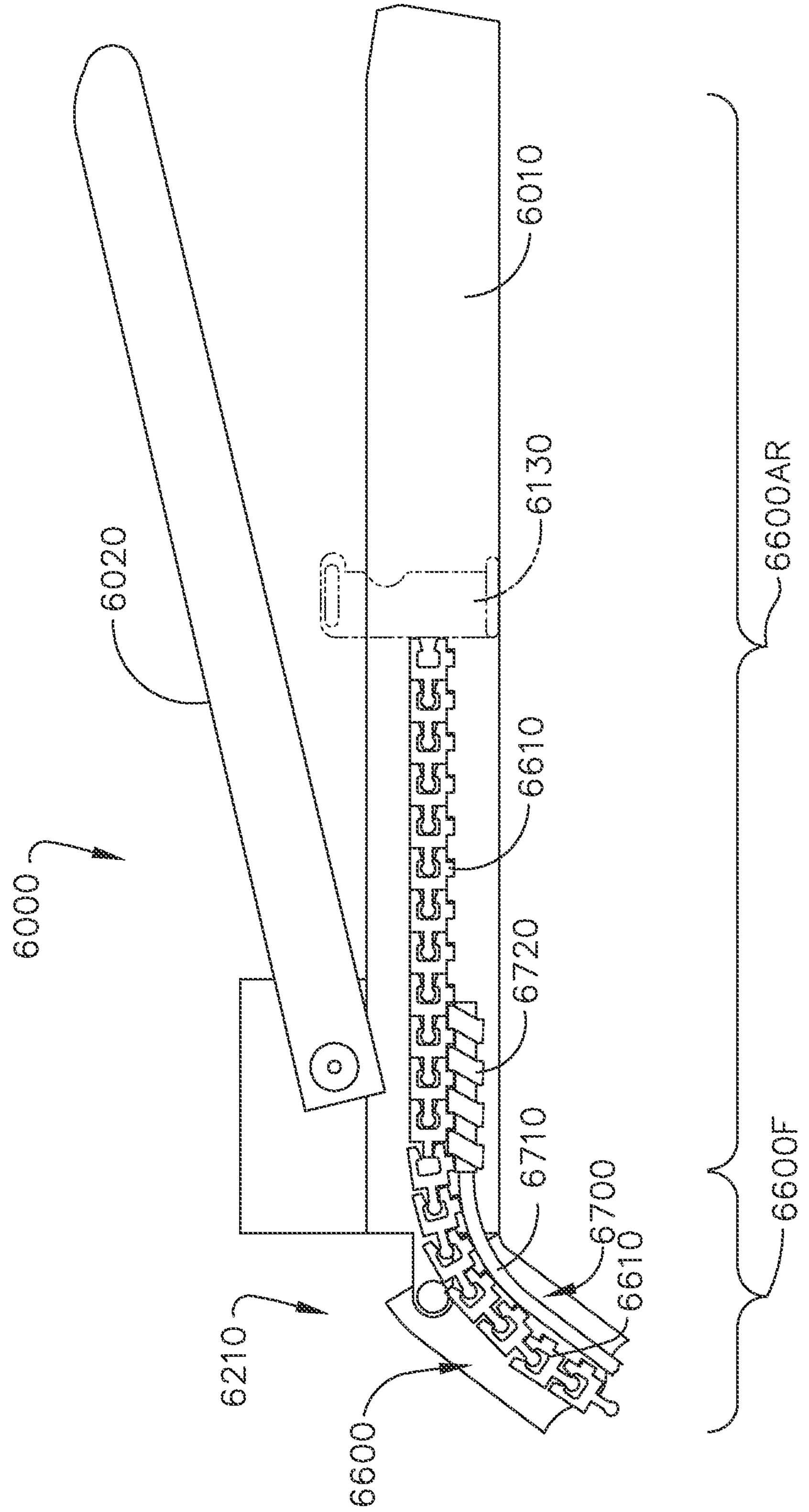
FIG. 73 is a partial side view of a surgical end effector of another surgical instrument that employs a series of flexibly linked drive components to drive a firing member through the surgical end effector.

As can be seen in FIG. 73, a flexible rotary drive system 6700 is employed to drive the series of 6600 drive components 6610. In one arrangement, the flexible rotary drive system 6700 comprises a flexible rotary drive shaft 6710 that can pass through the articulation joint 6210 and includes a rotary drive gear 6720 that is configured to threadably engage the thread segments 6620 on each drive component 6610. The flexible rotary drive shaft 6710 may be rotated by a motor/gear arrangement supported in a housing of a surgical instrument. The portion 6600F of the series 6600 of drive components 6610 that is proximal to the rotary drive gear 6720, remains flexibly linked or "floppy". As the drive components 6610 are threadably engaged by the rotary drive gear 6720 they are driven through a passage in the channel 6010 that causes the drive components to form the axially rigid series 6600AR for driving the firing member 6130 through the surgical end effector 6000.

Figure 77:
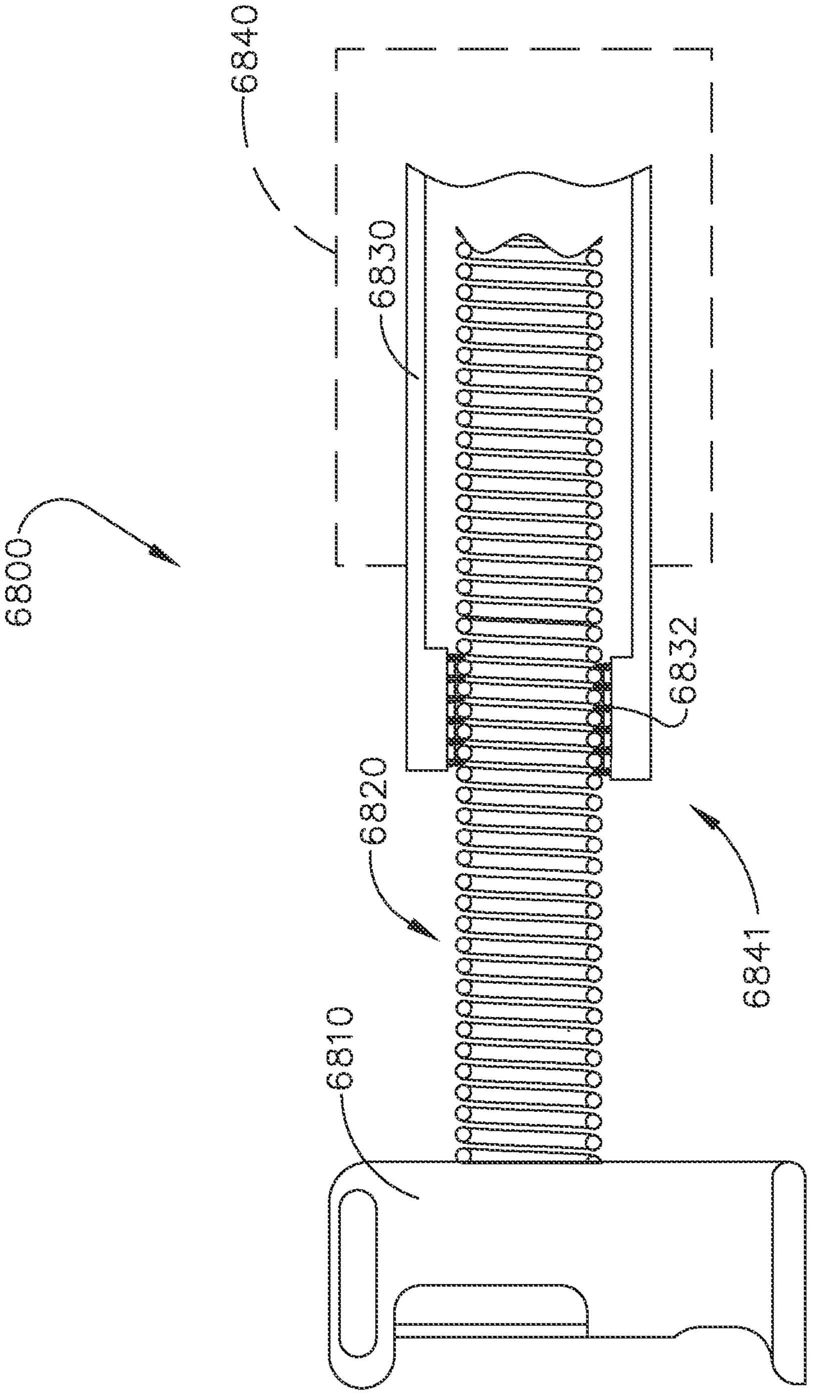
FIG. 77 is a side view of a portion of rotary firing system and firing member of another surgical instrument.

Torsional loads that are applied to firing system components as they traverse the articulation joint are less likely to de-articulate the articulation joint than axial loads. Various embodiments disclosed herein transfer torsional loads to longitudinal loads in a location that is distal of the articulation joint. Because the longitudinal loads are contained in the end effector, de-articulation is prevented. FIG. 77 illustrates one firing system 6800 example that can provide such advantages. The firing system 6800 comprises a firing member 6810 that is configured to be operably supported in a surgical end effector in the various manners described herein. A flexible spring-like driven member 6820 is attached to the firing member 6810. Such flexible, spring-like driven member 6820 can span an articulation joint area 6840 that can attain relatively large ranges of articulation. The flexible, spring-like driven member 6820 is configured to be driven axially by a flexible, spring-like torsion drive member 6830 that is rotatably supported to span the articulation joint area 6840. The flexible, spring-like torsion drive member 6830 includes a threaded insert 6832 that is configured to threadably engage the spring-like driven member 6820 at a location 6841 that is distal to the articulation joint area 6840. The flexible, spring-like torsion drive member 6830 may be rotated by a motor/gear arrangement supported in a housing of a surgical instrument. As the flexible, spring-like torsion drive member 6830 rotates in a first direction, the flexible, spring-like driven member 6820 translates longitudinally to drive the firing member 6810. Rotation of the flexible torsion drive member 6830 in a second direction will cause the flexible, spring-like driven member to move proximally.

Figure 78:
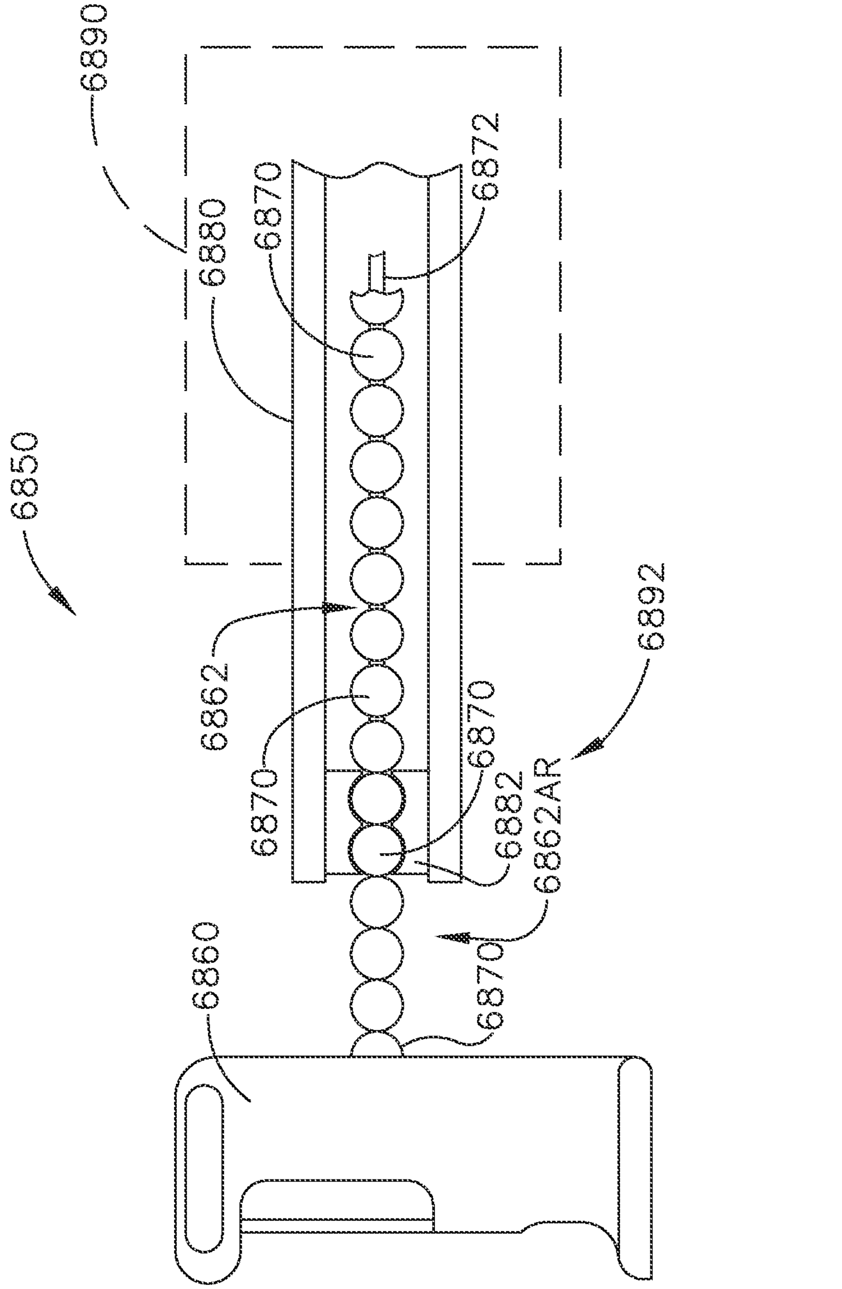
FIG. 78 is a side view of a portion of a rotary firing system and firing member of another surgical instrument.

FIG. 78 illustrates another firing system 6850 that comprises a firing member 6860 that is configured to be operably supported in a surgical end effector in the various manners described herein. The firing member 6860 is driven by firing member drive assembly 6861 which comprises a series 6862 of spherical ball members 6870 that are coupled together by a flexible cable 6872. Such series 6862 of flexible spherical ball members 6870 can span an articulation joint area 6840 that can attain relatively large ranges of articulation. The series 6862 of flexible spherical ball members 6870 is configured to be driven axially by a flexible torsion drive member 6880 that is rotatably supported to span an articulation joint area 6890. The flexible torsion drive member 6880 includes an insert 6882 that is configured to drivingly engage the spherical ball members 6870 at a location 6892 that is distal to the articulation joint area 6890. The flexible torsion drive member 6880 may be rotated by a motor/gear arrangement supported in a housing of a surgical instrument. As the flexible torsion drive member 6880 rotates in a first direction, the spherical ball members 6870 are driven distally into contact with each other to form an axially rigid series 6862AR that translates longitudinally to drive the firing member 6860 distally. Rotation of the flexible torsion drive member 6880 in a second direction will cause the series of spherical ball members 6870 to move proximally.

Figure 79:
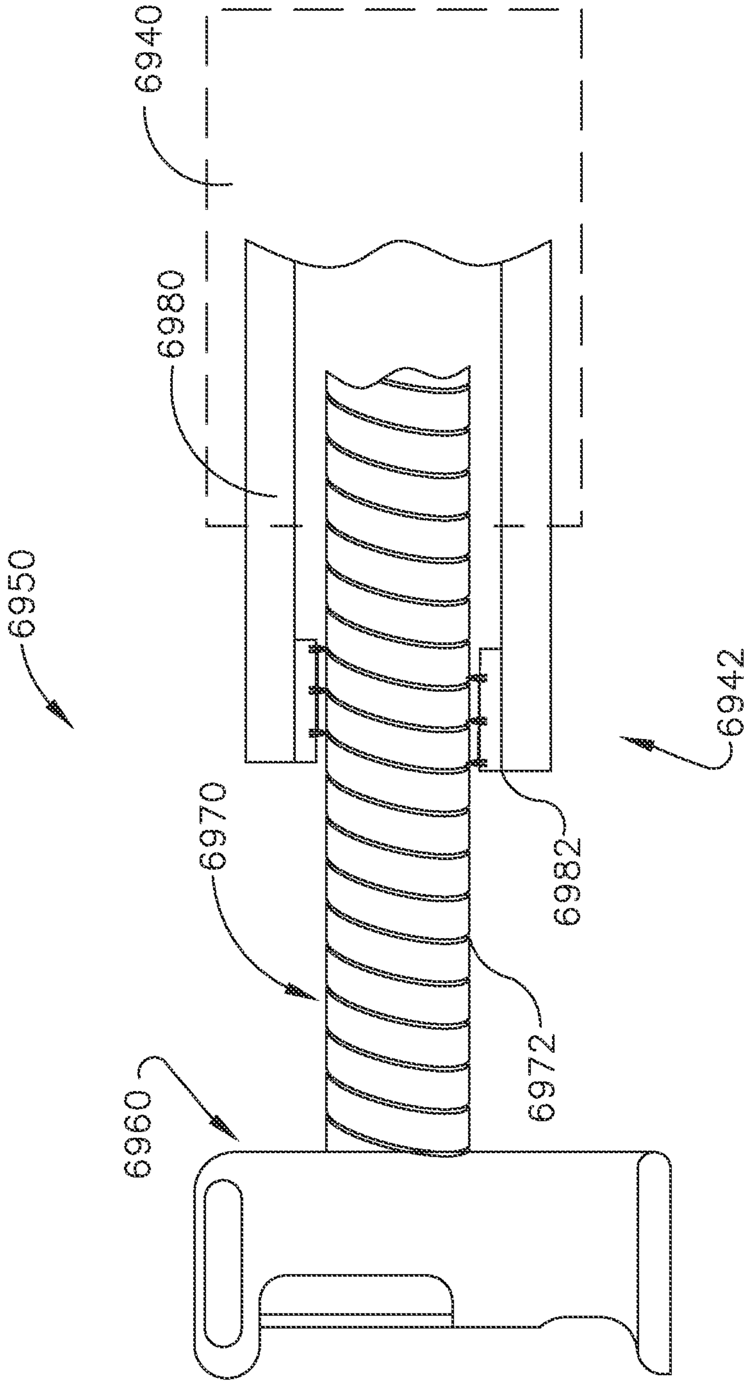
FIG. 79 is a side view of a portion of a rotary firing system and firing member of another surgical instrument.

FIG. 79 illustrates another firing system 6950 that comprises a firing member 6960 that is configured to be operably supported in a surgical end effector in the various manners described herein. A laser cut, hypotube driven member 6970 is attached to the firing member 6960. Such flexible driven member 6970 can span an articulation joint area 6940 that can attain relatively large ranges of articulation. The flexible driven member 6970 is configured to be driven axially by a flexible torsion drive member 6980 that is rotatably supported to span the articulation joint area 6940. The flexible torsion drive member 6980 includes a threaded insert 6982 that is configured to threadably engage the laser cuts 6972 on the flexible driven member 6970 at a location 6942 that is distal to the articulation joint area 6940. The flexible torsion drive member 6980 may be rotated by a motor/gear arrangement supported in a housing of a surgical instrument. As the flexible torsion drive member 6980 rotates in a first direction, the flexible driven member 6970 translates longitudinally to drive the firing member 6960. Rotation of the flexible torsion drive member 6980 in a second direction will cause the flexible driven member 6970 to move proximally.

Figures 80, 81:
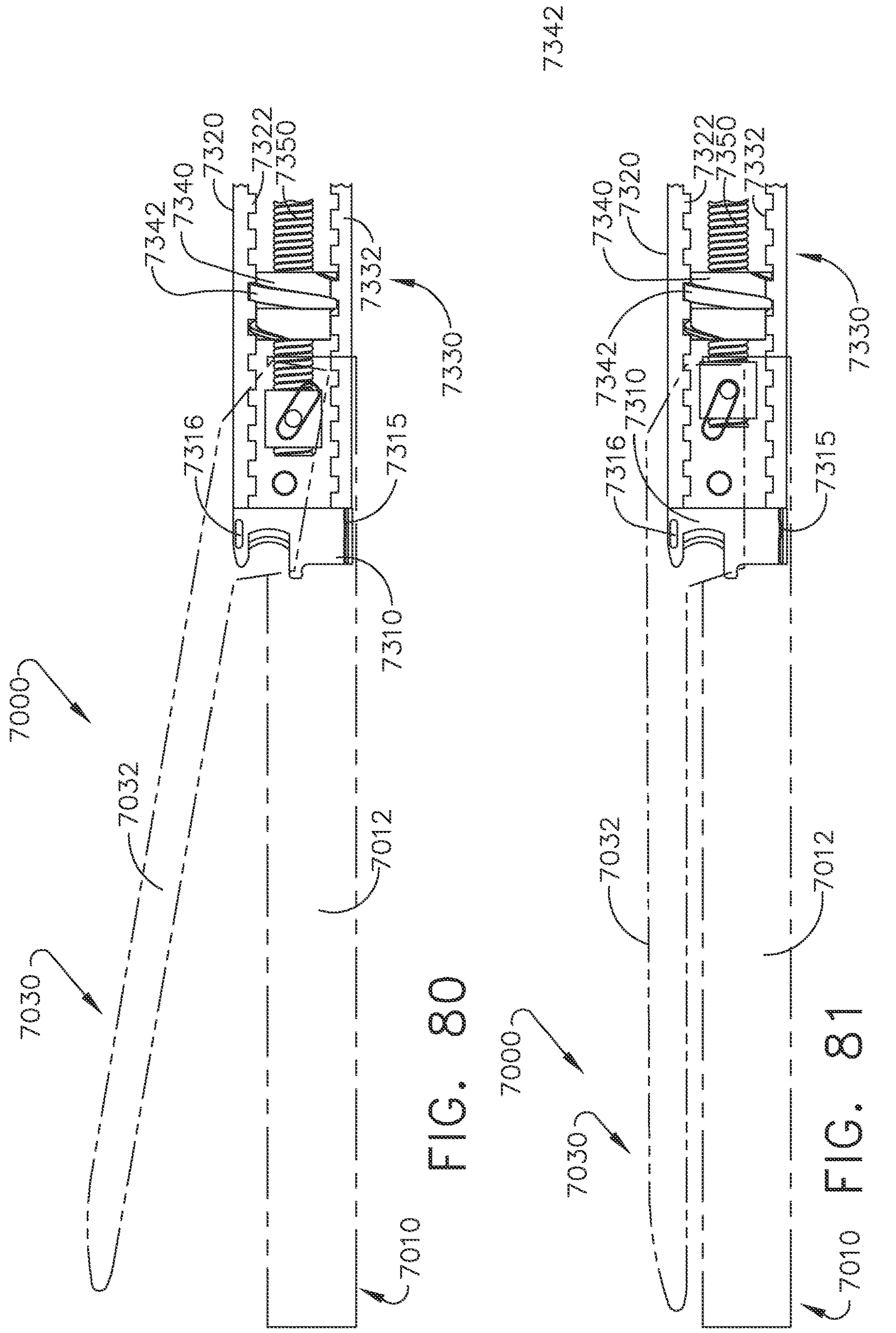
FIG. 80 is a partial view of another surgical instrument that employs a rotary driven firing system to drive a firing member through a surgical end effector with an anvil of the surgical end effector in an open position.
FIG. 81 is another partial side view of the surgical instrument and end effector of FIG. 80 with the anvil thereof in a closed position.
Figure 82:
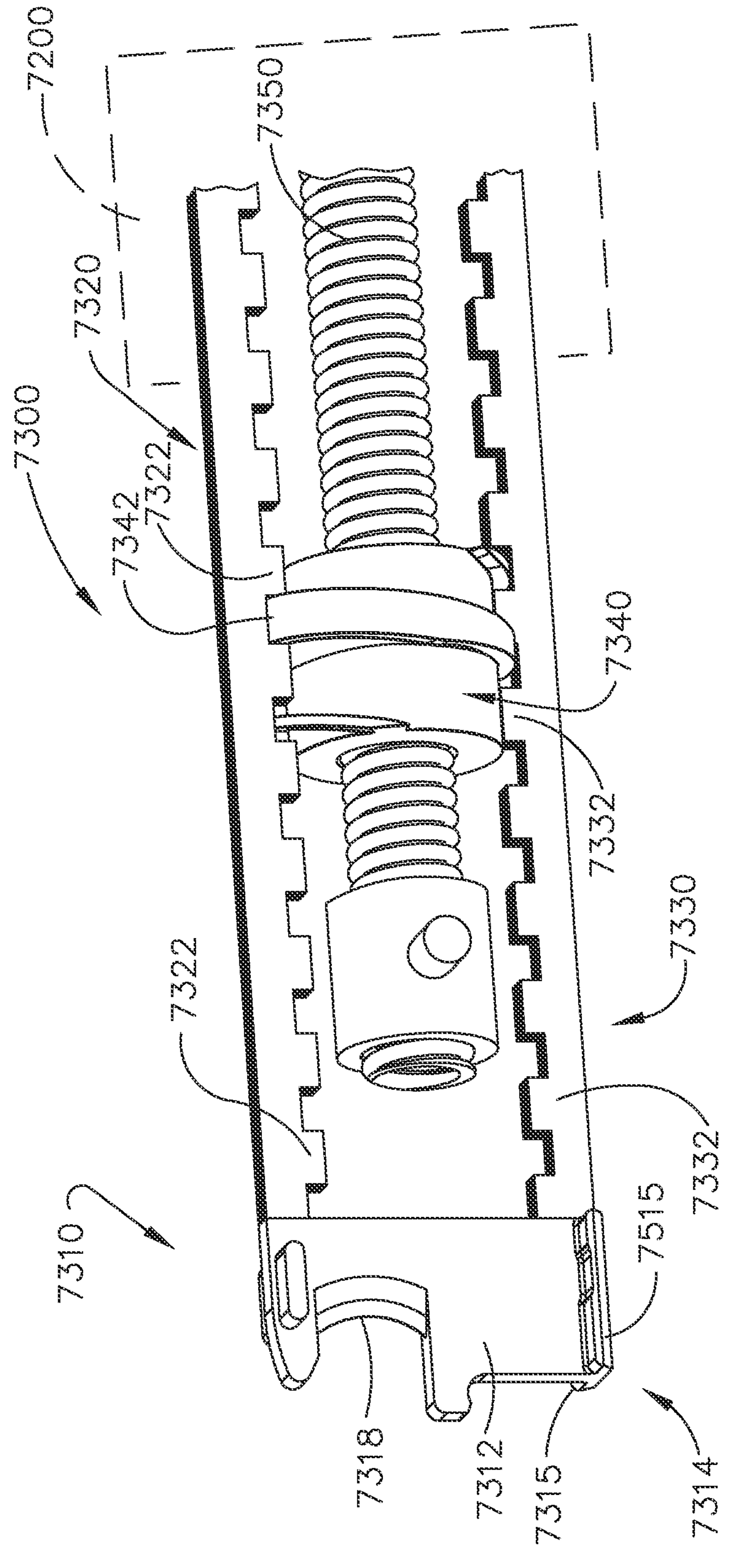
FIG. 82 is a perspective view of portions of the rotary driven firing system of the surgical instrument of FIG. 80.
Figure 83:
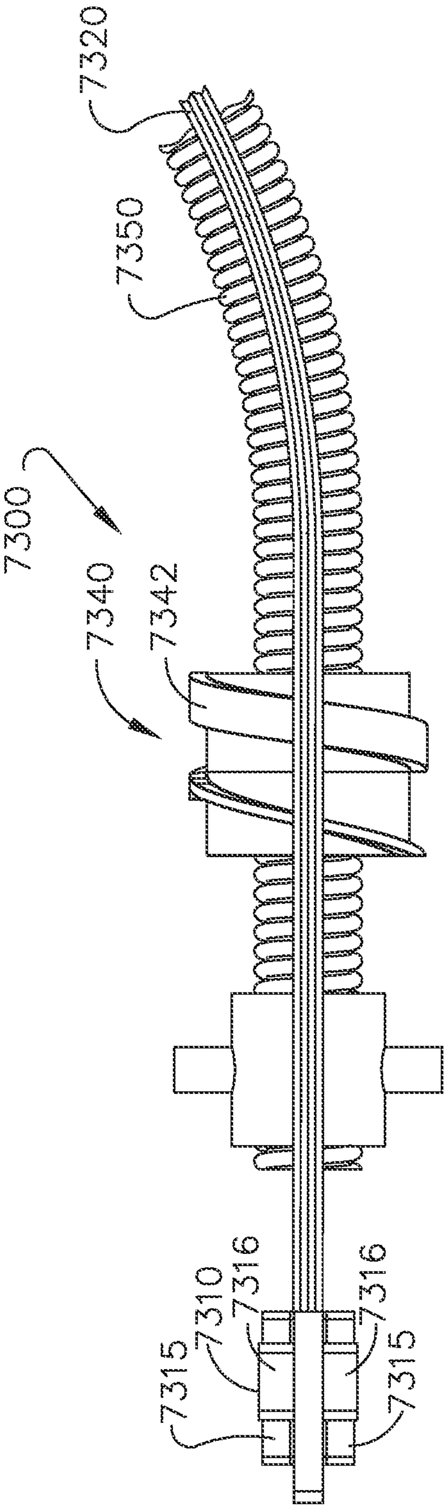
FIG. 83 is a top view of a portion of the rotary driven firing system depicted in FIG. 82.
Figure 84:
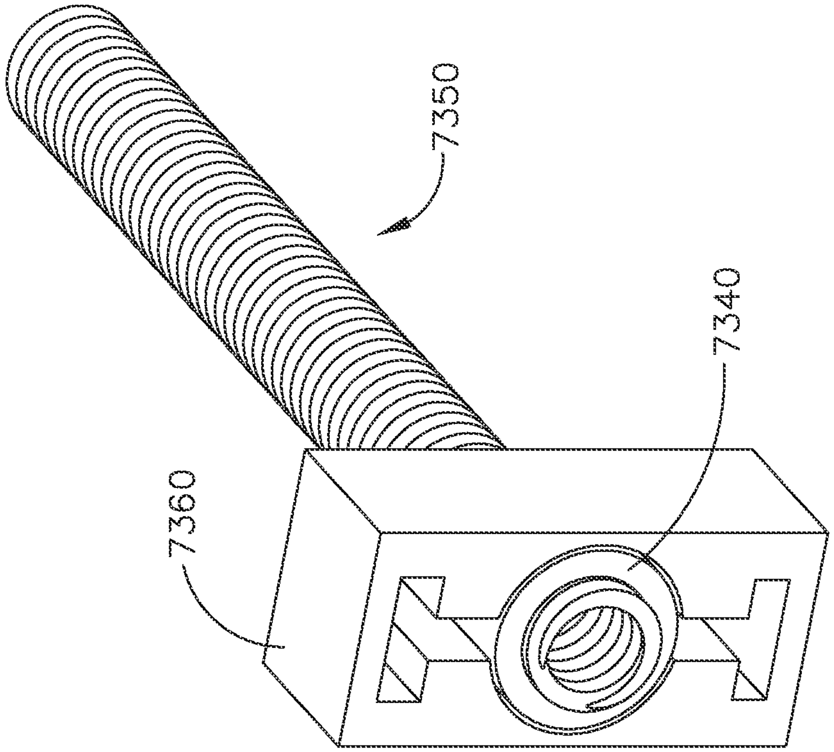
FIG. 84 is a perspective view of a guide member and rotary drive shaft of the rotary driven firing system of FIG. 83.

Pushing a firing beam forward in an articulating end effector generally requires a lot of force and such force needs to be balanced. For example, it is generally difficult to push a firing beam through an articulation joint that has been articulated to angles of greater than sixty degrees. As the firing beam traverses through the articulation joint, the firing beam can apply significant loads onto the articulation joint components which can cause the articulation joint to de-articulate. FIGS. 80-84 illustrate a firing drive system 7300 that comprises a flexible upper drive band 7320 and a flexible lower drive band 7330 that are attached to a firing member 7310 that is configured to move within a surgical end effector 7000 between a starting and ending position. As can be seen in FIGS. 80-82, the flexible upper drive band 7320 comprises a plurality of spaced upper drive teeth 7322 that are configured to threadably engage a helical thread 7342 on a rotary drive nut 7340. Similarly, the flexible lower drive band 7330 comprises a plurality of spaced lower drive teeth 7332 that are configured to threadably engage the helical thread 7342 on the rotary drive nut 7340. In at least one arrangement, the flexible upper drive band 7320 and the flexible lower drive band 7330 are formed from a metal material and are welded to or otherwise attached to the firing member 7310. Such arrangement serves to balance the firing loads that are applied to the firing member 7310.

The rotary drive nut 7340 is received on a flexible rotary drive shaft 7350 that is centrally disposed between the flexible upper drive band 7320 and the flexible lower drive band 7330 and traverses through the articulation joint area generally designated as 7200. The flexible rotary drive shaft 7350 may be rotated by a motor/gear arrangement supported in a housing of a surgical instrument. As the flexible rotary drive shaft 7350 rotates in a first direction, the flexible upper drive band 7320 and the flexible lower drive band 7330 will drive the firing member 7310 distally. Rotation of the flexible rotary drive shaft 7350 in a second direction will cause the flexible upper drive band 7320 and the flexible lower drive band 7330 to pull the firing member 7310 proximally. In at least one arrangement, flexible upper drive band 7320 and the flexible lower drive band 7330 pass through a guide member 7360 that surrounds the rotary drive nut 7340 to prevent the flexible upper drive band 7320 and the flexible lower drive band 7330 from bypassing the rotary drive nut 7340 during actuation of the flexible rotary drive shaft 7350. See FIG. 84.

In the illustrated arrangement, the firing member 7310 is configured to move through the surgical end effector 7000 that comprises a first jaw 7010 and a second jaw 7030 that is configured to move relative to the first jaw 7010. In one embodiment, the first jaw 7010 comprises an elongate channel 7012 that is configured to operably support a surgical staple cartridge therein. See FIGS. 80 and 81. The second jaw 7030 comprises an anvil 7032 that is pivotally supported on the elongate channel 7012 and is movable between an open position and a closed position relative to the elongate channel 7012. As can be seen in FIG. 82, in at least one form, the firing member 7310 comprises a shape that is commonly referred to as an “E-beam”. The firing member 7310 comprises a vertically extending firing member body 7312 that has a lower foot feature 7314 that comprises two laterally extending tabs 7315 that are configured to be slidably engage the elongate channel 7012 as the firing member is driven axially therein. In addition, a pair of upper tabs 7316 protrude from the upper portion of the firing member body 7312 to engage the anvil 7032 as the firing member 7310 is driven distally through the closed anvil 7032. During the firing stroke, the tabs 7315 and 7316 may serve to space the anvil 7032 relative to the surgical staple cartridge supported in the elongate channel 7012. The firing member body 7312 also comprises a tissue cutting feature 7318. The tabs 7316 may also serve to apply a closing motion to the anvil 7032 as the firing member 7310 is moved distally from the starting position.

In the illustrated example, the firing drive system 7300 may also be employed to apply opening and closing motions to the anvil 7032. As can be seen in FIGS. 80-83, a closure nut 7370 is threadably received on the flexible rotary drive shaft 7350. The closure nut 7370 comprises a cam pin 7372 that extends laterally from each side of the closure nut 7370 to be received in corresponding cam slots 7036 in an anvil mounting portion 7034 of the anvil 7032. See FIGS. 80 and 81. Such cam pins 7372 prevent the closure nut 7370 from rotating with the flexible rotary drive shaft 7350 such that rotation of the flexible rotary drive shaft 7350 causes the closure nut 7370 to move axially. Thus, rotation of the flexible rotary drive shaft 7350 in a first direction causes the closure nut 7370 to move distally and cam the anvil 7032 from the open position to the closed position. Rotation of the flexible rotary drive shaft 7350 in the second rotary direction will cause the closure nut 7370 to move proximally and cam the anvil 7032 back to the open position. Thus, alternating the rotation of the flexible rotary drive shaft 7350 may allow the surgeon to quickly open and close the anvil 7032 for grasping purposes, for example.

Figure 85:
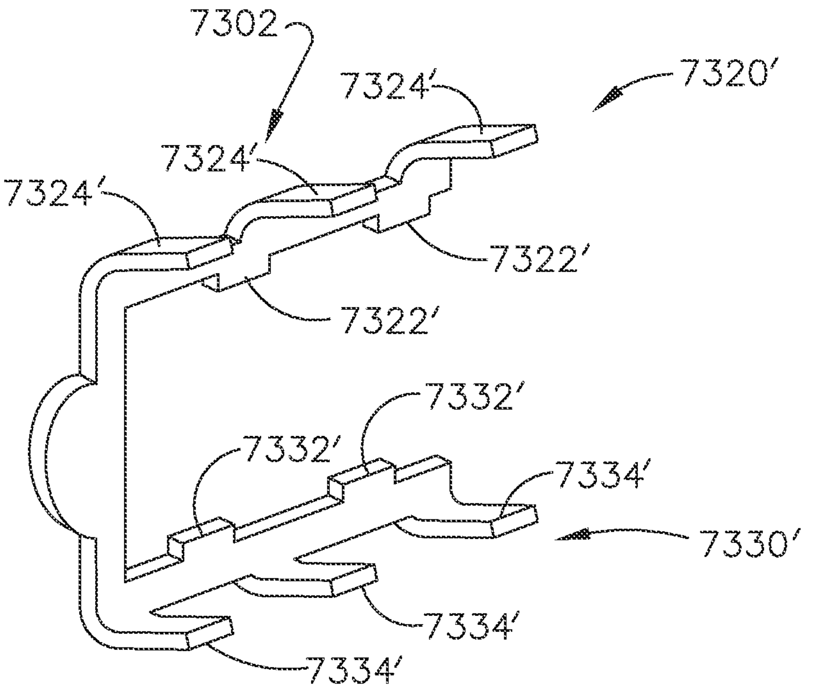
FIG. 85 is a perspective view of a portion of another flexible firing drive assembly that may be employed with the firing drive system of FIG. 83.
Figure 86:
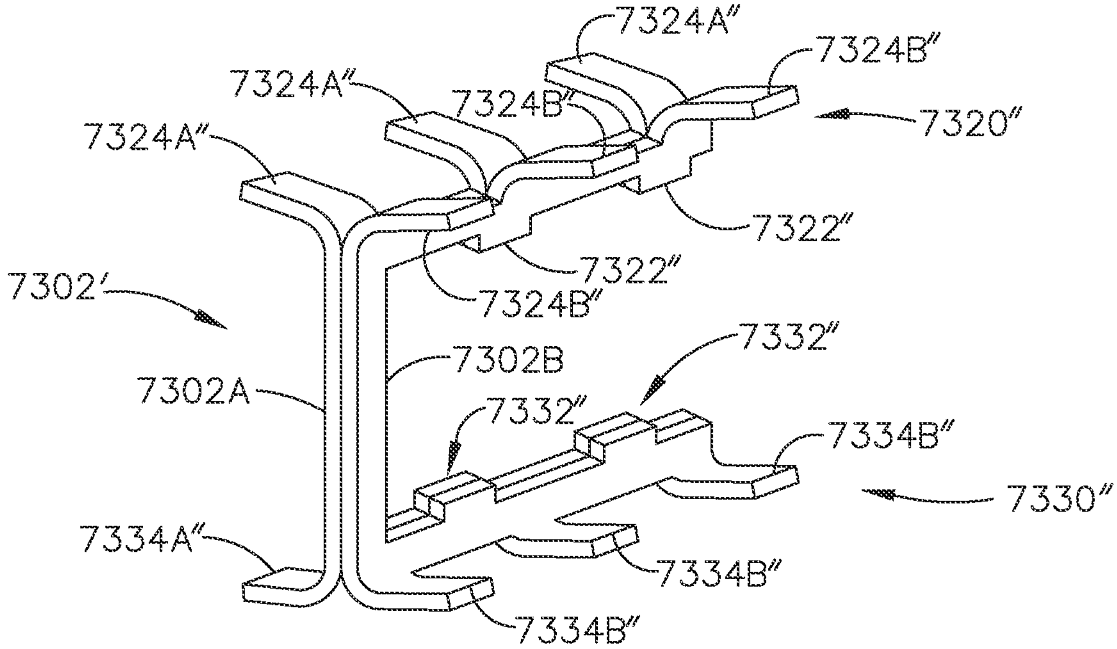
FIG. 86 is another perspective view of a portion of another flexible firing drive assembly embodiment that may be employed with the firing drive system of FIG. 83.

FIG. 85 illustrates an alternative firing drive assembly 7302 that comprises the flexible upper drive band 7320' that has upper drive teeth 7322' and a flexible lower drive band 7330' that has lower drive teeth 7332' that is formed out of one piece of material such as metal. The flexible upper drive band 7320' also includes upper strength tabs 7324' that are provided to pass through the anvil 7032 similar to the upper tabs 7316 on the firing member 7310 as well as lower strength tabs 7334 that are provided to pass through the channel 7012 similar to the tabs 7315 on the firing member 7310. FIG. 86 illustrates an alternative firing drive assembly 7302' that is fabricated from two band assemblies 7302A and 7302B that are laminated together to form the flexible upper drive band 7320" that has the upper drive teeth 7322" and a flexible lower drive band 7330" that has the lower drive teeth 7332". Each band assembly 7302A, 7302B also comprise upper strength tabs 7324A", 7324B" and lower strength tabs 7334A", 7334B" that are provided to pass through the anvil 7032 and the elongate channel 7012, respectively.

The firing drive system 7300 serves to apply a uniform drive motion to the firing member 7310 and can accommodate articulation angles that may be greater than seventy degrees, for example. In addition, because the rotary drive nut 7340 engages the flexible upper drive band 7320 and flexible lower drive band 7330 at a location that is distal to the articulation joint area 7200, the linear firing loads are confined to the end effector and do not go through the articulation joint.

Figure 87:
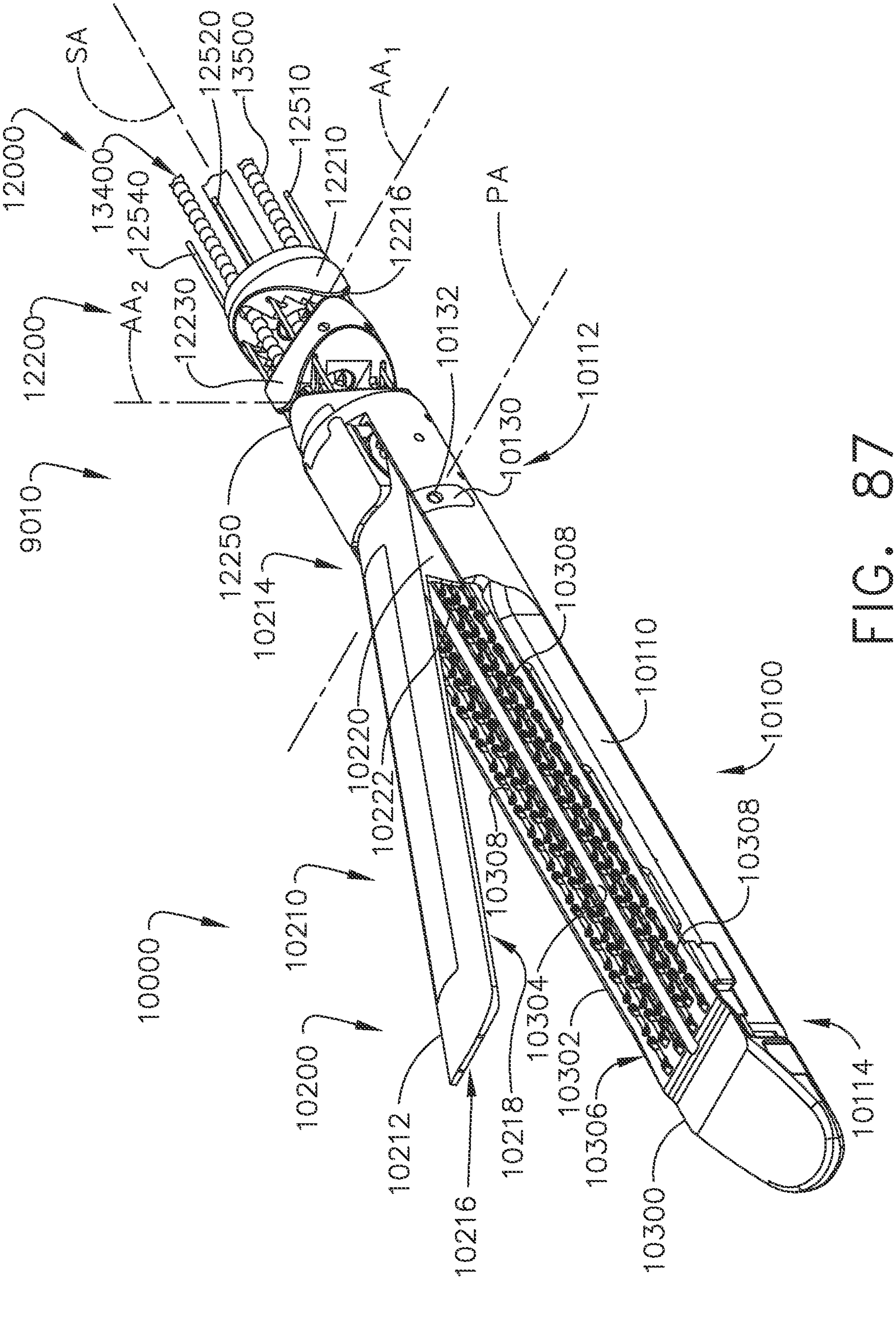
FIG. 87 is a perspective view of a surgical end effector of another surgical instrument with an anvil thereof in an open position and the surgical end effector in an unarticulated orientation.
Figure 88:
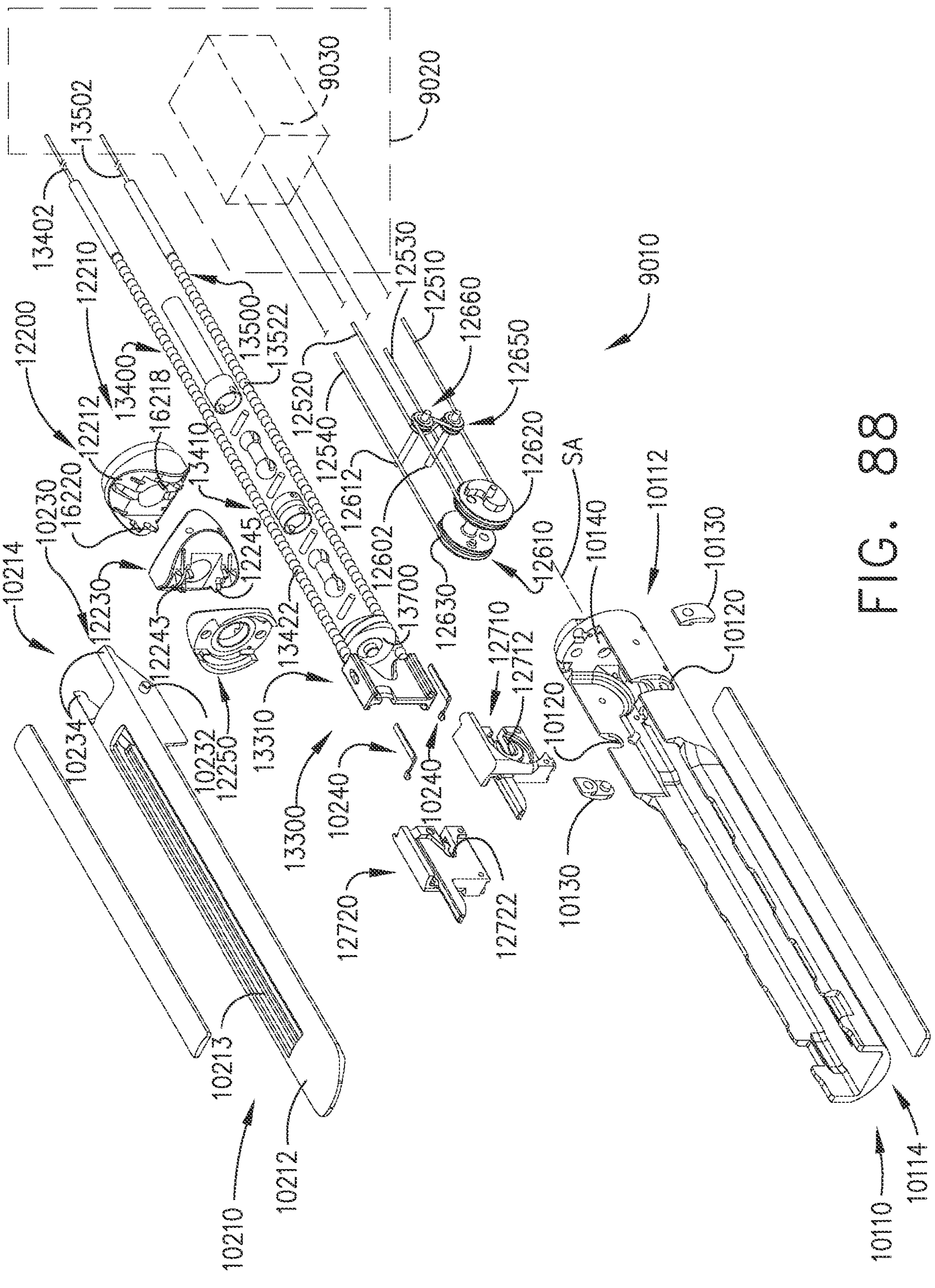
FIG. 88 is an exploded assembly view of the surgical end effector and surgical instrument of FIG. 87.
Figure 89:
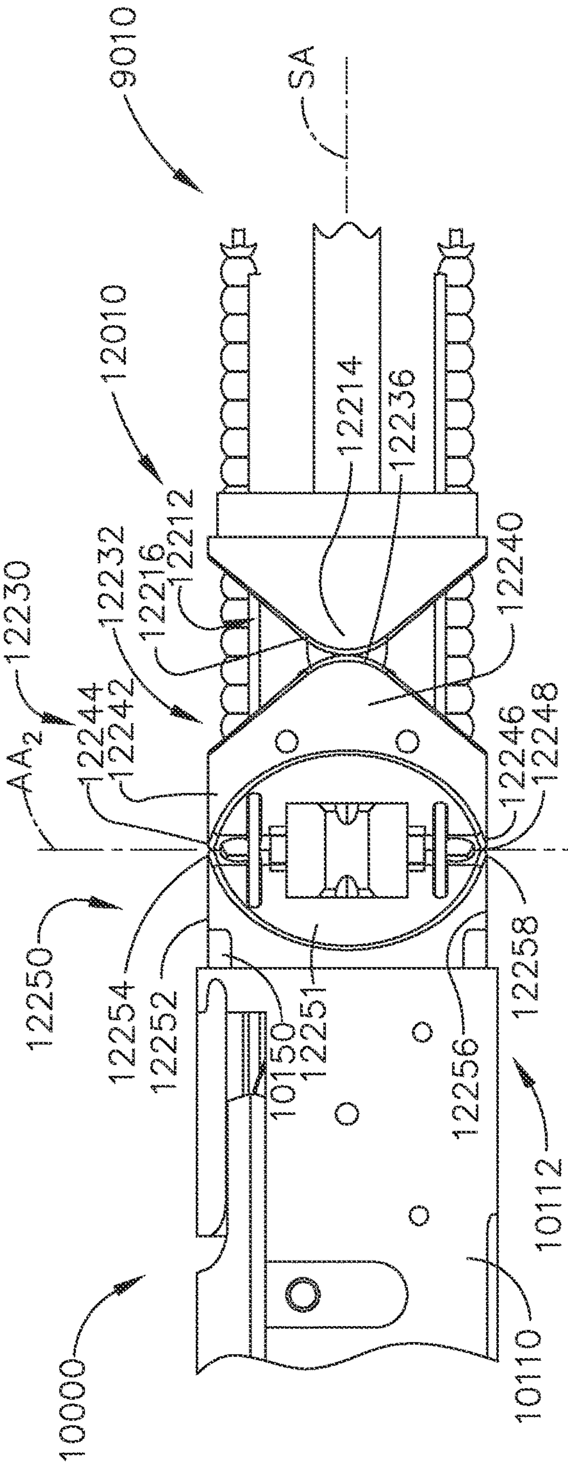
FIG. 89 is a side elevational view of an articulation joint of the surgical instrument of FIG. 87.

FIGS. 87-89 illustrate another form of surgical instrument 9010 that may address many of the challenges facing surgical instruments with end effectors that are articulatable to large articulation angles and that are configured to cut and fasten tissue. In various embodiments, the surgical instrument 9010 may comprise a handheld device. In other embodiments, the surgical instrument 9010 may comprises an automated system sometimes referred to as a robotically-controlled system, for example. In various forms, the surgical instrument 9010 comprises a surgical end effector 10000 that is operably coupled to an elongate shaft assembly 12000. The elongate shaft assembly 12000 may be operable attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be “housed” or contained in the housing or various components may be “associated with” a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 10000 comprises a first jaw 10100 and a second jaw 10200. In the illustrated arrangement, the first jaw 10100 comprises an elongate channel 10110 that comprises a proximal end 10112 and a distal end 10114 and is configured to operably support a surgical staple cartridge 10300 therein. The surgical staple cartridge 10300 comprises a cartridge body 10302 that has an elongate slot 10304 therein. A plurality of surgical staples or fasteners (not shown) are stored therein on drivers (not shown) that are arranged in rows on each side of the elongate slot 10304. The drivers are each associated with corresponding staple cavities 10308 that open through a cartridge deck surface 10306. The surgical staple cartridge 10300 may be replaced after the staples/fasteners have been discharged therefrom. Other embodiments are contemplated wherein the elongate channel 10110 and/or the entire surgical end effector 10000 is discarded after the surgical staple cartridge 10300 has been used.

In the illustrated arrangement, the second jaw 10200 comprises an anvil 10210 that comprises an elongate anvil body 10212 that has a proximal end 10214 and a distal end 10216. The anvil body 10212 comprises a staple-forming undersurface 10218 that faces the first jaw 10100 and may include a series of staple-forming pockets (not shown) that correspond to each of the staples or fasteners in the surgical staple cartridge 10300. The anvil body 10212 may further include a pair of downwardly extending tissue stop features 10220 that are formed adjacent the proximal end 10214 of the anvil body 10212. One tissue stop feature 10220 extends from each side of the anvil body 10212 such that a distal end 10222 on each tissue stop 10220 corresponds to the proximal-most staples/fasteners in the surgical staple cartridge 10300. When the anvil 10200 is moved to a closed position onto tissue positioned between the staple-forming undersurface 10218 of the anvil 10200 and the cartridge deck surface 10306 of the surgical staple cartridge 10300, the tissue contacts the distal ends 10222 of the tissue stops 10220 to prevent the tissue from migrating proximally past the proximal-most staples/fasteners to thereby ensure that the tissue that is cut is also stapled. When the surgical staple cartridge is “fired” as will be discussed in further detail below, the staples/fasteners supported within each staple cavity are driven out of the staple cavity 10308 through the clamped tissue and into forming contact with the staple forming undersurface 10218 of the anvil 10200.

As can be seen in FIG. 88, the proximal end 10214 of the anvil body 10212 comprises an anvil mounting portion 10230 that comprises a pair of laterally extending mounting pins 10232 that are configured to be received in corresponding mounting inserts 10130 that are configured to be retainingly received within mounting cradles 10120 formed in the proximal end 10112 of the elongate channel 10110. The mounting pins 10232 are pivotally received within pivot holes 10132 in the mounting inserts 10130 and then the mounting inserts 10130 are inserted into their corresponding cradle 10120 and affixed to the elongate channel 10110 by welding, adhesive, snap fit, etc. Such arrangement facilitates pivotal travel of the anvil 10210 relative to the elongate channel 10110 about a fixed (i.e., non-translating, non-moving) pivot axis PA. See FIG. 87.

In the illustrated arrangement, the elongate shaft assembly 12000 defines a shaft axis SA and comprises a hollow outer tube (omitted for clarity) that operably interfaces with a housing of the control portion (e.g., handheld unit, robotic tool driver, etc.) of the surgical instrument 9010. The elongate shaft assembly 12000 further comprises an articulation joint 12200 that may be attached to the hollow outer tube as well as the surgical end effector 10000 to facilitate selective articulation of the surgical end effector 10000 relative to the elongate shaft assembly 12000 about multiple articulation axes in multiple articulation planes. In at least one arrangement, for example, the articulation joint 12200 comprises a proximal joint member 12210, a central joint member 12230, and a distal joint member 12250. In one example, the central joint member 12230 operably interfaces with the proximal joint member 12210 such that the central joint member 12230 is selectively articulatable through a first or proximal articulation plane that is defined by a first or proximal articulation axis $AA_1$ that is transverse to the shaft axis SA. Also in one example, the distal joint member 12250 operably interfaces with the central joint member 12230 such that the distal joint member 12250 is selectively articulatable through a second or distal articulation plane that is defined by a second or distal articulation axis $AA_2$ that is transverse to the shaft axis SA and transverse to the first or proximal articulation axis $AA_1$.

Figure 90:
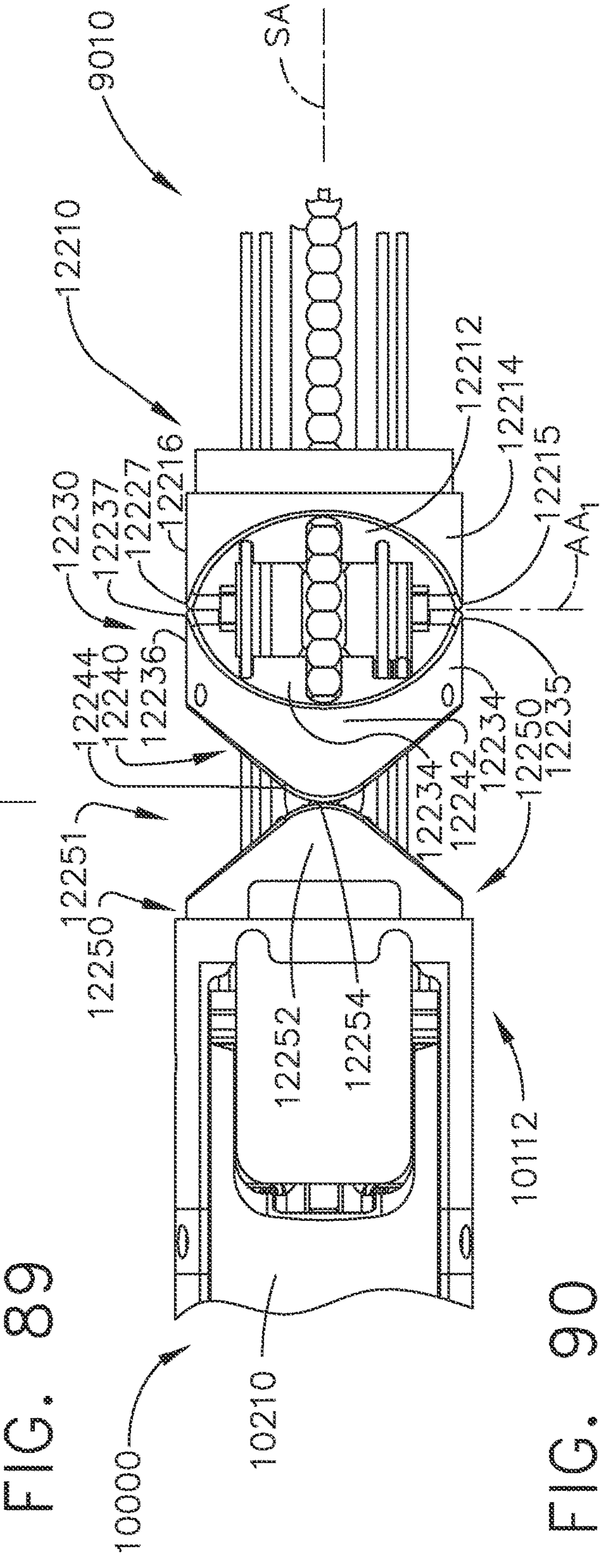
FIG. 90 is a top view of the articulation joint of FIG. 89.

As can be seen in FIGS. 89 and 90, the proximal joint member 12210 comprises a proximal joint distal face 12212 that defines two spaced, lateral apex portions 12214, 12216. The apex portion 12214 defines a radial surface 12215 and the apex portion 12216 defines a radial surface 12217 (FIG. 90). The central joint member 12230 comprises proximal face 12232 that defines two spaced lateral proximal apex portions 12234, 12236. The proximal apex portion 12234 defines a radial surface 12235 and the apex portion 12236 defines a radial surface 12237. As can be seen in FIG. 89, the proximal face 12232 of the central joint member 12230 confronts the proximal joint distal face 12212 of the proximal joint member 12210 such that the central joint member 12230 is articulatable through a first articulation plane defined by the first or proximal articulation axis $AA_1$ that extends between a point where the lateral apex portion 12214 on the proximal joint member contacts the proximal apex portion 12234 on the central joint member 12230 and the point where the lateral apex portion 12216 on the proximal joint member 12210 contacts the proximal apex portion 12236 on the central joint member 12230. In one arrangement, the radial surfaces 12215, 12217 on the lateral apex portions 12214, 12216, respectively, and the radial surfaces 12235 and 12237 on the proximal apex portions 12234, 12236, respectively, may act as rocker points/surfaces about which the central joint member 12230 may articulate relative to the proximal joint member 12210. Additionally, the central joint member 12230 comprises proximal first gear tooth segments that are configured to rotatably mesh with distal gear segments 12218, 12220 on the proximal joint member 12210. See FIG. 88. In various arrangements, the radial surface 12235 on the central joint member 12230 may be spaced from the radial surface 12215 on the proximal joint member 12210 and the radial surface 12237 on the central joint member 12230 may be spaced from the radial surface 12217 on the proximal joint member 12210.

Figure 92:
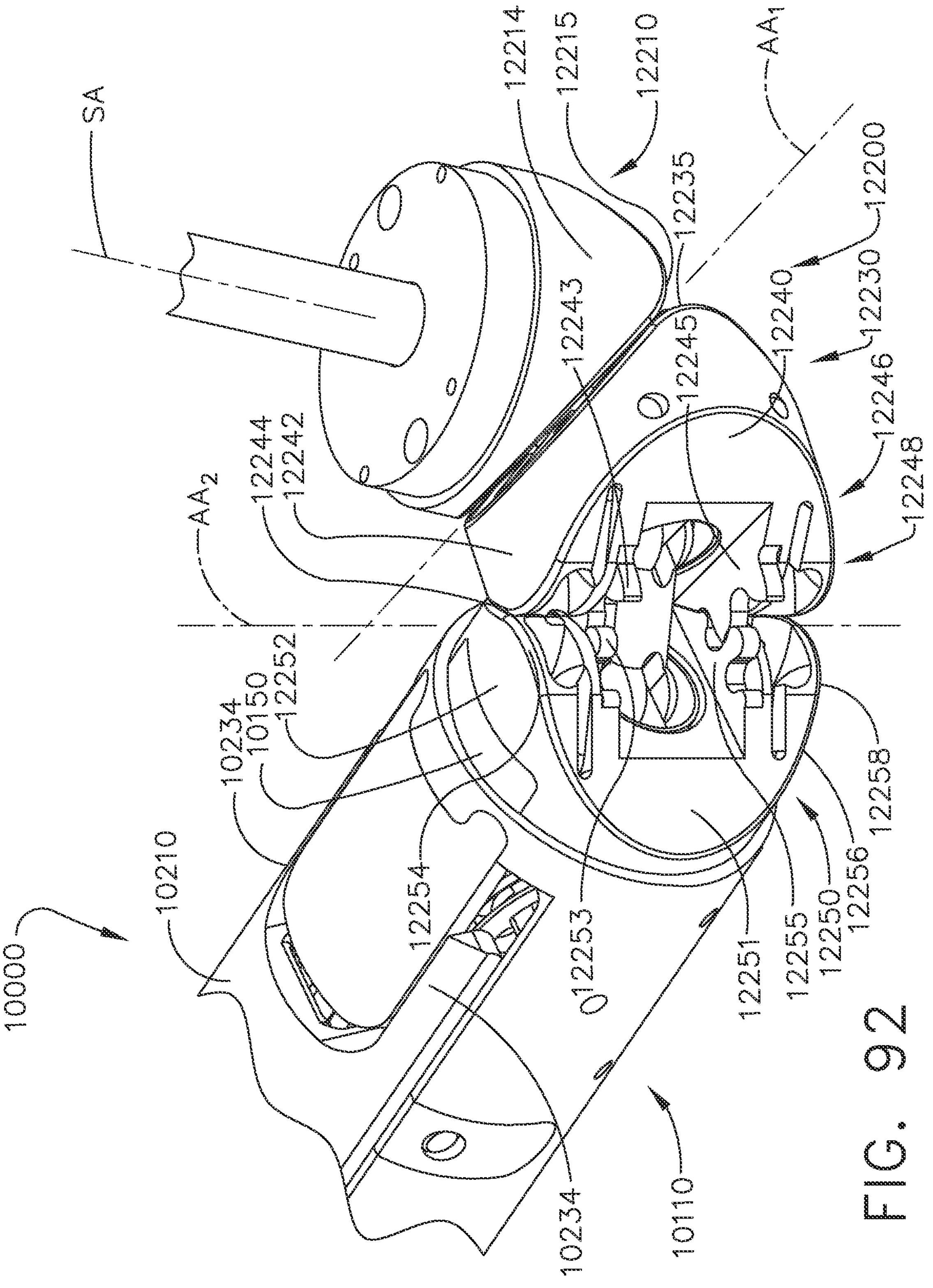
FIG. 92 is a perspective view of a portion of the surgical end effector of FIG. 89 articulated by the articulation joint of FIG. 89.
Figure 95:
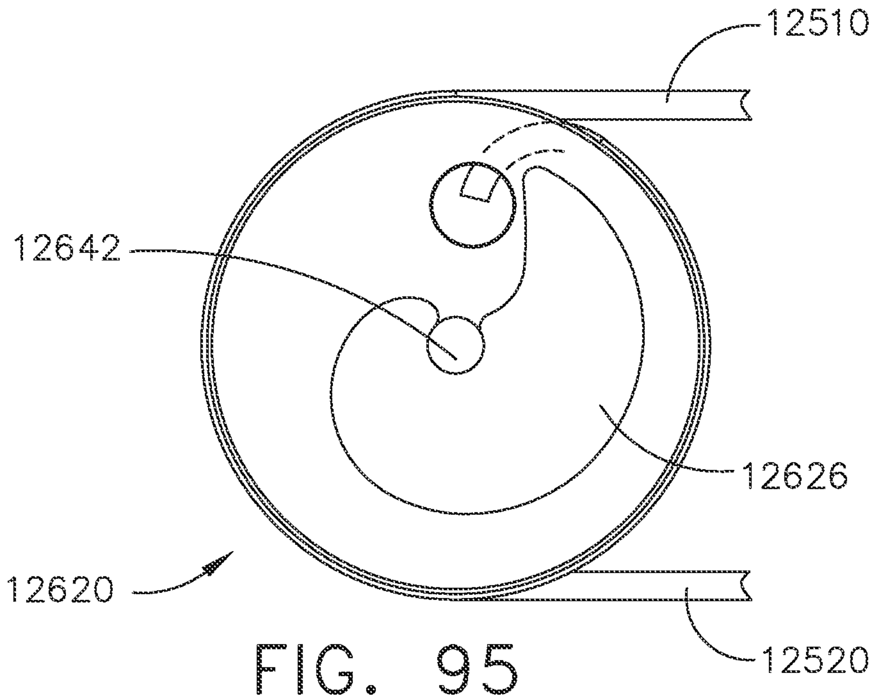
FIG. 95 is a side elevational view of a first lateral alpha wrap pulley of the pulley unit of FIG. 94.

The central joint member 12230 further comprises a central joint distal face 12240 that defines a centrally disposed upper apex portion 12242 that forms an upper radial surface 12244 and a lower apex portion 12246 that forms a lower radial surface 12248. See FIG. 89. The distal joint member 12250 is attached to the proximal end 10112 of the elongate channel 10110 by a mounting bushing 10150 and comprises a proximal face 12251 that faces or confronts the central joint distal face 12240 on the central joint member 12230. See FIGS. 89 and 92. As can be seen in FIGS. 89 and 92, the proximal face 12251 defines a centrally disposed upper apex portion 12252 that forms an upper radial surface 12254 that is configured to confront or abut the upper radial surface 12244 on the central joint member 12230. The proximal face 12251 further defines a centrally disposed lower apex portion 12256 that forms a lower radial surface 12258 that is configured to confront or abut the lower radial surface 12248 on the central joint member 12230. See FIG. 89. The distal joint member 12250 further comprises an upper gear tooth segment 12253 that is configured to rotatably mesh with an upper gear tooth segment 12243 on the central joint member 12230. In addition, the distal joint member 12250 comprises a lower gear tooth segment 12255 that is configured to rotatably mesh with a lower gear tooth segment 12245 on the central joint member 12230. See FIG. 92.

The distal joint member 12250 is configured to articulate through a second or distal articulation plane defined by the second or distal articulation axis $AA_2$ that extends between a point where the upper apex portion 12252 on the distal joint member 12250 contacts or confronts the upper apex portion 12242 on the central joint member 12230 and the point where the lower apex portion 12256 on the distal joint member 12250 contacts or confronts the lower apex portion 12246 on the central joint member 12230. See FIGS. 89 and 92. In one arrangement, the radial surfaces 12254, 12258 on the upper and lower apex portions 12252, 12256, respectively of the distal joint member 12250 and the radial surfaces 12244 and 12248 on the upper and lower apex portions 12242, 12246, respectively on the central joint member 12230 may act as rocker points/surfaces about which the distal joint member 12250 may articulate relative to the central joint member 12230. In alternative arrangements, however, the radial surface 12254 on the distal joint member 12250 is spaced from the radial surface 12244 on the central joint member 12230 and the radial surface 12258 on the distal joint member 12250 is spaced from the radial surface 12248 on the central joint member 12230.

Returning to FIG. 88, in the illustrated example, the articulation joint 12200 is operably controlled by a cable control system 9030 that comprises four cables 12510, 12520, 12530, and 12540 that extend through the elongate shaft assembly 12000. The cable control system 9030 may be supported within a housing 9020 of the surgical instrument 9010. The cable control system 9030 may comprise a plurality of cable support members/capstans, pulleys, etc. that are controlled by one or more corresponding motors that are controlled by a control circuit portion of the surgical instrument 9010. In various embodiments, the cable control system 9030 is configured to manage the tensioning (pulling) and paying out of cables at precise times during the articulation process. In addition, in at least one arrangement, the cable control system 9030 is employed to control the opening and closing of the anvil 10210 as will be discussed in further detail below.

As can be seen in FIG. 88, the cables 12510, 12520, 12530, and 12540 are configured to operably interface with a closure system 12600 that is rotatably mounted in the proximal end 10112 of the elongate channel 10110. In at least one arrangement, the closure system 12600 comprises a pulley unit 12610 that comprises a first lateral alpha wrap pulley 12620 and a second lateral alpha wrap pulley 12630 that are interconnected by a central shaft 12640. See FIGS. 93 and 94. The pulley unit 12610 is rotatably supported within the proximal end 10112 of the elongate channel 10110 by mounting brackets 12710 and 12720. See FIG. 88. More particularly, the proximal end 10112 of the elongate channel 10110 defines a firing member parking area 10140 that is proximal to the mounting cradles 10120 and is configured to operably support a firing member 12310 when in a starting position. Each mounting bracket 12710, 12720 is mounted within the firing member parking area 10140 on each side of the shaft axis SA to enable the firing member 12310 to be received in the parking area 10140 when the firing member 12310 is in a starting position. The mounting brackets 12710, 12720 may be attached to the proximal end 10112 of the elongate channel 10110 by welding, adhesive, snap features, etc. The mounting bracket 12710 comprises a first shaft cradle 12712 that is configured to rotatably support a first pivot shaft 12621 protruding from the first lateral alpha wrap pulley 12620 and the second mounting bracket 12720 comprises a second shaft cradle 12722 that is configured to rotatably support a second pivot shaft 12644 protruding from the second lateral alpha wrap pulley 12630. In addition, each mounting bracket 12710, 12720 further includes a relief area 12732 that is shaped to receive the corresponding first and second alpha wrap pulleys 12620, 12630 therein.

Figure 94:
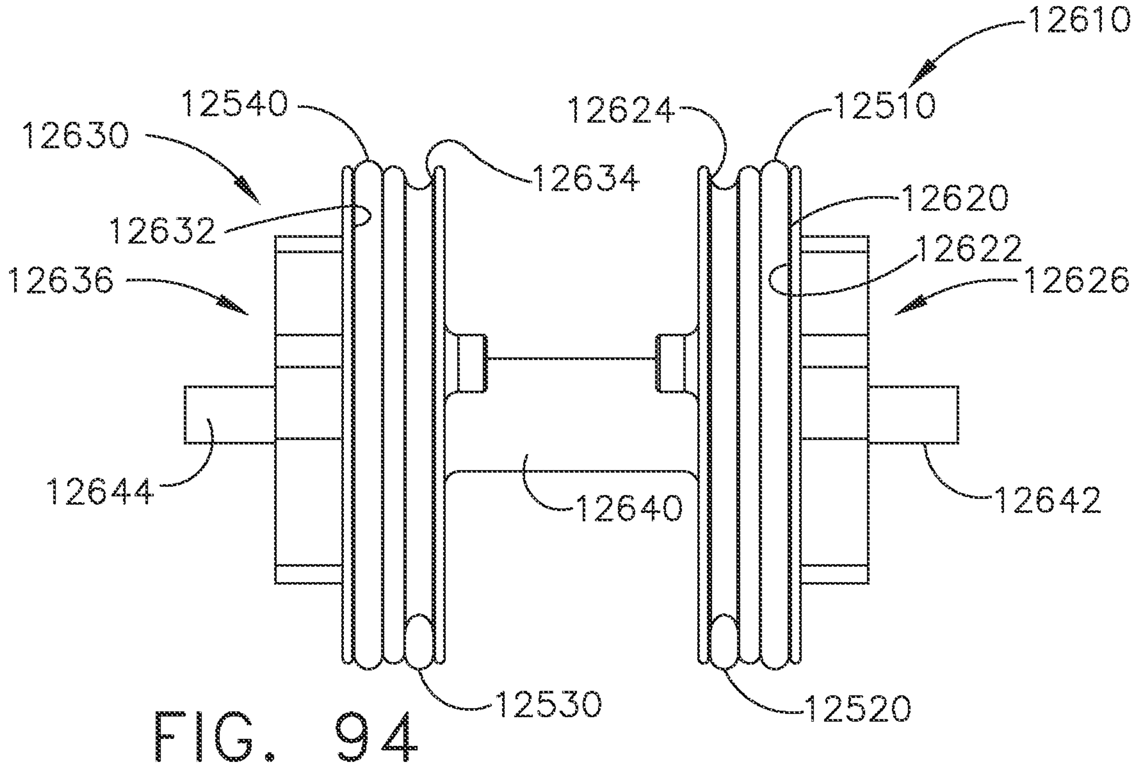
FIG. 94 is an end view of a pulley unit of the cable-controlled pulley system of FIG. 93.

As can be seen in FIG. 94, the first alpha wrap pulley 12620 comprises a first circumferential groove 12622 and a second circumferential groove 12624. In the illustrated example, the first cable 12510 is received in the first circumferential groove 12622 and is attached thereto and the second cable 12520 is received in the second circumferential groove 12624 and is attached thereto. Pulling on the first cable 12510 will result in the rotation of the first lateral alpha wrap pulley 12620 in a first direction and pulling the second cable 12520 will result in the rotation of the first lateral alpha wrap pulley 12620 in a second opposite direction. Similarly, the second lateral alpha wrap pulley 12630 comprises a first circumferential groove 12632 and a second circumferential groove 12634. In the illustrated arrangement, cable 12540 is received in the first circumferential groove 12632 and is attached thereto and the second cable 12520 is received in the second circumferential groove 12634 and is attached thereto. Pulling on the fourth cable 12540 will result in the rotation of the first second alpha wrap pulley 12630 in the first direction and pulling the third cable 12530 will result in the rotation of the second lateral alpha wrap pulley 12630 in the second opposite direction. The lateral alpha wrap pulleys 12620, 12630 can rotate approximately three hundred thirty degrees. This range of rotational travel is in contrast to a normal pulley that may have a range of rotational travel that is less than one hundred eighty degrees of rotation.

Figure 96:
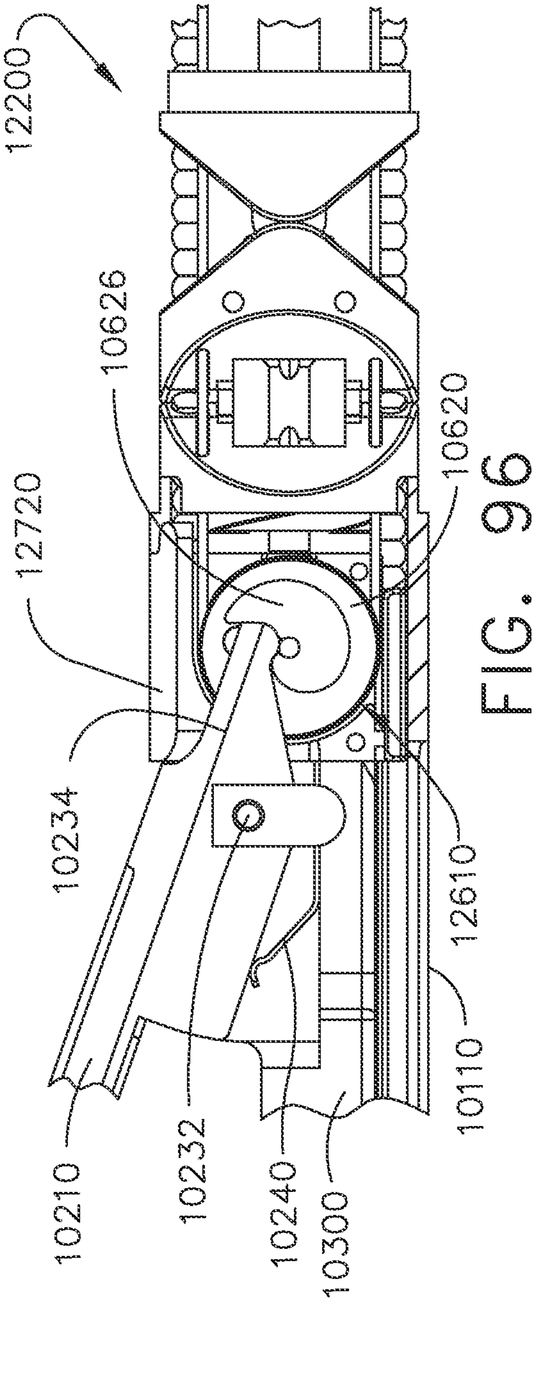
FIG. 96 is a side cross-sectional view of a portion of the surgical end effector of FIG. 89 with the anvil of the surgical end effector in an open position.
Figure 97:
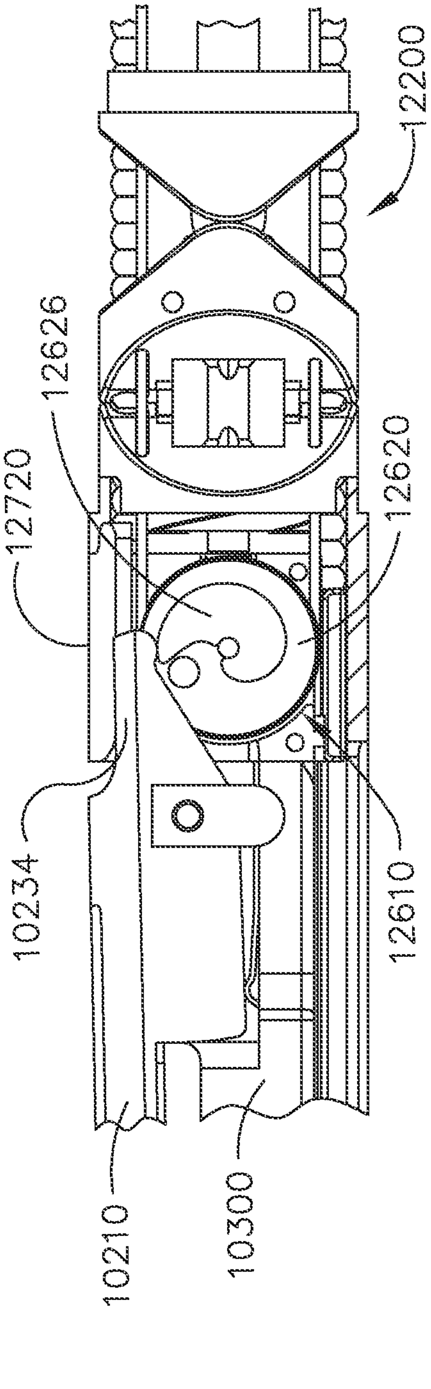
FIG. 97 is another side elevational view of the surgical end effector of FIG. 96 with the anvil in a closed position.

Each of the first and second lateral alpha wrap pulleys 12620, 12630 also comprises a corresponding spiral closure cam that is configured to apply closure motions to the anvil 10210. As can be seen in FIG. 94, the first lateral alpha wrap pulley 12620 includes a first spiral closure cam 12626 and the second lateral alpha wrap pulley 12630 has a second spiral closure cam 12636 thereon. The spiral closure cams 12626, 12636 are configured to cammingly interact with corresponding anvil closure arms 10234 on the anvil mounting portion 10230 of the anvil 10210 to apply closure motions thereto. FIG. 96 illustrates the position of a spiral closure cam 12626 on the first lateral alpha wrap pulley 12620 when the anvil 10210 is biased into the open position by an anvil spring 10240. Rotation of the pulley unit 12610 in a first rotary direction will cause the spiral closure cams 12626 to cam the anvil 1210 to the closed position shown in FIG. 97. To open the anvil 10210, the pulley unit 12610 is rotated in opposite direction back to the position shown in FIG. 96.

Figure 91:
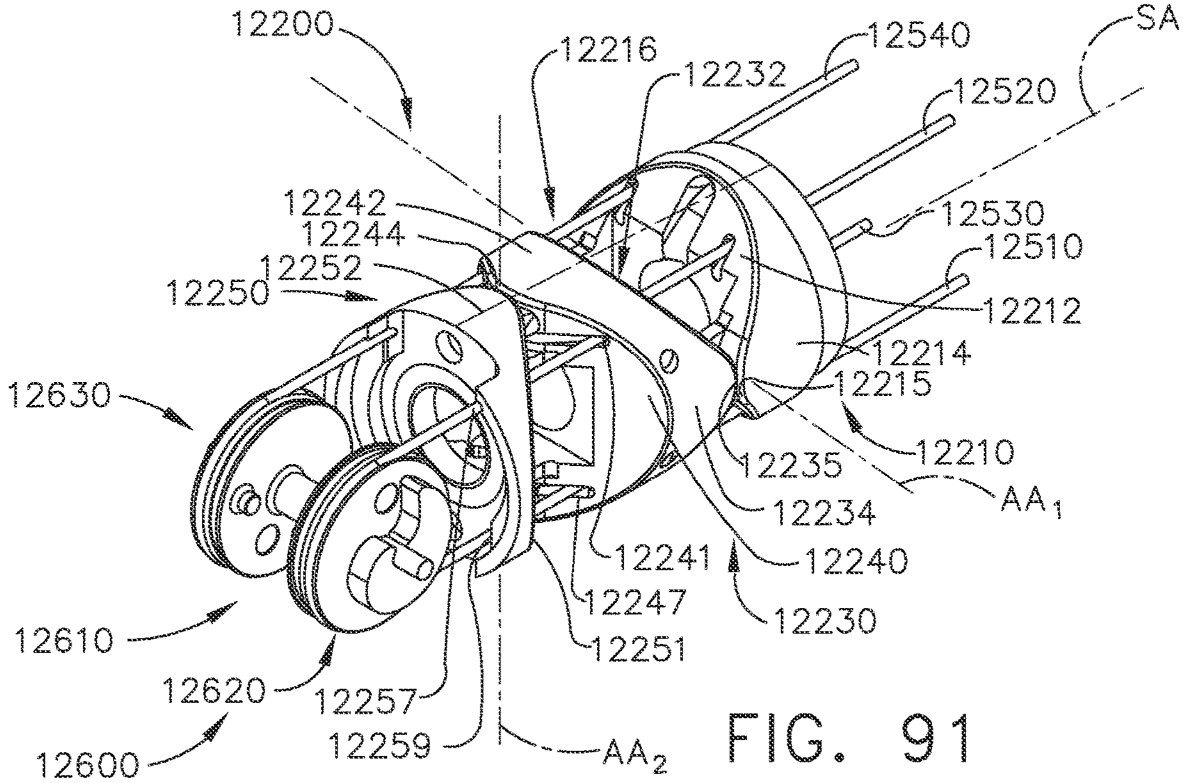
FIG. 91 is a perspective view of the articulation joint of FIG. 89 and a cable-controlled closure pulley system for applying closing motions to the anvil of the surgical end effector of FIG. 89.
Figure 93:
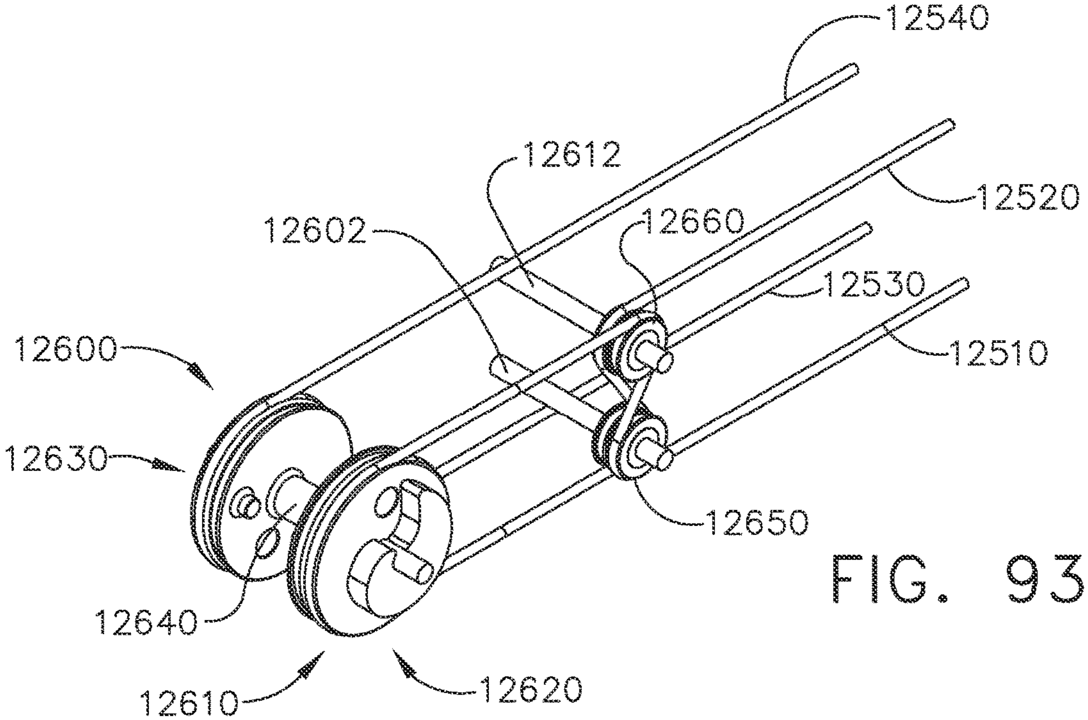
FIG. 93 is another perspective view of the cable-controlled closure pulley system of FIG. 91.

Referring now to FIGS. 91 and 93, the first cable 12510 extends from the cable control system through the elongate shaft assembly and through a passage in the proximal joint member 12210 and is looped around two redirect pulleys 12650, 12660 that are supported on shafts 12602, 12612 that are mounted in the central joint member 12230. The first cable 12510 exits the central joint member 12230 through passage 12231 and extends through passage 12257 in the distal joint member 12250 to be received within the first circumferential groove 12622 in the first lateral alpha wrap pulley 12620 where it is attached thereto. A second cable 12520 extends from the cable control system through the elongate shaft assembly and through passage 12213 in the proximal joint member 12210 to be looped around the redirect pulleys 12650, 12660 in the central joint member 12230. The second cable 12520 exits the central joint member 12230 through a corresponding passage 12241 and extends through passage 12259 in the distal joint member 12250 to be received within the second circumferential groove 12624 in the first lateral alpha wrap pulley 12620 where it is attached thereto.

In the illustrated example, the third cable 12530 extends from the cable control system 9030 through the elongate shaft assembly 12000 and through a corresponding passages in the proximal joint member 12210, the central joint member 12230, and the distal joint member 12250 to be received within a corresponding circumferential groove in the second lateral alpha wrap pulley 12630 where it is attached thereto. In addition, a fourth cable 12540 extends from the cable control system 9030 through the elongate shaft assembly 12000 and through corresponding passages in the proximal joint member 12210, the central joint member 12230, and the distal joint member 12250 to be received within a corresponding circumferential groove in the second lateral alpha wrap pulley 12630 where it is attached thereto.

Figure 98:
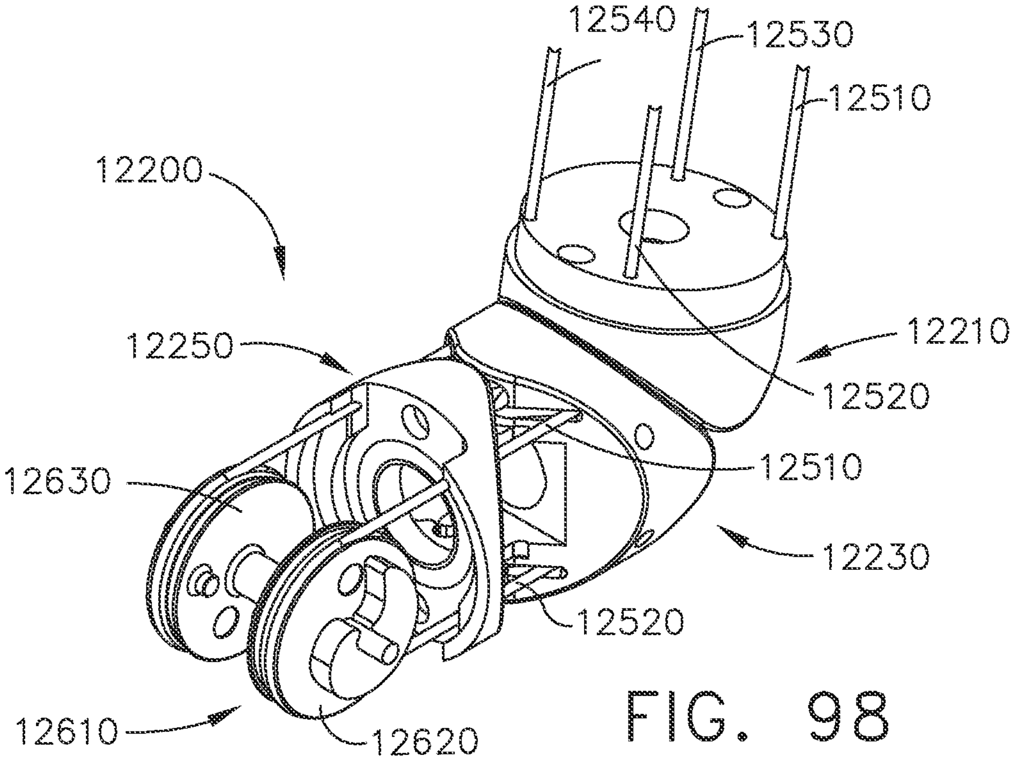
FIG. 98 is a perspective view of the articulation joint and cable-controlled closure system of the surgical instrument of FIG. 87 with a central joint member and a distal joint member articulated relative to a proximal joint member of the articulation joint.
Figure 99:
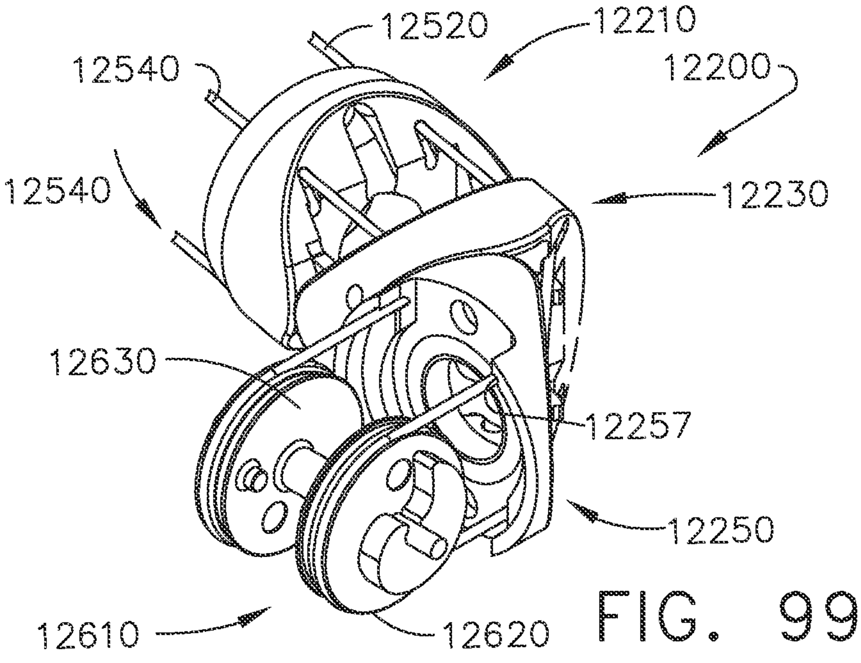
FIG. 99 is another perspective view of the articulation joint and cable-controlled closure system of the surgical instrument of FIG. 87 with the distal joint member articulated through a second articulation plane relative to a central joint member of the articulation joint.

In at least one example, to articulate the surgical end effector 10000 relative to the elongate shaft assembly 12000 through a first articulation plane that is defined by the first articulation axis $AA_1$, the cable control system 9030 is actuated to pull on the second cable 12520 and the fourth cable 12540 simultaneously with a same amount of tension being applied to each cable 12520 and 12540. Because the cables 12520, 12540 apply equal amounts of tension on both sides of the pulley unit 12610, the pulley unit 12610 does not rotate. However, the pulling action of the cables 12520 and 12540 is translated through the articulation joint 12200 to the surgical end effector 10000 which results in the articulation of the central joint member 12230 relative to the proximal joint member 12210 about the first articulation axis $AA_1$. See FIGS. 92 and 98. To articulate the surgical end effector 10000 through a second plane of articulation that is defined by the second articulation axis $AA_2$ and is transverse to the first plane of articulation, the cable control system 9030 is actuated to pull the third cable 12530 and the fourth cable 12540 simultaneously with a same amount of tension being applied to each cable 12530 and 12540. Because the cables 12530, 12540 apply equal amounts of tension on both sides of the second lateral alpha wrap pulley 12630 of the pulley unit 12610, the pulley unit 12610 does not rotate. However, the pulling action of the cables 12530 and 12540 is translated through the articulation joint 12200 to the surgical end effector 10000 which results in the articulation of the distal joint member 12250 relative to the central joint member 12230 about the second articulation axis $AA_2$. See FIGS. 92 and 99.

The cable control system 9030 may also be used to control the opening and closing of the anvil 10210 in the following manner. As indicated above, when the spiral cams 10626 on the first lateral alpha wrap pulley 10620 and the second lateral alpha wrap pulley 10630 are in the position shown in FIG. 96, the anvil 10210 is biased into the open position by the anvil spring 10240. To close the anvil 10210 from that position, the cable control system 9030 is actuated to pull the first cable 12510 and the fourth cable 12540 simultaneously with a same amount of tension being applied to each cable 12510 and 12540. These cables 12510 and 12540 will cause the pulley unit 12610 to rotate into the closure position shown in FIG. 97 which causes the closure cams 10626 to cammingly contact the anvil closure arms 10234 to pivot the anvil 10210 into the closed position. It will be appreciated that by applying equal amounts of tension into the cables 12510 and 12540, no moment is applied to the central joint member 12230 and/or distal joint member 12250 because there are equal amounts of tension being applied on each side of the articulation joint 12200. See FIG. 91. Such arrangement allows the jaw closure to be profiled as desired. This cable-controlled system 9030 allows for a faster closure when the anvil is fully open. The cable-controlled system 9030 can also function as a lower speed/higher force generating closure mechanism for clamping onto tissue. The present cable controlled system 9030 may also not produce the backlash that commonly occurs with other cable-controlled systems and thus can also be used to control the articulation position of the end effector. As will be further discussed below, this cable actuated closure and articulation system does not cross across the center axis or shaft axis of the articulation joint which provides critical space for a firing drive system 13000.

The above-described articulation joint 12200 and cable controlled system 9030 can facilitate two plane articulation while also supplying an additional actuation motion to the surgical end effector 10000 while keeping the central area of the articulation joint 12200 free for other control systems as will be discussed in further detail below. The articulation joint 12200 uses the last degree of freedom to actuate the jaw closure of the surgical end effector. In one aspect, the articulation joint 12200 comprises an N+1 joint, meaning that for N degrees of freedom, the joint requires N+1 cables to actuate it. Thus, in the above-described example, the articulation joint 12200 employs four actuation cables.

As can be seen in FIGS. 100-103, the firing drive system 13000 comprises a firing member 13310 that includes a vertically-extending firing member body 13312 that has two laterally extending tabs 13314 protruding from a bottom portion 13313 of the firing member body 13312. The tabs 13314 are configured to be slidably engage ledges 10113 in the elongate channel 10110 as the firing member 13310 is driven axially therein. In addition, a pair of upper tabs 13316 protrudes from a top portion 13315 of the firing member body 13312. The upper tabs 13316 are configured to engage ledges 10213 (FIG. 103) in the anvil body 10212 as the firing member 13310 is driven distally through the closed anvil 10210. During the firing stroke, the tabs 13314 and 13316 may serve to space the anvil 10210 relative to a surgical staple cartridge that is supported in the elongate channel 10110. The firing member body 13312 also comprises a tissue cutting feature 13318 and a proximally-facing notch 13319 that is configured to accommodate the central shaft 12640 of the pulley unit 12610 when the firing member 13310 is in its proximal-most starting position within the firing member parking area 10140 in the proximal end 10112 of the elongate channel 10110.

Figure 100:
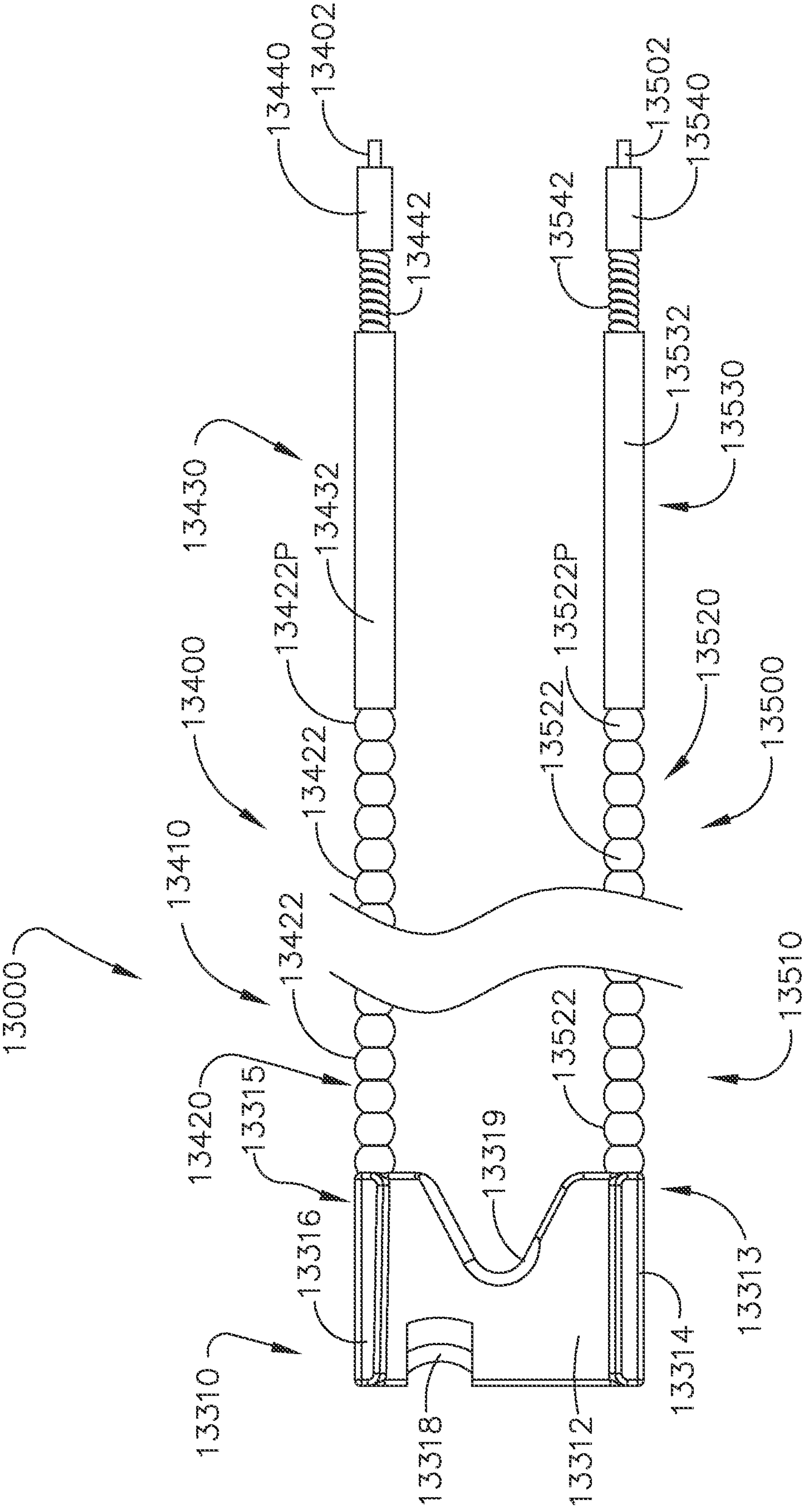
FIG. 100 is a side elevational view of portions of a firing drive system of the surgical instrument of FIG. 87.
Figure 101:
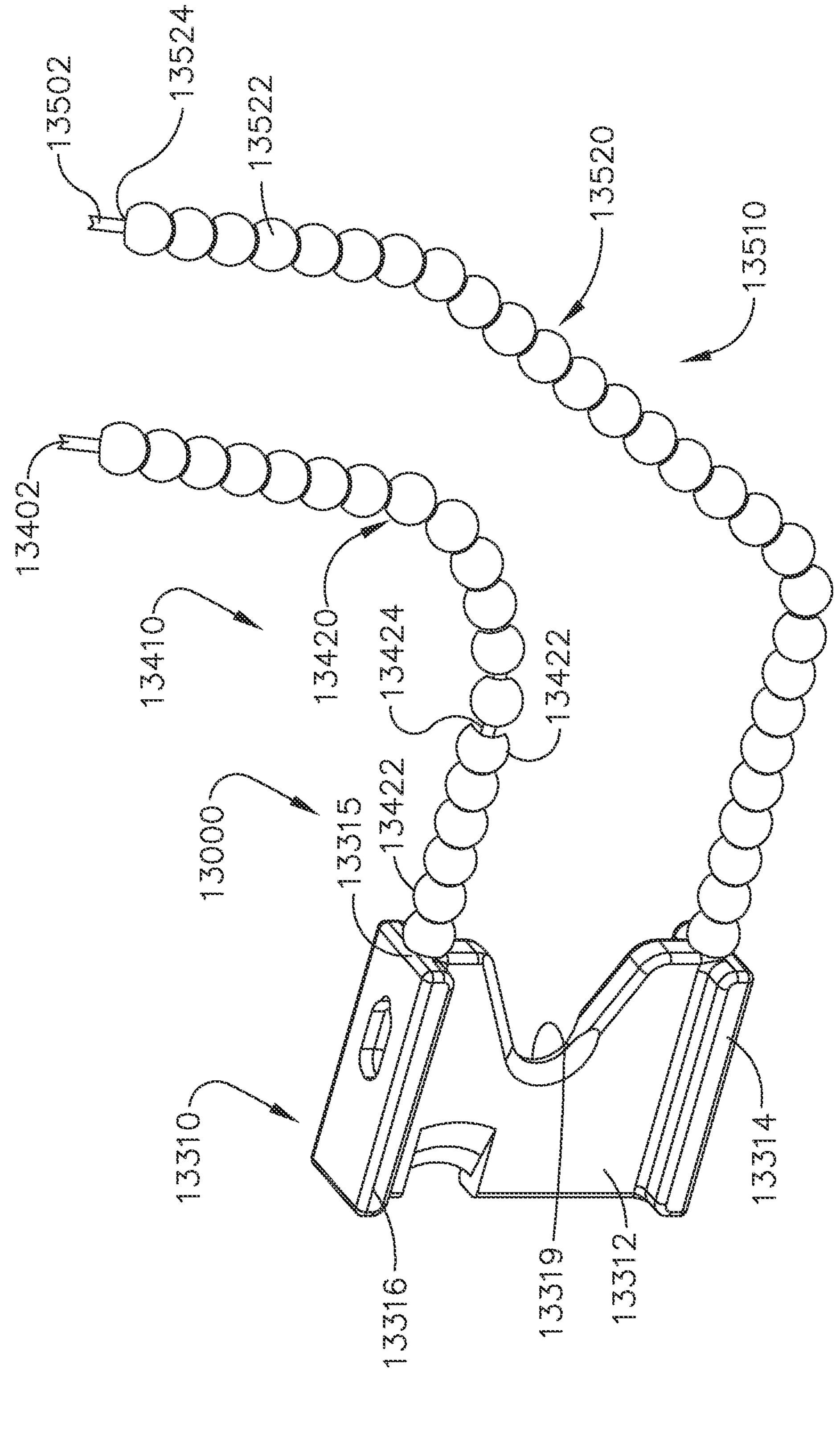
FIG. 101 is another perspective view of the firing drive system of FIG. 100 with upper chain link features and lower chain link features in articulated positions.
Figure 102:
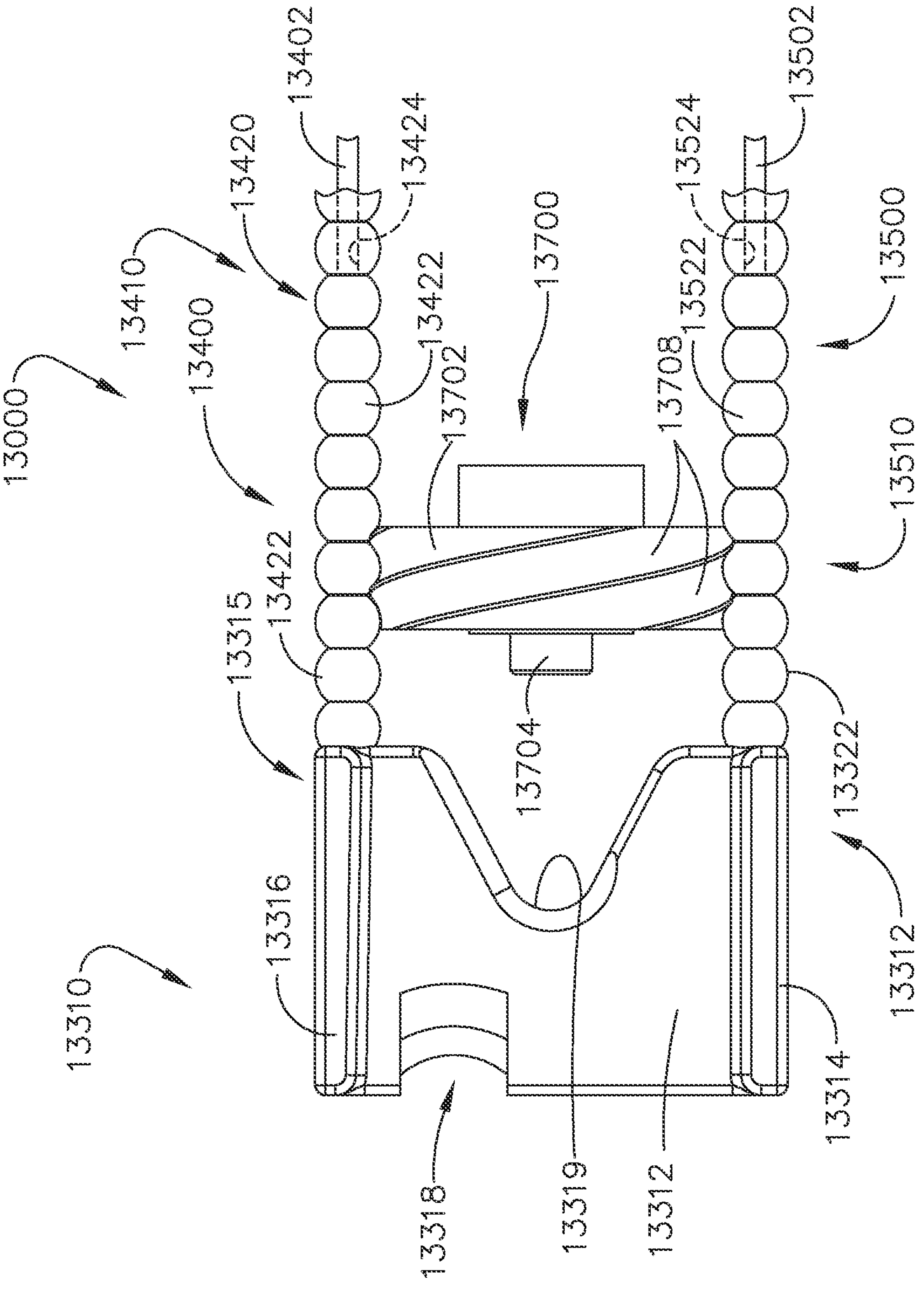
FIG. 102 is another side view of the firing drive system of FIG. 100 with the upper chain link features and lower chain link features in driving engagement with a rotary drive screw of the firing drive system.
Figure 103:
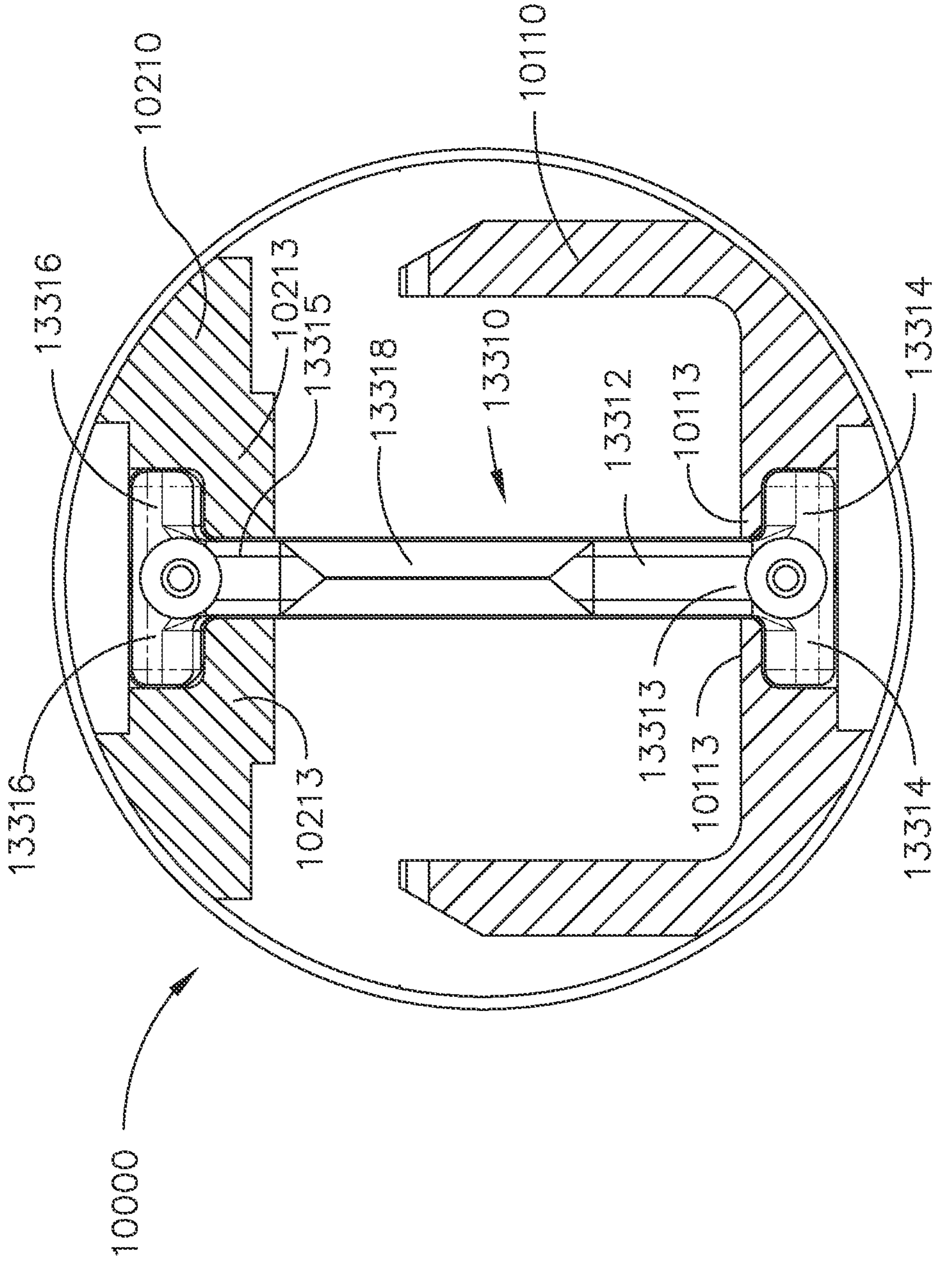
FIG. 103 is a cross-sectional end view of the surgical end effector of FIG. 87 with the anvil thereof in a closed position.

As shown in FIGS. 100-102, the firing drive system 13000 further comprises an upper flexible chain drive assembly 13400 that is operably coupled to the top portion 13315 of the firing member 13310 and a lower flexible chain drive assembly 13500 that is operably coupled to the bottom portion 13313 of the firing member 13310. In at least one embodiment, the upper flexible chain drive assembly 13400 comprises an upper series 13410 of upper chain link features 13420 that are loosely coupled together by an upper flexible coupler member 13402 that is attached to the top portion 13315 of the firing member 13310. In at least one example, each upper chain link feature 13420 comprises an upper ball or sphere 13422 that has an upper hollow passage 13424 therein that is configured to permit the upper flexible coupler member 13402 to pass therethrough. As can be seen in FIG. 100, the upper flexible chain drive assembly 13400 further comprises an upper compression assembly 13430 for compressing the upper balls 13422 in the upper series 13410 together. In one arrangement, the upper compression assembly 13430 comprises a hollow flexible compression tube 13432 that is received on the upper flexible coupler member 13402. An upper ferrule 13440 is crimped onto the upper flexible coupler member 13402 and an upper compression spring 13442 is journaled between the upper ferrule 13440 and the upper flexible compression tube 13432 to distally bias the upper flexible compression tube 13432 into contact with the proximal-most upper ball 13422P in the upper series 13410 of upper chain link features 13420.

Similarly, in at least one embodiment, the lower flexible chain drive assembly 13500 comprises a lower series 13510 of lower chain link features 13520 that are loosely coupled together by a lower flexible coupler member 13502 that is attached to the bottom portion 13313 of the firing member 13310. In at least one example, each lower chain link feature 13520 comprises a lower ball or sphere 13522 that has a lower hollow passage 13524 therein that is configured to permit the lower flexible coupler member 13502 to pass therethrough. The lower flexible chain drive assembly 13500 further comprises an upper compression assembly 13530 for compressing the lower balls 13522 in the lower series 13510 together. In one arrangement, the lower compression assembly 13530 comprises a hollow flexible compression tube 13532 that is received on the lower flexible coupler member 13502. A lower ferrule 13540 is crimped onto the lower flexible coupler member 13502 and a lower compression spring 13542 is journaled between the lower ferrule 13540 and the lower flexible compression tube 13532 to distally bias the lower flexible compression tube 13532 into contact with the proximal-most lower ball 13522P in the lower series 13510 of lower chain link features 13520.

Figure 104:
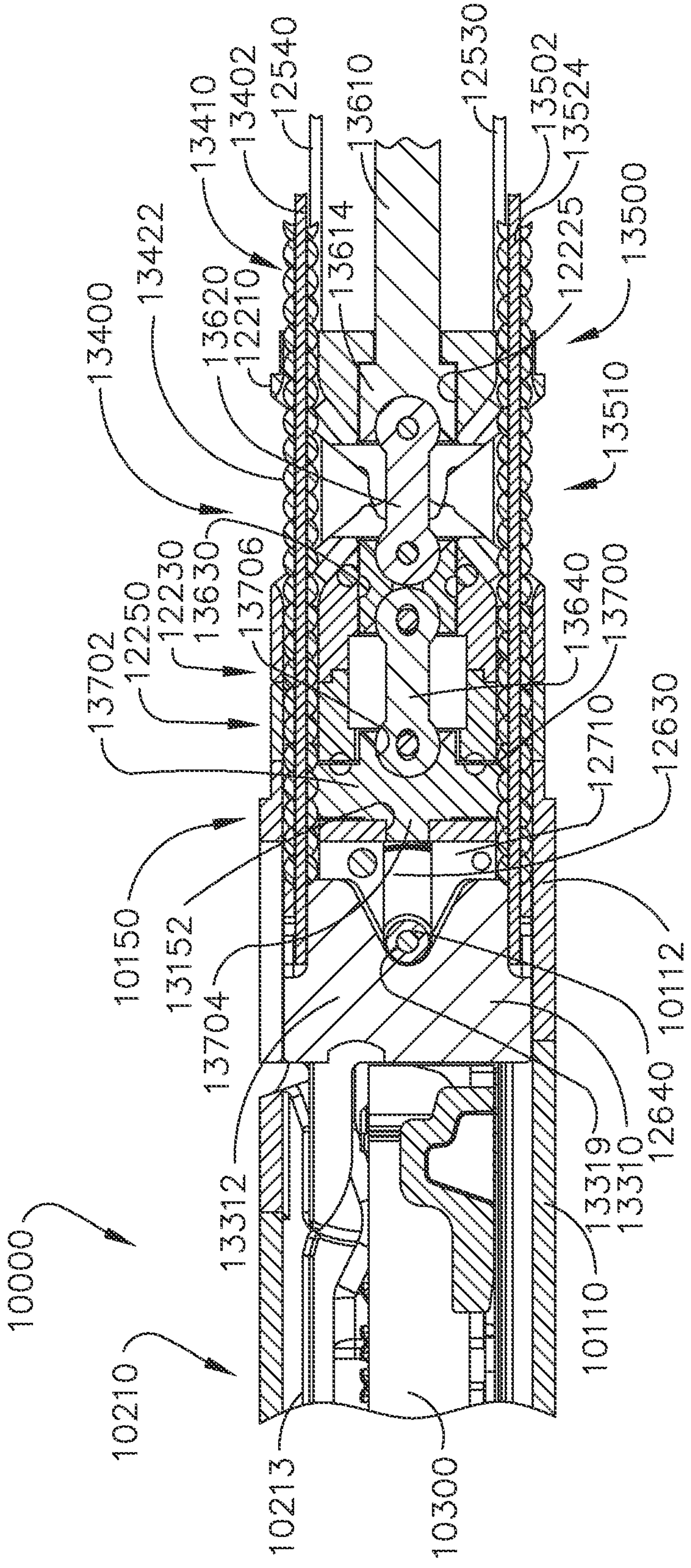
FIG. 104 is a cross-sectional side view of a portion of the surgical instrument of FIG. 87 with the firing member in a starting position and the anvil in a closed position.

Now turning to FIG. 104, in at least one arrangement, the firing drive system 13000 further comprises rotary drive screw 13700 that is configured to drivingly interface with the upper series 13410 of upper chain link features 13420 and the lower series 13510 of lower chain link features 13520. As can be seen in FIG. 104, in the illustrated arrangement, the rotary drive screw 13700 is rotatably supported in the mounting bushing 10150 that is attached to the proximal end 10112 of the elongate channel 10110. For example, the rotary drive screw 13700 comprises a body portion 13702 that has a central axle 13704 protruding therefrom that is rotatably mounted in a mounting hole 10152 in the mounting bushing 10150. Such arrangement permits the rotary drive screw 13700 to rotate about the shaft axis SA.

Figure 105:
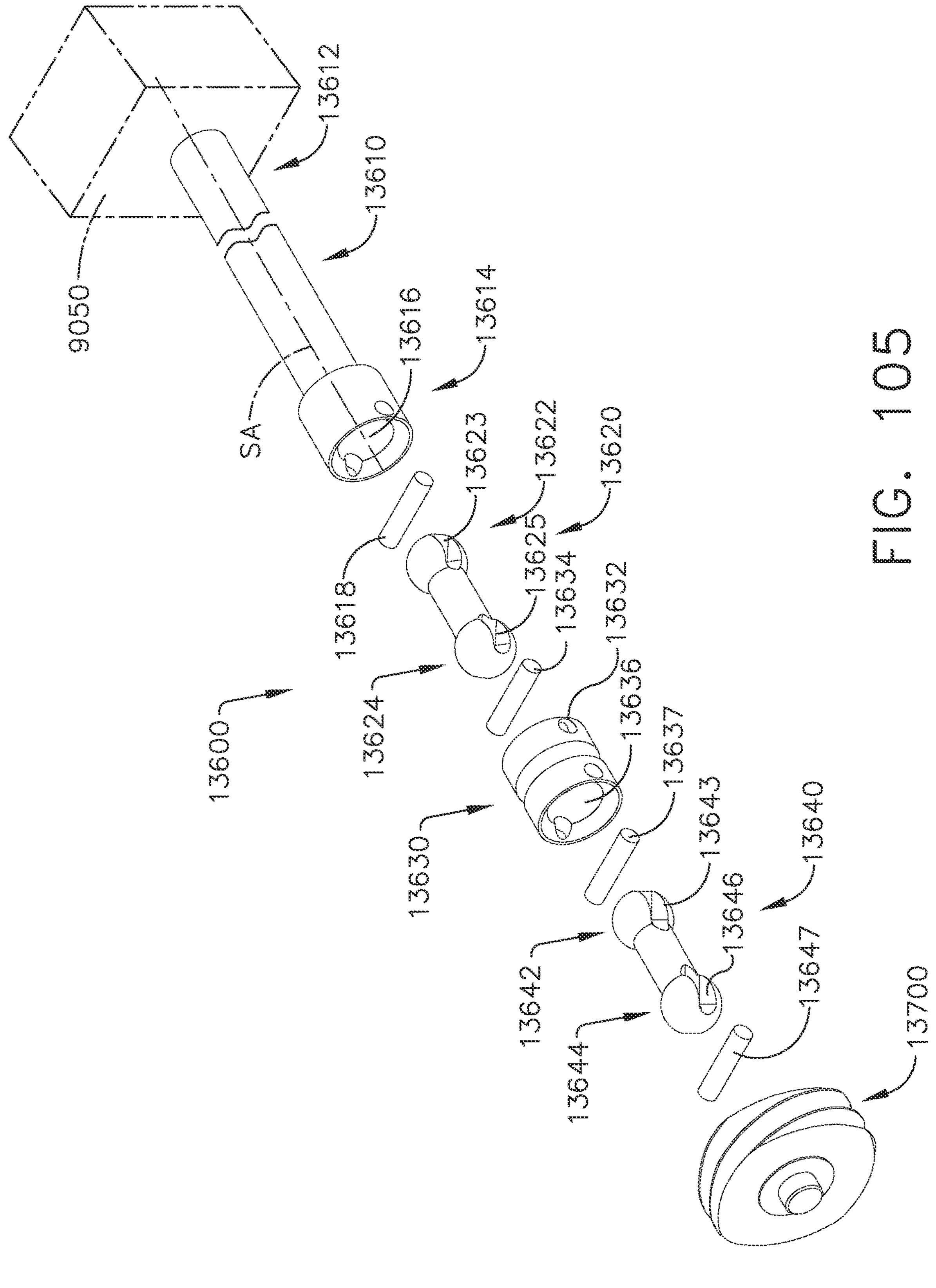
FIG. 105 is an exploded assembly view of a rotary drive system of the surgical instrument of FIG. 87.
Figure 106:
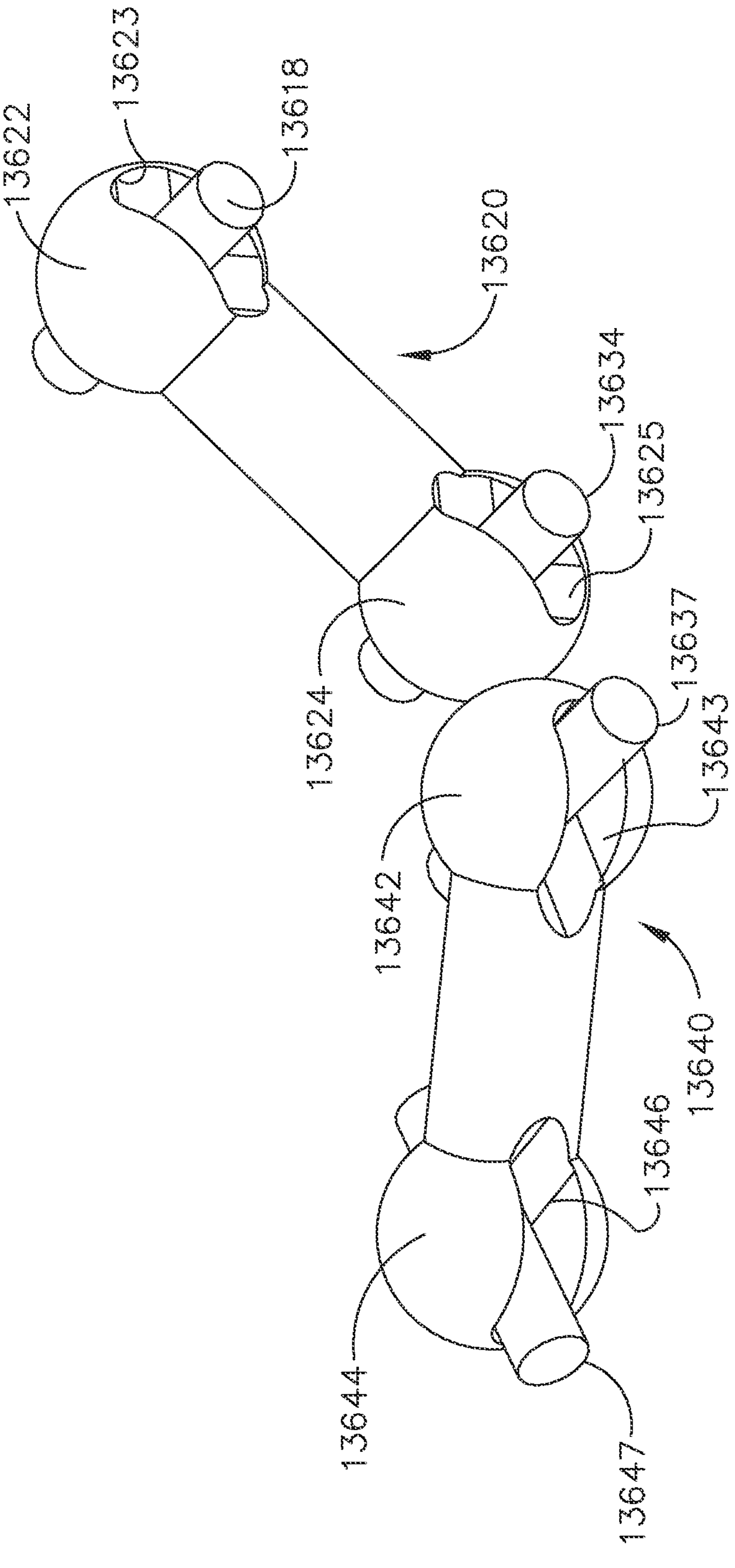
FIG. 106 is a perspective view of a first drive shaft segment and a second drive shaft segment of the rotary drive system of FIG. 105.
Figure 107:
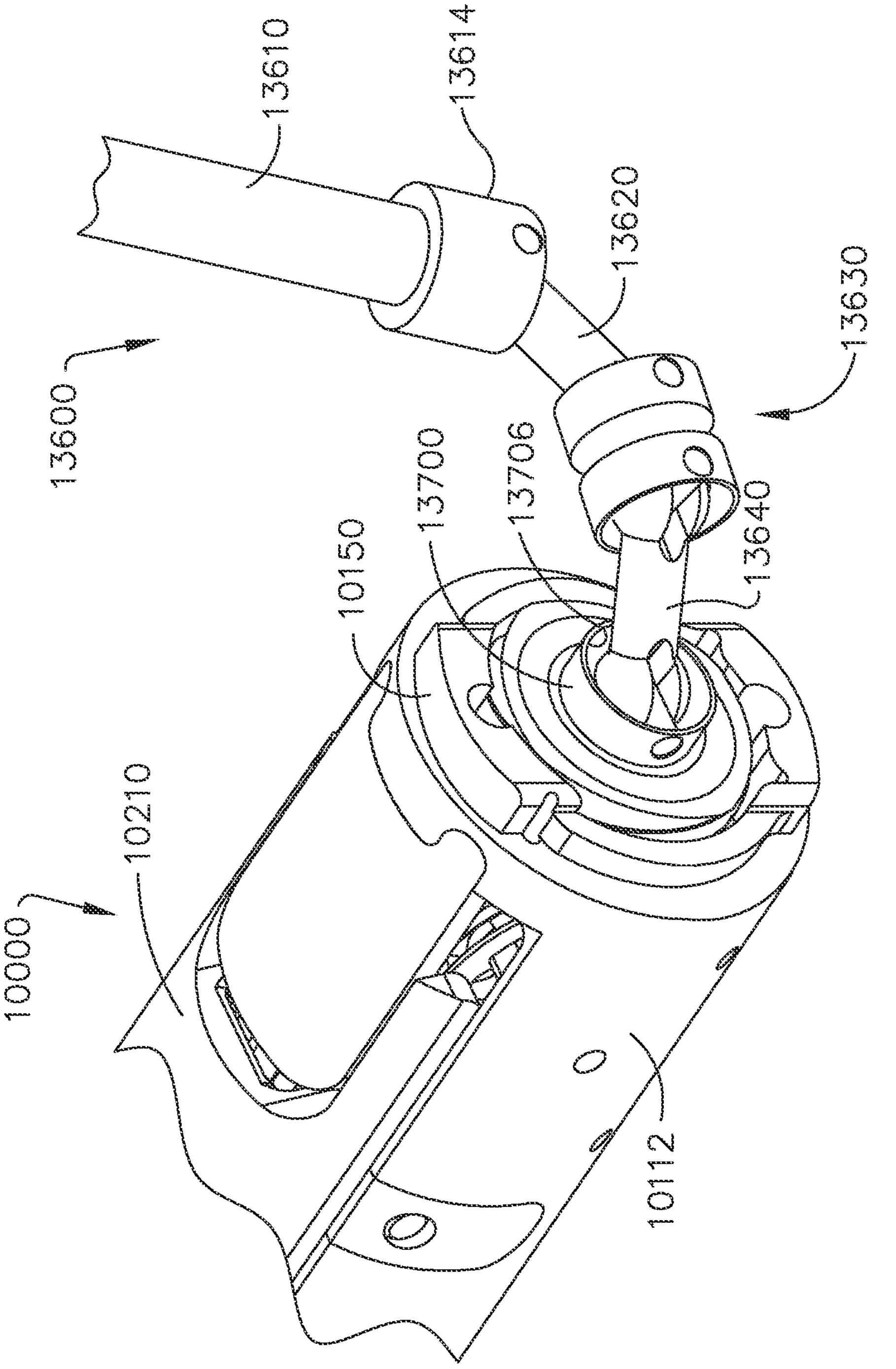
FIG. 107 is a perspective view of the surgical end effector of FIG. 87 with the rotary drive system in an articulated orientation.
Figure 108:
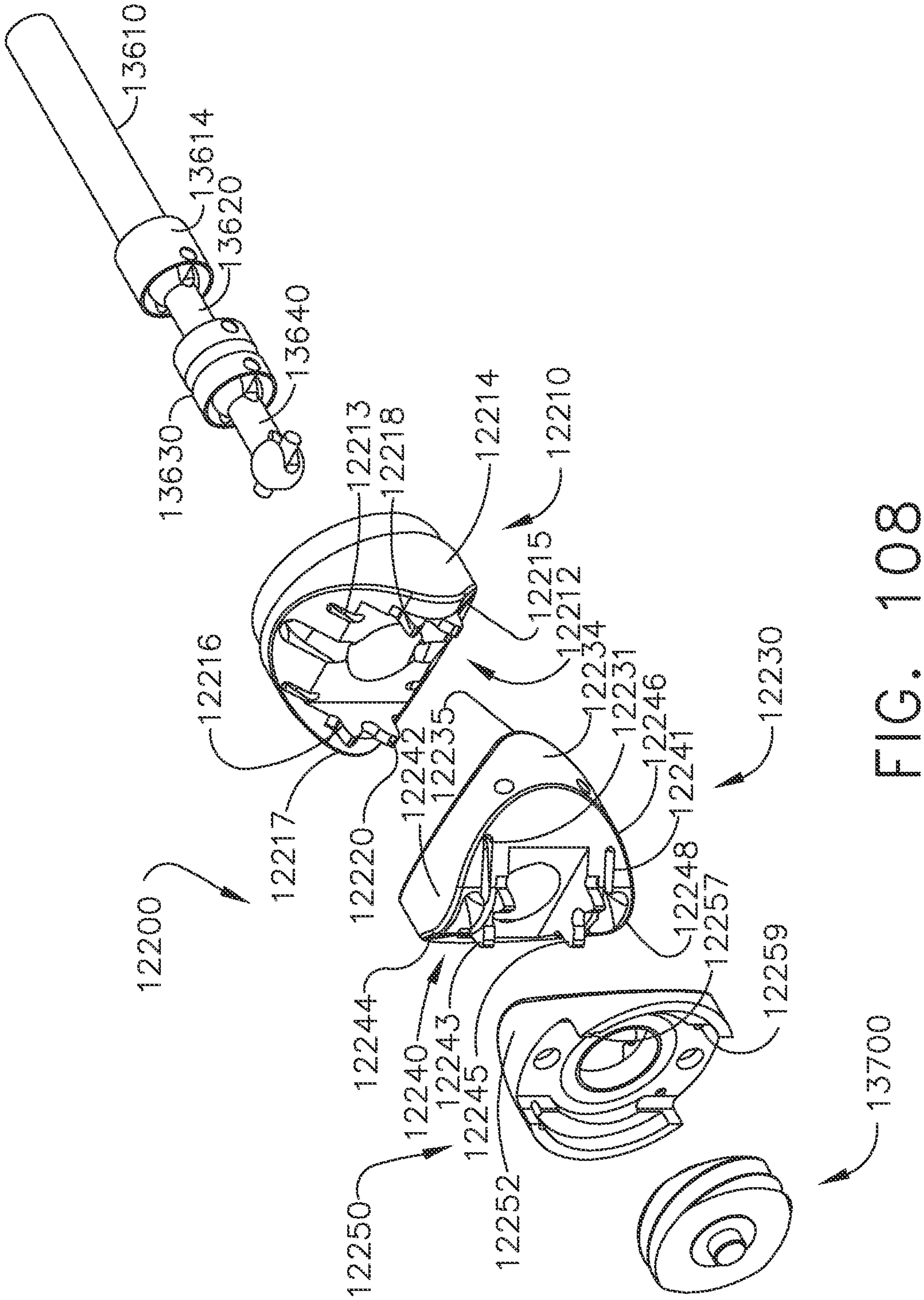
FIG. 108 is an exploded assembly view of an articulation joint and a portion of the rotary drive system of the surgical instrument of FIG. 87.
Figure 109:
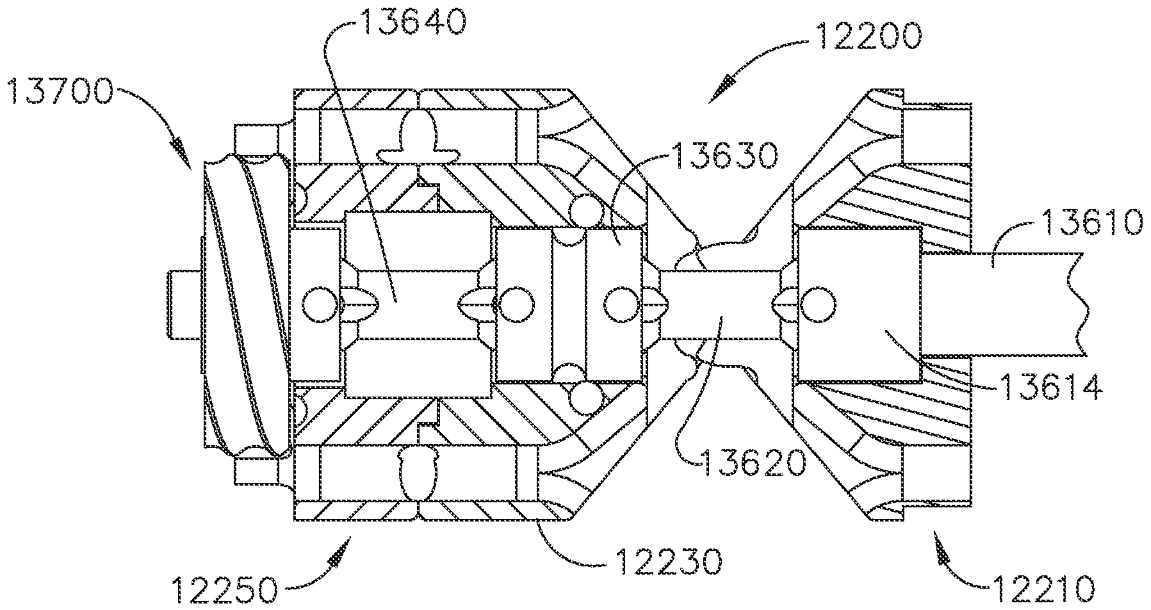
FIG. 109 is a cross-sectional view of the articulation joint and rotary drive system of FIG. 108 in an unarticulated orientation.
Figure 110:
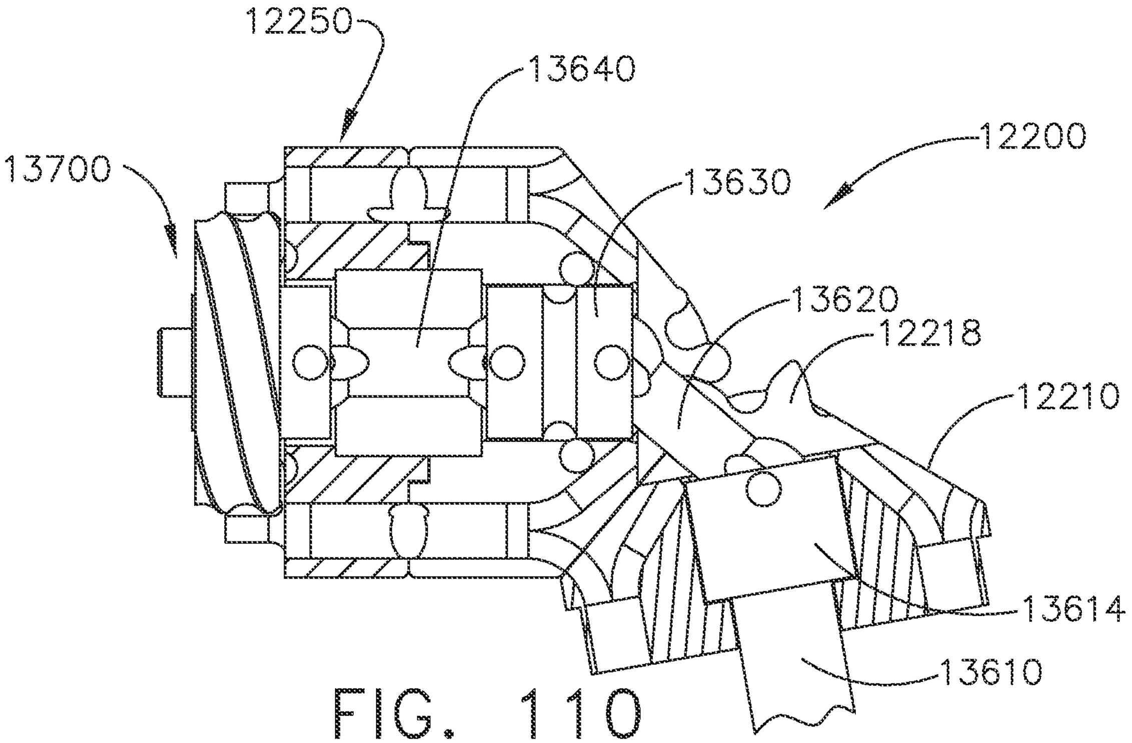
FIG. 110 is another cross-sectional view of the articulation joint and rotary drive system of FIG. 109 with a proximal joint member of the articulation joint articulated relative to a central joint member of the articulation joint.

In the illustrated example, the rotary drive screw 13700 is driven by a rotary drive system 13600 that comprises a proximal rotary drive shaft 13610 that is rotatably supported within an axial passage 12225 within the proximal joint member 12210. As can be seen in FIG. 105, the proximal rotary drive shaft 13610 comprises a proximal end 13612 and a distal end 13614. The proximal end 13612 may interface with a gear box/motor arrangement 9050 or other source of rotary motion housed in the housing 9020 of the surgical instrument 9010. Such source of rotary motion causes the proximal rotary drive shaft 13610 to rotate about the shaft axis SA within the axial passage 12225 in the proximal joint member 12210. See FIG. 104. As can be seen in FIG. 105, the distal end 13614 of the proximal rotary drive shaft 13610 is movably coupled to a first drive shaft segment 13620. In the illustrated example, the first drive shaft segment 13620 resembles a "dog bone" with a first spherical proximal end 13622 and a first spherical distal end 13624. See FIG. 106. The first spherical proximal end 13622 is movably pinned within a first distal socket 13616 formed in the distal end 13614 of the proximal rotary drive shaft 13610 by a first proximal pin 13618. The first proximal pin 13618 extends through an arcuate transverse slot 13623 in the first spherical proximal end 13622. Such arrangement permits the first spherical proximal end 13622 to move in multiple directions within the first distal socket 13616 while remaining attached thereto. The first spherical distal end 13624 is received within a first proximal socket 13632 in a central bearing housing 13630 that is mounted within the central joint member 12230. The first spherical distal end 13624 is movably pinned within the first proximal socket 13632 by a first distal pin 13634. The first distal pin 13634 extends through an arcuate transverse slot 13625 in the first spherical distal end 13624. Such arrangement permits the first spherical distal end 13624 to move in multiple directions within the first proximal socket 13632 while remaining attached to the central bearing housing 13630.

As can be seen in FIG. 105, the rotary drive system 13600 further comprises a second drive shaft segment 13640 that resembles the first drive shaft segment 13620 and includes a second spherical proximal end 13642 and a second spherical distal end 13644. The second spherical proximal end 13642 is movably pinned within a second distal socket 13636 that is formed in the central bearing housing 13630 by a second proximal pin 13637. The second proximal pin 13637 extends through an arcuate transverse slot 13643 in the second spherical proximal end 13642. Such arrangement permits the second spherical proximal end 13642 to move in multiple directions within the second distal socket 13636 while remaining attached thereto. The second spherical distal end 13644 is received within a second proximal socket 13706 in the rotary drive screw 13700 and is movably pinned within the second proximal socket 13706 by a second distal pin 13647. The second distal pin 13647 extends through a transverse slot 13646 in the second spherical distal end 13644. Such arrangement permits the second spherical distal end 13644 to move in multiple directions relative to the rotary drive screw 13700.

The double joint rotary drive maintains a linear velocity output by using the angle constraint of the joint members of the articulation joint. This universal rotary joint arrangement on its own may have a sinusoidal output based on the angle of the joint. If the angles are equal and the phases are aligned correctly, the sine output of the first universal joint will be canceled out by the second universal joint, producing a linear rotational velocity. This is an advantage to putting a constraint in the rotary drive because it decreases the complexity of the components and prevents the need to remove material from the components to attain the requisite clearance. Thus, the components of this embodiment are more robust and stronger than prior arrangements. Further, the constant velocity of the rotary drive system will allow for smoother firing and reduced wear that may be otherwise caused by vibration.

Returning to FIG. 102, the rotary drive screw 13700 comprises helical grooves or drive features 13708 formed on a circumference thereof that are configured to engage and drive the upper balls or spheres 13422 in the upper series 13410 of upper chain link features 13420 and the lower balls or spheres 13522 in the lower series 13510 of lower chain link features 13520. Thus, to drive the firing member 13310 from a starting position in the surgical end effector 10000 to an ending position within the end effector, the rotary drive system 13600 is actuated to apply a rotary drive motion to the rotary drive screw 13700. As the rotary drive screw 13700 rotates in the first rotary direction, the helical drive features 13708 engage the upper balls or spheres 13422 in the upper series 13410 of upper chain link features 13420 and the lower balls or spheres 13522 in the lower series 13510 of lower chain link features 13520 and drive the upper flexible chain drive assembly 13400 and the lower flexible chain drive assembly 13500 distally. As each upper ball 13422 and lower ball 13522 engage the rotary drive screw 13700, the upper balls 13422 in the upper series 13410 that are distal to the rotary drive screw 13700 (and the articulation joint 12200) and the lower balls 13522 in the lower series 13510 that are distal to the rotary drive screw 13700 (and the articulation joint 12200) are placed under compression to apply balanced axial drive forces to the firing member 13310. When the upper flexible chain drive assembly 13400 and the flexible lower chain drive assembly 13500 are in compression, they are constrained by the slots in the anvil 10210 and the elongate channel 10110, respectively. Such arrangement ensures that, when the upper flexible chain drive assembly 13400 and lower flexible chain drive assembly 13500 are compressed, they do not buckle.

This arrangement enables two degrees of articulation freedom for a few reasons. For example, the upper flexible chain drive assembly 13400 and lower flexible chain drive assembly 13500 can bend freely both in the pitch and yaw axes. Thus, the upper flexible chain drive assembly 13400 and lower flexible chain drive assembly 13500 can assume a variety of configurations that can accommodate various articulated positions that are attainable with the articulation joint 12200. Once the firing member 13310 has traveled through the surgical end effector 10000 distally to an ending position therein, the rotary drive system 13600 is actuated to apply a second rotary drive motion to the rotary drive screw 13700 to cause the rotary drive screw 13700 to rotate about the shaft axis in a second rotary direction. As the rotary drive screw 13700 rotates in the second rotary direction, the upper flexible chain drive assembly 13400 and the lower flexible chain drive assembly 13500 serve to retract the firing member 13310 in the proximal direction back to the starting position. As the upper flexible chain drive assembly 13400 and the lower flexible chain drive assembly 13500 retract the firing member 13310 proximally, a portion of the upper flexible chain drive assembly 13400 and the lower flexible chain drive assembly 13500 traverse back through the articulation joint 12200 and into the elongate shaft. Such arrangement allows the firing member 13310 to translate a long distance, without increasing the length of the end effector joint. Additionally, because the rotary drive screw 13700 drivingly engages the upper flexible chain drive assembly 13400 and the lower flexible chain drive assembly 13500 at a location that is distal to the articulation joint 12200, the high compressive loads are contained within the surgical end effector 10000 and do not create a moment on the articulation joint 12200. This arrangement may greatly reduce the strength requirements of the articulation joint. See FIG. 104.

Figure 111:
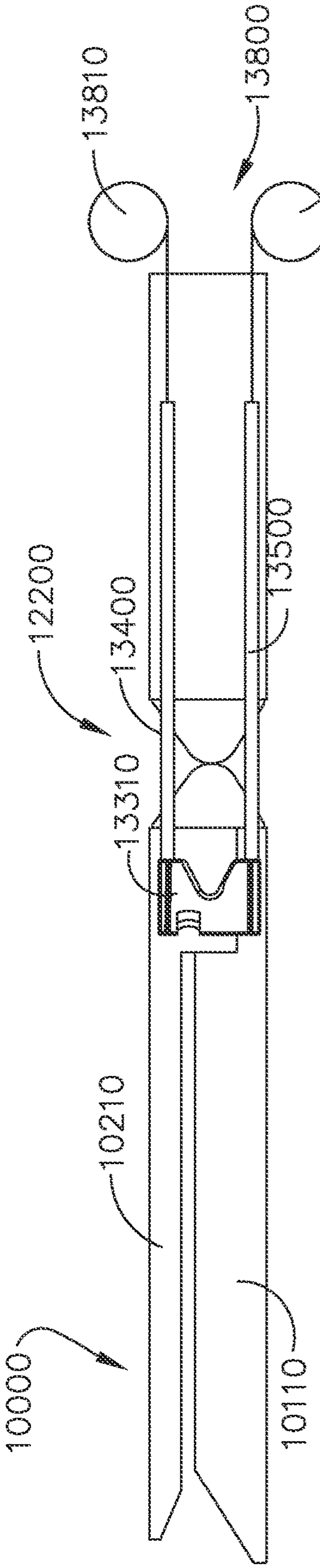
FIG. 111 is a partial side elevational view of the surgical instrument of FIG. 87 illustrating one form of a cable tensioning system with the surgical end effector in an unarticulated orientation.
Figure 112:
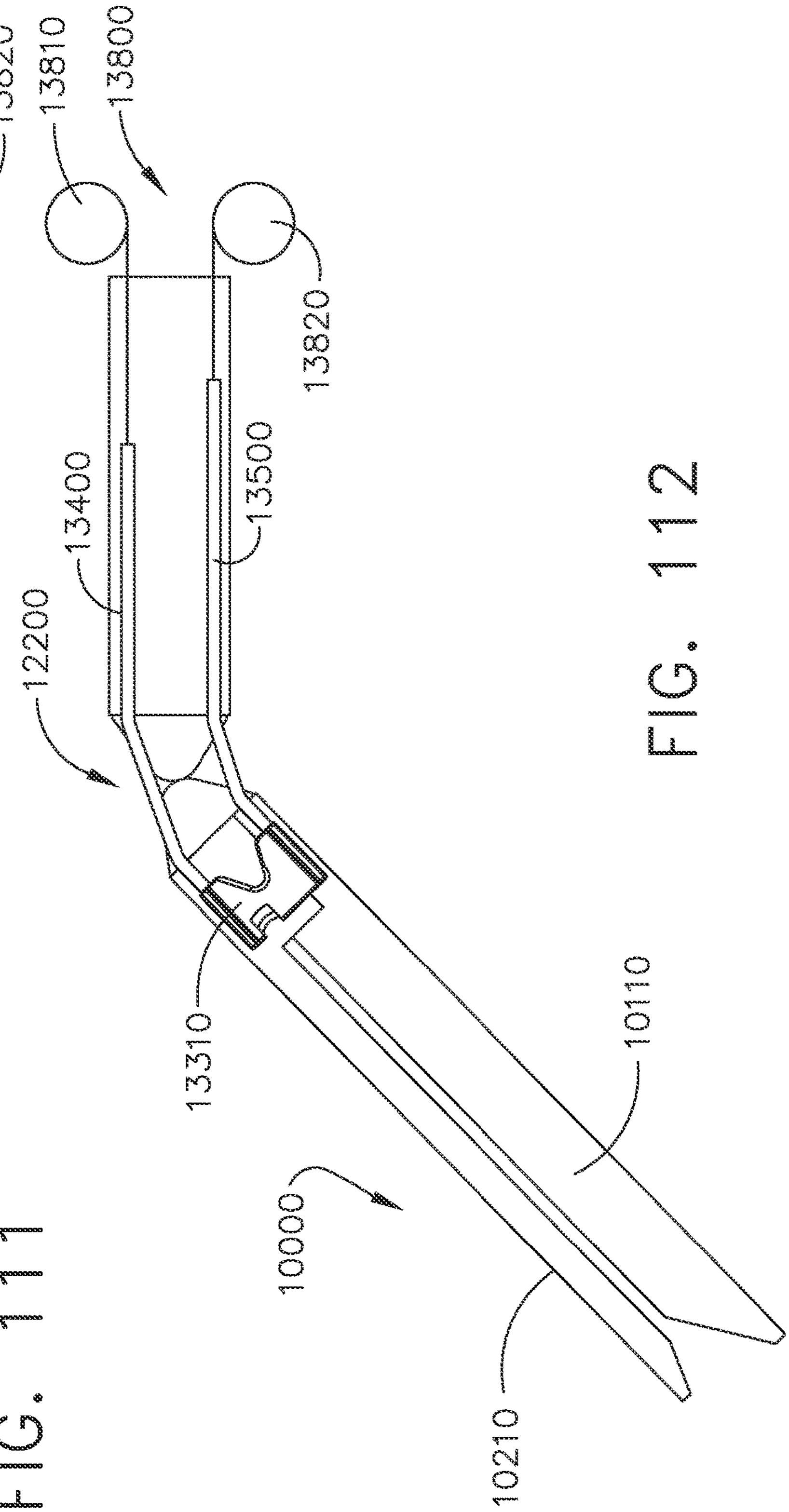
FIG. 112 is another partial side view of the surgical instrument and cable tensioning system of FIG. 111 with the surgical end effector in an articulated orientation.

In at least one arrangement, the surgical instrument 9010 may further comprise a cable tensioning system 13800 that is configured to maintain a desired amount of tension on the upper flexible chain drive assembly 13400 and the lower flexible chain drive assembly 13500 as they bend through the articulation joint 12200. Keeping the upper flexible chain drive assembly 13400 and the lower flexible chain drive assembly 13500 under a desired amount of tension as they traverse through the articulation joint 12200 may prevent slack from forming in those flexible chain drive assemblies 13400, 13500 which might otherwise cause them to undesirably bunch up in the articulation joint 12200. FIGS. 111 and 112 illustrate one form of cable tensioning system 13800 which comprises constant force spring arrangements 13810 and 13820. Such solution has the benefit of not requiring length conservation of the flexible chain drive assemblies 13400, 13500.

Figure 113:
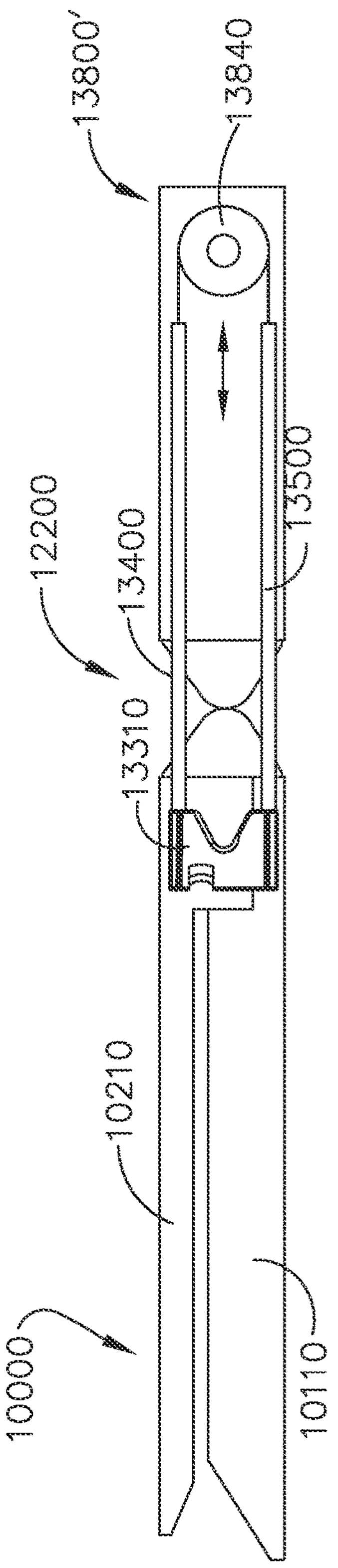
FIG. 113 is a partial side elevational view of the surgical instrument of FIG. 87 illustrating another form of a cable tensioning system with the surgical end effector in an unarticulated orientation.
Figure 114:
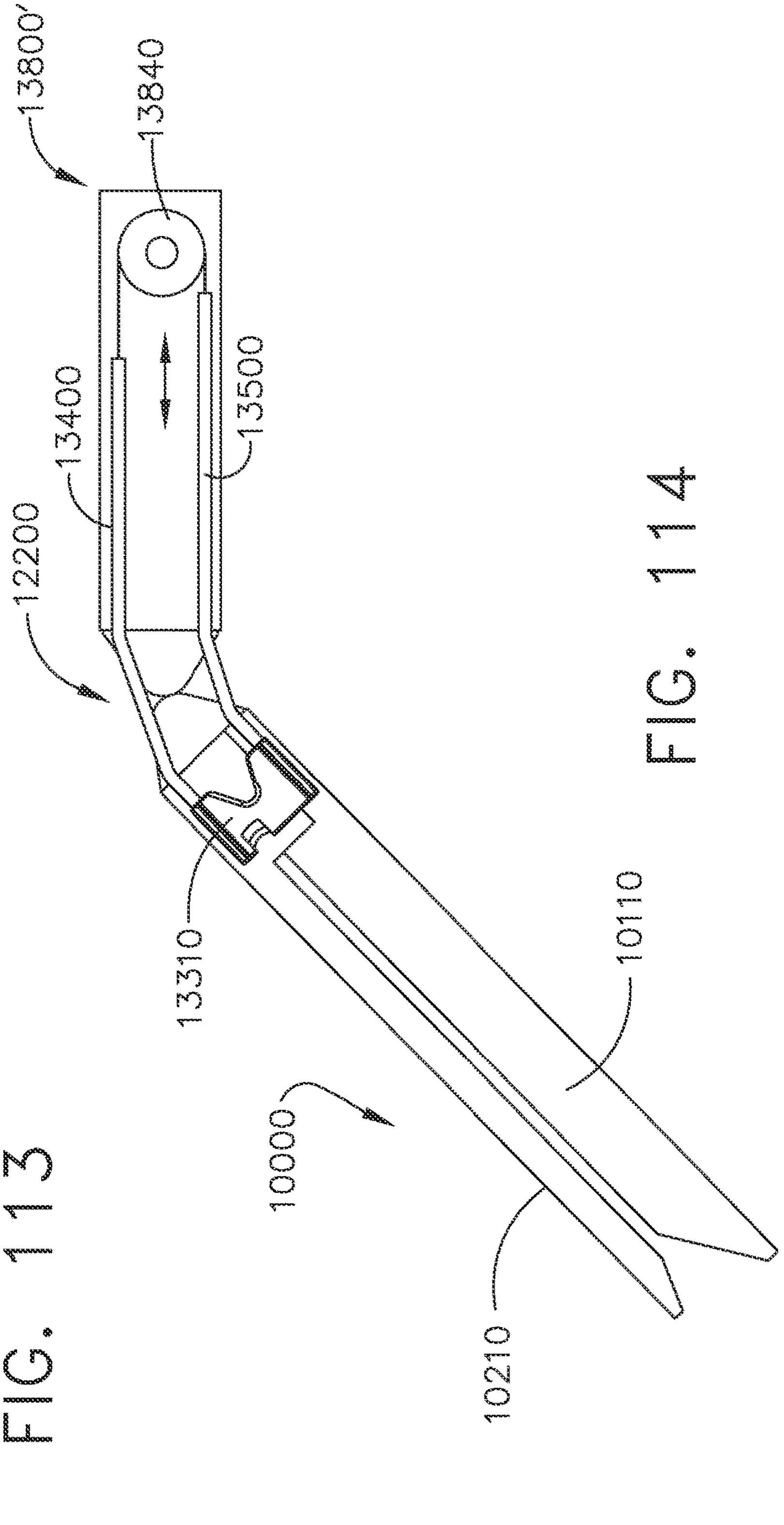
FIG. 114 is another partial side view of the surgical instrument and cable tensioning system of FIG. 113 with the surgical end effector in an articulated orientation.

Another cable management system 13800' is illustrated in FIGS. 113 and 114. In this arrangement, the proximal ends of the flexible chain drive assemblies 13400, 13500 are coupled together and journaled around a cable management pulley 13840 that is configured to translate with the firing member 13310. When the firing member 13310 is distally advanced during the firing stroke, the cable management pulley 13840 also translates distally maintaining tension in the flexible chain drive assemblies 13400, 13500. During articulation, a length of one of the flexible chain drive assemblies 13400, 13500 would increase, while the other would decrease. Such arrangement serves to minimize the lengths of the flexible chain drive assemblies 13400, 13500 required to fully actuate and articulate the surgical end effector 10000.

One method of using the surgical instrument 9010 may involve the use of the surgical instrument to cut and staple target tissue within a patient using laparoscopic techniques. For example, one or more trocars may have been placed through the abdominal wall of a patient to provide access to a target tissue within the patient. The surgical end effector 10000 may be inserted through one trocar and one or more cameras or other surgical instruments may be inserted through the other trocar(s). To enable the surgical end effector 10000 to pass through the trocar cannula, the surgical end effector 10000 is positioned in an unarticulated orientation (FIG. 63) and the jaws 10100 and 10200 must be closed. To retain the jaws 10100 in the closed position for insertion purposes, for example, the cable control system 9030 is actuated to pull the first cable 12510 and the fourth cable 12540 simultaneously which causes the pulley unit 12610 to rotate and cause the closure cams 10626, 10636 to contact the anvil closure arms 10234 to pivot the anvil 10210 into the closed position. See FIG. 97. The cable control system 9030 is deactivated to retain the anvil 10210 in the closed position. Once the surgical end effector 10000 has passed into the abdomen through the trocar, the cable control system 9030 is activated to rotate the pulley unit 12610 in an opposite direction to the position shown in FIG. 96 to permit the anvil 10210 to be biased open by the anvil springs 10240.

Once inside the abdomen and before engaging the target tissue, the surgeon may need to articulate the surgical end effector 10000 into an advantageous position. The cable control system 9030 may then be actuated to articulate the surgical end effector 10000 in one or more planes relative to a portion of the elongate shaft assembly 12000 that is received within the cannula of the trocar. Once the surgeon has oriented the surgical end effector 10000 in a desirable position, the cable control system 9030 is deactivated to retain the surgical end effector 10000 in the articulated orientation. Thereafter, the surgeon may activate the cable control system 9030 in the above-described manner to cause the anvil 10210 to rapidly close to grasp the tissue between the anvil 10210 and the surgical staple cartridge 10300. This process may be repeated as necessary until the target tissue has be properly positioned between the anvil 10210 and the surgical staple cartridge 10300.

Once the target tissue has been positioned between the anvil 10210 and the surgical staple cartridge 10300, the surgeon may activate the cable control system 9030 to close the anvil 10210 to clamp the target tissue in position. Thereafter, the firing process may be commenced by activating the rotary drive system 13600 to drive the firing member 13310 distally from the starting position. As the firing member 13310 moves distally, the firing member 13310 contacts a sled that is supported in the surgical staple cartridge 10300 and also drives the sled distally through the staple cartridge body. The sled serially drives rows of drivers supported in the staple cartridge toward the clamped target tissue. Each driver has supported thereon one or more surgical staples or fasteners which are then driven through the target tissue and into forming contact with the underside of the anvil 10210. As the firing member 13310 moves distally, the tissue cutting edge 13318 thereon cuts through the stapled tissue.

After the firing member 13310 has been driven distally to the ending position within the surgical end effector 10000, the rotary drive system 13600 is reversed which causes the firing member 13310 to retract proximally back to the starting position. Once the firing member 13310 has returned to the starting position, the cable control system 9030 may be activated to rotate the pulley unit 12610 back to an open position wherein the anvil springs 10240 can pivot the anvil 10210 to the open position to enable the surgeon to release the stapled tissue from the surgical end effector 10000. Once the stapled tissue has been released, the surgical end effector 10000 may be withdrawn out of the patient through the trocar cannula. To do so, the surgeon must first actuate the cable control system 9030 to return the surgical end effector 10000 to an unarticulated position and actuate the cable control system 9030 to pivot the anvil 10210 to the closed position. Thereafter, the surgical end effector 10000 may be withdrawn through the trocar cannula.

In previous endocutter arrangements, the firing member is pushed by a flexible beam. In such arrangements, the articulation joint must redirect the linear motion of the flexible beam as it enters the articulation joint back to that linear motion as it exits the articulation joint and enters the end effector. Because of the high loads required to push the flexible beam and the firing member, the flexible beam commonly experiences high amounts of friction as it exits the articulation joint and is linearly redirected into the end effector. This added amount of friction increases the amount of driving forces that are required to drive the firing member from the starting to ending position within the end effector while the end effector is articulated. Further, as the flexible beam traverses the articulation joint, it may apply de-articulation motions to the articulation joint components. Thus, the articulation joint components must be sufficiently robust so as to resist such de-articulation motions.

Other forms of surgical endocutters employ rotary forces to drive the firing member through the end effector. Such arrangements commonly employ a rotary drive screw that is housed within the channel that supports the staple cartridge. During use, the sled and tissue place large moments on the firing member which decrease the efficiency of the system and ultimately require higher rotary forces to actuate the firing member. It is difficult to move the rotary drive screw closer to the center of such forces because of the cartridge and the location of the tissue. It is also difficult to package a screw on top and bottom of the firing member without increasing the overall diameter of the surgical end effector. The various embodiments discussed above may address many if not all of these issues and challenges.

FIGS. 115-139 illustrate another form of surgical instrument 25010 that may address many of the challenges facing surgical instruments that comprise end effectors that are articulatable to large articulation angles and that are configured to cut and fasten tissue. In various embodiments, the surgical instrument 25010 may comprise a handheld device. In other embodiments, the surgical instrument 25010 may comprises an automated system sometimes referred to as a robotically-controlled system, for example. In various forms, the surgical instrument 25010 comprises a surgical end effector 26000 that is operably coupled to an elongate shaft assembly 28000. The elongate shaft assembly 28000 may be operable attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 119:
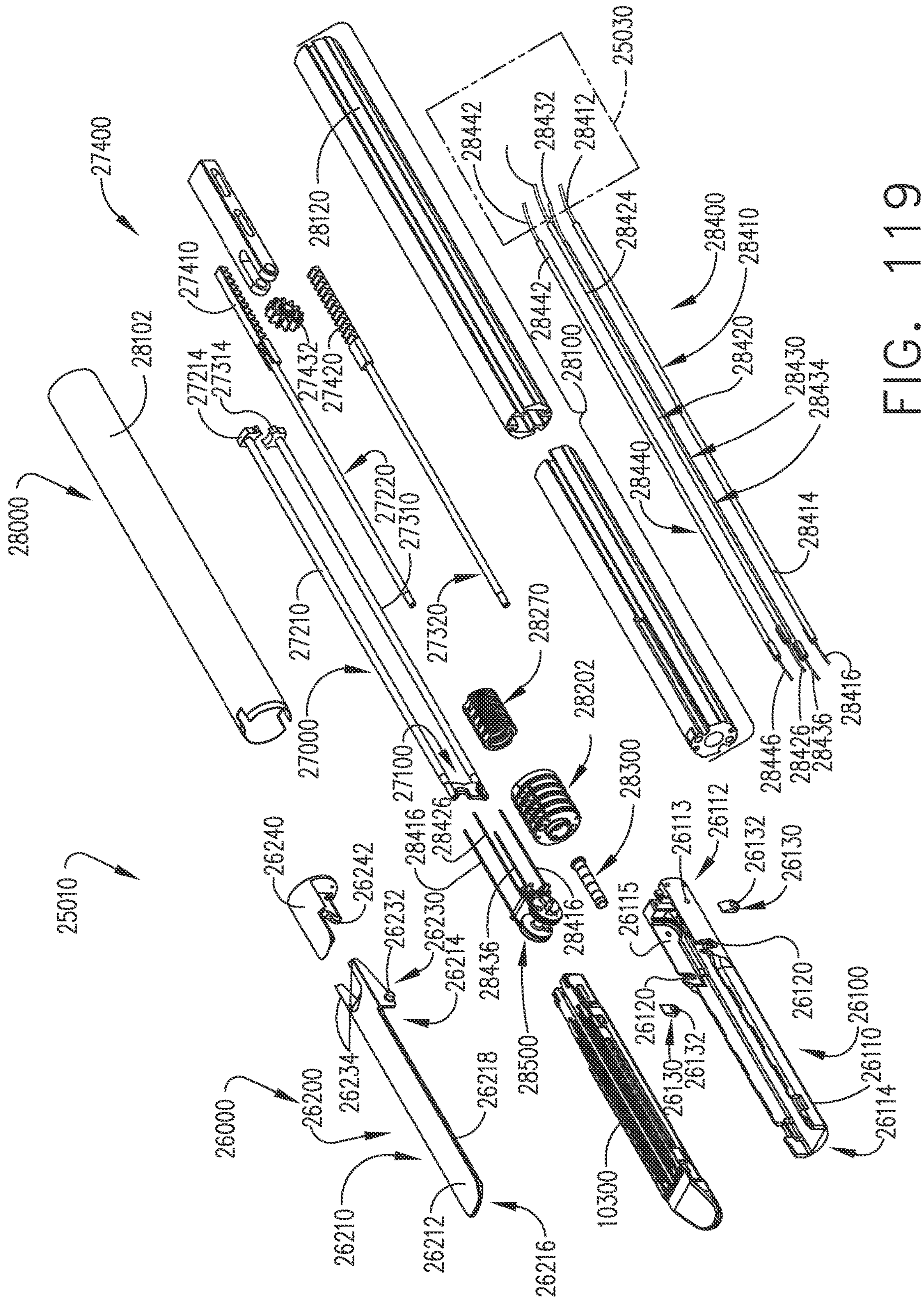

In one form, the surgical end effector 26000 comprises a first jaw 26100 and a second jaw 26200. In the illustrated arrangement, the first jaw 26100 comprises an elongate channel 26110 that comprises a proximal end 26112 and a distal end 26114 and is configured to operably support a surgical staple cartridge 10300 therein. An example of a surgical staple cartridge 10300 was described in detail above. The second jaw 26200 comprises an anvil 26210 that comprises an elongate anvil body 26212 that has a proximal end 26214 and a distal end 26216. The anvil body 26212 comprises a staple-forming undersurface 26218 that faces the first jaw 26100 and may include a series of staple-forming pockets (not shown) that corresponds to each of the staples or fasteners in the surgical staple cartridge 10300. As can be seen in FIG. 119, the proximal end 26214 of the anvil body 26212 comprises an anvil mounting portion 26230 that comprises a pair of laterally extending mounting pins 26232 that are configured to be received in corresponding mounting inserts 26130 that are configured to be retainingly received within mounting cradles 26120 formed in a proximal end 26112 of the elongate channel 26110. The mounting pins 26232 are pivotally received within pivot holes 26132 in the mounting inserts 26130 and then the mounting inserts 26130 are inserted into their corresponding cradle 26120 and affixed to the elongate channel 26110 by welding, adhesive, snap fit, etc. Such arrangement facilitates pivotal travel of the anvil 26210 relative to the elongate channel 26110 about a fixed pivot axis PA. See FIG. 115. As stated above, as used in this context, the term "fixed" means that the pivot axis PA is non-translating or non-moving relative to the elongate channel 26110.

In the illustrated arrangement, the elongate shaft assembly 28000 defines a shaft axis SA and comprises a shaft spine assembly 28100 that is received in a hollow outer shaft tube 28102. See FIG. 119. The shaft spine assembly 28100 may operably interface with a housing of the control portion (e.g., handheld unit, robotic tool driver, etc.) of the surgical instrument 25010 and in one example, comprises a proximal spine segment 28120 and a distal spine segment 28140.

Figure 120:
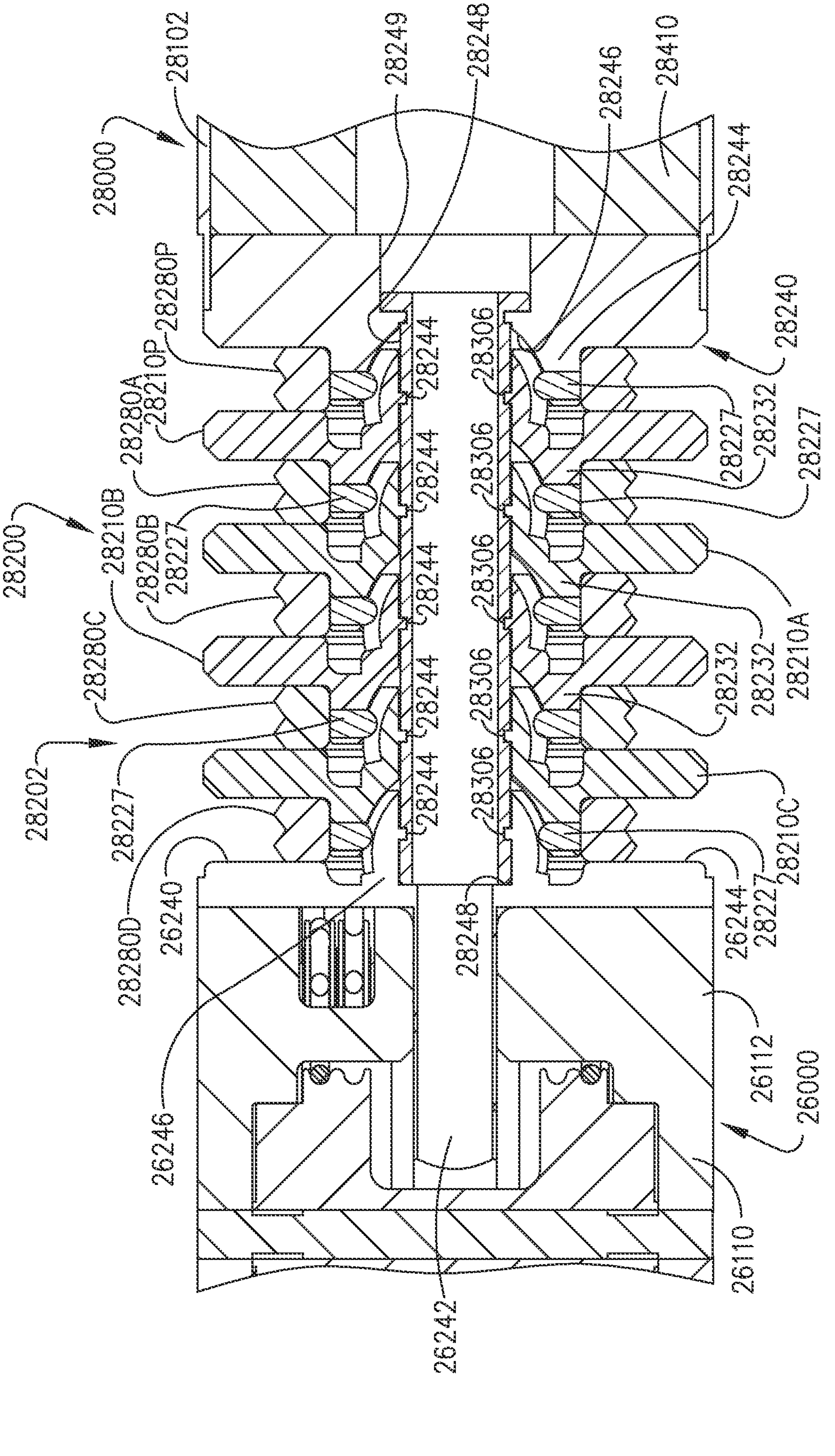
Figure 121:
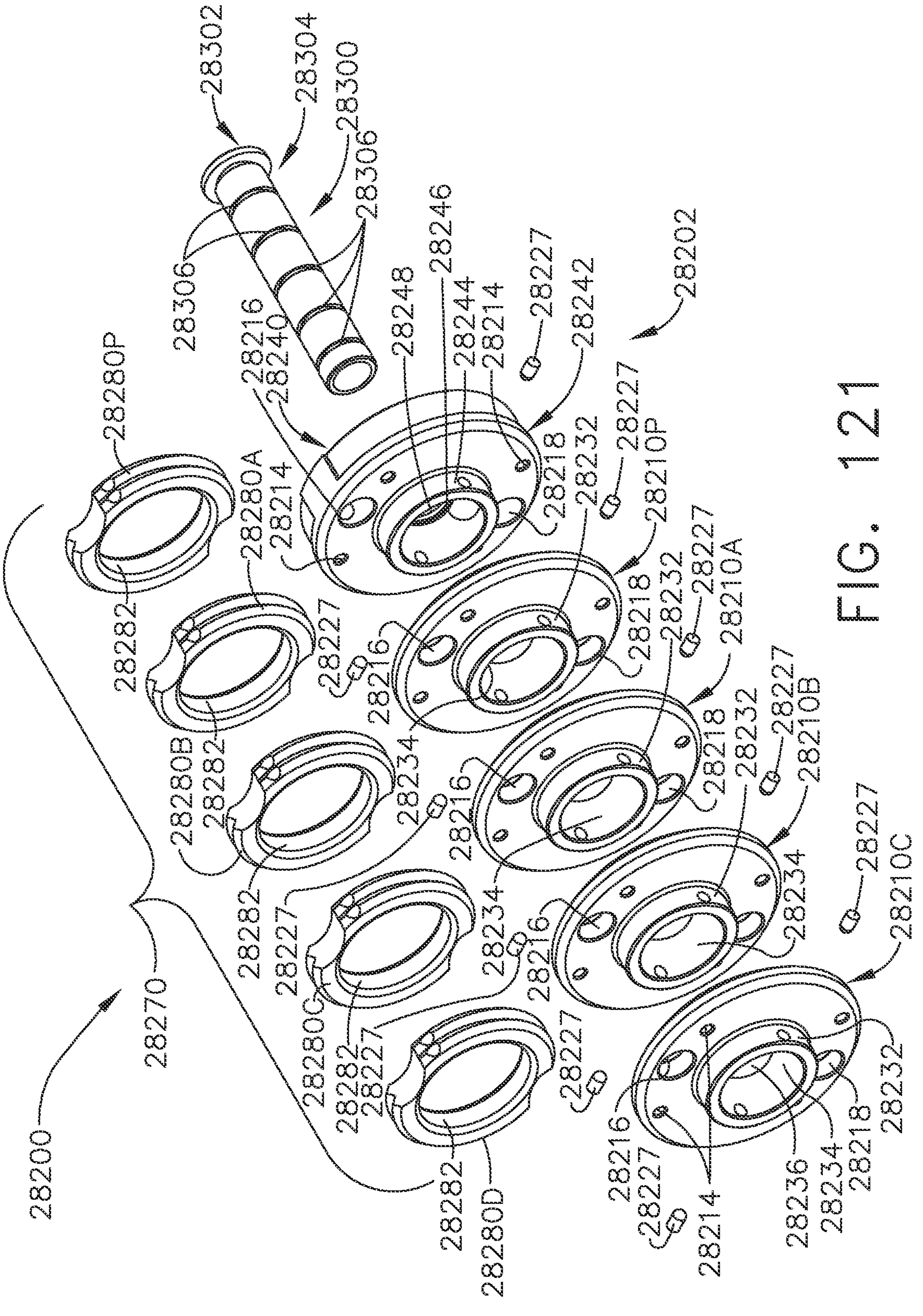
Figure 123:
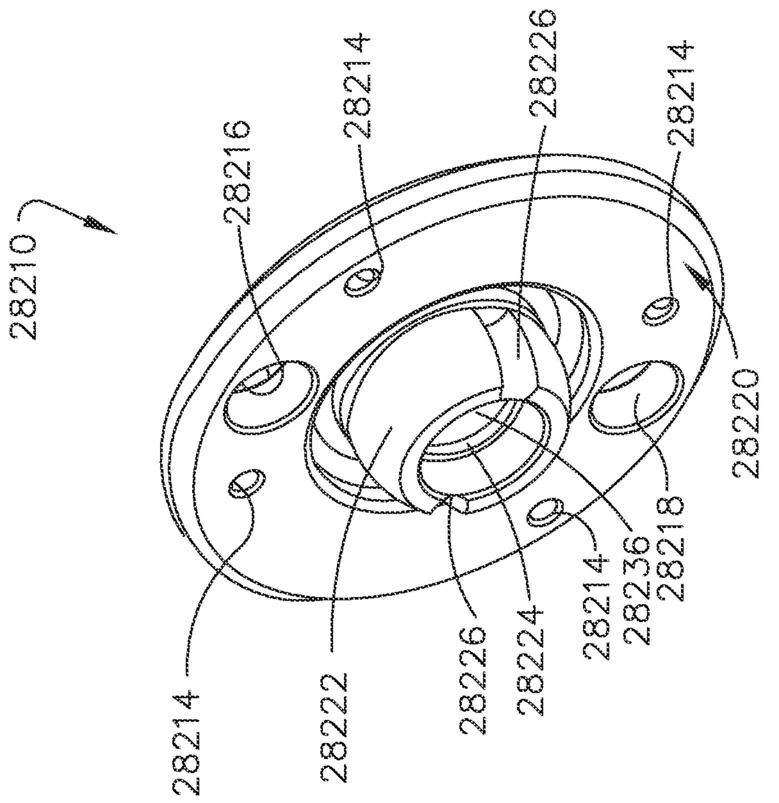
Figure 122:
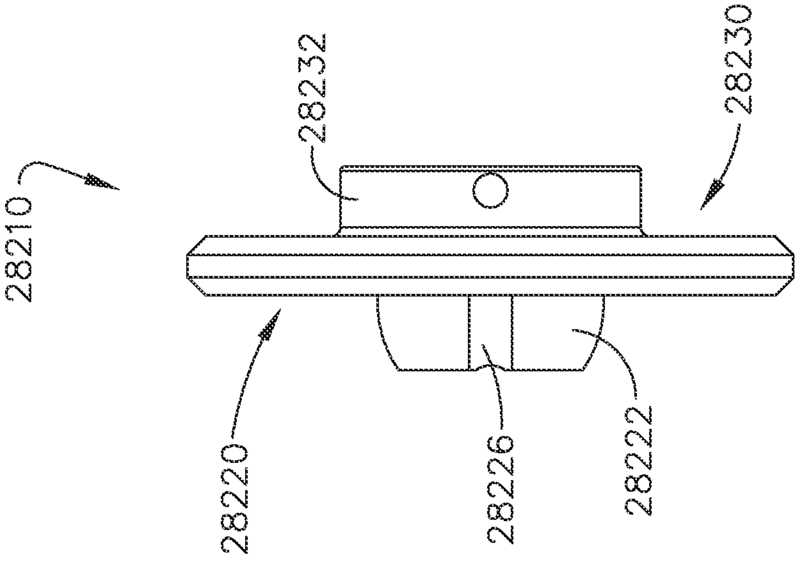
Figure 125:
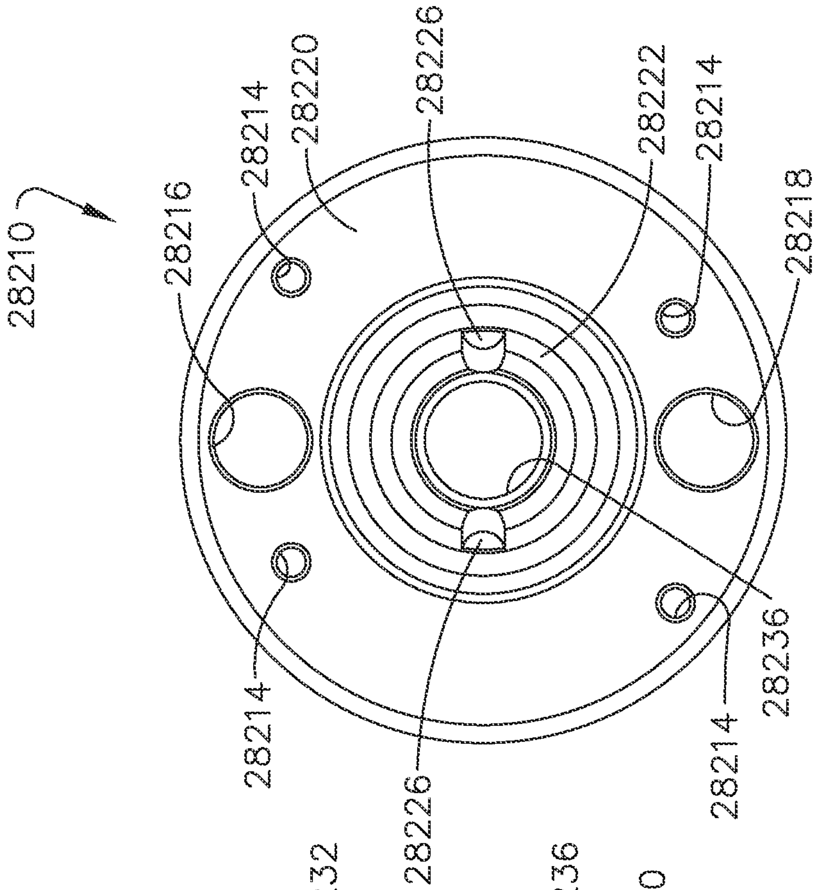
Figure 124:
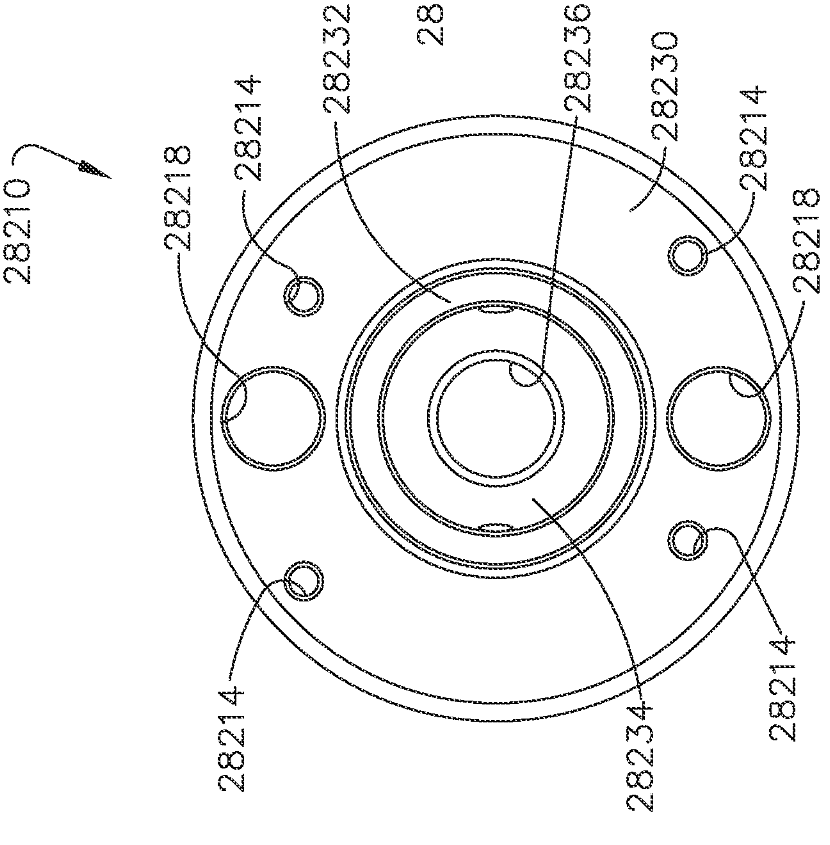

The elongate shaft assembly 28000 further comprises an articulation joint 28200 that may be attached to the distal spine segment 28140 as well as the surgical end effector 26000 to facilitate selective articulation of the surgical end effector 26000 relative to the elongate shaft assembly 28000 in multiple articulation planes. Turning now to FIGS. 120-125, the articulation joint 28200 comprises a series 28202 of movably interfacing annular disc members 28210. As can be seen in FIGS. 122, 123, and 125, each annular disc member 28210 comprises a "first" or proximal face 28220 that comprises a centrally-disposed spherical feature or protrusion 28222. Each annular disc member 28210 further comprises a second or distal face 28230 that comprises an annular hub portion 28232 that defines a concave socket 28234 therein. See FIGS. 122 and 124. Each annular disc member 28210 further has a central shaft passage 28236 therethrough. As can be seen in FIGS. 120 and 121, the articulation joint 28200 further comprises a proximal attachment disc assembly 28240 that is configured to be attached to a distal end of the distal spine segment 28140 by welding, adhesive, or other suitable fastener arrangement. The proximal attachment disc assembly 28240 comprises a distal face 28242 that includes an annular hub portion 28244 that defines a concave socket 28246 therein. The proximal attachment disc 28240 further has a central shaft passage 28248 therethrough. Also in the illustrated arrangement, the anvil mounting bracket 26240 is configured to operably interface with the articulation joint 28200. The anvil mounting bracket 26240 is attached to the proximal end 26112 of the elongate channel 26110 of the surgical end effector 26000 by welding, adhesive or other suitable fastener arrangements and comprises a proximal face 26244 that has a centrally-disposed spherical feature or protrusion 26246 protruding therefrom. See FIG. 120. The anvil mounting bracket 26240 further has a central shaft passage 26248 therethrough.

In at least one embodiment, the articulation joint further comprises a series 28270 of elastomeric annular spacer members 28280 that serve to space and provide elastic support between each annular disc member 28210. The elastomeric annular spacer members 28280 define a spacer opening 28282 such that each elastomeric spacer member 28280 may be journaled on an annular hub portion 28232 of a corresponding annular disc member 28210. Each annular disc member 28210 is journaled on a central elastomeric support or continuum shaft 28300 that is mounted to the proximal attachment disc assembly 28240 and the anvil mounting bracket 26240. In one arrangement, the central continuum shaft 28300 is fabricated from an elastomeric material (e.g., rubber, polymer, etc.) and comprises a flanged proximal end 28302 and a cylindrical body portion 28304. The cylindrical body portion 28304 comprises a series of annular grooves 28306 therein. Each annular groove 28306 corresponds to one of the annular disc members 28210. The annular disc members 28210 and annular spacer members 28280 are journaled on the central continuum shaft 28300 as shown in FIG. 120. The flanged proximal end 28302 of the central continuum shaft 28300 is supported in a proximal passage 28249 in the proximal attachment disc 28240. The cylindrical body portion 28304 of the central continuum shaft 28300 extends through the central passage 28236 in each of the annular disc members 28210 in the series 28202 of movably interfacing annular disc members 28210. Each centrally-disposed spherical feature or protrusion 28222 comprises an annular key member 28224 that is configured to be received in a corresponding annular groove 28306 in the central continuum shaft 28300. Such arrangement may serve to orient each annular disc member 28210 in a desired spacing orientation on the central continuum shaft 28300, for example.

Still referring to FIG. 120, a proximal-most elastomeric spacer member 28280P is journaled on the annular hub portion 28244 of the proximal attachment disc assembly 28240 such that it is positioned between a proximal-most annular disc member 28210P and the proximal attachment disc 28240. The annular key member 28224 of the proximal-most annular disc member 28210P is received within a corresponding annular groove 28306 in the central continuum shaft 28300 to position the centrally-disposed spherical feature or protrusion 28222 of the proximal-most annular disc member 28210P within the concave socket 28246 in the annular hub portion 28244 of the proximal attachment disc 28240. As can further be seen in FIG. 120, another elastomeric spacer member 28280A is journaled on the annular hub portion 28232 of the proximal-most annular disc member 28210P such that is positioned between the next annular disc member 28210A in the series 28202 of movably interfacing annular disc members 28202 and the proximal-most annular disc member 28210P. The annular key member 28224 of the annular disc member 28210A is received within a corresponding annular groove 28306 in the central continuum shaft 28300 to position the centrally-disposed spherical feature or protrusion 28222 of the annular disc member 28210A within the concave socket 28246 in the annular hub portion 28244 of the proximal attachment disc 28210P. Still referring to FIG. 120, another elastomeric spacer member 28280B is journaled on the annular hub portion 28232 of the annular disc member 28210A such that is positioned between the next annular disc member 28210B in the series 28202 of movably interfacing annular disc members 28210. The annular key member 28224 of the annular disc member 28210B is received within a corresponding annular groove 28306 in the central continuum shaft 28300 to position the centrally-disposed spherical feature or protrusion 28222 of the annular disc member 28210B within the concave socket 28246 in the annular hub portion 28244 of the annular disc member 28210A. Also in this arrangement, another elastomeric spacer member 28280C is journaled on the annular hub portion 28232 of the annular disc member 28210B such that is positioned between the distal-most annular disc member 28210C in the series of movably interfacing annular disc members 28202. The annular key member 28224 of the distal-most annular disc member 28210C is received within a corresponding annular groove 28306 in the central continuum shaft 28300 to position the centrally-disposed spherical feature or protrusion 28222 of the distal-most annular disc member 28210C within the concave socket 28246 in the annular hub portion 28244 of the annular disc member 28210B. Finally, another elastomeric spacer member 28280D is journaled on the annular hub portion 28232 of the distal-most annular disc member 28210C such that is positioned between the anvil mounting bracket 26240 and the distal-most annular disc member 28210C. The annular key member 28224 of the centrally-disposed spherical feature or protrusion 26246 of the anvil mounting bracket 26240 is received within a corresponding annular groove 28306 in the central continuum shaft 28300 to position the centrally-disposed spherical feature or protrusion 226246 of the anvil mounting bracket 26240 within the concave socket 28246 in the annular hub portion 28244 of the distal-most annular disc member 28210C.

In at least one arrangement, to limit pivotal travel of the annular disc members to a range of relative pivotal travel and prevent complete relative rotation of the annular disc members 28210 relative to each other, the centrally-disposed spherical feature or protrusion 28222 of each of the annular disc member 28210P, 28210A, 28210B, 28210C, as well as the distal spherical feature or protrusion 26246 of the anvil mounting bracket 26240, includes a pair of arcuate pin grooves 28226 therein. As can be seen in FIG. 120, a corresponding travel-limiting pin member 28227 is pressed into or otherwise attached to each annular hub portion 28232 and is received within the corresponding pin groove 28226 in the centrally-disposed spherical feature or protrusions 28222, 26246.

Returning to FIG. 119, in the illustrated example, the articulation joint 28200 may be operably controlled by an articulation system 28400 that comprises four cable assemblies 28410, 28420, 28430, and 28440 that extend through the elongate shaft assembly 28000. In one arrangement, the cable assembly 28410 comprises a proximal cable portion 28412 that is attached to an articulation rod 28414 that is supported in a corresponding axial groove in the shaft spine assembly 28100 for axial travel therein. A distal cable portion 28416 is attached to the articulation rod 28414. The cable assembly 28420 comprises a proximal cable portion 28422 that is attached to an articulation rod 28424 that is supported in a corresponding axial groove in the shaft spine assembly 28100 for axial travel therein. A distal cable portion 28426 is attached to the articulation rod 28414. The cable assembly 28430 comprises a proximal cable portion 28432 that is attached to an articulation rod 28434 that is supported in a corresponding axial groove in the shaft spine assembly 28100 for axial travel therein. A distal cable portion 28436 is attached to the articulation rod 28434. The cable assembly 28440 comprises a proximal cable portion 28442 that is attached to an articulation rod 28444 that is supported in a corresponding axial groove in the shaft spine assembly 28100 for axial travel therein. A distal cable portion 28446 is attached to the articulation rod 28444.

The proximal cable portions 28412, 28422, 28432, 28442 may operably interface with a portion of a cable control system 25030 that is supported within or is otherwise associated with a housing of the surgical instrument 25010. The cable control system 25030 may comprise a plurality of cable support members/capstans, pulleys, etc. that are controlled by one or more corresponding motors that are controlled by a control circuit portion of the surgical instrument 25010. In various embodiments, the cable control system 25030 is configured to manage the tensioning (pulling) and paying out of cables at precise times during the articulation process. In addition, in at least one arrangement, the cable control system 25030 may be employed to control the opening and closing of the anvil 26210 as will be discussed in further detail below.

Turning now to FIG. 126, the distal cable portions 28416, 28426, 28436, 28446 are configured to operably interface with a closure system 28500 that is rotatably mounted in the proximal end 26112 of the elongate channel 26110. As can be seen in FIG. 126, the closure system 28500 comprises a pulley unit 28510 that comprises a first lateral alpha wrap pulley 28520 and a second lateral alpha wrap pulley 28530 that are interconnected by a central shaft 28540. The pulley unit 28510 is rotatably supported within the proximal end 26112 of the elongate channel 26110 and retained therein by an anvil mounting bracket 26240 that is attached to the proximal end 26112 of the elongate channel 26112. See FIG. 119. The anvil mounting bracket 26240 may be attached to the proximal end 26112 of the elongate channel 26110 by welding, adhesive, snap features, etc. The anvil mounting bracket 26240 comprises a shaft cradle 26242 that is configured to rotatably support the central shaft 28540 within the elongate channel 26110. In the illustrated arrangement, a first pivot shaft 28521 protrudes from the first lateral alpha wrap pulley 28520 and is pivotally supported in a pivot hole 26113 in the proximal end of the elongate channel. Similarly, a second pivot shaft 28531 protrudes from the second lateral alpha wrap pulley 28530 and is pivotally supported in a pivot hole 26115 in the proximal end 26112 of the elongate channel 26110.

As can be seen in FIG. 126, the first alpha wrap pulley 28520 comprises a first circumferential groove 28522 and a second circumferential groove 28524. In the illustrated example, the first distal cable portion 28416 is received in the first circumferential groove 28522 and is attached thereto and the second distal cable portion 28426 is received in the second circumferential groove 28524 and is attached thereto. Pulling on the first distal cable portion 28416 will result in the rotation of the first lateral alpha wrap pulley 28520 in a first direction and pulling the second distal cable portion 28426 will result in the rotation of the first lateral alpha wrap pulley 28520 in a second opposite direction. Similarly, the second lateral alpha wrap pulley 28530 comprises a first circumferential groove 28532 and a second circumferential groove 28534. In the illustrated arrangement, the distal cable portion 28446 is received in the first circumferential groove 28532 and is attached thereto and the third distal cable portion 28436 is received in the second circumferential groove 28534 and is attached thereto. Pulling on the fourth distal cable portion 28446 will result in the rotation of the second alpha wrap pulley 28530 in the first direction and pulling the third distal cable portion 28436 will result in the rotation of the second lateral alpha wrap pulley 28530 in the second opposite direction. In accordance with one aspect, the lateral alpha wrap pulleys 28520, 28530 can rotate approximately three hundred thirty degrees. This range of rotational travel is in contrast to a normal pulley that may have a range of rotational travel that is less than one hundred eighty degrees of rotation.

Each of the first and second lateral alpha wrap pulleys 28520, 28530 also comprise a corresponding spiral closure cam that is configured to apply closure motions to the anvil 26210. As can be seen in FIG. 126, the first lateral alpha wrap pulley 28520 includes a first spiral closure cam 28526 and the second lateral alpha wrap pulley 28530 has a second spiral closure cam 28536 thereon. The spiral closure cams 28526, 28536 are configured to cammingly interact with corresponding anvil closure arms 26234 on the anvil mounting portion 26230 of the anvil 26210 to apply closure motions thereto. See FIG. 119. Rotation of the pulley unit 28510 in a first rotary direction will cause the spiral closure cams 28526, 28536 to cam the anvil 26210 to the closed position. To open the anvil 26210, the pulley unit 28510 is rotated in opposite direction to position the spiral closure cams 28526, 28536 in positions wherein the anvil 26210 can be pivoted open by an anvil spring (not shown).

Figure 127:
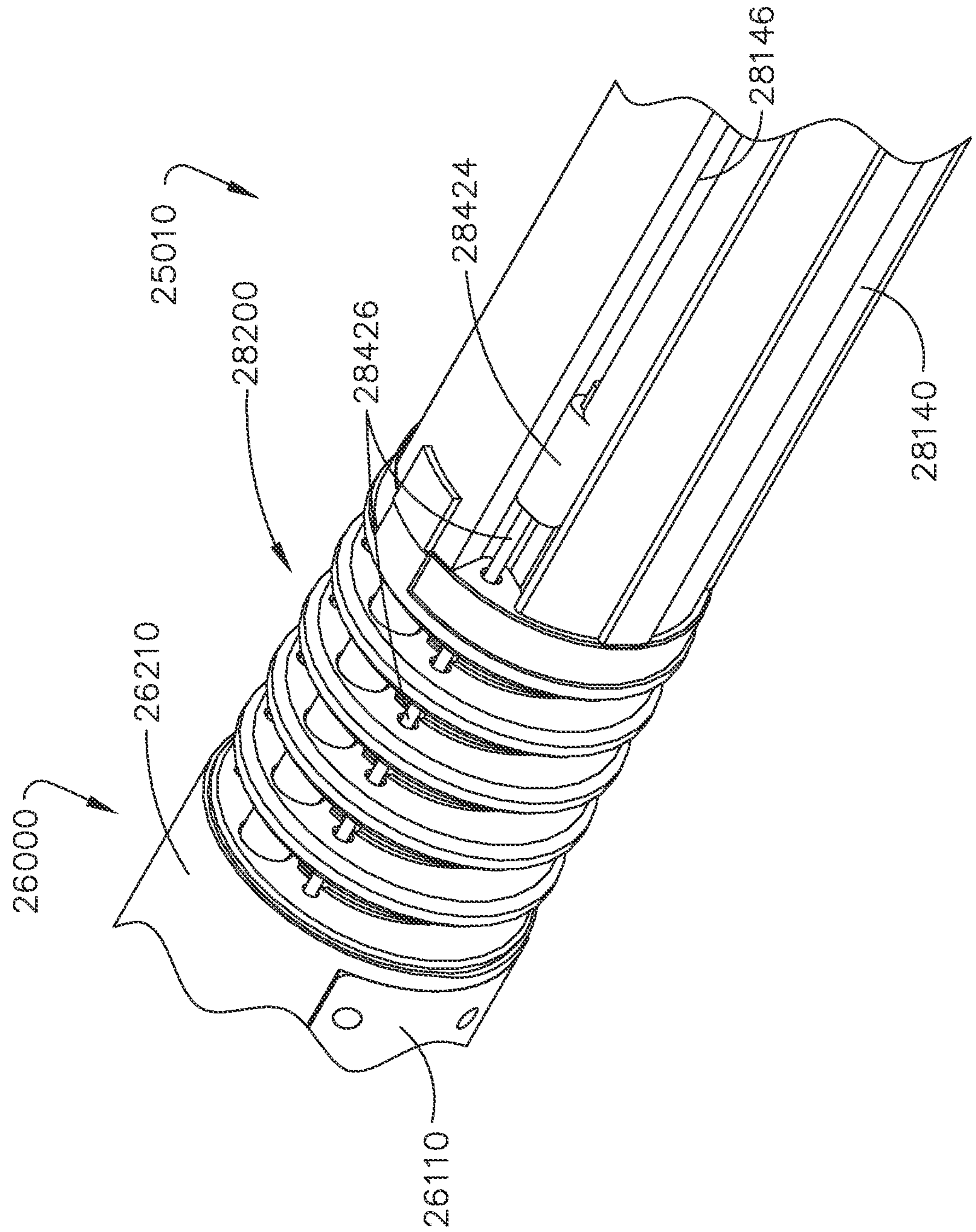
Figure 128:
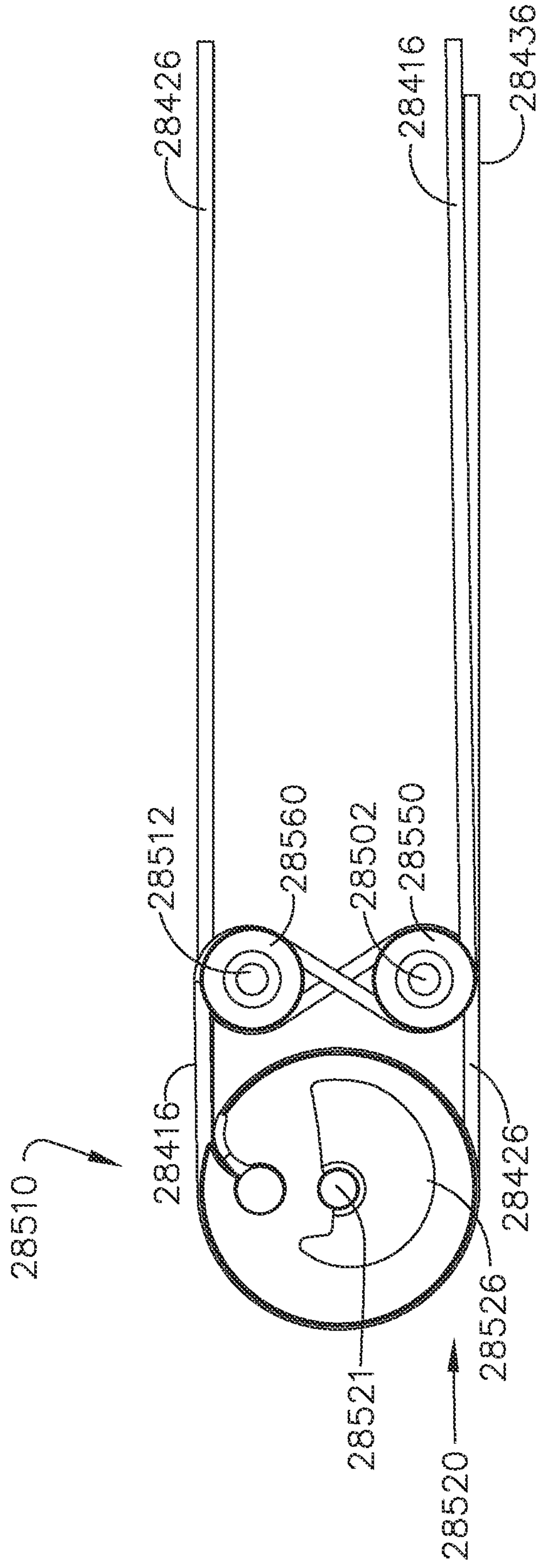
Figure 129:
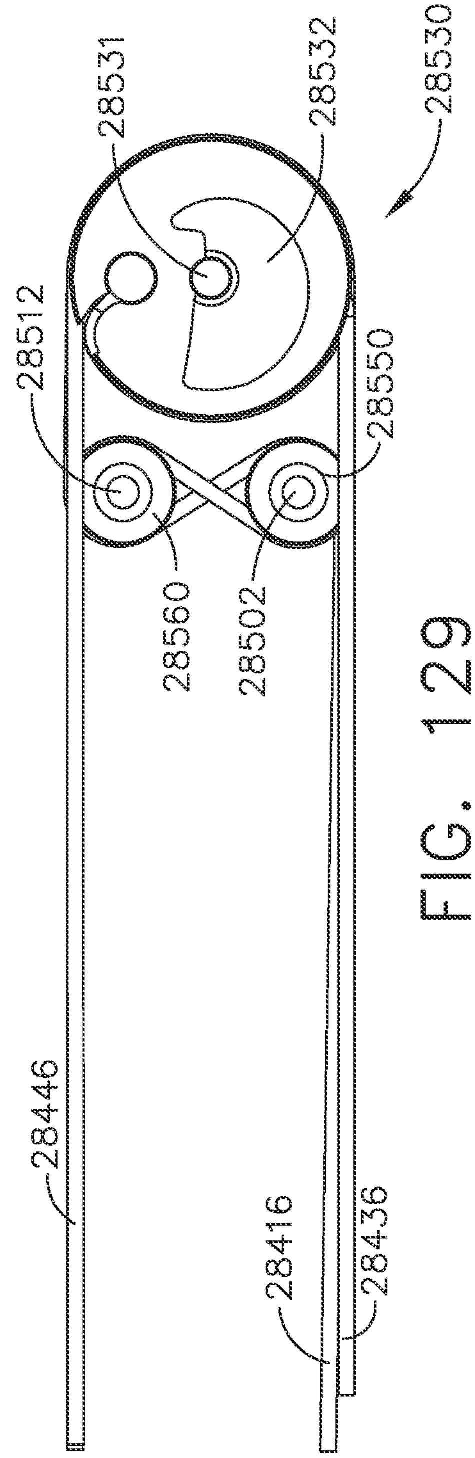
Figure 130:
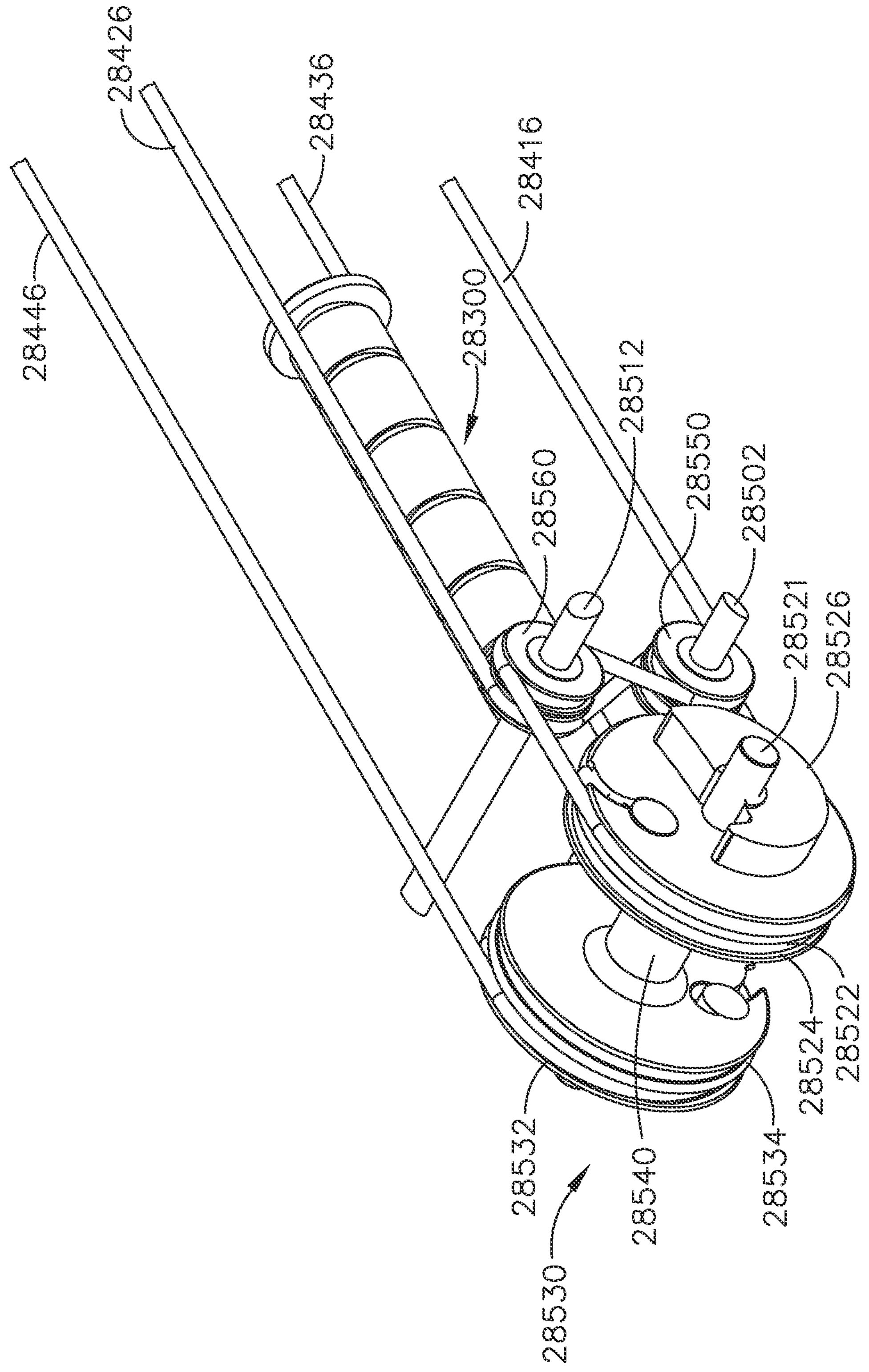

In the illustrated arrangement, the proximal attachment disc 28240, the proximal-most annular disc member 28210P, annular proximal disc members 28210A, 28210B, 28210C and anvil mounting bracket 26240 all include fourth articulation cable passages 28214 that are configured to permit each of the distal cable portions 28416, 28426, 28436, and 28446 to pass therethrough. FIG. 127 illustrates the articulation rod 28424 slidably supported in a corresponding axial groove 28146 in the distal spine segment 28140 for axial travel therein. Each of the other articulation rods 28414, 28434, 28444 is similarly supported in axial grooves in the distal spine segment 28140 as well as corresponding grooves in the proximal spine segment 28120.

Referring now to FIGS. 119 and 128-130, the distal cable portion 28416 extends from the articulation rod 28414 through the articulation joint 28200 and is looped around two redirect pulleys 28550, 28560 that are supported on shafts 28502, 28512 that are rotatably mounted in the proximal end 26112 of the elongate channel 26110. The distal cable portion 28416 exits the articulation joint 28200 to be received within the first circumferential groove 28522 in the first lateral alpha wrap pulley 28520 where it is secure therein. The distal cable portion 28426 extends from the articulation rod 28424 through the articulation joint 28200 to be looped around the redirect pulleys 28560, 28550 to be received within the second circumferential groove 28524 in the first lateral alpha wrap pulley 28520 where it is secure therein.

In the illustrated example, distal cable portion 28436 extends from the articulation rod 28434 through the articulation joint 28200 to be received within a corresponding circumferential groove 28534 in the second lateral alpha wrap pulley 28530 where it is secured therein. In addition, the distal cable portion 28446 extends from the articulation rod 28444 through the articulation joint 28200 to be received within a corresponding circumferential groove 28532 in the second lateral alpha wrap pulley 28530 where it is secure therein.

In at least one example, to articulate the surgical end effector 26000 relative to the elongate shaft assembly 28000 through a first articulation plane, the cable control system 25030 is actuated to pull on the distal cable portion 28426 and the distal cable portion 28446 simultaneously with a same amount of tension being applied to each distal cable portion 28426, 28446. Because the distal cable portions 28426, 28446 apply equal amounts of tension on both sides of the pulley unit 28510, the pulley unit 28510 does not rotate. However, the pulling action of the distal cable portions 28426, 28446 is translated through the articulation joint 28200 to the surgical end effector 26000 which results in the articulation of the articulation joint 28200 through a first articulation plane. To articulate the surgical end effector 26000 through a second plane of articulation that is transverse to the first plane of articulation, the cable control system 25030 is actuated to pull the distal cable portion 28436 and the distal cable portion 28446 simultaneously with a same amount of tension being applied to each distal cable portion 28436, 28446. Because the distal cable portions 28436, 28446 apply equal amounts of tension on both sides of the second lateral alpha wrap pulley 25830 of the pulley unit 28510, the pulley unit 28510 does not rotate. However, the pulling action of the distal cable portions 28436, 28446 is translated through the articulation joint 28200 to the surgical end effector 26000 which results in the articulation of the articulation joint 28200 in a second articulation plane.

The cable control system 25030 may also be used to control the opening and closing of the anvil 26210 in the following manner. As indicated above, when the spiral closure cams 28526 on the first lateral alpha wrap pulley 28520 and the second lateral alpha wrap pulley 28530 are in a first position, the anvil 26210 may be pivoted to an open position by an anvil spring or springs (not shown) that are positioned in the proximal end 26112 of the elongate channel 26110 and are position to contact the anvil mounting portion 26230 or anvil closure arms 26234 to pivot the anvil 26210 to the open position. To close the anvil 26210 from that position, the cable control system 25030 is actuated to pull the distal cable portion 28416 and the distal cable portion 28446 simultaneously with a same amount of tension being applied to each distal cable portion 28416 and 28446. These distal cable portions 28416, 28446 will cause the pulley unit 28510 to rotate causing the spiral closure cams 28526, 28536 to contact the anvil closure arms 26234 and cam the anvil 26210 to a closed position. It will be appreciated that by applying equal amounts of tension into the distal cable portions 28416, 28446, no moment is applied to the articulation joint 28200 because there are equal amounts of tension being applied on each side of the shaft axis SA. Such arrangement allows the jaw closure to be profiled as desired. This cable-control system 25030 may allow for a faster closure when the anvil 26210 is fully open. The cable-control system 25030 can also function as a lower speed/higher force generating closure mechanism for clamping onto tissue. The present cable controlled system 25030 may not produce the backlash that commonly occurs with other cable-controlled systems and thus can also be used to control the articulation position of the end effector. The above-described articulation joint 28200 and cable controlled system 25030 can facilitate multiple plane articulation while also supplying an additional actuation motion to the surgical end effector 26000.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 25010 employs a firing system 27000 that may address many if not all of such issues.

Referring now to FIGS. 133 and 134, in at least one embodiment, the firing system 27000 comprises a firing member 27100 that includes a vertically-extending firing member body 27112 that comprises a top firing member feature 27120 and a bottom firing member feature 27130. A tissue cutting blade 27114 is attached to or formed in the vertically-extending firing member body 27112. In at least one arrangement, the top firing member feature 27120 comprises a top tubular body 27122 that has a top axial passage 27124 extending therethrough. See FIG. 134. The bottom firing member feature 27130 comprises a bottom tubular body 27132 that has a bottom axial passage 27134 extending therethrough. In at least one arrangement, the top firing member feature 27120 and the bottom firing member feature 27130 are integrally formed with the vertically-extending firing member body 27112. In at least one example, the anvil body 26212 comprises an axially extending anvil slot that has a cross-sectional shape that resembles a "keyhole" to accommodate passage of the top firing member feature 27120 in the various manners discussed herein. Similarly, the elongate channel 26110 comprises an axially extending channel slot that also has a keyhole cross-sectional shape for accommodating passage of the bottom firing member feature 27130 as described above.

In the illustrated arrangement, the firing system 27000 comprises an upper firing assembly 27200 that operably interfaces with the top firing member feature 27120. The upper firing assembly 27200 includes an upper flexible outer tube or conduit 27210 that has a proximal end 27212 that is fixed to an upper insert 27214 that is non-movably attached to the shaft spine assembly 28100. For example, the upper insert 27214 may be welded to the shaft spine assembly 28100 or otherwise be attached thereto by adhesive or other appropriate fastening means. The flexible outer tube or conduit 27210 extends through upper passages 28216 provided through the proximal attachment disc assembly 28240, the proximal-most annular disc member 28210P, the annular disc members 28210A, 28210B, 28210C and the anvil mounting bracket 26240. A distal end 27216 of the flexible outer tube or conduit 27210 may be affixed to the anvil mounting bracket 26240.

In the illustrated embodiment, the upper firing assembly 27200 further includes an upper push rod 27220 that is slidably supported in a corresponding axial passage in the shaft spine assembly 28100. The upper firing assembly 27200 further comprises an upper push coil 27230 that is supported in an inner flexible upper sleeve 27240 which extends through the upper flexible outer tube or conduit 27210. A proximal end 27232 of the upper push coil 27230 and a proximal end 27242 of the inner flexible upper sleeve 27240 abut a distal end 27222 of the upper push rod 27220. The upper push coil 27230 is hollow and may comprise a coil spring that is fabricated from Nitinol, titanium, stainless steel, etc. In other arrangements, the upper push coil 27230 comprises a laser cut "hypotube" that essentially comprises a hollow tubular member with offset laser cuts therein which enable the hypotube to flex and bend while being capable of transmitting axial forces or motions. The inner flexible upper sleeve 27240 may be fabricated from a polymer or similar material and prevent tissue, fluid, and/or debris from infiltrating into the upper push coil 27230 which may hamper its ability to flex and bend during articulation of the surgical end effector relative to the elongate shaft assembly.

As can be seen in FIG. 134, a distal end 27234 of the upper push coil 27230 as well as a distal end 27244 of the inner flexible upper sleeve 27240 abut a proximal end 27123 of the top tubular body 27122 or the top firing member feature 27120. Also in the illustrated arrangement, the upper firing assembly further comprises an upper push coil cable 27250 that extends through the hollow upper push coil 27230. The upper push coil cable 27250 comprises an upper cable proximal end 27252 that is secured to the distal end 27222 of the upper push rod 27220 and an upper cable distal end 27254 that is secured within the top axial passage 27124 in the top tubular body 27122 of the top firing member feature 27120 by an upper attachment lug 27256. The upper push coil cable 27250 is held in tension between the top firing member feature 27120 an the upper push rod 27220 which serves to retain the distal end 27234 of the upper push coil 27230 as well as a distal end 27244 of the inner flexible upper sleeve 27240 in abutting contact with the proximal end 27123 of the top tubular body 27122 of the top firing member feature 27120 and the proximal end 27232 of the upper push coil 27230 and a proximal end 27242 of the inner flexible upper sleeve 27240 in abutting contact with the distal end 27222 of the upper push rod 27220.

In the illustrated example, the firing system 27000 further comprises a lower firing assembly 27300 that operably interfaces with the bottom firing member feature 27130. The lower firing assembly 27300 includes a lower flexible outer tube or conduit 27310 that has a proximal end 27312 that is fixed to a lower insert 27314 that is non-movably attached to the shaft spine assembly 28100. For example, the lower insert 27314 may be welded to the shaft spine assembly 28100 or otherwise be attached thereto by adhesive or other appropriate fastening means. The lower flexible outer tube or conduit 27310 extends through lower passages 28218 provided in each of the proximal attachment disc assembly 28240, the proximal-most annular disc member 28210P, annular disc members 28210A, 28210B, 28210C and anvil mounting bracket 26240. A distal end 27316 of the flexible outer tube or conduit 27310 is affixed to the anvil mounting bracket 26240.

In the illustrated embodiment, the lower firing assembly 27300 further includes a lower push rod 27320 that is slidably supported in a corresponding axial passage in the shaft spine assembly 28100. The lower firing assembly 27300 further comprises a lower push coil 27330 that is supported in an inner flexible lower sleeve 27340 which extends through the lower flexible outer tube or conduit 27310. A proximal end 27332 of the lower push coil 27330 and a proximal end 27342 of the inner flexible lower sleeve 27340 abut a distal end 27322 of the lower push rod 27320. The lower push coil 27330 is hollow and may comprise a coil spring that is fabricated from Nitinol, titanium, stainless steel, etc. In other arrangements, the lower push coil 27330 comprises a laser cut hypotube that essentially comprises a hollow tubular member with offset laser cuts therein which enable the hypotube to flex and bend. The inner flexible lower sleeve 27340 may be fabricated from a polymer or similar material and prevent tissue, fluid, and/or debris from infiltrating into the lower push coil 27330 which may hamper its ability to flex during articulation.

As can be seen in FIG. 134, a distal end 27334 of the lower push coil 27330 as well as a distal end 27344 of the inner flexible lower sleeve 27340 abut a proximal end 27133 of the bottom tubular body 27132 of the bottom firing member feature 27130. Also in the illustrated arrangement, the lower firing assembly 27300 further comprises a lower push coil cable 27350 that extends through the hollow lower push coil 27330. The lower push coil cable 27350 comprises a lower cable proximal end 27352 that is secured to the distal end 27322 of the lower push rod 27320 and a lower cable distal end 27354 that is secured within the bottom axial passage 27134 in the bottom tubular body 27132 of the bottom firing member feature 27130 by a lower attachment lug 27356. The lower push coil cable 27350 is held in tension between the bottom firing member feature 27130 an the lower push rod 27320 which serves to retain the distal end 27334 of the lower push coil 27330 as well as a distal end 27344 of the inner flexible lower sleeve 27340 in abutting contact with the proximal end 27133 of the bottom tubular body 27132 of the bottom firing member feature 27130 and the proximal end 27332 of the lower push coil

27330 and a proximal end 27342 of the inner flexible lower sleeve 27340 in abutting contact with the distal end 27322 of the lower push rod 27320.

In the illustrated arrangement, the firing system 27000 further comprises a differential drive assembly 27400 that is configured to axially drive the upper firing assembly 27200 and the lower firing assembly 27300. Turning to FIGS. 136-139, in at least one arrangement, a proximal end 27224 of the upper push rod 27220 is coupled to a first or upper gear rack 27410 of the differential drive assembly 27400. As can be seen in FIG. 136, the first or upper gear rack 27410 is slidably supported in an upper proximal axial cavity 28122 in the proximal spine segment 28120. Similarly, a proximal end 27324 of the lower push rod 27320 is coupled to a second or lower gear rack 27420 that is supported for axial travel within a lower proximal axial cavity 28124 in the proximal spine segment 28120. The differential drive assembly 27400 further comprises an axially movable carrier member 27430 that is centrally disposed between the first or upper gear rack 27410 and the second or lower gear rack 27420 and is supported for axial travel within a proximal axial cavity 28126 in the proximal spine segment 28120. See FIG. 136. Still referring to FIGS. 136-139, a pinion gear 27432 is pivotally pinned to the axially movable carrier member 27430 such that the pinion gear 27432 is meshing engagement with the first or upper gear rack 27410 and the second or lower gear rack 27420. The axially movable carrier member 27430 is driven axially within the proximal axial cavity 28126 in the proximal spine segment 28120 by a firing drive actuator 27440. See FIG. 137. In one arrangement, the firing drive actuator 27440 comprises a firing drive gear rack 27442 that drivingly interfaces with a drive gear 27444 that is driven by a firing motor 27446 that may be operably supported in or otherwise associated with the housing of the surgical instrument 25010. In other arrangements, the firing drive actuator 27440 may be axially driven distally and proximally by a cylinder arrangement or other suitable actuator interfacing therewith. As can be seen in FIGS. 137-139, the firing drive actuator 27440 may be attached to the axially movable carrier member 27430 by a pair of spaced coupler pins 27448 that are attached to the firing drive actuator 27440 and are received within corresponding axial slots 27434 in the axially movable carrier member 27430. Such arrangement permits some relative axial movement between the firing drive actuator 27440 and the axially movable carrier member 27430. For example, when the firing drive actuator 27440 is driven distally in the distal direction DD, the axially movable carrier member 27430 will not move distally until the coupler pins 27448 reach the distal ends of their corresponding axial slots 27434 at which point the axially movable carrier member 27430 will move distally. Likewise, the when the firing drive actuator 27440 is driven in the proximal direction PD, the axially movable carrier member 27430 will not move proximally until the coupler pins 27448 reach the proximal ends of their corresponding axial slots 27434 at which point the axially movable carrier member 27430 will move proximally.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The differential drive assembly 27400 described herein addresses and solves many, if not all of such challenges by employing two flexible outer tubes or conduits 27210, 27310 to constrain the paths of the flexible push coils 27230, 27330, respectively. As described herein, the upper flexible outer tube or conduit 27210 surrounds a portion of the upper push coil 27230 and the upper flexible outer tube or conduit 27310 surrounds a portion of the lower push coil 27330. Each of the outer tubes or conduits 27210, 27310 can bend but they also can resolve an axial tensile load. The ability to bend allows for the firing member force to be redirected through the articulated joint, and the ability to resolve tension allows for it to change the direction in which the push coil goes. When the push coil 27230, 27330 is put in compression, the flexible outer tube or conduit 27210, 27310 is put in tension. The outer tubes or conduits 27210, 27310 prevent the push coils 27230, 27330 from buckling. The outer tubes 27210, 27310 are terminated in a manner to resolve the tensile loads. As described above, the distal end 27216 of the flexible outer tube or conduit 27210 and the distal end 27316 of the flexible outer tube or conduit 27310 are both affixed to the anvil mounting bracket 26240. The proximal end 27212 of the flexible outer tube or conduit 27210 and the proximal end 27312 of the flexible outer tube or conduit 27310 are both affixed to the shaft spine assembly 28100. The pinion gear 27432 is in meshing engagement with the first or upper gear rack 27410 and the second or lower gear rack 27420 such that when one of the racks 27410, 27420 moves in one axial direction, the other rack 27410, 27420 axially moves in an opposite direction. As can be seen in FIGS. 138 and 139, during articulation, the pinion gear 27432 rotates so the flexible outer tubes or conduits 27210, 27310 can move to account for the change in path length. However, when the firing drive actuator 27440 is driven in the distal direction DD, the axially movable carrier member 27430 is actuated to push the push coils 27230, 27330 distally through the outer tubes or conduits 27210, 27310 to fire (i.e., drive the firing member 27100 distally) the tensile loads in the two flexible outer tubes or conduits 27210, 27310 react against one another without any motion of the pinion gear 27432.

In accordance with one general aspect, the upper passages 28216 form an upper pathway 28221 (FIG. 117) through the articulation joint 28200. Similarly, the lower passages 28218 form a lower pathway 28223 through the articulation joint 28200. When the surgical end effector 26000 is in an unarticulated position (i.e., the surgical end effector is axially aligned with the elongate shaft assembly 28000 on the shaft axis SA—FIGS. 115, 117, 118), the upper pathway 28221 and the lower pathway 28223 are parallel to each other. See FIG. 117. When the surgical end effector 26000 is in an articulated position relative to the elongate shaft assembly 28000, the upper pathway 28221 and the lower pathway 28223 are concentric to each other. See FIG. 116.

When the surgical end effector 26000 is in the unarticulated position, the firing system 27000 may be actuated to drive the firing member 27100 from a starting position within the proximal end 26112 of the elongate channel 26100 to an ending position within the distal end 26114 of the elongate channel 26110. When the surgical end effector 26000 is in the unarticulated position, and the firing system 27000 is actuated, the differential drive assembly 27400 drives the upper firing assembly 27200 and the lower firing assembly 27300 equal axial distances in a same axial direction (i.e., the distal direction DD) to apply an upper axial drive motion and a lower axial drive motion to the firing member 27100. The upper axial drive motion and the lower axial drive motion are substantially equal in magnitude which serves to distally advance the firing member 27100 through the surgical end effector 26000 without binding which might otherwise occur should the upper axial drive motion and the lower axial drive motions be different in magnitude. Similarly, when the surgical end effector 26000 is in an articulated position relative to the elongate shaft assembly 28000, the firing system 27000 may be actuated to drive the firing member 27100 from the starting position to the ending position. In such instances, the differential drive assembly 27400 is configured to permit the upper firing assembly 27200 and the lower firing assembly 27300 to move in substantially equal distances in opposite axial directions to accommodate the articulated position. The differential drive assembly 27400 may then apply an upper axial drive motion and a lower axial drive motion that are equal to each other to the firing member 27100. For example, depending upon the articulated position of the surgical end effector 26000 relative to the elongate shaft assembly 28000, the upper firing assembly 27200, upon articulation of the surgical end effector 26000, may be moved proximally a first distance and the lower firing assembly 27300 may be positioned relative thereto distally a second distance that is substantially equal to the first distance by the pinion gear 27432. Thereafter, distal actuation of the firing drive actuator 27440 will cause the upper firing assembly 27200 and the lower firing assembly 27300 to apply an upper axial drive motion and a lower axial drive motion that are equal to each other to the firing member 27100. As used herein, when the carrier is moved distally, the carrier may apply "axial control motions" to the upper firing assembly 27200 and the lower firing assembly 27300. Thus, when the surgical end effector 26000 is in an unarticulated configuration, the carrier may apply equal amounts of axial control motions to the upper firing member 27200 and the lower firing member 27300 in the same axial direction (distal direction DD) and when the surgical end effector 26000 is in an articulated configuration, the carrier may apply "other equal amounts" of axial control motions to the upper firing member 27200 and the lower firing member 27300 in the same axial direction (distal direction DD) to move the firing member 27100 from the starting position to the ending position.

FIGS. 140-152 illustrate another surgical instrument 30010 that employs another form of articulation joint 30200 for coupling a surgical end effector 31000 to an elongate shaft assembly 32000. The elongate shaft assembly 32000 may be identical or very similar to various other elongate shaft assemblies described herein. As can be seen in FIGS. 140-143, the articulation joint 30200 comprises a proximal joint member 30210 and a distal joint member 30250. The proximal joint member 30210 is configured to be attached to a distal end of the elongate shaft assembly 32000 that is coupled to a housing or other portion of a surgical instrument. The distal joint member 30250 is configured to be attached to the surgical end effector 31000. For example, the distal joint member 30250 may be attached to the elongate channel 31200 of the surgical end effector 31000. The end effector 31000 may be identical or very similar to various surgical end effectors disclosed herein.

As can be seen in FIGS. 143 and 150, the proximal joint member 30210 comprises a proximal face 30212 that defines a proximal apex 30218. Similarly, the distal joint member 30250 comprises a distal face 30252 that defines a distal apex 30254. See FIG. 151. The proximal joint member 30210 and the distal joint member 30250 are pivotally retained together with their respective apex portions 30218, 30254 in "rolling inter-engagement" by a linkage assembly 30300. As can be seen in FIGS. 141-143, the linkage assembly 30300 comprises a first link 30310 and a second link 30320. In the illustrated example, the first link 30310 and the second link 30320 are coupled to the proximal joint member 30210 by a proximal cross pin assembly 30330. In accordance with one aspect, the proximal cross pin assembly 30330 comprises a first proximal cross pin 30332 that defines a first proximal pivot axis FPPA. See FIG. 152. A proximal end 30312 of the first link 30310 is configured to receive a first proximal threaded fastener 30314 therethrough that is configured to be threadably received in a first threaded hole 30334 in the first proximal cross pin 30332. See FIG. 143. Likewise, a proximal end 30322 of the second link 30320 is configured to receive a second proximal threaded fastener 30324 therethrough that is configured to be threadably received in a second threaded hole 30336 in the first proximal cross pin 30332.

In at least one embodiment, the first proximal cross pin assembly 30330 further comprises a second proximal cross pin 30340 that is rotatably journaled on the first proximal cross pin 30332. In one arrangement, the first proximal cross pin 30332 may comprise a first proximal bushing or low friction sleeve 30338 that is configured to facilitate free rotation between the first proximal cross pin 30332 and the second proximal cross pin 30340. The second proximal cross pin 30340 defines a second proximal pivot axis SPPA that is transverse to the first proximal pivot axis FPPA and a shaft axis SA that is defined by the elongate shaft assembly 32000. As can be seen in FIG. 143, the second proximal cross pin 30340 is received within laterally aligned proximal pin openings 30220 in the proximal joint member 30210 to attach the linkage assembly 30300 to the proximal joint member 30210 such that the linkage assembly 30300 may pivot relative to the proximal joint member 30210 about the first proximal pivot axis FPPA and the second proximal pivot axis SPPA.

In the illustrated example, the first link 30310 and the second link 30320 are coupled to the distal joint member 30250 by a distal cross pin assembly 30350. In accordance with one aspect, the distal cross pin assembly 30350 comprises a first distal cross pin 30352 that defines a first distal pivot axis FDPA. A distal end 30316 of the first link 30310 is configured to receive a first distal threaded fastener 30318 therethrough that is configured to be threadably received in a third threaded hole 30354 in the first distal cross pin 30352. Likewise, a distal end 30326 of the second link 30320 is configured to receive a second distal threaded fastener 30328 therethrough that is configured to be threadably received in a fourth threaded hole 30356 in the first distal cross pin 30352.

In at least one embodiment, the first distal cross pin assembly 30350 further comprises a second distal cross pin 30360 that is rotatably journaled on the first distal cross pin 30352. In one arrangement, the first distal cross pin 30352 may comprise a first proximal bushing or low friction sleeve 30358 that is configured to facilitate free rotation between the first distal cross pin 30352 and the second distal cross pin 30360. The second distal cross pin 30360 defines a second distal pivot axis SDPA that is transverse to the first distal pivot axis FDPA and the shaft axis SA. As can be seen in FIG. 142, the second distal cross pin 30360 is received within laterally aligned distal pin openings 30256 in the distal joint member 30250 to attach the linkage assembly 30300 to the distal joint member 30250 such that the linkage assembly 30300 may pivot relative to the distal joint member 30250 about the first distal pivot axis FDPA and the second distal pivot axis SDPA.

Turning now to FIG. 150, the proximal face 30212 of the proximal joint member 30210 defines a proximal apex 30218 that comprises a plurality of radially-spaced recessed regions 30222 formed thereon. In the illustrated arrangement, six total recessed regions 30222 are equally spaced about a center 30219 of the proximal apex 30218. As can be seen in FIG. 151, the distal face 30252 of the distal joint member 30250 comprises a total of six distal fins or protuberances 30262 that are equally spaced about a center 30255 of the distal apex 30254 such that each fin 30262 is corresponds to one of the recessed regions 30222 when the surgical end effector is in an unarticulated position. For example, angle B may be approximately sixty degrees. See FIG. 151. Each of the fins 30262 and each of the recessed regions 30222 comprise rounded edges configured to facilitate rolling inter-engagement between the proximal apex 30218 and the distal apex 30254 during articulation of the surgical end effector 31000 relative to the elongate shaft assembly 32000. Such rolling inter-engagement may be somewhat similar to the rolling inter-engagement between the teeth of intermeshing bevel gears, for example such that the proximal apex 30218 and the distal apex 30254 remain in engagement with each other during articulation of the surgical end effector 31000.

Returning to FIG. 141, the surgical instrument 30010 also comprises an articulation system 30500 that is configured to apply articulation motions to the surgical end effector 31000 to articulate the surgical end effector 31000 relative to the elongate shaft assembly 32000. In at least one arrangement, the articulation system 30500 comprises four articulation cables 30510, 30520, 30530, and 30540 that extend through the elongate shaft assembly 32000. In the illustrated arrangement, the articulation cables 30510, 30520, 30530, and 30540 pass through the proximal joint member 30210 and the distal joint member 30250 and are secured to the surgical end effector 31000 in the various manners disclosed herein. The articulation cables 30510, 30520, 30530, and 30540 operably interface with an articulation control system that is supported in or otherwise associated with the housing of the surgical instrument 300010. For example, as was discussed above, a proximal portion of each cable 30510, 30520, 30530, and 30540 may be spooled on a corresponding rotary spool or cable-management system 2007 (FIG. 2) in the housing portion of the surgical instrument 30010 that is configured to payout and retract each cable 30510, 30520, 30530, and 30540 in desired manners. The spools/cable management system may be motor powered or manually powered (ratchet arrangement, etc.). FIGS. 140, 141, and 144-146 illustrate the position of the articulation joint 30200 when the surgical end effector is in an unarticulated position and FIGS. 142 and 147-149 illustrate various positions of the articulation joint 30200 when the surgical end effector has been articulated in various positions relative to the elongate shaft assembly 32000. The surgical instrument 30010 may also employ a firing system 30600 of the various types and constructions disclosed in detail herein to drive a firing member (not shown) within the surgical end effector 31000. For example, the proximal joint member 30210 may be provided with an upper proximal firing member passage 30214 that is configured to accommodate passage of an upper flexible firing assembly 30610 therethrough. The upper flexible firing assembly 30610 may span across an area generally designated as 30700 between the proximal face 30212 of the proximal joint member 30210 and the distal face 30252 of the distal joint member 30250 to and slidably pass through an upper distal firing member passage 30257 in the distal joint member 30250. Similarly, the proximal joint member 30210 is provided with a lower proximal firing member passage 30216 that is configured to accommodate passage of a lower flexible firing assembly 30620 member therethrough. The lower flexible firing assembly 30620 spans area 30700 and is received in a lower distal firing member passage 30259 in the distal joint member 30250. The upper flexible firing assembly 30610 and the lower flexible firing assembly 30620 operably interface with a firing member in the surgical end effector 31000. The upper flexible firing assembly 30610 and the lower flexible firing assembly 30620 may be identical or very similar in construction to the various flexible firing member drive arrangements disclosed herein.

FIG. 153 illustrates another form of articulation joint 30200' that is identical in construction and operation to articulation joint 30200 described above, except that the first link 30310 and the second link 30320 are connected together by an annular ring 30380 that is located in the area 30700 between the proximal face 30212 of the proximal joint member 30210 and the distal face 30252 of the distal joint member 30250. In at least one arrangement, the annular ring 30380 comprises an outer diameter which is equal to or less than an outer diameter of the proximal joint member 30210 and an outer diameter of the distal joint member 30250. In one arrangement, for example, the outer diameter of the distal joint member 30250 is equal to the outer diameter of the proximal joint member 30210 which is equal to or less than the maximum outer diameter of the elongate shaft assembly 32000. Thus, such arrangement permits the surgical instrument 30010 to be inserted into a patient through a trocar cannula that can accommodate the maximum outer diameter of the elongate shaft assembly 32000. The annular ring 30380 may be particularly advantageous as it may prevent tissue or a flexible exterior joint cover (not shown) from potentially getting caught between the joint components.

The articulation joints 30200, 30200' utilize an outer linkage assembly 30300 arrangement that connects the proximal cross pin assembly 30330 and the distal cross pin assembly 30350 together and resolve torsional and axial loads that are applied to the joint which may be particular important for resolving loads in the instrument during firing of the firing member. Such joint arrangement further leaves space between the proximal joint member and distal joint member to accommodate additional components/features. As can be seen in the various Figures, the proximal joint member and the distal joint member each are provided with clearance pockets/features/contours to accommodate the linkage assembly when the joint articulates.

FIGS. 154-156 illustrate another form of articulation joint 33000 that may be used to couple a surgical end effector of the various types disclosed herein to an elongate shaft assembly 34000 of a surgical instrument 33010. The elongate shaft assembly 34000 comprises a central spine member 34100 (FIG. 155) that may be coupled to or otherwise operably interfaces with a housing (not shown) of the surgical instrument 33010. The elongate shaft assembly 34000 further comprises an outer tube member 34110 that is extends over the central spine member 34100. In at least one form, the articulation joint 33000 comprises a proximal joint member 33100 that is attached to the central spine member 34100 and a distal joint member 33300 that is attached to a surgical end effector (not shown). For example, the distal joint member 33300 may be attached to an elongate channel of an endo-cutter arrangement in the various manners disclosed herein.

In the illustrated arrangement, the proximal joint member 33100 comprises a first or right half segment 33100A and a second or left half segment 33100B that are attached to a distal end of the central spine member 34100. The first half segment 33100A and the second half segment 33100B may be attached to the central spine member 34100 or other similar component of the elongate shaft assembly 34000 by welding, adhesive, mechanical fasteners, pins, etc. In accordance with one aspect, the surgical instrument 33010 comprises a firing system 35000 that comprises a distal differential drive assembly 35100 and a proximal differential drive assembly 35500.

As can be seen in FIG. 156, the proximal joint member 33100 operably supports the distal differential drive assembly 35100. In one arrangement, the distal differential drive assembly 35100 comprises an upper distal rack assembly 35110 that is supported for axial travel within the proximal joint member 33100. As can be seen in FIGS. 156, 157, and 158, the upper distal rack assembly 35110 is supported in meshing engagement with a distal differential gear 35130 that is rotatably supported on a pivot axle 35132 that is supported in the proximal joint member 33100. The upper distal rack assembly 35110 is supported for axial travel within the proximal joint member 33100. The distal differential drive assembly 35100 also comprises a lower distal rack assembly 35120 that is supported in meshing engagement with the distal differential gear 35130 and is configured to travel axially within the proximal joint member 33100.

In accordance with one aspect, the firing system 35000 further comprises an upper flexible firing assembly 35300 and a lower flexible firing assembly 35400 that are configured to operably interface with a firing member 35200. As can be seen in FIGS. 156 and 159, the firing member 35200 includes a vertically-extending firing member body 35212 that comprises a top firing member feature 35220 and a bottom firing member feature 35230. A tissue cutting blade 35214 is attached to or formed in the vertically-extending firing member body 35212. In at least one arrangement, the top firing member feature 35220 comprises a top finned portion 35222 that has a top axial passage 35224 extending therethrough. The bottom firing member feature 35230 comprises a bottom finned portion 35232 that has a bottom axial passage 35234 extending therethrough. In at least one arrangement, the top firing member feature 35220 and the bottom firing member feature 35230 are integrally formed with the vertically-extending firing member body 35212. In at least one example, the anvil body comprises an axially extending anvil slot that is configured to accommodate passage of the top firing member feature 35220 in the various manners discussed herein. Similarly, the elongate channel comprises an axially extending channel slot that is configured to accommodate passage of the bottom firing member feature 35230 as described herein.

In one example, the upper flexible firing assembly 35300 comprises an upper flexible tube or conduit 35310 that has a proximal end 35312 that is supported in a distal socket 3512 in the upper distal rack assembly 35110 and is secured thereto by welding, adhesive, etc. The upper flexible tube or conduit 35310 extends through an upper opening 33218 in the proximal joint member 33100 and spans across the articulation joint 33000. The upper flexible tube or conduit 35310 comprises a distal end 35314 that is received in an opening 33330 in the distal joint member 33300 and is terminated or secured therein by welding, adhesive, etc. The upper flexible firing assembly 35300 further comprises an upper push coil 35320. The upper push coil 35320 is hollow and may comprise a coil spring that is fabricated from Nitinol, titanium, stainless steel, etc. In other arrangements, the upper push coil 35320 comprises a laser cut hypotube that essentially comprises a hollow tubular member with offset laser cuts or spiral cuts therein which enable the hypotube to flex and bend. The upper push coil 35320 may additionally be received within an inner flexible upper sleeve 35330 that may be fabricated from a polymer or similar material and prevent tissue, fluid, and/or debris from infiltrating into the upper push coil 35320 which may hamper its ability to flex and bend during articulation.

The upper push coil 35320 extends through the upper flexible tube 35310 and through an axial passage in the upper distal rack 35110. An upper support beam 35140 is supported by the central spine member 34100 and has an upper passage 35142 to constrain and permit passage of the upper push coil 35320 therethrough. As can be seen in FIG. 159, a distal end 35322 of the upper push coil 35320 as well as a distal end 35332 of the inner flexible upper sleeve 35330 abut a proximal end 35223 of the top finned portion 35222 of the top firing member feature 35220. Also in the illustrated arrangement, the upper firing assembly 35300 further comprises an upper cable 35340 that extends through the hollow upper push coil 35320. The upper cable 35340 comprises an upper cable distal end 35342 that is secured within the top axial passage 35224 in the top finned portion 35222 of the top firing member feature 35220 by an upper attachment lug 35343.

Turning to FIGS. 156-161, the proximal differential drive assembly 35500 comprises an upper gear rack 35510 that is slidably supported within the central spine member 34100. The proximal differential drive assembly 35500 further comprises a lower proximal gear rack 35520 that is supported for axial travel within the central spine member 34100. The proximal differential drive assembly 35500 also comprises an axially movable carrier member 35530 that is centrally disposed between the upper proximal gear rack 35510 and the lower proximal gear rack 35520 and is supported for axial travel within the central spine member 34100. A proximal pinion gear 35532 is pivotally supported on a pin 35533 that is mounted to the axially movable carrier member 35530 such that the proximal pinion gear 35532 is meshing engagement with the upper proximal gear rack 35510 and the lower proximal gear rack 35520. The axially movable carrier member 35530 is driven axially within an axial cavity in the central spine member 34100 by a firing drive actuator 35540. As can be seen in FIG. 160, the firing drive actuator 35540 comprises a firing drive gear rack 35542 that drivingly interfaces with a drive gear 35544 that is driven by a firing motor 35546 that may be operably supported in the housing of the surgical instrument 33010. In other arrangements, the firing drive actuator 35540 may be axially driven distally and proximally by a cylinder arrangement or other suitable actuator interfacing therewith. As can be seen in FIGS. 156 and 160, the firing drive actuator 35540 may be attached to the axially movable carrier member 35530 by a pair of spaced coupler pins 35548.

In the illustrated arrangement, the upper proximal gear rack 35510 further comprises an upper cable attachment feature 35512 that protrudes therefrom and is configured to slide within the upper passage 35142 in the upper support beam 35140. In accordance with one aspect, the upper cable 35340 extends through the hollow upper push coil 35320 and a proximal end of the upper cable 35340 is secured to the upper cable attachment feature 35512. The upper cable 35340 is held in tension between the top firing member feature 35220 and the upper cable attachment feature 35512 which serves to retain the distal end 35322 of the upper push coil 35320 as well as a distal end 35332 of the inner flexible upper sleeve 35330 in abutting contact with the proximal end 35323 of the top finned portion 35222 of the top firing member feature 35220 and the proximal end of the upper push coil 35320 and a proximal end of the inner flexible upper sleeve 35330 in abutting contact with the distal end of the upper cable attachment feature 35512.

In one example, the lower flexible firing assembly 35400 comprises a lower flexible tube or conduit 35410 that has a proximal end 35412 that is supported in a distal socket 35122 in the lower distal rack 35120 and is secured thereto by welding, adhesive, etc. The lower flexible tube or conduit 35410 extends through a lower opening 33219 in the proximal joint member 33100 and spans across the articulation joint 33000. The lower flexible tube or conduit 35410 comprises a distal end 35414 that is received in an opening 33340 in the distal joint member 33300 and is terminated or secured therein by welding, adhesive, etc. The lower flexible firing assembly 35400 further comprises a lower push coil 35420. The lower push coil 35420 is hollow and may comprise a coil spring that is fabricated from Nitinol, titanium, stainless steel, etc. In other arrangements, the lower push coil 35420 comprises a laser cut hypotube that essentially comprises a hollow tubular member with offset laser cuts or spiral cuts therein which enable the hypotube to flex and bend. The lower push coil 35420 may additionally be received within an inner flexible lower sleeve 35430 may be fabricated from a polymer or similar material and prevent tissue, fluid, and/or debris from infiltrating into the lower push coil 35420 which may hamper its ability to flex and bend during articulation.

The lower push coil 35420 extends through the lower flexible tube 35410 and through an axial passage in the lower distal rack 35120. A lower support beam 35150 is supported by the central spine member 34100 and has a lower passage 35152 to constrain and permit passage of the lower push coil 35420 therethrough. As can be seen in FIG. 159, a distal end 35422 of the lower push coil 35420 as well as a distal end 35432 of the inner flexible lower sleeve 35430 abut a proximal end 35233 of the bottom finned portion 35232 of the bottom firing member feature 35230. Also in the illustrated arrangement, the lower flexible firing assembly 35400 further comprises a lower cable 35440 that extends through the hollow lower push coil 35420. The lower cable 35440 comprises a lower cable distal end 35442 that is secured within the bottom axial passage 35234 in the bottom finned portion 35232 of the bottom firing member feature 35230 by a lower attachment lug 35443. In accordance with one aspect, the lower cable 35440 extends through the hollow lower push coil 35420 and a distal end of the lower cable 35440 is secured to a lower cable attachment feature 35522 on the lower proximal gear rack 35520. The lower cable 35440 is held in tension between the bottom firing member feature 35230 and the lower cable attachment feature 35522 which serves to retain the distal end 35422 of the lower push coil 35420 as well as a distal end 35332 of the inner flexible upper sleeve 35330 in abutting contact with the proximal end 35233 of the bottom finned portion 35232 of the bottom firing member feature 35230 and the proximal end of the lower push coil 35420 and a proximal end of the inner flexible lower sleeve 35430 in abutting contact with the distal end of the lower cable attachment feature 35522.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The firing system 35000 described herein addresses and solves many, if not all of such challenges by employing two flexible tubes 35310, 35410 to constrain the paths of the push coils 35320, 35420, respectively. As described herein, the upper flexible tube 35310 surrounds the upper push coil 35320 and the lower flexible tube 35410 surrounds the lower push coil 35420. Each of the tubes 35310, 35410 can bend but they also can resolve an axial tensile load. See FIGS. 164 and 165. The ability to bend allows for the firing member force to be redirected through the articulated joint, and the ability to resolve tension allows for it to change the direction in which the push coil goes. When the push coil 35320, 35420 is put in compression, the flexible tube 35310, 35410 is put in tension. The tube 35310, 35410 prevents the push coil 35320, 35420 from buckling. To resolve the tensile loads the tubes 35310, 35410 need to be terminated in a manner to resolve the loads. In the illustrated example, the respective distal ends 35314, 35414 of the flexible tubes 35310, 35410, respectively are secured to the distal joint member 33300. The proximal ends 35312, 35412 of the flexible tubes 35310, 35410 are secured to the upper distal rack assembly 35110 and the lower distal rack 35120, respectively. The distal differential gear 35130 is in meshing engagement with each of the upper distal rack assembly 35110 and the lower distal rack 35120 such that when one of the rack assemblies 35110, 35120 moves in one axial direction, the other rack assembly 35110, 35120 would axially move in an opposite axial direction. As can be seen in FIGS. 163-165, during articulation, the distal differential gear 35130 rotates so the flexible tubes 35310, 35410 can move to account for the change in path length. However, when the firing drive system is actuated to push the push coils 35320, 35420 distally through the tubes 35310, 35410 to fire (i.e., drive the firing member distally) the tensile loads in the two flexible tubes 35310, 35410 react against one another without any motion of the distal differential gear 35130.

In accordance with one aspect, the upper flexible tube or conduit 35310 forms an upper pathway that spans the articulation joint 33000 and the lower flexible tube or conduit 35410 forms a lower pathway that spans the articulation joint 33000. The upper pathway supports the upper push coil 35320 for axial travel therethrough and the lower push coil 35420 for axial travel therethrough. When the surgical end effector to which the articulation joint 33000 is attached is in an unarticulated position (i.e., the surgical end effector is axially aligned articulated with the elongate shaft assembly along the shaft axis) the upper pathway and the lower pathway are parallel. Stated another way, when the surgical end effector is in an unarticulated position, an end effector axis is axially aligned with the shaft axis and the upper pathway and the lower pathway are parallel. When the surgical end effector is in an unarticulated position (i.e., the end effector axis is not axially aligned with the shaft axis), the upper pathway and the lower pathway are concentric to each other. When the surgical end effector is in the unarticulated position, the proximal differential drive assembly is configured to drive the upper push coil 35320 and the lower push coil 35420 equal distances in the same axial direction (distal direction DD) to apply an upper axial drive motion and a lower axial drive motion to the firing member. The upper axial drive motion and the lower axial drive motion are substantially equal in magnitude which serves to distally advance the firing member through the surgical end effector without binding which might otherwise occur should the upper axial drive motion and the lower axial drive motions be different in magnitude. Similarly, the when the surgical end effector is in an articulated position relative to the elongate shaft assembly, the proximal differential drive assembly is configured to permit the upper push coil 35320 and the lower push coil 35420 to move in substantially equal distances in opposite axial directions and thereafter apply an upper axial drive motion and a lower axial drive motion that are equal to each other to the firing member.

As can be seen in FIG. 156, the proximal joint member 33100 defines a proximal face 33200 that is configured to receive a spherical proximal end of 33410 of a central link member 33400. In the illustrated arrangement, the spherical proximal end 33410 is configured to be pivotally received in a proximal socket 33210 in the proximal face 33200 of the proximal joint member 33100. The spherical proximal end 33410 of the central link member 33400 is retained within the proximal socket 33210 by a proximal cross pin assembly 33500. In accordance with one aspect, the proximal cross pin assembly 33500 comprises a first proximal cross pin 33510 that defines a first proximal pivot axis FPPA. The first proximal cross pin 33510 is pivotally supported in a pair of attachment lugs 33220 formed on the proximal face 33200 of the proximal joint member 33100 and extends through two opposing arcuate slots 33412 to permit pivotal as well as rotational travel of the first proximal cross pin 33510 within the spherical proximal end 33410 of the central link member 33400. Stated another way, the spherical proximal end 33410 of the central link member 33400 is rotatable about the first proximal cross pin 33510 as well as pivotable through a proximal pivot angle PPA defined by the arcuate slots 33412.

The proximal cross pin assembly 33500 further comprises a second proximal cross pin 33520 that is rotatably journaled on the first proximal cross pin 33510 to permit relative pivotal rotation between the first proximal cross pin 33510 and the second proximal cross pin 33520. The second proximal cross pin 33520 is pivotally supported within the spherical proximal end 33410 of the central link member 33400 and defines a second proximal pivot axis SPPA. The first proximal pivot axis FPPA is transverse to the shaft axis SA. The second proximal pivot axis SPPA is transverse to the shaft axis SA as well as the first proximal pivot axis FPPA. The proximal cross pin assembly 33500 facilitates pivotal travel of the spherical proximal end 33410 of the central link member 33400 relative to the proximal joint member 33100 about the first proximal pivot axis FPPA as well as the second proximal pivot axis SPPA.

In the illustrated arrangement, the distal joint member 33100 defines a distal face 33310 that is configured to receive a spherical distal end 33420 of a central link member 33400. In the illustrated arrangement, the spherical distal end 33420 is configured to be pivotally received in a distal socket 33312 in the distal face 33310 of the distal joint member 33300. The spherical distal end 33420 of the central link member 33400 is retained within the distal socket 33312 by a distal cross pin assembly 33600. In accordance with one aspect, the distal cross pin assembly 33600 comprises a first distal cross pin 33610 that defines a first distal pivot axis FDPA. The first distal cross pin 33610 is pivotally supported in a pair of attachment lugs 33314 formed on the distal face 33312 of the distal joint member 33300 and extends through two opposing arcuate slots 33422 to permit pivotal as well as rotational travel of the first distal cross pin 33610 within the spherical distal end 33420 of the central link member 33400. Stated another way, the spherical distal end 33420 of the central link member 33400 is rotatable about the first distal cross pin 33610 as well as pivotable through a distal pivot angle DPA defined by the arcuate slots 33412.

The distal cross pin assembly 33600 further comprises a second distal cross pin 33620 that is rotatably journaled on the first distal cross pin 33610 to permit relative pivotal rotation between the first distal cross pin 33610 and the second distal cross pin 33620. The second distal cross pin 33620 is pivotally supported within the spherical distal end 33420 of the central link member 33400 and defines a second distal pivot axis SDPA. The first distal pivot axis FDPA is transverse to the shaft axis SA. The second distal pivot axis SDPA is transverse to the shaft axis SA as well as the first distal pivot axis FDPA. The distal cross pin assembly 33600 facilitates pivotal travel of the spherical distal end 33420 of the central link member 33400 relative to the distal joint member 33300 about the first distal pivot axis FDPA as well as the second distal pivot axis SDPA.

In accordance with at least one aspect, the articulation joint 33000 further comprises a flexible joint support assembly generally designated as 33700 which provides flexible support between the proximal joint member 33100 and the distal joint member 33200 during articulation as well as to assist the articulation joint 33000 in returning to an unarticulated position (FIGS. 155-158). In at least one arrangement, the flexible joint support assembly 33700 comprises a series of flexible members 33710, 33720, 33730, and 33740 that cross through a hollow central link portion 33430 that is attached to the spherical proximal end 33410 and the spherical distal end 33420 and extends therebetween. The flexible members 33710, 33720, 33730, and 33740 may comprise cables or spring members that are fabricated from, for example, spring steel, stainless steel, Nitinol, titanium, etc. More particularly and with reference to FIG. 166, a first flexible member 33710 comprises a central portion 33712 and a proximal end portion 33714 that is configured to be received in a corresponding attachment hole 33212 (FIG. 156) in the first or right half segment 33100A of the proximal joint member 33100 and attached or secured therein. The first flexible member 33710 further comprises a distal end portion 33716 that is configured to be received in a corresponding slotted hole 33320 in the distal joint member 33300 and be attached therein. In such arrangement, the central portion 33712 of the first flexible member 33710 extends diagonally through the hollow central link portion 33430. The second flexible member 33720 comprises a central portion 33722 and a proximal end portion 33724 that is configured to be received in a corresponding attachment hole 33214 (FIG. 156) in the second or left segment 33100B of the proximal joint member 33100 and be secured therein. The second flexible member 33720 further comprises a distal end portion 33726 that is configured to be received in a corresponding slotted hole 33322 in the distal joint member 33300 and be secured therein. In such arrangement, the central portion 33722 of the second flexible member 33720 extends diagonally through the hollow central link portion 33430. The third flexible member 33730 comprises a central portion 33732 and a proximal end portion (not shown) that is configured to be inserted into a corresponding attachment hole (not shown) in the first or right segment 33100A of the proximal joint member 33100 and be secured therein. The third flexible member 33730 further comprises a distal end portion 33736 that is configured to be received in a corresponding slotted hole 33324 in the distal joint member 33300 and be secured therein. In such arrangement, the central portion 33732 of the third flexible member 33730 extends diagonally through the hollow central link portion 33430. The fourth flexible member 33740 comprises a central portion 33742 and a proximal end portion 33744 that is configured to be inserted into a corresponding attachment hole 33216 in the second or left segment 33100B of the proximal joint member 33100 and be secured therein. The fourth flexible member 33740 further comprises a distal end portion 33746 that is configured to be received in a corresponding slotted hole 33326 in the distal joint member 33300 and be secured therein. In such arrangement, the central portion 33742 of the fourth flexible member 33740 extends diagonally through the hollow central link portion 33430.

The surgical instrument 33010 also comprises an articulation system 33800 that is configured to apply articulation motions to the surgical end effector to articulate the surgical end effector relative to the elongate shaft assembly 34000. In at least one arrangement, the articulation system 33800 comprises four articulation cables 33810, 33820, 33830, and 33840 that extend through the elongate shaft assembly 34000. In the illustrated arrangement, the articulation cables 33810, 33820, 33830, and 33840 pass through the proximal articulation joint member 33100 and the distal articulation joint member 33300 and are secured to the surgical end effector in the various manners disclosed herein. The articulation cables 33810, 33820, 33830, and 33840 operably interface with an articulation control system that is supported in or is otherwise associated with the housing of the surgical instrument 33010. For example, as was discussed above, a proximal portion of each cable 33810, 33820, 33830, and 33840 may be spooled on a corresponding rotary spool or cable-management system 2007 (FIG. 2) in the housing portion of the surgical instrument 330010 that is configured to payout and retract each cable 33810, 33820, 33830, and 33840 in desired manners. The spools/cable management system may be motor powered or manually powered (ratchet arrangement, etc.). FIGS. 154, 155, 157, 158, 162, and 167 illustrate the position of the articulation joint 33000 when the surgical end effector is in an unarticulated position and FIGS. 163 and 169 illustrate various positions of the articulation joint 33000 when the surgical end effector has been articulated in various positions relative to the elongate shaft assembly.

The articulation joint 33000 comprises a spherical pitch and yaw joint that is controlled by cables and is used for articulation of the surgical end effector. The articulation joint comprises a double spherical joint, meaning that it has a pair of joints that each can perform pitch and yaw. This arrangement creates redundancy in the joint as now there are two joints that can perform pitch and yaw. The flexible joint support assembly 33700 serves to constrain how each joint moves during articulation so that the four degrees of freedom act as two. The flexible joint support assembly 33700 ties the two spherical joints together such that if one rotates, the other one rotates the same amount. When a joint rotates it applies tension in the cable that forces the other joint to rotate as well. Such joint arrangement has a very compact form factor and very little backlash in the wrist design.

Example 1—A surgical instrument comprising an elongate shaft assembly that is coupled to a surgical end effector by an articulation joint that is configured to facilitate selective articulation of the surgical end effector relative to the elongate shaft assembly in multiple articulation planes. A firing member is supported for axial travel within the surgical end effector between a starting position and an ending position. A firing system is configured to selectively move the firing member between the starting position and the ending position. The firing system comprises an upper flexible firing assembly that comprises a flexible upper hollow member that has an upper proximal end and an upper distal end. The upper proximal end is supported within the elongate shaft assembly and the flexible upper hollow member spans the articulation joint and the upper distal end is fixed to the surgical end effector. The flexible firing assembly further comprises a flexible upper drive member that has an upper drive member proximal end that operably interfaces with a source of axial drive motions. The flexible upper drive member is slidably constrained in the flexible upper hollow member for axial movement therein. The flexible upper drive member spans the articulation joint and further comprises an upper drive member distal end that operably interfaces with an upper portion of the firing member to apply upper axial drive motions thereto to move the firing member from the starting position to the ending position. The firing system further comprises a lower flexible firing assembly that comprises a flexible lower hollow member that has a lower proximal end and a lower distal end. The lower proximal end is supported within the elongate shaft assembly and the flexible lower hollow member spans the articulation joint and the lower distal end is fixed to the surgical end effector. The lower flexible firing assembly further comprises a flexible lower drive member that has a lower drive member proximal end that operably interfaces with the source of axial drive motions. The flexible lower drive member is slidably constrained in the flexible lower hollow member for axial movement therein and spans the articulation joint and further comprises a lower drive member distal end that operably interfaces with a lower portion of the firing member to apply lower axial drive motions thereto to move the firing member from the starting position to the ending position.

Example 2—The surgical instrument of Example 1, wherein the flexible upper drive member comprises an upper hollow coiled member and the flexible lower drive member comprises a lower hollow coiled member.

Example 3—The surgical instrument of Examples 1 or 2, wherein the flexible upper hollow member forms an upper pathway that spans the articulation joint for slidably supporting the flexible upper drive member therethrough. The flexible lower hollow member forms a lower pathway that spans the articulation joint for slidably supporting the flexible lower drive member therethrough. The upper pathway and the lower pathway are parallel to each other when the surgical end effector is in an unarticulated position and the upper pathway and the lower pathway are concentric to each other when the surgical end effector is articulated relative to the elongate shaft assembly.

Example 4—The surgical instrument of Examples 1, 2 or 3, wherein the upper proximal end of the flexible upper hollow member and the lower proximal end of the flexible lower hollow member are coupled to a distal differential assembly that is operably supported by the elongate shaft assembly. The distal differential assembly is configured to enable the flexible upper hollow member and the flexible lower hollow member to move in opposite axial directions when the surgical end effector is articulated relative to the elongate shaft assembly.

Example 5—The surgical instrument of Example 4, wherein the distal differential assembly comprises an upper distal gear rack that is supported for axial travel in two axial directions and is coupled to the proximal end of the flexible upper hollow member. The distal differential assembly further comprises a lower distal gear rack that is supported for axial travel in the two axial directions and is coupled to the proximal end of the flexible lower hollow member. A distal pinion gear is rotatably supported in meshing engagement with the upper distal rack and the lower distal gear rack.

Example 6—The surgical instrument of Examples 4 or 5, wherein the source of axial drive motions comprises a proximal differential drive assembly that is supported proximal to the articulation joint and operably interfaces with the flexible upper drive member and the flexible lower drive member such that when the surgical end effector is in the unarticulated position, the proximal differential drive assembly is configured to drive the flexible upper drive member and the flexible lower drive member equal axial distances in a same axial direction to apply an upper axial drive motion and a lower axial drive motion that is equal to the upper axial drive motion to the firing member. When the surgical end effector is in an articulated position, the proximal differential drive assembly is configured to permit the flexible upper drive member and the flexible lower drive member to move equal distances in opposite axial directions while applying the upper axial drive motion and lower axial drive motion that is equal to the upper axial drive motion to the firing member.

Example 7—The surgical instrument of Example 6, wherein the proximal differential drive assembly comprises an upper proximal gear rack that operably interfaces with the flexible upper drive member and a lower proximal gear rack that operably interfaces with the flexible lower drive member. A carrier is supported for axial movement relative to the upper proximal gear rack and the lower proximal gear rack. The carrier comprises a rotatable proximal pinion gear in meshing engagement with the upper proximal gear rack and the lower proximal gear rack.

Example 8—The surgical instrument of Example 7, wherein the carrier further comprises a carrier rack in meshing engagement with a motor-driven drive gear.

Example 9—The surgical instrument of Examples 1, 2, 3, 4, 5, 6, 7 or 8, wherein the flexible upper drive member comprises an upper push coil and the flexible lower drive member comprises a lower push coil.

Example 10—The surgical instrument of Example 9, wherein the flexible upper drive member further comprises an upper push coil cable that extends through the upper push coil and comprises an upper cable distal end that is coupled to the top portion of the firing member and an upper cable proximal end that is coupled to the upper proximal gear rack. The flexible lower drive member further comprises a lower push coil cable that extends through the lower push coil and comprises a lower cable distal end that is coupled to the bottom portion of the firing member and a lower cable proximal end that is coupled to the lower proximal gear rack.

Example 11—The surgical instrument of Example 10, further comprising an upper support beam that is supported by the elongate shaft assembly and extends proximally from the upper distal gear rack. The upper support beam defines an upper axial passage therein that is configured to slidably constrain a portion of the upper push coil that extends from the distal upper gear rack to the proximal upper gear rack. The surgical instrument further comprises a lower support beam that is supported by the elongate shaft assembly and extends proximally from the lower distal gear rack. The lower support beam defines a lower axial passage therein that is configured to slidably constrain a portion of the lower push coil that extends from the distal gear rack to the proximal gear rack.

Example 12—The surgical instrument of Examples 9, 10 or 11, wherein the upper push coil is received within an upper flexible sleeve and the lower push coil is received within a lower flexible sleeve.

Example 13—The surgical instrument of Examples 1, 2, 3, 4, 5, 6, 7, 8, 9, 10, 11 or 12, wherein the articulation joint comprises a proximal joint member hat is attached to the elongate shaft assembly and a distal joint member that is attached to the surgical end effector. A linkage assembly pivotally couples the proximal joint member to the distal joint member.

Example 14—The surgical instrument of Example 13, further comprising a plurality of flexible articulation actuators that extend through the elongate shaft assembly and the proximal joint member and are attached to the distal articulation joint member.

Example 15—A surgical instrument comprising an elongate shaft assembly that has a surgical end effector coupled thereto by an articulation joint that is configured to facilitate selective articulation of the surgical end effector relative to the elongate shaft assembly in multiple articulation planes. A firing member is supported for axial travel within the surgical end effector between a starting position and an ending position. A firing system is configured to selectively move the firing member between the starting position and the ending position. The firing system comprises an upper flexible firing assembly that comprises a flexible upper hollow member that includes an upper proximal end and an upper distal end. The upper proximal end is supported within the elongate shaft assembly for axial travel in two directions. The flexible upper hollow member spans the articulation joint and the upper distal end is fixed to the surgical end effector. The upper flexible firing assembly further comprises a flexible upper push coil that operably interfaces with a source of axial drive motions. The flexible upper push coil is slidably constrained in the flexible upper hollow member for axial movement therein. The flexible upper push coil spans the articulation joint inside of the flexible upper hollow member and operably interfaces with an upper portion of the firing member to apply upper axial drive motions thereto to move the firing member from the starting position to the ending position. The firing system further comprises a lower flexible firing assembly that includes a flexible lower hollow member that comprises a lower proximal end and a lower distal end. The lower proximal end is supported within the elongate shaft assembly for axial travel in the two axial directions. The flexible lower hollow member spans the articulation joint and the lower distal end is fixed to the surgical end effector. The upper proximal end of flexible upper hollow member and the lower proximal end of the flexible hollow lower member are configured to move equal distances relative to each other in opposite axial directions when the surgical end effector is articulated relative to the elongate shaft assembly. The lower flexible firing assembly further comprises a flexible lower push coil that operably interfaces with the source of axial drive motions. The flexible lower push coil is slidably constrained in the flexible lower hollow member for axial movement therein. The flexible lower push coil spans the articulation joint inside of the flexible lower hollow member and operably interfaces with a lower portion of the firing member to apply lower axial drive motions thereto to move the firing member from the starting position to the ending position.

Example 16—The surgical instrument of Example 15, wherein the source of axial drive motions comprises a proximal differential drive assembly that is supported proximal to the articulation joint and operably interfaces with the flexible upper push coil and the flexible lower push coil such that when the surgical end effector is in an unarticulated position, the proximal differential drive assembly is configured to drive the flexible upper push coil and the flexible lower push coil equal axial distances in a same axial direction to apply an upper axial drive motion and a lower axial drive motion that is equal to the upper axial drive motion to the firing member. When the surgical end effector is in an articulated position, the proximal differential drive assembly is configured to permit the flexible upper push coil and the flexible lower push coil to move equally in opposite axial directions while applying the upper axial drive motion and lower axial drive motion that is equal to the upper axial drive motion to the firing member.

Example 17—The surgical instrument of Example 16, wherein the proximal differential drive assembly comprises an upper proximal gear rack that operably interfaces with the flexible upper push coil and a lower proximal gear rack that operably interfaces with the flexible lower push coil. A carrier is supported for axial movement relative to the upper proximal gear rack and the lower proximal gear rack. The carrier comprises a rotatable proximal pinion gear that is in meshing engagement with the upper proximal gear rack and the lower proximal gear rack.

Example 18—The surgical instrument of Example 17, wherein carrier further comprises a carrier rack in meshing engagement with a motor-driven drive gear.

Example 19—The surgical instrument of Examples 15, 16, 17 or 18, wherein the flexible upper push coil further comprises an upper push coil cable that extends through the flexible upper push coil and comprises an upper cable distal end that coupled to the top portion of the firing member and an upper cable proximal end that is coupled to the upper proximal gear rack. The flexible lower push cable further comprises a lower push coil cable that extends through the lower push coil and comprises a lower cable distal end that is coupled to the bottom portion of the firing member and a lower cable proximal end that is coupled to the lower proximal gear rack.

Example 20—The surgical instrument of Examples 15, 16, 17, 18 or 19, wherein the upper push coil is received within an upper flexible sleeve and the lower push coil is received within a lower flexible sleeve.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:

(a) an elongate shaft;

(b) a surgical end effector operatively coupled with said elongate shaft by an articulation joint, wherein said articulation joint is configured to facilitate selective articulation of said surgical end effector relative to said elongate shaft in multiple articulation planes;

(c) a firing driver supported for axial travel within said surgical end effector between a starting position and an ending position; and (d) a firing system configured to selectively move said firing driver between the starting position and the ending position, wherein said firing system comprises:

(i) an upper flexible firing assembly comprising:

(A) a flexible upper hollow guide comprising an upper proximal end and an upper distal end, wherein said upper proximal end is supported within said elongate shaft, wherein said flexible upper hollow guide spans said articulation joint and said upper distal end is fixed to said surgical end effector; and (B) a flexible upper driver comprising an upper driver proximal end operably interfacing with a source of axial drive motions, wherein said flexible upper driver is slidably constrained in said flexible upper hollow guide for axial movement therein, wherein said flexible upper driver spans said articulation joint and further comprises an upper driver distal end that operably interfaces with an upper portion of said firing driver to apply upper axial drive motions thereto to move said firing driver from the starting position to the ending position, wherein said flexible upper driver comprises an upper hollow coil; and (ii) a lower flexible firing assembly comprising:

(A) a flexible lower hollow guide comprising a lower proximal end and a lower distal end, wherein said lower proximal end is supported within said elongate shaft, wherein said flexible lower hollow guide spans said articulation joint and said lower distal end is fixed to said surgical end effector; and (B) a flexible lower driver comprising a lower driver proximal end operably interfacing with said source of axial drive motions, wherein said flexible lower driver is slidably constrained in said flexible lower hollow guide for axial movement therein, wherein said flexible lower driver spans said articulation joint and further comprises a lower driver distal end that operably interfaces with a lower portion of said firing driver to apply lower axial drive motions thereto to move said firing driver from the starting position to the ending position, wherein said flexible lower driver comprises a lower hollow coil.

2. The surgical instrument of claim 1, wherein said flexible upper hollow guide forms an upper pathway spanning said articulation joint for slidably supporting said flexible upper driver therethrough, wherein said flexible lower hollow guide forms a lower pathway spanning said articulation joint for slidably supporting said flexible lower driver therethrough, wherein said upper pathway and said lower pathway are parallel to each other when said surgical end effector is in an unarticulated position and wherein said upper pathway and said lower pathway are concentric to each other when said surgical end effector is articulated relative to said elongate shaft.

3. The surgical instrument of claim 2, wherein said upper proximal end of said flexible upper hollow guide and said lower proximal end of said flexible lower hollow guide are coupled to a distal differential assembly operably supported by said elongate shaft, wherein said distal differential assembly is configured to enable said flexible upper hollow guide and said flexible lower hollow guide to move in opposite axial directions when said surgical end effector is articulated relative to said elongate shaft.

4. The surgical instrument of claim 3, wherein said distal differential assembly comprises:

an upper distal gear rack supported for axial travel in two axial directions, wherein said upper distal gear rack is coupled to said proximal end of said flexible upper hollow guide;

a lower distal gear rack supported for axial travel in the two axial directions, wherein said lower distal gear rack is coupled to said proximal end of said flexible lower hollow guide; and a distal pinion gear rotatably supported in meshing engagement with said upper distal rack and said lower distal gear rack.

5. The surgical instrument of claim 3, wherein said source of axial drive motions comprises a proximal differential drive assembly supported proximal to said articulation joint and operably interfacing with said flexible upper driver and said flexible lower driver such that when said surgical end effector is in said unarticulated position, said proximal differential drive assembly is configured to drive said flexible upper driver and said flexible lower driver equal axial distances in a same axial direction to apply an upper axial drive motion and a lower axial drive motion that is equal to the upper axial drive motion to said firing driver, and wherein when said surgical end effector is in an articulated position, said proximal differential drive assembly is configured to permit said flexible upper driver and said flexible lower driver to move equal axial distances in opposite axial directions while applying the upper axial drive motion and lower axial drive motion that is equal to the upper axial drive motion to said firing driver.

6. The surgical instrument of claim 5, wherein, said proximal differential drive assembly comprises:

an upper proximal gear rack operably interfacing with said flexible upper driver; a lower proximal gear rack operably interfacing with said flexible lower driver; and a carrier supported for axial movement relative to said upper proximal gear rack and said lower proximal gear rack, wherein said carrier comprises a rotatable proximal pinion gear in meshing engagement with said upper proximal gear rack and said lower proximal gear rack.

7. The surgical instrument of claim 6, wherein said carrier further comprises a carrier rack in meshing engagement with a motor-driven drive gear.

8. The surgical instrument of claim 6, wherein said flexible upper driver comprises an upper push coil, and wherein said flexible lower driver comprises a lower push coil.

9. The surgical instrument of claim 8, wherein said flexible upper driver further comprises an upper push coil cable extending through said upper push coil and comprising an upper cable distal end coupled to said top portion of said firing driver and an upper cable proximal end coupled to said upper proximal gear rack, and wherein said flexible lower driver further comprises a lower push coil cable extending through said lower push coil and comprising a lower cable distal end coupled to said bottom portion of said firing driver and a lower cable proximal end coupled to said lower proximal gear rack.

10. The surgical instrument of claim 9, further comprising:

an upper support beam supported by said elongate shaft and extending proximally from said upper distal gear rack, wherein said upper support beam defines an upper axial passage therein configured to slidably constrain a portion of said upper push coil extending from said distal upper gear rack to said proximal upper gear rack; and a lower support beam supported by said elongate shaft and extending proximally from said lower distal gear rack, wherein said lower support beam defines a lower axial passage therein configured to slidably constrain a portion of said lower push coil extending from said distal gear rack to said proximal gear rack.

11. The surgical instrument of claim 8, wherein said upper push coil is received within an upper flexible sleeve, and wherein said lower push coil is received within a lower flexible sleeve.

12. The surgical instrument of claim 1, wherein said articulation joint comprises:

a proximal joint portion attached to said elongate shaft;

a distal joint portion attached to said surgical end effector; and a linkage assembly pivotally coupling said proximal joint portion to said distal joint portion.

13. The surgical end effector of claim 12, further comprising a plurality of flexible articulation actuators extending through said elongate shaft and said proximal joint portion and attached to said distal joint portion.

14. A surgical instrument, comprising:

(a) an elongate shaft;

(b) a surgical end effector operatively coupled with said elongate shaft by an articulation joint, wherein said articulation joint is configured to facilitate selective articulation of said surgical end effector relative to said elongate shaft in multiple articulation planes;

(c) a firing driver supported for axial travel within said surgical end effector between a starting position and an ending position; and (d) a firing system configured to selectively move said firing driver between the starting position and the ending position, wherein said firing system comprises:

(i) an upper flexible firing assembly comprising:

(A) a flexible upper hollow guide comprising an upper proximal end and an upper distal end, wherein said upper proximal end is supported within said elongate shaft for axial travel in two axial directions, wherein said flexible upper hollow guide spans said articulation joint and said upper distal end is fixed to said surgical end effector; and (B) a flexible upper push coil operably interfacing with a source of axial drive motions, wherein said flexible upper push coil is slidably constrained in said flexible upper hollow guide for axial movement therein, wherein said flexible upper push coil spans said articulation joint inside of said flexible upper hollow guide and operably interfaces with an upper portion of said firing driver to apply upper axial drive motions thereto to move said firing driver from the starting position to the ending position; and (ii) a lower flexible firing assembly comprising:

(A) a flexible lower hollow guide comprising a lower proximal end and a lower distal end, wherein said lower proximal end is supported within said elongate shaft for axial travel in the two axial directions, wherein said flexible lower hollow guide spans said articulation joint and said lower distal end is fixed to said surgical end effector, wherein said upper proximal end of flexible upper hollow guide and said lower proximal end of said flexible hollow lower guide are configured to move equal distances relative to each other in opposite axial directions when said surgical end effector is articulated relative to said elongate shaft; and (B) a flexible lower push coil operably interfacing with said source of axial drive motions, wherein said flexible lower push coil is slidably constrained in said flexible lower hollow guide for axial movement therein, wherein said flexible lower push coil spans said articulation joint inside of said flexible lower hollow guide and operably interfaces with a lower portion of said firing driver to apply lower axial drive motions thereto to move said firing driver from the starting position to the ending position.

15. The surgical instrument of claim 14, wherein said source of axial drive motions comprises a proximal differential drive assembly supported proximal to said articulation joint and operably interfacing with said flexible upper push coil and said flexible lower push coil such that when said surgical end effector is in an unarticulated position, said proximal differential drive assembly is configured to drive said flexible upper push coil and said flexible lower push coil equal axial distances in a same axial direction to apply an upper axial drive motion and a lower axial drive motion that is equal to the upper axial drive motion to said firing driver, and wherein when said surgical end effector is in an articulated position, said proximal differential drive assembly is configured to permit said flexible upper push coil and said flexible lower push coil to move equally in opposite axial directions while applying the upper axial drive motion and lower axial drive motion that is equal to the upper axial drive motion to said firing driver.

16. The surgical instrument of claim 15, wherein, wherein said proximal differential drive assembly comprises:

an upper proximal gear rack operably interfacing with said flexible upper push coil;

a lower proximal gear rack operably interfacing with said flexible lower push coil; and a carrier supported for axial movement relative to said upper proximal gear rack and said lower proximal gear rack, and wherein said carrier comprises a rotatable proximal pinion gear in meshing engagement with said upper proximal gear rack and said lower proximal gear rack.

17. The surgical instrument of claim 16, wherein said carrier further comprises a carrier rack in meshing engagement with a motor-driven drive gear.

18. The surgical instrument of claim 17, wherein said flexible upper push coil further comprises an upper push coil cable extending through said flexible upper push coil and comprising an upper cable distal end coupled to said top portion of said firing driver and an upper cable proximal end coupled to said upper proximal gear rack, and wherein said flexible lower push cable further comprises a lower push coil cable extending through said lower push coil and comprising a lower cable distal end coupled to said bottom portion of said firing driver and a lower cable proximal end coupled to said lower proximal gear rack.

19. The surgical instrument of claim 18, wherein said upper push coil is received within an upper flexible sleeve, and wherein said lower push coil is received within a lower flexible sleeve.

* * * * *